US010889865B2

(12) United States Patent
Fahey, III et al.

(10) Patent No.: US 10,889,865 B2
(45) Date of Patent: Jan. 12, 2021

(54) THYROID TUMORS IDENTIFIED

(71) Applicant: Cornell University, Ithaca, NY (US)

(72) Inventors: Thomas J. Fahey, III, Larchmont, NY (US); Nimmi Kapoor, Orange, CA (US); Theresa Scognamiglio, Brooklyn, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/440,489

(22) Filed: Feb. 23, 2017

(65) Prior Publication Data

US 2017/0166980 A1 Jun. 15, 2017

Related U.S. Application Data

(63) Continuation of application No. 14/087,812, filed on Nov. 22, 2013, now Pat. No. 9,587,279, which is a continuation of application No. 13/063,429, filed as application No. PCT/US2009/005091 on Sep. 11, 2009, now abandoned.

(60) Provisional application No. 61/191,845, filed on Sep. 12, 2008, provisional application No. 61/207,812, filed on Feb. 17, 2009.

(51) Int. Cl.
*C12Q 1/6883* (2018.01)
*C12Q 1/6886* (2018.01)

(52) U.S. Cl.
CPC ......... *C12Q 1/6886* (2013.01); *C12Q 1/6883* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 5,698,410 | A * | 12/1997 | Burstein .............. | G01N 33/574 435/7.2 |
| 9,587,279 | B2 | 3/2017 | Fahey, III et al. | |
| 2006/0035244 | A1 | 2/2006 | Riggins et al. | |
| 2007/0037186 | A1 * | 2/2007 | Jiang .................... | C12Q 1/6886 435/6.12 |
| 2007/0099209 | A1 | 5/2007 | Clarke et al. | |
| 2008/0044824 | A1 * | 2/2008 | Giordano ............ | C12Q 1/6886 435/6.16 |
| 2008/0292546 | A1 | 11/2008 | Clarke et al. | |
| 2009/0298061 | A1 | 12/2009 | Wirtz | |
| 2010/0131432 | A1 | 5/2010 | Kennedy et al. | |

(Continued)

FOREIGN PATENT DOCUMENTS

| | | |
|---|---|---|
| WO | WO-0063438 A2 | 10/2000 |
| WO | WO-2005085471 A2 | 9/2005 |

(Continued)

OTHER PUBLICATIONS

Whitehead et al. Genome Biology. 2005. 6(2): Article R13. (Year: 2005).*

(Continued)

*Primary Examiner* — Joseph G. Dauner
(74) *Attorney, Agent, or Firm* — Schwegman Lundberg & Woessner, P.A.

(57) ABSTRACT

The invention relates to methods and kits for detecting thyroid cancer by detecting differences in the expression of genes that are differentially expressed in thyroid cancer cells.

18 Claims, 5 Drawing Sheets

Specification includes a Sequence Listing.

(56) References Cited

U.S. PATENT DOCUMENTS

| | | | |
|---|---|---|---|
| 2010/0285979 A1 | 11/2010 | Zeiger et al. |
| 2011/0251091 A1 | 10/2011 | Fahey, III et al. |
| 2012/0172243 A1 | 7/2012 | Davicioni et al. |
| 2015/0167094 A1 | 6/2015 | Fahey, III et al. |

FOREIGN PATENT DOCUMENTS

| | | | |
|---|---|---|---|
| WO | WO-2005100608 A2 | 10/2005 |
| WO | WO-2006020269 A2 | 2/2006 |
| WO | WO-2010030365 A2 | 3/2010 |
| WO | WO-2010030365 A3 | 3/2010 |
| WO | WO-2010124372 A1 | 11/2010 |

OTHER PUBLICATIONS

Human Protein Atlas. Retrieved on Jun. 28, 2018 from the internet: https://www.proteinatlas.org. (Year: 2018).*

Affymetrix NetAffx. Retrieved on Jun. 28, 2018 from the internet: https://www.affymetrix.com/analysis/netaffx/showresults.affx#. (Year: 2018).*

""[HG-UI33A] Affymetrix Human Genome U133A Array"", GEO, XP002528459, (Mar. 11, 2002), 4 pgs.

"U.S. Appl. No. 13/063,429, Examiner Interview Summary dated Mar. 11, 2015", 2 pgs.

"U.S. Appl. No. 13/063,429, Final Office Action dated Sep. 2, 2014", 20 pgs.

"U.S. Appl. No. 13/063,429, Non Final Office Action dated Feb. 21, 2014", 24 pgs.

"U.S. Appl. No. 13/063,429, Preliminary Amendment filed Mar. 10, 2011", 3 pgs.

"U.S. Appl. No. 13/063,429, Response filed Jan. 21, 2014 to Restriction Requirement dated Nov. 22, 2013", 11 pgs.

"U.S. Appl. No. 13/063,429, Response filed May 20, 2014 to Non Final Office Action dated Feb. 21, 2014", 17 pgs.

"U.S. Appl. No. 13/063,429, Restriction Requirement dated Nov. 22, 2013", 11 pgs.

"U.S. Appl. No. 13/063,429, Supplemental Preliminary Amendment filed Feb. 4, 2013", 11 pgs.

"U.S. Appl. No. 13/063,429, Supplemental Preliminary Amendment filed May 31, 2011", 10 pgs.

"U.S. Appl. No. 13/063,429, Supplemental Preliminary Amendment filed Jun. 25, 2013", 11 pgs.

"U.S. Appl. No. 14/087,812, Advisory Action dated Oct. 22, 2015", 3 pgs.

"U.S. Appl. No. 14/087,812, Advisory Action dated Oct. 28, 2014", 3 pgs.

"U.S. Appl. No. 14/087,812, Examiner Interview Summary dated Jun. 29, 2015", 3 pgs.

"U.S. Appl. No. 14/087,812, Final Office Action dated Jun. 29, 2016", 10 pgs.

"U.S. Appl. No. 14/087,812, Final Office Action dated Aug. 12, 2014", 19 pgs.

"U.S. Appl. No. 14/087,812, Final Office Action dated Aug. 12, 2015", 7 pgs.

"U.S. Appl. No. 14/087,812, Non Final Office Action dated Mar. 9, 2016", 8 pgs.

"U.S. Appl. No. 14/087,812, Non Final Office Action dated Mar. 26, 2014", 21 pgs.

"U.S. Appl. No. 14/087,812, Non Final Office Action dated Mar. 31, 2015", 10 pgs.

"U.S. Appl. No. 14/087,812, Notice of Allowance dated Oct. 20, 2016", 9 pgs.

"U.S. Appl. No. 14/087,812, Response filed Jan. 6, 2016 to Advisory Action dated Oct. 22, 2015", 7 pgs.

"U.S. Appl. No. 14/087,812, Response filed Jun. 24, 2014 to Non Final Office Action dated Mar. 26, 2014", 18 pgs.

"U.S. Appl. No. 14/087,812, Response filed Jun. 25, 2015 to Non Final Office Action dated Mar. 31, 2015", 11 pgs.

"U.S. Appl. No. 14/087,812, Response filed Sep. 29, 2016 to Final Office Action dated Jun. 29, 2016", 8 pgs.

"U.S. Appl. No. 14/087,812, Response filed Oct. 13, 2014 to Final Office Action dated Aug. 12, 2014", 11 pgs.

"U.S. Appl. No. 14/087,812, Response filed Oct. 13, 2015 to Final Office Action dated Aug. 12, 2014", 8 pgs.

"U.S. Appl. No. 14/087,812, Response filed Nov. 19, 2014 to Advisory Action dated Oct. 28, 2014", 11 pgs.

"U.S. Appl. No. 14/087,812, Response filed Jun. 14, 2016 to Non Final Office Action dated Mar. 9, 2016", 20 pgs.

"International Application Serial No. PCT/US2009/005091, International Preliminary Report on Patentability dated Mar. 15, 2011", 9 pgs.

"International Application Serial No. PCT/US2009/005091, International Search Report dated Mar. 31, 2010", 9 pgs.

"International Application Serial No. PCT/US2009/005091, Invitation to Pay Additional Fee dated Jan. 11, 2010", 9 pgs.

"International Application Serial No. PCT/US2009/005091, Written Opinion dated Mar. 31, 2010", 9 pgs.

Arora, N., et al., "Identification of Borderline Thyroid Tumors by Gene Expression Array Analysis", Cancer, (2009), 11 pgs.

Durand, S, et al., "Evaluation of gene expression profiles in thyroid nodule biopsy material to diagnose thyroid cancer", Journal of Clinical Endocrinology & Metabolism, 93(4), (2008), 1195-1202.

Finley, D. J, et al., "Advancing the Molecular Diagnosis of Thyroid Nodules: Defining Benign Lesions by Molecular Profiling", Thyroid, 15(6), (2005), 562-568.

Finley, D. J, et al., "Discrimination of Benign and Malignant Thyroid Nodules by Molecular Profiling", Annuals of Surgery, 240(3), (2004), 425-437.

Finley, D. J, et al., "Molecular Profiling Distinguishes Papillary Carcinoma from Benign Thyroid Nodules", The Journal of Clinical Endrocrinology & Metabolism, 89(7), (Jul. 2004), 3214-3223.

Fontaine, J.-F., et al., "Microarray analysis refines classification of non-medullary thyroid tumours of uncertain malignancy", Oncogene, 27, (2008), 2228-2236.

Gombos, K., et al., "Characterization of microarray gene expression profiles of early stage thyroid tumours", Cancer Genomics & Proteomics, 4(6), (2007), 403-409.

Lubitz, C. C., et al., "Gene expression profiling of thyroid tumors—clinical applicability", Nature Clinical Practice—Endocrinology & Metabolism, 2(9), (2006), 472-473.

Lubitz, C. C., et al., "Microarray Analysis of Thyroid Nodule Fine-Needle Aspirates Accurately Classifies Benign and Malignant Lesions", Journal of Molecular Diagnostics, 8(4), (2006), 490-498.

Lubitz, C. C, et al., "Molecular analysis of minimally invasive follicular carcinomas by gene profiling", Surgery, 138(6), (2005), 1042-1048; Discussion 1048-1049.

Lubitz, C. C., et al., "The Differentiation of Benign and Malignant Thyroid Nodules", Advances in Surgery, vol. 39, (2005), 355-376.

Nikolova, D, et al., ""Genome-wide gene expression profiles of thyroid carcinoma: Identification of molecular targets for treatment of thyroid carcinoma"", Oncology Reports, 20(1), (2008), 105-121.

Puxeddu, E., et al., "Clinical implications of BRAF mutation in thyroid carcinoma", Trends in Endocrinology and Metabolism, 19(4), (2008), 138-145.

Stolf, B. S., et al., "Expres si on profil e of malignant and non-malignant diseases of the thyroid gland reveals altered expression of a common set of genes in goiter and papillary carcinomas", Cancer Letters, 227(1), (2005), 59-73.

* cited by examiner

THYROID TUMORS IDENTIFIED

CROSS-REFERENCE TO RELATED APPLICATIONS

This patent application is a continuation of U.S. patent application Ser. No. 14/087,812, filed Nov. 22, 2013, which is a continuation of U.S. patent application Ser. No. 13/063,429, filed Jun. 2, 2011, which is a National Stage application under 35 U.S.C. 371 of PCT/US2009/005091, filed Sep. 11, 2009 and published as WO 2010/030365 A2 on Mar. 18, 2010 which claims the benefit of priority, under 35 U.S.C. Section 119(e), to U.S. Provisional Patent Application Ser. No. 61/191,845 filed on Sep. 12, 2008, and U.S. Provisional Patent Application Ser. No. 61/207,812 filed Feb. 17, 2009, the contents of both of which applications are specifically incorporated by reference herein in their entireties.

FIELD OF THE INVENTION

The invention relates to detection and diagnosis of thyroid cancer. In some embodiments, the methods of the invention can be used to distinguish between benign thyroid cells or tissues, malignant thyroid cells or tissues, and follicular adenomas with nuclear atypia (FANA).

BACKGROUND OF THE INVENTION

Thyroid nodules are common in the United States, occurring in greater than 60% of individuals. Moreover, their incidence is steadily increasing, mainly because of the increased detection of smaller, asymptomatic nodules. Although the majority of these nodules are benign, a significant numbers of patients undergo surgical excision. Upon pathologic review of such thyroid tumors, clear-cut benign or malignant diagnoses often can be rendered. However, follicular lesions of the thyroid often pose a diagnostic challenge.

A particular diagnostic dilemma is presented in a subset of encapsulated follicular lesions with partial nuclear features of papillary thyroid carcinoma (PTC) (occasional nuclear grooves, focal nuclear clearing, and overlapping nuclei) and with histological features that fail to place them reliably in either the benign category or the malignant category. In the inventors' experience, these tumors represent approximately 10% of all follicular-patterned lesions observed at surgical pathology (see also, Arora et al. World J Surg. 32:1237-1246 (2008)). The difficulty of classifying this group of tumors is exemplified further by several studies in which poor interobserver agreement was demonstrated among expert endocrine pathologists ranging from 39% to 58% when they reviewed follicular-patterned lesions of the thyroid (Chan et al., Am J Clin Pathol. 117:16-18 (2002); Franc et al., Hum Pathol. 34:1092-1100 (2003); Lloyd et al., Am J Surg Pathol. 28:1336-1340 (2004); Saxen et al. Acta Pathol Microbiol Scand [A]. 1978; 86A:483-4864-8 (1978); Hirokawa et al. Am J Surg Pathol. 26:1508-1514 (2002)). This diagnostic difficulty in classifying such borderline tumors with standard terminology led Williams to propose the term well differentiated tumor of uncertain malignant potential (WDT-UMP) as a separate diagnostic category (Int J Surg Pathol. 8:181-183 (2000).

No matter what terminology is used for these tumors, additional tools are needed to determine whether thyroid nodules and/or tumors are actually malignant or simply benign, and/or whether such nodules and/or tumors can progress to become malignant tumors.

SUMMARY OF THE INVENTION

The invention relates to methods for improved diagnosis of thyroid cancer that can distinguish not only benign nodules from malignant thyroid tumors but can also identify borderline, pre-cancerous tumors (e.g., encapsulated follicular lesions that may have partial nuclear features of PTC) that may not need aggressive treatment. For example, in one study conducted by the inventors using the methods described herein, the majority of histologically uncertain tumors (66.7%) were determined to be premalignant tumors, while a smaller number of tumors were determined to be benign tumors (26.7%) and only a even smaller number of tumors were actually malignant tumors (6.7%). By using the methods and kits of the invention, the malignant thyroid tumors can be identified with greater certainty, thereby avoiding unnecessary, expensive and invasive medical procedures that might otherwise have been used to treat histologically uncertain tumors.

Thus, one aspect of the invention is a method of detecting whether thyroid cancer cells are present in a test tissue or cell sample which comprises (a) observing test levels of RNA or protein expression in the test tissue or cell sample for any differentially expressed gene, and (b) comparing the test levels of expression to one or more standard or control levels of expression, to ascertain whether higher or lower levels of expression of any of the genes is present in the test tissue or cell sample, and thereby detecting whether thyroid cancer cells are present in the test tissue or cell sample; wherein the differentially expressed gene is selected from the group consisting of ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC25A15, SLC4A4, SLIT1, SPTAN1, TFCP2L1, TIAM1, TIMP1, TNS3, TSPAN12, UPP1, and a combination thereof.

In some embodiments, the differentially expressed gene can be selected from the group consisting of DIO1, DTX4, GALNT7, HMGA2, IGFBP6, MET, PROS1, SDC4, SERPINA1, SLC4A4, TIAM1, TIMP1, UPP1 and a combination thereof. In other embodiments, the differentially expressed gene can be selected from the group consisting of ANK2, ARHGAP6, CDH16, CITED 1, CITED 2, COL9A3, ChGn, DUSP4, EFEMP1, ELMO1, FGFR2, FLRT1, FMOD, GATM, KIT, LRP4, MATN2, SLIT1, SPTAN1, TFCP2L1, PIP3-E, PSD3, TNS3, TSPANI2, TIAM1 and a combination thereof. In further embodiments, the differentially expressed gene can be selected from the group consisting of C11orf17, CAPN3, CAPN3, CKB, CSRP2, DAPK2, DPP4, HGD, MYH10, NAUK2, PFAAP5, PGF, PKNOX2, PRKACB, QPCT, RAB27A, RXRG, and SLC25A15 and a combination thereof.

Any methods available to one of skill in the art can be used to detect and/or quantify the test levels of RNA. For example, the test levels of RNA expressed can be detected by microarray analysis or by nucleic acid amplification. In some embodiments, the test levels of RNA expressed are detected by microarray analysis that includes use of one or more probes on the microarray that can hybridize to one or more of the differentially expressed genes, or an RNA or DNA copy of the one or more differentially expressed genes. For example, such methods can employ one or more probes that can hybridize to any of SEQ ID NO: 119-172. In some embodiments, the one or more probes hybridize to one or more of the differentially expressed genes, or an RNA or DNA copy of the one or more differentially expressed genes under moderate to highly stringent hybridization conditions. For example, the hybridization conditions can be highly stringent hybridization conditions.

In other embodiments, nucleic acid amplification can be employed. Such nucleic acid amplification can include reverse transcription polymerase chain reaction, real time polymerase chain reaction, or quantitative polymerase chain reaction. For example, the test levels of RNA expressed can be detected by nucleic acid amplification using one or more primers that hybridize to one or more of the differentially expressed genes, or an RNA or DNA copy of the one or more differentially expressed genes under moderate to highly stringent hybridization conditions. The one or more primers employed can, for example, hybridize to any of SEQ ID NO: 119-172. Such hybridization conditions can in some instances be highly stringent hybridization conditions.

The one or more standard or control levels of expression can include: an expression level observed for a malignant thyroid cancer cell or tissue; an expression level observed for a benign thyroid cell or tissue; an expression level observed for a follicular adenoma with nuclear atypia; an expression level observed for a borderline thyroid cell or tissue; an expression level observed for a normal non-cancerous thyroid cell or tissue; or an expression level observed for a constitutively expressed gene.

These methods can distinguish between benign, malignant and borderline thyroid cells or tissues. For example, these methods can distinguish between benign thyroid cells or tissues, malignant thyroid cells or tissues, and follicular adenomas with nuclear atypia (FANA). For example, the test tissue or cell sample is obtained from a patient with thyroid cancer or suspected of having thyroid cancer.

Another aspect of the invention is a kit comprising: (a) at least one set of oligonucleotide primers, wherein a first primer in the set contains a sequence complementary to a region in one strand of a nucleic acid sequence template and primes the synthesis of a first extension product, and a second primer contains a sequence complementary to a region in said first extension product and primes the synthesis of a nucleic acid strand complementary to said first extension product, and wherein the template is a differentially expressed gene, or an RNA or DNA copy of the differentially expressed gene; and (b) instructions for using the at least one set of oligonucleotide primers; wherein the differentially expressed gene is selected from the group consisting of ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC25A15, SLC4A4, SLIT1, SPTAN1, TFCP2L1, TIAM1, TIMP1, TNS3, TSPAN12, UPP1, and a combination thereof.

In some embodiments, the differentially expressed gene can be selected from the group consisting of DIO1, DTX4, GALNT7, HMGA2, IGFBP6, MET, PROS1, SDC4, SERPINA1, SLC4A4, TIAM1, TIMP1, UPP1 and a combination thereof. In other embodiments, the differentially expressed gene can be selected from the group consisting of ANK2, ARHGAP6, CDH16, CITED 1, CITED 2, COL9A3, ChGn, DUSP4, EFEMP1, ELMO1, FGFR2, FLRT1, FMOD, GATM, KIT, LRP4, MATN2, SLIT1, SPTAN1, TFCP2L1, PIP3-E, PSD3, TNS3, TSPAN12, TIAM1 and a combination thereof. In further embodiments, the differentially expressed gene can be selected from the group consisting of C11orf17, CAPN3, CAPN3, CKB, CSRP2, DAPK2, DPP4, HGD, MYH10, NAUK2, PFAAP5, PGF, PKNOX2, PRKACB, QPCT, RAB27A, RXRG, and SLC25A15 and a combination thereof. The first primer and/or the second primer can include a label. A container of nucleotides can also be included in the kit where the nucleotides are used as subunits in the synthesis of and amplified product. For example, the nucleotides can be ribonucleotides and/or deoxyribonucleotides. One or more of such nucleotides can include a label.

The instructions can describe a method for amplifying an mRNA, cRNA or cDNA corresponding to the differentially expressed gene(s). In some embodiments, the first primer and/or the second primer may hybridize to an mRNA, cRNA or cDNA corresponding to the differentially expressed gene under moderate to highly stringent hybridization conditions. For example, the hybridization conditions can be highly stringent hybridization conditions in some instances.

Another aspect of the invention is a kit that includes (a) a microarray with covalently attached probes that can hybridize to a differentially expressed gene selected from the group consisting of ANK2, ARHGAP6, C11orf17, CAPN3, CDHI6, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC25A15, SLC4A4. SLIT1, SPTAN1, TFCP2L1, TIAM1, TIMP1, TNS3, TSPAN12, UPP1, and a combination thereof; and (b) instructions for using the microarray.

In some embodiments, the differentially expressed gene can be selected from the group consisting of DIO1, DTX4, GALNT7, HMGA2, IGFBP6, MET, PROS1, SDC4, SERPINA1, SLC4A4, TIAM1, TIMP1, UPP1 and a combination thereof. In other embodiments, the differentially expressed gene can be selected from the group consisting of ANK2, ARHGAP6, CDH16, CITED 1, CITED 2, COL9A3, ChGn, DUSP4, EFEMP1, ELMO1, FGFR2, FLRT1, FMOD, GATM, KIT, LRP4, MATN2, SLIT1, SPTAN1, TFCP2L1, PIP3-E, PSD3, TNS3, TSPANI2, TIAM1 and a combination thereof. In further embodiments, the differentially expressed gene can be selected from the group consisting of C11orf17, CAPN3, CAPN3, CKB, CSRP2, DAPK2, DPP4, HGD, MYH10, NAUK2, PFAAP5, PGF, PKNOX2, PRKACB, QPCT, RAB27A, RXRG, and SLC25A15 and a combination thereof. Such probes can, in some embodiments, hybridize to an mRNA, cRNA or cDNA corresponding to the differentially expressed gene, for example, under moderate to highly stringent hybridization conditions. In some embodiments, the hybridization conditions are highly stringent hybridization conditions. Such a kit can also include one or more standard or control probes. For example, the kit can include one or more probes for a constitutively expressed gene.

Another aspect of the invention is a method of detecting a mutation in a human BRAF gene that includes: (a) obtaining a test sample of genomic DNA from a human; (b) amplifying a segment of BRAF DNA from the genomic DNA using primers with SEQ ID NO: 1 and SEQ ID NO:2; and (c) detecting whether the mutation exists in the segment amplified; wherein the mutation consists of a glutamate substituted for valine at codon 600.

Such a method can also include detecting or confirming whether the human has thyroid cancer by observing test levels of RNA or protein expression in the test tissue or cell sample for any of the differentially expressed genes described herein, using any of the methods and/or kits described herein.

DETAILED DESCRIPTION OF THE INVENTION

The invention relates to methods of detecting malignant thyroid tumors and/or distinguishing whether thyroid tumors are benign, malignant, and/or pre-cancerous borderline tumors. While currently available histological and/or cytological procedures can sometimes distinguish benign and malignant thyroid tumors, there are many thyroid tumors that cannot readily be classified as either malignant or benign by such histological procedures. Patients with such unclassified tumors are often aggressively treated as though their tumors were malignant. However, by employing the methods and kits described herein, these unclassified tumors can be properly identified as either benign, malignant, or pre-cancerous borderline tumors, thereby reducing the need for expensive, invasive and unpleasant medical treatment when it is unnecessary.

The application describes an analysis of fifty histologically-unequivocal benign and malignant tumors, which led to the identification of a list of sixty-one genes that are differentially expressed in benign and malignant thyroid tumors. These differentially expressed genes are listed in Table 1.

Figure 4:
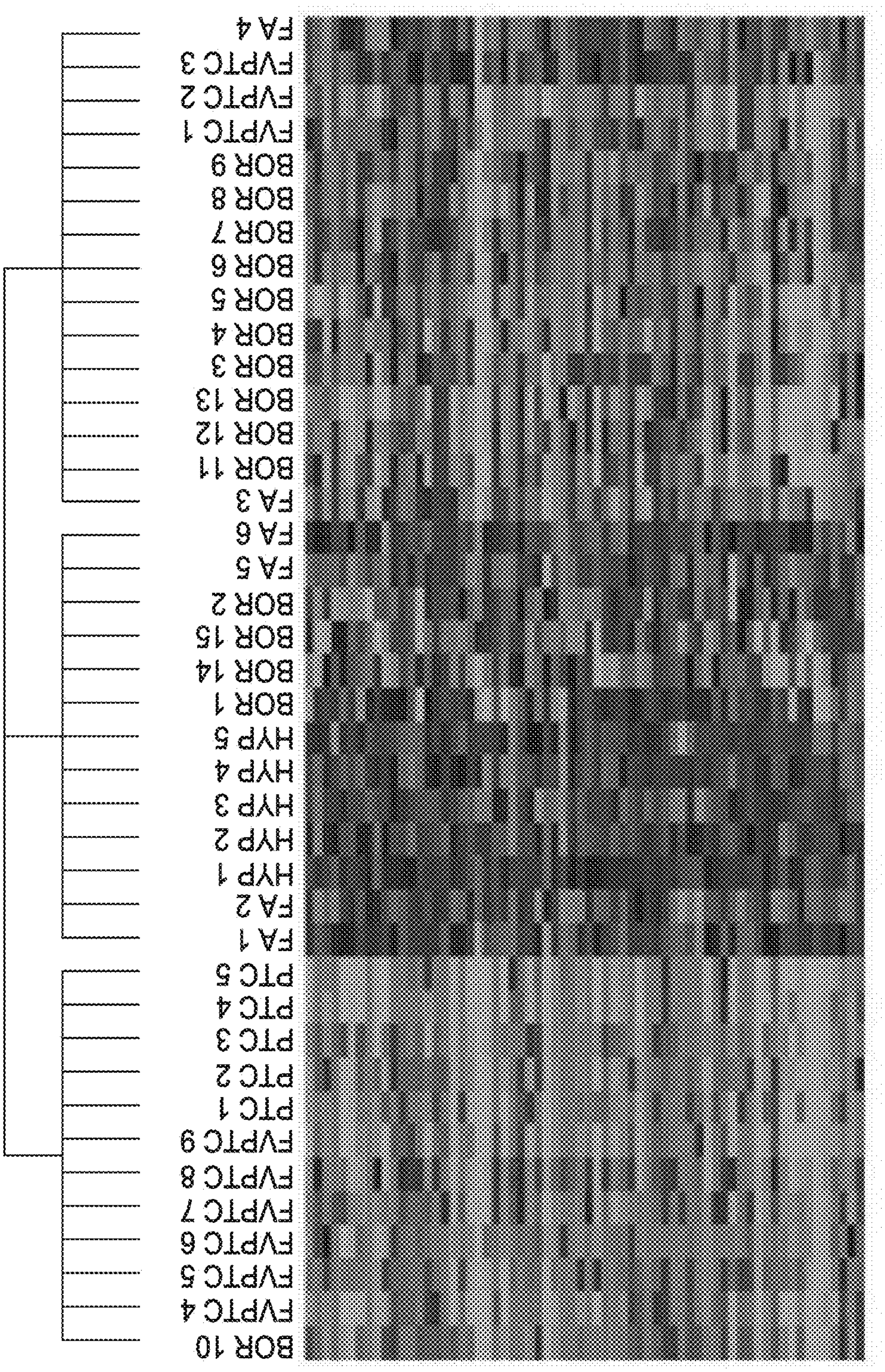
FIG. 4 is graphic generated by three-group K-means cluster analysis that identified 3 distinct groups of tumors based upon their gene expression patterns: malignant (left), benign (center), and intermediate (right). BOR indicates borderline tumor; FVPTC, follicular variant of papillary thyroid carcinoma; PTC, papillary thyroid carcinoma; FA, follicular adenoma; HYP, hyperplastic lesion.

By using probes for the fifty to sixty differentially expressed genes described herein, forty additional tumors were evaluated, including 15 histologically intermediate tumors, 11 benign tumors, and 14 papillary thyroid carcinomas (PTCs). Differential gene expression was used to detect whether the histologically intermediate thyroid tumors were malignant or not. As illustrated herein, the majority of histologically intermediate tumors (66.7%) were actually borderline, premalignant tumors that exhibited gene expression similarities with benign tumors (26.7%) and malignant tumors (6.7%) (FIG. 4). This third category of borderline tumors (encapsulated follicular tumors with cytological atypia) does not fit into previously proposed benign or malignant classification schemes using standard histological, immuno-histochemical, or mutation analyses. Instead, these borderline tumors are premalignant tumors that may warrant monitoring but do not generally need immediate aggressive medical treatment.

Twenty-seven genes were expressed differentially between the benign and borderline groups, including the cyclic AMP response element binding protein/p300-interactivator with glutamic acid/aspartic acid-rich carboxy-terminal domain 1 or CITED1 gene and the fibroblast growth factor receptor 2 or FGFR2 gene. Fourteen genes were expressed differentially between the borderline group and malignant tumors, for example, the met proto-oncogene and of the high-mobility group adenine/thymine-hook 2 or HMGA2 gene in malignancies. Mutations of the v-raf murine sarcoma viral oncogene homolog B1 or BRAF gene were identified in 4 of 14 malignant tumors but not in benign or borderline tumors.

Patients who had histologically or molecularly borderline tumors did not have metastasis or recurrences. These data indicate that encapsulated thyroid follicular lesions with partial nuclear features of PTC are biologically borderline tumors that are molecularly distinct from benign and malignant tumors. Moreover, the data indicate that such borderline tumors identified by the methods and kits of the invention are pre-cancerous with no immediate need for aggressive cancer treatment.

The gene expression profiling methods described herein are more accurate than existing procedures for diagnosing problematic thyroid tumors. For example, the methods of the invention can identify malignant thyroid tumors with greater than 90% sensitivity and 80% specificity. In some embodiments, the methods of the invention can identify malignant thyroid tumors with greater than 93% sensitivity and greater than 82% specificity.

Definitions

"Genes" are the units of heredity in living organisms. They are encoded in the organism's genetic material (DNA or RNA), and control the physical development and behavior of the organism. Genes encode the information necessary to construct the proteins (etc.) needed for the organism to function. The term "genes" generally refers to the region of DNA (or RNA, in the case of some viruses) that determines the structure of a protein (the coding sequence), together with the region of DNA that controls when and where the protein will be produced (the regulatory sequences).

As used herein, the phrase "expression profiling" refers to differential gene expression analysis/techniques. Examples of such techniques include microarray analyses, real time PCR and qPCR. Microarray technology allows for the comparison of gene expression between, for example, normal and diseased (e.g., cancerous) cells or cells which express different cell markers. There are several names for microarray technology including DNA microarrays, DNA arrays, DNA chips, gene chips, and others.

In this disclosure. "comprises," "comprising." "containing" and "having" and the like can have the meaning ascribed to them in U.S. patent law and can mean “includes,” “including,” and the like; “consisting essentially of” or “consists essentially” likewise has the meaning ascribed in U.S. patent law and the term is open-ended, allowing for the presence of more than that which is recited so long as basic or novel characteristics of that which is recited is not deleteriously changed by the presence of more than that which is recited.

Other definitions may appear throughout this disclosure in the appropriate context.

Genes that are Differentially Expressed in Benign and Malignant Thyroid Tumors

The expression levels of one or more of the genes listed in Table 1 can be detected using the methods and kits of the invention. In some embodiments, the expression levels of two or more, or three or more, or four or more, or five or more of the genes listed in Table 1 are detected to assess whether a thyroid nodule contains benign or malignant cancer cells. In other embodiments, the expression levels of seven or more, or eight or more, or ten or more, or twelve or more of the genes listed in Table 1 are detected to assess whether a thyroid nodule contains benign or malignant cancer cells. In further embodiments, the expression levels of no more than ten, no more than twelve, no more than fifteen, no more than twenty of the genes listed in Table 1 are detected to assess whether a thyroid nodule contains benign or malignant cancer cells.

Differential expression of these genes means that the mRNA or transcript levels produced by these genes increases or decreases in a test tissue or cell sample (e.g., a thyroid tissue biopsy) relative to a control, thereby indicating the presence of benign thyroid cells or tissues, malignant thyroid cells or tissues, and/or borderline tumors (e.g., encapsulated thyroid follicular lesions with partial nuclear features of PTC) in the test tissue or cell sample from which the RNA/transcripts were obtained.

Genes whose expression changes in thyroid tumor cells include one or more of the following genes: ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC4A4, SLC25A15, SLIT1, SPTAN1, TFCP2L1, TIAM1, TIMP1, TNS3, TSPAN12, UPP1, or a combination thereof.

The following genes were expressed at higher levels in malignant thyroid cancer tissues and cells than in benign thyroid lesions: CAPN3, CITED 1, DAPK2, DPP4, DUSP4, DTX4, GALNT7, HMGA2, IGFBP6, LRP4, MET, MYH10, PFAAP5, PROS1, PSD3, QPCT, RAB27A, RXRG, SERPINA1, SLIT1, SPTAN1, TIAM1, TIMP1, and UPP1. Thus, detection of an increase in the expression of one or more of these genes in a tissue or cell sample, relative to a benign control tissue sample, is indicative of thyroid cancer.

On the other hand, the following genes are expressed at lower levels in malignant thyroid cancer tissues than in benign thyroid lesions: ANK2, ARHGAP6, C11orf17, CDH16, CITED 2, COL9A3, ChGn, CKB, CSRP2, DIO1, EFEMP1, ELMO1, FGFR2, FLRT1, FMOD, GATM, HGD, KIT, MATN2, NAUK2, PGF, PIP3-E, PKNOX2, PRKACB, SDC4, SLC4A4, SLC25A15, TFCP2L1, TNS3, and TSPAN12. Thus, detection of a decrease in the expression of one or more of these genes in a tissue or cell sample, relative to a benign control tissue sample, is indicative of thyroid cancer.

However, as described herein, the inventors have discovered a third type of thyroid tumor that is pre-cancerous and may not need aggressive medical treatment when initially detected. As described herein, these borderline tumors can be distinguished from benign and malignant by their expression patterns.

The following genes are differentially expressed between malignant and borderline/benign tumors: DIO1, DTX4, GALNT7, HMGA2, IGFBP6, MET, PROS1, SDC4, SERPINA1, SLC4A4, TIAM1, TIMP1, and/or UPP1. Each of these genes exhibit increased expression in malignant tumors relative to borderline and benign tumors, except DIO1, SDC4, and SLC4A4, which are expressed at lower levels in malignant thyroid tissues and cells when compared to their expression in benign and borderline tumors. Thus, when differential expression of one or more of these genes is detected in a thyroid test or cell sample, such differential expression is indicative of the presence of malignant tumor cells.

The following genes are differentially expressed between benign and borderline/malignant lesions: ANK2, ARHGAP6, CDH16, CITED 1, CITED 2, COL9A3, ChGn, DUSP4, EFEMP1, ELMO1, FGFR2, FLRT1, FMOD, GATM, KIT, LRP4, MATN2, SLIT1, SPTAN1, TFCP2L1, PIP3-E, PSD3, TNS3, TSPAN12, and/or TIAM1. Each of these genes exhibit decreased expression in malignant tumors relative to borderline/malignant tumors, except CITED 1, DUSP4, LRP4, PSD3, SLIT1, SPTAN1, and TIAM1, which are expressed at higher levels in malignant tissues and cells compared to borderline/malignant tissues and cells. Thus, benign thyroid lesions can be identified and distinguished from borderline/malignant tumors by their differential expression patterns in a thyroid test tissue or cell sample.

The following genes are differentially expressed between benign and malignant lesions: C11orf17, CAPN3, CAPN3, CKB, CSRP2, DAPK2, DPP4, HGD, MYH10, NAUK2, PFAAP5, PGF, PKNOX2, PRKACB, QPCT, RAB27A, RXRG, and SLC25A15. Each of these genes are expressed at higher levels in malignant thyroid tumors relative to their expression levels in benign thyroid lesions, except the following genes: C11orf17, CKB, CSRP2, HGD, PGF, PKNOX2, PRKACB, and SLC25A15, which are expressed at lower levels in malignant thyroid tissues relative to benign thyroid lesions. Thus, to definitively distinguish between benign and malignant thyroid tissues, the expression of these genes can be evaluated.

The difference in expression levels between a differentially expressed gene in malignant thyroid tissues relative to the expression levels for that gene in a control (e.g., normal thyroid tissues) can be at least a 20% difference in expression levels, at least a 30% difference in expression levels, at least a 40% difference in expression levels, at least a 50% difference in expression levels, at least a 60% difference in expression levels, at least a 70% difference in expression levels, at least an 80% difference in expression levels, at least a 90% difference in expression levels, at least a 100% difference in expression levels, and/or a more than a 100% difference in expression levels. Thus, in some embodiments, the difference in expression levels between a differentially expressed gene in malignant thyroid tissues relative to the expression levels for that gene in a control (e.g., normal thyroid tissues) can be at least 1.5 fold, at least 1.7 fold, at least 1.8 fold, at least 2-fold, at least 2.2 fold, at least at least 2.3 fold, at least 2.4 fold, at least 2.5 fold, or more than 2.5 fold. Table 1 provides examples of the differences in expression levels that can readily be determined and observed.

Gene expression data may be gathered in any way that is available to one of skill in the art. For example, gene expression levels can be detected and quantified by employing an array of probes that hybridize to the different transcripts of one or more of the genes listed in Table 1, by using nucleic acid amplification (e.g., quantitative polymerase chain reaction) and through nucleic acid hybridization procedures. Other methods of determining expression of the genes include traditional Northern blotting, nuclease protection, RT-PCR and differential display methods can be used for detecting gene expression levels. Such methods are described in the following sections and in the Examples.

Probes and primers that can hybridize to an RNA, cDNA corresponding to any of the following genes can be used to detect differential gene expression: ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2, IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC4A4, SLC25A15, SLIT1, SPTAN1, TFCP2L1, TIAM1, TIMP1, TNS3, TSPAN12, UPP1, or a combination thereof.

Sequences for these differentially expressed genes are available and can be used to make probes and primers for detecting expression levels. Examples of sequences that can be used to make probes and primers for these are provided hereinbelow. Any probe or primer that can hybridize to an RNA or cDNA of any of these genes can be used in the methods of the invention. In some embodiments, such a probe or primer hybridizes such to an RNA or cDNA of a differentially expressed gene under moderately stringent conditions. In other embodiments, such a probe or primer hybridizes such to an RNA or cDNA of a differentially expressed gene under highly stringent conditions. Such conditions are known to one of skill in the art and are described herein.

RNA Manipulation

One of skill in the art will appreciate that in order to assess the mRNA transcript levels (and thereby the expression levels) of a gene or genes, it is desirable to provide a RNA sample or a nucleic acid sample derived from the mRNA transcript(s). As used herein, a nucleic acid derived from an mRNA transcript refers to a nucleic acid ultimately synthesized from the mRNA transcript. Thus, the original mRNA obtained from a test tissue or cell sample can serve as a template for generating a nucleic acid derived from an mRNA. For example, such a nucleic acid derived from an mRNA can be a cDNA reverse transcribed from an mRNA, an RNA transcribed from the cDNA, a DNA amplified from the cDNA, an RNA transcribed from the amplified DNA, and the like. Detection of such derived products is indicative of the presence and abundance of the original mRNA transcript in a test tissue or cell sample. Thus, suitable samples include, but are not limited to, mRNA transcripts of the gene or genes, cDNA reverse transcribed from the mRNA, cRNA transcribed from the cDNA, and the like.

Where it is desired to quantify the transcription level of one or more genes in a sample, the concentration of the mRNA transcript(s) of the gene or genes is proportional to the transcription level of that gene. Similarly, when hybridization is employed to quantify transcription levels, the hybridization signal intensity can be proportional to the amount of hybridized nucleic acid. As described herein, controls can be run to correct for variations introduced during sample preparation and/or hybridization.

The nucleic acid may be isolated from a test tissue or cell sample (and/or a control tissue sample) according to any of a number of methods well known to those of skill in the art. One of skill in the art will appreciate that where expression levels of a gene or genes are to be detected, RNA (mRNA) is isolated. Methods of isolating total mRNA are well known to those of skill in the art. For example, methods of isolation and purification of nucleic acids are described in Sambrook et al. (1989) Molecular Cloning: A Laboratory Manual, Cold Spring Harbor Laboratory Press; and Sambrook et al. (2001). Molecular Cloning: A Laboratory Manual (3rd ed.). Cold Spring Harbor Laboratory Press, which are both incorporated herein by reference in their entireties. Filter based methods for the isolation of mRNA are also available in the art and can be used for isolating mRNA from biological samples. Examples of commercially available filter-based RNA isolation systems include RNAqueous™ (Ambion) and RNeasy™ (Qiagen). One of skill in the art would appreciate that it is desirable to inhibit or destroy RNase present in homogenates of biological samples soon after obtaining the samples so that the mRNA is not degraded by nucleases during testing.

Frequently, it is desirable to amplify the nucleic acid sample prior to evaluation. If a quantitative result is desired care can be taken to use an amplification method that maintains or controls for the relative frequencies of the amplified nucleic acids.

Methods of "quantitative" amplification are well known to those of skill in the art. For example, quantitative PCR involves simultaneously co-amplifying a known quantity of an internal control nucleic acid. This provides an internal standard that may be used to calibrate the PCR reaction. Detection of the internal control sequence along with the mRNAs of interest (e.g., those from any of the genes in Table 1) allows one of skill in the art to monitor whether the mRNA isolation, purification and quantification procedures accurately reflect actual expression levels or whether there is a problem with any of these procedures (e.g., the mRNA has become degraded during one of the procedures).

Suitable amplification methods include, but are not limited to polymerase chain reaction (PCR) (Innis & Gelfand. *Optimization of PCRs*. In: PCR protocols: a guide to methods and applications (eds. M. A. Innis. et al.), pp. 3-12. Academic Press, San Diego (1990); ligase chain reaction (LCR) (see. Wu and Wallace, Genomics (1989)); Landegren, et al., *Science* 241: 1077-1080 (1988); Barringer, et al., *Gene* 89: 117-122 (1990); transcription amplification (Kwoh, et al., *Proc. Natl. Acad. Sci. USA* 86, 1173-1177 (1989)), and self-sustained sequence replication (Guatelli, et al., *Proc. Natl. Acad. Sci.* 87: 1874-1878 (1990)).

In one embodiment, a nucleic acid sample is the total mRNA isolated from a biological sample (e.g., a test tissue or cell sample). The term "biological sample." as used herein, refers to a sample obtained from an organism or from components (e.g., cells) of an organism, including normal tissue (e.g., as a control) and diseased tissue such as a tumor, a neoplasia or a hyperplasia. The sample may be of any biological tissue or fluid or cells from any organism as well as cells raised in vitro, such as cell lines and tissue culture cells. The biological sample may also be referred to as a "clinical sample" derived from a patient. Such samples include, but are not limited to, tissue biopsy or fine needle aspiration biopsy samples, blood, blood cells (e.g., white cells), urine, peritoneal fluid, and pleural fluid, or cells therefrom. Biological samples may also include sections of tissues such as frozen sections or formalin fixed sections taken for histological purposes.

In some embodiments, the sample mRNA is reverse transcribed with a reverse transcriptase, such as SuperScript II (Invitrogen), and a primer consisting of an oligo-dT to generate first-strand cDNA. Other desirable sequences can be incorporsated into the first-strand cDNA by linking those sequences onto the oligo-dT primer (e.g., a restriction site sequence, a sequence encoding a promoter such as a phage T7 promoter, etc.). A second-strand DNA is polymerized in the presence of a DNA polymerase, DNA ligase, and RNase H. The resulting double-stranded cDNA may be blunt-ended using T4 DNA polymerase and purified by phenol/chloroform extraction. The double-stranded cDNA can then be then transcribed into cRNA or amplified to generate a pool of amplified cDNAs. Methods for the in vitro transcription of RNA are known in the art and describe in, for example, Van Gelder, et al. (1990) and U.S. Pat. Nos. 5,545,522; 5,716,785; and 5,891,636, all of which are incorporated herein by reference.

If desired, a label may be incorporated into the cRNA or cDNA when it is transcribed. Those of skill in the art are familiar with methods for labeling nucleic acids. For example, the cRNA may be transcribed in the presence of biotin-ribonucleotides or the cDNA may be synthesized in the presence of biotin-deoxyribonucleotides. The BioArray High Yield RNA Transcript Labeling Kit (Enzo Diagnostics) is a commercially available kit for biotinylating cRNA.

It will be appreciated by one of skill in the art that the direct transcription method described above provides an antisense (aRNA) pool. Where antisense RNA is used with a microarray for detection, the antisense RNA can be the "target nucleic acid" that is hybridized to an array of the oligonucleotide probes provided in the microarray. In that case the oligonucleotide probes on the microarray are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense, or both senses, as the target nucleic acids include both sense and antisense strands.

To detect hybridization, it may be advantageous to employ nucleic acids in combination with an appropriate detection means. Recognition moieties incorporated into primers, incorporated into the amplified product during amplification, or attached to probes that can hybridize to the amplified product are useful in the identification of nucleic acid molecules. A number of different labels may be used for this purpose including, but not limited to, fluorophores, chromophores, radiophores, enzymatic tags, antibodies, chemiluminescence, electroluminescence, and affinity labels. One of skill in the art will recognize that these and other labels can be used with success in this invention.

Examples of affinity labels include, but are not limited to the following: an antibody, an antibody fragment, a receptor protein, a hormone, biotin, Dinitrophenyl (DNP), or any polypeptide/protein molecule that binds to an affinity label. Examples of enzyme tags include enzymes such as urease, alkaline phosphatase or peroxidase to mention a few. Colorimetric indicator substrates can be employed to provide a detection means visible to the human eye or spectrophotometrically, to identify specific hybridization with complementary nucleic acid-containing samples. Examples of fluorophores include, but are not limited to, Alexa 350, Alexa 430, AMCA, BODIPY 630/650, BODIPY 650/665, BODIPY-FL, BODIPY-R6G, BODIPY-TMR, BODIPY-TRX, Cascade Blue. Cy2, Cy3, Cy5, 6-FAM, Fluoroscein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

Means of detecting such labels are well known to those of skill in the art. For example, radiolabels may be detected using photographic film or scintillation counters. In other examples, fluorescent markers may be detected using a photodetector to detect emitted light. In still further examples, enzymatic labels are detected by providing the enzyme with a substrate and detecting the reaction product produced by the action of the enzyme on the substrate, and colorimetric labels are detected by simply visualizing the colored label or by use of spectrometer.

So called "direct labels" are detectable labels that are directly attached to or incorporated into the target (sample) nucleic acid prior to hybridization to a probe or microarray. In contrast, so called "indirect labels" are joined to the hybrid duplex after hybridization. In some embodiments, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin-bearing hybrid duplexes providing a label that is easily detected. For a detailed review of methods of labeling nucleic acids and detecting labeled hybridized nucleic acids see, for example, Peter C, van der Vliet & Shiv Pillai, eds., Laboratory Techniques in Biochemistry and Molecular Biology (1993).

Methods for Detecting Differential Expression

The present invention includes a method for detecting and/or quantifying expression of any combination of the genes listed in Table 1 (e.g., a target nucleic acid) in a biological sample.

Such detection and quantification methods can involve nucleic acid amplification (e.g., reverse transcription PCR, quantitative PCR and/or real-time PCR), wherein a sample containing a target nucleic acid that is to be amplified (e.g. a cDNA generated from an RNA sample by reverse transcription) is mixed with 1) primers that are complementary to sequences within the target sequence to be amplified, 2) a thermostable polymerase, and 3) four different nucleoside triphosphates. The normal steps of nucleic acid amplification are then followed—melting, annealing and synthesis—by thermal cycling of the mixture. The primers employed can be linked to a label. In some embodiments, a fluorescent intercalating agent is used in the reaction. The labeled primers and/or fluorescent intercalating agents allow quantification of the amounts of amplified products generated in various test reactions.

When nucleic acid amplification is used to detect gene expression, any procedure that amplifies RNA can be used, for example, reverse transcription-polymerase chain reaction (RT-PCR) assays, strand displacement amplification and other amplification procedures. Strand displacement amplification can be used as described in Walker et al (1992) Nucl. Acids Res. 20, 1691-1696. The term "polymerase chain reaction" ("PCR") refers to the method of K. B. Mullis U.S. Pat. Nos. 4,683,195, 4,683,202; and 4,965,188, hereby incorporated by reference, which describe a method for increasing the concentration of target nucleic acid in a mixture of genomic DNA or other DNA or RNA without cloning or purification.

The steps involved in PCR nucleic acid amplification method are described in more detail below. For ease of discussion, the nucleic acid to be amplified is described as being double-stranded. However, the process is readily adapted to amplify a single-stranded nucleic acid, such as an mRNA from any of the genes listed in Table 1. In the amplification of a single-stranded nucleic acid, the first step involves the synthesis of a complementary strand, for example, by reverse transcription so that two complementary target strands are available for amplification.

When PCR is performed on double-stranded DNA or cDNA generated from one or more of the RNAs expressed from the genes of Table 1, two primers are employed, each primer hybridizing to a different DNA strand at opposite ends of the DNA target. One of skill in the art can readily make and use probes and primers for the genes listed in Table 1, for example, by examining available nucleic acid sequences for these genes that are available in the sequence database maintained by the National Center for Biotechnology Information (see website at www.ncbi.nlm.nih.gov). Examples of some sequences for the genes listed in Table 1 are provided hereinbelow.

The PCR process for amplifying a target nucleic acid consists of introducing a large excess of the two primers to a mixture that may contain the mRNA (or cDNA generated therefrom) from any of the genes listed in Table 1, followed by a precise sequence of thermal cycling in the presence of a nucleic acid polymerase. For PCR amplification, each of the two primers is complementary to a distinct region in one of the two strands of the double stranded target sequence. Primers are selected so that they hybridize just outside the region of interest to be amplified and so that, upon primer extension, one primer will be extended towards the hybridization site of a second primer hybridized on the opposite target strand.

To effect amplification, the nucleic acid (RNA or cDNA) is denatured to open up double-stranded target sites and the temperature is lowered so that the primers anneal to their complementary sequences within the target molecule. Following annealing, the primers are extended with a polymerase. Such primer extension forms a new pair of complementary strands that likely have different ends than the original target. Such complementary strands can hybridize together to form an "amplicon" that can also be a target for amplification. The steps of denaturation, primer annealing and primer extension can be repeated many times. Each round of denaturation, annealing and extension constitutes one "cycle." There can be numerous cycles, and the amount of amplified DNA produced increases with the number of cycles. Hence, to obtain a high concentration of an amplified target nucleic acid, many cycles are performed.

The following steps are generally employed during nucleic acid amplification with the inhibitors of the invention:

(a) Each target nucleic acid strand is contacted with four different nucleoside triphosphates and one oligonucleotide primer, wherein each primer is selected to be substantially complementary to a portion the nucleic acid strand to be amplified (hmgn3), such that the extension product synthesized from one primer, when it is separated from its complement, can serve as a template for synthesis of the extension product of the other primer. To promote the proper annealing of primer(s) and the nucleic acid strands to be amplified, a selected primer-hybridization temperature is used that allows hybridization of each primer to a complementary nucleic acid strand. The inhibitors of the invention can be added or included in this melting/annealing reaction.

(b) After primer annealing, a nucleic acid polymerase is used for primer extension. The nucleic acid polymerase incorporates the nucleoside triphosphates into a growing nucleic acid strand to form a new strand that is complementary to the template strand hybridized by the primer. In general, this primer extension reaction is performed at a temperature and for a time effective to promote the activity of the nucleic acid enzyme and to synthesize a "full length" complementary nucleic acid strand that extends into and through a complete second primer binding site. However, the temperature is not so high as to separate each extension product from its nucleic acid template strand. The polymerase may be added after the first melting/annealing reaction.

(c) The mixture from step (b) is then heated for a time and at a temperature sufficient to separate the primer extension products from their complementary templates. The temperature chosen is not so high as to irreversibly denature the nucleic acid polymerase present in the mixture.

(d) The mixture from (c) is cooled for a time and at a temperature effective to promote hybridization of a primer to each of the single-stranded molecules produced in step (b).

(e) The mixture from step (d) is maintained at a temperature and for a time sufficient to promote primer extension by the polymerase to produce a "full length" extension product. The temperature used is not so high as to separate each extension product from the complementary strand template. Steps (c)-(e) are repeated until the desired level of amplification is obtained.

In some embodiments, real-time polymerase chain reaction (real time PCR; also called quantitative real time polymerase chain reaction (Q-PCR/qPCR) or kinetic polymerase chain reaction) is employed to quantify the expression of genes. Real-time PCR amplifies and simultaneously quantifies a targeted nucleic acid (e.g., an RNA expressed by one of the genes listed in Table 1). Thus, real-time PCR permits both detection and quantification (as absolute number of copies or relative amount when normalized to DNA input or additional normalizing genes) of a specific nucleic acid (e.g., RNA) in a sample.

Real-time PCR employs many of the same steps as polymerase chain reaction but the amplified DNA product is quantified as it accumulates in the reaction in real time after each amplification cycle. Methods that are often used to quantify the amplified DNA include the use of fluorescent dyes intercalate with double-stranded DNA product, and the use of modified DNA primers that fluoresce when hybridized with a complementary nucleic acid template.

For example, any of the SEQ ID NO:3-118 primers can be used in a real-time PCR assay for evaluating expression levels of the differentially expressed genes. One type of real-time PCR assay that can be employed involves use of SYBRGreen dye. SYBR Green is a dye that binds the minor groove of double stranded DNA. When SYBR Green dye binds to double stranded DNA, the intensity of the fluorescent emissions increases. As more double stranded amplicons are produced, SYBR Green dye signal will increase. During the PCR assay, such a fluorescent signal is directly proportional to the number of amplicons generated.

To detect RNA expression levels, real-time polymerase chain reaction is combined with reverse transcription PCR, where the RNA in a sample is first treated with reverse transcriptase to generate a cDNA that can then be amplified.

Reverse transcription PCR and real-time PCR can be used to quantify relative levels of expression from any of the genes listed in Table 1.

The present invention therefore includes a method for detecting and/or quantifying expression of any of the genes listed in Table 1 (a target nucleic acid) that involves nucleic acid amplification (e.g., reverse transcription PCR and real-time PCR), wherein a sample containing a target nucleic acid that is to be amplified (e.g. a cDNA generated from an RNA sample by reverse transcription) is mixed with 1) primers that are complementary to sequences within the target sequence to be amplified, 2) a thermostable polymerase, and 3) four different nucleoside triphosphates. The normal steps of nucleic acid amplification are then followed—melting, annealing and synthesis—by thermal cycling of the mixture. The primers employed can be linked to a label. In some embodiments, a fluorescent intercalating agent is used in the reaction. The labeled primers and/or fluorescent intercalating agents allow quantification of the amounts of amplified products generated in various test reactions.

Microarrays exploit the preferential binding of complementary nucleic acid sequences. A microarray is typically a glass slide, on to which DNA molecules are attached at fixed locations (spots or features). There may be tens of thousands of spots on an array, each containing a huge number of identical DNA molecules (or fragments of identical molecules), of lengths from twenty to hundreds of nucleotides. The spots on a microarray are either printed on the microarrays by a robot, or synthesized by photo-lithography (similar to computer chip productions) or by ink-jet printing. There are commercially available microarrays, however many labs produce their own microarrays.

Hybridization

Nucleic acid hybridization simply involves contacting a probe and target nucleic acid under conditions where the probe and its complementary target can form stable hybrid duplexes through complementary base pairing (see Lockhart et al., 1999, WO 99/32660, for example). The nucleic acids that do not form hybrid duplexes are then washed away leaving the hybridized nucleic acids to be detected, for example, through detection of an attached detectable label. It is generally recognized that nucleic acids are denatured by increasing the temperature and/or decreasing the salt concentration of the buffer containing the nucleic acids.

Under low stringency conditions (e.g., low temperature and/or high salt) hybrid duplexes (e.g., DNA-DNA, RNA-RNA or RNA-DNA) will form even where the annealed sequences are not perfectly complementary. Thus specificity of hybridization is reduced at lower stringency. Conversely, at higher stringency (e.g., higher temperature or lower salt) successful hybridization occurs with fewer mismatches.

One of skill in the art will appreciate that hybridization conditions may be selected to provide any degree of stringency. Stringency can also be increased by addition of agents such as formamide. Hybridization specificity may be evaluated by comparison of hybridization to the test probes with hybridization to the various controls that can be present (e.g., expression level control, normalization control mismatch controls, etc.).

In general, there is a tradeoff between hybridization specificity (stringency) and signal intensity. Thus, in some embodiments, the wash is performed at the highest stringency that produces consistent results and that provides a signal intensity greater than approximately 10% of the background intensity. To better distinguish between the signal and the background, the hybridized sequences (e.g., on a microarray) may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

As used herein, the terms "hybridize" and "hybridization" refer to the annealing of a complementary sequence to the target nucleic acid. i.e., the ability of two polymers of nucleic acid (polynucleotides) containing complementary sequences to anneal through base pairing. The terms "annealed" and "hybridized" are used interchangeably throughout, and are intended to encompass any specific and reproducible interaction between a complementary sequence and a target nucleic acid, including binding of regions having only partial complementarity. Certain bases not commonly found in natural nucleic acids may be included in the nucleic acids of the present invention and include, for example, inosine and 7-deazaguanine. Those skilled in the art of nucleic acid technology can determine duplex stability empirically considering a number of variables including, for example, the length of the complementary sequence, base composition and sequence of the oligonucleotide, ionic strength and incidence of mismatched base pairs. The stability of a nucleic acid duplex is measured by the melting temperature, or "$T_m$". The $T_m$ of a particular nucleic acid duplex under specified conditions is the temperature at which on average half of the base pairs have disassociated.

The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids which are not completely complementary to one another be hybridized or annealed together. The art knows well that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al. (1989); Nucleic Acid Hybridization, A Practical Approach, IRL Press, Washington D.C. 1985, for a general discussion of the methods).

The stability of nucleic acid duplexes is known to decrease with an increased number of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization include conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization include conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 g/ml denatured salmon sperm DNA followed by washing in a solution comprising 1.0× SSPE, 1.0% SDS at 42° C. when a probe of about 500 nucleotides in length is employed.

"Low stringency conditions" include conditions equivalent to binding or hybridization at 42EC in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400. Pharmacia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed.

The term "homology" refers to a degree of sequence identity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison. Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

The hybridization conditions selected also depend on the particular circumstances (depending, for example, on the G+C content, type of target nucleic acid, source of nucleic acid, and size of hybridization probe). Optimization of hybridization conditions for the particular application of interest is well known to those of skill in the art. Representative solid phase hybridization methods are disclosed in U.S. Pat. Nos. 5,843,663, 5,900,481, and 5,919,626, which are incorporated herein by reference in their entireties. Other methods of hybridization that may be used in the practice of the present invention are disclosed in U.S. Pat. Nos. 5,849,481, 5,849,486, and 5,851,772, which are also incorporated herein by reference in their entireties.

Signal Detection

The hybridized nucleic acids are typically detected by detecting one or more labels attached to either the nucleic acids derived from a test sample (e.g., an amplified product) or to a probe that is hybridized to the mRNA or an amplified product of the mRNA. The labels may be incorporated by any of a number of means well known to those of skill in the art (for example, see Affymetrix GeneChip™ Expression Analysis Technical Manual).

DNA arrays and gene chip technology provide a means of rapidly screening a large number of nucleic acid samples for their ability to hybridize to a variety of single stranded DNA probes immobilized on a solid substrate. These techniques involve quantitative methods for analyzing large numbers of genes rapidly and accurately. The technology capitalizes on the complementary binding properties of single stranded DNA to screen nucleic acid samples by hybridization (Pease et al., 1994; Fodor et al., 1991). Basically, a DNA array or gene chip consists of a solid substrate with an attached array of single-stranded DNA molecules. For screening, the chip or array is contacted with a single stranded nucleic acid sample (e.g., cRNA or cDNA), which is allowed to hybridize under stringent conditions. The chip or array is then scanned to determine which probes have hybridized.

Methods for directly synthesizing on or attaching polynucleotide probes to solid substrates are available in the art. See. e.g., U.S. Pat. Nos. 5,837,832 and 5,837,860, both of which are expressly incorporated by reference herein in their entireties. A variety of methods have been utilized to either permanently or removably attach the probes to the substrate. Exemplary methods include: the immobilization of biotinylated nucleic acid molecules to avidin/streptavidin coated supports (Holmstrom, 1993), the direct covalent attachment of short, 5'-phosphorylated primers to chemically modified polystyrene plates (Rasmussen et al., 1991), or the precoating of the polystyrene or glass solid phases with poly-L-Lys or poly L-Lys. Phe, followed by the covalent attachment of either amino- or sulfhydryl-modified oligonucleotides using bifunctional crosslinking reagents (Running et al., 1990; Newton et al., 1993). When immobilized onto a substrate, the probes are stabilized and therefore may be used repeatedly.

In general terms, hybridization is performed on an immobilized nucleic acid target or a probe molecule that is attached to a solid surface such as nitrocellulose, nylon membrane or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules).

The Affymetrix GeneChip system may be used for hybridization and evaluation of the probe arrays, where the probes have been selected to hybridize to any combination of the genes listed in Table 1 (or a cRNA or cDNA obtained from an mRNA generated by any of those genes). In some embodiments, the Affymetrix U95A or U133A array is used in conjunction with Microarray Suite 5.0 for data acquisition and preliminary analysis of gene expression patterns and/or levels.

Normalization Controls

Normalization controls are oligonucleotide probes that are complementary to labeled reference oligonucleotides that are added to the nucleic acid sample. The signals obtained from the normalization controls after hybridization provide a control for variations in hybridization conditions, label intensity. "reading" efficiency and other factors that may cause the hybridization signal to vary between arrays. For example, signals read from all other probes in the array can be divided by the signal from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few normalization probes are used and they are selected such that they hybridize well (i.e. no secondary structure) and do not match any target-specific probes. Normalization probes can be localized at any position in the array or at multiple positions throughout the array to control for spatial variation in hybridization efficiently.

In a some embodiments, a standard probe cocktail supplied by Affymetrix is added to the hybridization to control for hybridization efficiency when using Affymetrix Gene Chip arrays.

Expression Level Controls

Expression level controls are probes that hybridize specifically with constitutively expressed genes in the sample. The expression level controls can be used to evaluate the efficiency of cRNA preparation.

Virtually any constitutively expressed gene provides a suitable target for expression level controls. Typically expression level control probes have sequences complementary to subsequences of constitutively expressed "housekeeping genes."

In one embodiment, the ratio of the signal obtained for a 3' expression level control probe and a 5' expression level control probe that specifically hybridize to a particular housekeeping gene is used as an indicator of the efficiency of cRNA preparation. A ratio of 1-3 indicates an acceptable preparation.

Databases

Any appropriate computer platform may be used to perform the necessary comparisons between sequence information, gene expression information and any other information in a database or provided as an input. For example, a large number of computer workstations and programs are available from a variety of manufacturers, such as those available from Affymetrix.

Statistical Methods

Combining profiles of gene expression over a wide array of transcripts has potentially more classification prediction power than relying on any single gene. The significance of the difference between the levels of gene expression between tissue sample types can be assessed using expression data and any number of statistical tests such as those described in the Examples and by using published methods (e.g., the Significance Analysis of Microarrays (SAM) method, see, Tusher V G, et al., 2001, Proc. Natl. Acad. Sci. USA 98(9):5116-21). SAM identifies genes with statistically significant changes in expression by assimilating a set of gene-specific t-tests. Each gene is assigned a score on the basis of its change in gene expression relative to the standard deviation of repeated measurements for that gene. Genes with scores greater than a threshold are deemed potentially significant. The percentage of such genes identified by chance is the false discovery rate (FDR). To estimate the FDR, nonsense genes are identified by analyzing permutations of the measurements. The threshold can be adjusted to identify smaller or larger sets of genes, and FDRs are calculated for each set.

Kits

The methods described herein can be practiced using a kit. Such kits generally include probes and/or primers for detecting and/or quantifying expression of the differentially expressed genes described herein, and instructions for performing the detection and/or quantification methods.

Thus, one aspect of the invention is a kit that includes, for example, (a) at least one set of oligonucleotide primers, wherein a first primer in the set contains a sequence complementary to a region in one strand of a nucleic acid sequence template and primes the synthesis of a first extension product, and a second primer contains a sequence complementary to a region in said first extension product and primes the synthesis of a nucleic acid strand complementary to said first extension product, and wherein the template is a differentially expressed gene, or an RNA or DNA copy of the differentially expressed gene; and (b) instructions for using the at least one set of oligonucleotide primers: wherein differentially expressed gene is selected from the group consisting of ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD, HMGA2. IGFBP6, KIT, LRP4, MATN2, MET, MYH10, NAUK2, PFAAP5, PGF, PIP3-E, PKNOX2, PRKACB, PROS1, PSD3, QPCT, RAB27A, RXRG, SDC4, SERPINA1, SLC25A15, SLC4A4, SLIT1, SPTAN1, TFCP2L1, TIAM1, TIMP1, TNS3, TSPAN12, UPP1, and a combination thereof.

The first primer and/or the second primer provided in the kit can have a covalently attached label. For example, the first primer and/or the second primer can be selected from any of SEQ ID NO:3-118.

Another kit that can be made and/or used for detecting differential expression can include (a) a microarray with covalently attached probes that can hybridize to a differentially expressed gene selected from the group consisting of ANK2, ARHGAP6, C11orf17, CAPN3, CDHI6, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7, GATM, HGD. HMGA2, IGFBP6, KIT, LRP4, MATN2, MET, MYH10, NAUK2, PFAAP5, PGF, PIP3-E, PKNOX2, PRKACB, PROS1, PSD3, PSD3, QPCT, RAB27A, RXRG, SDC4, SERPINA1, SLC25A15, SLC4A4, SLIT1, SPTAN1, TFCP2L1, TIAM1, TIMP1, TNS3, TSPAN12, UPP1, and a combination thereof; and (b) instructions for using the microarray.

Probes useful in the microarray of this kit can hybridize to any of ANK2, ARHGAP6, C11orf17, CAPN3, CDH16, ChGn, CITED 1, CITED 2, CKB, COL9A3, CSRP2, DAPK2, DIO1, DPP4, DTX4, DUSP4, EFEMP1, ELMO1, FGFR2, FLRT1, FMOD, GALNT7. GATM, HGD, HMGA2, IGFBP6, KIT, LRP4, MATN2, MET, MYH10, NAUK2, PFAAP5, PGF, PIP3-E, PKNOX2, PRKACB, PROS1, PSD3. QPCT, RAB27A, RXRG, SDC4, SERPINA1, SLC25A15, SLC4A4, SLIT1, SPTAN1, TFCP2L1, TIAM1, TIMP1, TNS3, TSPAN12, UPP1, or a combination thereof The kit can include other useful components. For example, the kit can include a container of nucleotides for use as subunits in the synthesis of and amplified product. In some embodiments, the one or more nucleotides provided can have a covalently attached label. The nucleotides provided with the kit can be ribonucleotides or deoxyribonucleotides. Other components provided by the kit include reagents or devices for isolating and/or purifying mRNA, enzymes such as reverse transcriptase, ligase. DNA polymerase (e.g., Taq polymerase), solutions and buffers for performing enzymatic reaction, and/or solutions for performing hybridization. Thus, the kits can include one or more buffers, such as a DNA isolation buffers, an amplification buffer or a hybridization buffer. The kit may also contain compounds and reagents to prepare DNA templates and isolate RNA from a test sample. The kit may also include various labeling reagents and compounds.

The kit of can also include one or more standard or control probes. For example, one or more of the standard or control probes can be a probe or probes for one or more constitutively expressed genes.

In some embodiments the instructions provided with the kit can describe a method for amplifying an mRNA, cRNA or cDNA corresponding to the differentially expressed gene(s). One of skill in the art may choose to utilize the kit for detecting differential expression by hybridization of a first primer and/or a second primer to an mRNA, cRNA or cDNA corresponding to the differentially expressed gene under moderate to highly stringent hybridization conditions. When using the kit with the microarray, one of skill in the art may choose to utilize the kit for detecting differential expression by hybridization of a probe to an mRNA, cRNA or cDNA corresponding to the differentially expressed gene under moderate to highly stringent hybridization conditions. For example, the instructions provided in the kit can inform one of skill in the art to employ hybridization conditions that are moderately to highly stringent hybridization conditions.

The kit can include primers and/or probes for detecting some or all of the differentially expressed genes. For example, the kits can detect and/or quantify expression of a subset of differentially expressed genes such as any one of DIO1, DTX4, GALNT7, HMGA2, IGFBP6, MET, PROS1, SDC4, SERPINA1, SLC4A4, TIAM1, TIMP1, UPP1 or a combination thereof. The kits can detect and/or quantify expression of other subsets of differentially expressed genes, for example, any one of ANK2, ARHGAP6, CDH16, CITED 1, CITED 2, COL9A3, ChGn, DUSP4, EFEMP1, ELMO1, FGFR2, FLRT1, FMOD, GATM, KIT, LRP4, MATN2, SLIT1, SPTAN1, TFCP2L1, PIP3-E, PSD3, TNS3, TSPAN12, TIAM1 or a combination thereof. Alternatively, for example, the kits can be used to detect another subset of differentially expressed genes such as one or more of the following genes C11orf17, CAPN3, CAPN3, CKB, CSRP2, DAPK2, DPP4, HGD, MYH10, NAUK2, PFAAP5, PGF, PKNOX2, PRKACB, QPCT, RAB27A, RXRG, and SLC25A15 or a combination thereof.

Thus, probes and/or primers for detecting mRNA expression of any of the genes listed in Table 1 may be included in a kit. The kit may further include individual nucleic acids that can be amplified with the nucleic acids of interest. The kit can also include probes and/or primers for detecting particular control nucleic acid sequences. The control nucleic acids included in the kit can be mRNA(s) and/or control cDNA(s). The probes, primers and/or control RNA and/or DNA sequences can be provided on a microarray. Alternatively, the probes, primers and/or control RNA and/or DNA sequences can be provided in separate vials or wells of an assay plate (e.g., a microtiter plate).

Some of the components of the kits may be packaged either in aqueous media or in lyophilized form. When the components of the kit are provided in one and/or more liquid solutions, the liquid solution is an aqueous solution, with a sterile aqueous solution being particularly preferred. However, the components of the kit may also be provided as dried powder(s). When reagents and/or components are provided as a dry powder, the powder can be reconstituted by the addition of a suitable solvent. It is envisioned that the solvent may also be provided in another container or by the user.

The containers for the kits can include at least one vial, test tube, flask, bottle, syringe or other container means, into which a component may be placed, and/or suitably aliquoted. A labeling reagent and label may be included and packaged separately or together. There can be more than one component or container in the kit. For example, the kit can also contain a second, third or other additional container into which the additional components may be separately placed. However, various combinations of components may be included together in a vial. The kits of the present invention can also include a means for containing the nucleic acids, and any other reagent containers in close confinement for commercial sale. Such containers may include injection or blow-molded plastic containers into which the desired vials are retained.

A kit will also include instructions for employing the kit components as well the use of any other reagent not included in the kit. Instructions may include variations that can be implemented.

The following non-limiting examples further illustrate aspects of the invention.

Example 1: Materials and Methods

Tumor Samples

Tissue samples were collected at time of surgery, snap-frozen in liquid nitrogen, and stored at −80° C. Representative slides for all tumors were reviewed by two dedicated pathologists. A total of 90 thyroid tumor samples, including 16 papillary thyroid carcinoma (PTC), 22 follicular variants of papillary thyroid carcinoma (FVPTC), 15 hyperplastic nodules, 22 follicular adenomas, and 15 histologically borderline tumors were analyzed in this study. This study was approved by our Institutional Review Board.

Figure 1:
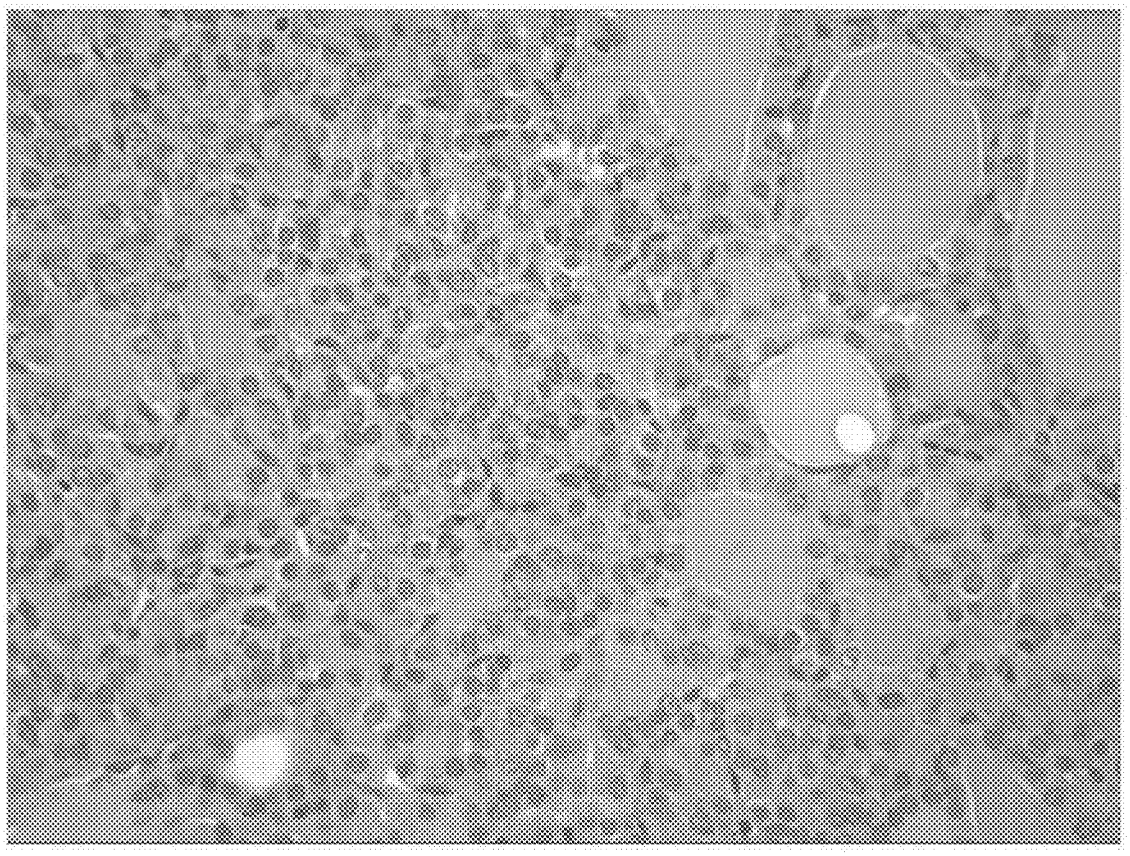
FIG. 1 is an image of a histologically borderline lesion. Note the follicular architecture with focal nuclear clearing and occasional nuclear grooves.

Borderline tumors were defined as encapsulated lesions with follicular architecture in which the morphologic features of papillary thyroid carcinoma were qualitatively incomplete and the lesions did not demonstrate evidence of capsular and/or vascular invasion. The incomplete features of papillary thyroid carcinoma were widespread in the lesions that were analyzed in this study and did not represent focal findings in an otherwise benign nodule. An example of such a borderline tumor sample is shown in FIG. 1. In essence, these cases could be classified as well differentiated tumors of uncertain malignant potential (WDT-UMP) as proposed by Williams et al. (*Int J Surg Pathol.* 8:181-183 (2000)). The officially reported final diagnosis of the 15 borderline tumors, all rendered prior to the onset of this study, was 7 follicular adeonomas and 8 FVPTCs.

RNA Isolation and GeneChip Hybridization

RNA was extracted using RNeasy Mini kit (Qiagen. Valencia, Calif.) from frozen tissue following manufacturer's protocol. RNA purity was confirmed by spectrophotometry. Total RNA was reverse transcribed to complementary DNA (cDNA) according to manufacturer's protocol (NuGEN Ovation RNA Amplification System V2) and then labeled with biotin, cDNA was then hybridized to genechips for microarray analysis, using either GeneChip U95A or U133A (Affymetrix, Santa Clara, Calif.).

Microarray Data Analysis

ArrayAssist 5.2.2 (Stratagene, Inc., La Jolla, Calif.) was used for gene chip analysis. Interchip and intrachip normalization was performed via robust multichip analysis (RMA). After RMA, hybridization signals underwent variance stabilization, log transformation, and baseline transformation. Advanced significance analysis was performed on 50 U95A GeneChips including 10 hyperplastic nodules, 16 follicular adenomas, 13 follicular variants of papillary thyroid carcinomas (FVPTCs), and 11 papillary thyroid carcinomas. This formed the training set. Gene expression of benign tumors was compared to that of malignant tumors. After Benjamini-Hochberg correction for false-discovery, gene probe sets with significant differential expression (2-fold or more with $p<0.05$) were identified. This probe list was then converted to correspond to probes on the U133A Gene Chips (array comparison software; available from Affymetrix.com). The remaining 40 tumor samples, all analyzed with U133A Gene Chips, formed the test set. The test set was then assessed using unsupervised hierarchical cluster analysis and K-means cluster analysis with both 2- and 3-group cluster algorithms. Genes that were differentially expressed between borderline tumors and classic benign and malignant tumors were further identified with advanced significance analysis.

Detection of BRAF Mutations

All 40 tumors forming the test group were analyzed for v-raf murine sarcoma viral oncogene homolog B1 (BRAF) mutations in which glutamate was substituted for valine at codon 600. One microgram of RNA was reverse-transcribed in a 20 μl reaction and a 1 μl aliquot of cDNA was used for polymerase chain reaction (PCR). The following PCR primers were used:

forward primer,5'-TGCTTGCTCTGATAGGAAAATG-3' (SEQ ID NO:1); and reverse primer, 5'-GACTTTCTAGTAACTCAGCAGC-3' (SEQ ID NO:2).

Amplification was carried out for 35 cycles (at 94° C. for 15 seconds, at 60° C. for 1 minute, and at 72° C. for 1 minute). All PCR products were visualized by electrophoresis on a 2% agarose gel and purified using a PCR purification kit (Qiagen Inc). BRAF mutations were detected by direct sequencing of PCR products. All sequencing was performed bidirectionally using the Big Dye Terminator cycle-sequencing kit and the Applied Biosystems Automated 3730 DNA Analyzer (Applied Biosystems. Foster City. Calif.).

Example 2: Accurate Diagnosis of Thyroid Tumors as Benign or Malignant

This Example illustrates that gene expression analysis can be used to identify whether tumors of uncertain malignancy are benign or malignant. Based on their benign clinical behavior, it is proposed that these encapsulated thyroid follicular lesions with partial nuclear features of papillary thyroid carcinoma be called 'follicular adenomas with nuclear atypia' and the data indicate that these lesions may not need to be treated as cancers.

Differentiation of Benign and Malignant Tumors

The training set consisted of 50 tumors including 26 unequivocal benign tumors (16 follicular adenoma and 10 hyperplastic nodules) and 24 unequivocal malignancies (11 PTC and 13 FVPTC). A total of 66 probe sets corresponding to 56 genes showed significant differential expression between benign and malignant tumors. Thirty-one genes had up-regulated expression in malignancies compared to benign tumors, and 30 genes were down-regulated (Table 1).

TABLE 1

Genes differentially expressed between benign, borderline, and/or malignant thyroid lesions

| Gene Name | Gene Symbol | Fold Change* | P |
|---|---|---|---|
| Differentially expressed between benign and borderline/malignant lesions | | | |
| Ankyrin 2, neuronal | ANK2 | −2.70 | .0281 |
| Rho GTPase activating protein 6 | ARHGAP6 | −2.42 | .0329 |
| Cadherin 16, kidney-specific cadherin | CDH16 | −2.28 | .0185 |
| Cbp/p300-interacting | CITED1 | +6.44 | .0252 |
| Cbp/p300-interacting | CITED2 | −2.06 | .0261 |
| Cbp/p300-interacting | CITED2 | −2.76 | .0182 |
| Collagen, type IX, alpha 3 | COL9A3 | −5.87 | .0160 |
| Chondroitin beta 1,4 | ChGn | −3.72 | .0111 |
| Dual-specificity phosphatase 4 | DUSP4 | +3.69 | .0206 |
| EGF-containing fibulin-like | EFEMP1 | −2.60 | .0464 |
| engulfment and cell motility 1 | ELMO1 | −2.60 | .0261 |
| Fibroblast growth factor receptor 2 | FGFR2 | −2.13 | .0343 |
| Fibronectin leucine rich transmembrane protein 1 | FLRT1 | −2.10 | .0252 |
| Fibromodulin | FMOD | −3.09 | .0063 |
| Glycine amidinotransferase | GATM | −2.41 | .0482 |
| V-kit Hardy-Zuckerman 4 feline | KIT | −3.85 | .0039 |
| Low-density lipoprotein | LRP4 | +5.89 | .016 |
| Matrilin 2 | MATN2 | −3.38 | .0127 |
| Slit homolog 1 (*Drosophila*) | SLIT1 | +3.35 | .0258 |
| Spectrin, alpha, nonerythrocytic 1 | SPTAN1 | +2.66 | .0160 |
| Transcription factor CP2-like 1 | TFCP2L1 | −3.54 | .0029 |
| Phosphoinositide-binding protein | PIP3-E | −3.14 | .0343 |
| Pleckstrin and Sec7 domain | PSD3 | +2.40 | .0169 |
| Pleckstrin and Sec7 domain | PSD3 | +2.55 | .0214 |
| Tensin 3 | TNS3 | −2.41 | .0029 |
| Tetraspanin 12 | TSPAN12 | −2.35 | .0047 |
| T-cell lymphoma invasion and metastasis | TIAM1 | +3.91 | .0160 |
| Differentially expressed between malignant and borderline/benign lesions | | | |
| Deiodinase, iodonthyronine, type 1 | DIO1 | −4.47 | .0321 |
| Deltex 4 homolog (*Drosophila*) | DTX4 | +3.68 | .0111 |
| Uridine diphosphate-N-acetyl-alpha-D-galactosamine | GALNT7 | +2.07 | .0213 |
| High-mobility group AT-hook 2 | HMGA2 | +3.56 | .0204 |
| Insulin-like growth factor binding protein 6 | IGFBP6 | +3.18 | .0160 |
| Met proto-oncogene | MET | +2.35 | .0182 |
| Protein S | PROS1 | +3.97 | .0089 |
| Syndecan 4 | SDC4 | −3.26 | .0049 |
| Serpin peptidase inhibitor, clade A | SERPINA1 | +5.64 | .0252 |
| Serpin peptidase inhibitor, clade A | SERPINA1 | +4.81 | .0233 |
| Solute carrier family 4 | SLC4A4 | −4.03 | .0034 |
| TIMP metallopeptidase inhibitor 1 | TIMP1 | +2.72 | .0446 |
| Uridine phosphorylase 1 | UPP1 | +2.25 | .0127 |
| T-cell lymphoma invasion and metastasis 1 | TIAM1 | +3.91 | .0160 |
| Differentially expressed only between benign and malignant lesions | | | |
| Chromosome 11 open reading frame 17 | C11orf17 | −2.12 | .0239 |
| Calpain 3 | CAPN3 | +2.00 | .0263 |
| Calpain 3 | CAPN3 | +2.10 | .0410 |
| Creatine kinase, brain | CKB | −2.46 | .0189 |
| Cysteine and glycine-rich protein 2 | CSRP2 | −2.41 | .0189 |
| Death-associated protein kinase | DAPK2 | +2.23 | .0322 |
| Dipeptidyl-peptidase 4 | DPP4 | +2.83 | .0127 |
| Dipeptidyl-peptidase 4 | DPP4 | +2.51 | .0117 |
| Homogentisate 1,2-dioxygenase | HGD | −3.17 | .0149 |
| Myosin, heavy chain 10 | MYH10 | +2.73 | .0214 |
| Phosphonoformate immunoassociated protein 5 | PFAAP5 | +2.59 | .0189 |
| Phosphonoformate immunoassociated protein 5 | PFAAP5 | +2.28 | .0258 |
| Placental growth factor | PGF | −2.22 | .0301 |
| Myosin, heavy chain 10 | MYH10 | +2.73 | .0214 |
| PBX/knotted 1 homeobox 2 | PKNOX2 | −2.31 | .0455 |

TABLE 1-continued

Genes differentially expressed between benign, borderline, and/or malignant thyroid lesions

| Gene Name | Gene Symbol | Fold Change* | P |
|---|---|---|---|
| Protein kinase, cAMP-dependent | PRKACB | −2.20 | .0241 |
| Glytaminyl-peptidecyclotransferase | QPCT | +3.43 | .0136 |
| RAB27A, member RAS oncogene | RAB27A | +2.41 | .0111 |
| RAB27A, member RAS oncogene | RAB27A | +2.08 | .0063 |
| Retinoid X receptor, gamma | RXRG | +2.57 | .0261 |
| Solute carrier family 25 | SLC25A15 | −2.75 | .0261 |

GTP indicates guanine triphosphate;
Cpb, cyclic adenosine monophosphate response element-binding protein;
EGF, epidermal growth factor;
Sec7, a guanine-nucleotide-exchange factor (also called ARNO3 and cytohesion 3);
AT, adenine and thymine;
TIMP, tissue inhibitor of metalloproteinase;
cAMP, cyclic adenosine monophosphate.
*Fold change is shown relative to benign lesions.

Unsupervised Hierarchical Cluster Analysis

Figure 2:
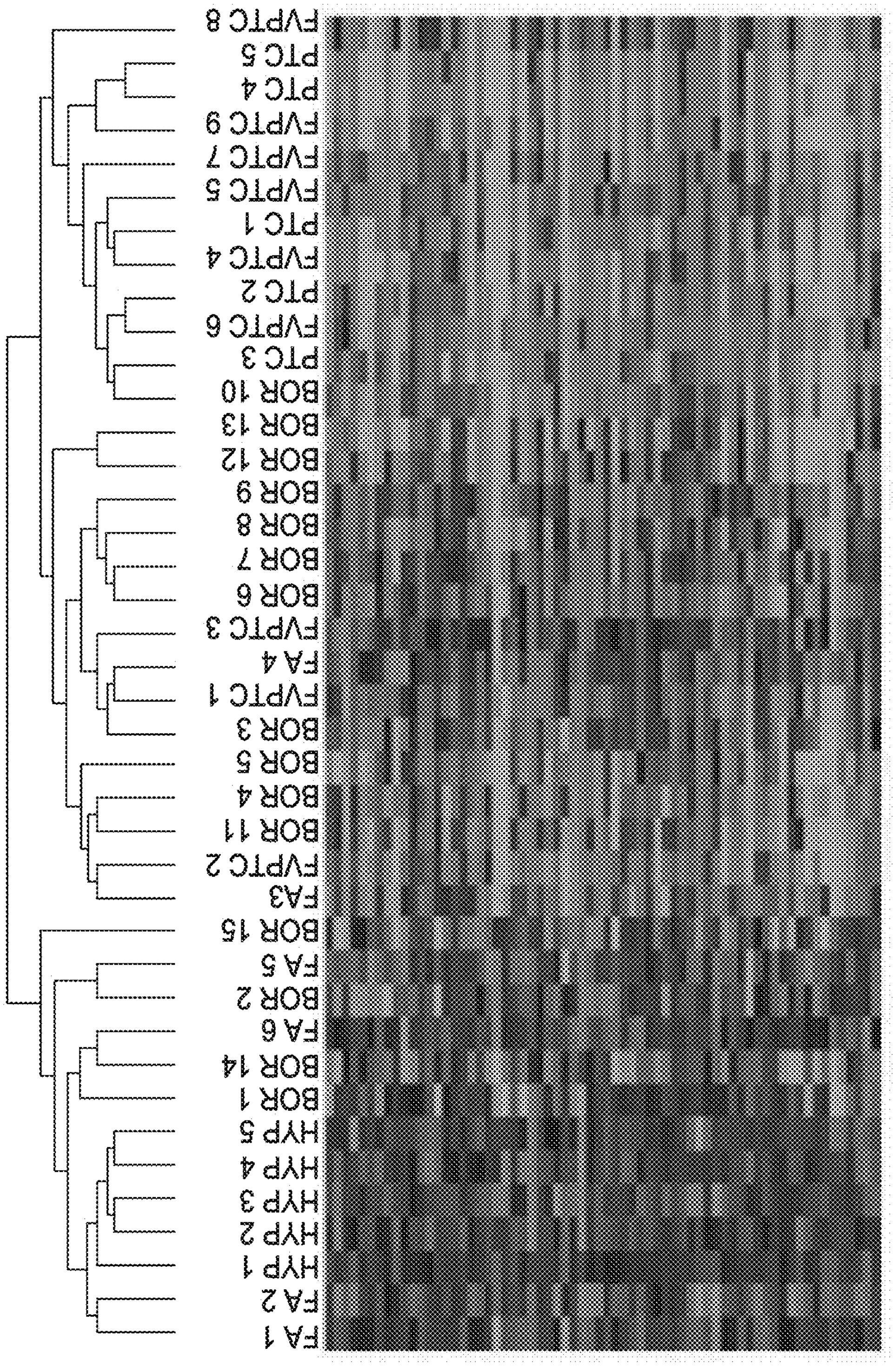
FIG. 2 is a graphic generated by an unsupervised hierarchical cluster analysis. FA indicates follicular adenoma; HYP, hyperplastic lesion; BOR, borderline tumor; FVPTC, follicular variant of papillary thyroid carcinoma; PTC, papillary thyroid carcinoma.

An independent set of 40 test samples was then characterized by observing the expression of genes from the list generated by the training set. The test set included 15 borderline tumors as well as a second group of unequivocal benign (n=11) and malignant (n=14) tumors, including 6 follicular adenomas, 5 hyperplastic nodules, 9 FVPTCs and 5 PTCs. In an unsupervised hierarchical cluster analysis, all benign tumors were distinguished from malignant tumors as expected (FIG. 2).

In addition to these two groups of tumor types, a third intermediate group was identified. This tumor group involved 15 tumors, where the vast majority (10 cases) were histologically borderline tumors. Three FVPTCs and 2 follicular adenomas were also identified in this borderline group of tumor types. Of the 5 remaining borderline tumors, 4 clustered with the benign group and 1 with the malignant group. It is noteworthy that these tumors were the most peripheral nodes in these two groups, indicating an expression profile closer to the intermediate group than other benign and malignant tumors (FIG. 2).

K-Means Cluster Analysis

Figure 3:
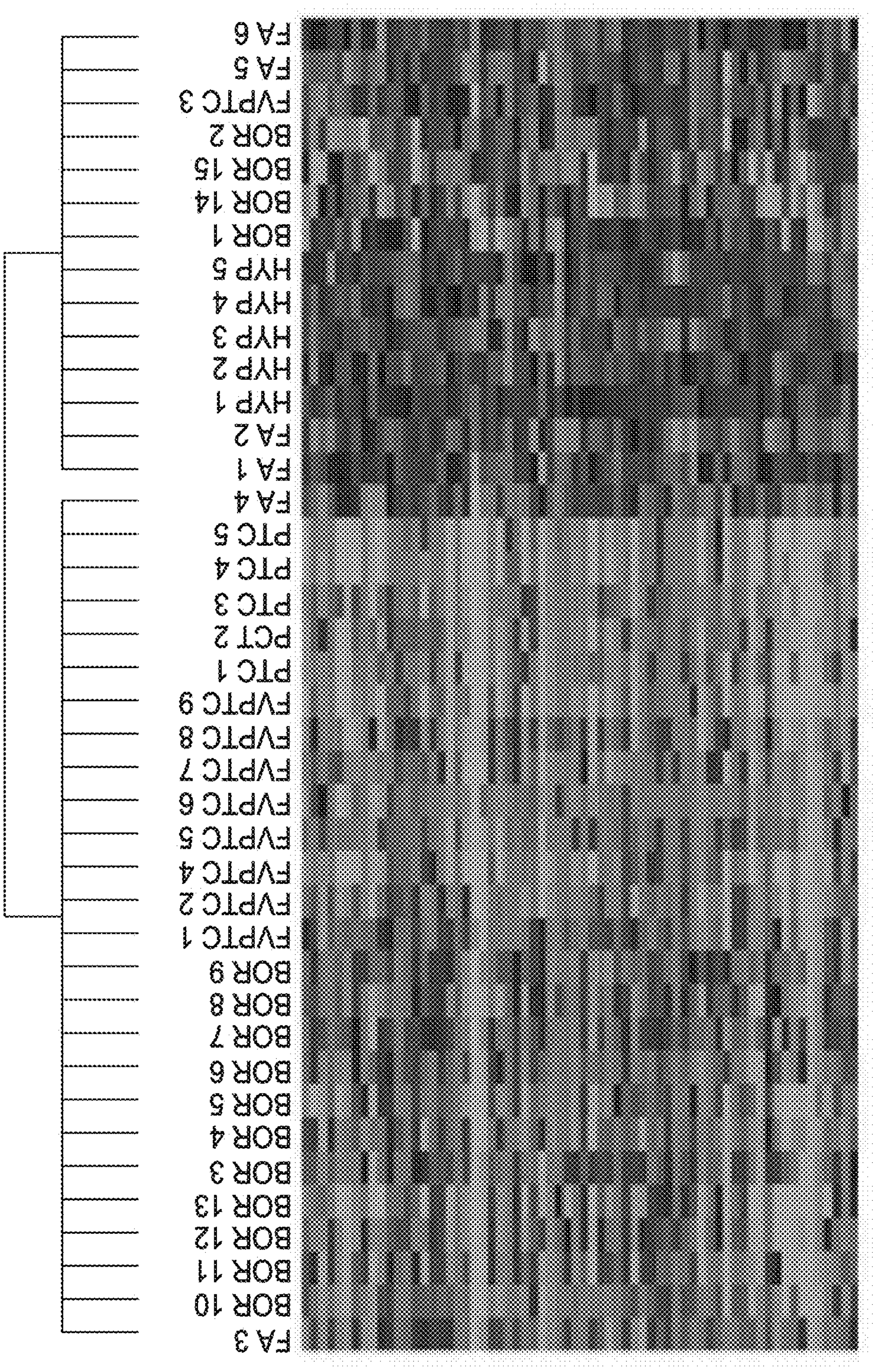
FIG. 3 is a graphic generated by a 2-group K-means cluster analysis. FA indicates follicular adenoma; BOR, borderline tumor; FVPTC, follicular variant of papillary thyroid carcinoma; PTC, papillary thyroid carcinoma; HYP, hyperplastic lesion.

To help elucidate the differences in gene expression between the three groups of tumors (benign, borderline and malignant), the test set was also subjected to K-means cluster analysis using both 2- and 3-groups. In the 2-group cluster algorithm, tumors were separated into two groups based on their gene expression of the genes of interest. This algorithm distinguished benign and malignant tumors with 93% sensitivity and 82% specificity (FIG. 3). Borderline tumors were divided, with four tumors (27%) grouped with benign tumors while eleven (73%) were grouped with the malignant tumors.

In the 3-group cluster algorithm, tumors were separated into three designated groups based on their expression profile. With this algorithm, malignant tumors primarily formed one group (with 1 borderline tumors), benign tumors formed a second group (with 4 borderline tumors), and a third group was composed of 10 borderline tumors, 2 follicular adenoma, and 3 FVPTC (FIG. 4). These 2 follicular adenomas were previously grouped with malignancies in the 2-group algorithm (FA-3 and FA-4) and one of the three FVPTCs that was grouped with the borderline tumors (FVPTC-3) had previously clustered with the benign tumors in the 2-group algorithm.

Correlation with Final Clinical Diagnosis and Patient Follow-Up

Of 15 borderline tumors included in this study, 7 tumors were officially diagnosed and reported as follicular adenomas (47%) and 8 (53%) as FVPTCs. Upon review of the 2-group K-means cluster analysis of these 15 borderline tumors, a correlation between the reported diagnosis and cluster group was observed in only 6 out of 15 tumors (40%), underscoring the diagnostic dilemmas that pathologists face with these tumors (Table 2).

TABLE 2

Comparison of Final Diagnosis with 2-Group Clustering of Borderline Tumor Samples BOR1-15

| Sample | Pathologic Diagnosis | Cluster Group | Concordance |
|---|---|---|---|
| BOR 1 | FVPTC | Benign | No |
| BOR 2 | FA | Benign | Yes |
| BOR 3 | FA | Malignant* | No |
| BOR 4 | FVPTC | Malignant* | Yes |
| BOR 5 | FA | Malignant* | No |
| BOR 6 | FA | Malignant* | No |
| BOR 7 | FVPTC | Malignant* | Yes |
| BOR 8 | FVPTC | Malignant* | Yes |
| BOR 9 | FA | Malignant* | No |
| BOR 10 | FA | Malignant | No |
| BOR 11 | FVPTC | Malignant* | Yes |
| BOR 12 | FVPTC | Malignant* | Yes |
| BOR 13 | FA | Malignant* | No |
| BOR 14 | FVPTC | Benign | No |
| BOR 15 | FVPTC | Benign | No |

None of the borderline tumors were associated with lymph node metastasis or distant metastasis. Of the 9 patients with histologically borderline tumors who were followed, 6 patients were officially diagnosed with FVPTC, and none developed a recurrence after surgery (mean follow-up 1.7 years; range 2 months to 4.4 years) based on thyroglobulin level, ultrasound studies, or a combination of both methods. Similarly, among the 3 patients with FVPTC in the molecularly intermediate group (FVPTC-1. FVPTC-2, and FVPTC-3), none had lymph node metastasis, extranodal extension, or recurrent disease at follow-up periods of 23 months, 23 months, and 25 months, respectively.

Gene Signature of Borderline Tumors

Figure 5:
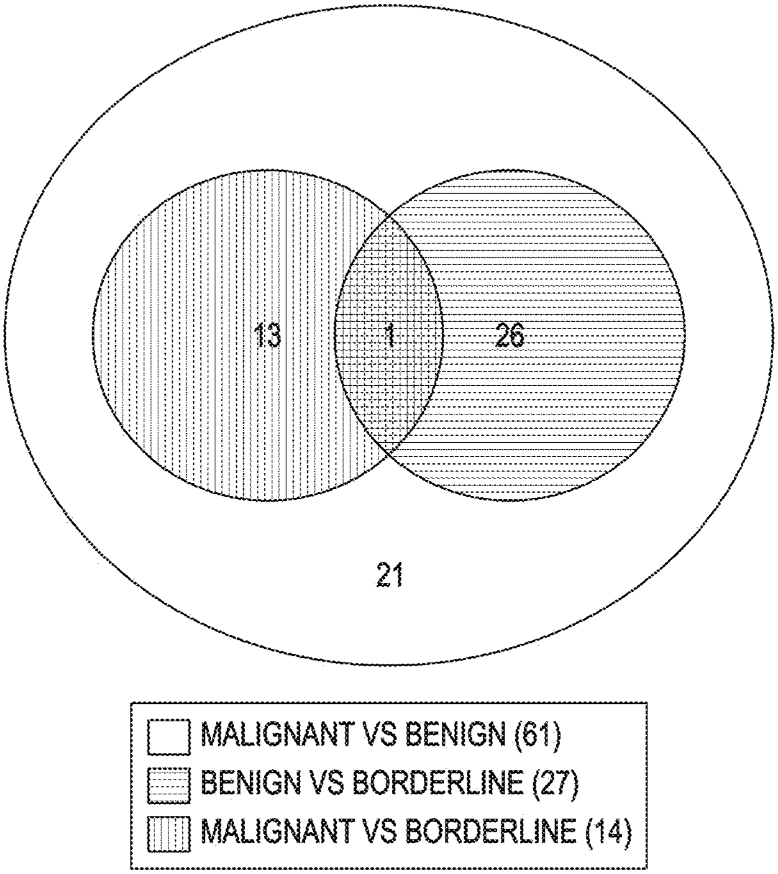
FIG. 5 shows a Venn diagram illustrating the differentially expressed genes relating 61 genes to benign, borderline, and malignant tumors.
Figure 6:
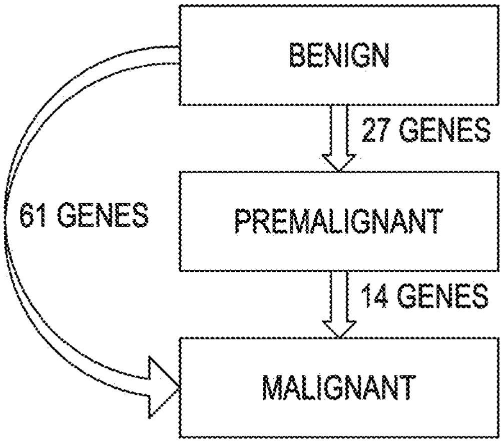
FIG. 6 is a schematic diagram showing proposed gene expression changes during tumorigenesis of follicular-patterned lesions of the thyroid.

To identify gene expression profiles that distinguish borderline tumors from either benign or malignant tumors, another advanced significance analysis was performed. Twenty-seven of the 61 genes had significant differential expression between benign and borderline tumors, while 14 of the 61 genes had significant differential expression between malignancies and borderline tumors. Only one of these genes, T-cell lymphoma invasion and metastasis 1 (TIAM1), overlapped between the two comparisons (FIG. 5). Of the 27 genes that distinguished benign from borderline tumors, 8 genes had up-regulated expression in borderline tumors including, CITED-1, and 19 genes were down-regulated including fibroblast growth factor receptor 2 (FGFR-2) (Table 1). Of the 14 genes that distinguished malignant tumors from borderline tumors, 11 genes were up-regulated in malignant tumors, including met proto-oncogene (MET) and the high-mobility group adenine/thymine-hook 2 gene (HMGA2), whereas 2 genes were relatively down-regulated, notably deiodinase-1 (DIO) (Table 1).

Mutational Analysis of v-Raf Murine Sarcoma Viral Oncogene Homolog B1

BRAF mutational analysis was performed on all tumors in the test set. BRAF mutations were identified in 4 of 14 of the malignant tumors (29%) (Table 3). No borderline tumors or benign tumors had BRAF mutations.

TABLE 3

Presence of BRAF mutation in tumors

| | BRAF mutation | Percent |
|---|---|---|
| PTC (n = 5) | 3 | 60% |
| FVPTC (n = 9) | 1 | 11% |
| BOR (n = 15) | 0 | 0% |
| Follicular Adenoma (n = 6) | 0 | 0% |
| Hyperplastic Nodule (n = 5) | 0 | 0% |

PTC = papillary thyroid carcinoma;
FVPTC = follicular variant of papillary thyroid carcinoma;
BOR = borderline tumor Encapsulated follicular lesions with cytologic atypia remain a diagnostic challenge for pathologists. The foregoing experiments employed molecular profiling to identify a third category of thyroid tumors that, based on gene expression data, is likely to be premalignant. This third category of encapsulated follicular tumors with cytologic atypia typically did not fit into previously proposed benign or malignant classification schemes using standard histology, immunohistochemistry, or mutation analysis. The majority of histologically borderline tumors (66.7%) fell into an intermediate group and only a small number share gene expression similarities with benign tumors (26.7%) or malignant tumors (6.7%; Kmeans cluster analysis) (FIG. 4).

Many genes that were expressed differentially between benign tumors and malignant tumors in the training set were classic markers of PTC, including CITED1; dipeptidyl-peptidase 4 (DPP4); FGFR2; and serpin peptidase inhibitor, clade A (SERPINA1) (see also, Prasad et al., Mod. Pathol. 2005; 18:48-57 (2005); Huang et al., Proc. Natl. Acad. Sci. USA. 98:15044-49 (2001); Jarzab et al., Cancer Res. 65:1587-1597 (2005)).

It is noteworthy that borderline tumors, like malignant tumors, exhibited up-regulated gene expression of CITED1 and pleckstrin and Sec7 domain 3 (PSD3) and down-regulated gene expression of FGFR2 relative to benign tumors (Table 1). These genes and others listed in Table 1 are potential markers of early tumorigenesis.

In contrast, some genes with expression that was consistently altered in malignant tumors exhibited unchanged expression in the borderline group of tumors. For example DIO1, a differentiation marker that was consistently lost in PTC, was retained in this borderline group. Conversely. MET, SERPINA1, tissue inhibitor of metalloproteinase 1 (TIMP1), and HMGA2, which are genes that were often activated or over-expressed in PTC, exhibited lower expression in the borderline group of tumors relative to the malignant group. These genes may represent gene expression changes that are involved in the later stages of cancer development. These findings indicate that the histologically borderline tumors are premalignant and still lack the complete phenotype of PTC.

The results of BRAF mutation analysis also were in agreement with other studies (see, Nikiforova et al., J Clin Endocrinol Metab. 2003; 88:5399-5404 (2003)), with mutations identified in 29% of malignancies. To date. BRAF mutations have not been identified in benign lesions or in borderline encapsulated follicular tumors (see, Arora et al., World J Surg. 32:1237-1246 (2008); Fontaine et al., Oncogene 27:2228-2236 (2008)). Some studies indicate that BRAF mutations are associated with more aggressive tumors (Frasca et al., Endocr Relat Cancer. 15:191-205 (2008); Kebebew et al., Ann Surg. 246:466-471 (2007)) indicating that borderline tumors are more likely to be indolent tumors.

The finding that BRAF mutation is more frequent in classic PTC than in FVPTC also indicates that, for FVPTCs derived from FAs, BRAF either is uninvolved in carcinogenesis or is involved only as a late event. In addition, because of its higher frequency in classic PTC versus FVPTC. BRAF mutational analysis remains of limited usefulness in the diagnostic evaluation of these lesions.

Of the 15 histologically-defined borderline tumors in this study, 10 were clustered in an intermediate group, separate from benign and malignant clusters (FIG. 3). It is noteworthy that not all borderline tumors were separated into this third group: One tumor was clustered with malignant tumors, and 4 tumors were clustered with benign tumors. Conversely, 3 histologically-unequivocal FVPTCs and 2 FAs were identified in the molecularly intermediate group. Given the data provided herein that FAs, borderline tumors, and FVPTCs are stages of a biologic continuum, such an imperfect correlation between the histological classification and molecular data illustrates that accurate diagnosis should not be based on histological analysis alone.

Immunohistochemical markers have been studied in a few well differentiated tumors of uncertain malignant potential (WDT-UMP) with variable results. Papotti et al. (Mod Pathol. 18:541-546 (2005)) studied the expression of galectin-3 and HBME1 in 13 WDT-UMPs and noted some degree of staining with either antibody in 12 of 13 tumors. Immunohistochemical staining for HBME1. Galectin-3, and CK19 (data not shown) in the histologically borderline tumors that were studied as described herein revealed heterogeneous staining patterns. This variability, again, may reflect the biologically borderline nature of these tumors.

Unfortunately, part of the problem with standard diagnostic tools is the need by clinicians to separate tumors into benign or malignant categories. Partially for that reason, the term WDT-UMP proposed by Williams and by Rosai has not been embraced in practice and certainly is not in use at most institutions (Williams et al., Int J Surg Pathol. 8:181-183 (2000); Rosai, Endocr Pathol. 16:279-283 (2005)). Consequently, the majority of borderline tumors, as in the current study, probably are diagnosed as FVPTCs because of pathologists' general preference to err on the side of over-diagnosis for potential legal concerns. Patients are then often subjected, perhaps unnecessarily, to completion thyroidectomies, central neck dissections, and even radioactive iodine therapy. With the current 2-tiered classification (benign and malignant), our 2-Kmeans cluster would place 73% of histologically borderline tumors in the malignant category. However, such classification is somewhat simplistic and does not correlate with the clinical behavior of these tumors.

Several groups have reviewed the outcome of patients with encapsulated PTC, including both classic PTC and FVPTC (Liu et al., Cancer. 107:1255-1264 (2006); Vickery et al., Am J Surg Pathol. 7: 797-807 (1983); Evans et al., Am J Surg Pathol. 11:592-597 (1987). Liu et al. reviewed the outcome data from 42 patients with encapsulated, noninvasive FVPTCs who had a median 10-year follow-up and reported that no patients had recurrences and that none had lymph node metastasis. Vickery identified 10 patients who had encapsulated papillary cancers; in those patients, none had a recurrence, and only 1 patient had developed lymph node metastasis at a median follow-up of 15 years. Evans identified 7 patients who had encapsulated PTC and reported no recurrences or distant metastases at a median follow-up of 13.5 years. The number of studies that specifically have investigated tumors with borderline features is limited, although no tumor recurrences have been reported (Fusco et al., Am J Pathol. 160:2157-2167 (2002)). Likewise, none of the patients with borderline tumors in the current study had lymph node metastasis, and none of those with clinical follow-up developed recurrent disease or distant metastasis. The data presented here provide evidence that borderline tumors represent a molecularly distinct group of tumors that may not need aggressive treatment.

Example 3: Real Time PCR Methods

This example describes procedures for performing reverse transcription, real-time, quantitative PCR (RT-qPCR).

Total RNA from human cells is isolated by a standard mini-column method, RNAeasy® Mini Kit (Qiagen. Valencia, Calif.). RNA sample quality is evaluated based on electrophoretic integrity of 18S and 28S rRNA bands on a 2100 Bioanalyzer instrument (Agilent, Santa Clara, Calif.) and by standard spectrophotometric absorbance methods at 230, 260 and 280 nm wavelengths on a NanoDrop 1000 (NanoDrop/fhermo Scientific. Wilmington, Del.).

Preparation of cDNA from the RNA samples is carried out using 1.0 µg of total RNA into a standard 20 µl MMLV reverse transcriptase (Promega. Madison, Wis.) reaction according to the manufacturer's instructions using Promega buffers with a combination of 50 µg/ml random hexamers (Integrated DNA Technologies. Coralville, Iowa) and 2.5 ng/µl oligo d(T16) (Integrated DNA Technologies, Coralville, Iowa) to prime the first strand synthesis. Upon completion of the reverse transcription protocol the cDNA sample is diluted with 91 µl nuclease-free water (~5 fold) so that 1 µl (~1/100) is used as the template for individual 25 µl PCR reactions.

SYBR® Green real-time PCR is set up by combining 12.5 µl 2×SYBR® Green PCR Master Mix (Applied Biosystems, Foster City, Calif.) with 1 µl cDNA sample, 1 µl PCR primer mix (10 µM each forward and reverse primers from Tables 4 and 5) and 10 µl nuclease-free water in an appropriate reaction tube or plate. Real-time PCR thermal cycling and detection is performed on either an ABI 7500 (Applied Biosystems, Foster City, Calif.) or Stratagene Mx3005P (Agilent, Santa Clara, Calif.) instrument for 1 cycle of 10 minutes at 95° C., then 40 cycles of 15 seconds at 95° C. and 60 seconds at 60° C. followed by the instrument specific dissociation analysis steps.

Using the instrument's software and a consistent selection of measurement variables. Ct values are determined and relative expression measurements obtained by the ΔΔCt calculation method (Livak, K J, Schmittgen. TD. 2001, *Methods* 25.402-408).

Example 4: Primers and Probes for Detection of Differential Expression

This Example describes primers and probes for detecting expression of the differentially expressed genes described herein.

Thus, the sequences of primers with SEQ ID NO:3-118 are shown below in Tables 4 and 5.

Examples of human sequences (SEQ ID NO: 119-172) for the differentially expressed genes ANK2, ARHGAP6, C11orf17, CAPN3, CDH16. ChGn. CITED 1, CITED 2, CKB, COL9A3, CSRP2, DAPK2, DIO1, DPP4, DTX4, DUSP4, EFEMP1, ELMO1, FGFR2, FLRT1. FMOD. GALNT7, GATM, HGD. HMGA2. IGFBP6, KIT, LRP4, MATN2, MET, MYH10, PFAAP5, PGF, PIP3-E, PKNOX2, PRKACB, PROS1, PSD3, QPCT, RAB27A, RXRG, SDC4, SERPINA1, SLC25A15. SLC4A4, SLIT1, SPTAN1, TFCP2L1, TIAM1. TIMP1, TNS3, TSPANI2, and UPP1 are shown in Table 6.

TABLE 4

Forward Primers for Nucleic Acid Amplification Of Differentially Expressed Genes

| Gene Symbol HGNC Standard | NIH/NCBI Transcript ID | Forward Primer Sequence | SEQ ID NO: |
|---|---|---|---|
| ANK2 | NM_001127493 | AATACTGTGAGAA GAAGTG | 3 |
| ARHGAP6 | NM_001174 | GTGCCAAAGGCTG AGGAAATG | 4 |
| C11orf17 | NM_182901 | CTCATGTGGTAGC AGTTGATTC | 5 |
| NAUK2 | NM_030952 | GAAGTCCCGCAAG GAGAATG | 6 |
| CAPN3 | NM_173090 | AGGCTGGCCTCAT CCAAAG | 7 |
| CDH16 | NM_004062 | GATCGTGTGTCGC TGCAAC | 8 |
| CSGALNACT1 (ChGn) | NR_024040 | AGGAAACTCATTC AGACTG | 9 |
| CITED1 | NM_004143 | ATGCCAACCAAGA GATGAG | 10 |
| CITED2 | NM_006079 | AATGGGCGAGCAC ATACAC | 11 |
| CITED2 | NM_006079 | TAATAGGGTGTGG AATGTC | 12 |
| CKB | NM_001823 | CTTCCTAACTTAT TGCCTG | 13 |
| COL9A3 | NM_001853 | GGATCTGCGACAC CTCAGC | 14 |
| CSRP2 | NM_001321 | GGCCTACAACAAA TCCAAAC | 15 |
| DAPK2 | NM_014326 | TAGGACACGCAGG AAAGACCAC | 16 |
| DIO1 | NM_000792 | TTAAACCTGTCCA CATTGGTG | 17 |
| DPP4 | NM_001935 | GATAAGAGGGATT AGGGAG | 18 |
| DTX4 | NM_015177 | ATTTCCTTTCTAA CACTGTG | 19 |
| DUSP4 | NM_001394 | TCTAGTTACAGTG GATTTAG | 20 |
| EFEMP1 | NM_001039348 | ATCCAGAGTGACA GTGAAC | 21 |
| ELMO1 | NM_001039459 | GACTAAACCTAAA TGCCTC | 22 |
| FGFR2 | NM_000141 | ATCCAGCCTCATA CCTACATCAG | 23 |

TABLE 4-continued

Forward Primers for Nucleic Acid Amplification Of Differentially Expressed Genes

| Gene Symbol HGNC Standard | NIH/NCBI Transcript ID | Forward Primer Sequence | SEQ ID NO: |
|---|---|---|---|
| FLRT1 | NM_013280 | GCTTATTCCATAC CATTTC | 24 |
| FMOD | NM_002023 | GGCTCTTCTCCCT CTCCCAG | 25 |
| GALNT7 | NM_017423 | GTTGGTAATATCA CTATGC | 26 |
| GATM | NM_001482 | GTAATTGGATTTC GCTATC | 27 |
| HGD | NM_000187 | GATGAGAACTACC ACAAGTGCTG | 28 |
| HMGA2 | NM_003483 | TGTACTTTGAATC GCTTGCTTGTTG | 29 |
| IGFBP6 | NM_002178 | TGCAGCAACTCCA GACTGAG | 30 |
| KIT | NM_001093772 | TTGTGTGTTGTCT TGAAAG | 31 |
| LRP4 | NM_002334 | GAAGCGATTCTCC CATGCTC | 32 |
| MATN2 | NM_030583 | TACGATAAAGTTT GCACAG | 33 |
| MET | NM_001127500 | GAAAGAACTGTCT CTACCAG | 34 |
| MYH10 | NM_005964 | ACTACAAGCAGAG ACTGAG | 35 |
| PFAAP5 | U50535 | CAAGGCAGGCAGA TTGTTTG | 36 |
| PFAAP5 | CR601845 | TTAGCGGACATGG GTCAATTTC | 37 |
| PGF | NM_002632 | GCTTGTACTGGGA CATTGTTC | 38 |
| IPCEF1 (PIP3-E) | NM_001130700 | GATCCAGGACATC TATCAG | 39 |
| PKNOX2 | NM_022062 | AGCACGGACACAC TGGCAC | 40 |
| PRKACB | NM_002731 | GTGAAAGCACCTT GTAAAC | 41 |
| PROS1 | NM_000313 | AGTAAGGAGGTAA GATTGC | 42 |
| PSD3 | NM_206909 | GGTAGTGTCTAAG TGGTATG | 43 |
| PSD3 | NM_206909 | TGACTTTCAACTA ACCTTG | 44 |
| QPCT | NM_012413 | GATATTGTGTCCT AAATTGC | 45 |
| RAB27A | NM_183236 | TGCCAATGGGACA AACATAAG | 46 |
| RAB27A | NM_183236 | GATGCCTGTTTGC TATTTGGTGGAAG | 47 |

TABLE 4-continued

Forward Primers for Nucleic Acid Amplification Of Differentially Expressed Genes

| Gene Symbol HGNC Standard | NIH/NCBI Transcript ID | Forward Primer Sequence | SEQ ID NO: |
|---|---|---|---|
| RXRG | NM_006917 | ATTGTACTCTTTA ACCCAG | 48 |
| SDC4 | NM_002999 | CTTCCTCAGTTGC ACTAACCAC | 49 |
| SERPINA1 | NM_000295 | TCTGCCAGCTTAC ATTTACCCAAAC | 50 |
| SLC25A15 | NM_014252 | GTGACCGCTCTTG CTCTTG | 51 |
| SLC4A4 | NM_003759 | AAGAGTGAATAGT TGCCTC | 52 |
| SLIT1 | NM_003061 | CTAGAGGCTGGTT TAGAAC | 53 |
| SPTAN1 | NM_003127 | AGTTTGTAGCCAA TGTGGAAG | 54 |
| TFCP2L1 | NM_014553 | TGATTTCCTGTTA TGAGTC | 55 |
| TIAM1 | NM_003253 | TTCCATATCATCT CCGGTTCG | 56 |
| TIMP1 | NM_003254 | GACTCTTGCACAT CACTAC | 57 |
| TNS3 | NM_022748 | TGTGCCCAACGCA TGTTATAG | 58 |
| TSPAN12 | NM_012338 | AGAAAGGACTTGT ATGCTG | 59 |
| UPP1 | NM_181597 | GTGTGTGTCACCC TCCTGAAC | 60 |

TABLE 5

Reverse Primers for Nucleic Acid Amplification of Differentially Expressed Genes

| Gene Symbol HGNC Standard | NIH/NCBI Transcript ID | Reverse Primer Sequence | SEQ ID NO: |
|---|---|---|---|
| ANK2 | NM_001127493 | TTGCAGCTATGT ATTGTTAG | 61 |
| ARHGAP6 | NM_001174 | GATGGCGATACG CTTCAGTA | 62 |
| C11orf17 | NM_182901 | AAGGTGATGTGA TGGCAGTG | 63 |
| NAUK2 | NM_030952 | TTGGCAGCTTGA GGTTGCTC | 64 |
| CAPN3 | NM_173090 | CTTGATCGGTCA TGCCTAGCC | 65 |
| CDH16 | NM_004062 | GTAGGCACCCTG GTAGCAA | 66 |
| CSGALNACT1 (ChGn) | NR_024040 | AAGAGATTGTTT GGTTCAC | 67 |

TABLE 5-continued

Reverse Primers for Nucleic Acid Amplification of Differentially Expressed Genes

| Gene Symbol HGNC Standard | NIH/NCBI Transcript ID | Reverse Primer Sequence | SEQ ID NO: |
|---|---|---|---|
| CITED1 | NM_004143 | CTCGGGATCTCC AATAGGCTCTC | 68 |
| CITED2 | NM_006079 | GTGCCCTCCGTT CACAGTC | 69 |
| CITED2 | NM_006079 | AGCTTTCAACAC AGTAGTATC | 70 |
| CKB | NM_001823 | ATAAACTCTACC AAGGGTG | 71 |
| COL9A3 | NM_001853 | CGTGAGGAAGCA AGTGACA | 72 |
| CSRP2 | NM_001321 | GAGAAGATAATT GGAGCTGGAA | 73 |
| DAPK2 | NM_014326 | CAATCTTAGACT CTGGCCTCAA | 74 |
| DIO1 | NM_000792 | GCTCTCTGTACC CTGAAATCTTC | 75 |
| DPP4 | NM_001935 | GTTTGAATAGTC TTTCTCAG | 76 |
| DTX4 | NM_015177 | GTCAAGGTAGTA GATGCAC | 77 |
| DUSP4 | NM_001394 | GCTACCTTGCAC ATATCTAC | 78 |
| EFEMP1 | NM_001039348 | GATACATCAAAG TAAAGCAG | 79 |
| ELMO1 | NM_001039459 | ATGATGTAAACT TGGATGTC | 80 |
| FGFR2 | NM_000141 | CAATAGCCGTGC AAGATGAATG | 81 |
| FLRT1 | NM_013280 | ATCGACTACATG ATTGTTC | 82 |
| FMOD | NM_002023 | GTATGAGACCTA CGAGCCTTACC | 83 |
| GALNT7 | NM_017423 | ACCCAGAATTAA GATATACG | 84 |
| GATM | NM_001482 | CTTAGATGACCA AAGATGC | 85 |
| HGD | NM_000187 | CTTTCTGGTAGT ATTGGAGGAGG | 86 |
| HMGA2 | NM_003483 | CAGAGGCTGTTA TGTTTATTGTG | 87 |
| IGFBP6 | NM_002178 | CATCGAGGCTTC TACCGGAA | 88 |
| KIT | NM_001093772 | AGAGCATAGAAC TCCAGTG | 89 |
| LRP4 | NM_002334 | CACTGGAGAGAT TGGACTTTC | 90 |
| MATN2 | NM_030583 | TATATCAAGGTA AAGTCCAG | 91 |

TABLE 5-continued

Reverse Primers for Nucleic Acid Amplification of Differentially Expressed Genes

| Gene Symbol HGNC Standard | NIH/NCBI Transcript ID | Reverse Primer Sequence | SEQ ID NO: |
|---|---|---|---|
| MET | NM_001127500 | CAAGTGTGTAGT CCTGTTG | 92 |
| MYH10 | NM_005964 | GGTTTCTTTCTT CTTCTTC | 93 |
| PFAAP5 | U50535 | AATGGCACGATC ATGGGTC | 94 |
| PFAAP5 | CR601845 | AAGTGTAGCCCA GGTTAAGAAC | 95 |
| PGF | NM_002632 | GAGAAACAGCTC AGCCAGTGG | 96 |
| IPCEF1 (PIP3-E) | NM_001130700 | AAGGTGATTTCT TGAGTTC | 97 |
| PKNOX2 | NM_022062 | CTGATGTATCCA CCAAACCAGTAC | 98 |
| PRKACB | NM_002731 | CAGTAGTGCATA GGAAATTC | 99 |
| PROS1 | NM_000313 | CAGTGAAACATC TGATACAC | 100 |
| PSD3 | NM_206909 | ATAGTCATGGAC ATTTACAG | 101 |
| PSD3 | NM_206909 | AAGTTACTAAGA CTGCACAG | 102 |
| QPCT | NM_012413 | CTATCGTTGAAT GAATGAAC | 103 |
| RAB27A | NM_183236 | CTGAAGGAGTGG TGCGATCAA | 104 |
| RAB27A | NM_183236 | GAAGACACTTTG GCAATGCAGCGG | 105 |
| RXRG | NM_006917 | GATACTTCTGCT TGGTGTAG | 106 |
| SDC4 | NM_002999 | GACGACCCTTGT CTCCCTG | 107 |
| SERPINA1 | NM_000295 | GCATCACTAAGG TCTTCAGCA | 108 |
| SLC25A15 | NM_014252 | GTGGTCAGTAGC CTTATGCACCT | 109 |
| SLC4A4 | NM_003759 | ATCATTTCTCTC TCCAAAG | 110 |
| SLIT1 | NM_003061 | GGAAGACAACAG ACAATATC | 111 |
| SPTAN1 | NM_003127 | GATTATGGCGAC ACTCTTGCC | 112 |
| TFCP2L1 | NM_014553 | TACAGTGATGAC AGACAGC | 113 |
| TIAM1 | NM_003253 | CTTGGAGAGGGT GCCATTGTC | 114 |
| TIMP1 | NM_003254 | GATAAACAGGGA AACACTG | 115 |

TABLE 5-continued

| Reverse Primers for Nucleic Acid Amplification of Differentially Expressed Genes | | | |
|---|---|---|---|
| Gene Symbol HGNC Standard | NIH/NCBI Transcript ID | Reverse Primer Sequence | SEQ ID NO: |
| TNS3 | NM_022748 | CTTGTAACGTCT TCTCTGCCT | 116 |
| TSPAN12 | NM_012338 | TATTGACTTGGA GACTATTG | 117 |
| UPP1 | NM_181597 | GAAGAAACTGAG CAAGGCC | 118 |

Sequences of the coding regions of ANK2, ARHGAP6, C11orf17, CAPN3, CDH16, ChGn, CITED 1, CITED 2, CKB, COL9A3, CSRP2, DAPK2, DIO1, DPP4, DTX4. DUSP4, EFEMP1, ELMO1, FGFR2, FLRT1, FMOD, GALNT7, GATM, HGD, HMGA2. IGFBP6, KIT, LRP4, MATN2, MET, MYHI0, NAUK2, PFAAP5, PGF, PIP3-E, PKNOX2, PRKACB, PROS1, PSD3, QPCT, RAB27A, RXRG, SDC4, SERPINA1, SLC25A15, SLC4A4, SLIT1, SPTAN1. TFCP2L1, TIAM1, TIMP1, TNS3, TSPAN12, and/or UPP1 can be used to develop probes and primers for detecting differential expression of these genes. Such sequences are available in the database maintained by the National Center for Biotechnology Information (NCBI). See website at ncbi.nlm.nih.gov. A few examples of such sequences are provided below.

One example of a nucleic acid sequence for human ANK2 is available as NCBI accession number NM_001148 (gi: 188595661). This sequence is recited below for easy reference as SEQ ID NO:119.

```
   1 ctcctcctcc tgctttcctc cagtaagtgc atacccgcta gtggtctgta caggcggcac
  61 ggtttgatgg cagagatatt ttctttccaa actgttcaaa atgatgaacg aagatgcagc
 121 tcagaaaagc gacagtggag agaagttcaa cggcagtagt cagaggagaa aaagacccaa
 181 gaagtctgac agcaatgcaa gcttcctccg tgctgccaga gcaggcaacc tggacaaagt
 241 tgtggaatat ctgaaggggg gcatagacat caatacctgc aatcagaatg gactcaacgc
 301 tctccatctg gctgccaagg aaggccacgt ggggctggtg caggagctgc tgggaagagg
 361 gtcctctgtg gattctgcca ctaagaaggg aaataccgct cttcacattg catctttggc
 421 tggacaagca gaagttgtca aagttcttgt taaggaagga gccaatatta atgcacagtc
 481 tcagaatggc tttactcctt tatacatggc tgcccaagag aatcacattg atgttgtaaa
 541 atatttgctg gaaaatggag ctaatcagag cactgctaca gaggatggct ttactcctct
 601 agctgtggca ctccagcaag gacacaacca ggcggtggcc atcctcttgg agaatgacac
 661 caaagggaaa gtgaggctgc cagctctgca tattgccgct aggaaagacg acaccaaatc
 721 tgccgcactt ctgcttcaga atgaccacaa tgctgacgta caatccaaga tgatggtgaa
 781 taggacaact gagagtggtt ttaccccttt gcacatagct gcacattacg gaaatgtcaa
 841 cgtggcaact cttcttctaa accggggagc tgctgtggac ttcacagcca ggaatggaat
 901 cactcctctg catgtggctt ccaaaagagg aaatacaaac atggtgaagc tcttactgga
 961 tcgaggcggt cagatcgatg ccaaaactag qgatgggttg acaccacttc actgtgctgc
1021 acgaagtggg catgaccaag tggtggaact tctgttggaa cggggtgccc ccttgctggc
1081 aaggactaag aatggctgt ctccactaca catggctgcc cagggagacc acgtggaatg
1141 tgtgaagcac ctgttacagc acaaggcacc tgttgatgat gtcaccctag actacctgac
1201 agccctccac gttgctgcgc actgtggcca ctaccgtgta accaaactcc ttttagacaa
1261 gagagaaaat ccgaacgcca gagccctgaa tggttttact acactgcaca ttgcatgaaa
1321 gaaaaaccgc atcsaagtca tggaactgct ggtgaaatat ggggcttcaa tccaagctat
1381 aacagagtct ggcctcacac caatacatgt ggctgccttc atgggccact tgaacattgt
1441 cctccttctg ctgcagaacg gagcctctcc agatgtcact aacattcgtg gtgagacggc
1501 actacacatg gcagcccgag ccgggcaggt ggaagtggtc cgatgcctcc tgagaaatgg
1561 tgcccttgtt gatgccagag ccagggagga acagacacct ttacatattg cctcccgcct
1621 gggtaagaca gaaattgtcc agctgcttct acaacatatg gctcatccag atgcggccac
1681 tacaaatggg tacacaccac tgcacatctc tgcccgggag ggccaggtgg atgtggcatc
```

-continued

```
1741 agtcctattg gaagcaggag cagcccactc cttagctacc aagaagggtt ttactcccct
1801 gcatgtagca gccaagtatg gaagcctgga tgtggcaaaa cttctcttgc aacgccgtgc
1861 tgccgcagat tctgcaggga agaacggcct taccccgctc catgttgctg ctcattatga
1921 caaccagaag gtggcgctgc tgttactgga gaagggtgct tcccctcatg ccactgccaa
1981 gaatggctat actccgttac atattgctgc caagaagaat caaatgcaga tagcttccac
2041 actcctgaac tatggagcag agacaaacat tgtgacaaag caaggagtaa ctccactcca
2101 tctggcctcg caggaggggc acacagatat ggttaccttg cttctggaca agggagccaa
2161 tatccacatg tcaactaaga gtggactcac atccttacac cttgcagccc aggaagataa
2221 agtgaatgtt gctgatattc tcaccaagca tggagctgat caggatgctc atacaaagct
2281 tggttacaca cctttaattg tggcctgtca ctatggaaat gtgaaaatgg tcaactttct
2341 tctgaagcag ggagcaaatg ttaacgcaaa aaccaagaac ggctacacgc ctttgcacca
2401 ggccgctcag cagggtcaca cgcacatcat caacgtcctg ctccagcatg gggccaagcc
2461 caacgccacc actgcgaatg gcaacactgc cttggcgatt gctaagcgtc tgggctacat
2521 ctccgtggtc gacaccctga aggttgtgac tgaggaggtc accaccacca ccacaactat
2581 tacagaaaaa cacaaactaa atgtacctga gacgatgact gaggttcttg atgtttctga
2641 tgaagagggt gatgacacaa tgactggtga tgggggagaa taccttaggc ctgaggacct
2701 aaaagaactg ggtgatgact cactacccag cagtcagttc ctggatggta tgaattacct
2761 gcgatacagc ttggagggag gacgatctga cagccttcga tccttcagtt ccgacaggtc
2821 tcacactctg agccatgcct cctacctgag ggacagtgcc gtgatggatg actcagttgt
2881 gattcccagt caccaggtgt caactctagc caaggaggca gaaaggaatt cttatcgcct
2941 aagctggggc actgagaact tagacaacgt ggctctttct tctagtccta ttcattcagg
3001 tttcctggtt agttttatgg tggatgcccg aggtggtgct atgcgaggat gcagacacaa
3061 tgggctccga atcattattc cacctcggaa atgtactgct ccaacgcgag tcacctgccg
3121 actggtcaag cgccacagac tggcaacaat gcctccaatg gtggaaggag aaggcctggc
3181 cagtcgcctg atcgaagttg gaccttctgg tgctcagttc cttggtaaac ttcacctgcc
3241 aacggctcct cccccactta atgagggaga aagtttggtc agccgcattc ttcagctggg
3301 gcctcctgga accaaattcc ttgggcctgt gatcgtggag atccctcact ttgcggccct
3361 tcgaggaaag gaaagggaac tggtggtcct gcgcagtgag aatggggaca gctggaaaga
3421 gcatttctgt gactacactg aagatgaatt gaatgaaatt cttaacggca tggatgaagt
3481 actggatagc ccagaagacc tagaaaagaa acgaatctgc cgcatcatca cccgagactt
3541 cccacagtac tttgcagtgg tgtctcgtat caaacaggac agcaatctga ttggcccaga
3601 aggaggtgta ctgagcagca cagtggtgcc ccaggtgcag gccgtcttcc cagagggggc
3661 actcaccaag cggatccgcg taggcctgca ggctcaacct atgcacagtg agctggttaa
3721 gaagatccta ggcaacaaag ctaccttcag ccctatagtc actttggaac ctagaagaag
3781 aaaattccac aaaccaatta ccatgaccat tcctgtcccc aaagcttcaa gtgatgtcat
3841 gttgaatggt tttgggggag atgcaccaac cttaagatta ctatgcagca taacaggtgg
3901 aaccacccct gcccagcggg aagatattac aggaactacg ccattaacat ttgtcaatga
3961 atgtgtttcc tttacaacaa acgtgtctgc caggttccgg ctgatagatt gtcgacagac
4021 ccaggaatcc gttacccttg catcacaagt atacagagaa attacctgcg taccttatat
4081 ggccaaattt gtagtgtttg ccaaatcaca tgaccccatt gaagccaggt tgaggtgttt
4141 ctgcatgact gatgataaag tggataagac ccttgaacaa caagaaaatt ttgctgaggt
```

-continued 4201 ggccagaagc agggatgtgg aggtgttaga aggaaaaccc atctacgttg attgtttcgg 4261 caacttggta ccattaacta aaagtggcca gcatcatata ttcagttttt ttgccttcaa 4321 agaaaataga cttcctctat ttgtcaaggt acgcgatacg actcaggaac cttgcggacg 4381 actatcattt atgaaggagc caaaatccac gagaggcctg gtgcatcaag ctatttgcaa 4441 cttaaacatc actttgccga tttatacaaa ggaatcagag tcagatcaag aacaggagga 4501 agagatcgat atgacatcag aaaaaaatga tgagacagaa tctacagaaa catctgtcct 4561 gaaaagtcac ctggttaatg aagttcctgt cctagcaagt ccggacttgc tctctgaagt 4621 ttctgagatg aaacaagatt tgatcaaaat gaccgccatc ttgaccacag atgtgtctga 4681 taaggcaggt tctattaaag tgaaggagct ggtgaaggct gctgaggaag agccaggaga 4741 gccttttgaa atcgttgaaa gagttaaaga ggacttagag aaagtgaatg aaatcctgag 4801 aagtggaacc tgcacaagag atgaaagcag tgtgcagagc tctcggtctg agagaggatt 4861 agttgaagag gaatgggtta ttgtcagtga tgaggaaata gaagaggcta ggcaaaaagc 4921 acctttagaa atcactgaat atccatgtgt agaagttaga atagataaag agatcaaagg 4981 aaaagtagag aaagactcaa ctgggctagt gaactacctt actgatgatc tgaatacctg 5041 tgtgcctctt cccaaagagc agctgcagac agttcaagat aaggcaggga agaaatgtga 5101 ggctctggct gttggcagga gctctgaaaa ggaagggaaa gacatacccc cagatgagac 5161 acagagtaca cagaaacagc acaaaccaag cttgggaata aagaagccag taagaaggaa 5221 attaaaagaa aagcagaaac aaaaagagga aggtttacaa gctagtgcag agaaagctga 5281 acttaaaaaa ggtagttcag aagagtcatt aggtgaagac ccaggtttag cccctgaacc 5341 ccttcccact gtcaaggcca catctccttt gatagaagaa actcccattg gttccataaa 5401 ggacaaagta aaggcccttc agaagcgagt ggaagatgaa cagaaaggtc gaagcaagtt 5461 gcccatcaga gtcaaaggca aggaggacgt gccaaaaaag accacccaca ggccacatcc 5521 agctgcgtca ccctctctga agtcagagag acatgcgcca gggtctccct cccctaaaac 5581 agaaagacac tctactcttt cctcttccgc aaaaactgaa aggcaccctc cagtatcacc 5641 atcaagtaaa actgagaaac actcacctgt gtcaccctct gcaaaaacgg aaagacattc 5701 acctgcgtca tcatcgagta aaactgagaa acactcacct gtatcaccct cgacaaaaac 5761 tgaaaggcac tctcctgtgt catctacaaa aacagaaaga cacccacctg tttcgccttc 5821 aggcaaaaca gacaaacgtc cacctgtatc gccctccggg aggacagaaa aacacccgcc 5881 agtatcgcct gggagaacag aaaaacgctt gcctgtttca ccctccggaa gaacggacaa 5941 gcaccaacct gtatcaacag ctgggaaaac tgagaagcac ctgcctgtgt caccttctgg 6001 caaaacagaa aagcaaccac ctgtatcccc cacttcaaaa acagagagga ttgaggaaac 6061 catgtctgtt cgggagctga tgaaggcttt ccagtcaggt caggacccct ctaaacataa 6121 aactggactc tttgagcaca aatcagcaaa acaaaagcag ccacaagaga aaggtaaagt 6181 tcgggtagaa aaagaaaagg ggccgatact aacccagaga gaagctcaga aaacagagaa 6241 tcagacaatc aaacgaggcc agagactccc ggtaacgggc acagcagaat ccaaaagagg 6301 agttcgtgtt tcctccatag gagttaagaa agaagatgca gctggaggaa aggagaaagt 6361 tctcagccac aaaatacctg aacctgttca gtcagtgcct gaagaagaaa gccacagaga 6421 gagcgaagtg cccaaagaaa agatggctga tgagcaggga gacatggatc tacagatcag 6481 cccagatagg aaaacctcca ctgacttctc tgaggtcatt aagcaagagt tggaagacaa 6541 tgacaaatac caacaattcc gcctgagtga ggagacagaa aaggcacagc ttcacttaga -continued

```
6601   ccaagtactc actagtcctt tcaacacaac atttccactc gactacatga aagatgagtt
6661   ccttccagct ctgtctttac aaagcggtgc tttagatggc agttctgaaa gcctaaagaa
6721   tgagggggta gccggctctc cgtgtggcag cctgatggag ggacccctc agattagttc
6781   agaagaaagc tataagcatg aaggcctagc agagacccct gagacgagcc cagaaagcct
6841   ttctttctca ccaaagaaaa gtgaggagca aactggggaa acaaaggaaa gcaccaagac
6901   agaaaccacc acagaaattc gttcagaaaa agagcatccc acgaccaaag acattactgg
6961   tggctctgaa gagcgaggtg ccacagtcac tgaggactca gagacctcta ctgagagttt
7021   tcagaaagag gccactctag gctctcccaa agacacaagc cctaaaagac aagatgattg
7081   cacaggcagc tgtagcgtag cattagctaa agagacacct acaggactga ctgaggaggc
7141   agcctgtgat gaaggtcaac gtacctttgg tagttcagcc cacaagacac aaactgatag
7201   tgaggttcaa gaatccacag ccacctcaga cgagacaaag gccttgccgc tgcctgaggc
7261   ttctgtaaag acagatacag gaactgaatc aaaacctcag ggagtcatta gaagtcccca
7321   agggttagaa cttgcactcc ctagccgaga tagcgaagtc ctcagcgctg tggctgatga
7381   ctcattagca gtgagccaca aagactctct ggaagccagc cctgtgctag aagataactc
7441   ttcacacaaa acccctgatt ctctggagcc aagtcctctg aaagaatccc cttgccgtga
7501   ctctctggaa agcagccctg ttgaaccaaa gatgaaggct ggaatttttc caagtcactt
7561   tcctcttcct gcagctgttg ccaaaacaga actcttgacg gaagtggcct ctgtgcggtc
7621   ccggctactc cgagaccctg atggcagtgc tgaggatgac agtcttgagc agacatcgct
7681   catggagagc tcagggaaga gcccccttc tcctgacacc cccagctctg aagaagtcag
7741   ctatgaggtt acacccaaaa ccacagatgt aagtacacca aaaccagctg tgattcatga
7801   atgtgcagag gaggatgatt cagaaaacgg ggagaaaaag aggttcacac ctqaagagga
7861   gatgtttaaa atggtaacca aaatcaaaat gtttgatgaa cttgaacaag aagcaaagca
7921   gaaaagggac tacaaaaaag aacccaaaca agaagaatct tcttcatctt ctgacccaga
7981   tgctgactgt tcagtagatg tggatgaacc aaaacataca ggcagtgggg aggatgaaag
8041   tggtgtccct gtgttagtaa cttcggagag caggaaggtg tcttcctcct cagaaagtga
8101   acctgagttg gcacagctta aaaaaggtgc tgactcaggc cttttaccag aaccagtgat
8161   tcgagtacaa cctccttctc cacttccatc aagcatggac tccaattcca gtccagaaga
8221   agtacaattc cagcctgtcg tttccaaaca atatactttc aagatgaacg aagatactca
8281   ggaagagcca ggcaaatcag aagaagaaaa agattctgaa tcccatttag ctgaagaccg
8341   tcatgctgtt tccactgagg ctgaagacag gtcttatgat aagctaaaca gagacactga
8401   tcagccaaaa atctgtgatg gccatggatg tgaggccatg agtcctagca gctcagctgc
8461   tcctgtctct tcaggtctac agagtccgac tggtgatgat gttgatgaac agccagtcat
8521   ctataaagaa tcattagctc tccaaggcac tcatgaaaaa gacacagagg gagaagagct
8581   cgatgtttct agagcagaat ctccacaagc agattgcccc agtgaaagct tttcatcttc
8641   atcctcttcg cctcattgtt tggtatctga aggaaaagaa ttagatgaag acatatctgc
8701   cacatcttct attcaaaaaa cagaggtcac aaaaaactgat gaaacatttg agaacttacc
8761   aaaggactgc ccctctcaag actcatccat tactactcaa acagatagat tttccatgga
8821   tgttcccgtg tctgacctag ctgagaatga tgaaatctat gatccacaaa tcactagccc
8881   ttatgaaaat gtcccttccc aatctttttt ctctagtgaa gaaagcaaaa cccaaacaga
8941   tgcaaatcac accacaagtc ttcactcttc tgaagtgtat tctgttacca tcacaccccc
9001   tgttgaagac gttgtagtgg caagctcctc tagtggaact gttttaagca aagaatctaa
```

-continued 9061 ttttgagggc caggacataa aaatqgaatc ccaacaggaa agtaccttgt gggaaatgca
9121 atcagacagt gtctcttcat ctttcgagcc tactatgtcc gctacaacaa cagttgttgg
9181 tgaacaaata agcaaagtca tcatcacaaa aactgatgtg gattctgatt cttggagtga
9241 aattcgggaa gacgacgaag cctctgaggc tcgtgtgaaa gaggaagaac aaaagatatt
9301 tggtttgatg gtagacagac aatcacaggg taccacccct gacaccactc ctgctaggac
9361 cccaactgaa gaggggaccc caacaagtga gcaaaaccca tttctgtttc aggaaggaaa
9421 attgtttgaa atgacccgaa gtggtgccat tgatatgacc aaaaggtcct atgcagatga
9481 aagttttcac tttttccaaa ttggtcaaga atccagggaa gagactctct ctgaagatgt
9541 gaaagaaggg gctactgggg ctgatcccct accgctggag acatcagctg aatcactagc
9601 actttcagaa tcaaaagaaa cagtggatga tgaggcagac ttacttccag atgacgtgag
9661 tgaggaagta gaggaaatac ctgcttcgga tgctcaactt aactcccaaa tggggatttc
9721 agcctccact gaaacaccta caaaagaagc tgttagtgta gggaccaagg acctccccac
9781 cgtgcaaacg ggtgatatac ctcctctctc tggtgtaaag cagacatcct gccccgactc
9841 ttctgaacca gctgtacaag tccagttaga cttttccaca ctcaccaggt ctgtttattc
9901 agataggggt gatgattctc ccgattcttc cccagaagaa cagaaatcag taatcgagat
9961 tcctactgca cccatggaga atgtgccttt tactgaaagc aaatccaaaa ttcctgtaag
10021 gactatgccc acttccaccc cagcacctcc atctgcagag tatgagagtt cagtttctga
10081 agattttcta tccagtgtag atgaggaaaa taaggcggat gaagcaaaac caaagtccaa
10141 actccctgtc aaagtacccc tccaaagagt tgaacagcag ctctcagacc tagacacctc
10201 tgtccagaag acagtggctc ctcagggaca ggacatggca agcatcgcac cagataatag
10261 aagcaaatct gaatctgatg ctagttcttt ggattcaaag accaaatgcc cagtaaaaac
10321 ccgaagttac actgagacag aaacagagag cagagagagg gccgaggaac ttgagttaga
10381 atcagaagaa ggggccacaa gaccaaagat acttacatcc cgactgccag ttaagagcag
10441 aagcactaca tcttcctgca ggggggcac gagccccaca aaagaaagta aggagcatcc
10501 ctttgacctt tacagaaatt ccatagaatt ctttgaggag attagtgatg aggcttccaa
10561 attagtggat aggctgacac agtcagagag ggagcaggaa atagtttcag acgatgaaag
10621 tagtagtgcc ctggaagtat cagtaattga aaatctgcca cctgttgaga ccgagcactc
10681 agttcctgag gacatctttg acacaaggcc catttgggat gagtctattg agactctgat
10741 tgaacgcatc cctgatgaaa atggccatga ccatgctgaa gatccacagg atgagcagga
10801 acggatcgag gaaaggctgg cttatattgc tgatcacctt ggcttcagct ggacagaatt
10861 agcaagagaa ctggatttca ctgaggagca aattcatcaa attcgaattg aaaatcccaa
10921 ctctcttcaa gaccagagtc atgcactgtt gaagtactgg ctagagaggg atgggaaaca
10981 tgctacagat accaacctcg ttgaatgtct caccaagatc aaccgaatgg atattgttca
11041 tctcatggag accaacacag aacctctcca ggagcgcatc agtcatagct atgcagaaat
11101 tgaacagacc attacactgg atcatagtga agggttctcg gtacttcaag aggagttatg
11161 cactgcacag cacaagcaga aagaggagca agctgtttct aaagaaagtg agacctgcga
11221 tcaccctcct atcgtctcag aggaagacat ttctgttggt tattccactt ttcaggatgg
11281 cgtccccaaa actgaggggg acagctcagc aacagcactc tttccccaaa ctcacaagga
11341 gcaagttcaa caggatttct cagggaaaat gcaagacctg cctgaagagt catctctgga
11401 atatcagcag gaatattttg tgacaactcc aggaacagaa acatcagaga ctcagaaggc -continued 11461 tatgatagta cccagctctc ccagcaagac acctgaggaa gttagcaccc ctgcagagga 11521 ggagaagctg taactccaga ccccaacatc cagcgagcgg ggaggctatc ccataataca 11581 agaacccgaa gagccctcag agcacagaga ggagagctct ccgcggaaaa ccagcctcgt 11641 aatagtggag tctgccgata accagcctga gacctgtgaa agactcgatg aagatgcagc 11701 ttttgaaaag ggagacgata tgcctgaaat acccccagaa acagtcacag aagaagaata 11761 cattgatgag catggacaca ccgtggtaaa gaaggttact aggaaaatca ttaggcggta 11821 tgtatcctct gaaggcacag agaaagaaga gattatggtg cagggaatgc cacaggaacc 11881 tgtcaacatc gaggaagggg atggctattc caaagttata aagcgtgttg tattgaagag 11941 tgacaccgag cagtcagagg acaacaatga gtaaagccat cacacagaag agggctgtgg 12001 tgaaggacca gcatggaaaa cgcattgact tggagcacct ggaggatgta ccagaagcac 12061 tagaccagga cgacctccag cgcgatctcc agcagctcct tcggcatttc tgcaaggagg 12121 acttgaagca agaggccaag tgaggggctg cccagttctc acaccagaaa ccacacattc 12181 actcaatatg cagcttcctg tttcagtagg ggagtgacct aactggccta attaatggga 12241 taccccgaca tttccactgt tagcaaatat acggcatttt gctttagttt tcccccatcc 12301 tctttaacta taaagctaat ttgtgaccaa agatggcatc cttcatactg gatgctgtat 12361 ccaatacttt gttgtgtctg tgctaacctg ggaactggcc acctccattg ttctttgctt 12421 ctgcacaaga tccatgaaaa tccattgatc agaagaactt cacctgcaga cctcttcaag 12481 tgacactatg taggaatcct tccaaggaat atctatgtac aatgtatata gctgaaatgc 12541 tcagatgaac aacatattaa aattaaaacc actgcctatt gtaactacac tgggcatcag 12601 aataaaaggc ctctagaaat tgctgaacaa tggttaatta agatattgct aacacaatcg 12661 agtgataata cagttttact gcaaaagaag cacttcaaac ctattatgtc cttagaactt 12721 ccagagtagc cactgctccc agttaaaggt gggtcagtag ccttgcagaa ctgtcctgag 12781 aagttattgc tggtgctggc cagccatggc ttaggactcc aacagccact ctgagggagg 12841 ggagaaggga gcagaggcca cgcagaatga accgatgggg tattcagttg ctggcagcta 12901 cattgtgtgg cattctagca tcttcaggtc tttagatctt ggacaagttg gcagggtatt 12961 ttaaaagcta taactactgt agttttccag ttttcattgc tgctttagca aaccacgctg 13021 tcttacagtg gtactttctt ctggccactg cactgtagat aattcattgg aaacaagatt 13081 tacccactac ataaaaggtt aaactccttc agtatgttgg agtggtttct tttttttttt 13141 ctttctttct tttttttctt caggtttata tcttctctaa tacctgcatg tggcgtttaa 13201 aaatcaagac cacggtcaaa cccctcttct aatcacatta attgtttcca ttctttttac 13261 cctgagtgag cactcctcac tttccagcta ggtctgtttt tcagcttgca gacaagattg 13321 agaaatcctt gaaaatttgg ttttggttaa aatttttggt ttatttattt gaaatccaca 13381 ctcccttgga aactcttaag tgcatttgtg cacttctgtt tgtttgtctc aaagaaggga 13441 ctgtaacaat ctgagtaatt tccatgtcct cttccttatt cctctagtgg ttgaagctgt 13501 gtagcatttt aacatatata tattcacaaa tatattcata taaacagtat acattttgaa 13561 tcagtcattt gttaaagaaa agtatattca atgaagatga aatttaaata aaaaaggaca 13621 gagtctataa tccagggatt gaacattttc caattatctg gtcttttcct gttgtgcaaa 13681 aatgactcat tgctccgaat gtcaaaaaca aatgcgacaa acaatggcac ttcatcattt 13741 aaagtaatgt tgccaagaga aaaaatttcc tgggagggag gtttcccaca agccaaatct 13801 cctaagcctc aaatgctagc actttttggc agttggatag gaaatgagac attctttggc 13861 agccaaaata agagaggccg acggtgaaac tttttgagac accctatagc cttcttgtca -continued 13921 aaaccttcac tggagctcaa gaaaagcatt tctgttgtgt tatttgcagt gcagatgatg 13981 tctgtgtaac aacataatgg ttattcacct ttttttgatt ttgatttttg ctgtgttatc 14041 aaaaacttga atactgtgag aagaagtgaa ttttcagttg acgaatcagc atcttgttcc 14101 catggtgata acactaattg aatatatcta tgagggcatg tattagttaa tggaaaaaaa 14161 aatacaacac taacaataca tagctgcaat gtgtacaatg gctgatttaa ttaaataaaa 14221 tgtacaagtg ttaaatgtgg caa One example of a nucleic acid sequence for human ARHGAP6 is available as NCBI accession number NM_013427 (gi: 95091874). This sequence is recited below for easy reference as SEQ ID NO: 120.

1 ggctgggctg cgaatagcgt gttcctctcc ggcggaacac acacacccgg ccttggggct 61 gtctcctgag ctccctcctc cacggagagc gctgagcgcc gccgggaatt ccatcccacc 121 gtgggcacgc agtctttgga ggtcccgggc gcagcacgct cggtgtcccc acactgcagc 181 aagacagaga ccccgcggga accttgagct tggaacaacc cttgagcctc tgcagtcgga 241 agagtgggcg cagcagccca gcggaggcca ggcgcgcaac ctcgggcgcc ggggcaagga 301 gagagtgcag ggaggcgcag ctcaggcgcc cggctcagga gcgggaggaa gttctcgcgg 361 cgccgggagc gcggtggacg cgccctgggc gcacgcccag gcagccttct ccctggccct 421 cgggactgtc ctcgggccgc aaggaggagc ttgctggagt cttagaggcc atccagagcc 481 agcgagcagg agcgctgcgt ctcccgcctc agctaggaag ggggagtggc gctggcaggc 541 tggagctggg aacccagcga gcgcctgacc ttcctcctcc tcttcctgac cctcttcgcg 601 tcttgggctc cggaggaagg ttctagcggc tgcaggaggt ccccagaccc atttcctag 661 aaggctggtg atggatctgc tgctcctgcc gccgccgggg cacttggagc gcaccggcgg 721 cgcgtgagct gggctttgct ctccactgcc ctgggcaaac cccgggccag ccccgcctgg 781 cacctttgcc tgagtccctt tcggttcccg acccaaagcc accagcgtcc agggagggag 841 gaggaggtgg tcctcaggtg cagccccgcc gagatgtccg cgcagagcct gctccacagc 901 gtcttctcct gttcctcgcc cgcttcaagt agcgcggcct cggccaaggg cttctccaag 961 aggaagctgc gccagacccg cagcctggac ccggccctga tcggcggctg cgggagcgac 1021 gaggcgggcg cggagggcag tgcgcgggga gccacggcgg gccgcctcta ctccccatca 1081 ctcccagccg agagtctcgg ccctcgcttg gcgtcctctt cccggggtcc gccccccagg 1141 gccaccaggc taccgcctcc tggacctctt tgctcgtcct tctacacacc cagcaccccg 1201 caggagaagt caccatccgg cagctttcac tttgactatg aggttcccct gggtcgcggc 1261 ggcctcaaga agagcatggc ctgggacctg ccttctgtcc tggccgggcc agccagtagc 1321 cgaagcgctt ccagcatcct ctgttcatcc gggggaggcc ccaatggcat cttcgcttct 1381 cctaggaggt ggctccagca gaggaagttc cagtccccac ccgacagtcg cgggcacccc 1441 tacgtcgtgt ggaaatccga gggtgatttc acctggaaca gcatgtcagg ccgcagtgta 1501 cggctgaggt cagtccccat ccagagtctc tcagagctgg agagggcccg gctgcaggaa 1561 gtggcttttt atcagttgca acaggactgt gacctgagct gtcagatcac cattcccaaa 1621 gatggacaaa agagaaagaa atctttaaga aagaaactgg attcactagg aaaggagaaa 1681 aacaaagaca aagaattcat cccacaggca tttggaatgc ccttatccca agtcattgcg 1741 aatgacaggg cctataaact caagcaggac ttgcagaggg acgagcagaa agatgcatct -continued

```
1801 gactttgtgg cttccctcct cccatttgga aataaaagac aaaacaaaga actctcaagc
1861 agtaactcat ctctcagctc aacctcagaa acaccgaatg agtcaacgtc cccaaacacc
1921 ccggaaccgg ctcctcgggc taggaggagg ggtgccatgt cagtggattc tatcaccgat
1981 cttgatgaca atcagcctcg actactagaa gctttacaac tttccttgcc tgctgaggct
2041 caaagtaaaa aggaaaaagc cagagataag aaactcagtc tgaatcctat ttacagacag
2101 gtccctaggc tggtggacag ctgctgtcag cacctagaaa aacatggcct ccagacagtg
2161 gggatattcc gagttggaag ctcaaaaaag agagtgagac aattacgtga ggaatttgac
2221 cgtgggattg atgtctctct ggaggaggag cacagtgttc atgatgtggc agccttgctg
2281 aaagagttcc tgagggacat gccagacccc cttctcacca gggagctgta cacagctttc
2341 atcaacactc tcttgttgga gccggaggaa cagctgggca ccttgcagct cctcatatac
2401 cttctacctc cctgcaactg cgacaccctc caccgcctgc tacagttcct ctccatcgtg
2461 gccaggcatg ccgatgacaa catcagcaaa gatgggcaag aggtcactgg gaataaaatg
2521 acatctctaa acttagccac catatttgga cccaacctgc tgcacaagca gaagtcatca
2581 gacaaagaat tctcagttca gagttcagcc cgggctgagg agagcacggc catcatcgct
2641 gttgtgcaaa agatgattga aaattatgaa gccctgttca tggttccccc agatctccag
2701 aacgaagtgc tgatcagcct gttagagacc gatcctgatg tcgtggacta tttactcaga
2761 agaaaggctt cccaatcatc aagccctgac atgctgcagt cggaagtttc cttttccgtg
2821 ggagggaggc attcatctac agactccaac aaggcctcca gcggagacat ctccccttat
2881 gacaacaact ccccagtgct gtctgagcgc tccctgctgg ctatgcaaga ggacgcggcc
2941 ccgggggggct cggagaagct ttacagagtg ccagggcagt ttatgctggt gggccacttg
3001 tcgtcgtcaa agtcaaggga aagttctcct ggaccaaggc ttgggaaaga tctgtcagag
3061 gagcctttcg atatctgggg aacttggcat tcaacattaa aaagcggatc caaagaccca
3121 ggaatgacag gttcctctgg agacattttt gaaagcagct ccctaagagc ggggccctgc
3181 tccctttctc aagggaacct gtccccaaat tggcctcggt ggcaggggag ccccgcagag
3241 ctggacagcg acacgcaggg ggctcggagg actcaggccg cagcccccgc gacggagggc
3301 agggcccacc ctgcggtgtc gcgcgcctgc agcacgcccc acgtccaggt ggcagggaaa
3361 gccgagcggc ccacggccag gtcggagcag tacttgaccc tgagcggcgc ccacgacctc
3421 agcgagagtg agctggatgt ggccgggctg cagagccggg ccacacctca gtgccaaaga
3481 ccccatggga gtgggaggga tgacaagcgg cccccgcctc catacccggg cccagggaag
3541 cccgcggaag cggcagcctg gatccagggg cccccggaag gcgtggagac acccacggac
3601 cagggaggcc aagcagccga gcgagagcag caggtcacgc agaaaaaact gagcagcgcc
3661 aactccctgc cagcgggcga gcaggacagt ccgcgcctgg gggacgctgg ctggctcgac
3721 tggcagagag agcgctggca gatctgggag ctcctgtcga ccgacaaccc cgatgccctg
3781 cccgagacgc tggtctgagc ccgcacccag ccgagccccc cctgccccga gcccccgcc
3841 ctccagccca ggggggaccg tgggtggtgg ccactggcac acttagtgtt cttctttcac
3901 acttctcaaa agtgacacaa gagaaatcca gttcacctac agaggtagag cactcacgcc
3961 cccgccattg agaataaggt tccattgcgt agccagcctt aggaaaaaca aacagaaccc
4021 aaaccagatg gcaatgtcca atctaaaaac gtccctcttg gctctataat ataagataca
4081 actcttgctt ggtatagcct aaccgtattt atgtgtcttc ggttttgact attgtgtatt
4141 ctgtaacaga ttatgtataa tcatatatga tatattcaca aagagaaaac aaaaggaact
4201 tttaaaaaaa aaatcacttc acttatatta agcaatgaga tatactaaac aatgagattc
```

-continued 4261 tatagaatgt tctagaatgt gcacaagcgg gtttctgtgc ttttgccata gctttataac 4321 tggggataac ccttccttcg ataccaaaca ctaacaagag gaagcagaat atgagaagcc 4381 atatttttac ataggagtca gatacaaaaa gaaaaatcac tgaatgcttt tagatattga 4441 atacgttttc aggaaaatgc taaatctgat agattacgaa atatattttt agaacttgtt 4501 tagaaaggat tcagttaacc aaacaagaaa aaggcagtgc ctcacaaaga aattaagaag 4561 ttgtccgtcc cacgttacat caaattcagt tttatatagg ccatatataa tatatattta 4621 taatgtataa tttttatgta tttttcaaaa ctacaaactg gaatccaact ataaagtgtt 4681 taagaatcta cacagaatat tcaaattata gaacatgttt tttccctttg ccccataatc 4741 agtatttgcc aaattacatg caattcctta aaaactaaat cacatttggt aaaaggccta 4801 cagctttgta cttacactgt gccaaaggct gaggaaatgt tttctttcgt aattttatgt 4861 gtattgtaaa atgttctacc gtactttagt agtttgaagt ttttcaagtg cataactatt 4921 tttgaccagc agatggcgat acgcttcagt attttatgca atttttttc acttctgaag 4981 ggaaagtgta ttataaaaaa agattttttt ttttttata aaacatgcta ctcttaattt 5041 tcatgttggt gatgaaattc ccagtggtgt ttcttaaggt tctatcttgt gccatgatga 5101 ataaaaagtt aagcaaag One example of a nucleic acid sequence for human C11orf17 is available as NCBI accession number NM_182901 (gi: 116174739). This sequence is recited below for easy reference as SEQ ID NO:121.

1 agatgaaaat ggaaggggcg ggcgcgctag gcctagtcct ggctgggctc ccgctggagt 61 gtgcgttggg ggcggaccag gagcggtggt ctccagggag gtcgaggctg gggctcccac 121 ccggatttgg agcagggtcg ccgcggccca gctgacccgc cggcgtttgt acgttgtgtg 181 cccactcagg gagccatgga caactgtttg gcggccgcag cgctgaatgg ggtggaccga 241 cgttccctgc agcgttcagc aaggctggct ctagaagtgc tggagagggc caagaggagg 301 gcggtggact ggcatgccct ggagcgtccc aaaggctgca tgggggtcct tgcccgggag 361 gcgcccccacc tagagaaaca gccggcagcc ggcccgcagc gcgttctccc gggagagaga 421 gaagagagac ccccaaccct tagtgcttcc ttcagaacaa tggctgaatt catggactat 481 acttcaagtc agtgtgggaa atattattca tctgtgccag aggaaggagg ggcaacccat 541 gtctatcgtt atcacagagg cgagtcgaag ctgcacatgt gcttggacat agggaatggt 601 cagagaaaag acagaaaaaa gacatccctt ggtcctggag gcagctatca aatatcagag 661 catgctccag aggcatccca gcctgctgag aacatctcta aggacctcta catagaagta 721 tatccaggga cctattctgt cactgtgggc tcaaatgact taaccaagaa gactcatgtg 781 gtagcagttg attctggaca aagcgtggac ctggtcttcc ctgtgtgatg ttgaccatca 841 ctgccatcac atcacctttt tttaagtagt aagaataaag ccactgtatg attctcttaa 901 tagctataca ttaatcctgt ttttagtgct gactgggtca gccttccggg aactggagtc 961 tgtctctttc agtgcttttt tgtttgtttg gttggttttt ttttgagaca gtctcactct 1021 gttgcccagg ctggagtgca gtggcgtgat ctcggctcac tgcaagttcc gcctcccggg 1081 ttcacaccat tctcctgcct cagcctcccg agtagctggc actacaggca cccgccacca 1141 tgcccggcta tttttttgt atttttagta gagacggggt ttcaccatgt tggccaggat 1201 ggtctcgatc tcttgacctc gtgatccacc caccttggcc tcccaaagtg ttgggattac -continued

```
1261 aggcgtgagc caccgcgccc ggcctcagtg cctttttttaa cttgagggtg tagaggtcct
1321 ccacgcttgt ttgcctgaaa gtaatataat gatgctgtct gaacaggttt tactgcttgc
1381 tttccaagta aaggttaatt atgataataa agagatttgg aaatgaa
```

One example of a nucleic acid sequence for human CAPN3 is available as NCBI accession number NM_000070 (gi: 27765081). This sequence is recited below for easy reference as SEQ ID NO: 122.

```
   1 cactctcttt ctctctccct ctggcatgca tgctgctggt aggagacccc caagtcaaca
  61 ttgcttcaga aatcctttag cactcatttc tcaggagaac ttatggcttc agaatcacag
 121 ctcggttttt aagatggaca taacctgtac gaccttctga tggctttca actttgaact
 181 ggatgtggac acttttctct cagatgacag aattactcca acttcccctt tgcagttgct
 241 tcctttcctt gaaggtagct gtatcttatt ttctttaaaa agctttttct tccaaagcca
 301 cttgccatgc cgaccgtcat tagcgcatct gtggctccaa ggacagcggc tgagccccgg
 361 tccccagggc cagttcctca cccggcccag agcaaggcca ctgaggctgg gggtggaaac
 421 ccaagtggca tctattcagc catcatcagc cgcaattttc ctattatcgg agtgaaagag
 481 aagacattcg agcaacttca caagaaatgt ctagaaaaga aagttcttta tgtggaccct
 541 gagttcccac cggatgagac ctctctcttt tatagccaga agttccccat ccagttcgtc
 601 tggaagagac ctccggaaat ttgcgagaat ccccgattta tcattgatgg agccaacaga
 661 actgacatct gtcaaggaga gctaggggac tgctggtttc tcgcagccat tgcctgcctg
 721 accctgaacc agcaccttct tttccgagtc ataccccatg atcaaagttt catcgaaaac
 781 tacgcaggga tcttccactt ccagttctgg cgctatggag agtgggtgga cgtggttata
 841 gatgactgcc tgccaacgta caacaatcaa ctggttttca ccaagtccaa ccaccgcaat
 901 gagttctgga gtgctctgct ggagaaggct tatgctaagc tccatggttc ctacgaagct
 961 ctgaaaggtg ggaacaccac agaggccatg gaggacttca caggaggggt ggcagagttt
1021 tttgagatca gggatgctcc tagtgacatg tacaagatca tgaagaaagc catcgagaga
1081 ggctccctca tgggctgctc cattgatgat ggcacgaaca tgacctatgg aacctctcct
1141 tctggtctga acatgggggga gttgattgca cggatggtaa ggaatatgga taactcactg
1201 ctccaggact cagacctcga ccccagaggc tcagatgaaa gaccgacccg gacaatcatt
1261 ccggttcagt atgagacaag aatggcctgc gggctggtca gaggtcacgc ctactctgtc
1321 acggggctgg atgaggtccc gttcaaaggt gagaaagtga agctggtgcg gctgcggaat
1381 ccgtggggcc aggtggagtg gaacggttct tggagtgata gatggaagga ctggagcttt
1441 gtggacaaag atgagaaggc ccgtctgcag caccaggtca ctgaggatgg agagttctgg
1501 atgtcctatg aggatttcat ctaccatttc acaaagttgg agatctgcaa cctcacggcc
1561 gatgctctgc agtctgacaa gcttcagacc tggacagtgt ctgtgaacga gggccgctgg
1621 gtacggggtt gctctgccgg aggctgccgc aacttcccag atactttctg gaccaaccct
1681 cagtaccgtc tgaagctcct ggaggaggac gatgaccctg atgactcgga ggtgatttgc
1741 agcttcctgg tggccctgat gcagaagaac cggcggaagg accggaagct aggggccagt
1801 ctcttcacca ttggcttcgc catctacgag gttcccaaag agatgcacgg gaacaagcag
1861 cacctgcaga aggacttctt cctgtacaac gcctccaagg ccaggagcaa aacctacatc
1921 aacatgcggg aggtgtccca gcgcttccgc ctgcctccca gcgagtacgt catcgtgccc
```

-continued

```
1981 tccacctacg agccccacca ggagggggaa ttcatcctcc gggtcttctc tgaaaagagg
2041 aacctctctg aggaagttga aaataccatc tccgtggatc ggccagtgaa aaagaaaaaa
2101 accaagccca tcatcttcgt ttcggacaga gcaaacagca acaaggagct gggtgtggac
2161 caggagtcag aggagggcaa aggcaaaaca agccctgata agcaaaagca gtccccacag
2221 ccacagcctg gcagctctga tcaggaaagt gaggaacagc aacaattccg gaacattttc
2281 aagcagatag caggagatga catggagatc tgtgcagatg agctcaagaa ggtccttaac
2341 acagtcgtga acaaacacaa ggacctgaag acacacgggt tcacactgga gtcctgccgt
2401 agcatgattg cgctcatgga tacagatggc tctggaaagc tcaacctgca ggagttccac
2461 cacctctgga acaagattaa ggcctggcag aaaattttca aacactatgacacagaccag
2521 tccggcacca tcaacagcta cgagatgcga aatgcagtca acgacgcagg attccacctc
2581 aacaaccagc tctatgacat cattaccatg cggtacgcag acaaacacat gaacatcgac
2641 tttgacagtt tcatctgctg cttcgttagg ctggagggca tgttcagagc ttttcatgca
2701 tttgacaagg atggagatgg tatcatcaag ctcaacgttc tggagtggct gcagctcacc
2761 atgtatgcct gaaccaggct ggcctcatcc aaagccatgc aggatcactc aggatttcag
2821 tttcaccctc tatttccaaa gccatttacc tcaaaggacc cagcagctac acccctacag
2881 gcttccaggc acctcatcag tcatgctcct cctccatttt accccctacc catccttgat
2941 cggtcatgcc tagcctgacc ctttagtaaa gcaatgaggt aggaagaaca aacccttgtc
3001 cctttgccat gtggaggaaa gtgcctgcct ctggtccgag ccgcctcggt tctgaagcga
3061 gtgctcctgc ttaccttgct ctaggctgtc tgcagaagca cctgccggtg gcactcagca
3121 cctccttgtg ctagagccct ccatcacctt cacgctgtcc caccatgggc caggaaccaa
3181 accagcactg ggttctactg ctgtggggta aactaactca gtggaatagg gctggttact
3241 ttgggctgtc caactcataa gtttggctgc attttgaaaa aagctgatct aaataaaggc
3301 atgtgtatgg ctggtc
```

One example of a nucleic acid sequence for human CDH16 is available as NCBI accession number NM_004062 (gi: 16507958). This sequence is recited below for easy reference as SEQ ID NO:123.

```
  1 gaaggagctc tcttcttgct tggcagctgg accaagggag ccagtcttgg gcgctggagg
 61 gcctgtcctg accatggtcc ctgcctggct gtggctgctt tgtgtctccg tcccccaggc
121 tctccccaag gcccagcctg cagagctgtc tgtggaagtt ccagaaaact atggtggaaa
181 tttcccttta tacctgacca agttgccgct gccccgtgag gggggctgaag gccagatcgt
241 gctgtcaggg gactcaggca aggcaactga gggcccattt gctatggatc cagattctgg
301 cttcctgctg gtgaccaggg ccctggaccg agaggagcag gcagagtacc agctacaggt
361 caccctggag atgcaggatg gacatgtctt gtggggtcca cagcctgtgc ttgtgcacgt
421 gaaggatgag aatgaccagg tgccccattt ctctcaagcc atctacagag ctcggctgag
481 ccggggtacc aggcctggca tcccccttcct cttccttgag gcttcagacc gggatgagcc
541 aggcacagcc aactcggatc ttcgattcca catcctgagc caggctccag cccagccttc
601 cccagacatg ttccagctgg agcctcggct gggggctctg gccctcagcc ccaaggggag
661 caccagcctt gaccacgccc tggagaggac ctaccagctg ttggtacagg tcaaggacat
721 gggtgaccag gcctcaggcc accaggccac tgccaccgtg gaagtctcca tcatagagag
781 cacctgggtg tccctagagc ctatccacct ggcagagaat ctcaaagtcc tataccccgca
```

-continued

```
 841 ccacatggcc caggtacact ggagtggggg tgatgtgcac tatcacctgg agagccatcc
 901 cccgggaccc tttgaagtga atgcagaggg aaacctctac gtgaccagag agctggacag
 961 agaagcccag gctgagtacc tgctccaggt gcgggctcag aattcccatg gcgaggacta
1021 tgcggcccct ctggagctgc acgtgctggt gatggatgag aatgacaacg tgcctatctg
1081 ccctccccgt gaccccacag tcagcatccc tgagctcagt ccaccaggta ctgaagtgac
1141 tagactgtca gcagaggatg cagatgcccc cggctccccc aattcccacg ttgtgtatca
1201 gctcctgagc cctgagcctg aggatggggt agaggggaga gccttccagg tggaccccac
1261 ttcaggcagt gtgacgctgg gggtgctccc actccgagca ggccagaaca tcctgcttct
1321 ggtgctggcc atggacctgg caggcgcaga gggtggcttc agcagcacgt gtgaagtcga
1381 agtcgcagtc acagatatca atgatcacgc ccctgagttc atcacttccc agattgggcc
1441 tataagcctc cctgaggatg tggagcccgg gactctggtg gccatgctaa cagccattga
1501 tgctgacctc gagcccgcct tccgcctcat ggattttgcc attgagaggg gagacacaga
1561 agggactttt ggcctggatt gggagccaga ctctgggcat gttagactca gactctgcaa
1621 gaacctcagt tatgaggcag ctccaagtca tgaggtggtg gtggtggtgc agagtgtggc
1681 gaagctggtg gggccaggcc caggccctgg agccaccgcc acggtgactg tgctagtgga
1741 gagagtgatg ccaccccccca agttggacca ggagagctac gaggccagtg tccccatcag
1801 tgccccagcc ggctctttcc tgctgaccat ccagccctcc gaccccatca gccgaaccct
1861 caggttctcc ctagtcaatg actcagaggg ctggctctgc attgagaaat tctccgggga
1921 ggtgcacacc gcccagtccc tgcagggcgc ccagcctggg gacacctaca cggtgcttgt
1981 ggaggcccag gatacagatg agccgagact gagcgcttct gcacccctgg tgatccactt
2041 cctaaaggcc cctcctgccc cagccctgac tcttgcccct gtgccctccc aatacctctg
2101 cacaccccgc caagaccatg gcttgatcgt gagtggaccc agcaaggacc ccgatctggc
2161 cagtgggcac ggtccctaca gcttcaccct tggtcccaac cccacggtgc aacgggattg
2221 gcgcctccag actctcaatg gttcccatgc ctacctcacc ttggccctgc attgggtgga
2281 gccacgtgaa cacataatcc ccgtggtggt cagccacaat gcccagatgt ggcagctcct
2341 ggttcgagtg atcgtgtgtc gctgcaacgt ggaggggcag tgcatgagca aggtgggccg
2401 catgaagggc atgcccacga agctgtcggc agtgggcatc cttgtaggca ccctggtagc
2461 aataggaatc ttcctcatcc tcattttcac ccactggacc atgtcaagga agaaggaccc
2521 ggatcaacca gcagacagcg tgccccctgaa ggcgactgtc tgaatggccc aggcagctct
2581 agctgggagc ttggcctctg gctccatctg agtcccctgg gagagagccc agcacccaag
2641 atccagcagg ggacaggaca gagtagaagc ccctccatct gccctggggt ggaggcacca
2701 tcaccatcac caggcatgtc tgcagagcct ggacaccaac tttatggact gcccatggga
2761 gtgctccaaa tgtcagggtg tttgcccaat aataaagccc cagagaactg ggctgggccc
2821 tatgggattg gta
```

One example of a nucleic acid sequence for human ChGn is available as NCBI accession number BC060772 (gi: 38174239). This sequence is recited below for easy reference as SEQ ID NO: 124.

```
  1 tggggcttgt tccgggatcc gcagccttgc tcaggctgtg cattggtgtg gccccgaatt
 61 gcacggagct gccttcctat ttcaaggaaa gacgccaagg taattttgac ccagaggagc
```

-continued

```
121 aatgatgtag ccacctccta accttccctt cttgaacccc caggtcccct cttgctgttg
181 gctgcacatc aggaaggctg tgatgggaat gaaggtgaaa acttggagat ttcacttcag
241 tcattgcttc tgcctgcaag atcatccttt aaaagtagag aagctgctct gtgtggtggt
301 taactccaag aggcagaact cgttctagaa ggaaatggat gcaagcagct ccgggggccc
361 caaacgcatg cttcctgtga tctagcccag ggaagccctt ccgtgggggc cccggctttg
421 agggatgcca ccggttctgg acgcatggct gattcctgaa tgatgatggt tcgccggggg
481 ctgcttgcgt ggatttcccg ggtggtggtt ttgctggtgc tcctctgctg tgctatctct
541 gtcctgtaca tgttggcctg caccccaaaa ggtgacgagg agcagctggc actgcccagg
601 gccaacagcc ccacggggaa ggaggggtac caggccgtcc ttcaggagtg ggaggagcag
661 caccgcaact acgtgagcag cctgaagcgg cagatcgcac agctcaagga ggagctgcag
721 gagaggagtg agcagctcag gaatgggcag taccaagcca gcgatgctgc tggcctgggt
781 ctggacagga gcccccccaga gaaaacccag gccgacctcc tggccttcct gcactcgcag
841 gtggacaagg cagaggtgaa tgctggcgtc aagctggcca cagagtatgc agcagtgcct
901 ttcgatagct ttactctaca gaaggtgtac cagctggaga ctggccttac ccgccacccc
961 gaggagaagc ctgtgaggaa ggacaagcgg gatgagttgg tggaagccat tgaatcagcc
1021 ttggagaccc tgaacaatcc tgcagagaac agccccaatc accgtcctta cacggcctct
1081 gatttcatag aagggatcta ccgaacagaa agggacaaag ggacattgta tgagctcacc
1141 ttcaaagggg accacaaaca tgaattcaaa cggctcatct tatttcgacc attcggcccc
1201 atcatgaaag tggaaaatga aaagctcaac atggccaaca cgcttatcaa tgttatcgtg
1261 cctctagcaa aaagggtgga caagttccgg cagttcatgc agaatttcag gcctgctgat
1321 gaagtttttta gatgtgtgcc tttaagccct tgattgtgcg gtgttggatc ttagaagctg
1381 tgatggctca gatgcacata ttggctgagg ataaccagct aagtgatttc accagcttgt
1441 tttaaacata gaaaatccta ctgtctaatt ataaatcttg aaagatcaag ctgatttttt
1501 atttcttttt ttttgagatg gagtcttact ctgtcaccca ggctggagtg cagtggcacg
1561 aactctgctc actgcaacct tcacctccca ggttcaggga gatgtgcatt gagcaggatg
1621 ggagagtcca tctcactgtt gtttactttg ggaaagaaga aataaatgaa gtcaaaggaa
1681 tacttgaaaa cacttccaaa gctgccaact tcaggaactt taccttcatc cagctgaatg
1741 gagaattttc tcggggaaag ggacttgatg ttggagcccg cttctggaag ggaagcaacg
1801 tccttctctt tttctgtgat gtggacatct acttcacatc tgaattcctc aatacgtgta
1861 ggctgaatac acagccaggg aagaaggtat tttatccagt tcttttcagt cagtacaatc
1921 ctggcataat atacggccac catgatgcag tccctccctt ggaacagcag ctggtcataa
1981 agaaggaaac tggattttgg agagactttg gatttgggat gacgtgtcag tatcggtcag
2041 acttcatcaa tataggtggg tttgatctgg acatcaaagg ctggggcgga gaggatgtgc
2101 acctttatcg caagtatctc cacagcaacc tcatagtggt acggacgcct gtgcgaggac
2161 tcttccacct ctggcatgag aagcgctgca tggacgagct gacccccgag cagtacaaga
2221 tgtgcatgca gtccaaggcc atgaacgagg catcccacgg ccagctgggc atgctggtgt
2281 tcaggcacga gatagaggct caccttcgca aacagaaaca gaagacaagt agcaaaaaaa
2341 catgaactcc cagagaagga ttgtgggaga cacttttttct ttccttttgc aattactgaa
2401 agtggctgca acagagaaaa gacttccata aaggacgaca aaagaattgg actgatgggt
2461 cagagatgag aaagcctccg atttctctct gttgggcttt ttacaacaga aatcaaaatc
2521 tccgctttgc ctgcaaaagt aacccagttg caccctgtga agtgtctgac aaaggcagaa
```

-continued 2581 tgcttgtgag attataagcc taatggtgtg gaggttttga tggtgtttac aatacactga
2641 gacctgttgt tttgtgtgct cattgaaata ttcatgattt aagagcagtt ttgtaaaaaa
2701 ttcattagca tgaaaggcaa gcatatttct cctcatatga atgagcctat cagcagggct
2761 ctagtttcta ggaatgctaa aatatcagaa ggcaggagag gagataggct tattatgata
2821 ctagtgagta cattaagtaa aataaaatgg accagaaaag aaaagaaacc ataaatatcg
2881 tgtcatattt tccccaagat taaccaaaaa taatctgctt atctttttgg ttgtcctttt
2941 aactgtctcc gtttttttct tttatttaaa aatgcacttt ttttcccttg tgagttatag
3001 tctgcttatt taattaccac tttgcaagcc ttacaagaga gcacaagttg gcctacattt
3061 ttatattttt taagaagata ctttgagatg cattatgaga actttcagtt caaagcatca
3121 aattgatgcc atatccaagg acatgccaaa tgctgattct gtcaggcact gaatgtcagg
3181 cattgagaca tagggaagga atggtttgta ctaatacaga cgtacagata ctttctctga
3241 agagtatttt cgaagaggag caactgaaca ctggaggaaa agaaaatgac actttctgct
3301 ttacagaaaa ggaaactcat tcagactggt gatatcgtga tgtacctaaa agtcagaaac
3361 cacattttct cctcagaagt agggaccgct ttcttacctg tttaaataaa ccaaagtata
3421 ccgtgtgaac caaacaatct cttttcaaaa cagggtgctc ctcctggctt ctggcttcca
3481 taagaagaaa tggagaaaaa tatatatata tatatatata ttgtgaaaga tcaatccatc
3541 tgccagaatc tagtgggatg gaagtttttg ctacatgtta tccaccccag gccaggtgga
3601 agtaactgaa ttattttta aattaagcag ttctactcga tcaccaagat gcttctgaaa
3661 attgcatttt attaccattt caaactattt tttaaaaata aatacagtta acatagagtg
3721 gtttcttcat tcatgtgaaa attattagcc agcaccagat gcatgagcta attatctctt
3781 tgagtccttg cttctgtttg ctcacagtaa actcattgtt taaaagcttc aagaacattc
3841 aagctgttgg tgtgttaaaa aatgcattgt attgatttgt actggtagtt tatgaaattt
3901 aattaaaaca caggccatga atggaaggtg gtattgcaca gctaataaaa tatgatttg
3961 ggatatgaaa aaaaaaaaaa aa One example of a nucleic acid sequence for human CITED1 is available as NCBI accession number NM_004143 (gi: 222136685). This sequence is recited below for easy reference as SEQ ID NO: 125.

1 acgagccagg acatgtgcta ataatgccct aagccggtta taaagacgtg gaaattgagg
61 ggagaaaaaa aaagggaaaa aaagggtctg tccttcctgg gattcctagc cgaggccagt
121 ctgctgccgt gtgcgtgtgc gtcagggctc tccgggcggc aatgggggct tgagagccgg
181 gtccccagcg ccgggaaggg agcgcggtgg ccgccaccgc caccgccccg gagtccggcg
241 ccgaagctgc gggagggcgg gcgggcacca gctcggtcag gggctgcttg gcgcggcact
301 gtgcggtgca gcggcggcgc ggcgcggtgc gggcttttcc caggcgcccc ggggtcgggt
361 ggccaacggc gcggccgcgg gcgctgagcg cgaccggttc gcggtagcgg tggcggcggc
421 gtgcgtgcca ggggctgggg gctccgccgc ctctcttgcg gctcaccgag ctccgcgctt
481 ccctctctcc agggcaggcg gcttctcaga gcacaacagc tccagctggc agcatcactt
541 cccgccaatt tatccaactt ctgccaaggc tctgaaatgc caacaacgtc gaggcctgca
601 cttgatgtca agggtggcac ctcacctgcg aaggaggatg ccaaccaaga gatgagctcc
661 gtggcctact ccaaccttgc ggtgaaagat cgcaaagcag tggccattct gcactaccct -continued 721 ggggtagcct caaatggaac caaggccagt ggggctccca ctagttcctc gggatctcca 781 ataggctctc ctacaaccac ccctcccact aaaccccat ccttcaacct gcaccccgcc 841 cctcacttgc tggctagtat gcacctgcag aaacttaata gccagtatca ggggatggct 901 gctgccactc caggccaacc cggggaggca ggacccctgc aaaactggga ctttggggcc 961 caggcgggag gggcagaatc actctctcct tctgctggtg cccagagccc tgctatcatc 1021 gattcggacc cagtggatga ggaagtgctg atgtcgctgg tggtggaact ggggttggac 1081 cgagccaatg agcttccgga gctgtggctg gggcagaatg agtttgactt cactgcggac 1141 tttccatcta gctgctaatg ccaagtgtcc ctaaagatgg aggaataaag ccaccaattc 1201 tgttgtaaat aaaaataaag ttacttacaa agagacgggc caaaaaaaaa a One example of a nucleic acid sequence for human CITED2 is available as NCBI accession number NM_006079 (gi: 51807294). This sequence is recited below for easy reference as SEQ ID NO: 126.

1 acagctcatt gttggcagct gccgggcggt cctgccgagc tgtgagggca acggaggga 61 aataaaaggg aacggctccg aatctgcccc agcggccgct gcgagacctc ggcgccgaca 121 tcgcgacagc gaagcgcttt gcacgccagg aaggtcccct ctatgtgctg ctgagccggt 181 cctggacgcg acgagcccgc cctcggtctt cggagcagaa atcgcaaaaa cggaaggact 241 ggaaatggca gaccatatga tggccatgaa ccacgggcgc ttccccgacg gcaccaatgg 301 gctgcaccat caccctgccc accgcatggg catggggcag ttcccgagcc cccatcacca 361 ccagcagcag cagccccagc acgccttcaa cgccctaatg ggcgagcaca tacactacgg 421 cgcgggcaac atgaatgcca cgagcggcat caggcatgcg atggggccgg ggactgtgaa 481 cggagggcac cccccgagcg cgctggcccc cgcggccagg tttaacaact cccagttcat 541 gggtcccccg gtggccagcc agggaggctc cctgccggcc agcatgcagc tgcagaagct 601 caacaaccag tatttcaacc atcacccccta cccccacaac cactacatgc cggatttgca 661 ccctgctgca ggccaccaga tgaacgggac aaaccagcac ttccgagatt gcaaccccaa 721 gcacagcggc ggcagcagca cccccggcgg ctcgggcggc agcagcaccc ccggcggctc 781 tggcagcagc tcgggcggcg gcgcgggcag cagcaacagc ggcggcggca gcggcagcgg 841 caacatgccc gcctccgtgg cccacgtccc cgctgcaatg ctgccgccca atgtcataga 901 cactgatttc atcgacgagg aagttcttat gtccttggtg atagaaatgg gtttggaccg 961 catcaaggag ctgcccgaac tctggctggg gcaaaacgag tttgatttta tgacggactt 1021 cgtgtgcaaa cagcagccca gcagagtgag ctgttgactc gatcgaaacc ccggcgaaag 1081 aaatcaaacc cccaacttct tcggcgtgaa ttaaaagaaa cattccctta gacacagtat 1141 ctcacttttc agatcttgaa aggtttgaga acttggaaac aaagtaaact ataaacttgt 1201 acaaattggt tttaaaaaaa attgctgcca cttttttttc ctgtttttgt ttcgtttttg 1261 tagccttgac attcacccac ctcccttatg tagttgaaat atctagctaa cttggtcttt 1321 ttcgttgttt gtttttactc ctttccctca ctttctccag tgctcaactg ttagatatta 1381 atcttggcaa actgcttaat cttgtggatt ttgtagatgg tttcaaatga ctgaactgca 1441 ttcagattta cgagtgaaag gaaaaattgc attagttggt tgcatgaact tcgaagggca 1501 gatattactg cacaaactgc catctcgctt catttttttta actatgcatt tgagtacaga 1561 ctaattttta aaatatgcta aactggaaga ttaaacagat gtgggccaaa ctgttctgga 1621 tcaggaaagt catactgttc actttcaagt tggctgtccc ccccgccgcc ccccccaccc -continued 1681 ccatatgtac agatgataat agggtgtgga atgtcgtcag tggcaaacat ttcacagatt 1741 tttattttgt ttctgtcttc aacatttttg acactgtgct aatagttata ttcagtacat 1801 gaaaagatac tactgtgttg aaagcttttt aggaaatttt gacagtattt ttgtacaaaa 1861 catttttttg aaaaaatact tgttaattta ttctatttta atttgccaat gtcaataaaa 1921 agttaagaaa One example of a nucleic acid sequence for human CKB is available as NCBI accession number M16451 (gi: 180571). This sequence is recited below for easy reference as SEQ ID NO: 127.

1 ccggccgccc gcccgccgcc gccatgccct tctccaacag ccacaacgca ctgaagctgc 61 gcttcccggc cgaggacgag ttccccgacc tgagcgccca caacaaccac atggccaagg 121 tgctgacccc cgagctgtac gcggacgtgc gcgccaagag cacgccgagc ggcttcacgc 181 tggacgacgt catccagaca ggcgtggaca acccgggcca cccgtacatc atgaccgtgg 241 gctgcgtggc gggcgacgag gagtcctacg aagtgttcaa ggatctcttc gaccccatca 301 tcgaggaccg gcaccggcgc tacaagccca gcgatgacga caagaccgac ctcaaccccg 361 acaacctgca gggcggcgac gacctggacc ccaactacgt gctgagctcg cgggtggcca 421 cgggccgcag catccgtggc ttctgcctcc ccccgcactg cagccgcggg gagcgccgag 481 ccatcgagaa gctcgcggtg gaagccctgt ccagcctgga cggcgacctg gcgggccgat 541 actacgcgct caagagcatg acggaggcgg agcagcagca gctcatcgac gaccacttcc 601 tcttcgacaa gcccgtgtcg cccctgctgc tggcctcggg catggcccgc gactggcccg 661 acgccgcgcg tatctggcac aatgacaata agaccttcct ggtgtgggtc aacgaggagg 721 accacctgcg ggtcatctcc atgcagaagg ggggcaacat gaaggaggtg ttcacccgct 781 tctgcaccgg cctcacccag attgaaactc tcttcaagtc taaggactat gagttcatgt 841 ggaaccctca cctgggctac atcctcacct gcccatccaa cctgggcacc gggctgcggg 901 caggtgtcga tatcaagctg cccaacctgg gcaagcatga gaagttctcg gaggtgctta 961 agcggctgcg acttcagaag cgaggcacag gcggtgtgga cacggctgcg gtgggcgggg 1021 tcttcgacgt ctccaacgct gaccgcctgg gcttctcaga ggtggagctg gtgcagatgg 1081 tggtggacgg agtgaagctg ctcatcgaga tggaacagcg gctggagcag ggccaggcca 1141 tcgacgacct catgcctgcc cagaaatgaa gcccggccca cacccgacac cagccctgct 1201 gcttcctaac ttattgcctg cagtgcccac catgcacccc tcgatgttgc cgtctggcga 1261 gcccttagcc ttgctgtaag gaaggcttcc gtcacccttg gtagagttta tttttttgat 1321 ggctaagata ctgctgatgc tgaaataaac tagggttttg gcctgcaaaa aa One example of a nucleic acid sequence for human COL9A3 is available as NCBI accession number NM_001853 (gi: 119508425). This sequence is recited below for easy reference as SEQ ID NO: 128.

1 gccatggccg ggccgcgcgc gtgcgccccg ctcctgctcc tgctcctgct cggggagctt 61 ctggcggccg ccggggcgca gagagtggga ctcccccggcc cccccggccc cccagggccg 121 cccgggaagc ccggccagga cggcattgac ggagaagctg gtcctccagg tctgcctggg 181 cccccgggac caaagggggc cccaggaaag ccggggaaac caggagaggc tgggctgccg -continued

```
241 ggactgccgg gtgtggatgg tctgactgga cgagatggac cccctggacc caagggtgcc
301 cctggggaac ggggaagtct gggacccccg gggccgcccg ggctgggggg caaaggcctc
361 cctggacccc ccggagaggc aggagtgagc ggcccccag gtgggatcgg cctccgcggc
421 cccccgggac cttctggact ccccggcctc cctggtcccc caggacctcc cggacccccct
481 ggacacccag gagtcctccc tgaaggcgct actgaccttc agtgcccaag tatctgcccg
541 ccaggtcccc cagggccccc tggaatgcca gggttcaagg gacccactgg ctacaaaggc
601 gagcaggggg aagtcggcaa ggacggcgag aagggtgacc ctggcccccc tgggcccgcc
661 ggcctcccgg gcagcgtggg gctgcagggc ccccggggat tacgaggact gccagggcca
721 ctcgggcccc ctggggaccg gggtcccatt gggttccgag ggccgcctgg gatcccagga
781 gcgcctggga aagcgggtga ccgaggcgag aggggcccag aagggttccg cggccccaag
841 ggtgacctcg gcagacctgg tcccaaggga acccccggag tggccgggcc aagcggagag
901 ccgggcatgc cgggcaagga cggccagaat ggcgtgccag gactcgatgg ccagaaggga
961 gaggctggtc gcaacggtgc tccgggagag aagggcccca acgggctgcc gggcctccct
1021 ggacgagcgg ggtccaaagg cgagaaggga gaacggggca gagctgggga gctgggtgag
1081 gccggcccct ctggagagcc aggcgtccct ggagatgctg gcatgcctgg ggagcgcggt
1141 gaggctggcc accggggctc agcgggggcc ctcggcccac aaggccctcc cggagcccct
1201 ggtgtccgag gcttccaggg ccagaagggc agcatgggag accccggcct tccaggcccc
1261 cagggcctcc gaggtgacgt gggcgaccgg ggtccgggag gtgccgcagg ccctaaggga
1321 gaccagggta ttgcaggttc cgacggtctt cctggggata aaggagaact gggtcccagc
1381 ggcctggtcg gacccaaagg agagtctggc agtcgagggg agctgggccc caaaggcacc
1441 cagggtccca acggcaccag cggtgttcag ggtgtccccg ggcccccccgg tcctctgggc
1501 ctgcagggcg tcccgggtgt tcctggcatc acggggaagc cgggagttcc ggggaaggag
1561 gccagcgagc agcgcatcag ggagctgtgt ggggggatga tcagcgaaca aattgcacag
1621 ttagccgcgc acctaaggaa gcctttggca cccgggtcca ttggtcggcc cggtccagct
1681 ggcccccctg ggcccccagg acccccaggc tccattggtc accctggcgc tcgaggaccc
1741 cctggatacc gcggtcccac tggggagctg ggagaccccg ggcccagagg aaaccagggt
1801 gacagaggag acaaaggcgc ggcaggagca gggctggacg ggcctgaagg agaccagggg
1861 ccccaaggac cccaaggcgt gcccggcacc agcaaggacg gccaggacgg tgctcccggc
1921 gagcctgggc ctcccggaga tcctgggctt ccaggtgcca ttggggccca ggggacaccg
1981 gggatctgcg acacctcagc ctgccaagga gccgtgttag gaggggtcgg ggagaaatca
2041 ggctctcgaa gctcataaaa ttcaacgtga ggaagcaagt gacaaggacg cccgaagcac
2101 agtggacggt catgaaggag cgggggtgtg gcaggcgggt gacgtccagg agagggagcg
2161 cccctggctg cccctcggcc gccgactgga cgcgcgggcc ttgccagcga gcaccctcat
2221 cgggctgtcg cctgacagca tacctcaaaa ggccctagct aataaacctg taagcccagc
2281 atttgagaga aggtagggtg tgtatatata aaaggttgtg tacaactcca cgaggtgaaa
2341 aatattcagt aacttgttta catagcattt gtgtaaagac tatgatctca tcccaataaa
2401 atgatatatt aaaccttcag attaatgact ggctacagag taacaaaaaa taaagaattt
2461 aatgtacagt aaattctctc ccata
```

One example of a nucleic acid sequence for human CSRP2 is available as NCBI accession number NM_001321 (gi: 4503100). This sequence is recited below for easy reference as SEQ ID NO:129.

```
  1 gggatctcgg actccctgga ccctccctcc agcccagcct cgctagctcc gcctgcggta
 61 cgtgctcccg cctccgactc aaaatgcctg tctggggagg tggaaacaag tgtggggcct
121 gtgggaggac cgtgtaccac gcagaagagg tgcagtgtga tggcaggagc ttccaccgct
181 gctgctttct ctgcatggtt tgcaggaaaa atttagatag cacaacagtg gcaattcacg
241 atgaagagat ctactgcaaa tcctgctacg gaaagaagta tgggccaaaa ggctacggtt
301 atggccaggg cgctggcacg cttaacatgg accgtggcga gaggctgggc atcaaaccag
361 agagtgttca gcctcacagg cctacaacaa atccaaacac ttctaaattt gctcagaaat
421 atggaggtgc tgagaagtgt tccagatgtg gggattctgt atatgctgcc gagaagataa
481 ttggagctgg aaagccctgg cacaaaaact gtttccgatg tgcaaagtgt gggaagagtc
541 ttgaatcaac aactctgact gaaaaagaag gtgaaatcta ttgtaaagga tgctatgcaa
601 agaactttgg gcccaaggga tttggctatg gccaaggagc aggggctctt gttcatgccc
661 agtaagatgt aaaccctgaa ctaaacatca cacactgaga atctcttcat aatctaggca
721 cagataatct ttaacactaa actactgtga aattctacca gcattaagta ctgtatatcg
781 ccctgtactt ggataggctg gctaactcgt aggaagagag cactgtatgg tatccttttg
841 ctttattcac cagcattttg gggaacatt tcttttacat tttaaataaa acttcagctt
901 g
```

One example of a nucleic acid sequence for human DAPK2 is available as NCBI accession number NM_0014326 (gi: 71774012). This sequence is recited below for easy reference as SEQ ID NO: 130.

```
   1 gaccgcggca gctcagcctc ccgccgattg tatgttccag gcctcaatga ggagtccaaa
  61 catggagcca ttcaagcagc agaaggtgga ggacttttat gacatcggag aggagctggg
 121 gagtggccag tttgccatcg tgaagaagtg ccgggagaag agcacggggc ttgagtatgc
 181 agccaagttc atcaagaagc ggcagagccg ggcgagccgg cgcggtgtga gccgggagga
 241 gatcgagcgg gaggtgagca tcctgcggca ggtgctgcac cacaatgtca tcacgctgca
 301 cgacgtctat gagaaccgca ccgacgtggt gctcatcctt gagctagtgt ctggaggaga
 361 gctcttcgat ttcctggccc agaaggagtc actgagtgag gaggaggcca ccagcttcat
 421 taagcagatc ctggatgggg tgaactacct tcacacaaag aaaattgctc actttgatct
 481 caagccagaa aacattatgt tgttagacaa gaatattccc attccacaca tcaagctgat
 541 tgactttggt ctggctcacg aaatagaaga tggagttgaa tttaagaata tttttgggac
 601 gccggaattt gttgctccag aaattgtgaa ctacgagccc ctgggtctgg aggctgacat
 661 gtggagcata ggcgtcatca cctacatcct cttaagtgga gcatcccctt tcctgggaga
 721 cacgaagcag gaaacactgg caaatatcac agcagtgagt tacgactttg atgaggaatt
 781 cttcagccag acgagcgagc tggccaagga ctttattcgg aagcttctgg ttaaagagac
 841 ccggaaacgg ctcacaatcc aagaggctct cagacacccc tggatcacgc cggtggacaa
 901 ccagcaagcc atggtgcgca gggagtctgt ggtcaatctg gagaacttca ggaagcagta
 961 tgtccgcagg cggtggaagc tttccttcag catcgtgtcc ctgtgcaacc acctcacccg
1021 ctcgctgatg aagaaggtgc acctgaggcc ggatgaggac ctgaggaact gtgagagtga
```

-continued

```
1081 cactgaggag gacatcgcca ggaggaaagc cctccaccca cggaggagga gcagcacctc
1141 ctaactggcc tgacctgcag tggccgccag ggaggtctgg gcccagcggg gctcccttct
1201 gtgcagactt ttggacccag ctcagcacca gcacccgggc gtcctgagca ctttgcaaga
1261 gagatgggcc caaggaattc agaagagctt gcaggcaagc caggagaccc tgggagctgt
1321 ggctgtcttc tgtggaggag gctccagcat tcccaaagct cttaattctc cataaaatgg
1381 gctttcctct gtctgccatc ctcagagtct ggggtgggag tgtggactta ggaaaacaat
1441 ataaaggaca tcctcatcat cacggggtga aggtcagact aaggcagcct tcttcacagg
1501 ctgagggggt tcagaaccag cctggccaaa aattacacca gagagacaga gtcctcccca
1561 ttgggaacag ggtgattgag gaaagtgaac cttgggtgtg agggaccaat cctgtgacct
1621 cccagaacca tggaagccag gacgtcaggc tgaccaacac ctcagacctt ctgaagcagc
1681 ccattgctgg cccgccatgt tgtaattttg ctcattttta ttaaacttct ggtttacctg
1741 atgcttggct tcttttaggg ctacccccat ctcatttcct ttagcccgtg tgcctgtaac
1801 tctgaggggg ggcacccagt ggggtgctga gtgggcagaa tctcagaagg tcctcctgaa
1861 ccgtccgcgc aggcctgcag tgggcctgcc tcctccttgc ttccctaaca ggaaggtgtc
1921 cagttcaaga gaacccaccc agagactggg agtggtggct cacgcctata atccctgcgc
1981 tttggcagtc cgaggcaggg gaattgcttg aactcaggag ttggagacca gcctgggcaa
2041 catggcaaaa cgcagtctgt acaaaaaata caaaaaatta gccaggtgta ggggtaggca
2101 cctggcatcc cagctactcc aggggctgag gtgacagcat tgcttaagcc cagaaggtcg
2161 aggctgcagt gagctgagat cacgccactg cactccagtc tgggtgacag agagagacca
2221 tatccaaaaa aaaaaaaagt tgccagagac gagtatgccc atgctccctc tacctcactg
2281 ccaccactcc tgctgttagg agctgagtgt gtctccctaa aatttctatg ttgaagtctt
2341 aacccttggt accacagaat atcactgtat ttggagatgg ggtctttaga aaggcactta
2401 aattaaaatg agctcactga tatgggcccc gatgcaatat aattggtgtc cttataagaa
2461 ggggaggtta ggacacgcag gaaagaccac atgaaggccc aggagtggga gggggaatag
2521 ccatcgacaa actaaggggg cctcagagga aaccaaccct gctgacacct caatcttaga
2581 ctctggcctc aaaaattgta agaaaataaa cttctgtctt ttaagcca
```

One example of a nucleic acid sequence for human DIO1 is available as NCBI accession number NM_00972 (gi: 89357933). This sequence is recited below for easy reference as SEQ ID NO: 131.

```
1 gagcttactc tggctttgcc gagatggggc tgccccagcc agggctgtgg ctgaagaggc
61 tctgggtgct cttggaggtg gctgtgcatg tggtcgtggg taaagtgctt ctgatattgt
121 ttccagacag agtcaagcgg aacatcctgg ccatgggcga gaagacgggt atgaccagga
181 acccccattt cagccacgac aactggatac caaccttttt cagcacccag tatttctggt
241 tcgtcttgaa ggtccgttgg cagcgactag aggacacgac tgagctaggg ggtctggccc
301 caaactgccc ggtggtccgc ctctcaggac agaggtgcaa catttgggag tttatgcaag
361 gtaataggcc actggtgctg aattttggaa gttgtacctg accttcattt atgttcaaat
421 ttgaccagtt caagaggctt attgaagact ttagttccat agcagatttt cttgtcattt
481 acattgaaga agcacatgca tcagatggct gggcttttaa gaacaacatg gacatcagaa
541 atcaccagaa ccttcaggat cgcctgcagg cagcccatct actgctggcc aggagccccc
601 agtgccctgt ggtggtggac accatgcaga accagagcag ccagctctac gcagcactgc
```

-continued

```
 661 ctgagaggct ctacataatc caggagggca ggatcctcta caagggtaaa tctggccctt
 721 ggaactacaa cccagaggaa gttcgtgctg ttctggaaaa gctccacagt taatctggac
 781 agatacctca attctaggtg accaacggga gggcttctca aggcttagct ctccctgaga
 841 cccagctggc ttttaccctt gacctgtgtc cctagctgaa tcactagctc agatttttct
 901 gatctaagca aacaactccc agctgaggaa tgcaggccac agcacccaat caagacaaat
 961 tgttattatc agaaaatgaa gcaacacttg agctgttcag gccagttccc tgttgaagaa
1021 acagttccct gttgaagaaa gtagagcctg acactgctcc cactttggag accacattcc
1081 ctgcacacgg tctttgagag agcagttgca ctctacaggc acacttctga ggtacggtat
1141 ctctctccag ccactctgat accaagtaat tcaagctggc attccttcta ttagggaaat
1201 tcattttacc caatttgcat ttatggaatt gatcatttaa gacactaaat tagtttttag
1261 aaccaattat gggaagaatt ccagttgtta ggaagagatg aggagttgga agaggaggga
1321 ttagaaacag gaggaggcag tcatcctctc cttgccaaaa gatttaaacc tgtccacatt
1381 ggtggtgatg atgggtgagt ttccatggta acacatccct aattttacca gggaagagga
1441 gagtactcac tttaccatct ttgaatatat ttcatagaaa tctagctctc tgtaccctga
1501 aatcttccac tagcctcact tttcaacaga gtcatctaga agggagggtt ggcttcccaa
1561 aagcataacc ttgaccaaac caaacaatag gcaccagcaa tgctgtcatt cagttatgca
1621 gaagctcatt tgtgaaattc tgtttctctg atttcttcgc aagtctctta atggtcattt
1681 gtgttagatt acatcaaact gatggatagc cattggtatt catctatttt aactctgtgt
1741 ctttacatat ttgtttatga tggccacagc ctaaagtaca cacggctgtg acttgattca
1801 aaagaaaatg ttataagatg cagtaaacta ataacagaat tattaaaata tatcaggcta
1861 aaaaaaaaaa aaaaaa
```

One example of a nucleic acid sequence for human DPP4 is available as NCBI accession number NM_001935 (gi: 47078262). This sequence is recited below for easy reference as SEQ ID NO: 132.

```
  1 ctttcactgg caagagacgg agtcctgggt ttcagttcca gttgcctgcg gtgggctgtg
 61 tgagtttgcc aaagtcccct gccctctctg ggtctcggtt ccctcgcctg tccacgtgag
121 gttggaggag ctgaacgccg acgtcatttt tagctaagag ggagcagggt ccccgagtcg
181 ccggcccagg gtctgcgcat ccgaggccgc gcgccctttc ccctccccca cggctcctcc
241 gggccccgca ctctgcgccc cggctgccgc ccagcgccct acaccgccct caggggggccc
301 tcgcgggctc cccccggccg ggatgccagt gccccgcgcc acgcgcgcct gctcccgcgc
361 cgcctgccct gcagcctgcc cgcggcgcct ttatacccag cgggctcggc gctcactaat
421 gtttaactcg gggccgaaac ttgccagcgg cgagtgactc caccgcccgg agcagcggtg
481 caggacgcgc gtctccgccg cccgcggtga cttctgcctg cgctccttct ctgaacgctc
541 acttccgagg agacgccgac gatgaagaca ccgtggaagg ttcttctggg actgctgggt
601 gctgctgcgc ttgtcaccat catcaccgtg cccgtggttc tgctgaacaa aggcacagat
661 gatgctacag ctgacagtcg caaaacttac actctaactg attacttaaa aaatacttat
721 agactgaagt tatactcctt aagatggatt tcagatcatg aatatctcta caaacaagaa
781 aataatatct tggtattcaa tgctgaatat ggaaacagct cagttttctt ggagaacagt
841 acatttgatg agtttggaca ttctatcaat gattattcaa tatctcctga tgggcagttt
```

-continued

```
901 attctcttag aatacaacta cgtgaagcaa tggaggcatt cctacacagc ttcatatgac
961 atttatgatt taaataaaag gcagctgatt acagaagaga ggattccaaa caacacacag
1021 tgggtcacat ggtcaccagt gggtcataaa ttggcatatg tttggaacaa tgacatttat
1081 gttaaaattg aaccaaattt accaagttac agaatcacat ggacggggaa agaagatata
1141 atatataatg gaataactga ctgggtttat gaagaggaag tcttcagtgc ctactctgct
1201 ctgtggtggt ctccaaacgg cacttttttta gcatatgccc aatttaacga cacagaagtc
1261 ccacttattg aatactcctt ctactctgat gagtcactgc agtacccaaa gactgtacgg
1321 gttccatatc caaaggcagg agctgtgaat ccaactgtaa agttctttgt tgtaaataca
1381 gactctctca gctcagtcac caatgcaact tccatacaaa tcactgctcc tgcttctatg
1441 ttgatagggg atcactactt gtgtgatgtg acatgggcaa cacaagaaag aatttctttg
1501 cagtggctca ggaggattca gaactattcg gtcatggata tttgtgacta tgatgaatcc
1561 agtggaagat ggaactgctt agtggcacgg caacacattg aaatgagtac tactggctgg
1621 gttggaagat ttaggccttc agaacctcat tttacccttg atggtaatag cttctacaag
1681 atcatcagca atgaagaagg ttacagacac atttgctatt tccaaataga taaaaaagac
1741 tgcacattta ttacaaaagg cacctgggaa gtcatcggga tagaagctct aaccagtgat
1801 tatctatact acattagtaa tgaatataaa ggaatgccag gaggaaggaa tctttataaa
1861 atccaactta gtgactatac aaaagtgaca tgcctcagtt gtgagctgaa tccggaaagg
1921 tgtcagtact attctgtgtc attcagtaaa gaggcgaagt attatcagct gagatgttcc
1981 ggtcctggtc tgcccctcta tactctacac agcagcgtga atgataaagg gctgagagtc
2041 ctggaagaca attcagcttt ggataaaatg ctgcagaatg tccagatgcc ctccaaaaaa
2101 ctggacttca ttattttgaa tgaaacaaaa ttttggtatc agatgatctt gcctcctcat
2161 tttgataaat ccaagaaata tcctctacta ttagatgtgt atgcaggccc atgtagtcaa
2221 aaagcagaca ctgtcttcag actgaactgg gccacttacc ttgcaagcac agaaaacatt
2281 atagtagcta gctttgatgg cagaggaagt ggttaccaag gagataagat catgcatgca
2341 atcaacagaa gactgggaac atttgaagtt gaagatcaaa ttgaagcagc cagacaattt
2401 tcaaaaatgg gatttgtgga caacaaacga attgcaattt ggggctggtc atatggaggg
2461 tacgtaacct caatggtcct gggatcggga agtggcgtgt tcaagtgtgg aatagccgtg
2521 gcgcctgtat cccggtggga gtactatgac tcagtgtaca cagaacgtta catgggtctc
2581 ccaactccag aagacaacct tgaccattac agaaattcaa cagtcatgag cagagctgaa
2641 aattttaaac aagttgagta cctccttatt catggaacag cagatgataa cgttcacttt
2701 cagcagtcag ctcagatctc caaagccctg gtcgatgttg gagtggattt ccaggcaatg
2761 tggtatactg atgaagacca tggaatagct agcagcacag cacaccaaca tatatatacc
2821 cacatgagcc acttcataaa acaatgtttc tctttacctt agcacctcaa aataccatgc
2881 catttaaagc ttattaaaac tcatttttgt tttcattatc tcaaaactgc actgtcaaga
2941 tgatgatgat ctttaaaata cacactcaaa tcaagaaact taaggttacc tttgttccca
3001 aatttcatac ctatcatctt aagtagggac ttctgtcttc acaacagatt attaccttac
3061 agaagtttga attatccggt cgggttttat tgttttaaat catttctgca tcagctgctg
3121 aaacaacaaa taggaattgt ttttatggag gctttgcata gattccctga gcaggatttt
3181 aatctttttc taactggact ggttcaaatg ttgttctctt ctttaaaggg atggcaagat
3241 gtgggcagtg atgtcactag ggcagggaca ggataagagg gattagggag agaagatagc
3301 agggcatggc tgggaaccca agtccaagca taccaacacg agcaggctac tgtcagctcc
```

-continued

```
3361 cctcggagaa gagctgttca cagccagact ggcacagttt tctgagaaag actattcaaa
3421 cagtctcagg aaatcaaata tgcaaagcac tgacttctaa gtaaaaccac agcagttgaa
3481 aagactccaa agaaatgtaa gggaaactgc cagcaacgca ggcccccagg tgccagttat
3541 ggctataggt gctacaaaaa cacagcaagg gtgatgggaa agcattgtaa atgtgctttt
3601 aaaaaaaaat actgatgttc ctagtgaaag aggcagcttg aaactgagat gtgaacacat
3661 cagcttgccc tgttaaaaga tgaaaatatt tgtatcacaa atcttaactt gaaggagtcc
3721 ttgcatcaat ttttcttatt tcatttcttt gagtgtctta attaaaagaa tattttaact
3781 tccttggact cattttaaaa aatggaacat aaaatacaat gttatgtatt attattccca
3841 ttctacatac tatggaattt ctcccagtca tttaataaat gtgccttcat tttttcagaa
3901 aaaaaaaaaa aaa
```

One example of a nucleic acid sequence for human DTX4 is available as NCBI accession number NM_015177 (gi: 148237497). This sequence is recited below for easy reference as SEQ ID NO: 133.

```
   1 gagcagcggc agcagcagcg gaccccggcg gcggcggcgg cgcgcggtcc cagccaggcg
  61 gccccggtgt cccggccccg gtggatgcac ggctggggag gagcccatgg gccggagctg
 121 aggctgcccg gggcggcggg gcgcggggca gggggcgcgg tcgaggcccg gaggcggcgg
 181 cgcaggagga agcggaggag gtcgggcgct cggggcccgg gaggcgggcc gcgcagcgcc
 241 gcagccccgg gctcgccatg ctcctggcct cggccgtggt ggtctgggaa tggctgaacg
 301 agcacggccg ctggcgtccc tacagcccag cggtgagcca ccacatcgag gcggtggtcc
 361 gcgccggccc ccgcgcgggg ggcagcgtgg tgctgggcca ggtggacagc cgtctcgcgc
 421 cctacatcat cgacctgcag tccatgaacc agttccgcca agacacggga actctccgcc
 481 cagttcgccg caactactac gacccctcct cggcccctgg gaagggcgtg gtgtgggagt
 541 gggagaacga caatggctcc tggacgccct acgacatgga agtgggcatc accatccagc
 601 atgcctatga gaagcagcac ccctggatcg acctcacttc cattggcttt agctacgtaa
 661 ttgacttcaa caccatgggc cagatcaacc gtcagaccca gcgccaacgc cgcgtccgcc
 721 ggcgcctcga cctcatctac cccatggtca cagggacctt gcctaaggct cagtcctggc
 781 cagtcagccc tgggccagcc acctcgcccc ccatgtcccc ctgctcctgt ccccagtgtg
 841 tcttggtgat gagtgttaag gcagccgtgg tcaatggcag cactgggccc ctacagctgc
 901 cagtgacccg caagaacatg ccgcctcctg gagtggtcaa gctaccccca ctgccaggct
 961 ctggggccaa gccactggac agcacaggca ccattcgagg cccactgaag accgccccat
1021 cgcaggtgat ccggagacaa gcctccagca tgcccactgg gacaaccatg ggctctcctg
1081 ccagtccccc aggacccaac agcaagaccg gaagggtggc cctggccacc ttgaatcgta
1141 ccaacctgca gcgactggcc attgcccagt cccgggtgct gatcgcctct ggggtcccca
1201 cagtcccagt gaagaaccta aatgggtcca gtcctgtcaa ccctgccttg gcaggaatca
1261 ctgggatcct catgagtgca gcggggctgc ctgtgtgtct caccaggcca ccaaagctgg
1321 tcctacaccc acccccccgtc agcaagagtg aaataaaatc catcccaggg gtttccaaca
1381 caagccgcaa gaccaccaaa aaacaagcca agaaaggtaa aaccccagag gaagtgctaa
1441 aaaaatatct acagaaagtc cggcacccac cagatgagga ctgcaccatc tgtatggaac
1501 gcctcacggc cccctcaggc tacaagggcc cgcagcctac ggtaaaacct gacctggtag
```

-continued 1561 ggaagctgtc cagatgcggc cacgtctacc acatctactg cttggttgcc atgtacaaca
1621 atgggaacaa ggatggaagt ttgcagtgtc caacctgcaa gaccatttat ggggtgaaga
1681 caggcaccca acctccaggg aagatggagt accacctcat cccccactcc ttgcctggcc
1741 acccagactg caaaaccatc cggatcatct acagcatccc ccccggcatt cagggaccgg
1801 aacacccgaa tcctgggaag agtttcagcg cccgaggctt cccacgacac tgttaccttc
1861 cggacagcga gaaagggaga aaagttctga agctgctgct cgtggcctgg gatcgccgcc
1921 tcatttttgc cattggcacc tccagcacca caggcgagtc agacaccgtc atctggaatg
1981 aggtccacca caagacagag tttggctcta atctcactgg ccatggctac ccagatgcca
2041 attacctgga taatgtgctg gctgaactgg ctgcccaggg catctctgag gacagcactg
2101 cccaggagaa ggactgaggc cagaaaagct ttgaggtggg aggggccatg gagactgcag
2161 gacaggaagt gaggagagtg agtcaatgta gaagaagttg gtgtcctgcc ctcccaactt
2221 tctatcctcc cctcctgccc tgtgtccatc cctcatccct cccaaccaca gtgggagcca
2281 gactgaatat agcgacatca ttcataaatc tcatccaaca caaagggaga tgggatgagg
2341 gccatcctgg gtctgttccc atggagtttt tggtgctggg taggcaggaa tcccctccct
2401 accccacctc ccaagtaggg gcatggtcag cacacctagg gtatgggcag tgcttaggca
2461 ctccatatcc tggctttggg aagccggggt ttcttgcctc agccggcttc ttgctacttc
2521 cactctgctt tgagactgga gtttctgcta ttctccctct gctggaggca gggagctctc
2581 actgtgcaag gttggggggt gggcaaaggg gtgaatcact aaactgctgt gacatcagaa
2641 actgatgcct tggtgtagag caaggaagca cttcttccca agagggtcgg agaaggaaaa
2701 gcctctggga gcacattctg ctgtcatcac agtccttggc ttctctgggc cctcctctcc
2761 tcctcacagc tctcacctgt ccaaagaggc atctggttct ctcatgtgga tggatggact
2821 ctggggttcc tctttggagt ggcatcccat gatgctgttt ctagaccctc tctgatcaaa
2881 ccagagcctg catcccactg agcatctgaa ctgtcctcag ggagaggagc ccacagcctt
2941 cttcccaact cattctagac cagctcaaag attccatgag tttcatcgag tcactgtgag
3001 tggagcccat gctgggctct gtgccctctg tgtctgtgca tgcgcgtgtg tgtgtgggcg
3061 tgtgtgcatt gctgggccag cttgaaggga aggcccgtca tgtccctgca ctctgttttg
3121 caagatgcca aaccccagtt ctgatggggc tccaacagcc aggctgtggt cctttgacgt
3181 tcctcacctg ttgccaacct atcccgtagt gaactgaaac cccaatgaag acagaactgt
3241 gcctggggag atgcaatgag gtgagggctg aactcatcct tttatatttc ttttcaagat
3301 tggatcagag ctcatctcca tccagtcttg tttctatgaa ggcttcaatc tgtttccatg
3361 caaatttgct aatcagagcc cagagctgct gggtccctca tctccctcat ctattataga
3421 ttgacttaca gcagggagag aatctcttta gctcattcct aatggagttg ggatcacaat
3481 atggtctggt ccaatctgca tcttgttgtg tcccaagacc ctatctcctc cccaacattc
3541 ttattgcctt tggctcccag taaggaacga attgggggcc agggaggaga acaggcggga
3601 tcaagaaggg aaacccaatt cccccttga aagtgggttc tttgaactat gtgtttgggg
3661 gaagttcctc tggatactaa tttgaattta tatacctcat gttttggggg tttgacgtat
3721 atatatatat atatatatgc atatatattt cataatattt ggaaggtttt tgatgctaga
3781 aaaatggaaa caagagaacc ttcaaaaatg gtacttagat gggaactgga ggccaatctt
3841 tcataaagcc agccccatag ctgcttgctg ttaggcctcc agccattttg acattggggt
3901 ggatagtcga ttcacctgcc tgtcagtcga ttcacctgcc tgtcacccag ttctgtggat
3961 gtgctggtgc tgagcctttg ctctctttcc aaatggttac agggatgttg atcagctcca -continued 4021 ccagagggag ctctgatggg aggaattgct ctgccatcct tgtccctgtg tctcctgtcg
4081 gcaggcagcc attgtatctc accagcagac caggagactg gtcccaaggt tactgcacca
4141 cagggcaatt tcctgccata gttaggaagg aaacacctga actaaatgga agagacatcc
4201 ctgcggtgtt taatatcaca cccatgccct ttgtcaggtt accatgtaca gagattactt
4261 ggagagcctc atgccgtctc taccttcgca cactggtcaa gtatctgctg agcttcttgg
4321 ccgcaaggat gcagaaatag gctgagggtc catgggaaga aagacacaat gaggcagtag
4381 gaggtgggga agaaaagaag acagactttc aaaatggaat taggcactgg ggagagatca
4441 gtttccccac atcagggaga agaaggtata ggtggggaag ggggtggcca ggagcagaag
4501 gaagaagact caagatggaa agggagccgc tgtgcctgtg gcaataccac ttggagaggt
4561 cgacttcata ccttcaagcc ttttcccctg ggcttttgat tgtgtctgtg ccccctttct
4621 tgtcctctct gcagatgccc agtaggggct acctcatcct cgtgctgttc ttgtgtggct
4681 ttctgggcag tagggatctt gaatttcctt tctaacactg tgcccggcaa ggcggggagc
4741 attcctctgc cctttgtctt gtgccaacct ggaaaggtgc agtctagatt tcagtgagaa
4801 ccctgccagc tgagccctgt gcatctacta ccttgacaca gagtgttttc ccactagaag
4861 ctctgctctg ctctcctggc ccaagtaggg gattccatgc cttccctttc atggtcttag
4921 caccagcagc ctagtttctc ccttccagag tctccaggga tgacaaattg gattggagac
4981 aaacctcgtc agatgctcat cccctaaaag gttaattgtg tatttgtggc tgcgtgtgcc
5041 tttgtgtttt cattctcttc ccatttttgt acattttggt cttctctgtg gttttatact
5101 tggtcaa.ag tactcgtctt ggtattgcac tgttgtgtgc atgagaaaac tgggggaagg
5161 ctcactggta caagaaagga cccctgaccc ctttccttct ctgtggtccc cggcattaga
5221 ttgggggttc tgggagaggc aggtgaatgt cctaagtgaa ttgttctgtt tgtaactgga
5281 atgtttttga agtctttggt gttgctccgt gaaaggacat cgccacctgg tgctcatgag
5341 gtgtctttgc agaacaataa atggcaaatg aacaaccaca aaattgttac tcttgttggc
5401 cttctgctgt ttgtagatta gtgcacctat ctgtgaggga tttgggttac ctccctgagt
5461 ctgtaagcaa ccacaagccc tgccactggg tgggggaagt ccctccccaa ccacttaaaa
5521 acaaattttc cacatattac ccacccacac atttgacctg gctagacttt gtttgcctaa
5581 aggaacagac cacattgctg ggaaaatgag taagtgaacg tgtgggagaa aaacactttt
5641 agaatcacga atattcactt ttaaaggtct ctttgcctgg ctgcaatata gtgtgtgttt
5701 aaattattta caggctgttg tttctcaaat aaatgtttaa tattaatcat tcccaaactg
5761 acaagaacac aaaaataaaa tgcaaataca gagcc One example of a nucleic acid sequence for human DUSP4 is available as NCBI accession number NM_001394 (gi: 58331238). This sequence is recited below for easy reference as SEQ ID NO: 134.

1 gctgagcgcc ggaggagcgt aggcagggca gagctggcgc cagtggcgac aggagccgcg
61 cgaccggcaa aaatacacgg gaggccgtcg ccgaaaagag tccgcggtcc tctctcgtaa
121 acacactctc ctccaccggc gcctccccct ccgctctgcg cgccgcccgg ctgggcgccc
181 gaggccgctc cgactgctat gtgaccgcga ggctgcggga ggaaggggac agggaagaag
241 aggctctccc gcgggagccc ttgaggacca agtttgcggc cacttctgca ggcgtccctt
301 cttagctctc gcccgcccct ttctgcagcc taggcggccc gggttctctt ctcttcctcg -continued 361 cgcgcccagc cgcctcggtt cccggcgacc atggtgacga tggaggagct gcgggagatg 421 gactgcagtg tgctcaaaag gctgatgaac cgggacgaga atggcggcgg cgcgggcggc 481 agcggcagcc acggcaccct ggggctgccg agcggcggca agtgcctgct gctggactgc 541 agaccgttcc tggcgcacag cgcgggctac atcctaggtt cggtcaacgt gcgctgtaac 601 accatcgtgc ggcggcgggc taagggctcc gtgagcctgg agcagatcct gcccgccgag 661 gaggaggtac gcgcccgctt gcgctccggc ctctactcgg cggtcatcgt ctacgacgag 721 cgcagcccgc gcgccgagag cctccgcgag gacagcaccg tgtcgctggt ggtgcaggcg 781 ctgcgccgca acgccgagcg caccgacatc tgcctgctca aaggcggcta tgagaggttt 841 tcctccgagt acccagaatt ctgttctaaa accaaggccc tggcagccat cccacccccg 901 gttcccccca gtgccacaga gcccttggac ctgggctgca gctcctgtgg gaccccacta 961 cacgaccagg ggggtcctgt ggagatcctt cccttcctct acctcggcag tgcctaccat 1021 gctgcccgga gagacatgct ggacgccctg ggcatcacgg ctctgttgaa tgtctcctcg 1081 gactgcccaa accactttga aggacactat cagtacaagt gcatcccagt ggaagataac 1141 cacaaggccg acatcagctc ctggttcatg gaagccatag agtacatcga tgccgtgaag 1201 gactgccgtg ggcgcgtgct ggtgcactgc caggcgggca tctcgcggtc ggccaccatc 1261 tgcctggcct acctgatgat gaagaaacgg gtgaggctgg aggaggcctt cgagttcgtt 1321 aagcagcgcc gcagcatcat ctcgcccaac ttcagcttca tggggcagct gctgcagttc 1381 gagtcccagg tgctggccac gtcctgtgct gcggaggctg ctagcccctc gggacccctg 1441 cgggagcggg gcaagacccc cgccaccccc acctcgcagt tcgtcttcag ctttccggtc 1501 tccgtgggcg tgcactcggc ccccagcagc ctgccctacc tgcacagccc catcaccacc 1561 tctcccagct gttagagccg ccctgggggc cccagaacca gagctggctc ccagcaaggg 1621 taggacgggc cgcatgcggg cagaaagttg ggactgagca gctgggagca ggcgaccgag 1681 ctccttcccc atcatttctc cttggccaac gacgaggcca gccagaatgg caataaggac 1741 tccgaataca taataaaagc aaacagaaca ctccaactta gagcaataac ggctgccgca 1801 gcagccaggg aagaccttgg tttggtttat gtgtcagttt cacttttccg atagaaattt 1861 cttacctcat ttttttaagc agtaaggctt gaagtgatga aacccacaga tcctagcaaa 1921 tgtgcccaac cagctttact aaagggggag gaagggaggg caaagggatg agaagacaag 1981 tttcccagaa gtgcctggtt ctgtgtactt gtccctttgt tgtcgttgtt gtagttaaag 2041 gaatttcatt ttttaaaaga aatcttcgaa ggtgtggttt tcatttctca gtcaccaaca 2101 gatgaataat tatgcttaat aataaagtat ttattaagac tttcttcaga gtatgaaagt 2161 acaaaaagtc tagttacagt ggatttagaa tatatttatg ttgatgtcaa acagctgagc 2221 accgtagcat gcagatgtca aggcagttag gaagtaaatg gtgtcttgta gatatgtgca 2281 aggtagcatg atgagcaact tgagtttgtt gccactgaga agcaggcggg ttgggtggga 2341 ggaggaagaa agggaagaat taggtttgaa ttgcttttta aaaaaaaaag aaaagaaaaa 2401 gacagcatct cactatgttg ccaaggctca tcttgagaag caggcgggtt gggtgggagg 2461 aggaagaaag ggaagaatta ggtttgaatt gcttttttt One example of a nucleic acid sequence for human EFEMP1 is available as NCBI accession number NM_004105 (gi: 86787911). This sequence is recited below for easy reference as SEQ ID NO: 135.

```
   1 cgaaggtagc gtgtcgggga cccagactga taagacaaaa gagaatcagt cgctttgggc
  61 tgcccctcca cacaacctgg gacttttaaa caaagctgtg cgcagagaaa ggcgtggaaa
 121 tgccactttg agagtttgtg ctgggggatg tgagaagctc tgagacatgt gagaaggtct
 181 agtattctac tagaactgga agattgctct ccgagttttg ttttgttatt ttgtttaaaa
 241 aataaaaagc ttgaggccaa ggcaattcat attggctcac aggtattttt gctgtgctgt
 301 gcaaggaact ctgctagctc aagattcaca atgttgaaag ccctttttcct aactatgctg
 361 actctggcgc tggtcaagtc acaggacacc gaagaaacca tcacgtacac gcaatgcact
 421 gacggatatg agtgggatcc tgtgagacag caatgcaaag atattgatga atgtgacatt
 481 gtcccagacg cttgtaaagg tggaatgaag tgtgtcaacc actatggagg atacctctgc
 541 cttccgaaaa cagcccagat tattgtcaat aatgaacagc ctcagcagga aacacaacca
 601 gcagaaggaa cctcaggggc aaccaccggg gttgtagctg ccagcagcat ggcaaccagt
 661 ggagtgttgc ccgggggtgg ttttgtggcc agtgctgctg cagtcgcagg ccctgaaatg
 721 cagactggcc gaaataactt tgtcatccgg cggaacccag ctgaccctca gcgcattccc
 781 tccaaccctt cccaccgtat ccagtgtgca gcaggctacg agcaaagtga acacaacgtg
 841 tgccaagaca tagacgagtg cactgcaggg acgcacaact gtagagcaga ccaagtgtgc
 901 atcaatttac ggggatcctt tgcatgtcag tgccctcctg gatatcagaa gcgaggggag
 961 cagtgcgtag acatagatga atgtaccatc cctccatatt gccaccaaag atgcgtgaat
1021 acaccaggct cattttattg ccagtgcagt cctgggtttc aattggcagc aaacaactat
1081 acctgcgtag atataaatga atgtgatgcc agcaatcaat gtgctcagca gtgctacaac
1141 attcttggtt cattcatctg tcagtgcaat caaggatatg agctaagcag tgacaggctc
1201 aactgtgaag acattgatga atgcagaacc tcaagctacc tgtgtcaata tcaatgtgtc
1261 aatgaacctg ggaaattctc atgtatgtgc ccccagggat accaagtggt gagaagtaga
1321 acatgtcaag atataaatga gtgtgagacc acaaatgaat gccgggagga tgaaatgtgt
1381 tggaattatc atggcggctt ccgttgttat ccacgaaatc cttgtcaaga tccctacatt
1441 ctaacaccag agaaccgatg tgtttgccca gtctcaaatg ccatgtgccg agaactgccc
1501 cagtcaatag tctacaaata catgagcatc cgatctgata ggtctgtgcc atcagacatc
1561 ttccagatac aggccacaac tatttatgcc aacaccatca atacttttcg gattaaatct
1621 ggaaatgaaa atggagagtt ctacctacga caaacaagtc ctgtaagtgc aatgcttgtg
1681 ctcgtgaagt cattatcagg accaagagaa catatcgtgg acctggagat gctgacagtc
1741 agcagtatag ggaccttccg cacaagctct gtgttaagat tgacaataat agtggggcca
1801 ttttcatttt agtcttttct aagagtcaac cacaggcatt taagtcagcc aaagaatatt
1861 gttaccttaa agcactattt tatttataga tatatctagt gcatctacat ctctatactg
1921 tacactcacc cataattcaa acaattacac catggtataa agtgggcatt taatatgtaa
1981 agattcaaag tttgtcttta ttactatatg taaattagac attaatccac taaactggtc
2041 ttcttcaaga gagctaagta tacactatct ggtgaaactt ggattctttc ctataaaagt
2101 gggaccaagc aatgatgatc ttctgtggtg cttaaggaaa cttactagag ctccactaac
2161 agtctcataa ggaggcagcc atcataacca ttgaatagca tgcaagggta agaatgagtt
2221 tttaactgct ttgtaagaaa atggaaaagg tcaataaaga tatatttctt tagaaaatgg
```

-continued

```
2281 ggatctgcca tatttgtgtt ggtttttatt ttcatatcca gcctaaaggt ggttgtttat
2341 tatatagtaa taaatcattg ctgtacaata tgctggtttc tgtagggtat ttttaatttt
2401 gtcagaaatt ttagattgtg aatattttgt aaaaaacagt aagcaaaatt ttccagaatt
2461 cccaaaatga accagatatc ccctagaaaa ttatactatt gagaaatcta tggggaggat
2521 atgagaaaat aaattccttc taaaccacat tggaactgac ctgaagaagc aaactcggaa
2581 aatataataa catccctgaa ttcaggactt ccacaagatg cagaacaaaa tggataaaag
2641 gtatttcact ggagaagttt taatttctaa gtaaaattta aatcctaaca cttcactaat
2701 ttataactaa aatttctcat cttcgtactt gatgctcaca gaggaagaaa atgatgatgg
2761 tttttattcc tggcatccag agtgacagtg aacttaagca aattaccctc ctacccaatt
2821 ctatggaata ttttatacgt ctccttgttt aaaatgtcac tgctttactt tgatgtatca
2881 tatttttaaa taaaaataaa tattccttta gaagatcaaa aaaaaaaaaa aaaaaa
```

One example of a nucleic acid sequence for human ELMO1 is available as NCBI accession number NM_014800 (gi: 86787650). This sequence is recited below for easy reference as SEQ ID NO: 136.

```
   1 aagtgagagc agcggcagcc ggcggtgcag cagccggccg acccagagtg taagtgcgtg
  61 tgctggggcg agcgggagcg ggcgaggatg ggcacaggat agaggcagag ccacccacgc
 121 cgccgcggcc ccacgctggg cgacagagcc tccagttccc cttcaatggt ggcgggtcgc
 181 cggagctctg atcgccggga acccttgccg ctgctgtcct gcgaccccaa gcaggtatag
 241 acacgtgtgg ccgtttacgc tgtaggatcc tcattcccac tggctttgaa cattttgggg
 301 acttacaatg ccgccacccg cggacatcgt caaggtggcc atagaatggc cgggcgccta
 361 ccccaaactc atggaaattg atcagaaaaa accactgtct gcaataataa aggaagtctg
 421 tgatgggtgg tctcttgcca accatgaata ttttgcactc cagcatgccg atagttcaaa
 481 cttctatatc acagaaaaga accgcaatga gataaaaaat ggcactatcc ttcgattaac
 541 cacatctcca gctcagaacg cccagcagct ccatgaacga atccagtcct cgagtatgga
 601 tgccaagctg gaagccctga aggacttggc cagcctctcc cgggatgtca cgtttgccca
 661 ggagtttata aacctggacg gtatctctct cctcacgcag atggtggaga gcggcactga
 721 gcgataccag aaattgcaga agatcatgaa gccttgcttt ggagacatgc tgtccttcac
 781 cctgacggcc ttcgttgagc tgatggacca tggcatagtg tcctgggata cattttcggt
 841 ggcgttcatt aagaagatag caagttttgt gaacaagtca gccatagaca tctcgatcct
 901 gcagcggtcc ttggccattt tggagtcgat ggtgctcaat agccatgacc tctaccagaa
 961 agtggcgcag gagatcacca tcggccagct cattccacac ctgcaagggt cagatcaaga
1021 aatccaaacc tatactattg cagtgattaa tgcgcttttc ctgaaggctc ctgatgagag
1081 gaggcaggag atggcgaata ttttggctca gaagcaactg cgttccatca ttttaacaca
1141 tgtcatccga gcccagcggg ccatcaacaa tgagatggcg caccagctgt atgttctaca
1201 agtgctcacc tttaacctcc tggaagacag gatgatgacc aaaatggacc cccaggacca
1261 ggctcagagg gacatcatat ttgaacttcg aagaattgct tttgatgctg agtctgaacc
1321 taacaacagc agtggcagca tggagaaacg caagtccatg tacacgcgag attataagaa
1381 gcttgggttc attaatcatg tcaaccctgc catggacttc acgcagactc cacctgggat
1441 gttggctctg gacaacatgc tgtactttgc caagcaccac caagatgcct acatccggat
```

-continued

```
1501 tgtgcttgag aacagtagtc gagaagacaa gcatgaatgt ccctttggcc gcagtagtat
1561 agagctgacc aagatgctat gtgagatctt gaaagtgggc gagttgccta gtgagacctg
1621 caacgacttc cacccgatgt tcttcaccca cgacagatcc tttgaggagt ttttctgcat
1681 ctgtatccag ctcctgaaca agacatggaa ggaaatgagg gcaacttctg aagacttcaa
1741 caaggtaatg caggtggtga aggagcaggt tatgagagca cttacaacca agcctagctc
1801 cctggaccag ttcaagagca aactgcagaa cctgagctac actgagatcc tgaaaatccg
1861 ccagtccgag aggatgaacc aggaagattt ccagtcccgc ccgattttgg aactaaagga
1921 gaagattcag ccagaaatct tagagctgat caaacagcaa cgcctgaacc gccttgtgga
1981 agggacctgc tttaggaaac tcaatgcccg gcggaggcaa gacaagtttt ggtattgtcg
2041 gctttcgcca aatcacaaag tcctgcatta cggagactta gaagagagtc ctcagggaga
2101 agtgccccac gattccttgc aggacaaact gccggtggca gatatcaaag ccgtggtgac
2161 gggaaaggac tgccctcata tgaaagagaa aggtgccctt aaacaaaaca aggaggtgct
2221 tgaactcgct ttctccatct tgtatgactc aaactgccaa ctgaacttca tcgctcctga
2281 caagcatgag tactgtatct ggacggatgg actgaatgcg ctactcggga aggacatgat
2341 gagcgacctg acgcggaatg acctggacac cctgctcagc atggaaatca agctccgcct
2401 cctggacctg gaaaacatcc agatccctga cgcacctccg ccgattccca aggagcccag
2461 caactatgac ttcgtctatg actgtaactg aagtggccgg gcccagacat gccccttcca
2521 aaactggaac acctagctaa caggagagag gaatgaaaac acacccacgc cttggaaccg
2581 tcctttggta aagggaagct gtgggtccac attcccttca gcatcacctc tagccctggc
2641 aactttcagc ccctagctgg catcttgctc accgccctga ttctgttcct cggctccact
2701 gcttcaggtc acttcccatg gctgcagtcc actggtggga caagagcaaa gcccactgcc
2761 agtaagaagg ccaaagggcc cttccatcct agccctctgc aggcatgccc ttccttccct
2821 tgggcaggaa agccagcagc cccagactgc ccaaaaactt gcccaccaga ccaagggcag
2881 tgccccaagg cccctgtctg gaggaaatgg cctagctatt tgatgagaag accaaacccc
2941 acatcctcct ttcccctctc tctagaatca tctcgcacca ccagttacac ttgaattaag
3001 atctgcgctc aaatctcctc ccacctctct ccctgctttt gccttgctct gttcctcttt
3061 ggtcccaaga gcagcagccg cagcctcctc gtgatcctcc ctagcataaa tttcccaaac
3121 agtccacagg tcccatgccc actttgcgtc tgcactgtga tcgtgacaaa tcttccctcc
3181 tcaccagcta gtctggggtt tcctctccct gccccaggcc agaactgcct tcttcatttc
3241 cacccacgct cccagcctct tagctgaaag cacaaatggt gaaatcagta gtctcgctcc
3301 atctctaata gactaaacct aaatgcctct aggacggact gttgctatcc aagcgtttgg
3361 tgttaccttc tcctgggagg tcctgctgca actcaagttc cacaggatgg tcaagctgtc
3421 agacatccaa gtttacatca ttgtaattat tactggtatt tacaatttgc aagagttttg
3481 ggttagtttt tttttttttt tttgctttgt ttttgtacaa aagagtctaa catttttttgc
3541 caaacagata tatatttaat gaaaagaaga gatacataaa tgtgtgaatt tccagttttt
3601 ttttaattat tttaatccca aacatcttcc tgaaaataac attcccttaa acatgctgtg
3661 gaataaaatg gattgtgatg atttggaaaa aaaaaaaaaa aaaaaaaaaa aaaaaaaaaa
3721 aaaaaaa
```

One example of a nucleic acid sequence for human FGFR2 is available as NCBI accession number NM_000141 (gi: 189083823). This sequence is recited below for easy reference as SEQ ID NO: 137.

```
   1 ggcggcggct ggaggagagc gcggtggaga gccgagcggg cgggcggcgg gtgcggagcg
  61 ggcgagggag cgcgcgcggc cgccacaaag ctcgggcgcc gcggggctgc atgcggcgta
 121 cctggcccgg cgcggcgact gctctccggg ctggcggggg ccggccgcga gccccggggg
 181 ccccgaggcc gcagcttgcc tgcgcgctct gagccttcgc aactcgcgag caaagtttgg
 241 tggaggcaac gccaagcctg agtcctttct tcctctcgtt ccccaaatcc gagggcagcc
 301 cgcgggcgtc atgcccgcgc tcctccgcag cctggggtac gcgtgaagcc cgggaggctt
 361 ggcgccggcg aagacccaag gaccactctt ctgcgtttgg agttgctccc cgcaaccccg
 421 ggctcgtcgc tttctccatc ccgacccacg cggggcgcgg ggacaacaca ggtcgcggag
 481 gagcgttgcc attcaagtga ctgcagcagc agcggcagcg cctcggttcc tgagcccacc
 541 gcaggctgaa ggcattgcgc gtagtccatg cccgtagagg aagtgtgcag atgggattaa
 601 cgtccacatg gagatatgga agaggaccgg ggattggtac cgtaaccatg gtcagctggg
 661 gtcgtttcat ctgcctggtc gtggtcacca tggcaacctt gtccctggcc cggccctcct
 721 tcagtttagt tgaggatacc acattagagc cagaagagcc accaaccaaa taccaaatct
 781 ctcaaccaga agtgtacgtg gctgcgccag gggagtcgct agaggtgcgc tgcctgctga
 841 aagatgccgc cgtgatcagt tggactaagg atggggtgca cttggggccc aacaatagga
 901 cagtgcttat tggggagtac ttgcagataa agggcgccac gcctagagac tccggcctct
 961 atgcttgtac tgccagtagg accgtagaca gtgaaacccg gtacctcatg gcgaatgtca
1021 cagatgccat ctcatccgga gatgatgagg atgacaccga tggtgcggaa gattttgtca
1081 gtgagaacag taacaacaag agagcaccat actggaccaa cacagaaaag acggaaaagc
1141 ggctccatgc tgtgcctgcg gccaacactg tcaagtttcg ctgcccagcc gggggaacc
1201 caatgccaac catgcggtgg ctgaaaaacg ggaaggagtt taagcaggag catcgcattg
1261 gaggctacaa ggtacgaaac cagcactgga gcctcattat gqaaagtgtg gtcccatctg
1321 acaaqgqaaa ttatacctgt gtagtggaga atgaatacgg gtccatcaat cacacgtacc
1381 acctggatgt tgtggagcga tcgcctcacc ggcccatcct ccaagccgga ctgccggcaa
1441 atgcctccac agtggtcgga ggagacgtag agtttgtctg caaggtttac agtgatgccc
1501 agccccacat ccagtggatc aagcacgtgg aaaagaacgg cagtaaatac gggcccgacg
1561 ggctgcccta cctcaaggtt ctcaaggccg ccggtgtcaa caccacggac aaagagattg
1621 aggttctcta tattcggaat gtaacttttg aggacgctgg ggaatatacg tgcttggcgg
1681 gtaattctat tgggatatcc tttcactctg catggttgac agttctgcca gcgcctggaa
1741 gagaaaagga gattacagct tccccagact acctggagat agccatttac tgcatagggg
1801 tcttcttaat cgcctgtatg gtggtaacag tcatcctgtg ccgaatgaag aacacgacca
1881 agaagccaga cttcagcagc cagccggctg tgcacaagct gaccaaacgt atcccctgc
1921 ggagacaggt aacagtttcg gctgagtcca gctcctccat gaactccaac accccgctgg
1981 tgaggataac aacacgcctc tcttcaacgg cagacacccc catgctggca ggggtctccg
2041 agtatgaact tccagaggac ccaaaatggg agtttccaag agataagctg acactgggca
2101 agcccctggg agaaggttgc tttgggcaag tggtcatggc ggaagcagtg ggaattgaca
2161 aagacaagcc caaggaggcg gtcaccgtgg ccgtgaagat gttgaaagat gatgccacag
2221 agaaagacct ttctgatctg gtgtcagaga tggaqatgat gaagatgatt gggaaacaca
```

-continued 2281 agaatatcat aaatcttctt ggagcctgca cacaggatgg gcctctctat gtcatagttg
2341 agtatgcctc taaaggcaac ctccgagaat acctccgagc ccggaggcca cccgggatgg
2401 agtactccta tgacattaac cgtgttcctg aggagcagat gaccttcaag gacttggtgt
2461 catgcaccta ccagctggcc agaggcatgg agtacttggc ctcccaaaaa tgtattcatc
2521 gagatttagc agccagaaat gttttggtaa cagaaaaoaa tgtgatgaaa atagcagact
2581 ttggactcgc cagagatatc aacaatatag actattacaa aaagaccacc aatgggcggc
2641 ttccagtcaa gtggatggct ccagaagccc tgtttgatag agtatacact catcagagtg
2701 atgtctggtc cttcggggtg ttaatgtggg agatcttcac tttagggggc tcgccctacc
2761 cagggattcc cgtggaggaa ctctttaagc cgctgaagga aggacacaga atggataagc
2821 cagccaactg caccaacgaa ctgtacatga tgatgaggga ctgttggcat gcagtgccct
2881 cccagagacc aacgttcaag cagttggtag aagacttgga tcgaattctc actctcacaa
2941 ccaatgagga atacttggac ctcagccaac ctctcgaaca gtattcacct agttaccctg
3001 acacaagaag ttcttgttct tcaggagatg attctgtttt ttctccagac cccatgcctt
3061 acgaaccatg ccttcctcag tatccacaca taaacggcag tgttaaaaca tgaatgactg
3121 tgtctgcctg tccccaaaca ggacagcact gggaacctag ctacactgag cagggagacc
3181 atgcctccca gagcttgttg tctccacttg tatatatgga tcagaggagt aaataattgg
3241 aaaagtaatc agcatatgtg taaagattta tacagttgaa aacttgtaat cttccccagg
3301 aggagaagaa ggtttctgga gcagtggact gccacaagcc accatgtaac ccctctcacc
3361 tgccgtgcgt actggctgtg gaccagtagg actcaaggtg gacgcgcgtt ctgccttcct
3421 tgttaatttt gtaataattg gagaagattt atgtcagcac acacttacag agcacaaatg
3481 cagtatatag gtgctggatg tatgtaaata tattcaaatt atgtataaat atatattata
3541 tatttacaag gagttatttt ttgtattgat tttaaatgga tgtcccaatg cacctagaaa
3601 attggtctct ctttttttaa tagctatttg ctaaatgctg ttcttacaca taatttctta
3661 atttccaccg agcagaggtg gaaaaacact tttgctttca gggaaaatgg tataacgtta
3721 atttattaat aaattggtaa tatacaaaac aattaatcat ttatagtttt ttttgtaatt
3781 taagtggcat ttctatgcag gcagcacagc agactagtta atctattgct tggacttaac
3841 tagttatcag atcctttgaa aagagaatat ctacaatata tgactaattt ggggaaaatg
3901 aagttttgat ttatttgtgt ttaaatgctg ctgtcagacg attgctctta gacctcctaa
3961 atgccccata ttaaaagaac tcattcatag gaaggtgcct cattttggtg tgcaaccctg
4021 tcattacgtc aacgcaacgt ctaactggac ttcccaagat aaatggtacc agcgtcctct
4081 taaaagatgc cttaatccat tccttgagga cagaccttag ttgaaatgat agcagaatgt
4141 gcttctctct ggcagctggc cttctgcttc tgagttgcac attaatcaga ttagcctgta
4201 ttctcttcag tgaattttga taatggcttc cagactcttt ggcgttggag acgcctgtta
4261 ggatcttcaa gtcccatcat agaaaattga aacacagagt cgttctgccg atagtcttgg
4321 ggatacgtcc atctttttaa gggattgctt tcatctaatt ctggcaggac ctcaccaaaa
4381 gatccagcct catacctaca tcagacaaaa tatcgccgtt gttccttctg tactaaagta
4441 ttgtgttttg ctttggaaac acccactcac tttgcaatag ccgtgcaaga tgaatgcaga
4501 ttacactgat cttatgtgtt acaaaattgg agaaagtatt taataaaacc tgttaatttt
4561 catactgaca ataaaaatgt ttctacagat attaatgcca acaagacaaa ataaatgtca
4621 cgcaacttat ttttttaata aaaaaaaaaa aaaa One example of a nucleic acid sequence for human FLRT1 is available as NCBI accession number NM_013280 (gi: 48762940). This sequence is recited below for easy reference as SEQ ID NO: 138.

```
   1  caaggaggct gctgattgtg gcccacagcc tcatctgaac gccaggagac caggataccg
  61  aggcaccgga tcccctctct gtgccctggg gagccccagt gctgcccagt caccccaggg
 121  ctgaggtctg cgtccctagt ggtgcaaggc ctggtaggac cacggggcag ggaatgtgag
 181  cgccatctga gctcacggtg tcctgagtcg cggcttcgtg actttggcag gggcctccgg
 241  accagtgacc ccagtcaaac ccagagggtc ttgggcggca gcgacgaagg aggtattcag
 301  gctccaggcc aggtggggcc ggacgccccc agccatccac catggtggtg gcacacccca
 361  ccgccactgc caccaccacg cccactgcca ctgtcacggc caccgttgtg atgaccacgg
 421  ccaccatgga cctgcgggac tggctgttcc tctgctacgg gctcatcgcc ttcctgacgg
 481  aggtcatcga cagcaccacc tgcccctcgg tgtgccgctg cgacaacggc ttcatctact
 541  gcaacgaccg gggactcaca tccatccccg cagatatccc tgatgatgcc accaccctct
 601  acctgcagaa caaccagatc aacaacgccg gcatccccca ggacctcaag accaaggtca
 661  acgtgcaggt catctaccta tacgagaatg acctggatga gttccccatc aacctgcccc
 721  gctccctccg ggagctgcac ctgcaggaca acaatgtgcg caccattgcc agggactcgc
 781  tggcccgcat cccgctgctg gagaagctgc acctggatga caactccgtg tccaccgtca
 841  gcattgagga ggacgccttc gccgacagca aacagctcaa gctgctcttc ctgagccgga
 901  accacctgag cagcatcccc tcggggctgc cgcacacgct ggaggagctg cggctggatg
 961  acaaccgcat ctccaccatc ccgctgcatg ccttcaaggg cctcaacagc ctgcggcgcc
1021  tggtgctgga cggtaacctg ctggccaacc agcgcatcgc cgacgacacc ttcagccgcc
1081  tacagaacct cacagagctc tcgctggtgc gcaattcgct ggccgcgcca cccctcaacc
1141  tgcccagcgc ccacctgcag aagctctacc tgcaggacaa tgccatcagc cacatcccct
1201  acaacacgct ggccaagatg cgtgagctgg agcggctgga cctgtccaac aacaacctga
1261  ccacgctgcc ccgcggcctg ttcgacgacc tggggaacct ggcccagctg ctgctcagga
1321  acaacccttg gttttgtggc tgcaacctca tgtggctgcg ggactgggtg aaggcacggg
1381  cggccgtggt caacgtgcgg ggcctcatgt gccagggccc tgagaaggtc cggggcatgg
1441  ccatcaagga cattaccagc gagatggacg agtgttttga gacggggccg cagggcggcg
1501  tggccaatgc ggctgccaag accacggcca gcaaccacgc ctctgccacc acgccccagg
1561  gttccctgtt taccctcaag gccaaaaggc cagggctgcg cctccccgac tccaacattg
1621  actaccccat ggccacgggt gatggcgcca agaccctggc catccacgtg aaggccctga
1681  cggcagactc catccgcatc acgtggaagg ccacgctccc cgcctcctct ttccggctca
1741  gttggctgcg cctgggccac agcccagccg tgggctccat cacggagacc ttggtgcagg
1801  gggacaagac agagtacctg ctgacagccc tggagcccaa gtccacctac atcatctgca
1861  tggtcaccat ggagaccagc aatgcctacg tagctgatga gacacccgtg tgtgccaagg
1921  cagagacagc cgacagctat ggccctacca ccacactcaa ccaggagcag aacgctggcc
1981  ccatggcgag cctgcccctg gcgggcatca tcggcggggc agtggctctg gtcttcctct
2041  tcctggtcct gggggccatc tgctggtacg tgcaccaggc tggcgagctg ctgacccggg
2101  agagggccca caaccggggc agcaggaaaa aggatgacta tatggagtca gggaccaaga
2161  aggataactc catcctggaa atccgcggcc ctgggctgca gatgctgccc atcaacccgt
2221  accgcgccaa agaggagtac gtggtccaca ctatcttccc ctccaacggc agcagcctct
```

-continued

```
2281   gcaaggccac acacaccatt ggctacggca ccacgcgggg ctaccgggac ggcggcatcc
2341   ccgacataga ctactcctac acatgatgcc cgcccacccg ggctgccccg cctcagcccc
2401   agctgccctg gcgtggccat gtggcttcgc ccagcctgct gcaatccaag agagcaagga
2461   agagaaattc catgggtgac tttcctccgc agaaagcaaa gtttggggag ggctgacgat
2521   tttgtagaac acaacagtga caattttttt taaaagaata gaaggcagga gggggaattc
2581   gacattgttg aagacataat ttataccaag ttatgccagt tggggaggga aggactaaaa
2641   ataatattgc aggcagggct gggttgggtt tttttttttt ccccccctgaa ctggaaggat
2701   actacctgta caacatctgt ggacacctca tgctctgttc aaggccatca caaaggaacc
2761   gccagggaga agcagccggc tctcaaagct cccacgcagc tctcccgcca ctggccactc
2821   gctggcgacc cgatggaagg ttttcaggct cctcacaaag gagagaggga agaaaagatc
2881   ttttgccctg gagatatggt cctgaaatct ctcccctggc ttattccata ccatttccct
2941   tgcagatttg cagaaacatg gcatctttca ctgcattctt tgaacaatca tgtagtcgat
3001   taaaaaaaaa aaacaaactt tttttcccta ggctgaagcc ctcttcagtt ccatgcacca
3061   cgctccgtag aagccccggc ggaagccgta gctttccctg ccacctggag gtgcatctgt
3121   ctgcctgtct atccctgtcg cggtgtctct aagtacagat gggtagatag agccacatgc
3181   acggtcctta ccgttcttct tgggtcagtt cttaccattt cctgaacaat agaattgtga
3241   aagtgttaaa aa
```

One example of a nucleic acid sequence for human FMOD is available as NCBI accession number NM_002023 (gi: 71040110). This sequence is recited below for easy reference as SEQ ID NO: 139.

```
   1   ggtctggcac aggcacgcac actctcagta gactctttca ctcctctctc tcttcctctc
  61   tcacacgttc tccaacccaa ggaggccaga cagagggacg tggtcactct ctgaaaagtt
 121   caacttgaga gacaaaatgc agtggacctc cctcctgctg ctggcagggc tcttctccct
 181   ctcccaggcc cagtatgaag atgaccctca ttggtggttc cactacctcc gcagccagca
 241   gtccacctac tacgatccct atgaccctta cccgtatgag acctacgagc cttacccccta
 301   tggggtggat gaagggccag cctacaccta cggctctcca tcccctccag atccccgcga
 361   ctgcccccag gagtgcgact gcccacccaa cttccccacg gccatgtact gtgacaatcg
 421   caacctcaag tacctgccct tcgttccctc ccgcatgaag tatgtgtact tccagaacaa
 481   ccagatcacc tccatccagg aaggcgtctt tgacaatgcc acagggctgc tctggattgc
 541   tctccacggc aaccagatca ccagtgataa ggtgggcagg aaggtcttct ccaagctgag
 601   gcacctggag aggctgtacc tggaccacaa caacctgacc cggatgcccg gtcccctgcc
 661   tcgatccctg agagagctcc atctcgacca caaccagatc tcacgggtcc ccaacaatgc
 721   tctggagggg ctggagaacc tcacggcctt gtacctccaa cacaatgaga tccaggaagt
 781   gggcagttcc atgaggggcc tccggtcact gatcttgctg gacctgagtt ataaccacct
 841   tcggaaggtg cctgatgggc tgccctcagc tcttgagcag ctgtacatgg agcacaacaa
 901   tgtctacacc gtccccgata gctacttccg gggggcgccc aagctgctgt atgtgcggct
 961   gtcccacaac agtctaacca acaatggcct ggcctccaac accttcaatt ccagcagcct
1021   ccttgagcta gacctctcct acaaccagct gcagaagatc cccccagtca acaccaacct
1081   ggagaacctc tacctccaag gcaataggat caatgagttc tccatcagca gcttctgcac
```

-continued

```
1141   cgtggtggac gtcgtgaact tctccaagct gcaggtgctg cgcctggacg ggaacgagat

1201   caagcgcagc gccatgcctg ccgacgcgcc cctctgcctg cgccttgcca gcctcatcga

1261   gatctgagca gccctggcac cgggtactgg gcggagagcc cccgtggcat ttggcttgat

1321   ggtttggttt ggcttttgct ggaaggtcca ggatggacca tgtgacagaa gtccacgggc

1381   accctctgta gtcttctttc ctgtaggtgg ggttaggggg ggcgatcagg gacaggcagc

1441   cttctgctga ggacataggc agaagctcac tcttttccag ggacagaagt ggtggtagat

1501   ggaaggatcc ctggatgttc caaccccata aatctcacgg ctcttaagtt cttcccaatg

1561   atctgaggtc acggaacttc aaaagtggca tgggcaatag tatataacca tacttttcta

1621   acaatccctg gctgtctgtg agcagcactt gacagctctc cctctgtgct gggctggtcg

1681   tgcagttact ctgggctccc atttgttgct tctcaaaata tacctcttgc ccagctgcct

1741   cttctgaaat ccacttcacc cactccactt tcctccacag atgcctcttc tgtgccttaa

1801   gcagagtcag gagaccccaa ggcatgtgag catctgccca gcaacctgtg gagacaaccc

1861   acactgtgtc tgagggtgaa aggacaccag gagtcacttc tatacctccc taacctcacc

1921   cctggaaagc caccagattg gaggtcacca gcatgatgat aatattcatg acctgatgtg

1981   ggaggagaca gccaacctca ggcttagatc aatgtatagg gctatatttt ggcagctggg

2041   tagctctttg aaggtggata agacttcaga agaggaaagg ccagactttg cttaccatca

2101   gcatctgcaa tgggccaaac acacctcaaa ttggctgagt tgagacagca gccccagtag

2161   ttccattctt gcccagcact ttctgcattc caaacagcat cctacctggg tttttatcca

2221   caaaggtagc ggccacatgg tttttaaagt atgagaaaca cagtttgtcc tctcctttta

2281   tccaagcagg aagattctat atcctgatgg tagagacaga ctccaggcag ccctggactt

2341   gctagcccaa agaaggagga tgtggttaat ctgtttcacc tggtttgtcc taaggccata

2401   gttaaaaagt accagctctg gctggggtcc gtgaagccca ggccaggcag ccaaatcttg

2461   cctgtgctgg gcatacaacc ctctgctttc acatctctga gctatatcct cattagtgaa

2521   ggtggctttt gctttatagt ttggctgggg agcacttaat tcttcccatt tcaaaaggta

2581   atgttgcctg gggcttaacc cacctgccct ttgggcaagg ttgggacaaa gccatctggg

2641   cagtcagggg caaggactgt tggaggagag ttagcccaag tataggctct gcccagatgc

2701   catcacatcc ctgatactgt gtatgctttg aagcaccttc cctgagaagg gaagagggga

2761   tctttggact acgttcttgg ctccagacct ggaatccaca aaagccaaac cagctcattt

2821   caacaaagga gctccgatgt gaggggcaag gctgccccct gccccagggc tcttcagaaa

2881   gcatctgcat gtgaacacca tcatgccttt ataaaggatc cttattacag gaaaagcatg

2941   agtggtggct aacctgacca ataaagttat tttatgattg catctaaaaa aaaaaaaaaa

3001   aaaaa
```

One example of a nucleic acid sequence for human GALNT7 is available as NCBI accession number NM_017423 (gi: 157502211). This sequence is recited below for easy reference as SEQ ID NO: 140.

```
   1   agagccggag gagggggaag gagggagggg agagcggtgg cggcggctgc gccgggctgt

  61   gagtctctcg ccgccggagg aagatgaggc tgaagattgg gttcatctta cgcagtttgc

 121   tggtggtggg aagcttcctg gggctagtgg tcctctggtc ttccctgacc ccgcggccgg

 181   acgacccaag cccgctgagc aggatgaggg aagacagaga tgtcaatgac cccatgccca

 241   accgaggcgg caatggacta gctcctgggg aggacagatt caaacctgtg gtaccatggc
```

-continued 301 ctcatgttga aggagtagaa gtggacttag agtctattag aagaataaac aaggccaaaa
361 atgaacaaga gcaccatgct ggaggagatt cccagaaags tatcatgcag aggcagtatc
421 tcacatttaa gcctcagaca ttcacctacc atgatcctgt gcttcgccca gggatcctcg
481 gtaactttga acccaaagaa cctgagcctc ctggagtggt tggtggccct ggagagaaag
541 ccaagccatt ggttttggga ccagaattca aacaagcaat tcaagccagc attaaagagu
601 ttggatttaa catggtggca agtgacatga tctcactgga ccgcagcgtc aatgacttac
661 gccaagaaga atgcaagtat tggcattatg atgaaaactt gctcacttcg agcgttgtca
721 ttgtcttcca taatgaagga tggtcaaccc tcatgagaac agtccacagt gtaattaaaa
781 ggactccaag gaaatattta gcagaaattg tgttaattga cgatttcagt aataaagaac
841 acttaaaaga aaaactggat gaatatatta agctgtggaa cggcctagcg aaggtatttc
901 gaaatgaaag aagggaaggt ttaattcaag cacgaagtat tggtgctcag aaggctaaac
961 ttggacaggt tttgatatac cttgatgccc actgtgaggt ggcagttaac tggtatgcac
1021 cacttgtagc tcccatatct aaggacagaa ccatttgcac tgtgccgctt atagatgtca
1081 taaatggcaa cacatatgaa attatacccc aaggggggtgg tgatgaagat gggtatgccc
1141 gaggagcatg ggattggagt atgctctgga aacgggtgcc tctgacccct caagagaaga
1201 gactgagaaa gacaaaaact gaaccgtatc ggtccccagc catggctggg ggattatttg
1261 ccattgaacg agagttcttc tttgaattgg gtctctatga tccaggtctc cagatttggg
1321 gtggtgaaaa ctttgagatc tcatacaaga tatggcagtg tggtggcaaa ttattatttg
1381 ttccttgttc tcgtgttgga catatctacc gtcttgaggg ctggcaagga aatcctccgc
1441 ccatttatgt tgggtcttct ccaactctga agaattatgt tagagttgtg gaggtttggt
1501 gggatgaata taaagactac ttctatgcta gtcgtcctga atcgcaggca ttaccatatg
1561 gggatatatc ggagctgaaa aaatttcgag aagatcacaa ctgcaaaagt tttaagtggt
1621 tcatggaaga aatagcttat gatatcacct cacactaccc tttgccaccc aaaaatgttg
1681 actgggggaga aatcagaggc ttcgaaactg cttactgcat tgatagcatg ggaaaaacaa
1741 atggaggctt tgttgaacta ggaccctgcc acaggatggg agggaatcag cttttcagaa
1801 tcaatgaagc aaatcaactc atgcagtatg accagtgttt gacaaaggga gctgatggat
1861 caaaagttat gattacacac tgtaatctaa atgaatttaa ggaatggcag tacttcaaga
1921 acctgcacag atttactcat attccttcag gaaagtgttt agatcgctca gaggtcctgc
1981 atcaagtatt catctccaat tgtgactcca gtaaaacgac tcaaaaatgg gaaatgaata
2041 acatccatag tgtttagaga gaaaaaaata aaccaataac ctacctactg acaagtaaat
2101 ttatacagga ctgaaaaccg cctgaaacct gctgcaacta ttgttattaa ctctgtatag
2161 ctccaaacct ggaacctcct gatcagtttg aaggacattg ataaactgtg attttacaat
2221 aacattatca tctgcagtta ctgtttacaa gactgctttt accttaaact ttgtagatgt
2281 ttacatcttt ttgttgtgtt ttaagatgat gttggtaatt tgtgccttta gctctgtttt
2341 attagacaga gttaaagcat gttgtcttct ttgggattac actcaggggt ctgaaaggca
2401 gtttgatttt tatttttaac acacttgaaa aaaggttgga gtagccagac tttcatatat
2461 aacttggtga ttatcaacct gttgtgtctt tatttaattt tacatctttt tgaagcactg
2521 ccacaggtta ttagccaagg tggccttcct tcacagtcat gctgcttttt tgaaaggtga
2581 atttcaacac atttagtgcc tctttcattt ctcagtatat atttcaagag cttgtgatga
2641 aatctatagg atggtaatga tggacttgtc acctgtatgg ggaatacttt tactactcag -continued

```
2701 aaatgaattt atgtgctgcc atttgctata aagttgaact ttgtatggct tgaaaaagaa
2761 atgacaatat ggaacatccc aaggctgtcc catagggttg gaagttgtgt agcattcact
2821 cccttaccta ctggcattcc cagtgccctc tgtccatacc tacttctagg attgcaaagg
2881 agtcttccaa ctagagaaaa attgtccact gacatttggg atttactttt ctccaatacc
2941 tgccaataca gaaaactatt atcagttgtt attgttatcc cttgaaagcg agggtgacaa
3001 aaacaacaaa acaccgttat aaacacatca aaggttcatt ctgactgagg taagactttc
3061 caagcccttg ttagattagg ccttataaaa cttgtgtgca ttataaccta agctgtgcaa
3121 cctgtgaagc caagagtgaa ctgatgtttc atttatattt tcatccaaat gacattatct
3181 gcacgttttt aaaatttaaa aacaaaggac tatttaaaaa tacagtttat taacaaacgt
3241 gaactacttt ctgttacatt aggtgttccc tagtgtttct taatttcttt ttagaaagtg
3301 tatttttatt agtatttttc cggtgaacag aagatttgtt tggatttaaa catttactaa
3361 gacagtacct attaggaaaa ccaaatattg caaatggtca attcgatttt aatttctcaa
3421 aagatactct gttatccaga agattaaaat gcctacattg agtgcttaaa aaaaaaaaaa
3481 caactgtgat gatgtgagca gaatggcaag taagttaagc atttttgatc ctgtaatcat
3541 ggtatcatta caatgaaagg aattcacaaa ctactgccag aggaagtttg ttttttaatt
3601 taagagggaa atataaccta taaatttgtt tcttccaagc ttagctctta aatttggaga
3661 ctcaaagtta aacatcctca acagagtttt atttataatt ttgaattgtc aatttgtatt
3721 ttgctactga tctgtgatca accattttaa ctttcatctc tagggatgtt taacatttat
3781 aattgcaaaa taaaccaact ataaaaaaag aaactaagag agaattggta ctttaattac
3841 ttgtgtgttt gcaaataggc tccattttcc atgttgagta gattataacc ttattaacta
3901 tgcataggcc taagaaaggt ggcaatgaac tgtgcatgta aattttaaat gggtactttg
3961 tgcaattcgt taaaagaaga tactctatga atatgattct atatattgaa atcagaaaac
4021 ctaccaaaca aaaacatcag aagctgctgc cataatgact attttctact gtaggctgct
4081 ttggaaataa ttcccatatc cttgctttgt aagttggtaa tatcactatg catttctaca
4141 cattttataa atttgattta tgcagatttt gatacactgt atgtttctgt agaaattgta
4201 taaatattca aaattttatt aggataaatt tgagaaactt acgtatatct taattctggg
4261 ttgcttgttt tttaggtgac aaaaataaaa tattgtattt taattcaaaa aaaaaaaaaa
4321 aaaaaaaaaa aaaaaaaaa
```

One example of a nucleic acid sequence for human GATM is available as NCBI accession number NM_001482 (gi: 126090880). This sequence is recited below for easy reference as SEQ ID NO: 141.

```
  1 ttgcgacgct cgggtctggg tccgggtccg gacgtgcaac agaagccgtc agtggccccg
 61 ctggctaaaa aagggcaagc atcggaggct cgagccagcg gccgcggcgc ttcccgacag
121 ttcctaattc ggggcgctac gccggcccca ccacctgttc ccggcagcca atggggccgc
181 gggggcggc cggggcggag cgcggctaca aaaggcctcg ggccccgcgc gcccgcccac
241 cccgctccgg gcgcgctctc gggaaggctt ggaccgacgc ggcccagagg ccaggaacat
301 tccgcgcgtg gaccagccgg gccagggcga tgctgcgggt gcggtgtctg cgcggcggga
361 gccgcggcgc cgaggcggtg cactacatcg gatctcggct tggacgaacc ttgacaggat
421 gggtgcagcg aactttccag agcacccagg cagctacggc ttcctcccgg aactcctgtg
481 cagctgacga caaagccact gagcctctgc ccaaggactg ccctgtctct tcttacaacg
```

-continued

```
541   aatgggaccc cttagaggaa gtgatagtgg gcagagcaga aaacgcctgt gttccaccgt
601   tcaccatcga ggtgaaggcc aacacatatg aaaagtactg gccattttac cagaagcaag
661   gagggcatta ttttcccaaa gatcatttga aaaaggctgt tgctgaaatt gaagaaatgt
721   gcaatatttt aaaaacggaa ggagtgacag taaggaggcc tgaccccatt gactggtcat
781   tgaagtataa aactcctgat tttgagtcta cgggtttata cagtgcaatg cctcgagaca
841   tcctgatagt tgtgggcaat gagattatcg aggctcccat ggcatggcgt tcacgcttct
901   ttgagtaccg agcgtacagg tcaattatca aagactactt ccaccgtggc gccaagtgga
961   caacagctcc taagcccaca atggctgatg agctttataa ccaggattat cccatccact
1021  ctgtagaaga cagacacaaa ttggctgctc agggaaaatt tgtgacaact gagtttgagc
1081  catgctttga tgctgctgac ttcattcgag ctggaagaga tatttttgca cagagaagcc
1141  aggttacaaa ctacctaggc attgaatgga tgcgtaggca tcttgctcca gactacagag
1201  tgcatatcat ctcctttaaa gatcccaatc ccatgcatat tgatgctacc ttcaacatca
1261  ttggacctgg tattgtgctt tccaaccctg accgaccatg tcaccagatt gatcttttca
1321  agaaagcagg atggactatc attactcctc caacaccaat catcccagac gatcatccac
1381  tctggatgtc atccaaatgg ctttccatga atgtcttaat gctagatgaa aaacgtgtta
1441  tggtggatgc caatgaagtt ccaattcaaa agatgtttga aaagctgggt atcactacca
1501  ctaaagttaa cattcgcaat gccaattccc tgggaggagg cttccattgc tggacctgcg
1561  atgtccggcg ccgaggcacc ttacagtcct acttggactg aacaggcctg atggagcttg
1621  tggctggcct cagatacacc taagaagctt aggggcaagg ttcattctcc tgctttaaaa
1681  agtgcatgaa ctgtagtgct ttaaacaatc atctccttaa caggggtcgt aagcctggtt
1741  tgcttctatt acttttcttt gacataaaga aaataacttc tgctaggtat tactctctac
1801  tcctaaagtt acctactatc tggcttcaag tataaaattt tggtgaatgt gtaccaagaa
1861  aaaattagtc acctgagtaa cttggccact aataattaac catctacctc tgtttttaat
1921  tttctttcca aaaggcagct tgaaatgttg gtcctaatct taattttttt tcctcttcta
1981  tagacttgag aatgtttttc tctaaatgag agaaagactt agaatgtaca cagatccaaa
2041  atagaatcag attatctctt tttttctaaa ggagagaaag acttagaaca tacacagatc
2101  ctaagtagaa ccaggtaatt gtcccttttt ctaataagga atttgggtaa tttttaattt
2161  tttgtttttt aaaaaataac ctagactatg caaaacatca aagtgaattt tccatgaatg
2221  tttttaatat tctcatctca acattgtgat atatgctact aaaaaccttt tcatatacat
2281  cttacctcat ttcaagtgaa ttattttaat ctttttctct ctttccaaaa atttaggaat
2341  gtttagtgta attggatttc gctatcagtt cccatcctta agttttgata ttcaatatct
2401  gatagataca ccgcatcttc ggtcatctaa gatctgttta caaatgtgca aattacttag
2461  agcatagact ttataagcat taaaaaaaac taatggaggt aaaacctaaa tgcgatgtga
2521  aataatttta gtgttgatac cgtatgtgta tttttattct aataaacttt tgtgttccag
2581  attgaaaaaa aaaaaaaaaa aa
```

One example of a nucleic acid sequence for human HGD is available as NCBI accession number NM_000187 (gi: 115527116). This sequence is recited below for easy reference as SEQ ID NO:142.

```
   1 ccacagttcc tttccccgat agcttcaaat tctctgcctt ttgaaataag cctactttta
  61 actggaataa ataattggtc aatctctacc tcaggtgaag aggaaccaag cctctggaaa
 121 cacttaggaa caaactgtaa aaaccaaagg caattgtgta accggttaaa taagcttgct
 181 ggactttgtc cctgtgtatg agttagacaa ttctttcagc tagtttgagt gacgcactga
 241 ccagtgaagc gcagtgaagc agtgggaacc ggaatatcca aagagtggtt tgaaggagaa
 301 agaagcattg tggctttata tcctctgggc ctgggtttcc tgaagtcacc acacatagag
 361 gagagagaaa atggctgagt taaagtacat ttctggattt gggaatgagt gttcttcaga
 421 ggatcctcgc tgcccaggtt ccctgccaga aggacagaat aatcctcagg tctgccccta
 481 caatctctat gctgagcagc tctcaggatc ggctttcact tgtccacgga gcaccaataa
 541 gagaagctgg ctgtatagga ttctaccttc agtttctcac aagcccttcg aatccattga
 601 cgaaggccaa gtcactcaca actgggatga agttgatcct gatcctaacc agcttagatg
 661 gaaaccattt gagattccaa aagcatctca gaagaaagta gactttgtga gtggcctgca
 721 taccttgtgt ggagctggag acataaagtc taacaatggg cttgctatcc acattttcct
 781 ctgcaatacc tccatggaga acagatgctt ttacaattca gatggggact tcttgattgt
 841 tccgcagaaa gggaaccttc tcatttacac cgagtttggc aagatgcttg tacagcccaa
 901 tgagatctgc gtcattcaga gaggaatgcg gttcagcata gatgtctttg aggagaccag
 961 gggctacatc ttggaggtct atggtgtcca ctttgagtta cctgaccttg gaccaattgg
1021 ggccaatggc ttggccaatc ctcgtgattt cttgataccc attgcctggt atgaggatcg
1081 ccaagtacca ggtggttaca cggtcattaa taaataccag ggcaagctgt ttgctgccaa
1141 acaggatgtc tccccgttca atgttgcggc ctggcacggg aattatacac cctacaagta
1201 caacctgaag aatttcatgg ttatcaactc agtggccttt gaccatgcag acccatccat
1261 tttcacagta ttgactgcta agtctgtccg ccctggagtg gccattgctg attttgtcat
1321 cttcccacct cgatgggggg ttgctgataa gaccttcagg cctcccttatt accataggaa
1381 ctgcatgagt gagttcatgg gactcatccg aggtcactat gaggcaaagc aaggtgggtt
1441 cctgccaggg ggagggagtc tacacagcac aatgaccccc catggacctg acgctgactg
1501 ctttgagaag gccagcaagg tcaagctggc acctgagagg attgccgatg gcaccatggc
1561 atttatgttt gaatcatctt taagtctggc ggtcacaaag tggggactca aggcctccag
1621 gtgtttggat gagaactacc acaagtgctg ggagccactc aagagccact tcactcccaa
1681 ctccaggaac ccagcagaac ctaattgaga ctggaacatt gctaccataa ttaagagtag
1741 atttgtgaag atttcttcag aatctcatgc tttctggtag tattggagga gggggttggt
1801 taaaatgaaa attcactttt catagtcaag taactcagaa cttttatgga aacgcatttg
1861 caaagttcta tggctgtcac cttaattact caataaactt gctggtgttc tgtggacgta
```

One example of a nucleic acid sequence for human HMGA2 is available as NCBI accession number NM_003483 (gi: 62912480). This sequence is recited below for easy reference as SEQ ID NO: 143.

```
   1  cttgaatctt ggggcaggaa ctcagaaaac ttccagcccg ggcagcgcgc gcttggtgca
  61  agactcagga gctagcagcc cgcccccctc cgactctccg gtgccgccgc tgcctgctcc
 121  cgccacccta ggaggcgcgg tgccacccac tactctgtcc tctgcctgtg ctccgtgccc
 181  gaccctatcc cggcggagtc tccccatcct cctttgcttt ccgactgccc aaggcacttt
 241  caatctcaat ctcttctctc tctctccctc tctctctctc tctctctctc tctctctctc
 301  tctccctctc gcagggtggg gggaagagga ggaggaattc cctccccgcc taacatttca
 381  agggacacaa ttcactccaa gtctcttccc tttccaagcc gcttccgaag tgctcccggt
 421  gcccgcaact cctgatccca acccgcgaga ggagcctctg cgacctcaaa gcctctcttc
 481  cttctccctc gcttccctcc tcctcttgct acctccacct ccaccgccac ctccacctcc
 541  ggcacccacc caccgccgcc gccgccaccg gcagcgcctc ctcctctcct cctcctcctc
 601  ccctcttctc tttttggcag ccgctggacg tccggtgttg atggtggcag cggcggcagc
 661  ctaagcaaca gcagccctcg cagcccgcca gctcgcgctc gccccgccgg cgtccccagc
 721  cctatcacct catctcccga aaggtgctgg gcagctccgg ggcggtcgag gcgaagcggc
 781  tgcagcggcg gtagcggcgg cgggaggcag gatgagcgca cgcggtgagg gcgcggggca
 841  gccgtccact tcagcccagg gacaacctgc cgccccagcg cctcagaaga gaggacgcgg
 901  ccgccccagg aagcagcagc aagaaccaac cggtgagccc tctcctaaga gacccagggg
 961  aagacccaaa ggcagcaaaa acaagagtcc ctccaaagca gctcaaaaga aagcagaagc
1021  cactggagaa aaacggccaa gaggcagacc taggaaatgg ccacaacaag ttgttcagaa
1081  gaagcctgct caggaggaaa ctgaagagac atcctcacaa gagtctgccg aagaggacta
1141  gggggcgcca acgttcgatt tctacctcag cagcagttgg atcttttgaa gggagaagac
1201  actgcagtga ccactcattc tgtattgcca tggtcttccc actttcatct ggggtggggt
1261  ggggtggggc gggggagggg ggggtggggt ggggagaaat cacataacct taaaaaggac
1321  tatattaatc accttctttg taatcccttc acagtcccag gtttagtgaa aaactgctgt
1381  aaacacaggg gacacagctt aacaatgcaa cttttaatta ctgttttctt ttttcttaac
1441  ctactaatag tttgttgatc tgataagcaa gagtgggcgg gtgagaaaaa ccgaattggg
1501  tttagccaat cactgcactg catgcaaaca agaaacgtgt cacacttgtg acgtcgggca
1561  ttcatatagg aagaacgcgg tgtgtaacac tgtgtacacc ccaaatacca ccccaaccca
1621  ctccctgtag tgaatcctct gtttagaaca ccaaagataa ggactagata ctactttctc
1681  tttttcgtat aatcttgtag acacttactt gatgattttt aactttttat ttctaaatga
1741  gacgaaatgc tgatgtatcc tttcattcag ctaacaaact agaaaaggtt atgttcattt
1801  ttcaaaaagg gaagtaagca aacaaatatt gccaactcct ctatttatgg atatcacaca
1861  tatcagcagg agtaacaaat ttactcacag cacttgtttt caggacaaca cctcattttc
1921  aggaaatcta cttcctacag agccaaaatg ccatttagca ataaataaca cttgtcagcc
1981  tcagagcatt taaggaaact agacaagtaa aattatcctc tttgtaattt aatgaaaagg
2041  tacaacagaa taatgcatga tgaactcacc taactatgag gtgggaggag cgaaatctaa
2101  atttcttttg ctatagttat acatcaattt aaaaagcaaa aaaaaaaaag gggggggcaa
2161  tctctctctg tgtctttctc tctctccctt cctctccctc cctcttttca ttgtgtatca
2221  gtttccatga aagacctgaa taccacttac ctcaaattaa gcatatgtgt tacttcaagt
```

-continued

```
2281   aatacgtttt gacataagat ggttgaccaa ggtgcttttc ttcggcttga gttcaccatc
2341   tcttcattca aactgcactt ttagccagag atgcaatata tccccactac tcaatactac
2401   ctctgaatgt tacaacgaat ttacagtcta gtacttacta catgctgcta tacacaagca
2461   atgcaagaaa aaaacccact gggcaggtga ttctaatcat ctgcagttct tcttgtacac
2521   ttaattacag ttaaagaagc aatctcctta ctgtgtttca gcatgactat gtatttttct
2581   atgttttttt aattaaaaat ttttaaaata cttgtttcag cttctctgct agatttctac
2641   attaacttga aaatttttta accaagtcgc tcctaggttc ttaaggataa ttttcctcaa
2701   tcacactaca catcacacaa gatttgactg taatatttaa atattaccct ccaagtctgt
2761   acctcaaatg aattctttaa ggagatggac taattgactt gcaaagacct acctccagac
2821   ctcaaaagga atgaacttgt tacttgcagc attcatttgt tttttcaatg tttgaaatag
2881   ttcaaactgc agctaaccct agtcaaaact atttttgtaa aagacatttg atagaaagga
2941   acacgttttt acatactttt gcaaaataag caaataacaa ataaaataaa agccaacctc
3001   caaagaaact tgaagctttg taggcgagat gcaacaagcc ctgctcttgc ataatgcaat
3061   caaaaatatg tgtttttaag attagttgaa tataagaaaa tgcttgacaa atattttcat
3121   gtattttaca caaatgtgat ttttgtaata tgtctcaacc agatttattt taaacgcttc
3181   ttatgtagag tttttatgcc tttctctcct agtgsgtgtg ctgacttttt aacatggtat
3241   tatcaactgg gccaggaggt agtttctcat gacggctttt gtcagtatgg cttttagtac
3301   tgaagccaaa tgaaactcaa aaccatctct cttccagctg cttcagggag gtagtttcaa
3361   aggccacata cctctctgag actggcagat cgctcactgt tgtgaatcac caaaggagct
3421   atggagagaa ttaaaactca acattactgt taactgtgcg ttaaataagc aaataaacag
3481   cggctcataa aaataaaagt cgcattccat atctttggat gggcctttta gaaacctcat
3541   cggccagccc ataaaatgga agcaattgct catgttggcc aaacatggtg caccgagtga
3601   tttccatctc tggtaaagtt acacttttat ttcctgtatg ttgtacaatc aaaacacact
3661   actacctctt aagtcccagt atacctcatt tttcatactg aaaaaaaaag cttgtggcca
3721   atggaacagt aagaacatca taaaattttt atatatatag tttattttcg tgggagataa
3781   atttcatagg actgttcttc gctgttgttg gtcgcagcta cataagactg gacatttaac
3841   ttttctacca tctctgcaag ttaggtatgt ttgcaggaga aaagtatcaa gacgtctaac
3901   tgcagttgac tttctccctg ttcctttgag tgtcttctaa ctttattctt tgttctttat
3961   gtagaattgc tgtctatgat tgtactttga atcgcttgct tgttgaaaat atttctctag
4021   cgtattatca ctgtctgttc tgcacaataa acataacagc ctctgtgatc cccatgtgtt
4081   ttgattcctg ctctttgtta cagttccatt aaatgagtaa taaagtttgg tcaaaacaga
4141   aaaaaaaaaa
```

One example of a nucleic acid sequence for human IGFBP6 is available as NCBI accession number NM_002178 (gi: 49574524). This sequence is recited below for easy reference as SEQ ID NO: 144.

```
  1   gcggcggcgg gcagcagctg cgctgcgact gctctggaag gagaggacgg ggcacaaacc
 61   ctgaccatga ccccccacag gctgctgcca ccgctgctgc tgctgctagc tctgctgctc
121   gctgccagcc caggaggcgc cttggcgcgg tgcccaggct gcgggcaagg ggtgcaggcg
181   ggttgtccag gggctgcgt ggaggaggag gatgggggt cgccagccga gggctgcgcg
```

-continued

```
241  gaagctgagg gctgtctcag gagggagggg caggagtgcg gggtctacac ccctaactgc
301  gccccaggac tgcagtgcca tccgcccaag gacgacgagg cgcctttgcg ggcgccgctg
361  ctcggccgag gccgctgcct tccggcccgc gcgcctgctg ttgcagagga gaatcctaag
421  gagagtaaac cccaagcagg cactgcccgc ccacaggatg cgaaccgcag agaccaacag
481  aggaatccag gcacctctac cacgccctcc cagcccaatt ctgcgggtgt ccaagacact
541  gagatgggcc catgccgtag acatctggac tcagtgctgc agcaactcca gactgaggtc
601  taccgagggg ctcaaacact ctacgtgccc aattgtgacc atcgaggctt ctaccggaag
661  cggcagtgcc gctcctccca ggggcagcgc cgaggtccct gctggtgtgt ggatcggatg
721  ggcaagtccc tgccagggtc tccagatggc aatggaagct cctcctgccc cactgggagc
781  agcggctaaa gctgggggat agagggggctg cagggccact ggaaggaaca tggagctgtc
841  atcactcaac aaaaaaccga ggccctcaat ccaccttcag gccccgcccc atgggcccct
901  caccgctggt tggaaagagt gttggtgttg gctggggtgt caataaagct gtgcttgggg
961  tcgccgaaaa aaaaaaaaaa
```

One example of a nucleic acid sequence for human KIT is available as NCBI accession number NM_000222 (gi: 148005048). This sequence is recited below for easy reference as SEQ ID NO: 145.

```
   1  tctgggggct cggctttgcc gcgctcgctg cacttgggcg agagctggaa cgtggaccag
  61  agctcggatc ccatcgcagc taccgcgatg agaggcgctc gcggcgcctg ggattttctc
 121  tgcgttctgc tcctactgcc tcgcgtccag acaggctctt ctcaaccatc tgtgagtcca
 181  ggggaaccgt ctccaccatc catccatcca ggaaaatcag acttaatagt ccgcgtgggc
 241  gacgagatta ggctgttatg cactgatccg ggctttgtca aatggacttt tgagatcctg
 301  gatgaaacga atgagaataa gcagaatgaa tggatcacgg aaaaggcaga agccaccaac
 361  accggcaaat acacgtgcac caacaaacac ggcttaagca attccattta tgtgtttgtt
 421  agagatcctg ccaagctttt ccttgttgac cgctccttgt atgggaaaga agacaacgac
 481  acgctggtcc gctgtcctct cacagaccca gaagtgacca attattccct caaggggtgc
 541  caggggaagc ctcttcccaa ggacttgagg tttattcctg accccaaggc gggcatcatg
 601  atcaaaagtg tgaaacgcgc ctaccatcgg ctctgtctgc attgttctgt ggaccaggag
 661  ggcaagtcag tgctgtcgga aaaattcatc ctgaaagtga ggccagcctt caaagctgtg
 721  cctgctgtgt ccgtgtccaa agcaagctat cttcttaggg aaggggaaga attcacagtg
 781  acgtgcacaa taaaagatgt gtctagttct gtgtactcaa cgtggaaaag agaaaacagt
 841  cagactaaac tacaggagaa atataatagc tggcatcacg gtgacttcaa ttatgaacgt
 901  caggcaacgt tgactatcag ttcagcgaga gttaatgact ctggagtgtt catgtgttac
 961  gccaataata cttttggatc agcaaatgtc acaacaacct tggaagtagt agataaagga
1021  ttcattaata tcttccccat gacaaacact acagtatccg taaacgatgg agaaaatgta
1081  gatttgattg ttgaatatga agcattcccc aaacctgaac accagcagtg gatctatatg
1141  aacagaacct tcactgataa atgggaagat tatcccaagt ctgagaatga aagtaatatc
1201  agatacgtaa gtgaacttca tctaacgaga ttaaaaggca ccgaaggagg cacttacaca
1261  ttcctagtgt ccaattctga cgtcaatgct gccatagcat ttaatgttta tgtgaataca
1321  aaaccagaaa tcctgactta cgacaggctc gtgaatggca tgctccaatg tgtggcagca
1381  ggattcccag agcccacaat agattggtat ttttgtccag gaactgagca gagatgctct
```

-continued 1441 gcttctgtac tgccagtgga tgtgcagaca ctaaactcat ctgggccacc gtttggaaag
1501 ctagtggttc agagttctat agattctagt gcattcaagc acaatggcac ggttgaatgt
1561 aaggcttaca acgatgtggg caagacttct gcctatttta actttgcatt taaaggtaac
1621 aacaaagagc aaatccatcc ccacaccctg ttcactcctt tgctgattgg tttcgtaatc
1681 gtagctggca tgatgtgcat tattgtgatg attctgacct acaaatattt acagaaaccc
1741 atgtatgaag tacagtggaa ggttgttgag gagataaatg gaaacaatta tgtttacata
1801 gacccaacac aacttcctta tgatcacaaa tgggagtttc ccagaaacag gctgagtttt
1861 gggaaaaccc tgggtgctgg agctttcggg aaggttgttg aggcaactgc ttatggctta
1921 attaagtcag atgcggccat gactgtcgct gtaaagatgc ccaagccgag tgcccacttg
1981 acagaacggg aagccctcat gtctgaactc aaagtcctga gttaccttgg taatcacatg
2041 aatattgtga atctacttgg agcctgcacc attggagggc ccaccctggt cattacagaa
2101 tattgttgct atggtgatct tttgaatttt ttgagaagaa aacgtgattc atttatttgt
2161 tcaaagcagg aagatcatgc agaagctgca ctttataaga atcttctgca ttcaaaggag
2221 tcttcctgca gcgatagtac taatgagtac atggacatga aacctggagt ttcttatgtt
2281 gtcccaacca aggccgacaa aaggagatct gtgagaatag gctcatacat agaaagagat
2341 gtgactcccg ccatcatgga ggatgacgag ttggccctag acttagaaga cttgctgagc
2401 ttttcttacc aggtggcaaa gggcatggct ttcctcgcct ccaagaattg tattcacaga
2461 gacttggcag ccagaaatat cctccttact catggtcgga tcacaaagat ttgtgatttt
2521 ggtccagcca gagacatcaa gaatgattct aattatgtgg ttaaaggaaa cgctcgacta
2581 cctgtgaagt ggatggcacc tgaaagcatt ttcaactgtg tatacacgtt tgaaagtgac
2641 gtctggtcct atgggatttt tctttgggag ctgttctctt taggaagcag cccctatcct
2701 ggaatgccgg tcgattctaa gttctacaag atgatcaagg aaggcttccg gatgctcagc
2761 cctgaacacg cacctgctga aacgtatgac ataatgaaga cttgctggga tgcagatccc
2821 ctaaaaagac caacactcaa gcaaattgtt cagctaaccg agaagcagat ttcagagagc
2881 accaatcata tttactccaa cttagcaaac tgcagcccca accgacagaa gcccgtggta
2941 gaccattctg tgcggatcaa ttctgtcggc agcaccgctt cctcctccca gcctctgctt
3001 gtgcacgacg atgtctgagc agaatcagtg tttgggtcac ccctccagga atgatctctt
3061 cttttggctt ccatgatggt tattttcttt tctttcaact tgcatccaac tccaggatag
3121 tgggcacccc actgcaatcc tgtctttctg agcacacttt agtggccgat gatttttgtc
3181 atcagccacc atcctattgc aaaggttcca actgtatata ttcccaatag caacgtagct
3241 tctaccatga acagaaaaca ttctgatttg gaaaaagaga gggaggtatg gactgggggc
3301 cagagtcctt tccaaggctt ctccaattct gcccaaaaat atggttgata gtttacctga
3361 ataaatggta gtaatcacag ttggccttca gaaccatcca tagtagtatg atgatacaag
3421 attagaagct gaaaacctaa gtcctttatg tggaaaacag aacaccatta gaacaaagga
3481 cagagtatga acacctgggc ttaagaaatc tagtatttca tgctgggaat gagacatagg
3541 ccatgaaaaa aatgatcccc aagtgtgaac aaaagatgct cttctgtgga ccactgcatg
3601 agcttttata ctaccgacct ggtttttaaa tagagtttgc tattagagca ttgaattgga
3661 gagaaggcct ccctagccag cacttgtata tacgcatcta taaattgtcc gtgttcatac
3721 atttgagggg aaaacaccat aaggtttcgt ttctgtatac aaccctggca ttatgtccac
3781 tgtgtataga agtagattaa gagccatata agtttgaagg aaacagttaa taccattttt -continued

```
3841  taaggaaaca atataaccac aaagcacagt ttgaacaaaa tctcctcttt tagctgatga
3901  acttattctg tagattctgt ggaacaagcc tatcagcttc agaatggcat tgtactcaat
3961  ggatttgatg ctgtttgaca aagttactga ttcactgcat ggctcccaca ggagtgggaa
4021  aacactgcca tcttagtttg gattcttatg tagcaggaaa taaagtatag gtttagcctc
4081  cttcgcaggc atgtcctgga caccgggcca gtatctatat atgtgtatgt acgtttgtat
4141  gtgtgtagac aaatatttgg aggggtattt ttgccctgag tccaagaggg tcctttagta
4201  cctgaaaagt aacttggctt tcattattag tactgctctt gtttcttttc acatagctgt
4261  ctagagtagc ttaccagaag cttccatagt ggtgcagagg aagtggaagg catcagtccc
4321  tatgtatttg cagttcacct gcacttaagg cactctgcta tttagactca tcttactgta
4381  cctgttcctt agaccttcca taatgctact gtctcaccga aacatttaaa tcttaccctt
4441  cagactgtag cctggatatt attcttgtag tttacctctt taaaaacaaa acaaaacaaa
4501  acaaaaaact ccccttcctc actgcccaat ataaaaggca aatgtgtaca tggcagagtt
4561  tgtgtgttgt cttgaaagat tcaggtatgt tgcctttatg gtttcccccct tctacatttc
4621  ttagactaca tttagagaac tgtggccgtt atctggaagt aaccatttgc actggagttc
4681  tatgctctcg cacctttcca aagttaacag attttggggt tgtgttgtca cccaagagat
4741  tgttgtttgc catactttgt ctgaaaaatt cctttgtgtt tctattgacc tcaatgatag
4801  taagaaaagt ggttgttagt tatagatgtc taggtacttc aggggcactt cattgagagt
4861  tttgtcttgg atattcttga aagtttatat ttttataatt ttttcttaca tcagatgttt
4921  ctttgcagtg gcttaatgtt tgaaattatt ttgtggcttt ttttgtaaat attgaaatgt
4981  agcaataatg tcttttgaat attcccaagc ccatgagtcc ttgaaaatat tttttatata
5041  cacagtaact ttatgtgtaa atacataagc ggcgtaagtt taaaggatgt tggtgttcca
5101  cgtgttttat tcctgtatgt tgtccaattg ttgacagttc tgaagaattc taataaaatg
5161  tacatatata aatcaaaaaa aaaaaaaaaa
```

One example of a nucleic acid sequence for human LRP4 is available as NCBI accession number NM_002334 (gi: 157384997). This sequence is recited below for easy reference as SEQ ID NO: 146.

```
   1  gcggcggcgg cccgagggcg acttgcgggg cgcgcaggcc gccgtgcacc cgggacgctt
  61  ccccctcggg gaccctccgc gggcttctcc gccgcgccgt ccggcgggag ccggcgggac
 121  cccgggcgag cggcgcgggc ggcaccatga ggcggcagtg gggcgcgctg ctgcttggcg
 181  ccctgctctg cgcacacggc ctggccagca gccccgagtg tgcttgtggc cggagccact
 241  tcscatgtgc agtgagtgct cttggagagt gtacctgcat ccctgcccag tggcagtgtg
 301  atggagacaa tgactgcggg gaccacagcg atgaggatgg atgtatacta cctacctgtt
 361  cccctcttga ctttcactgt gacaatggca agtgcatccg ccgctcctgg gtgtgtgacg
 421  gggacaacga ctgtgaggat gactcggatg agcaggactg tccccccccgg gagtgtgagg
 481  aggacgagtt tccctgccag aatggctact gcatccggag tctgtggcac tgcgatggtg
 541  acaatgactg tggcgacaac agcgatgagc agtgtgacat gcgcaagtgc tccgacaagg
 601  agttccgccg tagtgacgga agctgcattg ctgagcattg gtactgcgac ggtgacaccg
 661  actgcaaaga tggctccgat gaggagaact gtccctcagc agtgccagcg ccccccctgca
 721  acctggagga gttccagtgt gcctatggac gctgcatcct cgacatctac cactgcgatg
 781  gcgacgatga ctgtggagac tggtcagacg agtctgactg ctcctcccac cagccctgcc
```

-continued 841 gctctgggga gttcatgtgt gacagtggcc tgtgcatcaa tgcaggctgg cgctgcgatg 901 gtgacgcgga ctgtgatgac cagtctgatg agcgcaactg caccacctcc atgtgtacgg 961 cagaacagtt ccgctgtcac tcaggccgct gtgtccgcct gtcctggcgc tgtgatgggg 1021 aggacgactg tgcagacaac agcgatgaag agaactgtga gaatacagga agcccccaat 1081 gtgccttgga ccagttcctg tgttggaatg ggcgctgcat tgggcagagg aagctgtgca 1141 acggggtcaa cgactgtggt gacaacagcg acgaaagccc acagcagaat tgccggcccc 1201 ggacgggtga ggagaactgc aatgttaaca acggtggctg tgcccagaag tgccagatgg 1261 tgcgggggc agtgcagtgt acctgccaca caggctaccg gctcacagag qatgggcaca 1321 cgtgccaaga tgtgaatgaa tgtgccgagg aggggtattg cagccagggc tgcaccaaca 1381 gcgaaggggc tttccaatgc tggtgtgaaa caggctatga actacggccc gaccggcgca 1441 gctgcaaggc tctggggcca gagcctgtgc tgctgttcgc caatcgcatc gacatccggc 1501 aggtgctgcc acaccgctct gagtacacac tgctgcttaa caacctggag aatgccattg 1561 cccttgatct ccaccaccgc cgcgagcttg tcttctggtc agatgtcacc ctggaccgga 1621 tcctccgtgc caacctcaac ggcagcaacg tggaggaggt tgtgtctact gggctggaga 1681 gcccaggggg cctggccgtg gattgggtcc atgacaaact ctaccggacc gactcaggca 1741 cctcgaggat tgaggtggcc aatctggatg ggcccaccg gaaagtgttg ctgtggcaga 1801 acctggagaa gccccgggcc attgccttgc atcccatgga gggtaccatt tactggacag 1861 actggggcaa cacccccgt attgaggcct ccagcatgga tggctctgga cgccgcatca 1921 ttgccgatac ccatctcttc tggcccaatg gcctcaccat cgactatgcc gggcgccgta 1981 tgtactgggt ggatgctaag caccatgtca tcgagagggc caatctggat gggagtcacc 2041 gtaaggctgt cattagccag ggcctcccgc atcccttcgc catcacagtg tttgaagaca 2101 gcctgtactg gacagactgg cacaccaaga gcatcaatag cgctaacaaa tttacgggga 2161 agaaccagga aatcattcgc aacaaactcc acttccctat ggacatccac accttgcacc 2221 cccagcgcca acctgcaggg aaaaaccgct gtggggacaa caacggaggc tgcacgcacc 2281 tgtgtctgcc cagtggccag aactacacct gtgcctgccc cactggcttc cgcaagatca 2341 gcagccacgc ctgtgcccag agtcttgaca agttcctgct tttgcccga aggatggaca 2401 tccgtcgaat cagctttgac acagaggacc tgtctgatga tgtcatccca ctggctgacg 2461 tgcgcagtgc tgtggccctt gactgggact cccgggatga ccacgtgtac tggacagatg 2521 tcagcactga taccatcagc agggccaagt gggatggaac aggacaggag gtggtagtgg 2581 ataccagttt ggagagccca gctggcctgg ccactgattg ggtcaccaac aaactgtact 2641 ggacagatgc aggtacagac cggattgaag tagccaacac agatggcagc atgagaacag 2701 tactcatctg ggagaacctt gatcgtcctc gggacatcgt ggtggaaccc atgggcgggt 2761 acatgtattg gactgactgg ggtgcgagcc ccaagattga acgagctggc atggatgcct 2821 caggccgcca agtcattatc tcttctaatc tgacctggcc taatgggtta gctattgatt 2881 atgggtccca gcgtccatac tgggctgacg ccggcatgaa gacaattgaa tctgctggac 2941 tggatggcag taagaggaag gtgctgattg gaagccagct cccccaccca tttgggctga 3001 ccctctatgg agagcgcatc tattggactg actggcagac caagagcata cagagcgctg 3061 accggctgac agggctggac cgggagactc tgcaggagaa cctggaaaac ctaatggaca 3121 tccatgtctt ccaccgccgc cggcccccag tgtctacacc atgtgctatg gagaatggcg 3181 gctgtagcca cctgtgtctt aggtccccaa atccaagcgg actcagctgc acctgcccca -continued 3241 caggcatcaa cctgctgtct gatggcaaga cctgctcacc aggcatgaac agtttcctca 3301 tcttcgccag gaggatagac attcgcatgg tctccctgga catcccttat tttgctgatg 3361 tggtggtacc aatcaacatt accatgaaga acaccattgc cattggagta gacccccagg 3421 aaggaaaggt gtactggtct gacagcacac tgcacaggat cagtcgtgcc aatctggatg 3481 gctcacagca tgaggacatc atcaccacag ggctacagac cacagatggg cccgcggttg 3541 atgccattgg ccggaaagta tactggacag acacgggaac aaaccggatt gaagtgggca 3601 acctggacgg gtccatgcgg aaagtgttgg tgtggcagaa ccttgacagt ccccgggcca 3661 tcgtactgta ccatgagatg gggtttatgt actggacaga ctgggggggag aatgccaagt 3721 tagagcggtc cggaatggat ggctcagacc gcgcggtgct catcaacaac aacctaggat 3781 ggcccaatgg actgactgtg gacaaggcca gctcccaact gctatgggcc gatgcccaca 3841 ccgagcgaat tgaggctgct gacctgaatg gtgccaatcg gcatacattg gtgtcaccgg 3901 tgcagcaccc atatggcctc accctgctcg actcctatat ctactggact gactggcaga 3961 ctcggagcat ccaccgtgct gacaagggta ctggcagcaa tgtcatcctc gtgaggtcca 4021 acctgccagg cctcatggac atgcaggctg tggaccgggc acagccacta ggttttaaca 4081 agtgcggccc gagaaacggc ggctgctccc acctctgctt gcctcggcct cctggcttcc 4141 cctgtgcccg ccccactggc atccagctga agggagatgg gaagacctgt gatccctctc 4201 ctgagaccta cctgctcttc tccagccgtg gctccatccg gcgtatctca ctggacacca 4261 gtgaccacac cgatgtgcat gtccctgttc ctgagctcaa caatgtcatc tccctggact 4321 atgacagcgt ggatggaaag gtctattaca cagatgtgtt cctggatgtt atcaggcgag 4381 cagacctgaa cggcagcaac atggagacag tgaccgggcg agggctgaag accactgacg 4441 ggctggcagt ggactgggtg gccaggaacc tgtactggac agacacaggt cgaaatacca 4501 ttgaggcgtc caggctggat ggttcctgcc gcaaagtact gatcaacaat agcctggatg 4561 agccccgggc cattgctgtt ttccccagga aggggtacct cttctggaca gactggggcc 4621 acattgccaa gatcgaacgg gcaaacttgg atggttctga gcggaaggtc ctcatcaaca 4681 cagacctggg ttggcccaat ggccttaccc tggactatga tacccgcagg acctactggg 4741 tggatgcgca tctggaccgg atcgagagtg ctgacctcaa tgggaaactg cggcaggtct 4801 tggtcagcca tgtgtcccac ccctttgccc tcacacagca agacaggtgg atctactgga 4861 cagactggca gaccaagtca atccagcgtg ttgacaaata ctcaggccgg aacaaggaga 4921 cagtgctggc aaatgtggaa ggactcatgg atatcatcgt ggtttcccct cagcggcaga 4981 cagggaccaa tgcctgtggt gtgaacaatg gtggctgcac ccacctctgc tttgccagag 5041 cctcggactt cgtatgtgcc tgtcctgacg aacctgatag ccggccctgc tcccttgtgc 5101 ctggcctggt accaccagct cctagggcta ctggcatgag tgaaaagagc ccagtgctac 5161 ccaacacacc acctaccacc ttgtattctt caaccacccg gacccgcacg tctctggagg 5221 aggtggaagg aagatgctct gaaagggatg ccaggctggg cctctgtgca cgttccaatg 5281 acgctgttcc tgctgctcca ggggaaggac ttcatatcag ctacgccatt ggtggactcc 5341 tcagtattct gctgattttg gtggtgattg cagctttgat gctgtacaga cacaaaaaat 5401 ccaagttcac tgatcctgga atggggascc tcacctacag caacccctcc taccgaacat 5461 ccacacagga agtgaagatt gaagcaatcc ccaaaccagc catgtacaac cagctgtgct 5521 ataagaaaga gggagggcct gaccataact acaccaagga gaagatcaag atcgtagagg 5581 gaatctgcct cctgtctggg gatgatgctg agtgggatga cctcaagcaa ctgcgaagct 5641 cacggggggg cctcccccgg gatcatgtat gcatgaagac agacacggtg tccatccagg -continued

```
5701   ccagctctgg ctccccggat gacacagaga cggagcagct gttacaggaa gagcagtctg
5761   agtgtagcag cgtccatact gcagccactc cagaaagacg aggctctctg ccagacacgg
5821   gctggaaaca tgaacgcaag ctctcctcag agagccaggt ctaaatgccc acattctctt
5881   ccctgcctgc ctgttccttc tcctttatgg acgtctagtc cttgtgctcg cttacaccgc
5941   aggccccgct tctgtgtgct tgtcctcctc ctcctcccac cccataactg ttcctaagcc
6001   ttcaccggag ctgtttacca cgtgagccca taactacctg cgcacaagaa atgatggcac
6061   atcacgagaa tttagacctg gattttacca tgaacctcac atcttgtact ccatcctggg
6121   ccccctgaaa ctgcttattc gtgattcctc accagcgtag agctccacct cccctttccc
6181   cagtaccctc agtgcctgct tctcagtgct gatgcagctg atgacccagg actgcgctct
6241   gccccatcac agccagcatg actgcttctc tgagagaact tgcccatcag ggctgggac
6301   atgggggtgt gggtaaagac agggatgaag gatagaggct gagagaagaa ggaagaatca
6361   gcccagcagg tatgggcatc tgggaaacct ccagcctcaa gtgtgttggt aacatgaaaa
6421   agctttgggg ggtagttgga tctgggtgtc tggtccattg ctggcagtgg acattattct
6481   tgccctaaga gacactgcct tttcagcagc agatactggt gagatggggg tggctcaggc
6541   tgttcttcct cctcctagaa tgtctggagc tgtttctaca ttcagataac tgggtcccct
6601   atcacaaggc tactggctaa taggaactcc ctcccggtgc caccactggc cagtaccttt
6661   cctaagtctt tgctcaaatt aaccaggttg tgagccagtg gcttgagtga atgttaggcc
6721   ttgggggctg agtctctgaa aagtctaaga agctctgcct agaccaaata tggtatacct
6781   cctgacccct ctctccctca tgtcctggga ttctggggaa gagacctaga aacaagcttt
6841   caaagaaaaa ccagaagttg tcataaatgg tcagaaagaa cgatcaggtt ggagacttgg
6901   gaaacccagg gcctaaagag aagtatccat gagggtcaaa cttcctgttg aacttcctat
6961   gttctttctc aagtgctcag ggatctaagt tagtggacag caagcctgtg gctacggggt
7021   ggtgatgttc ctcttccagc tgtcccctca gctaaggggc ttagtttcca tgtgggatgc
7081   catcacttgg ttcatgctca ttcacacaaa gggcacgtgt ctcagcctgg tatcagggaa
7141   attgagactt atttttgccc taaaacgtct ccctagctgt tcttcgtggg gttttttttgt
7201   ttgtcttttt gcctaatttg ctttttctga ccaagccttg tggcaccagc aatctccaaa
7261   gtcctgtggt gggagggctg aataaataaa aatacaaaga ggtgggtaag gagtaggaag
7321   gtagagagca ccactgatga ggccctccta gcccatggca gacccagacc tcttctcccc
7381   caggaattag aagtggcagg agagaacaac aggggctggg aatggagggg agaatttcta
7441   ggggaagttc cctgagttga aacttctcct gtggttactg gtattgagaa atcagctacc
7501   aaagtgaaaa aggacaagat caactctttt ctagtcagtt ctaagactgc tagagagaga
7561   taccaggccc ttagccttgc tctcagtagc gtcagcccca gttctgagcc tccccacatt
7621   acacttaaca agcagtaaag gagtgagcac tttgggtcct tagactcatg tctggggagg
7681   aagagcaagt agaaaagtgg cattttcttg attggaaagg gggaaggatc ttattgcact
7741   tgggctgttc agaatgtaga aaggacatat ttgaggaagt atctatttga gcactgattt
7801   actctgtaaa aagcaaaatc tctctgtcct aaactaatgg aagcgattct cccatgctca
7861   tgtgtaatgg ttttaacgtt actcactgga gagattggac tttctggagt tatttaacca
7921   ctatgttcag tattttagga ctttatgata atttaatata aatttagctt ttcttaatca
7981   aaaaaaaaaa aaaaaaaa
```

One example of a nucleic acid sequence for human MATN2 is available as NCBI accession number NM_002380 (gi: 62548859). This sequence is recited below for easy reference as SEQ ID NO: 147.

```
   1  gcgagcgaag ggagcgctct gggatgggac ttggagcaag cggcggcggc ggagacagag
  61  gcagaggcag aagctggggc tccgtcctcg cctcccacga gcgatccccg aggagagccg
 121  cggccctcgg cgaggcgaag aggccgacga ggaagacccg ggtggctgcg cccctgcctc
 181  gcttcccagg cgccggcggc tgcagccttg cccctcttgc tcgccttgaa aatggaaaag
 241  atgctcgcag gctgctttct gctgatcctc ggacagatcg tcctcctccc tgcagaggcc
 301  agggagcggt cacgtgggag gtccatctct aggggcagac acgctcggac ccacccgcag
 361  acggcccttc tggagagttc ctgtgagaac aagcgggcag acctggtttt catcattgac
 421  agctctcgca gtgtcaacac ccatgactat gcaaaggcca aggagctcat cgtggacatc
 481  ttgcaattct tggacattgg tcctgatgtc acccgagtgg gcatgctaaa atatggcagc
 541  actgtcaaga atgagttctc cctcaagacc ttcaagagga agtccgaggt ggagcgtgat
 601  gtcaagagga tgcggcatct gtccacgggc accatgactg ggctggccat ccagtatgcc
 661  ctgaacatcg cattctcaga agcagagggg gcccggcccc tgagggagaa tgtgccacgg
 721  gtcataatga tcgtgacaga tgggagacct caggactccg tggccgaggt ggctgctaag
 781  gcacgggaca cgggcatcct aatctttgcc attggtgtgg gccaggtaga cttcaacacc
 841  ttgaagtcca ttgggagtga gccccatgag gaccatgtct tccttgtggc caatttcagc
 901  cagattgaga cgctgacctc cgtgttccag aagaagttgt gcacggccca catgtgcagc
 961  accctggagc ataactgtgc ccacttctgc atcaacatcc ctggctcata cgtctgcagg
1021  tgcaaacaag gctacattct caactcggat cagacgactt gcagaatcca ggatctgtgt
1081  gccatggagg accacaactg tgagcagctc tgtgtgaatg tgccgggctc cttcgtctgc
1141  cagtgctaca gtggctacgc cctggctgag gatgggaaga ggtgtgtggc tgtggactac
1201  tgtgcctcag aaaaccacgg atgtgaacat gagtgtgtaa atgctgatgg ctcctacctt
1261  tgccagtgcc atgaaggatt tgctcttaac ccagataaaa aaacgtgcac aaagatagac
1321  tactgtgcct catctaatca cggatgtcag cacgagtgtg ttaacacaga tgattcctat
1381  tcctgccact gcctgaaagg ctttaccctg aatccagata agaaaacctg cagaaggatc
1441  aactactgtg cactgaacaa accgggctgt gagcatgagt gcgtcaacat ggaggagagc
1501  tactactgcc gctgccaccg tggctacact ctggacccca atggcaaaac ctgcagccga
1561  gtggaccact gtgcacagca ggaccatggc tgtgagcagc tgtgtctgaa cacggaggat
1621  cccttcgtct gccagtgctc agaaggcttc ctcatcaacg aggacctcaa gacctgctcc
1681  cgggtggatt actgcctgct gagtgaccat ggttgtgaat actcctgtgt caacatggac
1741  agatcctttg cctgtcagtg tcctgaggga cacgtgctcc gcagcgatgg gaagacgtgt
1801  gcaaaattgg actcttgtgc tctgggggac cacggttgtg aacattcgtg tgtaagcagt
1861  gaagattcgt ttgtgtgcca gtgctttgaa ggttatatac tccgtgaaga tggaaaaacc
1921  tgcagaagga aagatgtctg ccaagctata gaccatggct gtgaacacat ttgtgtgaac
1981  agtgatgact catacacgtg cgagtgcttg gagggattcc ggctcgctga ggatgggaaa
2G41  cgctgccgaa ggaaggatgt ctgcaaatca acccaccatg gctgcgaaca catttgtgtt
2101  aataatggga attcctacat ctgcaaatgc tcagagggat ttgttctagc tgaggacgga
2161  agacggtgca agaaatgcac tgaaggccca attgacctgg tctttgtgat cgatggatcc
2221  aagagtcttg gagaagagaa ttttgaggtc gtgaagcagt ttgtcactgg aattatagat
```

-continued

```
2281   tccttgacaa tttcccccaa agccgctcga gtggggctgc tccagtattc cacacaggtc
2341   cacacagagt tcactctgag aaacttcaac tcagccaaag acatgaaaaa agccgtggcc
2401   cacatgaaat acatgggaaa gggctctatg actgggctgg ccctgaaaca catgtttgag
2461   agaagtttta cccaaggaga aggggccagg cccctttcca caagggtgcc cagagcagcc
2521   attgtgttca ccgacggacg ggctcaggat gacgtctccg agtgggccag taaagccaag
2581   gccaatggta tcactatgta tgctgttggg gtaggaaaag ccattgagga ggaactacaa
2641   gagattgcct ctgagcccac aaacaagcat ctcttctatg ccgaagactt cagcacaatg
2701   gatgagataa gtgaaaaact caagaaaggc atctgtgaag ctctagaaga ctccgatgga
2761   agacaggact ctccagcagg ggaactgcca aaaacggtcc aacagccaac agaatctgag
2821   ccagtcacca taaatatcca agacctactt tcctgttcta attttgcagt gcaacacaga
2881   tatctgtttg aagaagacaa tcttttacgg tctacacaaa agctttccca ttcaacaaaa
2941   ccttcaggaa gccctttgga agaaaaacac gatcaatgca aatgtgaaaa ccttataatg
3001   ttccagaacc ttgcaaacga agaagtaaga aaattaacac agcgcttaga agaaatgaca
3061   cagagaatgg aagccctgga aaatcgcctg agatacagat gaagattaga aatcgcgaca
3121   catttgtagt cattgtatca cggattacaa tgaacgcagt gcagagcccc aaagctcagg
3181   ctattgttaa atcaataatg ttgtgaagta aaacaatcag tactgagaaa cctggtttgc
3241   cacagaacaa agacaagaag tatacactaa cttgtataaa tttatctagg aaaaaaatcc
3301   ttcagaattc taagatgaat ttaccaggtg agaatgaata agctatgcaa ggtattttgt
3361   aatatactgt ggacacaact tgcttctgcc tcatcctgcc ttagtgtgca atctcatttg
3421   actatacgat aaagtttgca cagtcttact tctgtagaac actggccata ggaaatgctg
3481   tttttttgta ctggacttta ccttgatata tgtatatgga tgtatgcata aaatcatagg
3541   acatatgtac ttgtggaaca agttggattt tttatacaat attaaaattc accacttcag
3601   agaatggtat tcagtgcaaa aattcttagt ttaactttaa atggaagata tgtatgtatg
3661   agaaatggcc aacatgccta tgaaaaaaat gctgaatctc atcagtaatc aggaaaatgc
3721   aggttaaaac aataccattt ttcacccatc agcttagcaa aaatgagtat attttttaac
3781   aagtgttggt aaggatgtgg aaatgtgagg ttcttgtagt aagaatgcaa atggcactct
3841   ttgtagagta agtctgttga catctcataa aactgaaaat gcacacaacc ctgtaaatct
3901   agcaactgca ctcagttgat ttcagcccat acatacaaag agacctgcat aagaatgtta
3961   ctaggctttg taaaagcaaa aaataaggaa caacttaaac atcatcagaa ggggaactga
4021   taaactctgg tgtaatccat accacagaaa tacaacaccg catgtacagg aatgtgctac
4081   atctatacaa ataaatggtc aaactcaaaa aaaaaaaaaa aa
```

One example of a nucleic acid sequence for human MET is available as NCBI accession number NM_001127500 (gi: 188595715). This sequence is recited below for easy reference as SEQ ID NO: 148.

```
   1   gccctcgccg cccgcggcgc cccgagcgct ttgtgagcag atgcggagcc gagtggaggg
  61   cgcgagccag atgcggggcg acagctgact tgctgagagg aggcggggag gcgcggagcg
 121   cgcgtgtggt ccttgcgccg ctgacttctc cactggttcc tgggcaccga aagataaacc
 181   tctcataatg aaggcccccg ctgtgcttgc acctggcatc ctcgtgctcc tgtttacctt
 241   ggtgcagagg agcaatgggg agtgtaaaga ggcactagca aagtccgaga tgaatgtgaa
```

-continued 301 tatgaagtat cagcttccca acttcaccgc ggaaacaccc atccagaatg tcattctaca 361 tgagcatcac attttccttg gtgccactaa ctacatttat gttttaaatg aggaagacct 421 tcagaaggtt gctgagtaca agactgggcc tgtgctggaa cacccagatt gtttcccatg 481 tcaggactgc agcagcaaag ccaatttatc aggaggtgtt tggaaagata acatcaacat 541 ggctctagct gtcgacacct actatgatga ccaactcact agctgcggca gcgtcaacag 601 agggacctgc cagcgacatg tctttcccca caatcatact gctgacatac agtcggaggt 661 tcactgcata ttctccccac agatagaaga gcccagccag tgtcctgact gtgtggtgag 721 cgccctggga gccaaagtcc tttcatctgt aaaggaccgg ttcatcaact tctttgtagg 781 caataccata aattcttctt atttcccaga tcatccattg cattcgatat cagtgagaag 841 gctaaaggaa acgaaagatg gttttacgtt tttgacggac cagtcctaca ttgatgcttt 901 acctgagttc agagattctt accccattaa gtatgtccat gcctttgaaa gcaacaattt 961 tatttacttc ttgacggtcc aaagggaaac tctagatgct cagacttttc acacaagaat 1021 aatcaggttc tgttccataa actctggatt gcattcctac atggaaatgc ctctggagtg 1081 tattctcaca gaaaagagaa aaaagagatc cacaaagaag gaagtgttta atatacttca 1141 ggctgcgtat gtcagcaagc ctggggccca gcttgctaga caaacaggag ccagcctgaa 1201 tgatgacatt cttttcgggg tgttcgcaca aagcaagcca gattctgccg aaccaatgga 1261 tcgatctgcc atgtgtgcat tccctatcaa atatgtcaac gacttcttca acaagatcgt 1321 caacaaaaac aatgtgagat gtctccagca tttttacgga cccaatcatg agcactgctt 1381 taataggaca cttctgagaa attcatcagg ctgtgaagcg cgccgtgatg aatatcgaac 1441 agagcttacc acagctttgc agcgcgccga cttattcatg ggtcaattca gcgaagccct 1501 cttaacatct atatccacct tcattaaagg agacctcacc atagctaatc ttgggacatc 1561 agagggtcgc ttcatgcagg ttgtggtttc tcgatcagga ccatcaaccc ctcatgtgaa 1621 ttttctcctg gactcccatc cagtgtctcc agaagtgact gtggagcata cattaaacca 1681 aaatggctac acactggtta tcactgggaa gaagatcacg aagatcccat tgaatggctt 1741 gggctgcaga catttccagt cccgcagtca atgcctctct gccccaccct ttgttcagtg 1801 tggctggtgc cacgacaaat gtgtgcgatc ggaggaatgc ctgagcggga catggactca 1861 acagatctgt ctgcctgcaa tctacaaggt tttcccaaat agtgcacccc ttgaaggagg 1921 gacaaggctg accatatgtg gctgggactt tggatttcgg aggaataata aatttgattt 1981 aaagaaaact agagttctcc ttggaaatga gagctgcacc ttgactttaa gtgagagcac 2041 gatgaataca ttgaaatgca cagttggtcc tgccatgaat aagcatttca atatgtccat 2101 aattatttca aatggccacg ggacaacaca atacagtaca ttctcctatg tggatcctgt 2161 aataacaagt atttcgccga aatacggtcc tatggctggt ggcactttac ttactttaac 2221 tggaaattac ctaaacagtg ggaattctag acacatttca attggtggaa aaacatgtac 2281 tttaaaaagt gtgtcaaaca gtattcttga atgttatacc ccagcccaaa ccatttcaac 2341 tgagtttgct gttaaattga aaattgactt agccaaccga gagacaagca tcttcagtta 2401 ccgtgaagat cccattgtct atgaaattca tccaaccaaa tcttttatta gtacttggtg 2461 gaaagaacct cccaacattg tcagttctct attttgcttt gccagtggtg ggagcacaat 2521 aacaggtgtt gggaaaaacc tgaattcagt tagtgtcccg agaatggtca taaatgtgca 2581 tgaagcagga aggaacttta cagtggcatg tcaacatcgc tctaattcag agataatctg 2641 ttgtaccact ccttccctgc aacagctgaa tctgcaactc cccctgaaaa ccaaagcctt 2701 tttcatgtta gatgggatcc ttcccaaata ctttgatctc atttatgtac ataatcctgt -continued 2761 gtttaagcct tttgaaaagc cagtgatgat ctcaatgggc aatgaaaatg tactggaaat
2821 taagggaaat gatattgacc ctgaagcagt taaaggtgaa gtgttaaaag ttggaaataa
2881 gagctgtgag aatatacact tacattctga agccgtttta tgcacggtcc ccaatgacct
2941 gctgaaattg aacagcgagc taaatataga gtggaagcaa gcaatttctt caaccgtcct
3001 tggaaaagta atagttcaac cagatcagaa tttcacagga ttgattgctg gtgttgtctc
3061 aatatcaaca gcactgttat tactacttgg gtttttcctg tggctgaaaa agagaaagca
3121 aattaaagat ccgggcagtg aattagctcg ctacgatgca agagtacaca ctcctcattt
3181 ggataggctt gtaagtgccc gaagtgtaag cccaactaca gaaatggttt caaatgaatc
3241 tgtagactac cgagctactt ttccagaaga tcagtttcct aattcatctc agaacggttc
3301 atgccgacaa gtgcagtatc ctctgacaga catgtccccc atcctaacta gtggggactc
3361 tgatatatcc agtccattac tgcaaaatac tgtccacatt gacctcagtg ctctaaatcc
3421 agagctggcc caggcagtgc agcatgtagt gattgggccc agtagcctga tcgtgcattc
3481 caatgaagcc ataggaagag ggcattttgg ttgtgtatat catgggactt tgttggacaa
3541 tgatggcaag aaaattcact gtgctgtgaa atccttgaac agaatcactg acataggaga
3601 agtttcccaa tttctgaccg agggaatcat catgaaagat tttagtcatc ccaatgtcct
3661 ctcgctcctg ggaatctgcc tgcgaagtga agggtctccg ctggtggtcc taccacacat
3721 gaaacatgga gatcttcgaa atttcactcg aaatgagact cataatccaa ctgtaaaaga
3781 tcttattggc tttggtcttc aagtagccaa aggcatgaaa tatcttgcaa gcaaaaagtt
3841 tgtccacaga gacttggctg caagaaactg tatgctggat gaaaaattca cagtcaaggt
3901 tgctgatttt ggtcttgcca gagacatgta tgataaagaa tactatagtg tacacaacaa
3961 aacaggtgca aagctgccag tgaagtggat ggctttggaa agtctgcaaa ctcaaaagtt
4021 taccaccaag tcagatgtgt ggtcctttgg cgtgctcctc tgggagctga tgacaagagg
4081 agccccacct tatcctgacg taaacacctt tgatataact gtttacttgt tgcaagggag
4141 aagactccta caacccgaat actgcccaga cccccttatat gaagtaatgc taaaatgctg
4201 gcaccctaaa gccgaaatgc gcccatcctt ttctgaactg gtgtcccgga tatcagcgat
4261 cttctctact ttcattgggg agcactatgt ccatgtgaac gctacttatg tgaacgtaaa
4321 atgtgtcgct ccgtatcctt ctctgttgtc atcagaagat aacgctgatg atgaggtgga
4381 cacacgacca gcctccttct gggagacatc atagtgctag tactatgtca aagcaacagt
4441 ccacactttg tccaatggtt ttttcactgc ctgaccttta aaaggccatc gatattcttt
4501 gctcttgcca aaattgcact attataggac ttgtattgtt atttaaatta ctggattcta
4561 aggaatttct tatctgacag agcatcagaa ccagaggctt ggtcccacag gccacggacc
4621 aatggcctgc agccgtgaca acactcctgt catattggag tccaaaactt gaattctggg
4681 ttgaattttt taaaaatcag gtaccacttg atttcatatg ggaaattgaa gcaggaaata
4741 ttgagggctt cttgatcaca gaaaactcag aagagatagt aatgctcagg acaggagcgg
4801 cagccccaga acaggccact catttagaat tctagtgttt caaaacactt ttgtgtgttg
4861 tatggtcaat aacatttttc attactgatg gtgtcattca cccattaggt aaacattccc
4921 ttttaaatgt ttgtttgttt tttgagacag gatctcactc tgttgccagg gctgtagtgc
4981 agtggtgtga tcatagctca ctgcaacctc cacctcccag gctcaagact aaagaatagga
5041 tgggactaca ggcgcacacc accatccccg gctaattttt gtattttttg tagagacggg
5101 gttttgccat gttgccaagg ctggtttcaa actcctggac tcaagaaatc cacccacctc -continued

```
5161   agcctcccaa agtgctagga ttacaggcat gagccactgc gcccagccct tataaatttt

5221   tgtatagaca ttcctttggt tggaagaata tttataggca atacagtcaa agtttcaaaa

5281   tagcatcaca casaacatgt ttataaatga acaggatgta atgtacatag atgacattaa

5341   gaaaatttgt atgaaataat ttagtcatca tgaaatattt agttgtcata taaaaaccca

5401   ctgtttgaga atgatgctac tctgatctaa tgaatgtgaa catgtagatg ttttgtgtgt

5461   attttttttaa atgaaaactc aaaataagac aagtaatttg ttgataaata tttttaaaga

5521   taactcagca tgtttgtaaa gcaggataca ttttactaaa aggttcattg gttccaatca

5581   cagctcatag gtagagcaaa gaaagggtgg atggattgaa aagattagcc tctgtctcgg

5641   tggcaggttc ccacctcgca agcaattgga aacaaaactt ttggggagtt ttattttgca

5701   ttagggtgtg ttttatgtta agcaaaacat actttagaaa caaatgaaaa aggcaattga

5761   aaatcccagc tatttcacct agatggaata gccaccctga gcagaacttt gtgatgcttc

5821   attctgtgga attttgtgct tgctactgta tagtgcatgt ggtgtaggtt actctaactg

5881   gttttgtcga cgtaaacatt taaagtgtta tattttttat aaaaatgttt atttttaatg

5941   atatgagaaa aattttgtta ggccacaaaa acactgcact gtgaacattt tagaaaaggt

6001   atgtcagact gggattaatg acagcatgat tttcaatgac tgtaaattgc gataaggaaa

6061   tgtactgatt gccaatacac cccaccctca ttacatcatc aggacttgaa gccaagggtt

6121   aacccagcaa gctacaaaga gggtgtgtca cactgaaact caatagttga gtttggctgt

6181   tgttgcagga aaatgattat aactaaaagc tctctgatag tgcagagact taccagaaga

6241   cacaaggaat tgtactgaag agctattaca atccaaatat tgccgtttca taaatgtaat

6301   aagtaatact aattcacaga gtattgtaaa tggtggatga caaaagaaaa tctgctctgt

6361   ggaaagaaag aactgtctct accagggtca agagcatgaa cgcatcaata gaaagaactc

6421   ggggaaacat cccatcaaca ggactacaca cttgtatata cattcttgag aacactgcaa

6481   tgtgaaaatc acgtttgcta tttataaact tgtccttaga ttaatgtgtc tggacagatt

6541   gtgggagtaa gtgattcttc taagaattag atacttgtca ctgcctatac ctgcagctga

6601   actgaatggt acttcgtatg ttaatagttg ttctgataaa tcatgcaatt aaagtaaagt

6661   gatgcaacat cttgtaaaaa aaaaaaaaaa aaaaa
```

One example of a nucleic acid sequence for human MYH10 is available as NCBI accession number NM_005964 (gi: 41406063). This sequence is recited below for easy reference as SEQ ID NO:149.

```
  1 actgaggcgc tggatctgtg gtcgcggctg gggacgtgcg cccgcgccac catcttcggc

 61 tgaagaggca attgcttttg gatcgttcca tttacaatgg cgcagagaac tggactcgag

121 gatccagaga ggtatctctt tgtggacagg gctgtcatct acaaccctgc cactcaagct

181 gattggacag ctaaaaagct agtgtggatt ccatcagaac gccatggttt tgaggcagct

241 agtatcaaag aagaacgggg agatgaagtt atggtggagt tggcagagaa tggaaagaaa

301 gcaatggtca acaaagatga tattcagaag atgaacccac ctaagttttc caaggtggag

361 gatatggcag aattgacatg cttgaatgaa gcttccgttt tacataatct gaaggatcgc

421 tactattcag gactaatcta tacttattct ggactcttct gtgtagttat aaacccttac

481 aagaatcttc caatttactc tgagaatatt attgaaatgt acagagggaa gaagcgtcat

541 gagatgcctc cacacatcta tgctatatct gaatctgctt acagatgcat gcttcaagat

601 cgtgaggacc agtcaattct ttgcacgggt gagtcaggtg ctgggaagac agaaaataca
```

-continued 661 aagaaagtta ttcagtacct tgcccatgtt gcttcttcac ataaaggaag aaaggaccat
721 aatattcctg ggaacttgga acggcagctt ttgcaagcaa atccaattct ggaatcattt
781 ggaaatgcga agactgtgaa aaatgataac tcatctcgtt ttggcaaatt tattcggatc
841 aactttgatg taactggcta tatcgttggg gccaacattg aaacatacct tctggaaaag
901 tctcgtgctg ttcgtcaagc aaaagatgaa cgtacttttc atatctttta ccagttgtta
961 tctggagcag gagaacacct aaagtctgat ttgcttcttg aaggatttaa taactacagg
1021 tttctctcca atggctatat tcctattccg ggacagcaag acaaagataa tttccaggag
1081 accatggaag caatgcacat aatgggcttc tcccatgaag agattctgtc aatgcttaaa
1141 gtagtatctt cagtgctaca gtttggaaat atttctttca aaaaggagag aaatactgat
1201 caagcttcca tgccagaaaa tacagttgcg cagaagctct gccatcttct tgggatgaat
1261 gtgatggagt ttactcgggc catcctgact ccccggatca aggtcggccg agactatgtg
1321 caaaaagccc agaccaaaga acaggcagat tttgcagtag aagcattggc aaaagctacc
1381 tatgagcggc tctttcgctg gctcgttcat cgcatcaata aagctctgga taggaccaaa
1441 cgtcagggag catctttcat tggaatcctg gatattgctg gatttgaaat ttttgagctg
1501 aactcctttg aacaactttg catcaactac accaatgaga agctgcagca gctgttcaac
1561 cacaccatgt ttatcctaga acaagaggaa taccagcgcg aaggcatcga gtggaacttc
1621 atcgatttcg ggctggatct gcagccatgc atcgacctaa tagagagacc tgcgaaccct
1681 cctggtgtac tggccctttt ggatgaagaa tgctggttcc ctaaagccac agataaaacc
1741 tttgttgaaa aactggttca agagcaaggt tcccactcca agtttcagaa acctcgacaa
1801 ttaaaagaca aagctgattt ttgcattata cattatgcag ggaaggtgga ctataaggca
1861 gatgagtggc tgatgaagaa tatggacccc ctgaatgaca acgtggccac ccttttgcac
1921 cagtcatcag acagatttgt ggcagagctt tggaaagatg tggaccgtat cgtgggtctg
1981 gatcaagtca ctggtatgac tgagacagct tttggctccg catataaaac caagaagggc
2041 atgtttcgta ccgttgggca actctacaaa gaatctctca ccaagctgat ggcaactctc
2101 cgaaacacca accctaactt tgttcgttgt atcattccaa atcacgagaa gagggctgga
2161 aaattggatc cacacctagt cctagatcag cttcgctgta atggtgtcct ggaagggatc
2221 cgaatctgtc gccagggctt ccctaaccga atagttttcc aggaattcag acagagatat
2281 gagatcctaa ctccaaatgc tattcctaaa ggttttatgg atggtaaaca ggcctgtgaa
2341 cgaatgatcc gggctttaga attggaccca aacttgtaca gaattggaca gagcaagata
2401 tttttcagag ctggagttct ggcacactta gaggaagaaa gagatttaaa aatcaccgat
2461 atcattatct tcttccaggc cgtttgcaga ggttacctgg ccagaaaggc ctttgccaag
2521 aagcagcagc aactaagtgc cttaaaggtc ttgcagcgga actgtgccgc gtacctgaaa
2581 ttacggcact ggcagtggtg gcgagtcttc acaaaggtga agccgcttct acaagtgact
2641 cgccaggagg aagaacttca ggccaaagat gaagagctgt tgaaggtgaa ggagaagcag
2701 acgaaggtgg aaggagagct ggaggagatg gagcggaagc accagcagct tttagaagag
2761 aagaatatcc ttgcagaaca actacaagca gagactgagc tctttgctga agcagaagag
2821 atgagggcaa gacttgctgc taaaaagcag gaattagaag agattctaca tgacttggag
2881 tctagggttg aagaagaaga agaaagaaac caaatcctcc aaaatgaaaa gaaaaaaatg
2941 caagcacata ttcaggacct ggaagaacag ctagacgagg aggaaggggc tcggcaaaag
3001 ctgcagctgg aaaaggtgac agcagaggcc aagatcaaga agatggaaga ggagattctg -continued 3061 cttctcgagg accaaaattc caagttcatc aaagaaaaga aactcatgga agatcgcatt 3121 gctgagtgtt cctctcagct ggctgaagag gaagaaaagg cgaaaaactt ggccaaaatc 3181 aggaataagc aagaagtgat gatctcagat ttagaagaac gcttaaagaa ggaagaaaag 3241 actcgtcagg aactggaaaa ggccaaaaga aaactcgacg gggagacgac cgacctgcag 3301 gaccagatcg cagagctgca ggcgcagatt gatgagctca agctgcagct ggccaagaag 3361 gaggaggagc tgcagggcgc actggccaga ggtgatgatg aaacactcca taagaacaat 3421 gcccttaaag ttgtgcgaga gctacaagcc caaattgctg aacttcagga agactttgaa 3481 tccgagaagg cttcacggaa caaggccgaa aagcagaaaa gggacttgag tgaggaactg 3541 gaagctctga aaacagagct ggaggacacg ctggacacca cggcagccca gcaggaacta 3601 cgtacaaaac gtgaacaaga agtggcagag ctgaagaaag ctcttgagga ggaaactaag 3661 aaccatgaag ctcaaatcca ggacatgaga caaagacacg caacagccct ggaggagctc 3721 tcagagcagc tggaacaggc caagcggttc aaagcaaatc tagagaagaa caagcagggc 3781 ctggagacag ataacaagga gctggcgtgt gaggtgaagg tcctgcagca ggtcaaggct 3841 gagtctgagc acaagaggaa gaagctcgac gcgcaggtcc aggagctcca tgccaaggtc 3901 tctgaaggcg acaggctcag ggtggagctg gcggagaaag caagtaagct gcagaatgag 3961 ctagataatg tctccaccct tctggaagaa gcagagaaga agggtattaa atttgctaag 4021 gatgcagcta gtcttgagtc tcaactacag gatacacagg agcttcttca ggaggagaca 4081 cgccagaaac taaacctgag cagtcggatc cggcagctgg aagaggagaa gaacagtctt 4141 caggagcagc aggaggagga ggaggaggcc aggaagaacc tggagaagca agtgctggcc 4201 ctgcagtccc agttggctga taccaagaag aaagtagatg acgacctggg aacaattgaa 4261 agtctggaag aagccaagaa gaagcttctg aaggacgcgg aggccctgag ccagcgcctg 4321 gaggagaagg cactggcgta tgacaaactg gagaagacca agaaccgcct gcagcaggag 4381 ctggacgacc tcacggtgga cctggaccac cagcgccagg tcgcctccaa cttggagaag 4441 aagcagaaga agtttgacca gctgttagca gaagagaaga gcatctctgc tcgctatgcc 4501 gaagagcggg accgggccga agccgaggcc agagagaaag aaaccaaagc cctgtcactg 4561 gcccgggccc tcgaggaagc cctggaggcc aaggaggagt ttgagaggca gaacaagcag 4621 ctccgagcag acatggaaga cctcatgagc tccaaagatg atgtgggaaa aaacgttcac 4681 gaacttgaaa aatccaaacg ggccctagag cagcaggtgg aggaaatgag gacccagctg 4741 gaggagctgg aagacgaact ccaggccacg gaagatgcca agcttcgtct ggaggtcaac 4801 atgcaggcca tgaaggcgca gttcgagaga gacctgcaaa ccagggatga gcagaatgaa 4861 gagaagaagc ggctgctgat caaacaggtg cgggagctcg aggcggagct ggaggatgag 4921 aggaaacagc gggcgcttgc tgtagcttca aagaaaaaga tggagataga cctgaaggac 4981 ctcgaagccc aaatcgaggc tgcgaacaaa gctcgggatg aggtgattaa gcagctccgc 5041 aagctccagg ctcagatgaa ggattaccaa cgtgaattag aagaagctcg tgcatccaga 5101 gatgagattt ttgctcaatc caaagagagt gaaaagaaat tgaagagtct ggaagcagaa 5161 atccttcaat tgcaggagga acttgcctca tctgagcgag cccgccgaca cgccgagcag 5221 gagagagatg agctggcgga cgagatcacc aacagcgcct ctggcaagtc cgcgctgctg 5281 gatgagaagc ggcgtctgga agctcggatc gcacagctgg aggaggagct ggaagaggag 5341 cagagcaaca tggagctgct caacgaccgc ttccgcaaga ccactctaca ggtggacaca 5401 ctgaacgccg agctagcagc cgagcgcagc gccgcccaga agagtgacaa tgcacgccag 5461 caactggagc ggcagaacaa ggagctgaag gccaagctgc aggaactcga gggtgctgtc -continued 5521 aagtctaagt tcaaggccac catctcagcc ctggaggcca agattgggca gctggaggag 5581 cagcttgagc aggaagccaa ggaacgagca gccgccaaca aattagtccg tcgcactgag 5641 aagaagctga aagaaatctt catgcaggtt gaggatgagc gtcgacacgc ggaccagtat 5701 aaagagcaga tggagaaggc caacgctcgg atgaagcagc ttaaacgcca gctggaggaa 5761 gcagaagaag aagcgacgcg tgccaacgca tctcggcgta aactccagcg ggaactggat 5821 gatgccaccg aggccaacga gggcctgagc cgcgaggtca gcaccctgaa gaaccggctg 5881 aggcggggtg gccccatcag cttctcttcc agccgatctg gccggcgcca gctgcacctt 5941 gaaggagctt ccctggagct ctccgacgat gacacagaaa gtaagaccag tgatgtcaac 6001 gagacgcagc caccccagtc agagtaaagt tgcaggaagc cagaggaggc aatacagtgg 6061 gacagttagg aatgcacccg gggcctcctg cagatttcgg aaattggcaa gctacgggat 6121 tccttcctga aagatcaact gtgtcttaag gctctccagc ctatgcatac tgtatcctgc 6181 ttcagactta ggtacaattg ctcccctttt tatatataga cacacacagg acacatatat 6241 taaacagatt gtttcatcat tgcatctatt ttccatatag tcatcaagag accattttat 6301 aaaacatggt aagacccttt ttaaaacaaa ctccaggccc ttggttgcgg gtcgctgggt 6361 tattggggca gcgccgtggt cgtcactcag tcgctctgca tgctctctgt catacagaca 6421 ggtaacctag ttctgtgttc acgtggcccc cgactcctca gccacatcaa gtctcctaga 6481 ccactgtgga ctctaaactg cacttgtctc tctcatttcc ttcaaataat gatcaatgct 6541 atttcagtga gcaaactgtg aaaggggctt tggaaagagt aggaggggtg ggctggatcg 6601 gaagcaacac ccatttgggg ttaccatgtc catcccccaa ggggggccct gcccctcgag 6661 tcgatggtgt cccgcatcta ctcatgtgaa ctggccttgg cgagggctgg tctgtgcata 6721 gaagggatag tggccacact gcagctgagg ccccaggtgg cagccatgga tcatgtagac 6781 ttccagatgg tctcccgaac cgcctggctc tgccggcgcc ctcctcacgt caggagcaag 6841 cagccgtgga cccctaagcc gagctggtgg aaggcccctc cctgtcgcca gccgggccct 6901 catgctgacc ttgcaaattc agccgctgct ttgagcccaa aatgggaata ttggttttgt 6961 gtccgaggct tgttccaagt ttgtcaatga ggtttatgga gcctccagaa cagatgccat 7021 cttcctgaat gttgacatgc cagtgggtgt gactccttca tttttccttc tcccttccct 7081 ttggacagtg ttacagtgaa cacttagcat cctgtttttg gttggtagtt aagcaaactg 7141 acattacgga aagtgcctta gacactacag tactaagaca atgttgaata tatcattcgc 7201 ctctataaca atttaatgta ttcagttttg actgtgcttc atatcatgta cctctctagt 7261 caaagtggta ttacagacat tcagtgacaa tgaatcagtg ttaattctaa atccttgatc 7321 ctctgcaatg tgcttgaaaa cacaaacctt ttgggttaaa agctttaaca tctattagga 7381 agaatttgtc ctgtgggttt ggaatcttgg attttccccc tttatgaact gtactggctg 7441 ttgaccacca gacacctgac cgcaaatatc ttttcttgta ttcccatatt tctagacaat 7501 gatttttgta agacaataaa tttattcatt atagatattt gcgcctgctc tgtttacttg 7561 aagaaaaaag cacccgtgga gaataaagag acctcaataa acaagaataa tcatgtgaa One example of a nucleic acid sequence for human PFAAP5 is available as NCBI accession number AF530063 (gi: 33329092). This sequence is recited below for easy reference as SEQ ID NO: 150.

```
   1 atgtcttatg gtgaaattga aggtaaattc ttgggaccta gagaagaagt aacgagtgag
  61 ccacgctgta aaaaattgaa gtcaaccaca gagtcgtatg tttttcacaa tcatagtaat
 121 gctgattttc acagaatcca agagaaaact ggaaatgatt gggtccctgt gaccatcatt
 181 gatgtcagag gacatagtta tttgcaggag aacaaaatca aaactacaga tttgcataga
 241 cctttgcatg atgagatgcc tggtaataga ccagatgtta ttgaatccat tgattcacag
 301 gttttacagg aagcacgtcc tccattagta tccgcagacg atgagatata tagcacaagt
 361 aaagcattta taggacccat ttacaaaccc cctgagaaaa agaaacgtaa tgaagggagg
 421 aatgaggcac atgttctaaa tggtataaat gacagaggag gacaaaaaga gaaacagaaa
 481 tttaactctg aaaaatcaga gattgacaat gaattattcc agttttacaa agaaattgaa
 541 gagcttgaaa aggaaaaaga tggttttgag aacagttgta aagaatctga accttctcag
 601 gaacaatttg ttccatttta tgagggtcat aataatggtc tcttaaaacc tgatgaagaa
 661 aagaaagatc ttagtaataa agctatgcca tcacattgtg attatcagca gaacttgggg
 721 aatgagccag acaaatatcc ctgtaatgga caagtaatac ctacattttg tgacacttca
 781 tttacttctt tcaggcctga atggcagtca gtatatcctt ttatagtgcc ctatggtccc
 841 cctcttccca gtttgaacta tcatttaaac attcagagat tcagtggtcc accaaatcca
 901 ccatcaaata ttttccaagc ccaagatgac tctcagatac aaaatggata ttatgtaaat
 961 aattgtcatg ttaactggaa ttgcatgact tttgatcaga acaatgaata tactgactgt
1021 agtgagaata ggagtagtgt tcatccctct ggaaatggct gcagtatgca agatcgatat
1081 gtgagtaatg gtttctgtga agtcagagaa agatgctgga aagatcattg tatggacaag
1141 cataatggaa cagacaggtt tgtgaaccag cagtttcaag aggaaaagtt aaataaattg
1201 cagaagttac ttattctttt tagaggtctg cctggttctg ggaaaacaac attgtctcga
1261 attctgcttg gtcagaatcg tgatggcatt gtgttcagca ctgatgacta ttttcaccat
1321 caagatgggt acaggtataa tgttaatcaa cttggtgatg cccatgactg gaaccagaac
1381 agagcaaaac aagctatcga tcagggaaga tctccagtta taatagataa cactaatata
1441 caagcttggg aaatgaagcc atatgtggaa gtggccatag gaaaaggata cagagtagag
1501 tttcatgaac ctgaaacttg gtggaaattt gatcctgaag aattagaaaa gaggaataaa
1561 catggtgtgt ctcgaaagaa gattgctcag atgttggatc gttatgaata tcaaatgtcc
1621 atttctattg taatgaattc agtggaacca tcacacaaaa gcacacaaag acctcctcct
1681 ccacagggga gacagaggtg gggaggctct cttggctcac ataatcgtgt ctgtgtcaca
1741 aataatcatt aa
```

One example of a nucleic acid sequence for human PGF is available as NCBI accession number NM_002632 (gi: 56676307). This sequence is recited below for easy reference as SEQ ID NO: 151.

```
   1 ctgctgtctg cggaggaaac tgcatcgacg gacggccgcc cagctacggg aggacctgga
  61 gtggcactgg gcgcccgacg gaccatcccc gggacccgcc tgcccctcgg cgccccgccc
 121 cgcccggccg ctccccgtcg ggttccccag ccacagcctt acctacgggc tcctgactcc
 181 gcaaggcttc cagaagatgc tcgaaccacc ggccggggcc tcggggcagc agtgagggag
```

-continued

```
 241 gcgtccagcc ccccactcag ctcttctcct cctgtgccag gggctccccg ggggatgagc
 301 atggtggttt tccctcggag ccccctggct cgggacgtct gagaagatgc cggtcatgag
 361 gctgttccct tgcttcctgc agctcctggc cgggctggcg ctgcctgctg tgcccccccca
 421 gcagtgggcc ttgtctgctg ggaacggctc gtcagaggtg gaagtggtac ccttccagga
 481 agtgtggggc cgcagctact gccgggcgct ggagaggctg gtggacgtcg tgtccgagta
 541 ccccagcgag gtggagcaca tgttcagccc atcctgtgtc tccctgctgc gctgcaccgg
 601 ctgctgcggc gatgagaatc tgcactgtgt gccggtggag acggccaatg tcaccatgca
 661 gctcctaaag atccgttctg ggaccggccc ctcctacgtg gagctgacgt tctctcagca
 721 cgttcgctgc gaatgccggc ctctgcggga gaagatgaag ccggaaagga ggagacccaa
 781 gggcaggggg aagaggagga gagagaagca gagacccaca gactgccacc tgtgcggcga
 841 tgctgttccc cggaggtaac ccaccccttg gaggagagag accccgcacc cggctcgtgt
 901 atttattacc gtcacactct tcagtgactc ctgctggtac ctgccctcta tttattagcc
 961 aactgtttcc ctgctgaatg cctcgctccc ttcaagacga ggggcaggga aggacaggac
1021 cctcaggaat tcagtgcctt caacaacgtg agagaaagag agaagccagc cacagacccc
1081 tgggagcttc cgctttgaaa gaagcaagac acgtggcctc gtgaggggca agctaggccc
1141 cagaggccct ggaggtctcc aggggcctgc agaaggaaag aagggggccc tgctacctgt
1201 tcttgggcct caggctctgc acagacaagc agcccttgct ttcggagctc ctgtccaaag
1261 tagggatgcg gatcctgctg gggccgccac ggcctggctg gtgggaaggc cggcagcggg
1321 cggacmggat ccagccactt ccccctcttc ttctgaagat cagaacattc agctctggag
1381 aacagtggtt gcctgggggc ttttgccact ccttgtcccc cgtgatctcc cctcacactt
1441 tgccatttgc ttgtactggg acattgttct ttccggccaa ggtgccacca ccctgccccc
1501 cctaagagac acatacagag tgggccccgg gctggagaaa gagctgcctg gatgagaaac
1561 agctcagcca gtggggatga ggtcaccagg ggaggagcct gtgcgtccca gctgaaggca
1621 gtggcagggg agcaggttcc ccaagggccc tggcaccccc acaagctgtc cctgcagggc
1681 catctgactg ccaagccaga ttctcttgaa taaagtattc tagtgtggaa aaaaaaaaaa
1741 aaaaaaaaaa aaaaaaaa
```

One example of a nucleic acid sequence for human PIP3-E is available as NCBI accession number AJ310566 (gi: 18307480). This sequence is recited below for easy reference as SEQ ID NO: 152.

```
   1 gtttaagtag aatcctcaag cttggcctca gagtactatg aggcttctga atccaggaat
  61 aagactgctc ttggatttac tctctttgta ttgcatgtca aaggcaacag aactggacca
 121 agaaaattca taacttttttg cgtttgtttc tactaagatg acatcataca tggctattga
 181 tggcagtgct cttgttccct tgcgtcagaa gcccaggagg aaaactcaag gttttctcac
 241 gatgagtcgg aggaggatat cgtgtaaaga tctgggccat gctgactgcc aagggtggct
 301 gtataagaaa aaggaaaagg gaagtttcct aagcaacaaa tggaaaaagt tctgggtgat
 361 actgaagggg tcgtcactgt actggtatag caatcaaatg gcagagaaag ctgatggatt
 421 tgtcaacctg cctgatttca ctgtggaaag agcatctgaa tgcaagaaaa agcatgcttt
 481 taagatcagc catccacaga tcdagacctt ttattttgca gctgagaatg tgcaggaaat
 541 gaacgtgtgg ttaaataaac ttggatcggc tgtaatccat caggaatcca ctacaaagga
 601 tgaagaatgt tacagtgaaa gtgaacagga agatccagaa atagctgcgg agacaccacc
```

-continued

```
 661 ccctcctcac gcttcccaga ctcagtcttt gactgcacag caggcatctt catcctcacc

 721 cagcctgagt ggaacgtcgt attctttctc ttccctggaa aatacagtga agacacccag

 781 cagttttcct tcctccttat ctaaagagag acaatccttg cctgacacag ttaacagttt

 841 gtctgctgct gaagatgagg gacaaccaat aacgtttgct gtgcaagttc attcacctgt

 901 accctcagag gcaggcatcc acaaggccct ggaaaacagt tttgtcacat cagaaagtgg

 961 atttttgaac tctttatcta gtgatgatac ttcttcattg agtagcaatc atgaccatct

1021 tactgtccca gataagcctg ctggatcaaa gatcatggac aaagaagaga caaaagtgtc

1081 tgaagatgat gaaatggaga agctgtacaa atcattagag caagctagtc tatctcctct

1141 tggggaccga cgaccttcga ctaaaaagga gttgagaaaa tcctttgtta agcggtgtaa

1201 aaatccatct ataaacgaga aactccacaa aatccgaaca ttgaatagca cattaaagtg

1261 taaagaacat gatctggcca tgattaacca gttgctggat gacccgaagc tgacagccag

1321 gaaatacaga gagtggaaag tcatgaacac cctgctgatc caggacatct atcagcagca

1381 gcgggcttcg cctgcccctg atgacactga tgacaccccc caggaactca agaaatcacc

1441 ttcttctccc tctgttgaaa attccatttg agacaaagtc agggttttct cctcttatat

1501 tttatcacaa gcaactcttc aagatgttgc aaaagcttac atttttcctt aaaaggaaaa

1561 ctgaaaccca gtccttcaag catcagcttc ccatctaaag atgcacgtta gatgaagata

1621 at
```

One example of a nucleic acid sequence for human PKNOX2 is available as NCBI accession number NM_022062 (gi: 116812643). This sequence is recited below for easy reference as SEQ ID NO:153.

```
   1 gtgtgaaggg ggggtccggg gggcgggtcc ctgtgccgct gacgtcccga gcagtgctgg

  61 gaagtatagg ctgtgttgtc acgccggtgt cagtctgatg aagattggca tcaggtgaag

 121 tctggagcag gacttctgag gctttctatc ctccatgctg ctcactagaa aaggggctgt

 181 gaactgtgct ttggctctag cagacaggaa gaaattctgg cccagctgga agtagaaaga

 241 ggggagtgag tctcctgagg accatctcag aggccccggg atcacccgaa cagtcctcca

 301 tgtgaatcaa tcccatgatg caacatgcct ccccagcccc cgctctgacg atgatggcca

 361 cgcagaatgt cccgccccca ccctaccagg acagcccaca gatgacggca accgcccagc

 421 caccctccaa ggcccaggct gtccacatct ctgccccctc agctgctgcc agcacacctg

 481 tgcccagtgc ccccatcgac ccccaggccc agctggaggc tgacaagcga gctgtataca

 541 ggcaccctct tttcccgctc ctgacgctgc tgtttgagaa atgtgaacag gccacccagg

 601 gctctgagtg catcacctcc gccagctttg atgtggacat cgagaacttt gtccaccagc

 661 aggaacagga gcacaaaccc ttcttcagcg atgacccaga actggacaat ctgatggtga

 721 aggcaatcca ggtcctgaga atccacctgc tggagctgga gaaagtcaat gaactctgca

 781 aggacttttg taaccgttac atcacctgcc tcaaaaccaa gatgcacagc gacaacctgc

 841 tcaggaatga tctagggggg ccctactccc ccaaccagcc ctccatcaac cttcactcac

 901 aggacctcct gcagaattcc cccaattcca tgtccggagt ctccaataac ccccacmgga

 961 ttgtggtccc agcctcagcg ctccagcagg gcaacatcgc catgacaacc gtcaactcac

1021 aagttgtgtc aggtggagcc ttataccaac cggttaccat ggtaacctcc cagggtcagg

1081 tggtcaccca agcaatcccc cagggagcca tccagatcca gaacacacag gttaaccttg
```

-continued 1141 acctcacctc cctcctggac aatgaggata agaagtccaa gaacaaacga ggagtcttgc 1201 ccaagcatgc caccaatata atgcgttctt ggctcttcca gcatctcatg cacccctacc 1261 ccacggagga tgagaagagg cagatcgcag cccagaccaa cctcaccctc ctgcaagtaa 1321 acaactggtt catcaatgcc cggaggcgca tcctgcagcc catgcttgat gccagcaacc 1381 cagatcctgc ccccaaagcc aagaagatca agtctcagca ccggcccacc caaagattct 1441 ggcccaactc catcgctgcg gggtgctgc agcagcaggg cggtgcccca gggacaaacc 1501 ccgatggttc catcaacttg gacaacctgc agtccctgtc ctcagacagt gccaccatgg 1561 ccatgcagca ggctatgatg gctgcacacg atgactcatt ggatgggaca gaagaagagg 1621 atgaggatga gatggaagag gaggaggagg aggagctgga ggaggaggtc gacgagctgc 1681 agacgacaaa tgtcagcgac ctgggcttgg aacacagtga ctccctggag tagtcgggca 1741 gcccagatgg cactgatcac tgagcaggag aggagtgtcg ccgggaggcc ttcagggtgg 1801 gggggaaggg gacatgggca ggaagcaccg agggagttgg gccctagctt ccccaaatca 1861 gtagcttgaa gaaaggcaaa ggagacacct gttccttccc aaccaccgag cttcaatgag 1921 gaccccagcc ccacttccct ggaactgccg aggactctgt ttggcggggc cagtcgagca 1981 gcctgtgtgg aaagacagga gtgagatctg gactcaccaa atccctgagg atagatggca 2041 cccatggccc ccacccacgg aaggacttga gttgtttaca agccctgcac tgaggcagat 2101 tggtgctgtt cgcagagtag gcctttgccc gggggcagac ttagaaggaa ggggagagac 2161 aaagggggac tgagtttcat ccccagaagt ttctcagctc ctttgacaga cattcaaggg 2221 caggagggag ccccaaagca taaccagtgg ccagaggagt gggagggcct gaggcatcac 2281 atcttgcaga tcagaatggg atggaatcca ccaggctcca gctcatccct ccaaggccct 2341 gtctctgcgc acagcaacca tggacatggg agaaagggat gggagccaca gtgcccttca 2401 ctctctcctg gaaaccaact gtaagctggt gggctcaacc tgtgggaggt taagaggagt 2461 cccttctggg ttgactccaa gagccaagga gatggcagac cctgggctag gaaccatatg 2521 gaggtgactt tgaggccaca gctgtcccta ggtgatcaca gaacttagct cctttaacaa 2581 caggacaatg gtttttttacc ctagatgttc ccaccttcag tgctccacgc cctccataga 2641 ccttcagaga aggtgaaacc aggttatctg ggaatctttc cagcccgcag gtcgccacgg 2701 ccatcccttt gctcccagcc tggctccatc agcctccagc ttcctttctt cattctgtcc 2761 ttcagggaag gcagaagaaa cattggaaag catctagtcc agtgggaagc caggggttgg 2821 agaaggtgct acatccctct tcccatcaat atcctaaatg tgggggaggg cccagagaat 2881 ggcacccaag agcctgcggg gatgcccatc ccacacaccc cacccagctg ttctaaccct 2941 gctatccaca gccctggagg aactggggct cctggaagga ggaggaggct ctccactgtc 3001 caccctaaca catacctcc cacccacctt ccagaccccc ttggttggca ccctctcctc 3061 cggttccctc tcaccccatg gctgtgaatg acaggacagg tcacacgtgt gttttccatt 3121 gggtttaatt taatggacgt gcagtttcat ttgtaaattg tgcattggcc acctccttca 3181 gtggcaggat gtgagtggct acctggctca actggagggg accccttggg ccctctgggg 3241 cttcccctcc cccacctggt tggggtagag caaaaggatg gtcactcttc cgaggtctcc 3301 ctgaaatgaa tgtatttctc ccccaaaaga gctgatattt ddtgttttaa taaggatttt 3361 tgagaaacaa ataaccttat ttataatctg ggtgatccaa tcattttttta ctccctttttg 3421 atgccataca tagaggaaag tctagctttt ttggcgtgag acttttgcaa tgtgcagtgg 3481 gataaaatgc atttcctttt ctggttcgtt tttcttgtta acacgcgcac acagacacac 3541 acacacaccg ttccactcac cacctggaca ggcgtccccc agcacggaca cactggcaca -continued 3601 caggtgccca catctcttcc tctcagcccc tccacctgcc taatgttatg caacctcctt 3661 ctgatgtatc caccaaacca gtactgaatg tggccgagac gttttcagta aatcttatta 3721 cctaccgtaa One example of a nucleic acid sequence for human PRKACB is available as NCBI accession number NM_182948 (gi: 46909585). This sequence is recited below for easy reference as SEQ ID NO: 154.

1 acacatgcat agctcttagc ttctgtgtaa gaagttgtga gctccttctg gaaacatttg 61 cagttacatt aagtaaagtg taaatgcaca tgaatggcag cttatagaga accaccttgt 121 aaccagtata caggtacaac tacagctctt cagaaattgg aaggttttgc tagccggtta 181 tttcatagac actctaaagg tactgcacat gatcagaaaa cagctctgga aaatgacagc 241 cttcatttct ctgaacatac tgccttatgg gacagatcaa tgaaagagtt tctagccaaa 301 gccaaagaag actttttgaa aaaatgggag aatccaactc agaataatgc cggacttgaa 361 gattttgaaa ggaaaaaaac ccttggaaca ggttcatttg gaagagtcat gttggtaaaa 421 cacaaagcca ctgaacagta ttatgccatg aagatcttag ataagcagaa ggttgttaaa 481 ctgaagcaaa tagagcatac tttgaatgag aaaagaatat tacaggcagt gaattttcct 541 ttccttgttc gactggagta tgcttttaag gataattcta atttatacat ggttatggaa 601 tatgtccctg gggtgaaat gttttcacat ctaagaagaa ttggaaggtt cagtgagccc 661 catgcacggt tctatgcagc tcagatagtg ctaacattcg agtacctcca ttcactagac 721 ctcatctaca gagatctaaa acctgaaaat ctcttaattg accatcaagg ctatatccag 781 gtcacagact ttgggtttgc caaaagagtt aaaggcagaa cttggacatt atgtggaact 841 ccagagtatt tggctccaga aataattctc agcaagggct acaataaggc agtggattgg 901 tgggcattag gagtgctaat ctatgaaatg gcagctggct atcccccatt ctttgcagac 961 caaccaattc agatttatga aaagattgtt tctggaaagg tccgattccc atcccacttc 1021 agttcagatc tcaaggacct tctacggaac ctgctgcagg tggatttgac caagagattt 1081 ggaaatctaa agaatggtgt cagtgatata aaaactcaca agtggtttgc cacgacagat 1141 tggattgcta tttaccagag gaaggttgaa gctccattca taccaaagtt tagaggctct 1201 ggagatacca gcaactttga tgactatgaa gaagaagata tccgtgtctc tataacagaa 1261 aaatgtgcaa aagaatttgg tgaattttaa agaggaacaa gatgacatct gagctcacac 1321 tcagtgittg cactctgttg agagataagg tagagctgag accgtccttg ttgaagcagt 1381 tacctagttc cttcattcca acgactgagt gaggtcttta ttgccatcat cccgtgtgcg 1441 cactctgcat ccacctatgt aacaaggcac cgctaagcaa gcattgtctg tgccataaca 1501 cagtactaga ccactttctt acttctcttt gggttgtctt tctcctctcc tatatccatt 1561 tcttcctttt ccaatttcat tggttttctc taaacagtgc tccattttat tttgttggtg 1621 tttcagatgg gcagtgttat ggctacgtga tatttgaagg gaaggataag tgttgctttc 1681 agtagttatt gccaatattg ttgttggtca atggcttgaa gataaacttt ctaataatta 1741 ttatttcttt gagtagctca gacttggttt tgccaaaact cttggtaatt tttgaagata 1801 gactgtctta tcaccaagga aatttataca aattaagact aactttcttg gaattcacta 1861 ttctggcaat aaattttggt agactaatac agtacagcta gacccagaaa tttggaaggc 1921 tgtagatcag aggttctagt tccctttccc tccttttata tcctcctctc cttgagtaat -continued 1981 gaagtgacca gcctgtgtag tgtgacaaac gtgtctcatt cagcaggaaa aactaatgat 2041 atggatcatc acccagattc tctcacttgg taccagcatt tctgtaggta ttagagaaga 2101 gttctaagtt ttctaaacct taactgttcc ttaaggattt tagccagtat tttaatagaa 2161 catgattaat gaaagtgaca aattttaaat tttctctaat agtcctcatc ataaactttt 2221 taaaggaaaa tacgcaaact aaaaagaaca ttggtttaga taaatactta tactttgcaa 2281 agtcaaaaat ggcttgattt ttggaaacaa tatagaggta ttcatattta aatgagggtt 2341 tacatttgtt ttgttttgta accgttaaaa agaagttgtt tccagctaat tattgtggtg 2401 tactatattt gtgagcctag ggtaggggca ctgctgcaac ttctgctttc atcccatgcc 2461 tcatcaatga ggaaagggaa caaagtgtat aaaactgcca caattgtatt ttaattttga 2521 ggtatgatat tttcagatat ttcataattt ctaacctctg ttctctcagt aaacagaatg 2581 tctgatcgat catgcagata caatgttggt atttgagagg ttagtttttt tcctacactt 2641 ttttttgcca actgacttaa caacattgct gtcaggtgga aatttcaagc acttttgcac 2701 atttagttca gtgtttgttg agaatccatg gcttaaccca cttgttttgc tatttttttc 2761 tttgctttta attttcccca tctgatttta tctctgcgtt tcagtgacct accttaaaac 2821 aacacacgag aagagttaaa ctgggttcat tttaatgatc aatttacctg catataaaat 2881 ttatttttaa tcaagctgat cttaatgtat ataatcattc tatttgcttt attatcggtg 2941 caggtaggtc attaacacca cttcttttca tctgtaccac accctggtga aacctttgaa 3001 gacataaaaa aaacctgtct gagatgttct ttctaccaat ctatatgtct ttcggttatc 3061 aagtgtttct gcatggtaat gtcatgtaaa tgctgatatt gatttcactg gtccatctat 3121 atttaaaacg tgcaagaaaa aaataaaata ctctgctcta gcaagttttg tgtaacaaag 3181 gcatatcgtc atgttaataa atttaaaaca tcattcgtat aaaatatttt aattttcttg 3241 tatttcattt agacccaaga acatgctgac caatgtgttc tatatgtaaa ctacaaattc 3301 tatggtagct ttgttgtata ttattgtaaa attattttaa taagtcatgg ggatgacaat 3361 ttgattatta caatttagtt ttcagtaatc aaaaagattt ctatgaattc taaaaaatat 3421 ttttttctat gaaattacta gtgcccagct gtagaatcta ccttaggtag atgatcccta 3481 gacatacgtt ggttttgagg gctattcagc cattccattt tactctctat ttaaaggccg 3541 tgagcaagct tgtcatgagc aaatatgtca agggagtcaa tttctgacca atcaagtaca 3601 ctaaattaga atatttttaa agtatgtaac attcccagtt tcagccacaa tttagccaag 3661 aataagataa aaacttgaat aagaagtaag tagcataaat cagtatttaa cctaaaatta 3721 catatttgaa acagaagata ttatgttatg ctcagtaaat aattaagaga tggcattgtg 3781 taagaaggag ccctagactg aaagtcaaga catctgaatt tcaggctgga aaactatcag 3841 tatgatctca gcctcagttc tcttgtctgt aaaatggaag aactggatta ggcagtttgt 3901 aagattcctc ctaactttca cagtcgatga caagattgtc tttttatctg atattttgaa 3961 gggtatattg ctttgaagta agtctcaata aggcaatata ttttagggca tctttcttct 4021 tatctctgac agtgttctta aaattatttg aatatcataa gagccttggt gtctgtccta 4081 attcctttct cactcaccga tgctgaatac ccagttgaat caaactgtca acctaccaaa 4141 aacgatattg tggcttatgg gtattgctgt ctcattcttg gtatattctt gtgttaactg 4201 cccattggcc tgaaaatact cattgtaagc ctgaaaaaaa aaatctttcc cactgttttt 4261 tctgcttgtt gtaagaatca aatgaaataa tgtatgtgaa agcaccttgt aaactgtaac -continued 4321 ctatcaatgt aaaatgttaa ggtgtgttgt tatttcatta attacttctt tgtttagaat 4381 ggaatttcct atgcactact gtagctagga aatgctgaaa acaactgtgt tttttaatta 4441 atcaataact gcaaaattaa agtaccttca atggataaga caaaaaaaaa aaaaaaaaa One example of a nucleic acid sequence for human PROS1 is available as NCBI accession number NM_000313 (gi: 223671900). This sequence is recited below for easy reference as SEQ ID NO: 155.

1 tttggaaacg tcacactgtg gaggaaaagc agcaactagg gagctggtga agaaggatgt 61 ctcagcagtg tttactaggc ctccaacact agagcccatc ccccagctcc gaaaagcttc 121 ctggaaatgt ccttgttatc acttcccctc tcgggctggg cgctgggagc gggcggtctc 181 ctccgccccc ggctgttccg ccgaggctcg ctgggtcgct ggcgccgccg cgcagcacgg 241 ctcagaccga ggcgcacagg ctcgcagctc cgcggcgcct agcgctccgg tccccgccgc 301 gacgcgccac cgtccctgcc ggcgcctccg cgcgcttcga aatgagggtc ctgggtgggc 361 gctgcggggc gctgctggcg tgtctcctcc tagtgcttcc cgtctcagag gcaaactttt 421 tgtcaaagca acaggcttca caagtcctgg ttaggaagcg tcgtgcaaat tctttacttg 481 aagaaaccaa acagggtaat cttgaaagag aatgcatcga agaactgtgc aataaagaag 541 aagccaggga ggtctttgaa aatgacccgg aaacggatta tttttatcca aaatacttag 601 tttgtcttcg ctcttttcaa actgggttat tcactgctgc acgtcagtca actaatgctt 661 atcctgacct aagaagctgt gtcaatgcca ttccagacca gtgtagtcct ctgccatgca 721 atgaagatgg atatatgagc tgcaaagatg gaaaagcttc ttttacttgc acttgtaaac 781 caggttggca aggagaaaag tgtgaatttg acataaatga atgcaaagat ccctcaaata 841 taaatggagg ttgcagtcaa atttgtgata atacacctgg aagttaccac tgttcctgta 901 aaaatggttt tgttatgctt tcaaataaga aagattgtaa agatgtggat gaatgctctt 961 tgaagccaag catttgtggc acagctgtgt gcaagaacat cccaggagat tttgaatgtg 1021 aatgccccga aggctacaga tataatctca aatcaaagtc ttgtgaagat atagatgaat 1081 gctctgagaa catgtgtgct cagctttgtg tcaattaccc tggaggttac acttgctatt 1141 gtgatgggaa gaaaggattc aaacttgccc aagatcagaa gagttgtgag gttgtttcag 1201 tgtgccttcc cttgaacctt gacacaaagt atgaattact ttacttggcg gagcagtttg 1261 caggggttgt tttatattta aaatttcgtt tgccagaaat cagcagattt tcagcagaat 1321 ttgatttccg gacatatgat tcagaaggcg tgatactgta cgcagaatct atcgatcact 1381 cagcgtggct cctgattgca cttcgtggtg gaaagattga agttcagctt aagaatgaac 1441 atacatccaa aatcacaact ggaggtgatg ttattaataa tggtctatgg aatatggtgt 1501 ctgtggaaga attagaacat agtattagca ttaaaatagc taaagaagct gtgatggata 1561 taaataaacc tggacccctt tttaagccgg aaaatggatt gctggaaacc aaagtatact 1621 ttgcaggatt ccctcggaaa gtggaaagtg aactcattaa accgattaac cctcgtctag 1681 atggatgtat acgaagctgg aatttgatga agcaaggagc ttctggaata aaggaaatta 1741 ttcaagaaaa acaaaataag cattgcctgg ttactgtgga gaagggctcc tactatcctg 1801 gttctggaat tgctcaattt cacatagatt ataataatgt atccagtgct gagggttggc 1861 atgtaaatgt gaccttgaat attcgtccat ccacgggcac tggtgttatg cttgccttgg 1921 tttctggtaa caacacagtg ccctttgctg tgtccttggt ggactccacc tctgaaaaat -continued 1981 cacaggatat tctgttatct gttgaaaata ctgtaatata tcggatacag gccctaagtc 2041 tatgttccga tcaacaatct catctggaat ttagagtcaa cagaaacaat ctggagttgt 2101 cgacaccact taaaatagaa accatctccc atgaagacct tcaaagacaa cttgccgtct 2161 tggacaaagc aatgaaagca aaagtggcca catacctggg tggccttcca gatgttccat 2221 tcagtgccac accagtgaat gccttttata atggctgcat ggaagtgaat attaatggtg 2281 tacagttgga tctggatgaa gccatttcta aacataatga tattagagct cactcatgtc 2341 catragtttg gdaaaagaca aagaattctt aaggcatctt ttctctgctt ataatacctt 2401 ttccttgtgt gtaattatac ttatgtttca ataacagctg aagggtttta tttacaatgt 2461 gcagtctttg attattttgt ggtcctttcc tgggattttt aaaaggtcct ttgtcaagga 2521 aaaaaattct gttgtgatat aaatcacagt aaagaaattc ttacttctct tgctatctaa 2581 gaatagtgaa aaataacaat tttaaatttg aatttttttc ctacaaatga cagtttcaat 2641 ttttgtttgt aaaactaaat tttaatttta tcatcatgaa ctagtgtcta aatacctatg 2701 ttttttttcag aaagcaagga agtaaactca aacaaaagtg cgtgtaatta aatactatta 2761 atcataggca gatactattt tgtttatgtt tttgtttttt tcctgatgaa ggcagaagag 2821 atggtggtct attaaatatg aattgaatgg agggtcctaa tgccttattt caaaacaatt 2881 cctcaggggg aacagctttg gcttcatctt tctcttgtgt ggcttcacat ttaaaccagt 2941 atctttattg aattagaaaa caagtgggac atattttcct gagagcagca caggaatctt 3001 cttcttggca gctgcagtct gtcaggatga gatatcagat taggttggat aggtggggaa 3061 atctgaagtg ggtacatttt ttaaattttg ctgtgtgggt cacacaaggt ctacattaca 3121 aaagacagaa ttcagggatg gaaaggagaa tgaacaaatg tgggagttca tagttttcct 3181 tgaatccaac ttttaattac cagagtaagt tgccaaaatg tgattgttga agtacaaaag 3241 gaactatgaa aaccagaaca aattttaaca aaaggacaac cacagaggga tatagtgaat 3301 atcgtatcat tgtaatcaaa gaagtaagga ggtaagattg ccacgtgcct gctggtactg 3361 tgatgcattt caagtggcag ttttatcacg tttgaatcta ccattcatag ccagatgtgt 3421 atcagatgtt tcactgacag tttttaacaa taaattcttt tcactgtatt ttatatcact 3481 tataataaat cggtgtataa ttttaaaatg catgtgaata tctttattat atcaactgtt 3541 tgaataaaac aaaattacat aatagacatt taactcttca aaaaaaaaaa aaaaa One example of a nucleic acid sequence for human PSD3 is available as NCBI accession number NM_015310 (gi: 117606359). This sequence is recited below for easy reference as SEQ ID NO: 156.

1 aacaaagagc acgcggcgct ggccgccggc actcgcgccc tgaggctgcg gccccggagc 61 gcccggcggc ggtttcggcg cgcggccggg ctggcgatgg aagatggaag gaaggagcgc 121 agcggcagag acatttgttt gggtgaacaa tgcatctgca cattcccaga gtgttgccaa 181 ggccaaatat gaatttttdt ttggcagatc tgaagggaaa gctccagata ctagtgatca 241 tggaggaagc actttactcc caccaaatgt cacaaatgaa tttccagaat atgggaccat 301 ggaggaaggt ggagaaggcc taagggcttc tctggaattt gatggtgagg ctctgccatg 361 ccacccacaa gagcagcagg gtgtccagcc tcttactggc tgccactctg ggctcgacag 421 tgttacagaa ggaccaaaag atgtcagaga ggccccctct caaagtcatc tcaaggaaca 481 aagtttacag cccattgact ctttgatttc agctctgaaa gccacagaag ccagaatcat 541 ttccggaaca ttacaggcta caaaggtact ggaccaagat gctgtttcta gtttttcagt -continued 601 tcagcaggtg gaaaaagagc tggacactgc cagtcgtaaa acacagagag tcaacaaaac 661 gctccctgct ggccaaaaaa atttaccaga aatacctctt tcagctgaag taacaacgga 721 ggaaagtttt tatttgagca tccagaaaga tctcaccgcg ctgttaactg gagacactca 781 ggcagagatt tcccagataa tgaataatgg gaggaaaggg gctgtctgtg tgcaggagcc 841 atcttgtcct ttggcctccc tcgggagctc agcagtgacc tgccactctg caggcagtgt 901 tggtttcttg aaagagcaga ggtctgctct tgggagagag cacccagggg gatgtgatcg 961 aagcagctcc atgggacgcc caggccgggt caaacatgtg gaatttcaag gagtggaaat 1021 actgtggaca ggaggagaca agagagagac ccagcatcct atagattttg agacatcact 1081 gcaaagaaca gcctctcctg acagcaaaga gtcttccaaa gtgccacgcc atctcatctc 1141 atcagctggt ttgtgtaatt caagtagttt aactgagaat gtttgggatg aatcctggaa 1201 agctccttca gagaggcctg gcactagctc ggggacattt tcccctgtgc gtcttgatga 1261 gagtggagag gatgaagtct tcctacagga aaacaaacag catcttgaga agacacctaa 1321 accagagaga gacagggaaa ggatcagcga acaagaggag cacgttaagg gggaagatga 1381 agacatcctt gggcctggat atacggagga ctccaccgac gtgtacagct cccagtttga 1441 aaccattttg gacaacactt ctttatacta cagtgcagag tccctggaga cattatactc 1501 agagcctgat agctatttta gctttgaaat gcccctcact ccaatgatac aacagcgcat 1561 taaagaaggt ggtcagttct tggagaggac atcaggggga ggacatcagg atatcctgag 1621 tgtgtctgca gatggtggca tcgtgatggg ctattctagt ggcgtcacca atgggctgaa 1681 tgatgccagc gactccatct acacgaaagg caccccggag attgctttct ggggaagcaa 1741 tgctggggtg aaaacaacac ggctagaagc tcattctgaa atggggagca ctgaaatttt 1801 ggaaaaggag accccagaaa atctcagtaa tggtaccagc agcaatgtgg aagcagccaa 1861 aaggttggcc aaacgccttt atcagctgga cagattcaaa agatcagatg ttgcaaaaca 1921 ccttggcaag aacaacgaat ttagcaaact agttgcagaa gaatatctga agtttttga 1981 ttttacagga atgacgctgg atcagtcact caggtatttc tttaaagcat tctctcttgt 2041 gggagaaact caagaacgag agagagtttt aatacacttc tccaatagat atttttattg 2101 taacccagat accattgctt cacaagatgg agtccattgc cttacctgtg caataatgct 2161 tcttaatacc gatctacatg gccacaatat tggaaagaag atgacctgtc aggagttcat 2221 tgcaaatctg caaggggtaa atgagggtgt tgatttctcc aaggatctgc tgaaagctct 2281 gtacaactca atcaagaatg agaagcttga atgggcagta gatgatgaag agaaaaaaaa 2341 gtctccctca gaaagtactg aggagaaagc taacggaaca catccaaaga ccatcagtcg 2401 tattggaagt actactaacc catttttgga cattcctcat gatccaaatg ctgctgtgta 2461 caaaagtgga ttcttggctc ggaaaattca tgcagatatg gatggaaaga agactccaag 2521 aggaaaacga ggatggaaaa ccttttatgc tgtactgaag ggaacagttc tttacttgca 2581 aaaggatgaa tacaagccag aaaaggcctt gtctgaagag gacttgaaaa acgctgtgag 2641 tgtgcaccac gcattggcat ccaaggccac ggactatgag aagaaaccaa acgtgtttaa 2701 acttaaaact gccgactgga gggtcttgct ttttcaaact cagagcccag aggaaatgca 2761 agggtggata aacaaaatca attgtgtggc agctgtattt tctgcaccac catttccagc 2821 agcaatcggc tctcagaaga agtttagccg cccacttctg cctgccacta caacaaaact 2881 gtctcaggag gagcaactga agtcacatga aagtaagctg aagcagatca ccaccgagct 2941 ggccgagcac cgctcatatc cccccgacaa gaaggtcaaa gccaaggacg tcgatgagta -continued 3001 caaactgaaa gaccactatc tggagtttga gaaaacccgc tatgaaatgt atgtcagcat 3061 tctcaaggaa ggaggcaaag agctactgag taacgatgaa agcgaggctg caggactgaa 3121 gaagtcgcac tcgagtcctt cgctgaaccc ggatacttct ccaatcactg ccaaagtcaa 3181 gcgtaacgtg tcagagagga aggatcaccg acctgaaaca ccaagcatta agcaaaaagt 3241 tacttagagt ccatctgcgg ccaggaagtg ctggtcatgg agcaaaatag ggtttttcaa 3301 gatctttctg gtaatccgtg aatatattta aaaaaaaaaa gtctgtgaca aaacggtgca 3361 ttagtaattt tttctattgt atatttttgt tagtttctgt acagattgtc tttgctcttg 3421 atttcttttg ctttgatgat ttttgcaact tgatagctaa tgcacctttt ctgtgaggag 3481 gaggggatcg tgatttcaga atgaattatg tatcccttct cttttggttt tctcttgttt 3541 gcagtctgct cagttgtttt atgtattctc atatcaactg ttaaactttt ttttaaggtt 3601 aaagaattta atccattgtg aaacacttaa ctggacaaac tgtagtttta gtaaattcta 3661 gctggagtta atatacgcct ttatatgtga aatcttgccc agtcacagag gtagaattga 3721 gcactcacag atgctccagt aagaatcaca gtgctgggaa tctagttgct ccaatatgag 3781 gcagcttcat gtgcagctta gcacttgttg ttgagatcgg accctgctgg aagcagggaa 3841 aagaagcgtg aagatcgtag gattgagaac ttagggaagc acattagctt gcttgaagtg 3901 ctgattccat ttcagccaag caagggaaag aggaagtgga gtcattttgc ctttgaaggc 3961 tgaggaaaga ttgataccca gttaattttg tttgctaaag gatgggggca ataatcggcc 4021 cttgaggagc tgcagcagta ggcatgtgct cagtctgcag gaattgttac ctcactccca 4081 cagggtctag actagaaatc catcatctct atcgttgata tccttccatc caggaataga 4141 tttttcttac tctacatatg tgtgtgtgcg tgcgtgtgtg tgcgtgtgtg ggcatggggt 4201 tgtgtcctgg ttgtgatatt gaggtcttcc ttcctaacaa attaatacta aaatgaaaca 4261 gctttttcttg tgtccttaag acaaaataag gaaggaaaac gtagctgcag ttgtccacga 4321 tggatattgg ttctttaaaa tatatctgaa agtagtagtc agaatgaatt atggttggaa 4381 aactgaggaa tcttctggtt gcaggtgcaa agtgactttg tttattcttg tctcagtctc 4441 cttgatagcc acttcactct gctactactc aactttctcc taaaaatact tcatctattt 4501 tcagtccttt ctttctgtct actcaaaatg gttctattaa ctttgcagtc atgagcttgt 4561 tccagttaca gtccctttga agttcagggt gataaacaga atattcttct gtagaggaag 4621 agaaaggagt gaaagtttag cccactgaga cctagagctt tgtgatttcc taaccttgaa 4681 actctgtaat ccctaaagtt aaaatctccg caagtggcac aacttcagaa ctaatagtat 4741 cactttgatt tttcttttttc ctcccttaga aagtttctct agttctatag tttatttgtt 4801 gaaggtacta tgaccaaaga atcagctgct ctacaggaat agcatggttc cagtgaatta 4861 gagaaaacct gctgtaaagc catggtagtg tctaagtggt atgttattat gatgtactag 4921 catttattta cagaattatt tattaacgtt tacttccttc ccctctgtaa atgtccatga 4981 ctattgccca gagaaggctt acccctctct agggttgcag ttgctttctt tgtaataagt 5041 attttgccac acctgtaaaa aaaaaaacct cacttttaac tctctgcctt gtttgggtaa 5101 aggcagtaac taagtttatg tttcagaact gcaaaacaaa caggatagtt accaatatgg 5161 cccatgtatc agattgattt ttgtagcctc tcactgaatc caacatatcc acaagcaagt 5221 tatctgtctt tctacctgat aatctaaatt atcaggatat ttgttttctg cctaaatgtt 5281 tatactaagc cgaggggaga gaggtaccta gaccatgtca tctacaagct tcagtaacta 5341 aagaaaaagg aacttccctg agtggcttga atgtgtttgc ccacagtcta tatctatgta 5401 tatagaatgt ctgtatgtat tttacttatt taatatacat tgaatggtac cttgctacag -continued 5461 tatttctgac atttagagta gtgttgaaat actcggctag catcagcacc actatagcac 5521 tgtccgtgtc atatgagtca ctaatattaa ctccagggac ttctggatag gctaatagat 5581 cattggatac gaagggctct tttgaagctt cagtatacca tgtttgcata gtttatcttt 5641 aaaaacaact ttaaaggttc ttttgtgagc caggatctca gactgccgta gcatgatgct 5701 gtccatcttt agcgcatggg ctgagaacac ctcttccctg aggcttctga aggttgctgt 5761 ctgtcatgag tgcatgaagg aggccaagag tttatgctat gggaggaaac agtcactgat 5821 ttgcctagat tctgagagtc tggcccatag ccaaccacat tttcctttgg gataatttat 5881 ttcctgtggc atctagccag aagaaattga ggatgtttcc tttcacagct gctccaagcc 5941 tgttgcccaa ttcacggtac aagggagcac cccttccctt tcctctgaag gtacgccacc 6001 cacctccgtc gcccacctca gcgcccagga gccttgggac ttccttccat atgataaatc 6061 attcttcttc acgtcaatac acttcatatt aatttctagt acagaaaatc ttgacagcta 6121 tcagaatgcc ttggtcatag tgttgttgca aaattgacca tacaggtggc ccatgtataa 6181 aatctgaatt ttaggggttt gtccccacct cgcatgctgg cttttacagg gaggtgtctg 6241 ggattcctca ttagcaatca aaacttaatt actgggatgc agagtcctta ctttatcgcc 6301 agcccgtagg catttctgaa gtgcactttt ttgaaacatc attttgctaa ctctcagcag 6361 tgtctaatta aactgagcaa tacttttgtg aattttaatt aatctcagca aaaccatgat 6421 gggagagagt cctctgatgg aaatgtagtc cctggattat gtgtaacctt tttattcctc 6481 ttagatgcag aggatagaaa gcatttttttg gtgcagtggt cttgtggcaa acacaagacc 6541 ctctatgcgt ctccaactgt tatcctaatc tagaaaatga ggactggccc ctgggcaaaa 6601 gtgacatgag gaatttactc tggaagagga aaatctgggt ggctttccaa ggctaagata 6661 ggtttgtatt tcaccctgtg gccaagctac agaacttctg agattgtgga agaatttttg 6721 caaccagcag ggaaagaggc ctcttactgc ctaaacacaa agttacactg agcttttcta 6781 ctgtcctttg cctattgctc cctctatcat gtaaagatct gggaaggatg agaggcaggg 6841 cctgcttgtc atgagctgca ctcttttctt tttaactaat cattgacaat tggaagaaaa 6901 ttgacgttaa agaagtttct ccattgtctt actaacaaaa ccttttgggt ttcattaatt 6961 gtccttgaaa ttgagttcct ttggcatttt tccttgcagt catcagttaa gcatgttgca 7021 tcctgaattc acagaagttt agctttgcag gtttgaatct ctgtaattta actcccgtgg 7081 acttggtcga gttttcagca ggttgggagc cacctctctt catttcagca gtgagtcatc 7141 ccttgacttt tcaaatgaca gaattttttc caattgtaaa attagcactg taaaacaaag 7201 aaccaaagtg gcatcctaag agttgttaaa cctgaagtct agtttatgag gaattgtcca 7261 agttggagtt taaatagtat ctgcttttgt ctcaaagcat ctaagttatt ctgacagaaa 7321 atggtaagtc agctttgcag gcagatgcgc ctctgggcct cctaccttgc tccacagctt 7381 tctggccatc ttgtctccca ggccatgcca ctgctctgcc acatgtcagc aaatttcttt 7441 ccaccagtct tatagcatct tacatgatca aatcatcaca gaataacccc gtgatagatt 7501 attgatagca atagagaggg gctttgtcac tgatttttct ctcagattcc ttttccatct 7561 ctcatccata aaggaaggac tgaaatccaa aggcattctc cttttgtacc tacagtatcc 7621 agaacccacg tgggcagcct tctgcttatg acaataattg gcccattgca tgcagagaga 7681 atgtcttcat agagagaatg tcattaaata cttgaatctg catgacagtt tgacttgaat 7741 gcaacagcag gaaaattttg caagttacat aattgtatat acagtaggtt ttcttaagtc 7801 tcttcggttc atcctttgta atttgtgtgt gtatctgtag tattgcaggc ttttggagac -continued

```
7861 tattcttaca ggcagtatgt cagtcatcaa agaaaatgct gtcacctgcc attgttgtat
7921 ttgtgggtat ttatagttgt atgtatgtaa atgcatcagt gtgtagattg catatcagtg
7981 tatggtacat gtacatcaaa attatttttg tccttaatca gtgtgatatg aaaagcaagt
8041 acaacctcat aggactgatt atataatgaa gttgttgaga gtatatatag tggtattgtt
8101 ttattaaact taaactcaaa taatattttg attaaaattt ttaataagac tttatgctag
8161 aaaattcttt gagctttgaa tcaccagggc aaaaatgact ttcaactaac cttgtgaatc
8221 ttttgcagtg tactgtgtgc aataccaagg gcatagctcc ctgtaatttg ggaaatacag
8281 aaagaaaaga aaaaaaaaaa aaaaggcagc ctgtgcagtc ttagtaactt tagtattaag
8341 agcacttaaa gtcaaactga caattttggg cttattacaa aatgtgatgc tttaaagcac
8401 acgttcttta ttgttgttgt aattagtcca taaaaaatat agctttcgga agaattaagt
8461 acccaccata tcatttatgt atttgtgtat gttttacggg agatcaaacc actctcgtgg
8521 tgccgcatcc gtactcgctt gacttggaag aaatatcaca agcactaaag tatatcaggg
8581 catcccagga ttgggtactg tatcctaggt ttgcagttgc agaaattagc atctagtgtc
8641 acaggtaaaa gaatttcagg accaggttta aactttattt taaatatttt tatacttagg
8701 tctcttttc ctgcctctcc ccaaagaaga gccactggcc ttagttgttt gagcttactg
8761 cttatattat agagtgtaaa taggtaacta gagactaaaa ttttattaac cagcatgttt
8821 ggtatattta aagcagtgac tgagtgtgtt tgagtgagtg gctgagtgca gtgtcttttg
8881 tttaaacaca ctgcctcgtg tctttgtagc tgattcagag agtttgaatt gtggggtggg
8941 agactaactt cagctccagg ctgcagtaat gtgttggtag ttacacttga ggcatttttt
9001 tgttgttgtt aattaactct atagtctcaa actatttttg caaatatatc atttttccta
9061 attggttctt gacgtgcagt ggactggctc tgtgaatgat tggcagggtc ttagttttgc
9121 gagagtattt ccttctaaga attattgtga tctgcagaaa cagccatttg attcaaaaat
9181 catgtagaaa aggagtagga gaagcaaaac gtttcatttt tgggccttaa ccatttgaaa
9241 tgtttggact ttaaacataa agccatggag tttataaagc caagtaacca tttgatatgg
9301 ataataatat ctactctaga gagagtatat atatgcacat tgatttttaa tgctgttaag
9361 atacttttgt aaaactgtag gaacaagagt aattagacca aattgaagct taggggacag
9421 taaagtggtt gctttccatt tagggtaacc atgcatgtgg ttagtcctct cctcctgaga
9481 ttcagaacca gttgactgtc cccttaggtg tataaggaga aaagttgaca tgtctgggac
9541 ctctgacatg tgtacacatg cttgcacaca tgcacacaca gtgaatgttt taagttatac
9601 aaacataaga ccttaagatg caaagagcca gaatattcta aagaggtgat gaacagaggg
9661 ggtggaaact gcatcacaga tgttttccaa gggccagggt ggaatctgag ctctagtgtc
9721 tgactttgag atgcattata tttttaacac ataaatgagg ggatccatat cacattcttt
9781 cttgtggacc accaaattga aggctttctt gtaattcaca agcagcagct ctccagcatc
9841 tctccgtagc ctgggtgaag tcccagaagc tggtgtgcat catttAccaa ggtggcagag
9901 ctgcttgctc tgcagatcat tcctttgaga gaggagtaca agtgaagaaa caaggaggca
9961 cttcctgtag gagcactgat gtgccttgtc cacactcccc tctgagcttt actggtaaga
10021 gagctccgac tgaacatgct gagcagttga gcacttttcc atcagcaaca acagcgagga
10081 tggaaatgga aaggaaccga actaaaatgc atttcccttt gcagggcaga gagctaagct
10141 cttaggaata gtgttataga aataagcacc ctaacttcaa ttcctgaaaa tgttggttaa
10201 tggagagaat tttggagttt cacttaatat tttcccatcg gtcgccataa ataagtcttc
10261 aggcgctcct agaagagtcc cagcccaagg ctcgattaag gaccacactg caggtctgag
```

-continued 10321 gctcactgct ctgagtcctg aacaccagag ccctgcagag agtggtgata acacatcatc 10381 tctgcaaaga ggaacctctc cccaggccgc cacttcactc aggcttctac tgagcagcaa 10441 ggacagcctg ggtttcaaat gccacttccc ctgctttagg gatccaggtg tcctgatagc 10501 gtgaccctgc tgaggcaagg tatcaactcc gayagtgact gagtcactga gcgtcmcaca 10561 tgaacaaacg tcatgacaaa gattctctga gtgaagttaa caccacgtat tttacctttg 10621 caaaaaacaa actggcaccc tgagttctaa ctacggacgg acgatatctt tgcctccaca 10681 cccagattcc tggaaatggc taacgtttcc tttctagggg aagggtcgag gaatactcaa 10741 gtgctagctt agcagctttg ttcagtccag atcagagctg ttaggtaaag gcctaaccac 10801 ctccctgcag tctcttatat ctcaagcttt aggaacccat ttctaaatgt acactagcgg 10861 agaatttata ttgtcagcct tgattaccat aggacaggca gaaaggcgat aatttgtatc 10921 ttttaatata aaagaagctt ttaacttttc cagcctatta taataactga gttatattca 10981 ctgtggctca aactaattgg cattgtggaa catttcttta ccttcaaagt tttctccacc 11041 aatcatttca gttctattgc agtcctggtg ccatatgtcc cctgcaaatt gtgaaagtaa 11101 ttagtgacaa aatagcagcc tgctcctttt caatggcgaa actgtcggca ttagcagttt 11161 tgggtaagct ggcggtacta taacacgtac tggaaacctg ttcctcatca ccacctacca 11221 gattctggaa atgccgtctt ctagaaaacg atggcgtttg tggtggtctt cttttgaaag 11281 gaacagtaat ttgtgtggat attgttaaag tgtttaaaga atattttgac aattaagttt 11341 acattttaca attgctttat tttttattaa aatagttgta tataaatatt accctatttc 11401 actgttgttc aagtaaatct aaaccttgta gacaagtgag tcatctgata tgtatagaag 11461 ctgtgatata tagagtacat ttattgtgta aatgtttatg aatataattg ttcctgtgtt 11521 tttataagtt ggggatattt tgttgtttta cggcaacaaa atttattgca tttaaatggt 11581 ttttatgtaa tagaaatcac gcaaaatagt gaaggattta aaatatgtat atgatacatg 11641 taaatgtaca aactttagaa agaaataaat ccaacaaatt tcaatca One example of a nucleic acid sequence for human QPCT is available as NCBI accession number NM_012413 (gi: 68216098). This sequence is recited below for easy reference as SEQ ID NO: 157.

1 ggcgatggga aggcgggcgc agtcgaccca agggtggaga agagggaagg cgaaggacgc 61 gcgttcccgg gctcgtgacc gccagcggcc cggggaaccc gctcccagac agactcggag 121 agatggcagg cggaagacac cggcgcgtcg tgggcaccct ccacctgctg ctgctggtgg 181 ccgccctgcc ctgggcatcc aggggggtca gtccgagtgc ctcagcctgg ccagaggaga 241 agaattacca ccagccagcc attttgaatt catcggctct tcggcaaatt gcagaaggca 301 ccagtatctc tgaaatgtgg caaaatgact tacagccatt gctgatagag cgatacccgg 361 gatcccctgg aagctatgct gctcgtcagc acatcatgca gcgaattcag aggcttcagg 421 ctgactgggt cttggaaata gacaccttct tgagtcagac accctatggg taccggtctt 481 tctcaaatat catcagcacc ctcaatccca ctgctaaacg acatttggtc ctcgcctgcc 541 actatgactc caagtatttt tcccactgga acaacagagt gtttgtagga gccactgatt 601 cagccgtgcc atgtgcaatg atgttggaac ttgctcgtgc cttagacaag aaactccttt 661 ccttaaagac tgtttcagac tccaagccag atttgtcact ccagctgatc ttctttgatg 721 gtgaagaggc ttttcttcac tggtctcctc aagattctct ctatgggtct cgacacttag -continued

```
 781 ctgcaaagat ggcatcgacc ccgcacccac ctggagcgag aggcaccagc caactgcatg
 841 gcatggattt attggtctta ttggatttga ttggagctcc aaacccaacg tttcccaatt
 901 tttttccaaa ctcagccagg tggttcgaaa gacttcaagc aattgaacat gaacttcatg
 961 aattgggttt gctcaaggat cactctttgg aggggcggta tttccagaat tacagttatg
1021 gaggtgtgat tcaggatgac catattccat ttttaagaag aggtgttcca gttctgcatc
1081 tgataccgtc tcctttccct gaagtctggc acaccatgga tgacaatgaa gaaaatttgg
1141 atgaatcaac cattgacaat ctaaacaaaa tcctacaagt ctttgtgttg gaatatcttc
1201 atttgtaata ctctgattta gtttaggata attggttcta gaattgaatt caaaagtcaa
1261 ggcatcattt aaaataatct gatttcagac aaatgctgtg tggaaacatc tatcctatag
1321 atcatcctat tcttatgtgt ctttggttat cagatcaatt acagaataat tgtgttgtga
1381 tattgtgtcc taaattgctc attaattttt atttacagat tgaaaaagag ggaccgtgta
1441 aagaaaatgg aaaataaata tctttcaaag actcttttag ataaacacga tgaggcaaaa
1501 tcaggttcat tcattcaacg atagtttctc aacagtactt aaatagcggt tggaaaacgt
1561 agccttcatt ttatgatttt ttcatatgtg gaaatctatt acatgtaata caaaacaaac
1621 atgtagtttg aaggcggtca gatttctttg agaaatcttt gtagagttaa ttttatggaa
1681 attaaaatca gaattaaatg ctaaaaaaaa aaaaaaaaa
```

One example of a nucleic acid sequence for human RAB27A is available as NCBI accession number NM_004580 (gi: 34485707). This sequence is recited below for easy reference as SEQ ID NO: 158.

```
   1 gttttgaaag ttgatggagc gaactgcttt tccaaagact cttttgaaaa actttttaag
  61 taggccattc tgactttaac atttctcttt gtcttaacat tagacaaaaa gtaaccttcc
 121 tgaagaggac atgtgattgg aagttgtcaa ttgttgaagc attggtaact ccagtctcta
 181 acgttttaga aaatcataac aagcggttct ctaccctgta aaggtgaact actgagttct
 241 tcattatgtc tgatggagat tatgattacc tcatcaagtt tttagctttg ggagactctg
 301 gtgtagggaa gaccagtgta ctttaccaat atacagatgg taaatttaac tccaaattta
 361 tcacaacagt gggcattgat ttcagggaaa aaagagtggt gtacagagcc agtgggccgg
 421 atggagccac tggcagaggc cagagaatcc acctgcagtt atgggacaca gcagggcagg
 481 agaggtttcg tagcttaacg acagagttct tcagagatgc tatgggtttt cttctacttt
 541 ttgatctgac aaatgagcaa agtttcctca atgtcagaaa ctggataagc cagctacaga
 601 tgcatgcata ttgtgaaaac ccagatatag tgctgtgtgg aaacaagagt gatctggagg
 661 accagagagt agtgaaagag gaggaagcca tagcactcgc agagaaatat ggaatcccct
 721 actttgaaac tagtgctgcc aatgggacaa acataagcca agcaattgag atgcttctgg
 781 acctgataat gaagcgaatg gaacggtgtg tggacaagtc ctggattcct gaaggagtgg
 841 tgcgatcaaa tggtcatgcc tctacggatc agttaagtga agaaaaggag aaaggggcat
 901 gtggctgttg agaagtcaag taagcgacat agtagttcag gtggcccatg cctgggatct
 961 tctctatgat tgatacatgg cacagtgaga gattaatggg cattgtgtac aaattgcttc
1021 tcaccatccc cattagacct acgaataaag catccggttc taaaattaat ttgttgcagc
1081 tttgtaaata tttctttaag attcagcctg agagttagga gaaatatttc agagccaaaa
1141 gtgccttata caaccttagc ctattatagt aaatcattca aggattcaga attttgcagt
1201 cacagaagag tgtatttatt atgtagaatg aatgagggta ctgtcacctg ccttaatgta
```

-continued

```
1231 ggtaggccca gagtcttaca tttaagatct tacatgcagt tataaaaccg ccacagtctt
1321 caatccagat ttgaagactc atgccatagg tgacattcta aaataccatt aaagccactt
1381 aaatgttaaa taagaatata catgcacatc agctcaatgt ctttgagtat taattttatg
1441 taagcattct atttaacatg aatataggac aaatcatggc tatatctata gaccttggat
1501 aaactggatt gaccaattat acactcacgg tgactttttt attggtggga aggggattgg
1561 ggtggggcag gctggcttaa tgtaatatga gcaaccaaag tgggacttct gtctccccgc
1621 tatattccca ttgctctgaa tggttgattg aagggtcagg gaactagatt ttatggcttt
1681 agttcactgt gattgtacat ttatacttgg cctatgtgct ggccgcacct gaacatagct
1741 ggtgcttatg ccgagttatt tgcgatgagt aaatatttag tttctttttc ttcatattta
1801 taatgttgat ctggcatcct caggctgcag ctttattagc ttataactta ctcatctcta
1861 tctttaccag caggctctgt attgttgata tttgcaactt gttttgcttt tccattggtg
1921 gaattgaaat aattagtttt taattacata agatgcctgt ttgctatttg gtggaagata
1981 gatgttcata ttgaagcagt cacatttgta ctgtagttca ataaaagaaa aatgaagtat
2041 tctgtagcct atatttttca tagagctcat gagcatttac tgtacttgct gggtcttgcc
2101 aagatcattt attccgctgc attgccaaag tgtcttcata ccaaattaaa ggtggtttta
2161 atatatgttt catggaagtt gtttataaaa ttcaaaggta tttcatttag gtgaaaagtc
2221 ttatttatta aagtggtttg aataaagtag atcaaaactt ccagagatct taatggctat
2281 ataggaagaa atatcactca ccataattta aataaagaat aaaaatactt gtattttgtg
2341 gtggcaaatg tttggtagaa ctgtaattag aaaaatacaa gtatatttgc gtgatggtta
2401 cactagaagc ccagacttta cgactacaca atatattcat gtatctaaac tgtacttgta
2461 ccccctaaat ttatttttaa aaaaggaaaa ataaaagtat catgaaaaaa cctatttttt
2521 tttccactgt ccttccacta ctcccataac aaacttatcc atggttggta aaattttaca
2581 tatttctatc cttgaaatga aggcttcttt taaattccaa agaagtcatg gaggcctgtg
2641 catttgaatt gtatatgcta gtgaggaaaa gatttagaca tttcaagagc agggttggcc
2701 aggcgcggtg gctcacacct gtaatcccag cactttggga ggccgaggag ggcggatcac
2761 gaggtcagga gatcgagacc atcctggcta acacagtgaa accccatctc tactaaaaaa
2821 aaaa
```

One example of a nucleic acid sequence for human RXRG is available as NCBI accession number NM_006917 (gi: 58331205). This sequence is recited below for easy reference as SEQ ID NO:159.

```
   1 gtggcaagag tagcggtgac ggcggcggcg gcggcggcgg cagcattatg cgtgattact
  61 gacaggcacc agctgctgcc gccacagccg tctcaaacgc actatgtgga ctctccgatc
 121 tagaggcaga ttcctgacta atcccagagg gctggcccag cctgtgctcc ccgggctgct
 181 aggaagcgat gaccactctt gttagcccaa gttgaagaaa gccgggctgt gcctgggagc
 241 cgagagaggc ggtaatattt agaagctgca caggagagga acatgaactg acgagtaaac
 301 atgtatggaa attattctca cttcatgaag tttcccgcag gctatggagg ctcccctggc
 361 cacactggct ctacatccat gagcccatca gcagccttgt ccacagggaa gccaatggac
 421 agccaccccca gctacacaga taccccagtg agtgccccac ggactctgag tgcagtgggg
 481 accccccctca atgccctggg ctctccatat cgagtcatca cctctgccat gggcccaccc
```

-continued

```
 541 tcaggagcac ttgcagcgcc tccaggaatc aacttggttg ccccacccag ctctcagcta

 601 aatgtggtca acagtgtcag cagttcagag gacatcaagc ccttaccagg gcttcccggg

 661 attggaaaca tgaactaccc atccaccagc cccggatctc tggttaaaca catctgtgcc

 721 atctgtggag acagatcctc aggaaagcac tacggggtat acagttgtga aggctgcaaa

 781 gggttcttca agaggacgat aaggaaggac ctcatctaca cgtgtcggga taataaagac

 841 tgcctcattg acaagcgtca gcgcaaccgc tgccagtact gtcgctatca gaagtgcctt

 901 gtcatgggca tgaagaggga agctgtgcaa gaagaaagac agaggagccg agagcgagct

 961 gagagtgagg cagaatgtgc taccagtggt catgaagaca tgcctgtgga gaggattcta

1021 gaagctgaac ttgctgttga accaaagaca gaatcctatg gtgacatgaa tatggagaac

1081 tcgacaaatg accctgttac caacatatgt catgctgctg acaagcagct tttcaccctc

1141 gttgaatggg ccaagcgtat tccccacttc tctgacctca ccttggagga ccaggtcatt

1201 ttgcttcggg cagggtggaa tgaattgctg attgcctctt tctcccaccg ctcagtttcc

1261 gtgcaggatg gcatccttct ggccacgggt ttacatgtcc accggagcag tgcccacagt

1321 gctggggtcg gctccatctt tgacagagtc ctaactgagc tggtttccaa aatgaaagac

1381 atgcagatgg acaagtcgga actgggatgc ctgcgagcca ttgtactctt taacccagat

1441 gccaagggcc tgtccaaccc ctctgaggtg gagactctgc gagagaaggt ttatgccacc

1501 cttgaggcct acaccaagca gaagtatccg gaacagccag gcaggtttgc caagctgctg

1561 ctgcgcctcc cagctctgcg ttccattggc ttgaaatgcc tggagcacct cttcttcttc

1621 aagctcatcg gggacacccc cattgacacc ttcctcatgg agatgttgga gaccccgctg

1681 cagatcacct gagccccacc agccacagcc tccccaccca ggatgacccc tgggcaggtg

1741 tgtgtggacc cccaccctgc actttcctcc acctcccacc ctgacccccct tcctgtcccc

1801 aaaatgtgat gcttataata aagaaaacct ttctacacat gaaaaaaaaa aaaaaa
```

One example of a nucleic acid sequence for human SDC4 is available as NCBI accession number NM_002999 (gi: 38201674). This sequence is recited below for easy reference as SEQ ID NO: 160.

```
   1 actcgccgca gcctgcgcgc cttctccagt ccgcggtgcc atggcccccg cccgtctgtt

  61 cgcgctgctg ctgttcttcg taggcggagt cgccgagtcg atccgagaga ctgaggtcat

 121 cgacccccag gacctcctag aaggccgata cttctccgga gccctaccag acgatgagga

 181 tgtagtgggg cccgggcagg aatctgatga ctttgagctg tctggctctg gagatctgga

 241 tgacttggaa gactccatga tcggccctga agttgtccat cccttggtgc ctctagataa

 301 ccatatccct gagagggcag ggtctgggag ccaagtcccc accgaaccca agaaactaga

 361 ggagaatgag gttatcccca agagaatctc acccgttgaa gagagtgagg atgtgtccaa

 421 caaggtgtca atgtccagca ctgtgcaggg cagcaacatc tttgagagaa cggaggtact

 481 ggcagctctg attgtgggtg gcatcgtggg catcctcttt gccgtcttcc tgatcctact

 541 gctcatgtac cgtatgaaga agaaggatga aggcagctat gacctgggca agaaacccat

 601 ctacaagaaa gcccccacca atgagttcta cgcgtgaagc ttgcttgtgg gcactggctt

 661 ggactttagc ggggagggaa gccaggggat tttgaagggt ggacattagg gtagggtgag

 721 gtcaacctaa tactgacttg tcagtatctc cagctctgat tacctttgaa gtgttcagaa

 781 gagacattgt cttctactgt tctgccaggt tcttcttgag ctttgggcct cagttgccct

 841 ggcagaaaaa tggattcaac ttggcctttc tgaaggcaag actgggattg gatcacttct
```

-continued

```
 901 taaacttcca gttaagaatc taggtccgcc ctcaagccca tactgaccat gcctcatcca
 961 gagctcctct gaagccaggg ggctaacgga tgttgtgtgg agtcctggct ggaggtcctc
1021 ccccagtggc cttcctccct tcctttcaca gccggtctct ctgccaggaa atgggggaag
1081 gaactagaac cacctgcacc ttgagatgtt tctgtaaatg ggtacttgtg atcacactac
1141 gggaatctct gtggtatata cctggggcca ttctaggctc tttcaagtga cttttggaaa
1201 tcaacctttt ttatttgggg gggaggatgg ggaaaagagc tgagagttta tgctgaaatg
1261 gatttataga atatttgtaa atctattttt agtgtttgtt cgttttttta actgttcatt
1321 cctttgtgca gagtgtatat ctctgcctgg gcaagagtgt ggaggtgccg aggtgtcttc
1381 attctctcgc acatttccac agcacctgct aagtttgtat ttaatggttt ttgtttttgt
1441 ttttgtttgt ttcttgaaaa tgagagaaga gccggagaga tgatttttat taattttttt
1501 tttttttttt tttttttact atttatagct ttagataggg cctcccttcc cctcttcttt
1561 ctttgttctc tttcattaaa ccccttcccc agtttttttt ttatacttta aaccccgctc
1621 ctcatggcct tggccctttc tgaagctgct tcctcttata aaatagcttt tgccgaaaca
1681 tagttttttt ttagcagatc ccaaaatata atgaagggga tggtgggata tttgtgtctg
1741 tgttcttata atatattatt attcttcctt ggttctagaa aaatagataa atatattttt
1801 ttcaggaaat agtgtggtgt ttccagtttg atgttgctgg gtggttgagt gagtgaattt
1861 tcatgtggct gggtgggttt ttgccttttt ctcttgccct gttcctggtg ccttctgatg
1921 gggctggaat agttgaggtg gatggttcta ccctttctgc cttctgtttg ggacccagct
1981 ggtgttcttt ggtttgcttt cttcaggctc tagggctgtg ctatccaata cagtaaccac
2041 atgcggctgt ttaaagttaa gccaattaaa atcacataag attaaaaatt ccttcctcag
2101 ttgcactaac cacgtttcta gaggcgtcac tgtatgtagt tcatggctac tgtactgaca
2161 gcgagagcat gtccatctgt tggacagcac tattctagag aactaaactg gcttaacgag
2221 tcacagcctc agctgtgctg ggacgaccct tgtctccctg ggtagggggg ggggaatggg
2281 ggagggctga tgaggcccca gctggggcct gttgtctggg accctccctc tcctgagagg
2341 ggaggcctgg tggcttagcc tgggcaggtc gtgtctcctc ctgaccccag tggctgcggt
2401 gaggggaacc accctccctt gctgcaccag tggccattag ctcccgtcac cactgcaacc
2461 cagggtccca gctggctggg tcctcttctg cccccagtgc ccttcccctt gggctgtgtt
2521 ggagtgagca cctcctctgt aggcacctct cacactgttg tctgttactg attttttttg
2581 ataaaaagat aataaaacct ggtactttct aaaaaaaaaa aaaaaaaaaa aaaaaaaaaa
```

One example of a nucleic acid sequence for human SERPINA1 is available as NCBI accession number NM_001127707 (gi: 189163541). This sequence is recited below for easy reference as SEQ ID NO:161.

```
  1 tgggcaggaa ctgggcactg tgcccagggc atgcactgcc tccacgcagc aaccctcaga
 61 gtcctgagct gaaccaagaa ggaggagggg gtcgggcctc cgaggaaggc ctagccgctg
121 ctgctgccag gaattccagg ttggaggggc ggcaacctcc tgccagcctt caggccactc
181 tcctgtgcct gccagaagag acagagcttg aggagagctt gaggagagca ggaaagcctc
241 ccccgttgcc cctctggatc cactgcttaa atacggacga ggacagggcc ctgtctcctc
301 agcttcaggc accaccactg acctgggaca gtgaatcgac aatgccgtct tctgtctcgt
361 ggggcatcct cctgctggca ggcctgtgct gcctggtccc tgtctccctg gctgaggatc
```

-continued

```
421 cccacmgaga tgctgcccag aagacagata catcccacca tgatcaggat cacccaacct
481 tcaacaagat cacccccaac ctggctgagt tcgccttcag cctataccgc cagctggcac
541 accagtccaa cagcaccaat atcttcttct ccccagtgag catcgctaca gcctttgcaa
601 tgctctccct ggggaccaag gctgacactc acgatgaaat cctggagggc ctgaatttca
661 acctcacgga gattccggag gctcagatcc atgaaggctt ccaggaactc ctccgtaccc
721 tcaaccagcc agacagccag ctccagctga ccaccggcaa tggcctgttc ctcagcgagg
781 gcctgaagct agtggataag tttttggagg atgttaaaaa gttgtaccac tcagaagcct
841 tcactgtcaa cttcggggac accgaagagg ccaagaaaca gatcaacgat tacgtggaga
901 agggtactca agggaaaatt gtggatttgg tcaaggagct tgacagagac acagtttttg
961 ctctggtgaa ttacatcttc tttaaaggca aatgggagag accctttgaa gtcaaggaca
1021 ccgaggaaga ggacttccac gtggaccagg tgaccaccgt gaaggtgcct atgatgaagc
1081 gtttaggcat gtttaacatc cagcactgta agaagctgtc cagctgggtg ctgctgatga
1141 aatacctggg caatgccacc gccatcttct tcctgcctga tgaggggaaa ctacagcacc
1201 tggaaaatga actcacccac gatatcatca ccaagttcct ggaaaatgaa gacagaaggt
1261 ctgccagctt acatttaccc aaactgtcca ttactggaac ctatgatctg aagagcgtcc
1321 tgggtcaact gggcatcact aaggtcttca gcaatggggc tgacctctcc ggggtcacag
1381 aggaggcacc cctgaagctc tccaaggccg tgcataaggc tgtgctgacc atcgacgaga
1441 aagggactga agctgctggg gccatgtttt tagaggccat acccatgtct atcccccccg
1501 aggtcaagtt caacaaaccc tttgtcttct taatgattga acaaaatacc aagtctcccc
1561 tcttcatggg aaaagtggtg aatcccaccc aaaaataact gcctctcgct cctcaacccc
1621 tcccctccat ccctggcccc ctccctggat gacattaaag aagggttgag ctggtccctg
1681 cctgcatgtg actgtaaatc cctcccatgt tttctctgag tctccctttg cctgctgagg
1741 ctgtatgtgg gctccaggta acagtgctgt cttcgggccc cctgaactgt gttcatggag
1801 catctggctg ggtaggcaca tgctgggctt gaatccaggg gggactgaat cctcagctta
1861 cggacctggg cccatctgtt tctggagggc tccagtcttc cttgtcctgt cttggagtcc
1921 ccaagaagga atcacagggg aggaaccaga taccagccat gaccccaggc tccaccaagc
1981 atcttcatgt ccccctgctc atcccccact cccccccacc cagagttgct catcctgcca
2041 gggrtggctg tgcccacccc aaggctgccc tcctgggggc cccagaactg cctgatcgtg
2101 ccgtggccca gttttgtggc atctgcagca acacaagaga gaggacaatg tcctcctctt
2161 gacccgctgt cacctaacca gactcgggcc ctgcacctct caggcacttc tggaaaatga
2221 ctgaggcaga ttcttcctga agcccattct ccatggggca acaaggacac ctattctgtc
2281 cttgtccttc catcgctgcc ccagaaagcc tcacatatct ccgtttagaa tcaggtccct
2341 tctccccaga tgaagaggag ggtctctgct ttgtAttctc tatctcctcc tcagacttga
2401 ccaggcccag caggccccag aagaccatta ccctatatcc cttctcctcc ctagtcacat
2461 ggccataggc ctgctgatgg ctcaggaagg ccattgcaag gactcctcag ctatgggaga
2521 ggaagcacat cacccattga cccccgcaac ccctcccttt cctcctctga gtcccgactg
2581 gggccacatg cagcctgact tctttgtgcc tgttgctgtc cctgcagtct tcagagggcc
2641 accgcagctc cagtgccacg gcaggaggct gttcctgaat agcccctgtg gtaagggcca
2701 ggagagtcct tccatcctcc aaggccctgc taaaggacac agcagccagg aagtcccctg
2761 ggcccctagc tgaaggacag cctgctccct ccgtctctac caggaatggc cttgtcctat
2821 ggaaggcact gccccatccc aaactaatct aggaatcact gtctaaccac tcactgtcat
```

-continued 2881 gaatgtgtac ttaaaggatg aggttgagtc ataccaaata gtgatttcga tagttcaaaa
2941 tggtgaaatt agcaattcta catgattcag tctaatraat ggataccgac tgtttcccac
3001 acaagtctcc tgttctctta agcttactca ctgacagcct ttcactctcc acaaatacat
3061 taaagatatg gccatcacca agccccctag gatgacacca gacctgagag tctgaagacc
3121 tggatccaag ttctgacttt tccccctgac agctgtgtga ccttcgtgaa gtcgccaaac
3181 ctctctgagc cccagtcatt gctagtaaga cctgcctttg agttggtatg atgttcaagt
3241 tagataacaa aatgtttata cccattagaa cagagaataa atagaactac atttcttgca One example of a nucleic acid sequence for human SLC25A15 is available as NCBI accession number NM_014252 (gi: 237649033). This sequence is recited below for easy reference as SEQ ID NO: 162.

1 tgggggcggt ggcagggccg gtgggcggtg gcggctcccg gtctcggctc gggcacggcc
61 ctgggcaggc cgcccgccag ccgcaggggc gctcctgagc ttcgcggggc cgcagtccgg
121 gatgcctgcg cgaagggagg ggcgaagggc cggccgttgc cgacgtgggt gttaagtggc
181 cgccccagcc ggcgacccgg agccgagagc gggcggcgga gcctgagctg gacgcggcca
241 cgccggcgcg gcgggatatg tggtgcctgt cataagctcc agagagctgc cttccacaag
301 accagcagaa gagtgggcaa acatgaaatc caatcctgct atccaggctg ccattgacct
361 cacagcgggg gctgcaggag gtacagcatg tgtactgacc gggcagccct ttgacacaat
421 gaaagtgaag atgcagacgt tccctgacct gtaccggggc ctcaccgact gctgcctgaa
481 gacttactcc caggtgggct tccgtggctt ctacaagggt accagtccag cactaatcgc
541 caacatcgct gagaactcag tcctcttcat gtgctacggc ttctgccagc aggtggtgcg
601 gaaagtggct ggattggaca agcaggcaaa gctgagtgat ctgcagaatg cagccgccgg
661 ttccttcgcc tctgcctttg ctgcactggt gctctgcccc acggagctcg tgaagtgccg
721 gctgcagacc atgtatgaga tggagacatc agggaagata gccaagagcc agaatacagt
781 gtggtctgtc atcaaaagta ttcttaggaa agatggcccc ttggggttct accatggact
841 ctcaagcact ttacttcgag aagtaccagg ctatttcttc ttcttcggtg gctatgaact
901 gagccggtcc ttttttgcat cagggagatc aaaagatgaa ttaggccctg tacctttgat
961 gttaagtggt ggagttggtg ggatttgcct ctggcttgcg gtatacccag tggattgtat
1021 caaatccaga attcaagttc tttccatgtc tggaaaacag gcaggattta tcagaacctt
1081 tataaatgtt gtgaaaaatg aaggaataac ggccttatat tctggactga aacctactat
1141 gattcgagca ttccctgcca atggagcact ctttttggcc tacgaatata gcaggaagtt
1201 gatgatgaac cagttggaag catactgaag tgtcttggtg ggcctgagcc aagcacaggt
1261 gtttgaggac tacagttcat ctcagggttt cttggagtac aagaccagtg tgaagttatt
1321 ctgatttctt gggaattttg ctttttgtct tcccttctac cctacatctt aaactttatg
1381 gaagaacctc tattttgcat catatcattt ctgtccataa ttgtactgaa atagaaaagt
1441 gaccgctctt gctcttggta aaatatagag tggtcagtag ccttatgcac ctaattcaaa
1501 aggtggaata tagttctgtc agggctttta cgtaaacctc cacttgtaca tgcaatttgg
1561 acagttatgt gttgagggaa atacagtttg gtaccttgtt tatttcaaat atcagaaaaa
1621 cccagaggtg atcatttctc atgaagatgc ttataaatgg ttgcttaacc cattctagat
1681 gtagggtctg cttaatgtgt gtacttttct aagtggttga ttattttta tttttttgat -continued 1741 acagagtctc actctgtcac ccagactgga gtgcagtggc acgatctcgg ctcactgcaa 1801 cctccgcctc ctgggttcaa gcgattctct cacctcagcc tcctgagtag ctgggattac 1861 aggtacgcgc caccatgtcc agctaatttt ttttggtatt ttttgtagag acgaggtttc 1921 accatgttgt ccaggttggt ctcgaactcc tgacctcaag tgatccgccc acctcggcct 1981 cccaaagtgc tgggattact ggtgtgagcc accatgccca gccagtggtt gaatttttta 2041 aaaagtgttc atggggtgct tgaaaactaa aatatccttc tagatttgta agacagtata 2101 cctgcatact ggtgtggctt ccacacttga gtaaaagctt cagagtaggt atcctagatt 2161 tccccaagat gctctactct taaaatagtg ccattcattt tctaggtggg atcatattcc 2221 acgctgacta tattgctagg ggtggcccag agggtcaggc ctttgggaaa tagcatggcc 2281 tttaccagct tcccttctct cccaaagaac ttcccttctt gggctttaga ttgaggaagg 2341 ggctgagtgg taggcggtgc tgctgtgctc tgatgaagac ccatgtggct agcaacagcg 2401 cttacctttt gtctctgggt cctggcctgg ggccatcaat ccactttggg ccactcactg 2461 tctgctctgc ctccaccaat cagaaaccct tccaaggaac agtgagagcc aaagccaaga 2521 gaagccttct tccctgtttg gtgattgtgt gacagtgggt gaacctctct cagagagaac 2581 tagaaagaac tcagtgcttg tactccacag tgagtaatgt caggtctgac ccatcctgaa 2641 gcctgtcttg ccatgctttt acagtgttgg aggcttctac atttggtact tgcagtcagt 2701 aagtcttaat gatgactgta tatgtgatat gagtttataa agcaatggaa cataagaaaa 2761 gcaattgtag gccaggcgca gtggctcacg cctataatcc cagcactttg ggaggctgag 2821 gcgggcgggt cacaaggtca ggagttcgag aacagcctga ccaacatggt gaaaccccat 2881 ctctactaaa aatacaaaaa ttagctgggc gtggtggcac gtgcctgtaa tcccagctac 2941 tcaggaggct gaggcaggag aatcgcttga acccgggagg cagaggttgc agtgaactga 3001 gattgtgcca ctgcactcca gactgggtga cacagcgaga cttcatctca aaaaaaaaaa 3061 gaaaagaaaa gcaattgtac ttcactatgc catatgtatg tattcactga ccaaaaattc 3121 actgaccaac caaccaaact ccacacttca tctgatcccc catagacttg gggatggaca 3181 gctgttcttt ggccatatgg tataagagga tcattcttgt cactacttaa gttagcctca 3241 tcattttgtg ctgctccaac accagcaggg tatctcccaa taaagtgttc ctaagcagcc 3301 tgtatactga gtgcaagcag gctatcaatt ttaataatag tccataccat gtatgtgttt 3361 ctgtcagcag aatgtacatg ttgtacaaaa cctccaggtt ccttaagctt tttgctgtcc 3421 atgaatcctc tgtggcaact gtaatcacag agccagaagc cagagggcca gggatatgag 3481 aggctgacaa acatcagggg acatctgggg aggagatccc tgtcatgtct cttgtgccat 3541 ggagctatta tggctggtct tccatttgct ttttctttaa gtgaaaacca tttttctact 3601 ttgcttttct ctccatactt aaatggtcag tagctactga gtggtgcttt atctgaatag 3661 gcctggatcg aagtaaaata gaaatgggac tggctttcca caggaagtaa actgcttcag 3721 agcccacagt cccctgctca gtgtccggaa agaagtcagt catccctgtt ggcagtaaat 3781 cttcccacag gccgtccatt agagatttaa ctagatatgt tcaatagaaa gagtctgagg 3841 caagtggaaa tgaggaacgg aaacttaggt tgggagaata tttttttttt attcattctg 3901 tttgcttaat tcagagtaca gtttgtgcta tttcatatct gtactccagg cagaaatata 3961 acttgaaaat actgtgtcta aagaaatttc agtgttctat cattaaatta tttacttaat 4021 aaaaaaaaaa aaaaaaaa One example of a nucleic acid sequence for human SLC4A4 is available as NCBI accession number NM_001098484 (gi: 197927157). This sequence is recited below for easy reference as SEQ ID NO: 163.

```
   1 gcggcggcgg ccgcggtggc agcgaaggcg gcggcggcgg cggcagtggc agtggccgct
  61 gcagccccac actccgccgc caaactggag gagcgacgga agccagaccc caggaggatg
 121 gaggatgaag ctgtcctgga cagaggggct tccttcctca agcatgtgtg tgatgaagaa
 181 gaagtagaag gccaccatac catttacatc ggagtccatg tgccgaagag ttacaggaga
 241 aggagacgtc acaagagaaa gacagggcac aaagaaaaga aggaaaagga gagaatctct
 301 gagaactact ctgacaaatc agatattgaa aatgctgatg aatccagcag cagcatccta
 361 aaacctctca tctctcctgc tgcagaacgc atccgattca tcttgggaga ggaggatgac
 421 agcccagctc cccctcagct cttcacggaa ctggatgagc tgctggccgt ggatgggcag
 481 gagatggagt ggaaggaaac agccaggtgg atcaagtttg aagaaaaagt ggaacagggt
 541 ggggaaagat ggagcaagcc ccatgtggcc acattgtccc ttcatagttt atttgagctg
 601 aggacatgta tggagaaagg atccatcatg cttgatcggg aggcttcttc tctcccacag
 661 ttggtggaga tgattgttga ccatcagatt gagacaggcc tattgaaacc tgaacttaag
 721 gataaggtga cctatacttt gctccggaag caccggcatc aaaccaagaa atccaacctt
 781 cggtccctgg ctgacattgg gaagacagtc tccagtgcaa gtaggatgtt taccaaccct
 841 gataatggta gcccagccat gacccatagg aatctgactt cctccagtct gaatgacatt
 901 tctgataaac cggagaagga ccagctgaag aataagttca tgaaaaaatt gccacgtgat
 961 gcagaagctt ccaacgtgct tgttggggag gttgactttt tggatactcc tttcattgcc
1021 tttgttaggc tacagcaggc tgtcatgctg ggtgccctga ctgaagttcc tgtgcccaca
1081 aggttcttgt tcattctctt aggtcctaag gggaaagcca agtcctacca cgagattggc
1141 agagccattg ccaccctgat gtctgatgag gtgttccatg acattgctta taaagcaaaa
1201 gacaggcacg acctgattgc tggtattgat gagttcctag atgaagtcat cgtccttcca
1261 cctggggaat gggatccagc aattaggata gagcctccta agagtcttcc atcctctgac
1321 aaaagaaaga atatgtactc aggtggagag aatgttcaga tgaatgggga tacgccccat
1381 gatggaggtc acggaggagg aggacatggg gattgtgaag aattgcagcg aactggacgg
1441 ttctgtggtg gactaattaa agacataaag aggaaagcgc cattttttgc cagtgatttt
1501 tatgatgctt taaatattca agctctttcg gcaattctct tcatttatct ggcaactgta
1561 actaatgcta tcacttttgg aggactgctt ggggatgcca ctgacaacat gcagggcgtg
1621 ttggagagtt tcctgggcac tgctgtctct ggagccatct tttgcctttt tgctggtcaa
1681 ccactcacta ttctgagcag caccggacct gtcctagttt ttgagaggct tctatttaat
1741 ttcagcaagg acaataattt tgactatttg gagtttcgcc tttggattgg cctgtggtcc
1801 gccttcctat gtctcatttt ggtagccact gatgccagct tcttggttca atacttcaca
1861 cgtttcacgg aggagggctt ttcctctctg attagcttca tctttatcta tgatgctttc
1921 aagaagatga tcaagcttgc agattactac cccatcaact ccaacttcaa agtgggctac
1981 aacactctct tttcctgtac ctgtgtgcca cctgacccag ctaatatctc aatatctaat
2041 gacaccacac tggccccaga gtatttgcca actatgtctt ctactgacat gtaccataat
2101 actacctttg actgggcatt tttgtcgaag aaggagtgtt caaaatacgg aggaaacctc
2161 gtcgggaaca actgtaattt tgttcctgat atcacactca tgtcttttat cctcttcttg
2221 ggaacctaca cctcttccat ggctctgaaa aaattcaaaa ctagtcctta ttttccaacc
```

-continued 2281 acagcaagaa aactgatcag tgattttgcc attatcttgt ccattctcat cttttgtgta
2341 atagatgccc tagtaggcgt ggacacccca aaactaattg tgccaagtga gttcaagcca
2401 acaagtccaa accgaggttg gttcgttcca ccgtttggag aaaacccctg gtgggtgtgc
2461 cttgctgctg ctatcccggc tttgttggtc actatactga ttttcatgga ccaacaaatt
2521 acagctgtga ttgtaaacag gaaagaacat aaactcaaga aaggagcagg gtatcacttg
2581 gatctctttt gggtggccat cctcatggtt atatgctccc tcatggctct tccgtggtat
2641 gtagctgcta cggtcatctc cattgctcac atcgacagtt tgaagatgga gacagagact
2701 tctgcacctg gagaacaacc aaagtttcta ggagtgaggg aacaaagagt cactggaacc
2761 cttgtgttta ttctgactgg tctgtcagtc tttatggctc ccatcttgaa gtttataccc
2821 atgcctgtac tctatggtgt gttcctgtat atgggagtag catcccttaa tggtgtgcag
2881 ttcatggatc gtctgaagct gcttctgatg cctctgaagc atcagcctga cttcatctac
2941 ctgcgtcatg ttcctctgcg cagagtccac ctgttcactt tcctgcaggt gttgtgtctg
3001 gccctgcttt ggatcctcaa gtcaacggtg gctgctatca tttttccagt aatgatcttg
3061 gcacttgtag ctgtcagaaa aggcatggac tacctcttct cccagcatga cctcagcttc
3121 ctggatgatg tcattccaga aaaggacaag aaaaagaagg aggatgagaa gaaaaagaaa
3181 aagaagaagg gaagtctgga cagtgacaat gatgattctg actgcccata ctcagaaaaa
3241 gttccaagta ttaaaattcc aatggacatc atggaacagc aacctttcct aagcgatagc
3301 aaaccttctg acagagaaag atcaccaaca ttccttgaac gccacacatc atgctgataa
3361 aattcctttc cttcagtcac tcggtatgcc aagtcctcct agaactccag taaaagttgt
3421 gcctcaaatt agaatagaac ttgaacctga agacaatgat tatttctgga ggagcaaggg
3481 aacagaaact acattgtaac ctgtttgtct ttcttaaaac tgacatttgt tgttaatgtc
3541 atttgttttt gtttggctgt ttgtttattt tttaactttt atttcgtctc agtttttggt
3601 cacaggccaa ataatacagc gctctctctg cttctctctt gcatagatac aatcaagaca
3661 atagtgcacc gttccttaaa aacagcatct gaggaatccc ccttttgttc ttaaactttc
3721 agatgtgtcc tttgataacc aaattctgtc actcaagaca cagacacgca cagaccctgt
3781 cctttgcctc tattaagcag aggatggaag tattaaggat tttgtaacac cttttatgaa
3841 aatgttgaag gaacttaaaa ctttagcttt ggagctgtgc ttactggctt gtctttgtct
3901 ggtagaacaa accttgacct ccagacagag tcccttctca cttatagagc tctccaggac
3961 tggaaaaagt gctgctattt taacttgctc ttgcttgtaa atcctaatct tagagttatc
4021 aaaagaagaa aaaactgaag gtactttact ccctatagag aaaccattgc catcattgta
4081 gcaagtgctg gaatgtccct tttttcctat gcaacttttt ttaacccttt aatgaactta
4141 tctgttgagt acattgaaga atatttttct tcctagattt tgttgtttaa attatggggc
4201 ctaacctgcc acttattttt tgtcaatttt taaaactttt ttttaattac tgtaaagaaa
4261 atgaattttt tcctgcagca ggaaacatag ttttgagtag ttctacctct tatttgtagc
4321 tgccaggctt tctgtaaaaa ttgtattgta tataatgtga tttttacaca tacatacaca
4381 cacaaataca caatctctag ggtaagccag aaggcaagat cagattaaaa acaccatgtt
4441 tctaagcatc catttttccc tttctttaaa agaaacttaa ctgttctatg aaggagattg
4501 agggagaaga gacaaactcc tatgtcatga gaataaccga tgttctgata atagtagcat
4561 ctaggtacag atgctggttg tattaccacg tcaatgtcct atgcagtatt gttagacatt
4621 ttctcatttt gaaatatttg tgtgtttgtg tatgtgctct gtgccatggc tggtgtatat -continued 4681 atgtgcaatg ttagaaggca aaagagtgat ggtaggcaga gggcaaagtc attgaatctc 4741 ttatgccagt tttcataaaa cccaaaccac atatgaaaaa atccattaag ggtccaagaa 4801 gtctgtccat atgaaaatga gggtaaatat agtttatttc ccaggtatca gtcattataa 4861 ttgatataat agctctaaca tgcaatataa aattcatagg agtattaata gcccatttac 4921 acatctataa aatgtaatgg gattgcagag ctgcagagta cagtgtaaca gtactctcat 4981 gcaatttttt tcaggatgca aaggcaatta ttctttgtaa gcgggacatt tagaatatat 5041 ttgtgtacat attatatgta tgtatatttc aaagtaccac actgaaaatt agacatttat 5101 taaccaaatt taacgtggta tttaaaggta atatttttaa tatgatacat tacatattgt 5161 gaatgtatac taaaaaaaca ttttaaatgt taaaattata atttcagatt catataacca 5221 caactgtgat atatcctaac tataaccagt tgttgagggg tatactagaa gcagaatgaa 5281 accacatttt ttggtttgat aatatgcact tattgactcc cactcattgt tatgttaatt 5341 aagttattat tctgtctcct tgtaattttg attacaaaaa ttttattatc ctgagttagc 5401 tgttactttt acagtacctg atactcctaa aacttttaac ttatacaaat tagtcaataa 5461 tgaccccaat tttttcatta aaataatagt ggtgaattat atgttattgt gttaaaacct 5521 cacttgccaa attctggctt cacatttgta tttagggcta tccttaaaat gatgagtcta 5581 tattatctag ctttctatta ccctaatata aactggtata agaagacttt ccttttttct 5641 ttatgcatgg aagcatcaat aaattgttta aaaaccatgt atagtaaatt cagcttaacc 5701 cgtgatcttc ttaagttaaa ggtacttttg ttttataaaa gctctagata aaactttctt 5761 ttctgatcat gaatcaagta tctgtggttt catgcccctc tctatacctt tcaaagaact 5821 cctgaagcaa cttaactcat catttcagcc tctgagtaga ggtaaaacct atgtgtactt 5881 ctgtttatga tccatattga tatttatgac atgaacacag aatagtacct tacatttgct 5941 aaacagacag ttaatatcaa atcctttcaa tattctggga acccagggaa gtttttaaaa 6001 atgtcattac tttcaaagga acagaagtag ttaaccaaac taacaagcaa aacctgaggt 6061 ttacctagtg acaccaaatt atcggtattt taactgaatt tacccattga ctaagaatga 6121 accagatttg gtggtggttt tgtttctatg caaactggac acaaattaca acagtaaatt 6181 tttttataag tgcttctccc ttctccatga tgtgacttcc ggagataaag gattcaaaag 6241 ataaagacaa agtacgctca gagttgttaa ccagaaagtc ctggctgtgg ttgcagaaac 6301 actgttggaa gaaaagagat gactaagtca agtgtctgcc ttatcaaaag agcaaaaatg 6361 cctctggttt tgtgtttggg agaaaaatat cttggacgca ctgttttcct tgataaaagt 6421 catcttctct actgtgtgaa atgaatactt ggaattctaa ttgttttgtg tgccaggggc 6481 agtaatgtcc ctgcctcttc tcccaatcaa ggttgaggag tggggctggg gagaggactt 6541 aactgactta agaagtagga aaacaaaaac ctctctcctc agccttccac ctccaagaga 6601 ggaggaaaaa cagttgtctg ctgtctgtaa ttcagtttgc gtgtatttta tgctcatgca 6661 ccaacccata cagagtaaat cttttatcaa ctatatactg gtgtttaata gagaatgatt 6721 gtcttccgag ttttttggtt cctttttaa ctgtgttaaa gtacttgaaa tgtattgact 6781 gctgactata ttttaaaaac aaaatgaaat aatttgagtt gtattacaga ggttgacatt 6841 gttcagggat gggacaaagc cttcttcaat ccttttcata ctacttaatg attttggtgc 6901 aggaacctga gatttctga tttatatttc atgatatttc acatttgctc ttcacagcat 6961 gagcatgaag cccagtggca ccaaatggct gggtacaatc aagtgatatt ttgtagcacc 7021 tcactatctg aaaggccatg agttttcaga tgatttcatt gagcttcatt gcagcctgaa 7081 attttaaaaa agttgtgtaa tacgccaacc agtcaagttg tgttttggcc agagatttag -continued 7141 atatgtccaa tttcctggct catttcattg tgctctatgg gtacgtataa aaagcaagaa
7201 ttctgtttcc taggcaaaca ttgcaactca gggctaaagt catccagtga aacttttaga
7261 gccagaagta actttgtccc agtcctacaa tgtgaaaaga gtgaatagtt gcctcttttt
7321 agccattttc atggctggta catattcgta cgcattactt ttcagaatca atacgcactt
7381 tcagatattc ttatttttat tctcttaagt ctttattaac tttggagaga gaaatgatgc
7441 attttttat tttaaatgaa gtagatcaac atggtggaac aaaatgataa agaacagaaa
7501 acatttcaat atattactaa taactttttc caatataaat cctaaaattc ctataacata
7561 gtattttaca gttttatgaa gctttctatt gtgactttta tggaattaag agatgaagaa
7621 gatgagatat tttagcattt atatttttca aaattatatg tatacttaaa aataaagtaa
7681 ctttatgcat tta One example of a nucleic acid sequence for human SLIT1 is available as NCBI accession number NM_003061 (gi: 188528674). This sequence is recited below for easy reference as SEQ ID NO: 164.

1 gggagaggga gacgcaggcg gcgaaacggc agaggagccg agccccctcc gcccaaggcg
61 ccctccctcc gtccgcgcac aggcgccgtc gcttggagga gcaaggtgcc tcccagcccg
121 caggggcgcc gcgcgcaagc ccgcgggctc ttcggtggct ctgccccggg actgcacctg
181 gaggcggccc cggacgggga tggtcagcgg ctgctgccgt ctggctcgcg agcgggacgc
241 tgtgagggca ccatggcgct gactcccggg tgggggtcct cggcggggcc ggtccggccg
301 gagctctggc tgctgctgtg ggcagccgcg tggcgcctgg gtgcctcggc gtgccccgcc
361 ctctgcacct gcaccggaac cacggtggac tgccacggca cggggctgca ggccattccc
421 aagaatatac ctcggaacac cgagcgcctg gaactcaatg gcaacaacat cactcggatc
481 cataagaatg actttgcggg gctcaagcag ctgcgggtgc tgcagctgat ggagaaccag
541 attggagcag tggaacgtgg tgcttttgat gacatgaagg agctggagcg gctgcgactg
601 aaccgaaacc agctgcacat gttaccggaa ctgctgttcc agaacaacca ggctttgtca
661 agactggact tgagtgagaa cgccatccag gccatcccca ggaaagcttt tcggggagct
721 acggacctta aaaatttaca gctggacaag aaccagatca gctgcattga ggaagggggcc
781 ttccgtgctc tgcgggggct ggaggtgctg accctgaaca acaacaatat caccaccatc
841 cccgtgtcca gcttcaacca tatgcccaag ctacggacct tccgcctgca ctccaaccac
901 ctgttttgcg actgccacct ggcctggctc tcgcagtggc tgaggcagcg gccaaccatc
961 gggctcttca cccagtgctc gggcccagcc agcctgcgtg gcctcaatgt ggcagaggtc
1021 cagaagagtg agttcagctg ctcaggccag ggagaagcgg ggcgcgtgcc cacctgcacc
1081 ctgtcctccg gctcctgccc ggccatgtgc acctgcagca atggcatcgt ggactgtcgt
1141 ggaaaaggcc tcactgccat cccggccaac ctgcccgaga ccatgacgga gatacgcctg
1201 gagctgaacg gcatcaagtc catccctcct ggagccttct caccctacag aaagctacgg
1261 aggatagacc tgagcaacaa tcagatcgct gagattgcac ccgacgcctt ccagggcctc
1321 cgctccctga actcgctggt cctctatgga aacaagatca cagacctccc ccgtggtgtg
1381 tttggaggcc tatacaccct acagctcctg ctcctgaatg ccaacaagat caactgcatc
1441 cggcccgatg ccttccagga cctgcagaac ctctcactgc tctccctgta tgacaacaag
1501 atccagagcc tcgccaaggg cactttcacc tccctgcggg ccatccagac tctgcacctg -continued 1561 gcgcagaacc ctttcatttg cgactgtaac ctcaagtggc tggcagactt cctgcgcacc 1621 aatcccatcg agacgagtgg tgcccgctgt gccagtcccc ggcgcctcgc caacaagcgc 1681 atcgggcaga tcaagagcaa gaagttccgg tgctcagcca aagagcagta cttcattcca 1741 ggcacggagg attaccagct gaacagcgag tgcaacagcg acgtggtctg tccccacaag 1801 tgccgctgtg aggccaacgt ggtggagtgc tccagcctga agctcaccaa gatccctgag 1861 cgcatccccc agtccacggc agaactgcga ttgaataaca atgagatttc catcctggag 1921 gccactggga tgtttaaaaa acttacacat ctgaagaaaa tcaatctgag caacaacaag 1981 gtgtcagaaa ttgaagatgg ggccttcgag ggcgcagcct ctgtgagcga gctgcaccta 2041 actgccaacc agctggagtc catccggagc ggcatgttcc ggggtctgga tggcttgagg 2101 accctaatgc tgcggaacaa ccgcatcagc tgcatccaca acgacagctt cacgggcctg 2161 cgcaacgtcc ggctcctctc gctctacgac aaccagatca ccaccgtatc cccaggagcc 2221 ttcgacaccc tccagtccct ctccacactg aatctcctgg ccaacccttt caactgcaac 2281 tgccagctgg cctggctagg aggctggcta cggaagcgca agatcgtgac ggggaacccg 2341 cgatgccaga accctgactt tttgcggcag attcccctgc aggacgtggc cttccctgac 2401 ttcaggtgtg aggaaggcca ggaggagggg ggctgcctgc cccgcccaca gtgcccacag 2461 gagtgcgcct gcctggacac cgtggtccga tgcagcaaca agcacctgcg ggccctgccc 2521 aagggcattc ccaagaatgt cacagaactc tatttggacg ggaaccagtt cacgctggtt 2581 ccgggacagc tgtctacctt caagtacctg cagctcgtgg acctgagcaa caacaagatc 2641 agttccttaa gcaattcctc cttcaccaac atgagccagc tgaccactct gatcctcagc 2701 tacaatgccc tgcagtgcat cccgcctttg gccttccagg gactccgctc cctgcgcctg 2761 ctgtctctcc acggcaatga catctccacc ctccaagagg gcatctttgc agacgtgacc 2821 tccctgtctc acctggccat tggtgccaac cccctatact gtgactgcca cctccgctgg 2881 ctgtccagct gggtgaagac tggctacaag gaaccgggca ttgctcgttg tgctgggccc 2941 caggacatgg agggcaagct gctcctcacc acgcctgcca agaagtttga atgccaaggt 3001 cctccaacgc tggctgtcca ggccaagtgt gatctctgct tgtccagtcc gtgccagaac 3061 cagggcacct gccacaacga ccccccttgag gtgtacaggt gcgcctgccc cagcggctat 3121 aagggtcgag actgtgaggt gtccctggac agctgttcca gtggcccctg tgaaaatggg 3181 ggcacctgcc atgcacagga gggcgaggat gccccgttca cgtgctcctg tcccaccggc 3241 tttgaaggac caacctgtgg ggtgaacaca gatgactgtg tggatcatgc ctgtgccaat 3301 gggggcgtct gtgtggatgg tgtgggcaac tacacctgcc agtgccccct gcagtatgag 3361 ggaaaggcct gtgagcagct ggtggacttg tgctctccgg atctgaaccc atgtcaacac 3421 gaggcccagt gtgtgggcac cccggatggg cccaggtgtg agtgcatgcc aggttatgca 3481 ggtgacaact gcagtgagaa ccaggatgac tgcagggacc accgctgcca gaatggggcc 3541 cagtgtatgg atgaagtcaa cagctactcc tgcctctgtg ctgagggcta cagtggacag 3601 ctctgtgaga tccctcccca tctgcctgcc cccaagagcc cctgtgaggg gactgagtgc 3661 cagaatgggg ccaactgtgt ggaccagggc aacaggcctg tgtgccagtg cctcccaggc 3721 ttcggtggcc ctgagtgtga gaagttgctc agtgtcaact ttgtggatcg ggacacttac 3781 ctgcagttca ctgacctgca aaactggcca cgggccaaca tcacgttgca ggtctccacg 3841 gcagaggaca atgggatcct tctgtacaac ggggacaacg accacattgc agttgagctg 3901 taccagggcc atgtgcgtgt cagctacgac ccaggcagct accccagctc tgccatctac 3961 agtgctgaga cgatcaacga tgggcaattc cacaccgttg agctggttgc ctttgaccag -continued 4021 atggtgaatc tctccattga tggcgggagc cccatgacca tggacaactt tggcaaacat
4081 tacacgctca acagcgaggc gccactctat gtgggaggga tgcccgtgga tgtcaactca
4141 gctgccttcc gcctgtggca gatcctcaac ggcaccggct tccacggttg catccgaaac
4201 ctgtacatca acaacgagct gcaggacttc accaagacgc agatgaagcc aggcgtggtg
4261 ccaggctgcg aaccctgccg caagctctac tgcctgcatg gcatctgcca gcccaatgcc
4321 accccagggc ccatgtgcca ctgcgaggct ggctgggtgg gcctgcactg tgaccagccc
4381 gctgacggcc cctgccatgg ccacaagtgt gtccatgggc aatgcgtgcc cctcgacgct
4441 ctttcctaca gctgccagtg ccaggatggg tactcggggg cactgtgcaa ccaggccggg
4501 gccctggcag agccctgcag aggcctgcag tgcctgcatg gccactgcca ggcctcaggc
4561 accaaggggg cacactgtgt gtgtgacccc ggcttttcgg gcgagctgtg tgagcaagag
4621 tccgagtgcc ggggggaccc tgtccgggac tttcaccagg tccagagggg ctatgccatc
4681 tgccagacca cgcgccccct gtcatgggtg gagtgccggg gctcgtgccc aggccagggc
4741 tgctgccagg gccttcggct gaagcggagg aagttcacct ttgagtgcag cgatgggacc
4801 tcttttgccg aggaggtgga aaagcccacc aagtgtggct gtgccctctg cgcatagcgc
4861 tgggcgtgga caggccggtg agggcgggca aggggcccca gccgctgcag cagcggagac
4921 agtcgccagc agctgggctg gggtgcaggt catcacagga cggctcctgg gcagctgggc
4981 cctcctgggt ggggtggtgc cagagcagcc ttttaaaagc aaattgcgcc atagctgggg
5041 gcagcggggg tgggcgaggc ctgagctgcg ggctgccctc tccggaagtg ccttgcacaa
5101 ataggcgctt aataaatatt tgttgagtga atgtgtgcgt gaggtcaggc caagaagtgc
5161 agaacgatga cacccctcct tacctgctat ctgaatctgg agaagaaaaa tgacagcctt
5221 ccaaaccaac ccttcccttt ggcctgtggc ccaggctggc ttggaactgg gtctgtggcc
5281 ccagaagcct cttacccctc tgcgggcaac catgaagtac tgtcagcctc cccgggaagc
5341 cagcctggtt cattctgctg ctacagaatc tgctggtggt aggccaggct ctggagcggg
5401 ggtgccgcct cctgctggcc agggagggtc ggacccttgc cccctgggct gactggcagc
5461 tctgcagcca cggcttggga acgaggctgt gggtggaggt ggttcttagg accaggcctc
5521 tgaatcctaa agttctagca tgactactgt agctgcgagg gcttatgtgg aggaaacagt
5581 cacaggggct gctcagggtg gcagacccca ctaaagaggg cagagggttc tttgctctag
5641 ataaacaaac atcatctgcc tccagacact ggccacagta ggagtattgg tcctgggctt
5701 ccccagccac cagtcagcca caagctgtcg gtgacctatt ggtagaggga ctgggtgtga
5761 gggtctgggc cagggtgctt gacctgggag cagctggttc agagtccttc acaccgcagg
5821 ccagtaggga gcagtggaag ggacagtgct ccaggcattg ggaagtccct gctggctcta
5881 tcactcgggg caaacttctc cccacctggg ccttgggttc ttcagctata aaatggccag
5941 aggtgggggg cgggatgact aaaggaacag tgcagactcc cccactgtgg tcttgggagg
6001 ccagaggagt tagaagacct atctatctat ctatctatct acattgatca catcaaaagt
6061 atttatgtgc ctaacccggg gctggggatt gtggacgttc tggcctaatg gacagatgtg
6121 aactcatccc agagcatcgc aggaatgacc aggatgcccg gggagagttg agctgagtgg
6181 gggctccagc cacagacagc ggcccaggcc agggagttgc tggcaacgaa ggagccagtg
6241 gtggaagaag aagaggccct gaatatacga ttgcctgccc acgttgtctt ctcttccata
6301 cacagtgaaa atgtagaaag atggtttgtg aggccaaact gtgaatgggc taaagggagg
6361 caaagttgca ctctccttcc ccagagggct caccaagagg gcacaccccc gggggttctg -continued

```
6421 gtgggcaacg ggggtgagca tgtccctgcc ctggctccct ccatctgtga ccaggaggca
6481 tggctgggtg tatgttcagg tgaggctcag agtggcattg tgtccctgtc ccctgcccag
6541 ggcagtgagg ggagcccttg atgctgatta gaaggctaga actggggtag aggtgcctgg
6601 catgtctcat gccatgggga ctcaatctag caactgtgag tcctggggtc cctgtgatgg
6661 gaagagggca gtgccctgcc caatgtggca ggtgtcctca tggcaggatc tgcccctcac
6721 cagggggctg ggatctactt gcttggagct ctgagcaagg ccacaatgcc cgccccccacc
6781 cccaagtaga ctgcagcctg ggcctcatgg ggcttctccc aggcccacat ggcatccctc
6841 tctgagtttc caggccaccg tgggaccctg cagagcatct gcaccgggct ggatagggca
6901 gaaaagctca agggcagcta gcttgcctct tccctggaag aaaggtgctc tgggactcac
6961 caaccctgag aaagatagct ttcctggcca ccaccattcc ccaccaccct ggagaagcca
7021 attcccaggc ttgaagggca ctggctggca ggaggcctct tcattctgca ggaggtggaa
7081 aggacacctg tagacaggtg atgctcaccc ctcacctggc gccatggggc tgggaggtga
7141 gcggctggca tgtttgttcc tagggagcac catgtgagct taaggctccc ctgaccggcc
7201 ccaccacatg gcccagcctc ctagcacagc agcgctgacc tcagtgcagt ctgaggattg
7261 gaatccacca tgagatgatg tgagagctgt gtgccccagg atcaactttt tctccaactt
7321 ggccatcagc cagcgagttg ctaaggacct gagtcagcac tcacgttgcc tattcacact
7381 ccgcttgaaa gtccggaagg tggctactgc aaaatcaccc ctctgagaag tcctctctcc
7441 acatcttgtc cccctttgtg aagaccccta gttcgctctg cattttaggc atgaagagat
7501 acagcagggt gcgtccggag ggagctgtgg ccttgcaaca ccactggcaa cagggccggg
7561 gctcccggtg aaggtgtcag gaagtggaaa aggctggact ttgtctcctc tttgcctgct
7621 ggtagcctaa ccgcaaaagt atctctttat acagaatact tacagattct aatatatatt
7681 tgtatttcat tttgttacag tatttttata tgttaaagtc aacatccagc gtcttgtttt
7741 gcctttcaga tgctatgtgg tcgtggcacg ttttgttggg ggtttctgta gtcgtcttgt
7801 ttggatcaac tcctagaggc tggtttagaa caggcccatg agggagctgc acctgccctg
7861 gaagtattgt tttagactat gtcgatattg tctgttgtct tccatgtgaa catgacattg
7921 agtcactctg caaaaaaaaa aaaaaaaaa
```

One example of a nucleic acid sequence for human SPTAN1 is available as NCBI accession number NM_001130438 (gi: 194595508). This sequence is recited below for easy reference as SEQ ID NO: 165.

```
  1 gccactaccc gctgcggagt gaacggtgtg gagcggaggc cgcggaggct cctaggtcct
 61 tcagcacccc tcggcccgac gcacccacgc ccctcacccc ccgagagccg aaaatggacc
121 caagtggggt caaagtgctg gaaacagcag aggacatcca ggagaggcgg cagcaggtcc
181 tagaccgata ccaccgcttc aaggaactct caacccttag gcgtcagaag ctggaagatt
241 cctatcgatt ccagttcttt caaagagatg ctgaagagct ggagaaatgg atacaggaaa
301 aacttcagat tgcatctgat gagaattata aagacccaac caacttgcag ggaaagcttc
361 agaagcatca agcatttgaa gctgaagtgc aggccaactc aggagccatt gttaagctgg
421 atgaaactgg aaacctgatg atctcagaag ggcattttgc atctgaaacc atacggaccc
481 gtttgatgga gctgcaccgc cagtgggaat tacttttgga gaagatgcga gaaaaaggaa
541 tcaaactgct gcaggcccag aagttggtgc agtacttacg agaatgtgag gacgtgatgg
601 actggatcaa tgacaaggaa gcaattgtta cttctgaaga gctgggccag gatctggagc
```

-continued 661 atgtagaggt tttacagaag aaatttgaag agtttcaaac agatatggct gctcatgaag
721 aaagagttaa tgaagtgaac cagtttgctg ccaaactcat acaggagcag caccctgagg
781 aggaactgat caagactaag caggatgaag tcaatgcagc ctggcagcgg ctgaagggcc
841 tggctctgca gaggcagggg aagctctttg gggcagcaga agttcagcgc tttaacaggg
901 atgtggatga gactatcagt tggattaagg aaaaggagca gttaatggcc tctgatgatt
961 ttggccgaga cctggcaagt gttcaggctc tgcttcggaa gcacgagggt ctggagagag
1021 atcttgctgc tctagaagac aaggtcaaag ccctgtgtgc tgaggctgac cgcctgcaac
1081 agtcccaccc tctgagtgca acacagattc aagtgaagcg agaggaactg attacaaact
1141 gggagcagat ccgcaccttg gcggcagaga gacatgcacg gctcaatgat tcatacaggc
1201 ttcaacgctt ccttgctgac ttccgtgacc tcaccagctg ggtgactgag atgaaagccc
1261 tcatcaatgc agatgagctt gccagtgatg tggctggggc tgaagccctg ctagatagac
1321 accaagagca caagggtgaa attgatgccc atgaagacag cttcaaatct gcagatgaat
1381 ctggacaggc actgcttgct gctggtcact atgcctcaga tgaagtgagg gagaagctga
1441 ccgtcctttc cgaggagaga gcggcgctgc tggagctgtg ggagctgcgc aggcagcagt
1501 acgagcagtg catggacctg cagctcttct accgggacac tgagcaggtg gacaactgga
1561 tgagcaagca ggaggcgttc ctgttgaatg aagacttggg agattccttg gatagtgtgg
1621 aagcgcttct taagaagcac gaagactttg agaaatccct tagtgcccag gaggaaaaga
1681 ttacagcatt agatgaattt gcaaccaagc taattcagaa caaccactat gcaatggaag
1741 atgtggccac tcgccgagat gctctgttga gccgccgcaa tgcccttcac gagagagcca
1801 tgcgtcgccg ggcccagcta gccgattctt tccatctgca gcagtttttc cgtgattctg
1861 atgagctcaa gagttgggtc aatgagaaga tgaaaactgc cacagatgaa gcttataaag
1921 atccatccaa cctacaagga aaagtacaga agcatcaggc ttttgaggct gagctctcag
1981 caaaccagag ccgaattgat gccttggaga aagctggcca aaagctgatt gatgtcaacc
2041 actatgccaa ggatgaagtg gcagctcgta tgaatgaggt gatcagtttg tggaagaaac
2101 tgctagaggc cactgaactg aaaggaataa agcttcgtga agccaaccag caacagcaat
2161 ttaatcgcaa tgttgaggat attgaattgt ggctatatga agtagaaggt cacttggctt
2221 cggatgatta cggcaaagat cttaccaatg tgcagaacct ccagaagaaa catgccctgc
2281 tagaggcaga tgtggctgct caccaggacc gaattgatgg catcaccatt caggcccgcc
2341 agttccaaga tgctggccat tttgatgcag aaaacatcaa gaagaaacag gaagccctcg
2401 tggctcgcta tgaggcactc aaggagccca tggttgcccg gaagcagaag ctggccgatt
2461 ctctgcggtt gcagcagctc ttccgggatg ttgaggatga ggagacgtgg attcgagaga
2521 aagagcccat tgccgcatct accaacagag gtaaggattt aattggggtc cagaatctgc
2581 taaagaaaca tcaagcctta caagcagaaa ttgctggaca tgaaccacgc atcaaagcag
2641 ttacacagaa ggggaatgcc atggtggagg aaggccattt tgctgcagag gatgtgaagg
2701 ccaagcttca cgagctgaac caaaagtggg aggcactgaa agccaaagct tcccagcgtc
2761 ggcaggacct ggaggactct ctgcaggccc agcagtactt tgctgatgct aacgaggctg
2821 aatcctggat gcgggagaag gaacccattg tgggcagcac tgactatggc aaggacgaag
2881 actctgctga ggctctactg aagaaacacg aagctttgat gtcagatctc agtgcctacg
2941 gcagcagcat ccaggctttg cgagaacaag cacagtcctg ccggcaacaa gtggccccca
3001 cggatgatga gactgggaag gagctggtct tggctctcta cgactatcag gagaagagtc -continued 3061 cccgagaggt caccatgaag aagggagata tccttacctt actcaacagc accaacaagg
3121 attggtggaa agtggaagtg aacgatcgtc agggttttgt gccggctgcg tacgtgaaga
3181 aattggaccc cgcccagtca gcctcccggg agaatctcct ggaggagcaa ggcagcatag
3241 cactgcggca ggagcagatt gacaatcaga cacgcataac taaggaggcc ggcagtgtat
3301 ctctgcgtat gaagcaggtg gaagaactat atcattctct gctggaactg ggtgagaagc
3361 gtaaaggcat gttggagaag agttgcaaga agtttatgtt gttccgtgaa gcgaatgaac
3421 tacagcaatg gatcaatgag aaggaagccg ctctgacaag tgaggaggtc ggagcagact
3481 tggagcaggt tgaggtgctc cagaagaagt ttgatgactt ccagaaggac ctgaaggcca
3541 atgagtcacg gttgaaggac attaacaagg tagctgaaga cctggagtct gaaggtctca
3601 tggcagagga ggtgcaggct gtgcaacaac aggaagtgta tggcatgatg cccagggatg
3661 aaactgattc caagacagcc tccccgtgga agtctgctcg tctgatggtt cacaccgtgg
3721 ccacctttaa ttccatcaag gagctgaatg agcgctggcg gtccctacag cagctggccg
3781 aggaacggag ccagctcttg ggcagcgccc atgaagtaca gaggttccac agagatgctg
3841 atgaaaccaa agaatggatt gaagagaaga atcaagctct aaacacagac aattatggac
3901 atgatctcgc cagtgtccag gccctgcaac gcaagcatga gggcttcgag agggaccttg
3961 cggctctcgg tgacaaggta aactcccttg gtgaaacagc agagcgcctg atccagtccc
4021 atcccgagtc agcagaagac ctgcaggaaa agtgcacaga gttaaaccag gcctggagca
4081 gcctggggaa acgtgcagat cagcgcaagg caaagttggg tgactcccac gacctgcagc
4141 gcttccttag cgatttccgg gacctcatgt cttggatcaa tggaatacgg gggttggtgt
4201 cctcagatga gctagccaag gatgtcaccg gagctgaggc attgctggag cgacaccagg
4261 aacaccggac agaaatcgat gccagggctg gcactttcca ggcatttgag cagtttggac
4321 agcagctgtt ggctcacgga cactatgcca gccctgagat caagcagaaa cttgatattc
4381 ttgaccagga gcgtgcagac ctggagaagg cctgggttca gcgcaggatg atgctggatc
4441 agtgccttga actgcagctg ttccatcggg actgtgagca agctgagaac tggatggctg
4501 ccagggaggc cttcttgaat accgaagaca aaggagactc actggacagc gtagaggctc
4561 tgatcaaaaa acatgaagac tttgacaaag cgattaacgt ccaggaagag aagattgctg
4621 ctctgcaggc ctttgccgac cagctcatcg ctgccggcca ttatgccaag ggagacattt
4681 ctagccggcg caatgaggtc ttggacaggt ggcgacgtct gaaagcccag atgattgaga
4741 aaaggtcaaa gctaggagaa tctcaaaccc tccaacagtt cagccgggat gtggatgaga
4801 ttgaggcttg gatcagtgaa aaattgcaaa cagcgagtga tgagtcgtac aaggatccca
4861 ccaacatcca gctttccaag ctgctgagca agcaccagaa gcaccaggct tttgaagcag
4921 agctgcatgc caacgctgac cggatccgtg gggttatcga catgggcaac tccctcattg
4981 aacgtggagc ctgtgccggc agtgaggatg ctgtcaaggc ccgcctggct gccttagctg
5041 accagtggca gttcttggtg caaaagtcag cggaaaagag ccagaaactg aaagaagcca
5101 acaagcagca gaacttcaac acagggatca aggactttga cttctggctg tctgaggtgg
5161 aggccctgct ggcatccgaa gattatggca aagacctggc ttctgtgaac aacctgctga
5221 aaaagcatca actgctggaa gcagatatat ctgcccatga ggatcgcrtg aaggacctga
5281 acagccaggc agacagcctg atgaccagca gtgccttcga cacctcccaa gtaaaggaca
5341 agagggacac catcaacggg cgcttccaga agatcaagag catggcggcc tcccggcgag
5401 ccaagctgaa tgaatcccat cgcctgcacc agttcttccg ggacatggat gacgaggagt
5461 cctggatcaa ggagaagaag ctgctggtgg gctcagagga ctacggccgg gacctaaccg -continued 5521 gcgtgcagaa cctgaggaag aagcacaagc ggctggaagc agaactggct gcgcatgagc
5581 cggctattca gggtgtcctg gacactggca agaagctgtc cgatgacaac accatcggga
5641 aagaggagat ccagcagcgg ctggcgcagt ttgtggagca ctggaaagag ctgaagcagc
5701 tggcagctgc ccggggtcag cggctggaag agtccttgga atatcagcag tttgtagcca
5761 atgtggaaga ggaagaagcc tggatcaatg agaaaatgac cctggtggcc agcgaagatt
5821 atggcgacac tcttgccgcc atccagggct tactgaagaa acatgaagct tttgagacag
5881 acttcaccgt ccacaaggat cgcgtgaatg atgtctgcac caatggacaa gacctcatta
5941 agaagaacaa tcaccatgag gagaacatct cttcaaagat gaagggcctg aacgggaaag
6001 tgtcagacct ggagaaagct gcagcccaga gaaaggcgaa gctggatgag aactcggcct
6061 tccttcagtt caactggaag gcggacgtgg tggagtcctg gatcggtgaa aaggagaaca
6121 gcttgaagac agatgattat ggccgagacc tgtcttctgt gcagacgctc ctcaccaaac
6181 aggaaacttt tgacgctggg ctgcaggcct tccagcagga aggcattgcc aacatcactg
6241 ccctcaaaga tcagcttctc gccgccaaac acgttcagtc caaggccatc gaggcccggc
6301 acgcctccct catgaagagg tggagccagc ttctggccaa ctcagccgcc cgcaagaaga
6361 agcttctgga ggctcagagt cacttccgca aggtggagga cctcttcctg accttcgcca
6421 aaaaggcttc tgccttcaac agctggtttg aaaatgcaga ggaggactta acagaccccg
6481 tgcgctgcaa ctccttggaa gaaatcaaag ctttgcgcga ggcccacgac gccttccgct
6541 cctccctcag ctctgcccag gctgacttca accagctggc cgagctggac cgccagatca
6601 agagcttccg cgtagcctcc aaccccctaca cctggtttac catggaggcc ctggaggaga
6661 cctggaggaa cctacagaaa atcatcaagg agagggagct ggagctgcag aaggaacagc
6721 ggcggcagga ggagaacgac aagctgcgcc aggagtttgc ccagcacgcc aacgccttcc
6781 accagtggat ccaagagacc aggacatacc tcctcgatgg gtcctgtatg gtggaagagt
6841 cggggaccct cgaatcccag cttgaagcta ccaaacgcaa gcaccaggaa atccgagcca
6901 tgagaagtca gctcaaaaag atcgaggacc tgggggccgc catggaggag gccctcatcc
6961 tggacaacaa gtacacggag cacagcaccg tgggcctcgc ccagcagtgg gaccagctgg
7021 accagctggg catgcgcatg cagcacaacc tggagcagca gatccaggcc aggaacacaa
7081 caggtgtgac tgaggaggcc ctcaaagaat tcagcatgat gtttaaacac tttgacaagg
7141 acaagtctgg caggctgaac catcaggagt tcaaatcttg cctgcgctcc ctgggctatg
7201 acctgcccat ggtggaggaa ggggaacctg accctgagtt cgaggcaatc ctggacacgg
7261 tggatccgaa cagagatggc catgtctcct tgcaagaata catggctttc atgatcagcc
7321 gcgaaactga gaacgtcaag tccagcgagg agattgagag cgccttccgg gccctcagct
7381 cagagggaaa gccttacgtg accaaggagg agctctacca gaacctgacc cgggaacaag
7441 ccgactactg cgtctcccac atgaagccct acgtggacgg caagggccgc gagctcccca
7501 ccgcgttcga ctacgtggag ttcacccgct cgcttttcgt gaactgagcc actccctggg
7561 tcacccaccc ctcgctgctt gccctgcgtc gccttgctgc atgtccgctc ctctgtgtgc
7621 tctcactttc cactgtaacc ttaagcctgc ttagcttgga ataagactta ggagaaaatg
7681 gtgcttcact aacccgcttc cggtccagtc acaatcatca tgtcactgtg gggacccaga
7741 tctgtgtctt gaagcagctg ccctcattcc gacttcagaa aatcgaagca gctggctcct -continued

```
7801 ccccttgttc tctctcccac cctcccccaa atctgttttc atgtaaaaga caaataaatg
7861 atgacttccc ccaaaaaaaa aaaaaaaaaa aaaaaaaaaa aaaaaaaaaa aaaaaaaaaa
7921 aaaa
```

One example of a nucleic acid sequence for human TFCP2L1 is available as NCBI accession number NM_014553 (gi: 212276201). This sequence is recited below for easy reference as SEQ ID NO: 166.

```
   1 gggttcggag cgcgaagccg ccgctgggtc ctcggcgcgc cccgcgtctg cgcttgctgc
  61 cgcgccccgg tcggcgcgct gggagttcca gccatgctct tctggcacac gcagcccgag
 121 cactacaacc agcacaactc cggcagctac ctgcgtgatg tgctcgctct gcccatcttc
 181 aagcaggagg aaccccagct gtcccccgag aacgaggccc gcctgccacc cctgcaatat
 241 gtgttgtgtg ctgccacgtc cccagccgtg aagctgcatg aagagacgct gacctacctc
 301 aaccaaggtc agtcttatga aatccgacta ctggagaatc ggaagctggg agactttcaa
 361 gatctgaaca caaaatatgt caagagcatr atccgtgtgg tcttccatga ccgccggctg
 421 cagtatacgg agcaccagca gctggagggc tggcggtgga gtcggccagg ggaccggatc
 481 ctggacatcg atattccact gtctgttggt atcttggacc ccagggccag cccgacccag
 541 ctgaatgcag tcgagttttt gtgggaccct gcgaagagag cttctgcatt cattcaggta
 601 cactgcatca gcacagaatt cacccccagg aagcacgggg gcgagaaggg agtgccattt
 661 cgagtccaga ttgacacgtt taagcagaac gagaatgggg agtacacgga gcacctgcac
 721 tcagccagct gccagatcaa ggtgttcaag ccgaagggag ccgatcggaa acagaagact
 781 gaccgggaga agatggagaa aagaactgcc caagagaagg agaaatacca gccgtcctat
 841 gaaaccacca tcctcacaga gtgctctcca tggcccgacg tggcctacca ggtgaacagc
 901 gccccgtccc caagctacaa tggttctcca aacagctttg gcctcggcga aggcaacgcc
 961 tctccgaccc acccggtgga ggccctgccc gtgggcagtg accacctgct cccatcagct
1021 tcgatccagg atgcccagca gtggcttcac cgcaacaggt tctcgcagtt ctgccggctc
1081 tttgccagct tctcaggtgc tgacttgctg aagatgtccc gagatgattt ggtccagatc
1141 tgtggtcccg cagatgggat ccggctcttc aacgccatca aaggccggaa tgtgaggcca
1201 aagatgacca tttatgtctg tcaggagctg gagcagaatc gagtgcccct gcagcagaag
1261 cgggacggca gtggagacag caacctgtct gtgtaccacg ccatcttcct ggaagagctg
1321 accaccttgg agctgattga gaagatcgcc aacctgtaca gcatctcccc ccagcacatc
1381 cacggagtct accggcaggg ccccacgggc atccatgtgg tggtgagcaa cgagatggtg
1441 cagaacttcc aagatgaatc ctgttttgtc ctcagcacaa ttaaagctga gagcaatgat
1501 ggctaccaca tcatcctgaa atgtggactc tgagcagcag tggacctcat acctgtctcc
1561 agctcccagc cctgtggatc cccgtggatg tagacattgc cccactgtaa gctgtggcct
1621 caccaggcaa gctgaggcca ggagggaccc tgcccagtct gtgaaagcta cagagcacca
1681 accagcagaa gcctgtggac accaagtacg gtgtacagaa agccagtggc tcctttctcc
1741 cttcctcttg gcctccagat tttgaatggt tccttgttct tttctattgg tccaaccctg
1801 acgttctaaa agggcaaaca gtggagacgt ctgctctgaa atccctcatc ccttagttgg
1861 aagctgattg ggtatcttgg tgctgcctgt attggtccct tctgaccact ctcctgcctc
1921 cagagaaagc tctgcttcac cctggaagct ggtaccttta cctcctcctc tgggagttgg
```

-continued 1981 ctgcatggcc agcactgccg acttgatggg agcagtttgc cctcattctc ctgtttcagg 2041 tttgcttccc ttctcagtga ccctggtgag catccgcctt tcctgttctt ggatgaattg 2101 atgggagtgg ggctattctg tgccttctac ctctttcttc tctacgttgt ttctaaggat 2161 ctgctgctgc ggaacccaaa gatgtgctcc tgtctctgca ctggcgcatt ggcatggtag 2221 atgccacaat gtatgtgcac ggcctttctc agagacatta gttctgaggc cctttgtggg 2281 gaggttaggg ggatggtaat agaaaaagac tattttattt cctggcaatc acgggtaagg 2341 aggattagga atgagtattc cattcctagg tgtcatcaga tgaccttgac caccacaata 2401 ccaggccctc ttggatggac ttatagaaag ttagagaaga ccttgttgaa ccgctgctaa 2461 acttgccaca ggagcgatgt gttttctctg agtgcccctc acttacatgt ttatctttgt 2521 ttgtagaggc tatgtttagg atattttgcc tgcatcagaa tgggtgcatc atctttctta 2581 atggcctaac tatcgggaaa tttgagtgtc agtaactgtg gtagactcag aaattcgtct 2641 ttgtcttgcc tctggttcct gggatccagt gatctctact ggcccagggc ttcagctctt 2701 ggttaattta ggttcatggg gaaccctctg accacctgaa tgggatgtca tagcttctaa 2761 atggagcttc tgtggaatga agtgctagac tgaaggacta ccagaataaa acagggtcta 2821 caatggggag aacttgtttt atagatgagg aaaccaaggc tcagaggggc aaagtcacct 2881 gcatggtagc acatagtgat agggtagcga tataaattta tcatataaac caggacatct 2941 cggaataaaa ggggctctgt tagtcattat gttgggtaat agccgtggca ttcctacaga 3001 acagagtgag gacaggctcc tgattcctct tccttcttta gaggagaagc ggggagtggg 3061 ttaactaaca gctttattga gatgtcattc acatgccatt cagtttaccc attgctagtg 3121 tccaattgta ttcacagaac caccatcaat tcacagaatt acagtcaacg ttggtacatt 3181 ttcatcaccc ccagtaaaac cccgtaccct tggtctgtca ctcctgcttt cctaactcct 3241 gcagtccaag gcagccatga atctactttc tatgtaagat taacctactc tggacatttc 3301 atatatctgg aatcatgtga tatctctttt gtgactggct tcttccactg aatgttttct 3361 agggccgtcc aagttgagga tgtatcagta cttcattctt ttgtattgct gaataatact 3421 tcattgtata gatagaccac atttgtttat tgattcatca gttgatggac atttgtgtgt 3481 ttttactttt tggctactct gaatgatgct gctatgaaca tatttctaca agattttgtg 3541 tggacatatg ttttcatttc ttttagcaat atacatagga gtggaattgc taggtcttac 3601 agtaactccg tgttttaact ttttgagaaa ctgccagact gttttctata gcagctgtac 3661 cattttacat tcccaccagc aatgtatcca ggtttcaatt tgtctacatc ctcatcaaca 3721 cttgctatta tctgtctttt tgcttttagc atcctaatga gtatgaaatg ctatcttgtg 3781 gttttgattt gcattcccct gatggcaact gatgctgagt gtcttttcct gtgcttacgg 3841 gccatgcgta tttctttgga gaaaggtcta tccaggtcct ttgcctattt ttaattgagt 3901 tgtctttttt tttttaagtt ttctgttttc ctaaccacta gactaccagg gatgagcctt 3961 ctttttatta ttgagttggg tgagctattt gtatattcta gacgccagtc ttttatcagg 4021 tatatgactg gtaaaaatgt tctccccttc tgtggattgt tttcagtttc ttgttggtgt 4081 cctttgagac acaaaacttt ttaactttga tgatttccaa gatacgtatt ttttttctat 4141 tgtcacttgt gcttttggtg ccatatctag aaaaccattg cctaatccaa ggtcaagaag 4201 attaatgcct gtgttttctt ctaagaacta tacttttagt tctcacaatg gtctttgatc 4261 catttcgagt atatttttat atatgatgtg atgtaggggt ccagcttcat tcttttgctt 4321 gtggatctcc acttgtccca ctgctgatta ttgagaaaaa tatcctttct ccacggaatt 4381 gtcttggcat ccttgctaaa ggcctctgct tcttactgga tcttctttcc tgggacatgg -continued 4441 tgtcgttggg aagcttacct tttttttttt tttacttagt ctgtgtttgg ttccaccagt 4501 tttatgctgc ctttctactc tgttcttgct gtctccctct ttacctgagt caacggtact 4561 gagtcctatc tctctctgat gttccccagt cttccttggt gcatgttcta gctccacaca 4621 ctagtccttg gaggaaggtt gagaccaatg atttcctgtt atgagtcatg aggaaactga 4681 atcacctaga agtggaataa tgtgctcagg gtcaccatag cccattagtg gaaggaccag 4741 gactagacct ttagtcttct gaggtccagc cccttaggct gtctgtcatc actgtaccca 4801 agtgatgtca ctaccaaggc caaatgatgg tgggctaaat tttaattctc aaaagtgtag 4861 gaggctaata ttgtcttcta agttccaaaa gaagatgtaa taaaagtctg ttaccttaag 4921 tgtgctatta gtagagtctt ccatttttct ggcatgcccc tggcatctgc tcttcttacc 4981 ttctcgtggt tgtagttaaa gcttatagct tatgaaagaa tagaaaataa taaataccaa 5041 aaaaaagtac acatggtaat ttggtaccaa aatatctcag ctgcctaatt tagcagctca 5101 tcccttccac aggggtcaga tgagctaaag ctccaggttt tatttttcat ttgattgaca 5161 tacagaaaag ccatagccct tcccacagct gtccagggtc tttcctgtga gtccggaggt 5221 gctggcctat tgagcaggac agctcttccc agggcattcc caccaacctg tggcttctga 5281 actgtagctt ctttttacag tgaaccccag agggaaataa gacagacaca tgtgctcagg 5341 ccaccatctt gaactggaag cccaaagctg agttccttac tcttaggtcg tcacggtttt 5401 tgcggggtat ctgcaaggtt gagataaacc ctttcctgtt taccaggttg tcctttctgg 5461 atgaagggac agaggctgtt gaatggagga ataataggtt tgctggagga ggggcatggt 5521 atgcctgtgg aaaggacagg atggggtggg gaggtcgagg ctttgacttg gggtcctaaa 5581 caaaggtcag gtgttgccct agtgacctct tgcccagaca gcccagagcc ccttacacag 5641 agctattaac ctagggaagg ctttaccagc agtggactgg agccagccag ggtcacaagt 5701 ttccaagtcc agcattgctt caggggctgg cctgagtaac tgaagatctg aaaatcatta 5761 acaagtcgat gaaataaacg gaaaagcctc ttaggctgtt gtcagtggag cagagggaga 5821 aagtccctag gcgctcagag ggggtgagaa agcagtggat gattgggcgg gggtggggga 5881 ttagatgttg acactgcctg gggtgtagga agaggaacag agaacccaga gtcagggtcc 5941 tagatcccag accctcgctc agtatgagtc tctttgcctc tctgggtctc tatctcctcc 6001 tcttacaaat acaggcttgg tgatctctga agatggcacc aacctgccat gaaatgaatc 6061 tgaggggttt tcccattttt ccctccatca aaatcgtaca aaaagctgga cgtggtggcc 6121 catgcctcta atcctagcat tttgggaggc cgaggtggga gaatcacttg acgccaagag 6181 ttcgagacca gcctgggcat cgtagtgaga ctccatctct gtctttttga aaataaaaaa 6241 tctttgaaaa ttgcacaaca ggcaggagac ctttacgtgt gcccatcctg gttgtacaca 6301 gtgccaccag tgctcctgca gtgcaaggcg gcatgcttct tgacatgggt cagattgtgt 6361 ccatcgtgtc tttgggaatc agccctagct cctaactggg ctgactactt cctccgcaaa 6421 cttatggggg ctcccagata ttccttgcca gccaggggcc agacacagtg caggcacagt 6481 ctgtgtcatt ggtgcacatg tgcgtgttta catgtgtacc tgggttcctt cccttgccca 6541 tgaatttgcc atgagcacag ccagaagcag cctcagcttg gcaaggtgtg gagatgactg 6601 ctgttccctt cgcatttggg gaaaacaggc tccctcggta gctcgatgat cctcttttga 6661 tcttgtgtga cctcctggag agtggatgaa gctggtggcc ttagcttttc tagacagtgt 6721 aagtggcact gggcaaggcc cccagagcag ggcaaggtct ctagagcggg tctcccacat 6781 gactggcttc acacaggcac ttccgctcgg gttgcatgct ctgtgtcatc ttaccggtcc -continued 6841 agggttgcag gtaggaaatg tttgtaccct cttctgattg ccacctcctt cccatcgccc 6901 cttagggaca gggcttgagg gccagtgagg cgctggtcag gcaccccagg cctccttggg 6961 acctgcccag gggcaccctg agagctcctg aaaccccccac ttagcttcca gacctttctg 7021 caaaagctcc tcctggcttt cctccctccc ccaatctatg ggtcacagct aacagatctg 7081 agggcaactg ctgtgctagt ggccagggct gcacctgcca tccccggctc tgccacttta 7141 gggccttcta gaggcagtgt ccttaggaag tagctctgag gcatgggttt tctgctcctg 7201 tgcagggcag ctgatgggat aaggtgggga aggacggtca gtgcttgggc cccagctggc 7261 cagcctggcg atggggaaac caaaccatgt cccccagcga agggccagag tgggaacctg 7321 tcctcatgcc cttcgtcctg aggagccctg aggtgggcag caggggccag gggaagtttt 7381 caggccttca tcaaagagaa caacatcctc agctccgcac ccctcatcct gtatcagcac 7441 ttaccggtgt gtgactgccc ttgtcagcta gcatacggtg ggcccacctg gcccactggc 7501 tgtttatgcc actgatttat gatagggaat attatctttg aacccaatga agtgttttct 7561 cccccatcac aaaaaaaaaa attcttattt ttagtagaca tgtatttacc aaaaatatgt 7621 actcaattat tgtattttgg attttatcaa tttaaaaatt gtggaaattt gtttgctctt 7681 acgccaacat aatattgatt ttgcctcttg gctctgaaag cccaaaatat ttaccgtcta 7741 gcccgttaca gaaaaagtct gctgactact gagccagacc tccattacct ccatccctgt 7801 tggattattt aaagaaagcc tcagacagta agggcttttt taaaagaata aaatgacttg 7861 gtttgcgctt ggaagcaggg gaagcattca gatgagcggt ttctgcatta accctgccta 7921 tcacgcatct cgtgtcctgt gtgtctggcg agcccccctt ggaaggttct ggtgcttcag 7981 ctggctcctg cagagtccac cccgcctcgt ggtgggaatg cagagccctt tgctttcctt 8041 cttgccgcct gcttcctgtt cctggggacc cgctgggcct ttggtctgca tcccctggcc 8101 aggtccctca gggttgatgc gtggagaagg actttgagca gtggtgggca gcagtggcct 8161 cctggccagc tcacactctt gtcctgggag gggcagcctg atctcacctc cacctagtac 8221 cttggggact gaggaccttt tggcttctct ggagcctgca agcctcttcc catgtgtcca 8281 gctgctcttc ctgctacaaa ggggactgct cacagtggcc tcagcttggt ggttttgagg 8341 ggccgccccc cggccctcca taagggtatc ctgggcctga gaattctgca tctgccattg 8401 gaggatggac agcctcaaat ggaaggagtc ccacgggaga tgggtccgag gtccggctgt 8461 ggccatccag ccccctgtgg cttgtccagc ctctgtgcac ccctggtgtc ttcactccag 8521 gggcagacag cagccactgc agttcctttc ttcgtgagta acagtagtga tagcagctgg 8581 ggctaacagg ctaggctttg tgttctgcgc atttggtcag cttctcactc gatcctccct 8641 aaagcaatgg ggaggccccc actagcccag ttttcaggaa gtcaactggg aggttagatg 8701 ggggccaggg tcccacagct actgatggcc cgagccaggt tgagcttcct ggtgtccagt 8761 ccggatccca cttgcagatc tcatgctctc agataggtgg gacaagttct tttgtcacag 8821 tgctggctct gtcctgaggc ctcattgctg gctgggtgtg ctctgctggg aaaagctttg 8881 cggggcttgc ttggttaacc acagaagaga aggggactgt ttggggtgcc tctctgcagc 8941 ctccccgtgc tgggtggaag cacggttact gtgttctcta atgttcatgt atttaaaatg 9001 atttctttct aaagatgtaa cctccacacc tttctccaga ttgggtgact cttttctaaa 9061 ggtggtggga gtatctgtcg ggtggtgtgg gcccttggat gggtcaggtg ggtgtgagag 9121 gtcctgggga ggtgggcgtt gagctcaaag ttgtcctact gccatgtttt tgtacctgaa -continued 9181 ataaagcata ttttgcactt gttactgtac catagtgcgg acgagaagtc tgtatgtggg 9241 atctgtgctt gggttagaat gcaaataaaa ctcacatttg taagaaaaaa aaaaaaaaaa 9301 aaaaaa One example of a nucleic acid sequence for human TIAM1 is available as NCBI accession number NM_003253 (gi: 115583669). This sequence is recited below for easy reference as SEQ ID NO: 167.

1 gccccgcatc gtgcccggcc ccgtcgcgga gatcccggac gaccgtcgcg ggttgatggt 61 cgcattccag atgtaaacag cttcagaagc ctgacggtca tatggtagaa tcactgtgga 121 ctgagaccca cctttctaga cctgaagccc aggaggagga agaggaggct ggttggtacc 181 atgggcataa tgctctgaat cctagtctct cacctagtat gtgagcagtc cctgcagatg 241 gcccatttgg agatcttgac aaagcctctt ctgtttccaa tggggttttt ggcgcattct 301 cacagactta gatgaaactg tgatggccac cgcagggggc aggtgctgac atcgtcccca 361 gccctgtggc tgttcatccg gacatcattt ccaacctcaa tatctaaatg ccacagtgct 421 cttggagcaa gttgggctgg ggaccactgt tgccttttaa gaccataaaa ccatgggaaa 481 cgcagaaagt caacatgtag agcacgagtt ttatggagaa aagcatgcca gcctggggcg 541 caagcacact tcccgctccc tgcgcctctc gcacaagacg cggaggacca ggcacgcttc 601 ctcggggaag gtgatccaca ggaactccga agtgagcacc cgatccagca gcacccccag 661 catcccccag tccctggctg aaaatggcct ggagcccttc tcccaagatg gtaccctaga 721 agacttcggg agccccatct gggtggaccg agtggacatg ggcttgagac ctgtgtctta 781 cactgactct tctgtcactc ccagcgtaga cagcagcatc gtcctcacag cagcctctgt 841 gcagagcatg ccagacactg aggagagcag gctttacggg gatgacgcta catatttggc 901 tgagggaggc aggaggcagc attcctatac atccaatggg cccactttca tggagacggc 961 gagctttaag aagaaacgct ccaaatctgc agacatctgg cgggaggaca gcctggaatt 1021 ctcactctct gatctgagcc aagaacattt aacaagcaac gaagaaatct tgggttccgc 1081 cgaagagaag gactgcgagg aggctcgggg gatggaaacg cgggcgagtc cgcggcagct 1141 cagcacctgt cagagagcca attccttggg tgacttgtat gctcagaaaa actctggagt 1201 gacagcaaac gggggccgg ggagcaaatt tgcaggctac tgtcggaatt tggtgtctga 1261 tattcccaat cttgcaaacc ataagatgcc accagctgct gctgaagaga ctcctccgta 1321 cagtaattat aacacacttc cctgtaggaa atctcactgt ctctctgaag gtgccaccaa 1381 cccacaaatt agccatagca acagcatgca aggcagaaga gctaaaacaa ctcaggatgt 1441 taatgcaggc gagggcagtg agtttgcaga cagtgggatt gaaggggcca ctaccgacac 1501 ggacctcctg tccaggcgat ctaatgccac caactccagc tactcaccca ccacaggccg 1561 ggcctttgtg ggcagcgaca gcggcagcag ctccaccggg gatgcggctc gtcagggggt 1621 gtacgagaac ttccggcggg agctggagat gagcaccacc aacagcgaga gcctggagga 1681 ggccggctcg gcgcacagcg atgagcagag cagcggcacc ctgagctctc cgggccagtc 1741 ggacatcctg ctgaccgccg cacagggcac ggtgcgcaag gccggcgccc tggccgtcaa 1801 gaacttcctg gtgcacaaga agaacaagaa ggtggagtca gccacccgga ggaagtggaa 1861 gcactactgg gtgtccctga aggatgcac gctatttttc tacgagagcg acggcaggtc 1921 tgggatagac cacaacagca tccccaaaca cgccgtctgg gtggagaaca gcattgtgca -continued 1981 ggcggtgcct gagcacccca agaaggactt tgtcttctgc ctcagcaatt ccctgggtga 2041 tgccttcctt tttcagacca ctagccagac ggagcttgaa aactggatca ccgccatcca 2101 ctctgcctgc gccactgcgg tcgcgaggca ccaccacaag gaagacacgc tccgactcct 2161 gaaatcagag atcaaaaaac tggaacagaa gattgacatg gatgaaaaga tgaagaaaat 2221 gggtgaaatg cagctgtctt cagtcactga ctcaaagaaa aagaaaacaa tattagatca 2281 gatctttgtc tgggagcaaa atctcgagca gttccaaatg gacctgtttc gtttccgctg 2341 ttatttagcc agccttcagg gtggggagct gccaaacccc aaaaggcttc tcgcttttgc 2401 aagtcgacca acgaaagtgg ccatgggccg ccttggaatc ttttcggtat catcgtttca 2461 tgccctggtg gcagcacgca ctggtgaaac tggagtgaga agacgtactc aggccatgtc 2521 cagatccgcg agcaagcgaa ggagcaggtt ttcttctctg tggggtctgg atactacctc 2581 caaaaagaag cagggacggc caagcatcaa tcaggtgttt ggagagggaa ccgaagctgt 2641 aaagaaatct ttagagggaa tatttgatga cattgttcca gatggcaaga gggagaaaga 2701 agtggtctta cctaacgttc accagcacaa ccctgactgc gacatttggg tccacgagta 2761 tttcactcca tcctggttct gtctgcccaa taatcagcct gccctgacgg tcgtccggcc 2821 aggcgacact gcacgggaca ccctggagct gatttgcaag acacatcaac tggatcattc 2881 tgctcattac ctgcgcctga aatttctaat agaaaacaaa atgcagctct atgttccaca 2941 gcc.gaggaa gacatctatg agctgctgta caaagaaatt gaaatctgtc caaaagtcac 3001 tcagagcatc cacattgaga agtcagatac agctgctgat acttacgggt tttcactttc 3061 ttctgtggaa gaagatggta ttcgaaggct gtacgtgaat agtgtgaagg aaaccggttt 3121 agcttccaag aaaggcctga aagcaggaga tgagattctt gagatcaata atcgtgctgc 3181 tgacgccctg aactcttcta tgctcaaaga tttcctctca cagccctcgc tgggcctcct 3241 ggtgaggacc taccccgagc tggaggaagg agtggagctg ctggaaagcc cgccccaccg 3301 agtggacggc cctgccgacc ttggcgagag ccccctcgcc tttctcacca gcaacccagg 3361 gcacagcctt tgcagcgagc agggcagcag tgctgagacc gctccagagg agaccgaggg 3421 gccagacttg gaatcctcag atgagactga tcacagcagc aagagtacag aacaggtggc 3481 cgcattttgc cgcagtttgc atgagatgaa cccctctgac cagagcccat ctcctcagga 3541 ctccacgggg cctcagctgg cgaccatgag acaactctcg gatgcagata agctgcgcaa 3601 ggtgatctgc gagctcctgg agacggagcg cacctacgtg aaggatttaa actgtcttat 3661 ggagagatac ctaaagcctc ttcaaaaaga aacttttctc acccaggatg agcttgacgt 3721 gctttttgga aatttaacgg aaatggtaga gtttcaagta gaattcctta aaactctaga 3781 agatggagtg agactggtac ctgatttgga aaagcttgag aaggttgatc aatttaagaa 3841 agtgctgttc tctctggggg gatcattcct gtattatgct gaccgcttca agctctacag 3901 tgccttctgc gccagccaca caaaagttcc caaggtcctg gtgaaagcca agacagacac 3961 ggctttcaag gcattcttgg atgcccagaa cccgaagcag cagcactcat ccacgctgga 4021 gtcgtacctc atcaagccca tccagaggat cctcaagtac ccacttctgc tcagggagct 4081 gttcgccctg accgatgcgg agagcgagga gcactaccac ctggacgtgg ccatcaagac 4141 catgaacaag gttgccagtc acatcaatga gatgcagaaa atccatgaag agtttggggc 4201 tgtgtttgac cagctgattg ctgaacagac tggtgagaaa aaagaggttg cagatctgag 4261 catgggagac ctgcttttgc acactaccgt gatctggctg aacccgccgg cctcgctggg 4321 caagtggaaa aaggaaccag agttggcagc attcgtcttc aaaactgctg tggtccttgt 4381 gtataaagat ggttccaaac agaagaagaa acttgtagga tctcacaggc tttccattta -continued 4441 tgaggactgg gaccccttca gatttcgaca catgatcccc acggaagcgc tgcaggttcg
4501 agctttggcg agtgcagatg cagaggcaaa tgccgtgtgt gaaattgtcc atgtaaaatc
4561 cgagtctgaa gggaggccgg agagggtctt tcacttgtgc tgcagctccc cagagagccg
4621 aaaggatttc ctaaaggctg tgcattcaat cctgcgtgat aagcacagaa gacagctcct
4681 caaaaccgag agccttccct catcccagca atatgtccct tttggaggca aaagattgtg
4741 tgcactgaag gggccaggc cggccatgag cagggcagtg tctgccccaa gcaagtctct
4801 tgggaggagg aggcggcggc tggctcgaaa caggtttacc attgattctg atgccgtctc
4861 cgcaagcagc ccggagaaag agtcccagca gccccccggt ggtggggaca ctgaccgatg
4921 ggtagaggag cagtttgatc ttgctcagta tgaggagcaa gatgacatca aggagacaga
4981 catcctcagt gacgatgatg agttctgtga gtccgtgaag ggtgcctcag tggacagaga
5041 cctgcaggag cggcttcagg ccacctccat cagtcagcgg gaaagaggcc ggaaaaccct
5101 ggatagtcac gcgtcccgca tggcacagct caagaagcaa gctgccctgt cggggatcaa
5161 tggaggcctg gagagcgcaa gcgaggaagt catttgggtt aggcgtgaag actttgcccc
5221 ctccaggaaa ctgaacactg agatctgact gcgtcacctg ccccgtagag aatgtgtgta
5281 gatacttcct gccctaactc tgcccaccct cctgtaccgt cgacaagaat gtccccttag
5341 gtcgcgctct tgcacacacg gttttggcag ctgacttggt tctgaagcca tgtagccacc
5401 caactttgtc attttcaaca acatcagaaa gaattgatca gaatcccaaa taagcttgag
5461 tcctatcttc tgtatattac taagggcttt tatttattct caataaatca gggcctgaac
5521 aattaaaaga aaaaagattc tatagcactg gaaagcaaat caccccagga gttaacggat
5581 gtacaacaga ttaatttaag ggatagtagc acacacacga tccttctatc tgaaatcagt
5641 ctcctagctg gggaaacctc tttcacacac aaaatgaaat gtgtacagct tgccgtgttc
5701 tgactgtacc cttccctctt ccatgtctga gaatctccgt gtattttaag aatgtgtgag
5761 gagagggtgg cgattcatgt ttcaatgagc ctcttttttt ttttccttcc tgttttggtc
5821 tatggctggt cttactctgt gtccatgttc ggaagctcta gttttgcata gaattataga
5881 gatgccaaac tctttgaaaa gagatccaaa tttatcgctt gagagaaaga aaagaaacac
5941 tattttttgt attttacctg agatacaggg gcacaaatag atgagaattt tacagtgtta
6001 gtgtatgtat ccctgagcct aaaaaatgag gatataacct tttacagaga gagtgaggcg
6061 tggtggtttt atatttatat atgaaaggcc agcaagctca tgcgaaggat atacttttct
6121 tccaaaaagc ggattttttt tttttaatgt ttgaatctat atttgagatg ggagtttggt
6181 tggattaaac atgacacccc ggtgggcggt gtgtgtgtct gttgcacatg gcagggaggg
6241 gagcctcctt ctcatggggt tgccatggtg atcattggtt tttccatcaa aattgcatct
6301 tcatccatag attaccttcc ccttccctga cagtccataa ccaaaccttt aaacagaaca
6361 acctctttaa aaacttctct tgtgtttaac actttcttca tgccaacgaa acagggtaaa
6421 catgctcaaa acattaacag tctaaacaga tatccaaata ctaagaagaa aaacaagtta
6481 tagcactttc aatttttttt tttttttaa aaaaaggttt atagcttttt cttttcccat
6541 gtcacaatgt ccacttccta agaagggttt aaaatactat gaaaactttc tttttgggga
6601 aaatatctat ttggtgtttg acacatcagt aggtacttta aagacctgaa ttttatagta
6661 gctttaggag ttatatttta taaaaatcag ttatgacttt atatttccag acaatagaga
6721 gttcagtaca tcatgctctt gtgcctctgc ctgcttttcc tgcgttccca ccctgtattc
6781 cccccgcctt tcgggtttcc agggcttcga gcttgatctt ttgaaagttt tattctatta -continued 6841 aatttttgct atatcttctg gttttctgaa aaagctttag aatggtttct ataccctttg 6901 tatcactgca tttttccata tcatctccgg ttcgatcgcg tccagatgga aaacggaagc 6961 agaggcttct aatcgtcgca tttactggct ccagtgcaac acatccatct gaaaacactc 7021 ggaagtctgg tgcttggaga gggtgccatt gtctcttgta cataaggtca tgacgtgtct 7081 atgtcaaaag ttcttatata tttcttttat aagctgaaag aaggtctatt tttatgtttt 7141 taggtctatg aatggaacgt tgtaaatgct tgtcaaacaa taaaaataac gaaaagtgaa 7201 aaaaaaaaaa aaaaaaaa One example of a nucleic acid sequence for human TIMP1 is available as NCBI accession number NM_003254 (gi: 73858576). This sequence is recited below for easy reference as SEQ ID NO:168.

1 tttcgtcggc ccgccccttg gcttctgcac tgatggtggg tggatgagta atgcatccag 61 gaagcctgga ggcctgtggt ttccgcaccc gctgccaccc ccgcccctag cgtggacatt 121 tatcctctag cgctcaggcc ctgccgccat cgccgcagat ccagcgccca gagagacacc 181 agagaaccca ccatggcccc ctttgagccc ctggcttctg gcatcctgtt gttgctgtgg 241 ctgatagccc ccagcagggc ctgcacctgt gtcccacccc acccacagac ggccttctgc 301 aattccgacc tcgtcatcag ggccaagttc gtggggacac cagaagtcaa ccagaccacc 361 ttataccagc gttatgagat caagatgacc aagatgtata aagggttcca agccttaggg 421 gatgccgctg acatccggtt cgtctacacc cccgccatgg agagtgtctg cggatacttc 481 cacaggtccc acaaccgcag cgaggagttt ctcattgctg gaaaactgca ggatggactc 541 ttgcacatca ctacctgcag ttttgtggct ccctggaaca gcctgagctt agctcagcgc 601 cggggcttca ccaagaccta cactgttggc tgtgaggaat gcacagtgtt tccctgttta 661 tccatcccct gcaaactgca gagtggcact cattgcttgt ggacggacca gctcctccaa 721 ggctctgaaa agggcttcca gtcccgtcac cttgcctgcc tgcctcggga gccagggctg 781 tgcacctggc agtccctgcg gtcccagata gcctgaatcc tgcccggagt ggaagctgaa 841 gcctgcacag tgtccaccct gttcccactc ccatctttct tccggacaat gaaataaaga 901 gttaccaccc agcagaaaaa aaaaaaaaaa a One example of a nucleic acid sequence for human TNS3 is available as NCBI accession number NM_022748 (gi: 134152712). This sequence is recited herein below for easy reference as SEQ ID NO:169.

1 agaatgggaa actgccttgg gagaagcccc aagtgagccc aagggcgcag agcagaagga 61 ccctggagtg taagagccta gattgcaagc ctggcaggag gagccggaag aattaacctc 121 gagtctgcac gcttttaaga acaaggcctt taaaaaatcc aaagtgtgtg gagtttgcaa 181 acaaattatt gacggtcaag gtatttcatg ccgagcctgc aagtattcct gccacaagaa 241 atgtgaagcc aaggtggtga ttccctgcgg tgtgcaagtc cgactggaac aggctccagg 301 gagttccacg ctgtccagtt ctctctgccg tgataaacct ctgcggcccg tcatcctgag 361 tcccaccatg gaggagggcc atgggctgga cctcacttac atcacggagc gcatcatcgc 421 tgtgtccttc cctgccggct gctctgagga gtcctacctg cacaacctac aggaggtcac 481 gcgcatgctc aagtccaagc acggggacaa ctacctggta ttaaaccttt cagaaaagag 541 atatgacctt acgaagctta acccaaagat catggatgtg ggctggccag agctccacgc -continued 601 accgcccctg gataagatgt gtaccatatg caaggcgcag gagtcctggc tgaacagcaa
661 cctccagcat gtggtcgtca ttcactgcag ggcgggaaa ggacgcatag gagtggtcat
721 atcatcctac atgcatttca ccaacgtctc agccagcgcc gaccaggccc ttgacaggtt
781 tgcaatgaag aagttttatg atgacaaagt ttcagcttta atgcagcctt cccaaaaacg
841 gtatgttcag ttcctcagtg ggctcctgtc cggatcggtg aaaatgaatg cctctcccct
901 gttcctgcat tttgtcatcc tccacggcac ccccaacttc gacacaggtg gagtgtgccg
961 gccctttctg aagctctacc aagccatgca gcctgtgtac acctccggga tctacaacgt
1021 tggcccagaa aaccccagca ggatctgcat cgtcatcgag ccggcccagc ttctgaaggg
1081 agatgtcatg gtgaaatgct accacaagaa ataccgctcg gccacccgtg acgtcatttt
1141 ccgcctgcag tttcacactg ggctgtgca gggctacggg ctggtgtttg ggaaggagga
1201 tctggacaat gccagcaaag atgaccgttt tcctgactat gggaaggttg aattagtctt
1261 ctctgccacg cctgagaaga ttcaagggtc cgaacacttg tacaacgacc acggtgtgat
1321 tgtggactac aacacaacag acccactgat acgctgggac tcgtacgaga acctcagtgc
1381 agatggagaa gtgctacaca cgcagggccc tgtcgatggc agcctttacg cgaaggtgag
1441 gaagaaaagc tcctcggatc ctggcatccc aggtggcccc caggcaatcc cggccaccaa
1501 cagcccagac cacagtgacc acaccttgtc tgtcagcagt gactccggcc actctacagc
1561 ctctgccagg acggataaga cggaagagcg cctggcccca ggaaccagga ggggcctgag
1621 tgcccaggag aaggcagagt tggaccagct gctcagtggc tttggcctgg aagatcctgg
1681 aagctccctc aaggaaatga ctgatgctcg aagcaagtac agtgggaccc gccacgtggt
1741 gccagcccag gttcacgtga atggagacgc tgctctgaag gatcgggaga cagacattct
1801 ggatgacgag atgccccacc acgacctgca cagtgtggac agccttggga ccctgtcctc
1861 ctcggaaggg cctcagtcgg cccacctggg tcccttcacc tgccacaaga gcagccagaa
1921 ctcactccta tctgacggtt ttggcagcaa cgttggtgaa gatccgcagg gcaccctcgt
1981 tccggacctg ggccttggca tggacggccc ctatgagcgg gagcggactt ttgggagtcg
2041 agagcccaag cagccccagc ccctgctgag aaagccctca gtgtccgccc agatgcaggc
2101 ctatgggcag agcagctact ccacacagac ctgggtgcgc cagcagcaga tggttgtagc
2161 tcaccagtat agcttcgccc cagatgggga ggcccggctg gtgagccgct gccctgcaga
2221 caatcctggc ctcgtccagg cccagcccag agtgccactc acccccaccc gagggaccag
2281 cagtagggtg gctgtccaga ggggtgtagg cagtgggcca catccccctg acacacagca
2341 gccctctccc agcaaagcgt tcaaacccag gtttccagga gaccaggttg tgaatggagc
2401 cggcccagag ctgagcacag gcccctcccc aggctcgccc accctggaca tcgaccagtc
2461 catcgagcag ctcaacaggc tgatcctgga gctggatccc accttcgagc ccatccctac
2521 ccacatgaac gccctcggta gccaggccaa tggctctgtg tctccagaca gcgtgggagg
2581 tgggctccgg gcaagcagca ggctgcctga cacaggagag ggccccagca gggccaccgg
2641 gcggcaaggc tcctctgctg aacagcccct gggcgggaga ctcaggaagc tgagcctggg
2701 gcagtacgac aacgatgctg gggggcagct gcccttctcc aaatgtgcat ggggaaaggc
2761 tggtgtggac tatgccccaa acctgccggc attcccctca ccagcggacg tcaaagagac
2821 gatgacccct ggctatcccc aggacctcga tattatcgat ggcagaattt taagtagcaa
2881 ggagtccatg tgttcaactc cagcatttcc tgtgtctcca gagacaccgt atgtgaaaac
2941 agcgctgcgc catcctccgt tcagcccacc tgagcccccg ctgagcagcc cagccagtca -continued 3001 gcacaaagga ggacgtgaac cacgaagctg ccctgagacg ctcactcacg ctgtggggat 3061 gtcagagagc cccatcggac ccaaatccac gatgctccgg gctgatgcgt cctcgacgcc 3121 ctcctttcag caggcttttg cttcttcctg caccatttcc agcaacggcc ctgggcagag 3181 gagagagagc tcctcttctg cagaacgcca gtgggtggag agcagcccca agcccatggt 3241 ttccctgctg ggagcggcc ggcccaccgg aagtcccctc agcgctgagt tctccggtac 3301 caggaaggac tccccagtgc tgtcctgctt cccgccgtca gagctccagg ctcctttcca 3361 cagccatgag ctgtccctag cagagccacc ggactccctg gcgcctccca gcagccaggc 3421 cttcctgggc ttcggcaccg ccccagtggg aagtggcctt ccgcccgagg aggacctggg 3481 ggccttgctg gccaattctc atggagcgtc accgaccccc agcatcccgc tgacagcgac 3541 aggggctgcc gacaatggct tcctgtccca caactttctc acggtggcgc ctggacacag 3601 cagccaccac agtccaggcc tgcagggcca gggtgtgacc ctgcccgggc agccacccct 3661 ccctgagaag aagcgggcct cggaggggga tcgttctttg ggctcagtct ctccctcctc 3721 cagtggcttc tccagcccgc acagcgggag caccatcagt atccccttcc caaatgtcct 3781 tcccgacttt tccaaggctt cagaagcggc ctcacctctg ccagatagtc caggtgataa 3841 acttgtgatc gtgaaatttg ttcaagacac ttccaagttc tggtacaagg cggatatttc 3901 aagagaacaa gccatcgcca tgttgaagga caaggagccg ggctcattca ttgttcgaga 3961 cagccattcc ttccgagggg cctatggcct ggccatgaag gtggccacgc cccccacttc 4021 agtcctgcag ctgaacaaga aagctggaga tttggccaat gaactcgtcc ggcacttttt 4081 gatcgagtgt accccgaagg gagtgcggtt gaaagggtgc tcgaatgaac catatttcgg 4141 gagcctgacg gccttggtgt gccagcattc catcacgccc ttggccttgc cgtgcaagct 4201 gcttatccca gagagagatc cattggagga aatagcagaa agttctcccc agacggcagc 4261 caattcagca gctgagctgt tgaagcaggg ggcagcctgc aatgtgtggt acttgaactc 4321 tgtggagatg gagtccctca ccggccacca ggcgatccag aaggccctga gcatcaccct 4381 ggtccaggag cctccacctg tgtccacagt tgtgcacttc aaggtgtcag cccagggcat 4441 caccctgaca gacaatcaga ggaagctctt cttccggagg cattaccccg tgaacagtgt 4501 gattttctgt gccttggacc cacaagacag gaagtggatc aaagatggcc cttcctcaaa 4561 agtctttgga tttgtggccc ggaagcaggg cagtgccacg gataatgtgt gccacctgtt 4621 tgcagagcat gaccctgagc agcctgccag tgccattgtc aacttcgtat caaaggtcat 4681 gattggttcc ccaaagaagg tctgagaact cccctccctc cctggaccca ccgatgcctc 4741 tcgaagccct ggagacagcc gttgggtgag ggtggggccc ccactttttta ccaaactagt 4801 aaacctgaca ttccaggccc atgaggggaa agaggatctt ccagctctgc aaaaacaaga 4861 acaaacaaca tcaccgtgaa ttggcctttc ctgaaagtga cttatctgac acatctctgt 4921 agccacatgc tttttgggta gaagaagctg ggcatgggtg caccccaccc cctagggtcc 4981 ccatgggaaa gggacatgca aggaaacagc acagaacacg aggtggtccc catgtccctg 5041 gcacactagc attccggggg atgaggaatc cccagccctt gaggcagagg tgccgagtga 5101 ctgccatgct tcgcccgtcc gcatgggcgc ttctgtccag ctgcacccga ggccgggggt 5161 ttccctcacc tcggtcttcc caagatggag atgctaacga aactgagaag gggcgtatg 5221 tttgacgaag gtttgtgcaa gtcaggccct tctggaacac agcagggcct acaacgaggg 5281 gcctttgcga tgggctgtga ggatgggggt ggtgggaaga attggccacg ttggagaccc 5341 catgccaccc caccatggtg agtgctctgt gcctcctgct cacctgtggt gagctgggcg 5401 agctgggcga gctgggcgag ctgggctggg gagagcctgt gaggaccgag aggagaaatg -continued 5461 agaagaagga acaaaaatat tatttctatg taatttatat tttacttatg ccaaattatt
5521 tatgataatt tgccattgct atactgtacc agtgtcaaat gctgcagcct gccaagctgt
5581 gattttgtga ggcttgtccc tatgtaggat gcaccgcagg cccctggcca ctgaaagagt
5641 gtgcagtgga ctgtgggtct cccatatgcg gtgccgccca aaggtggctt tgcctcaagc
5701 aacctaccct gatgttttac tcattggaat gtttttcccc gattgtggat gacttctttt
5761 ctgatggaga gagtccagga gggatggaaa actcctggat ttaagctcag catcccccac
5821 atgggctttt cgatcatctt caggcctgaa gctgcacgac ctgaagttcg cctgcattta
5881 tcagccctct ttgtgctgct ccttgccacc ttggggttcc tgctggggac catgtgtggt
5941 tgtggcatgt gtgagcagaa gggaggatga ggaaaaagag aagaaacccc ggtactgaca
6001 agctgttttt gagtgccact gtttgccatc atctaagcca ctgaatcaag tgtatttcag
6061 gcttatttca acattccaat gccctggttt tcctgcttga atctgttcgt ggtcaaaggt
6121 ttgggggaat ttgtgaccct ggaacatccc cagagtgaaa gatggagctg ggccacatca
6181 gaataaggcc ttggccccat cctctcacag cctaggtgct ctgcaggcat gctgactgtc
6241 ctgattgcga tccagcccga aattccctcc tctgctttca aaagtcaaat cccccattct
6301 taggccacac tggtgtcaca agctcctgtc agggagctgg ggtttgggaa tgtgctttgt
6361 gaactctgct ttaaagtgag gggccgagga aaacttagaa acaggcagag ttggaagcag
6421 ccaaatcaca gtgggtgttg tgtgtgtgtg cgtgtgtgca tgcgtgcgtg tatgcgtgtg
6481 tgaaagcagg tggaccattc cactttttag ctcctattga tgcaccaaac caagtgcctc
6541 atttctgtgc caaatgtttg ccttggtcgt tgtggacctc cttctctaac ttgcggtggc
6601 atgactgtca ggaggtgctg gcattttcag cagatcctca tgtgttgacc ctgatgtctt
6661 tagcagaggc ctctagcatc tcggtttttc atccactgca ggaatgtggc cacagggagc
6721 agaggtttgt actttcccca agaggtcctc atcctgagac ggtctctacc catgtttaac
6781 ccaaagagtg caggccaggt tccttatcct tctgatgaag gatgagagag ctcatttaga
6841 agtcagagca aactagggtc tcagtattga gaaacgcagc ctgccaggga atcacagaga
6901 catcggggtg cccgcgatgg ccctcatgaa gccatgcctc gacggcattc aggaagccct
6961 gcaaacgtgc tttttgaact cattggccag gtgtgatttt tacacaaggt aaacgtggtc
7021 aagggcatcg gggaatttgc tccaagcaga tagctccctc tgaggaacca aaggaagcaa
7081 gtttccacga tttctgaaga gctggtatag gaagtttctt tcttcctttt gtgttacatg
7141 tgcattaaac agaacaagct gtgtgtcatc acagattgta ctgtgggctc agaaaccgtg
7201 agagagcccc caccgtggac accggctcta gggccacagg aaaaggaacg tttccaggca
7261 ttttgtctcc agggctcccg ctggacaggc acgtactgcc ctggggagta aatgcggaga
7321 gttcacgaac tgtgcccaac gcatgttata gccagggtcc tactaactac tcagtaaaag
7381 aacgtattgt tgtattcctc cagtgttaag ctatagccat gttaaaagtc actgtgcatt
7441 tattctcagc atcaaatacc ttgtaacgtc ttctctgcct tgttagtgca tatttttact
7501 tttctgatac tgtaaagaat atatccagta tgtaaatgaa tgttctataa atcttttgta
7561 tagtcatttt ctctgctcct taaatatcat ctctattcag agtataataa aattatgaac
7621 ttggtaaaaa aaaaaaaaaa aaaaaaaaaa aaaaaaaaaa aaaaaaaaaa aaaaaaaaaa
7681 aaaaaaaaaa aaaaaaa One example of a nucleic acid sequence for human TSPAN12 is available as NCBI accession number NM_012338 (gi: 48255911). This sequence is recited below for easy reference as SEQ ID NO: 170.

```
   1 ggccctggct gccgccgctg cctcgtccgg actcggagag gacttgggag ggacagcggc
  61 gctgggaggt ggcttagcag agactttcca gcaactgctg cccaggactt tttttttttt
 121 ttttcttttt cccaggaggc ggcgacggcg gcggcggggg gagaggaaga gaaagaagcg
 181 tctccagctg aagccaatgc agccctccgg ctctccgcga agaagttccc tgccccgatg
 241 agcccccgcc gtgcgtcccc gactatcccc aggcgggcgt ggggcaccgg gcccagcgcc
 301 gacgatcgct gccgttttgc ccttgggagt aggatgtggt gaaaggatgg ggcttctccc
 361 ttacggggct cacaatggcc agagaagatt ccgtgaagtg tctgcgctgc ctgctctacg
 421 ccctcaatct gctcttttgg ttaatgtcca tcagtgtgtt ggcagtttct gcttggatga
 481 gggactacct aaataatgtt ctcactttaa ctgcagaaac gagggtagag gaagcagtca
 541 ttttgactta ctttcctgtg gttcatccgg tcatgattgc tgtttgctgt ttccttatca
 601 ttgtggggat gttaggatat tgtggaacgg tgaaaagaaa tctgttgctt cttgcatggt
 661 actttggaag tttgcttgtc attttctgtg tagaactggc ttgtggcgtt tggacatatg
 721 aacaggaact tatggttcca gtacaatggt cagatatggt cactttgaaa gccaggatga
 781 caaattatgg attacctaga tatcggtggc ttactcatgc ttggaatttt tttcagagag
 841 agtttaagtg ctgtggagta gtatatttca ctgactggtt ggaaatgaca gagatggact
 901 ggcccccaga ttcctgctgt gttagagaat tcccaggatg ttccaaacag gcccaccagg
 961 aagatctcag tgacctttat caagagggtt gtgggaagaa aatgtattcc tttttgagag
1021 gaaccaaaca actgcaggtg ctgaggtttc tgggaatctc cattggggtg acacaaatcc
1081 tggccatgat tctcaccatt actctgctct gggctctgta ttatgataga agggagccgg
1141 ggacagacca aatgatgtcc ttgaagaatg acaactctca gcacctgtca tgtccctcag
1201 tagaactgtt gaaaccaagc ctgtcaagaa tctttgaaca cacatccatg gcaaacagct
1261 ttaatacaca ctttgagatg gaggagttat aaaaagaaat gtcacagaag aaaaccacaa
1321 acttgtttta ctggacttgt gaatttttga gtacatacta tgtgtttcag aaatatgtag
1381 aaataaaaat gttgccataa aataacacct aagcatatac tattctatgc tttaaaatga
1441 ggatggaaaa gtttcatgtc ataagtcacc acctggacaa taattgatgc ccttaaaatg
1501 ctgaagacag atgtcatacc cactgtgtag cctgtgtatg acttttactg aacacagtta
1561 tgttttgagg cagcatggtt tgattagcat ttccgcatcc atgcaaacga gtcacatatg
1621 gtgggactgg agccatagta aaggttgatt tacttctacc aactagtata taaagtacta
1681 attaaatgct aacataggaa gttagaaaat actaataact tttattactc agcgatctat
1741 tcttctgatg ctaaataaat tatatatcag aaaactttca atattggtga ctacctaaat
1801 gtgatttttg ctggttacta aaatattctt accacttaaa agagcaagct aacacattgt
1861 cttaagctga tcagggattt tttgtatata agtctgtgtt aaatctgtat aattcagtcg
1921 atttcagttc tgataatgtt aagaataacc attatgaaaa ggaaaatttg tcctgtatag
1981 catcattatt tttagccttt cctgttaata aagctttact attctgtcct gggcttatat
2041 tacacatata actgttattt aaatacttaa ccactaattt tgaaaattac cagtgtgata
2101 cataggaatc attattcaga atgtagtctg gtctttagga agtattaata agaaaatttg
2161 cacataactt agttgattca gaaaggactt gtatgctgtt tttctcccaa atgaagactc
2221 tttttgacac taaacacttt ttaaaaagct tatctttgcc ttctccaaac aagaagcaat
```

-continued 2281 agtctccaag tcaatataaa ttctacagaa aatagtgttc tttttctcca gaaaaatgct 2341 tgtgagaatc attaaaacat gtgacaattt agagattctt tgttttattt cactgattaa 2401 tatactgtgg caaattacac agattattaa attttttac aagagtatag tatatttatt 2461 tgaaatggga aaagtgcatt ttactgtatt ttgtgtattt tgtttatttc tcagaatatg 2521 gaaagaaaat taaaatgtgt caataaatat tttctagaga gtaaaaaaaa aaaaaaaaa One example of a nucleic acid sequence for human UPP1 is available as NCBI accession number NM_003364 (gi: 31742506). This sequence is recited below for easy reference as SEQ ID NO:171.

1 ggtcagctga gttcgccggc ccagggcagg cggggcccga gcctagcggt aacccccggg 61 cagggcgggg ccgctcgcag actccatatg agattcacct cgcaggtggt tccctcattc 121 gagtgctccg gcgcacagac ccgcgccccg ccgtctgcga gcctcccgag agccgtccct 181 tcgtccggcc ctggagcatt gcgtttgtcg caggtgtcgc agtgcgagga tggcgccgcg 241 ggtgtagcgg ctctctgcgc aggccgagtg ggcccagaga agcgaggaac tccgcagctc 301 gtcgacacgt ctcgtctcct gtcccaattc agggcttggt gaggtgactc gcggtcgcgg 361 gtgactcgcc ggcaggacac tgcctggaac gcctggagcg cctcccactg cagacgtctg 421 tccgcctcca gccgctctcc tctgacgggt cctgcctcag ttggcggaat ggcggccacg 481 ggagccaatg cagagaaagc tgaaagtcac aatgattgcc ccgtcagact tttaaatcca 541 aacatagcaa aaatgaaaga agatattctc tatcatttca atctcaccac tagcagacac 601 aatttcccag ccttgtttgg agatgtgaag tttgtgtgtg ttggtggaag cccctcccgg 661 atgaaagcct tcatcaggtg cgttggtgca gagctgggcc ttgactgccc aggtagagac 721 tatcccaaca tctgtgcggg aactgaccgc tatgccatgt ataaagtagg accggtgctg 781 tctgtcagtc atggtatggg cattccttct atctcaatca tgttgcatga gctcataaag 841 ctgctgtact atgcccggtg ctccaacgtc actatcatcc gcattggcac ttctggtggg 901 ataggtctgg agcccggcac tgtggtcata acagagcagg cagtggatac ctgcttcaag 961 gcagagtttg agcagattgt cctggggaag cgggtcatcc ggaaaacgga ccttaacaag 1021 aagctggtgc aggagctgtt gctgtgttct gcagagctga gcgagttcac cacagtggtg 1081 gggaacacca tgtgcacctt ggacttctat gaagggcaag gccgtctgga tggggctctc 1141 tgctcctaca cggagaagga caagcaggcg tatctggagg cagcctatgc agccggcgtc 1201 cgcaatatcg agatggagtc ctcggtgttt gccgccatgt gcagcgcctg cggcctccaa 1261 gcggccgtgg tgtgtgtcac cctcctgaac cgcctggaag gggaccagat cagcagccct 1321 cgcaatgtgc tcagcgagta ccagcagagg ccgcagcggc tggtgagcta cttcatcaag 1381 aagaaactga gcaaggcctg agcgctgccc tgcacctccg cagacctgct gtgatgactt 1441 gccattaaaa gcattgtcca aaatcccctg ttgtgtggac tttgagcaca ctttacacaa 1501 gaatctagaa aatcagatcg cgattaagag acagagaatc ttggattaac cgcatgggag 1561 atgttcttcc ttttgaagtt tcattggagc attttcaatg atgttagcct gatttggggt 1621 ttcttcaaga acattctacc aaatttttgt actatttcta gggaaatttt tcagacttta 1681 aaattctaat ggtagtcaga tttcatgtca ctaaacaaga aatctgacaa tagtgccagg 1741 aaactaattt cctgatacat taaaaaaatt ccatgcaaaa aaaaaaaaaa aaaaaa One example of a nucleic acid sequence for human NAUK2 is available as NCBI accession number NM_030952 (gi: 13569921). This sequence is recited below for easy reference as SEQ ID NO:172.

```
   1 gtgctttact gcgcgctctg gtactgctgt ggctccccgt cctggtgcgg gacctgtgcc
  61 ccgcgcttca gccctccccg cacagcctac tgattcccag gccgcccttg ctcacctcct
 121 gctcgccatg gagtcgctgg ttttcgcgcg gcgctccggc ccccactccct cggccgcaga
 181 gctagcccgg ccgctggcgg aagggctgat caagtcgccc aagcccctaa tgaagaagca
 241 ggcggtgaag cggcaccacc acaagcacaa cctgcggcac cgctacgagt tcctggagac
 301 cctgggcaaa ggcacctacg ggaaggtgaa gaaggcgcgg gagagctcgg ggcgcctggt
 361 ggccatcaag tcaatccgga aggacaaaat caaagatgag caagatctga tgcacatacg
 421 gagggagatt gagatcatgt catcactcaa ccaccctcac atcattgcca tccatgaagt
 481 gtttgagaac agcagcaaga tcgtgatcgt catggagtat gccagccggg gcgaccttta
 541 tgactacatc agcgagcggc agcagctcag tgagcgcgaa gctaggcatt tcttccggca
 601 gatcgtctct gccgtgcact attgccatca gaacagagtt gtccaccgag atctcaagct
 661 ggagaacatc ctcttggatg ccaatgggaa tatcaagatt gctgacttcg gcctctccaa
 721 cctctaccal caaggcaagt tcctgcagac attctgtggg agcccccctct atgcctcgcc
 781 agagattgtc aatgggaagc cctacacagg cccagaggtg gacagctggt ccctgggtgt
 841 tctcctctac atcctggtgc atggcaccat gccctttgat gggcatgacc ataagatcct
 901 agtgaaacag atcagcaacg gggcctaccg ggagccacct aaaccctctg atgcctgtgg
 961 cctgatccgg tggctgttga tggtgaaccc cacccgccgg gccaccctgg aggatgtggc
1021 cagtcactgg tgggtcaact ggggctacgc cacccgagtg ggagagcagg aggctccgca
1081 tgagggtggg caccctggca gtgactctgc ccgcgcctcc atggctgact ggctccggcg
1141 ttcctcccgc cccctgctgg agaatggggc caaggtgtgc agcttcttca agcagcatgc
1201 acctggtggg ggaagcacca cccctggcct ggagcgccag cattcgctca agaagtcccg
1261 caaggagaat gacatggccc agtctctcca cagtgacacg gctgatgaca ctgcccatcg
1321 ccctggcaag agcaacctca agctgccaaa gggcattctc aagaagaagg tgtcagcctc
1381 tgcagaaggg gtacaggagg accctccgga gctcagccca atccctgcga gcccagggca
1441 ggctgccccg ctgctcccca agaagggcat tctcaagaag ccccgacagc gcgagtctgg
1501 ctactactcc tctcccgagc ccagtgaatc tggggagctc ttggacgcag gcgacgtgtt
1561 tgtgagtggg gatcccaagg agcagaagcc tccgcaagct tcagggctgc tcctccatcg
1621 caaaggcatc ctcaaactca atggcaagtt ctcccagaca gccttggagc tcgcggcccc
1681 caccaccttc ggctccctgg atgaactcgc cccacctcgc cccctggccc gggccagccg
1741 accctcaggg gctgtgagcg aggacagcat cctgtcctct gagtcctttg accagctgga
1301 cttgcctgaa cggctcccag agcccccact gcggggctgt gtgtctgtgg acaacctcac
1861 ggggcttgag gagccccccct cagagggccc tggaagctgc ctgaggcgct ggcggcagga
1921 tcctttgggg gacagctgct tttgcctgac agactgccag gaggtgacag cgacctaccg
1981 acaggcactg agggtctgct caaagctcac ctgagtggag taggcattgc cccagcccgg
2041 tcaggctctc agatgcagct ggttgcaccc cgaggggaga tgccttctcc cccacctccc
2101 aggacctgca tcccagctca gaaggctgag agggtttgca gtggagccct gagcagggct
2161 ggatatggga agtaggcaaa tgaaatgcgc caagggttca gtgtctgtct tcagccctgc
2221 tgaacgaaga ggatactaaa gagaggggaa cgggaatgcc cgggacagag tccacattgc
```

-continued

```
2281 ctgtttcttg tgtacatggg ggggccacag agacctggaa agagaactct cccagggccc
2341 atctcctgca tcccatgaat actctgtaca catggtgcct tctaaggaca gctccttccc
2401 tactcattcc ctgcccaagt ggggcgagac ctctttacac acacattccc gttcctacca
2461 accaccagaa ctggatggtg gcacccctaa tgtgcatgag gcatcctggg aatggtctgg
2521 agtaacgctt cgttattttt atttttattt ttatttattt atttattttt ttgagacgga
2581 gtttcgctct tggtgcccag gctagagtgc aatggcgcga tctcagctca cctcaacctc
2641 cgcctcccgg gttcaagcga ttctcctgcc tcagcctccc tagtagctgg gattacaggc
2701 gcccgccacc atgcccggct aattttgtat ttttagtaga gacagggttt ctccatgttg
2761 gtcaggctgg tctcaaactc ccgacctcag gtgatccacc cacctcggcc tcccaaagtg
2821 ctgggattac aggcgtgagc caccgcgccc cacctaaccc ttccttattt agcctaggag
2881 taagagaaca caatctctgt ttcttcaatg gttctcttcc cttttccatc ctccaaacct
2941 ggcctgagcc tcctgaagtt gctgctgtga atctgaaaga cttgaaaagc ctccgcctgc
3001 tgtgtggact tcatctcaag gggcccagcc tcctctggac tccaccttgg acctcagtga
3061 ctcagaactt ctgcctctaa gctgctctaa agtccagact atggatgtgt tctctaggcc
3121 ttcaggactc tagaatgtcc atatttattt ttatgttctt ggctttgtgt tttaggaaaa
3181 gtgaatcttg ctgttttcaa taatgtgaat gctatgttct gggaaaatcc actatgacat
3241 ctaagttttg tgtacagaga gatatttttg caactatttc cacctcctcc cacaaccccc
3301 cacactccac tccacactct tgagtgtctt tacctaatgg tctctaccta atggacctcc
3361 gtggccaaaa agtaccatta aaaccagaaa ggtgattgga aaaaaaaaaa aaaaaaaaaa
3421 aaaaaaaaaa aaaaaaaaaa aaa
```

REFERENCES

1. Mazzaferri E L, Solitary thyroid nodule. 2. Selective approach to management. Postgrad Med. 1981; 70:107-109,112, 116.
2. Davies L, Welch H G, Increasing incidence of thyroid cancer in the United States, 1973-2002. JAMA. 2006; 295:2164-2167.
3. Arora N, Scognamiglio T, Zhu B, Fahey T J 3rd. Do benign thyroid nodules have malignant potential? An evidence-based review. World J Surg. 2008; 32:1237-1246.
4. Chan J K. Strict criteria should be applied in the diagnosis of encapsulated follicular variant of papillary thyroid carcinoma. Am J Clin Pathol. 2002; 117:16-18.
5. Franc B, de la Salmoniere P. Lange F. et al. Interobserver and intraobserver reproducibility in the histopathology of follicular thyroid carcinoma. Hum Pathol. 2003:34:1092-1100.
6. Lloyd R V, Erickson L A, Casey M B, et al. Observer variation in the diagnosis of follicular variant of papillary thyroid carcinoma. Am J Surg Pathol. 2004; 28:1336-1340.
7. Saxen E, Franssila K, Bjarnason O, Normann T, Ringertz N, Observer variation in histologic classification of thyroid cancer. Acta Pathol Microbiol Scand [A]. 1978; 86A:483-486.
8. Hirokawa M, Carney J A, Goellner J R, et al. Observer variation of encapsulated follicular lesions of the thyroid gland. Am J Surg Pathol. 2002; 26:1508-1514.
9. Williams E D, Guest editorial: two proposals regarding the terminology of thyroid tumors. Int J Surg Pathol. 2000; 8:181-183.
10. Miettinen M, Karkkainen P, Differential reactivity of HIBME-1 and CD15 antibodies in benign and malignant thyroid tumours. Preferential reactivity with malignant tumours. Virchows Arch. 1996; 429(4-5):213-219.
11. Cheung C C, Ezzat S, Freeman J L, Rosen I B, Asa S L, Immunohistochemical diagnosis of papillary thyroid carcinoma. Mod Pathol. 2001; 14:338-342.
12. Choi Y L, Kim M K, Suh J W, et al. Immunoexpression of HBME-1, high molecular weight cytokeratin, cytokeratin 19, thyroid transcription factor-1, and E-cadherin in thyroid carcinomas. J Korean Med Sci. 2005; 20:853-859.
13. de Matos P S, Ferreira A P, de Oliveira Facuri F, Assumpcao L V, Metze K, Ward L S, Usefulness of HBME-1, cytokeratin 19 and galectin-3 immunostaining in the diagnosis of thyroid malignancy. Histopathology. 2005; 47:391-401.
14. Papotti M, Rodriguez J, De Pompa R, Bartolazzi A, Rosai J, Galectin-3 and HBME-1 expression in well differentiated thyroid tumors with follicular architecture of uncertain malignant potential. Mod Pathol. 2005; 18:541-546.
15. Prasad M L, Pellegata N S, Huang Y. Nagaraja H N, de la Chapelle A, Kloos R T, Galectin-3, fibronectin-1, CITED-1, HBME1 and cytokeratin-19 immunohistochemistry is useful for the differential diagnosis of thyroid tumors. Mod Pathol. 2005; 18:48-57.
16. Scognamiglio T, Hyjek E, Kao J, Chen Y T, Diagnostic usefulness of HBME1, galectin-3, CK19, and CITED and evaluation of their expression in encapsulated lesions with questionable features of papillary thyroid carcinoma. Am J Clin Pathol. 2006; 126:700-708.

17. Fusco A, Chiappetta G, Hui P, et al. Assessment of RET/PTC oncogene activation and clonality in thyroid nodules with incomplete morphological evidence of papillary carcinoma: a search for the early precursors of papillary cancer. Am J Pathol. 2002; 160:2157-2167.

18. Chevillard S, Ugolin N, Vielh P, et al. Gene expression profiling of differentiated thyroid neoplasms: diagnostic and clinical implications. Clin Cancer Res. 2004; 10:6586-6597.

19. Finley D J, Zhu B, Barden C B, Fahey T J 3rd. Discrimination of benign and malignant thyroid nodules by molecular profiling. Ann Surg. 2004; 240:425-436: discussion 436-437.

20. Huang Y, Prasad M, Lemon W J, et al. Gene expression in papillary thyroid carcinoma reveals highly consistent profiles. Proc Natl Acad Sci USA. 2001; 98:15044-15049.

21. Mazzanti C, Zeiger M A, Costouros N G, et al. Using gene expression profiling to differentiate benign versus malignant thyroid tumors. Cancer Res. 2004; 64:2898-2903.

22. Lubitz C C, Ugras S K, Kazam J J, et al. Microarray analysis of thyroid nodule fine-needle aspirates accurately classifies benign and malignant lesions. J Mol Diagn. 2006; 8:490-498; quiz 528.

23. Jarzab B, Wiench M, Fujarewicz K, et al. Gene expression profile of papillary thyroid cancer: sources of variability and diagnostic implications. Cancer Res. 2005; 65:1587-1597.

24. Nikiforova M N, Kimura E T, Gandhi M, et al. BRAF mutations in thyroid tumors are restricted to papillary carcinomas and anaplastic or poorly differentiated carcinomas arising from papillary carcinomas. J Clin Endocrinol Metab. 2003; 88:5399-5404.

25. Fontaine J F, Mirebeau-Prunier D, Franc B, et al. Microarray analysis refines classification of non-medullary thyroid tumours of uncertain malignancy. Oncogene. 2008; 27:2228-2236.

26. Frasca F, Nucera C, Pellegriti G, et al. BRAF(V600E) mutation and the biology of papillary thyroid cancer. Endocr. Relat. Cancer. 2008; 15:191-205.

27. Kebehew E, Weng J, Bauer J, et al. The prevalence and prognostic value of BRAF mutation in thyroid cancer. Ann. Surg. 2007; 246:466-470; discussion 470-471.

28. Trovisco V, Vieira de Castro I, Soares P, et al. BRAF mutations are associated with some histological types of papillary thyroid carcinoma. J Pathol. 2004; 202:247-251.

29. Zhu X L, Zhou X Y, Zhu X Z, [BRAFV599E mutation and RET/PTC rearrangements in papillary thyroid carcinoma]. Zhonghua Bing Li Xue Za Zhi. 2005; 34:270-274.

30. Pennelli N, Pennelli G, Merante Boschin I, Pelizzo M R, Thyroid intrafollicular neoplasia (TIN) as a precursor of papillary microcarcinoma. Ann Ital Chir. 2005; 76:219-224.

31. Vasko V V, Gaudart J, Allasia C, et al. Thyroid follicular adenomas may display features of follicular carcinoma and follicular variant of papillary carcinoma. Eur J Endocrinol. 2004; 151:779-786.

32. Prasad M L, Huang Y, Pellegata N S, de la Chapelle A, Kloos R T, Hashimoto's thyroiditis with papillary thyroid carcinoma (PTC)-like nuclear alterations express molecular markers of PTC. Histopathology. 2004; 45:39-46.

33. Arif S, Blanes A, Diaz-Cano S J, Hashimoto's thyroiditis shares features with early papillary thyroid carcinoma. Histopathology. 2002; 41:357-362.

34. Nikiforov Y E, RET/PTC rearrangement—a link between Hashimoto's thyroiditis and thyroid cancer . . . or not. J Clin Endocrinol Metab. 2006; 91:2040-2042.

35. Rhoden K J, Unger K, Salvatore G, et al. RET/papillary thyroid cancer rearrangement in nonneoplastic thyrocytes: follicular cells of Hashimoto's thyroiditis share low-level recombination events with a subset of papillary carcinoma. J. Clin Endocrinol Metab. 2006; 91:2414-2423.

36. Rosai J. Handling of thyroid follicular patterned lesions. Endocr Pathol. 2005; 16:279-283.

37. Liu J, Singh B, Tallini G, et al. Follicular variant of papillary thyroid carcinoma: a clinicopathologic study of a problematic entity. Cancer. 2006; 107:1255-1264.

38. Vickery A L Jr. Thyroid papillary carcinoma. Pathological and philosophical controversies. Am J Surg Pathol. 1983; 7:797-807.

39. Evans H L. Encapsulated papillary neoplasms of the thyroid. A study of 14 cases followed for a minimum of 10 years. Am J Surg Pathol. 1987; 11:592-597.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method comprising:

measuring levels of RNA expressed by genes consisting of DPP4, MATN2, PROS1, RXRG, TIMP1, SERPINA1, ChGn, and SLC4A4 in a test thyroid tissue or thyroid cell sample from one or more patients by microarray analysis and/or quantitative polymerase chain reaction using primers or probes specific for DPP4, MATN2, PROS1, RXRG, TIMP1, SERPINA1, ChGn, and SLC4A4; and treating the one or more patients that have a test thyroid tissue or thyroid cell sample exhibiting at least a 2.5-fold increase in each measured RNA expression level of DPP4, SERPINA1, PROS1, RXRG, and TIMP1, and at least a 2.5-fold decrease in each measured expression level of MATN2, ChGn, and SLC4A4 RNA, compared to respective RNA expression levels of DPP4, MATN2, PROS1, RXRG, TIMP1, SERPINA1, ChGn, and SLC4A4 genes in a benign thyroid standard sample, where the treatment comprises thyroidectomy, central neck dissection, or radioactive iodine therapy.

2. The method of claim 1, further comprising measuring RNA expression of no more than ten of the following genes ANK2, ARHGAP6, Clorf17, CAPN3, CDH16, CITED 1, CITED 2, CKB, COL9A3, CSRP2, DAPK2, DIO1, DTX4 DUSP4, EFEMP1, ELMO1, FGFR2, FLRT1, FMOD, GALNT7, GATM, HGD, HMGA2, IGFBP6, KIT, LRP4, MET, MYH10, PFAAP5, PGF, PIP3-E, PKNOX2, PRKACB, PSD3, QPCT, RAB27A, RAB27A, SDC4, SLC25A15, SLIT1, SPTAN1, TFCP2L1, TIAM1, TNS3, TSPAN12, and UPP1.

3. The method of claim 1, further comprising performing fine needle aspiration to obtain the test thyroid tissue or thyroid cell sample.

4. The method of claim 1, wherein the test thyroid tissue or thyroid cell sample is obtained from a patient with thyroid cancer or suspected of having thyroid cancer.

5. The method of claim 1, wherein the test thyroid tissue or thyroid cell sample is an unclassified tumor sample.

6. The method of claim 1, wherein the test thyroid tissue or thyroid cell sample sample is a formalin fixed test tissue or cell sample.

7. The method of claim 1, wherein thyroid cancer cells are detected in the test thyroid tissue or thyroid cell sample when each of the RNA expression levels of each of DPP4, SERPINA1, MATN2, ChGn, RXRG, TIMP1, and PROS1 is at least 2.5 fold different compared to the respective levels of RNA expression of DPP4, SERPINA1, MATN2, ChGn, RXRG, TIMP1 and PROS1 in a benign thyroid standard sample.

8. The method of claim 1, wherein the method treats malignant tumors.

9. A method comprising:

obtaining a test thyroid tissue sample from a subject by fine needle aspirate;

measuring levels of expression of RNA from genes consisting of DPP4, MATN2, PROS1, RXRG, TIMP1, SERPINA1, SLC4A4, and ChGn genes in the test thyroid tissue sample by microarray analysis and/or quantitative polymerase chain reaction using primers or probes specific for DPP4, MATN2, PROS1, RXRG, TIMP1, SERPINA1, ChGn, and SLC4A4; and treating thyroid cancer in the subject with the test thyroid tissue sample exhibiting at least a 2.5-fold increase in the measured levels of RNA expression of DPP4, SERPINA1, PROS1, RXRG, and TIMP1 genes, and at least a 2.5-fold decrease in the measured level of MATN2, ChGn, and SLC4A4 RNA expression compared to RNA expression levels of DPP4, MATN2, PROS1, RXRG, SERPINA1, SLC4A4, ChGn, and TIMP1 genes in a benign thyroid standard sample, where the treatment comprises thyroidectomy, central neck dissection, or radioactive iodine therapy.

10. The method of claim 9, further comprising measuring RNA expression of no more than ten of the following genes ANK2, ARHGAP6, C11orf17, CAPN3, CDH16, CITED 1, CITED 2, CKB, COL9A3, CSRP2, DAPK2, DIO1, DTX4, DUSP4, EFEMP1, ELMO1, FGFR2, FLRT1, FMOD, GALNT7, GATM, HGD, HMGA2, IGFBP6, KIT, LRP4, MET, MYH10, PFAAP5, PGF, PIP3-E, PKNOX2, PRKACB, PROS1, PSD3, QPCT, RAB27A, RAB27A, SDC4, SLC25A15, SLIT1, SPTAN1, TFCP2L1, TIAM1, TNS3, TSPAN12, and UPP1.

11. The method of claim 9, wherein the test thyroid tissue sample is obtained from a patient with thyroid cancer or suspected of having thyroid cancer.

12. The method of claim 9, wherein the test thyroid tissue sample is an unclassified tumor sample.

13. The method of claim 9, wherein the test thyroid tissue sample is a formalin fixed test tissue or cell sample.

14. The method of claim 9, wherein malignant thyroid cancer cells are detected in the test thyroid tissue sample when each of the RNA expression levels of DPP4 and RXRG is at least 2.5-fold different as compared to RNA expression of DPP4 and RXRG, respectively in a benign thyroid standard sample.

15. The method of claim 9, wherein the method treats malignant tumors.

16. The method of claim 9, wherein malignant thyroid cancer cells are detected in the test thyroid tissue sample when each of the RNA expression levels of SERPINA1, TIMP1 and PROS1 is at least 2.5-fold different as compared to RNA expression of SERPINA1, TIMP1, and PROS1, respectively in a benign thyroid standard sample.

17. A method comprising: measuring levels of RNA expressed by genes consisting of DPP4, MATN2, PROS1, RXRG, TIMP1, SERPINA1, ChGn, and SLC4A4 in a test thyroid tissue sample or thyroid cell sample from one or more patients by microarray analysis and/or quantitative polymerase chain reaction using primers or probes specific for DPP4, MATN2, PROS1, RXRG, TIMP1, SERPINA1, ChGn, and SLC4A4.

18. The method of claim 17, where the primers comprise:

SEQ ID NOs:18 and 76 for DPP4;
SEQ ID NOs:33 and 91 for MATN2;
SEQ ID NOs:42 and 100 for PROS1;
SEQ ID NOs:48 and 106 for RXRG;
SEQ ID NOs:57 and 115 for TIMP1;
SEQ ID NOs:50 and 108 for SERPINA1;
SEQ ID NOs:9 and 67 for ChGn; and
SEQ ID NOs:52 and 110 for SLC4A4.

* * * * *

UNITED STATES PATENT AND TRADEMARK OFFICE

CERTIFICATE OF CORRECTION

PATENT NO. : 10,889,865 B2
APPLICATION NO. : 15/440489
DATED : January 12, 2021
INVENTOR(S) : Fahey, III et al.

It is certified that error appears in the above-identified patent and that said Letters Patent is hereby corrected as shown below:

In the Claims

In Column 461, Line 44, in Claim 2, delete “Clorf17,” and insert --C11orf17-- therefor In Column 461, Line 61, in Claim 2, delete “sample sample” and insert --sample-- therefor Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 172

<210> SEQ ID NO 1
<211> LENGTH: 22
<212> TYPE: DNA
<213> ORGANISM: Homo sapiens

<400> SEQUENCE: 1
tgcttgctct gataggaaaa tg 22

<210> SEQ ID NO 2
<211> LENGTH: 22
<212> TYPE: DNA
<213> ORGANISM: Homo sapiens

<400> SEQUENCE: 2
gactttctag taactcagca gc 22

<210> SEQ ID NO 3
<211> LENGTH: 19
<212> TYPE: DNA
<213> ORGANISM: Homo sapiens

<400> SEQUENCE: 3
aatactgtga gaagaagtg 19

<210> SEQ ID NO 4
<211> LENGTH: 21
<212> TYPE: DNA
<213> ORGANISM: Homo sapiens

<400> SEQUENCE: 4
gtgccaaagg ctgaggaaat g 21

<210> SEQ ID NO 5
<211> LENGTH: 22
<212> TYPE: DNA
<213> ORGANISM: Homo sapiens

<400> SEQUENCE: 5
ctcatgtggt agcagttgat tc 22

<210> SEQ ID NO 6
<211> LENGTH: 20
<212> TYPE: DNA
<213> ORGANISM: Homo sapiens

<400> SEQUENCE: 6
gaagtcccgc aaggagaatg 20

<210> SEQ ID NO 7
<211> LENGTH: 19
<212> TYPE: DNA
<213> ORGANISM: Homo sapiens

<400> SEQUENCE: 7
aggctggcct catccaaag 19

<210> SEQ ID NO 8
<211> LENGTH: 19
<212> TYPE: DNA
<213> ORGANISM: Homo sapiens

<400> SEQUENCE: 8
gatcgtgtgt cgctgcaac 19

<210> SEQ ID NO 9
<211> LENGTH: 19
<212> TYPE: DNA
<213> ORGANISM: Homo sapiens

<400> SEQUENCE: 9
aggaaactca ttcagactg 19

<210> SEQ ID NO 10
<211> LENGTH: 19
<212> TYPE: DNA
<213> ORGANISM: Homo sapiens

<400> SEQUENCE: 10
atgccaacca agagatgag 19

<210> SEQ ID NO 11
<211> LENGTH: 19
<212> TYPE: DNA
<213> ORGANISM: Homo sapiens

<400> SEQUENCE: 11
aatgggcgag cacatacac 19

<210> SEQ ID NO 12
<211> LENGTH: 19
<212> TYPE: DNA
<213> ORGANISM: Homo sapiens

<400> SEQUENCE: 12
taatagggtg tggaatgtc 19

<210> SEQ ID NO 13
<211> LENGTH: 19
<212> TYPE: DNA
<213> ORGANISM: Homo sapiens

<400> SEQUENCE: 13
cttcctaact tattgcctg 19

<210> SEQ ID NO 14
<211> LENGTH: 19
<212> TYPE: DNA
<213> ORGANISM: Homo sapiens

<400> SEQUENCE: 14
ggatctgcga cacctcagc 19

<210> SEQ ID NO 15
<211> LENGTH: 20
<212> TYPE: DNA
<213> ORGANISM: Homo sapiens

<400> SEQUENCE: 15
ggcctacaac aaatccaaac 20

<210> SEQ ID NO 16
<211> LENGTH: 22
<212> TYPE: DNA
<213> ORGANISM: Homo sapiens

<400> SEQUENCE: 16
taggacacgc aggaaagacc ac 22

<210> SEQ ID NO 17
<211> LENGTH: 21
<212> TYPE: DNA
<213> ORGANISM: Homo sapiens

<400> SEQUENCE: 17
ttaaacctgt ccacattggt g 21

<210> SEQ ID NO 18
<211> LENGTH: 19
<212> TYPE: DNA
<213> ORGANISM: Homo sapiens

<400> SEQUENCE: 18
gataagaggg attagggag 19

<210> SEQ ID NO 19
<211> LENGTH: 20
<212> TYPE: DNA
<213> ORGANISM: Homo sapiens

<400> SEQUENCE: 19
atttcctttc taacactgtg 20

<210> SEQ ID NO 20
<211> LENGTH: 20
<212> TYPE: DNA
<213> ORGANISM: Homo sapiens

<400> SEQUENCE: 20
tctagttaca gtggatttag 20

<210> SEQ ID NO 21
<211> LENGTH: 19
<212> TYPE: DNA
<213> ORGANISM: Homo sapiens

<400> SEQUENCE: 21
atccagagtg acagtgaac 19

<210> SEQ ID NO 22
<211> LENGTH: 19
<212> TYPE: DNA
<213> ORGANISM: Homo sapiens

<400> SEQUENCE: 22
gactaaacct aaatgcctc 19

<210> SEQ ID NO 23
<211> LENGTH: 23
<212> TYPE: DNA

<213> ORGANISM: Homo sapiens

<400> SEQUENCE: 23
atccagcctc atacctacat cag 23

<210> SEQ ID NO 24
<211> LENGTH: 19
<212> TYPE: DNA
<213> ORGANISM: Homo sapiens

<400> SEQUENCE: 24
gcttattcca taccatttc 19

<210> SEQ ID NO 25
<211> LENGTH: 20
<212> TYPE: DNA
<213> ORGANISM: Homo sapiens

<400> SEQUENCE: 25
ggctcttctc cctctcccag 20

<210> SEQ ID NO 26
<211> LENGTH: 19
<212> TYPE: DNA
<213> ORGANISM: Homo sapiens

<400> SEQUENCE: 26
gttggtaata tcactatgc 19

<210> SEQ ID NO 27
<211> LENGTH: 19
<212> TYPE: DNA
<213> ORGANISM: Homo sapiens

<400> SEQUENCE: 27
gtaattggat ttcgctatc 19

<210> SEQ ID NO 28
<211> LENGTH: 23
<212> TYPE: DNA
<213> ORGANISM: Homo sapiens

<400> SEQUENCE: 28
gatgagaact accacaagtg ctg 23

<210> SEQ ID NO 29
<211> LENGTH: 25
<212> TYPE: DNA
<213> ORGANISM: Homo sapiens

<400> SEQUENCE: 29
tgtactttga atcgcttgct tgttg 25

<210> SEQ ID NO 30
<211> LENGTH: 20
<212> TYPE: DNA
<213> ORGANISM: Homo sapiens

<400> SEQUENCE: 30
tgcagcaact ccagactgag 20

<210> SEQ ID NO 31
<211> LENGTH: 19

<212> TYPE: DNA
<213> ORGANISM: Homo sapiens

<400> SEQUENCE: 31
ttgtgtgttg tcttgaaag 19

<210> SEQ ID NO 32
<211> LENGTH: 20
<212> TYPE: DNA
<213> ORGANISM: Homo sapiens

<400> SEQUENCE: 32
gaagcgattc tcccatgctc 20

<210> SEQ ID NO 33
<211> LENGTH: 19
<212> TYPE: DNA
<213> ORGANISM: Homo sapiens

<400> SEQUENCE: 33
tacgataaag tttgcacag 19

<210> SEQ ID NO 34
<211> LENGTH: 20
<212> TYPE: DNA
<213> ORGANISM: Homo sapiens

<400> SEQUENCE: 34
gaaagaactg tctctaccag 20

<210> SEQ ID NO 35
<211> LENGTH: 19
<212> TYPE: DNA
<213> ORGANISM: Homo sapiens

<400> SEQUENCE: 35
actacaagca gagactgag 19

<210> SEQ ID NO 36
<211> LENGTH: 20
<212> TYPE: DNA
<213> ORGANISM: Homo sapiens

<400> SEQUENCE: 36
caaggcaggc agattgtttg 20

<210> SEQ ID NO 37
<211> LENGTH: 22
<212> TYPE: DNA
<213> ORGANISM: Homo sapiens

<400> SEQUENCE: 37
ttagcggaca tgggtcaatt tc 22

<210> SEQ ID NO 38
<211> LENGTH: 21
<212> TYPE: DNA
<213> ORGANISM: Homo sapiens

<400> SEQUENCE: 38
gcttgtactg ggacattgtt c 21

<210> SEQ ID NO 39

<211> LENGTH: 19
<212> TYPE: DNA
<213> ORGANISM: Homo sapiens

<400> SEQUENCE: 39
gatccaggac atctatcag 19

<210> SEQ ID NO 40
<211> LENGTH: 19
<212> TYPE: DNA
<213> ORGANISM: Homo sapiens

<400> SEQUENCE: 40
agcacggaca cactggcac 19

<210> SEQ ID NO 41
<211> LENGTH: 19
<212> TYPE: DNA
<213> ORGANISM: Homo sapiens

<400> SEQUENCE: 41
gtgaaagcac cttgtaaac 19

<210> SEQ ID NO 42
<211> LENGTH: 19
<212> TYPE: DNA
<213> ORGANISM: Homo sapiens

<400> SEQUENCE: 42
agtaaggagg taagattgc 19

<210> SEQ ID NO 43
<211> LENGTH: 20
<212> TYPE: DNA
<213> ORGANISM: Homo sapiens

<400> SEQUENCE: 43
ggtagtgtct aagtggtatg 20

<210> SEQ ID NO 44
<211> LENGTH: 19
<212> TYPE: DNA
<213> ORGANISM: Homo sapiens

<400> SEQUENCE: 44
tgactttcaa ctaaccttg 19

<210> SEQ ID NO 45
<211> LENGTH: 20
<212> TYPE: DNA
<213> ORGANISM: Homo sapiens

<400> SEQUENCE: 45
gatattgtgt cctaaattgc 20

<210> SEQ ID NO 46
<211> LENGTH: 21
<212> TYPE: DNA
<213> ORGANISM: Homo sapiens

<400> SEQUENCE: 46
tgccaatggg acaaacataa g 21

<210> SEQ ID NO 47
<211> LENGTH: 26
<212> TYPE: DNA
<213> ORGANISM: Homo sapiens

<400> SEQUENCE: 47
gatgcctgtt tgctatttgg tggaag 26

<210> SEQ ID NO 48
<211> LENGTH: 19
<212> TYPE: DNA
<213> ORGANISM: Homo sapiens

<400> SEQUENCE: 48
attgtactct ttaacccag 19

<210> SEQ ID NO 49
<211> LENGTH: 22
<212> TYPE: DNA
<213> ORGANISM: Homo sapiens

<400> SEQUENCE: 49
cttcctcagt tgcactaacc ac 22

<210> SEQ ID NO 50
<211> LENGTH: 25
<212> TYPE: DNA
<213> ORGANISM: Homo sapiens

<400> SEQUENCE: 50
tctgccagct tacatttacc caaac 25

<210> SEQ ID NO 51
<211> LENGTH: 19
<212> TYPE: DNA
<213> ORGANISM: Homo sapiens

<400> SEQUENCE: 51
gtgaccgctc ttgctcttg 19

<210> SEQ ID NO 52
<211> LENGTH: 19
<212> TYPE: DNA
<213> ORGANISM: Homo sapiens

<400> SEQUENCE: 52
aagagtgaat agttgcctc 19

<210> SEQ ID NO 53
<211> LENGTH: 19
<212> TYPE: DNA
<213> ORGANISM: Homo sapiens

<400> SEQUENCE: 53
ctagaggctg gtttagaac 19

<210> SEQ ID NO 54
<211> LENGTH: 21
<212> TYPE: DNA
<213> ORGANISM: Homo sapiens

<400> SEQUENCE: 54
agtttgtagc caatgtggaa g 21

<210> SEQ ID NO 55
<211> LENGTH: 19
<212> TYPE: DNA
<213> ORGANISM: Homo sapiens

<400> SEQUENCE: 55
tgatttcctg ttatgagtc 19

<210> SEQ ID NO 56
<211> LENGTH: 21
<212> TYPE: DNA
<213> ORGANISM: Homo sapiens

<400> SEQUENCE: 56
ttccatatca tctccggttc g 21

<210> SEQ ID NO 57
<211> LENGTH: 19
<212> TYPE: DNA
<213> ORGANISM: Homo sapiens

<400> SEQUENCE: 57
gactcttgca catcactac 19

<210> SEQ ID NO 58
<211> LENGTH: 21
<212> TYPE: DNA
<213> ORGANISM: Homo sapiens

<400> SEQUENCE: 58
tgtgcccaac gcatgttata g 21

<210> SEQ ID NO 59
<211> LENGTH: 19
<212> TYPE: DNA
<213> ORGANISM: Homo sapiens

<400> SEQUENCE: 59
agaaaggact tgtatgctg 19

<210> SEQ ID NO 60
<211> LENGTH: 21
<212> TYPE: DNA
<213> ORGANISM: Homo sapiens

<400> SEQUENCE: 60
gtgtgtgtca ccctcctgaa c 21

<210> SEQ ID NO 61
<211> LENGTH: 20
<212> TYPE: DNA
<213> ORGANISM: Homo sapiens

<400> SEQUENCE: 61
ttgcagctat gtattgttag 20

<210> SEQ ID NO 62
<211> LENGTH: 20
<212> TYPE: DNA
<213> ORGANISM: Homo sapiens

<400> SEQUENCE: 62
gatggcgata cgcttcagta 20

<210> SEQ ID NO 63
<211> LENGTH: 20
<212> TYPE: DNA
<213> ORGANISM: Homo sapiens

<400> SEQUENCE: 63
aaggtgatgt gatggcagtg 20

<210> SEQ ID NO 64
<211> LENGTH: 20
<212> TYPE: DNA
<213> ORGANISM: Homo sapiens

<400> SEQUENCE: 64
ttggcagctt gaggttgctc 20

<210> SEQ ID NO 65
<211> LENGTH: 21
<212> TYPE: DNA
<213> ORGANISM: Homo sapiens

<400> SEQUENCE: 65
cttgatcggt catgcctagc c 21

<210> SEQ ID NO 66
<211> LENGTH: 19
<212> TYPE: DNA
<213> ORGANISM: Homo sapiens

<400> SEQUENCE: 66
gtaggcaccc tggtagcaa 19

<210> SEQ ID NO 67
<211> LENGTH: 19
<212> TYPE: DNA
<213> ORGANISM: Homo sapiens

<400> SEQUENCE: 67
aagagattgt ttggttcac 19

<210> SEQ ID NO 68
<211> LENGTH: 23
<212> TYPE: DNA
<213> ORGANISM: Homo sapiens

<400> SEQUENCE: 68
ctcgggatct ccaataggct ctc 23

<210> SEQ ID NO 69
<211> LENGTH: 19
<212> TYPE: DNA
<213> ORGANISM: Homo sapiens

<400> SEQUENCE: 69
gtgccctccg ttcacagtc 19

<210> SEQ ID NO 70
<211> LENGTH: 21
<212> TYPE: DNA
<213> ORGANISM: Homo sapiens

<400> SEQUENCE: 70

-continued agctttcaac acagtagtat c 21

<210> SEQ ID NO 71
<211> LENGTH: 19
<212> TYPE: DNA
<213> ORGANISM: Homo sapiens

<400> SEQUENCE: 71
ataaactcta ccaagggtg 19

<210> SEQ ID NO 72
<211> LENGTH: 19
<212> TYPE: DNA
<213> ORGANISM: Homo sapiens

<400> SEQUENCE: 72
cgtgaggaag caagtgaca 19

<210> SEQ ID NO 73
<211> LENGTH: 22
<212> TYPE: DNA
<213> ORGANISM: Homo sapiens

<400> SEQUENCE: 73
gagaagataa ttggagctgg aa 22

<210> SEQ ID NO 74
<211> LENGTH: 22
<212> TYPE: DNA
<213> ORGANISM: Homo sapiens

<400> SEQUENCE: 74
caatcttaga ctctggcctc aa 22

<210> SEQ ID NO 75
<211> LENGTH: 23
<212> TYPE: DNA
<213> ORGANISM: Homo sapiens

<400> SEQUENCE: 75
gctctctgta ccctgaaatc ttc 23

<210> SEQ ID NO 76
<211> LENGTH: 20
<212> TYPE: DNA
<213> ORGANISM: Homo sapiens

<400> SEQUENCE: 76
gtttgaatag tctttctcag 20

<210> SEQ ID NO 77
<211> LENGTH: 19
<212> TYPE: DNA
<213> ORGANISM: Homo sapiens

<400> SEQUENCE: 77
gtcaaggtag tagatgcac 19

<210> SEQ ID NO 78
<211> LENGTH: 20
<212> TYPE: DNA
<213> ORGANISM: Homo sapiens

<400> SEQUENCE: 78
gctaccttgc acatatctac 20

<210> SEQ ID NO 79
<211> LENGTH: 20
<212> TYPE: DNA
<213> ORGANISM: Homo sapiens

<400> SEQUENCE: 79
gatacatcaa agtaaagcag 20

<210> SEQ ID NO 80
<211> LENGTH: 20
<212> TYPE: DNA
<213> ORGANISM: Homo sapiens

<400> SEQUENCE: 80
atgatgtaaa cttggatgtc 20

<210> SEQ ID NO 81
<211> LENGTH: 22
<212> TYPE: DNA
<213> ORGANISM: Homo sapiens

<400> SEQUENCE: 81
caatagccgt gcaagatgaa tg 22

<210> SEQ ID NO 82
<211> LENGTH: 19
<212> TYPE: DNA
<213> ORGANISM: Homo sapiens

<400> SEQUENCE: 82
atcgactaca tgattgttc 19

<210> SEQ ID NO 83
<211> LENGTH: 23
<212> TYPE: DNA
<213> ORGANISM: Homo sapiens

<400> SEQUENCE: 83
gtatgagacc tacgagcctt acc 23

<210> SEQ ID NO 84
<211> LENGTH: 20
<212> TYPE: DNA
<213> ORGANISM: Homo sapiens

<400> SEQUENCE: 84
acccagaatt aagatatacg 20

<210> SEQ ID NO 85
<211> LENGTH: 19
<212> TYPE: DNA
<213> ORGANISM: Homo sapiens

<400> SEQUENCE: 85
cttagatgac caaagatgc 19

<210> SEQ ID NO 86
<211> LENGTH: 23
<212> TYPE: DNA
<213> ORGANISM: Homo sapiens

<400> SEQUENCE: 86
ctttctggta gtattggagg agg 23

<210> SEQ ID NO 87
<211> LENGTH: 23
<212> TYPE: DNA
<213> ORGANISM: Homo sapiens

<400> SEQUENCE: 87
cagaggctgt tatgtttatt gtg 23

<210> SEQ ID NO 88
<211> LENGTH: 20
<212> TYPE: DNA
<213> ORGANISM: Homo sapiens

<400> SEQUENCE: 88
catcgaggct tctaccggaa 20

<210> SEQ ID NO 89
<211> LENGTH: 19
<212> TYPE: DNA
<213> ORGANISM: Homo sapiens

<400> SEQUENCE: 89
agagcataga actccagtg 19

<210> SEQ ID NO 90
<211> LENGTH: 21
<212> TYPE: DNA
<213> ORGANISM: Homo sapiens

<400> SEQUENCE: 90
cactggagag attggacttt c 21

<210> SEQ ID NO 91
<211> LENGTH: 20
<212> TYPE: DNA
<213> ORGANISM: Homo sapiens

<400> SEQUENCE: 91
tatatcaagg taaagtccag 20

<210> SEQ ID NO 92
<211> LENGTH: 19
<212> TYPE: DNA
<213> ORGANISM: Homo sapiens

<400> SEQUENCE: 92
caagtgtgta gtcctgttg 19

<210> SEQ ID NO 93
<211> LENGTH: 19
<212> TYPE: DNA
<213> ORGANISM: Homo sapiens

<400> SEQUENCE: 93
ggtttctttc ttcttcttc 19

<210> SEQ ID NO 94
<211> LENGTH: 19
<212> TYPE: DNA
<213> ORGANISM: Homo sapiens

<400> SEQUENCE: 94
aatggcacga tcatgggtc 19

<210> SEQ ID NO 95
<211> LENGTH: 22
<212> TYPE: DNA
<213> ORGANISM: Homo sapiens

<400> SEQUENCE: 95
aagtgtagcc caggttaaga ac 22

<210> SEQ ID NO 96
<211> LENGTH: 21
<212> TYPE: DNA
<213> ORGANISM: Homo sapiens

<400> SEQUENCE: 96
gagaaacagc tcagccagtg g 21

<210> SEQ ID NO 97
<211> LENGTH: 19
<212> TYPE: DNA
<213> ORGANISM: Homo sapiens

<400> SEQUENCE: 97
aaggtgattt cttgagttc 19

<210> SEQ ID NO 98
<211> LENGTH: 24
<212> TYPE: DNA
<213> ORGANISM: Homo sapiens

<400> SEQUENCE: 98
ctgatgtatc caccaaacca gtac 24

<210> SEQ ID NO 99
<211> LENGTH: 20
<212> TYPE: DNA
<213> ORGANISM: Homo sapiens

<400> SEQUENCE: 99
cagtagtgca taggaaattc 20

<210> SEQ ID NO 100
<211> LENGTH: 20
<212> TYPE: DNA
<213> ORGANISM: Homo sapiens

<400> SEQUENCE: 100
cagtgaaaca tctgatacac 20

<210> SEQ ID NO 101
<211> LENGTH: 20
<212> TYPE: DNA
<213> ORGANISM: Homo sapiens

<400> SEQUENCE: 101
atagtcatgg acatttacag 20

<210> SEQ ID NO 102
<211> LENGTH: 20
<212> TYPE: DNA

<213> ORGANISM: Homo sapiens

<400> SEQUENCE: 102
aagttactaa gactgcacag 20

<210> SEQ ID NO 103
<211> LENGTH: 20
<212> TYPE: DNA
<213> ORGANISM: Homo sapiens

<400> SEQUENCE: 103
ctatcgttga atgaatgaac 20

<210> SEQ ID NO 104
<211> LENGTH: 21
<212> TYPE: DNA
<213> ORGANISM: Homo sapiens

<400> SEQUENCE: 104
ctgaaggagt ggtgcgatca a 21

<210> SEQ ID NO 105
<211> LENGTH: 24
<212> TYPE: DNA
<213> ORGANISM: Homo sapiens

<400> SEQUENCE: 105
gaagacactt tggcaatgca gcgg 24

<210> SEQ ID NO 106
<211> LENGTH: 20
<212> TYPE: DNA
<213> ORGANISM: Homo sapiens

<400> SEQUENCE: 106
gatacttctg cttggtgtag 20

<210> SEQ ID NO 107
<211> LENGTH: 19
<212> TYPE: DNA
<213> ORGANISM: Homo sapiens

<400> SEQUENCE: 107
gacgaccctt gtctccctg 19

<210> SEQ ID NO 108
<211> LENGTH: 21
<212> TYPE: DNA
<213> ORGANISM: Homo sapiens

<400> SEQUENCE: 108
gcatcactaa ggtcttcagc a 21

<210> SEQ ID NO 109
<211> LENGTH: 23
<212> TYPE: DNA
<213> ORGANISM: Homo sapiens

<400> SEQUENCE: 109
gtggtcagta gccttatgca cct 23

<210> SEQ ID NO 110
<211> LENGTH: 19

-continued

<212> TYPE: DNA
<213> ORGANISM: Homo sapiens

<400> SEQUENCE: 110
atcatttctc tctccaaag 19

<210> SEQ ID NO 111
<211> LENGTH: 20
<212> TYPE: DNA
<213> ORGANISM: Homo sapiens

<400> SEQUENCE: 111
ggaagacaac agacaatatc 20

<210> SEQ ID NO 112
<211> LENGTH: 21
<212> TYPE: DNA
<213> ORGANISM: Homo sapiens

<400> SEQUENCE: 112
gattatggcg acactcttgc c 21

<210> SEQ ID NO 113
<211> LENGTH: 19
<212> TYPE: DNA
<213> ORGANISM: Homo sapiens

<400> SEQUENCE: 113
tacagtgatg acagacagc 19

<210> SEQ ID NO 114
<211> LENGTH: 21
<212> TYPE: DNA
<213> ORGANISM: Homo sapiens

<400> SEQUENCE: 114
cttggagagg gtgccattgt c 21

<210> SEQ ID NO 115
<211> LENGTH: 19
<212> TYPE: DNA
<213> ORGANISM: Homo sapiens

<400> SEQUENCE: 115
gataaacagg gaaacactg 19

<210> SEQ ID NO 116
<211> LENGTH: 21
<212> TYPE: DNA
<213> ORGANISM: Homo sapiens

<400> SEQUENCE: 116
cttgtaacgt cttctctgcc t 21

<210> SEQ ID NO 117
<211> LENGTH: 20
<212> TYPE: DNA
<213> ORGANISM: Homo sapiens

<400> SEQUENCE: 117
tattgacttg gagactattg 20

<210> SEQ ID NO 118

<211> LENGTH: 19
<212> TYPE: DNA
<213> ORGANISM: Homo sapiens

<400> SEQUENCE: 118
gaagaaactg agcaaggcc 19

<210> SEQ ID NO 119
<211> LENGTH: 14243
<212> TYPE: DNA
<213> ORGANISM: Homo sapiens

<400> SEQUENCE: 119
ctcctcctcc tgctttcctc cagtaagtgc atacccgcta gtggtctgta caggcggcac 60
ggtttgatgg cagagatatt ttctttccaa actgttcaaa atgatgaacg aagatgcagc 120
tcagaaaagc gacagtggag agaagttcaa cggcagtagt cagaggagaa aaagacccaa 180
gaagtctgac agcaatgcaa gcttcctccg tgctgccaga gcaggcaacc tggacaaagt 240
tgtggaatat ctgaaggggg gcatagacat caatacctgc aatcagaatg gactcaacgc 300
tctccatctg gctgccaagg aaggccacgt ggggctggtg caggagctgc tgggaagagg 360
gtcctctgtg gattctgcca ctaagaaggg aaataccgct cttcacattg catctttggc 420
tggacaagca gaagttgtca aagttcttgt taaggaagga gccaatatta atgcacagtc 480
tcagaatggc tttactcctt tatacatggc tgcccaagag aatcacattg atgttgtaaa 540
atatttgctg gaaaatggag ctaatcagag cactgctaca gaggatggct ttactcctct 600
agctgtggca ctccagcaag gacacaacca ggcggtggcc atcctcttgg agaatgacac 660
caaagggaaa gtgaggctgc cagctctgca tattgccgct aggaaagacg acaccaaatc 720
tgccgcactt ctgcttcaga atgaccacaa tgctgacgta caatccaaga tgatggtgaa 780
taggacaact gagagtggtt ttaccccttt gcacatagct gcacattacg gaaatgtcaa 840
cgtggcaact cttcttctaa accggggagc tgctgtggac ttcacagcca ggaatggaat 900
cactcctctg catgtggctt ccaaaagagg aaatacaaac atggtgaagc tcttactgga 960
tcgaggcggt cagatcgatg ccaaaactag ggatgggttg acaccacttc actgtgctgc 1020
acgaagtggg catgaccaag tggtggaact tctgttggaa cggggtgccc ccttgctggc 1080
aaggactaag aatgggctgt ctccactaca catggctgcc cagggagacc acgtggaatg 1140
tgtgaagcac ctgttacagc acaaggcacc tgttgatgat gtcaccctag actacctgac 1200
agccctccac gttgctgcgc actgtggcca ctaccgtgta accaaactcc ttttagacaa 1260
gagagccaat ccgaacgcca gagccctgaa tggttttact ccactgcaca ttgcctgcaa 1320
gaaaaaccgc atcaaagtca tggaactgct ggtgaaatat ggggcttcaa tccaagctat 1380
aacagagtct ggcctcacac caatacatgt ggctgccttc atgggccact tgaacattgt 1440
cctccttctg ctgcagaacg gagcctctcc agatgtcact aacattcgtg gtgagacggc 1500
actacacatg gcagcccgag ccgggcaggt ggaagtggtc cgatgcctcc tgagaaatgg 1560
tgcccttgtt gatgccagag ccagggagga acagacacct ttacatattg cctcccgcct 1620
gggtaagaca gaaattgtcc agctgcttct acaacatatg gctcatccag atgcggccac 1680
tacaaatggg tacacaccac tgcacatctc tgcccgggag ggccaggtgg atgtggcatc 1740
agtcctattg gaagcaggag cagcccactc cttagctacc aagaagggtt ttactcccct 1800
gcatgtagca gccaagtatg gaagcctgga tgtggcaaaa cttctcttgc aacgccgtgc 1860
tgccgcagat tctgcaggga agaacggcct taccccgctc catgttgctg ctcattatga 1920

-continued

```
caaccagaag gtggcgctgc tgttactgga gaagggtgct tcccctcatg ccactgccaa   1980
gaatggctat actccgttac atattgctgc caagaagaat caaatgcaga tagcttccac   2040
actcctgaac tatggagcag agacaaacat tgtgacaaag caaggagtaa ctccactcca   2100
tctggcctcg caggaggggc acacagatat ggttaccttg cttctggata agggagccaa   2160
tatccacatg tcaactaaga gtggactcac atccttacac cttgcagccc aggaagataa   2220
agtgaatgtt gctgatattc tcaccaagca tggagctgat caggatgctc atacaaagct   2280
tggttacaca cctttaattg tggcctgtca ctatggaaat gtgaaaatgg tcaactttct   2340
tctgaagcag ggagcaaatg ttaacgcaaa aaccaagaac ggctacacgc ctttgcacca   2400
ggccgctcag cagggtcaca cgcacatcat caacgtcctg ctccagcatg gggccaagcc   2460
caacgccacc actgcgaatg gcaacactgc cttggcgatt gctaagcgtc tgggctacat   2520
ctccgtggtc gacaccctga aggttgtgac tgaggaggtc accaccacca ccacaactat   2580
tacagaaaaa cacaaactaa atgtacctga gacgatgact gaggttcttg atgtttctga   2640
tgaagagggt gatgacacaa tgactggtga tgggggagaa taccttaggc ctgaggacct   2700
aaaagaactg ggtgatgact cactacccag cagtcagttc ctggatggta tgaattacct   2760
gcgatacagc ttggagggag gacgatctga cagccttcga tccttcagtt ccgacaggtc   2820
tcacactctg agccatgcct cctacctgag ggacagtgcc gtgatggatg actcagttgt   2880
gattcccagt caccaggtgt caactctagc caaggaggca gaaaggaatt cttatcgcct   2940
aagctggggc actgagaact tagacaacgt ggctctttct tctagtccta ttcattcagg   3000
tttcctggtt agttttatgg tggatgcccg aggtggtgct atgcgaggat gcagacacaa   3060
tgggctccga atcattattc cacctcggaa atgtactgct ccaacgcgag tcacctgccg   3120
actggtcaag cgccacagac tggcaacaat gcctccaatg gtggaaggag aaggcctggc   3180
cagtcgcctg atcgaagttg gaccttctgg tgctcagttc cttggtaaac ttcacctgcc   3240
aacggctcct cccccactta atgagggaga aagtttggtc agccgcattc ttcagctggg   3300
gcctcctgga accaaattcc ttgggcctgt gatcgtggag atccctcact ttgcggccct   3360
tcgaggaaag gaaagggaac tggtggtcct gcgcagtgag aatggggaca gctggaaaga   3420
gcatttctgt gactacactg aagatgaatt gaatgaaatt cttaacggca tggatgaagt   3480
actggatagc ccagaagacc tagaaaagaa acgaatctgc cgcatcatca cccgagactt   3540
cccacagtac tttgcagtgg tgtctcgtat caaacaggac agcaatctga ttggcccaga   3600
aggaggtgta ctgagcagca cagtggtgcc ccaggtgcag gccgtcttcc cagagggggc   3660
actcaccaag cggatccgcg taggcctgca ggctcaacct atgcacagtg agctggttaa   3720
gaagatccta ggcaacaaag ctaccttcag ccctatagtc actttggaac ctagaagaag   3780
aaaattccac aaaccaatta ccatgaccat tcctgtcccc aaagcttcaa gtgatgtcat   3840
gttgaatggt tttgggggag atgcaccaac cttaagatta ctatgcagca taacaggtgg   3900
aaccacccct gcccagtggg aagatattac aggaactacg ccattaacat ttgtcaatga   3960
atgtgtttcc tttacaacaa acgtgtctgc caggttctgg ctgatagatt gtcgacagat   4020
ccaggaatcc gttacttttg catcacaagt atacagagaa attatctgcg taccttatat   4080
ggccaaattt gtagtgtttg ccaaatcaca tgaccccatt gaagccaggt tgaggtgttt   4140
ctgcatgact gatgataaag tggataagac ccttgaacaa caagaaaatt ttgctgaggt   4200
ggccagaagc agggatgtgg aggtgttaga aggaaaaccc atctacgttg attgtttcgg   4260
```

-continued

```
caacttggta ccattaacta aaagtggcca gcatcatata ttcagttttt ttgccttcaa   4320
agaaaataga cttcctctat ttgtcaaggt acgcgatacg actcaggaac cttgcggacg   4380
actatcattt atgaaggagc caaaatccac gagaggcctg gtgcatcaag ctatttgcaa   4440
cttaaacatc actttgccga tttatacaaa ggaatcagag tcagatcaag aacaggagga   4500
agagatcgat atgacatcag aaaaaaatga tgagacagaa tctacagaaa catctgtcct   4560
gaaaagtcac ctggttaatg aagttcctgt cctagcaagt ccggacttgc tctctgaagt   4620
ttctgagatg aaacaagatt tgatcaaaat gaccgccatc ttgaccacag atgtgtctga   4680
taaggcaggt tctattaaag tgaaggagct ggtgaaggct gctgaggaag agccaggaga   4740
gccttttgaa atcgttgaaa gagttaaaga ggacttagag aaagtgaatg aaatcctgag   4800
aagtggaacc tgcacaagag atgaaagcag tgtgcagagc tctcggtctg agagaggatt   4860
agttgaagag gaatgggtta ttgtcagtga tgaggaaata gaagaggcta ggcaaaaagc   4920
acctttagaa atcactgaat atccatgtgt agaagttaga atagataaag agatcaaagg   4980
aaaagtagag aaagactcaa ctgggctagt gaactacctt actgatgatc tgaatacctg   5040
tgtgcctctt cccaaagagc agctgcagac agttcaagat aaggcaggga agaaatgtga   5100
ggctctggct gttggcagga gctctgaaaa ggaagggaaa gacatacccc cagatgagac   5160
acagagtaca cagaaacagc acaaaccaag cttgggaata aagaagccag taagaaggaa   5220
attaaaagaa aagcagaaac aaaaagagga aggtttacaa gctagtgcag agaaagctga   5280
acttaaaaaa ggtagttcag aagagtcatt aggtgaagac ccaggtttag cccctgaacc   5340
ccttcccact gtcaaggcca catctccttt gatagaagaa actcccattg gttccataaa   5400
ggacaaagta aaggcccttc agaagcgagt ggaagatgaa cagaaaggtc gaagcaagtt   5460
gcccatcaga gtcaaaggca aggaggacgt gccaaaaaag accacccaca ggccacatcc   5520
agctgcgtca ccctctctga agtcagagag acatgcgcca gggtctccct cccctaaaac   5580
agaaagacac tctactcttt cctcttccgc aaaaactgaa aggcaccctc cagtatcacc   5640
atcaagtaaa actgagaaac actcacctgt gtcaccctct gcaaaaacgg aaagacattc   5700
acctgcgtca tcatcgagta aaactgagaa acactcacct gtatcaccct cgacaaaaac   5760
tgaaaggcac tctcctgtgt catctacaaa aacagaaaga cacccacctg tttcgccttc   5820
aggcaaaaca gacaaacgtc cacctgtatc gccctccggg aggacagaaa aacacccgcc   5880
agtatcgcct gggagaacag aaaaacgctt gcctgtttca ccctccggaa gaacggacaa   5940
gcaccaacct gtatcaacag ctgggaaaac tgagaagcac ctgcctgtgt caccttctgg   6000
caaaacagaa aagcaaccac ctgtatcccc cacttcaaaa acagagagga ttgaggaaac   6060
catgtctgtt cgggagctga tgaaggcttt ccagtcaggt caggaccctt ctaaacataa   6120
aactggactc tttgagcaca aatcagcaaa acaaaagcag ccacaagaga aaggtaaagt   6180
tcgggtagaa aaagaaaagg ggccgatact aacccagaga gaagctcaga aaacagagaa   6240
tcagacaatc aaacgaggcc agagactccc ggtaacgggc acagcagaat ccaaaagagg   6300
agttcgtgtt tcctccatag gagttaagaa agaagatgca gctggaggaa aggagaaagt   6360
tctcagccac aaaatacctg aacctgttca gtcagtgcct gaagaagaaa gccacagaga   6420
gagcgaagtg cccaaagaaa agatggctga tgagcaggga gacatggatc tacagatcag   6480
cccagatagg aaaacctcca ctgacttctc tgaggtcatt aagcaagagt tggaagacaa   6540
tgacaaatac caacaattcc gcctgagtga ggagacagaa aaggcacagc ttcacttaga   6600
ccaagtactc actagtcctt tcaacacaac atttccactc gactacatga aagatgagtt   6660
```

-continued

```
ccttccagct ctgtctttac aaagcggtgc tttagatggc agttctgaaa gcctaaagaa   6720
tgagggggta gccggctctc cgtgtggcag cctgatggag gggacccctc agattagttc   6780
agaagaaagc tataagcatg aaggcctagc agagacccct gagacgagcc cagaaagcct   6840
ttctttctca ccaaagaaaa gtgaggagca aactggggaa acaaaggaaa gcaccaagac   6900
agaaaccacc acagaaattc gttcagaaaa agagcatccc acgaccaaag acattactgg   6960
tggctctgaa gagcgaggtg ccacagtcac tgaggactca gagacctcta ctgagagttt   7020
tcagaaagag gccactctag gctctcccaa agacacaagc cctaaaagac aagatgattg   7080
cacaggcagc tgtagtgtag cattagctaa agagacacct acaggactga ctgaggaggc   7140
agcctgtgat gaaggtcaac gtacctttgg tagttcagcc cacaagacac aaactgatag   7200
tgaggttcaa gaatccacag ccacctcaga cgagacaaag gccttgccgc tgcctgaggc   7260
ttctgtaaag acagatacag gaactgaatc aaaacctcag ggagtcatta gaagtcccca   7320
agggttagaa cttgcactcc ctagccgaga tagcgaagtc ctcagcgctg tggctgatga   7380
ctcattagca gtgagccaca aagactctct ggaagccagc cctgtgctag aagataactc   7440
ttcacacaaa acccctgatt ctctggagcc aagtcctctg aaagaatccc cttgccgtga   7500
ctctctggaa agcagccctg ttgaaccaaa gatgaaggct ggaatttttc caagtcactt   7560
tcctcttcct gcagctgttg ccaaaacaga actcttgacg gaagtggcct ctgtgcggtc   7620
ccggctactc cgagaccctg atggcagtgc tgaggatgac agtcttgagc agacatcgct   7680
catggagagc tcagggaaga gccccctttc tcctgacacc cccagctctg aagaagtcag   7740
ctatgaggtt acacccaaaa ccacagatgt aagtacacca aaaccagctg tgattcatga   7800
atgtgcagag gaggatgatt cagaaaacgg ggagaaaaag aggttcacac ctgaagagga   7860
gatgtttaaa atggtaacca aaatcaaaat gtttgatgaa cttgaacaag aagcaaagca   7920
gaaaagggac tacaaaaaag aacccaaaca agaagaatct tcttcatctt ctgacccaga   7980
tgctgactgt tcagtagatg tggatgaacc aaaacataca ggcagtgggg aggatgaaag   8040
tggtgtccct gtgttagtaa cttcggagag caggaaggtg tcttcctcct cagaaagtga   8100
acctgagttg gcacagctta aaaaaggtgc tgactcaggc cttttaccag aaccagtgat   8160
tcgagtacaa cctccttctc cacttccatc aagcatggac tccaattcca gtccagaaga   8220
agtacaattc cagcctgtcg tttccaaaca atatactttc aagatgaatg aagatactca   8280
ggaagagcca ggcaaatcag aagaagaaaa agattctgaa tcccatttag ctgaagaccg   8340
tcatgctgtt tccactgagg ctgaagacag gtcttatgat aagctaaaca gagacactga   8400
tcagccaaaa atctgtgatg gccatggatg tgaggccatg agtcctagca gctcagctgc   8460
tcctgtctct tcaggtctac agagtccgac tggtgatgat gttgatgaac agccagtcat   8520
ctataaagaa tcattagctc tccaaggcac tcatgaaaaa gacacagagg gagaagagct   8580
tgatgtttct agagcagaat ctccacaagc agattgcccc agtgaaagct tttcatcttc   8640
atcctctttg cctcattgtt tggtatctga aggaaaagaa ttagatgaag acatatctgc   8700
cacatcttct attcaaaaaa cagaggtcac aaaaaactgat gaaacatttg agaacttacc   8760
aaaggactgc cctctcaag actcatccat tactactcaa acagatagat tttccatgga   8820
tgttcccgtg tctgacctag ctgagaatga tgaaatctat gatccacaaa tcactagccc   8880
ttatgaaaat gtcccttccc aatctttttt ctctagtgaa gaaagcaaaa cccaaacaga   8940
tgcaaatcac accacaagtt ttcactcttc tgaagtgtat tctgttacca tcacatcccc   9000
```

-continued

```
tgttgaagac gttgtagtgg caagctcctc tagtggaact gttttaagca aagaatctaa   9060
ttttgagggc caggacataa aaatggaatc ccaacaggaa agtaccttgt gggaaatgca   9120
atcagacagt gtctcttcat ctttcgagcc tactatgtcc gctacaacaa cagttgttgg   9180
tgaacaaata agcaaagtca tcatcacaaa aactgatgtg gattctgatt cttggagtga   9240
aattcgggaa gacgatgaag cctttgaggc tcgtgtgaaa gaggaagaac aaaagatatt   9300
tggtttgatg gtagacagac aatcacaggg taccacccct gacaccactc ctgctaggac   9360
cccaactgaa gaggggaccc caacaagtga gcaaaaccca tttctgtttc aggaaggaaa   9420
attgtttgaa atgacccgaa gtggtgccat tgatatgacc aaaaggtcct atgcagatga   9480
aagttttcac tttttccaaa ttggtcaaga atccagggaa gagactctct ctgaagatgt   9540
gaaagaaggg gctactgggg ctgatcccct accgctggag acatcagctg aatcactagc   9600
actttcagaa tcaaaagaaa cagtggatga tgaggcagac ttacttccag atgacgtgag   9660
tgaggaagta gaggaaatac ctgcttcgga tgctcaactt aactcccaaa tggggatttc   9720
agcctccact gaaacaccta caaaagaagc tgttagtgta gggaccaagg acctccccac   9780
cgtgcaaacg ggtgatatac ctcctctctc tggtgtaaag cagatatcct gccccgactc   9840
ttctgaacca gctgtacaag tccagttaga tttttccaca ctcaccaggt ctgtttattc   9900
agataggggt gatgattctc ccgattcttc cccagaagaa cagaaatcag taatcgagat   9960
tcctactgca cccatggaga atgtgccttt tactgaaagc aaatccaaaa ttcctgtaag  10020
gactatgccc acttccaccc cagcacctcc atctgcagag tatgagagtt cagtttctga  10080
agattttcta tccagtgtag atgaggaaaa taaggcggat gaagcaaaac caaagtccaa  10140
actccctgtc aaagtacccc tccaaagagt tgaacagcag ctctcagatc tagacacctc  10200
tgtccagaag acagtggctc ctcagggaca ggacatggca agcatcgcac cagataatag  10260
aagcaaatct gaatctgatg ctagttcttt ggattcaaag accaaatgcc cagtaaaaac  10320
ccgaagttac actgagacag aaacagagag cagagagagg gccgaggaac ttgagttaga  10380
atcagaagaa ggggccacaa gaccaaagat acttacatcc cgattgccag ttaagagcag  10440
aagcactaca tcttcctgca ggggggggcac gagccccaca aaagaaagta aggagcattt  10500
ctttgacctt tacagaaatt ccatagaatt ctttgaggag attagtgatg aggcttccaa  10560
attagtggat aggctgacac agtcagagag ggagcaggaa atagtttcag acgatgaaag  10620
tagtagtgcc ctggaagtat cagtaattga aaatctgcca cctgttgaga ccgagcactc  10680
agttcctgag gacatctttg acacaaggcc catttgggat gagtctattg agactctgat  10740
tgaacgcatc cctgatgaaa atggccatga ccatgctgaa gatccacagg atgagcagga  10800
acggatcgag gaaaggctgg cttatattgc tgatcacctt ggcttcagct ggacagaatt  10860
agcaagagaa ctggatttca ctgaggagca aattcatcaa attcgaattg aaaatcccaa  10920
ctctcttcaa gaccagagtc atgcactgtt gaagtactgg ctagagaggg atgggaaaca  10980
tgctacagat accaacctcg ttgaatgtct caccaagatc aaccgaatgg atattgttca  11040
tctcatggag accaacacag aacctctcca ggagcgcatc agtcatagtt atgcagaaat  11100
tgaacagacc attacactgg atcatagtga agggttctcg gtacttcaag aggagttatg  11160
cactgcacag cacaagcaga aagaggagca agctgtttct aaagaaagtg agacctgcga  11220
tcaccctcct atcgtctcag aggaagacat ttctgttggt tattccactt ttcaggatgg  11280
cgtccccaaa actgaggggg acagctcagc aacagcactc tttccccaaa ctcacaagga  11340
gcaagttcaa caggatttct cagggaaaat gcaagacctg cctgaagagt catctctgga  11400
```

atatcagcag gaatattttg tgacaactcc aggaacagaa acatcagaga ctcagaaggc 11460
tatgatagta cccagctctc ccagcaagac acctgaggaa gttagcaccc ctgcagagga 11520
ggagaagctg tacctccaga ccccaacatc cagcgagcgg ggaggctctc ccatcataca 11580
agaacccgaa gagccctcag agcacagaga ggagagctct ccgcggaaaa ccagcctcgt 11640
aatagtggag tctgccgata accagcctga gacctgtgaa agactcgatg aagatgcagc 11700
ttttgaaaag ggagacgata tgcctgaaat acccccagaa acagtcacag aagaagaata 11760
cattgatgag catggacaca ccgtggtaaa gaaggttact aggaaaatca ttaggcggta 11820
tgtatcctct gaaggcacag agaaagaaga gattatggtg cagggaatgc cacaggaacc 11880
tgtcaacatc gaggaagggg atggctattc caaagttata aagcgtgttg tattgaagag 11940
tgacaccgag cagtcagagg acaacaatga gtaaagccat cacacagaag agggctgtgg 12000
tgaaggacca gcatggaaaa cgcattgact tggagcacct ggaggatgta ccagaagcac 12060
tagaccagga cgacctccag cgcgatctcc agcagctcct tcggcatttc tgcaaggagg 12120
acttgaagca agaggccaag tgaggggctg cccagttctc acaccagaaa ccacacattc 12180
actcaatatg cagcttcctg tttcagtagg ggagtgacct aactggccta attaatggga 12240
taccccgaca tttccactgt tagcaaatat acggcatttt gctttagttt tcccccatcc 12300
tctttaacta taaagctaat ttgtgaccaa agatggcatc cttcatactg gatgctgtat 12360
ccaatacttt gttgtgtctg tgctaacctg ggaactggcc acctccattg ttctttgctt 12420
ctgcacaaga tccatgaaaa tccattgatc agaagaactt cacctgcaga cctcttcaag 12480
tgacactatg taggaatcct tccaaggaat atctatgtac aatgtatata gctgaaatgc 12540
tcagatgaac aacatattaa aattaaaacc actgcctatt gtaactacac tgggcatcag 12600
aataaaaggc ctctagaaat tgctgaacaa tggttaatta agatattgct aacacaatcg 12660
agtgataata cagttttact gcaaaagaag cacttcaaac ctattatgtc cttagaactt 12720
ccagagtagc cactgctccc agttaaaggt gggtcagtag ccttgcagaa ctgtcctgag 12780
aagttattgc tggtgctggc cagccatggc ttaggactcc aacagccact ctgagggagg 12840
ggagaaggga gcagaggcca cgcagaatga accgatgggg tattcagttg ctggcagcta 12900
cattgtgtgg cattctagca tcttcaggtc tttagatctt ggacaagttg gcagggtatt 12960
ttaaaagcta taactactgt agttttccag ttttcattgc tgctttagca aaccacgctg 13020
tcttacagtg gtactttctt ctggccactg cactgtagat aattcattgg aaacaagatt 13080
tacccactac ataaaaggtt aaactccttc agtatgttgg agtggtttct tttttttttt 13140
ctttctttct tttttttctt caggtttata tcttctctaa tacctgcatg tggcgtttaa 13200
aaatcaagac cacggtcaaa cccctcttct aatcacatta attgtttcca ttctttttac 13260
cctgagtgag cacttttcac tttccagcta ggtctgtttt tcagcttgca gacaagattg 13320
agaaatcctt gaaaatttgg ttttggttaa aatttttggt ttatttattt gaaatccaca 13380
ctcccttgga aactcttaag tgcatttgtg cacttctgtt tgtttgtctc aaagaaggga 13440
ctgtaacaat ctgagtaatt tccatgtcct cttccttatt cctctagtgg ttgaagctgt 13500
gtagcatttt aacatatata tattcacaaa tatattcata taaacagtat acattttgaa 13560
tcagtcattt gttaaagaaa agtatattca atgaagatga aatttaaata aaaaaggaca 13620
gagtctatcc tccagggatt gaacattttc caattatctg gtcttttcct gttgtgcaaa 13680
aatgactcat tgctccgaat gtcaaaaaca aatgcgacaa acaatggcac ttcatcattt 13740

```
aaagtaatgt tgccaagaga aaaaatttcc tgggagggag gtttcccaca agccaaatct  13800

cctaagcctc aaatgctagc actttttggc agttggatag gaaatgagac attctttggc  13860

agccaaaata agagaggccg atggtgaaac tttttgagac accctatggc cttcttgtca  13920

aaaccttcac tggagctcaa gaaaagcatt tctgttgtgt tatttgcagt gcagatgatg  13980

tctgtgtaac aacataatgg ttattcacct ttttttgatt ttgatttttg ctgtgttatc  14040

aaaaacttga atactgtgag aagaagtgaa ttttcagttg acgaatcagc atcttgttcc  14100

catggtgata acactaattg aatatatcta tgagggcatg tattagttaa tggaaaaaaa  14160

aatacaacac taacaataca tagctgcaat gtgtacaatg gctgatttaa ttaaataaaa  14220

tgtacaagtg ttaaatgtgg caa                                          14243
```

<210> SEQ ID NO 120
<211> LENGTH: 5118
<212> TYPE: DNA
<213> ORGANISM: Homo sapiens

<400> SEQUENCE: 120

```
ggctgggctg cgaatagcgt gttcctctcc ggcggaacac acacacccgg ccttggggct     60

gtctcctgag ctccctcctc cacggagagc gctgagcgcc gccgggaatt ccatcccacc    120

gtgggcacgc agtctttgga ggtcccgggc gcagcacgct cggtgtcccc acactgcagc    180

aagacagaga ccccgcggga accttgagct tggaacaacc cttgagcctc tgcagtcgga    240

agagtgggcg cagcagccca gcggaggcca ggcgcgcaac ctcgggcgcc ggggcaagga    300

gagagtgcag ggaggcgcag ctcaggcgcc cggctcagga gcgggaggaa gttctcgcgg    360

cgccgggagc gcggtggacg cgccctgggc gcacgcccag gcagccttct ccctggccct    420

cgggactgtc ctcgggccgc aaggaggagc ttgctggagt cttagaggcc atccagagcc    480

agcgagcagg agcgctgcgt ctcccgcctc agctaggaag ggggagtggc gctggcaggc    540

tggagctggg aacccagcga gcgcctgacc ttcctcctcc tcttcctgac cctcttcgcg    600

tcttgggctc cggaggaagg ttctagcggc tgcaggaggt ccccagaccc attttcctag    660

aaggctggtg atggatctgc tgctcctgcc gccgccgggg cacttggagc gcaccggcgg    720

cgcgtgagct gggctttgct ctccactgcc ctgggcaaac cccgggccag ccccgcctgg    780

cacctttgcc tgagtccctt tcggttcccg acccaaagcc accagcgtcc agggagggag    840

gaggaggtgg tcctcaggtg cagccccgcc gagatgtccg cgcagagcct gctccacagc    900

gtcttctcct gttcctcgcc cgcttcaagt agcgcggcct cggccaaggg cttctccaag    960

aggaagctgc gccagacccg cagcctggac ccggccctga tcggcggctg cgggagcgac   1020

gaggcgggcg cggagggcag tgcgcgggga gccacggcgg gccgcctcta ctccccatca   1080

ctcccagccg agagtctcgg ccctcgcttg gcgtcctctt cccggggtcc gccccccagg   1140

gccaccaggc taccgcctcc tggacctctt tgctcgtcct tctccacacc cagcaccccg   1200

caggagaagt caccatccgg cagctttcac tttgactatg aggttcccct gggtcgcggc   1260

ggcctcaaga agagcatggc ctgggacctg ccttctgtcc tggccgggcc agccagtagc   1320

cgaagcgctt ccagcatcct ctgttcatcc gggggaggcc ccaatggcat cttcgcttct   1380

cctaggaggt ggctccagca gaggaagttc cagtccccac ccgacagtcg cgggcacccc   1440

tacgtcgtgt ggaaatccga gggtgatttc acctggaaca gcatgtcagg ccgcagtgta   1500

cggctgaggt cagtccccat ccagagtctc tcagagctgg agagggcccg gctgcaggaa   1560

gtggcttttt atcagttgca acaggactgt gacctgagct gtcagatcac cattcccaaa   1620
```

-continued

```
gatggacaaa agagaaagaa atctttaaga aagaaactgg attcactagg aaaggagaaa   1680
aacaaagaca aagaattcat cccacaggca tttggaatgc ccttatccca agtcattgcg   1740
aatgacaggg cctataaact caagcaggac ttgcagaggg acgagcagaa agatgcatct   1800
gactttgtgg cttccctcct cccatttgga aataaaagac aaaacaaaga actctcaagc   1860
agtaactcat ctctcagctc aacctcagaa acaccgaatg agtcaacgtc ccaaacacc    1920
ccggaaccgg ctcctcgggc taggaggagg ggtgccatgt cagtggattc tatcaccgat   1980
cttgatgaca atcagtctcg actactagaa gctttacaac tttccttgcc tgctgaggct   2040
caaagtaaaa aggaaaaagc cagagataag aaactcagtc tgaatcctat ttacagacag   2100
gtccctaggc tggtggacag ctgctgtcag cacctagaaa aacatggcct ccagacagtg   2160
gggatattcc gagttggaag ctcaaaaaag agagtgagac aattacgtga ggaatttgac   2220
cgtgggattg atgtctctct ggaggaggag cacagtgttc atgatgtggc agccttgctg   2280
aaagagttcc tgagggacat gccagacccc cttctcacca gggagctgta cacagctttc   2340
atcaacactc tcttgttgga gccggaggaa cagctgggca ccttgcagct cctcatatac   2400
cttctacctc cctgcaactg cgacaccctc caccgcctgc tacagttcct ctccatcgtg   2460
gccaggcatg ccgatgacaa catcagcaaa gatgggcaag aggtcactgg gaataaaatg   2520
acatctctaa acttagccac catatttgga cccaacctgc tgcacaagca gaagtcatca   2580
gacaaagaat tctcagttca gagttcagcc cgggctgagg agagcacggc catcatcgct   2640
gttgtgcaaa agatgattga aaattatgaa gccctgttca tggttccccc agatctccag   2700
aacgaagtgc tgatcagcct gttagagacc gatcctgatg tcgtggacta tttactcaga   2760
agaaaggctt cccaatcatc aagccctgac atgctgcagt cggaagtttc cttttccgtg   2820
ggagggaggc attcatctac agactccaac aaggcctcca gcggagacat ctccccttat   2880
gacaacaact ccccagtgct gtctgagcgc tccctgctgg ctatgcaaga ggacgcggcc   2940
ccgggggggct cggagaagct ttacagagtg ccagggcagt ttatgctggt gggccacttg   3000
tcgtcgtcaa agtcaaggga aagttctcct ggaccaaggc ttgggaaaga tctgtcagag   3060
gagcctttcg atatctgggg aacttggcat tcaacattaa aaagcggatc caaagaccca   3120
ggaatgacag gttcctctgg agacattttt gaaagcagct ccctaagagc ggggccctgc   3180
tccctttctc aagggaacct gtccccaaat tggcctcggt ggcaggggag ccccgcagag   3240
ctggacagcg acacgcaggg ggctcggagg actcaggccg cagcccccgc gacggagggc   3300
agggcccacc ctgcggtgtc gcgcgcctgc agcacgcccc acgtccaggt ggcagggaaa   3360
gccgagcggc ccacggccag gtcggagcag tacttgaccc tgagcggcgc ccacgacctc   3420
agcgagagtg agctggatgt ggccgggctg cagagccggg ccacacctca gtgccaaaga   3480
ccccatggga gtgggaggga tgacaagcgg cccccgcctc catacccggg cccagggaag   3540
cccgcggcag cggcagcctg gatccagggg cccccggaag gcgtggagac acccacggac   3600
cagggaggcc aagcagccga gcgagagcag caggtcacgc agaaaaaact gagcagcgcc   3660
aactccctgc cagcgggcga gcaggacagt ccgcgcctgg gggacgctgg ctggctcgac   3720
tggcagagag agcgctggca gatctgggag ctcctgtcga ccgacaaccc cgatgccctg   3780
cccgagacgc tggtctgagc ccgcacccag ccgagccccc cctgccccga gccccccgcc   3840
ctccagccca ggggggaccg tgggtggtgg ccactggcac acttagtgtt cttctttcac   3900
acttctcaaa agtgacacaa gagaaatcca gttcacctac agaggtagag cactcacgcc   3960
```

cccgccattg agaataaggt tccattgcgt agccagcctt aggaaaaaca aacagaaccc 4020
aaaccagatg gcaatgtcca atctaaaaac gtccctcttg gctctataat ataagataca 4080
actcttgctt ggtatagcct aaccgtattt atgtgtcttc ggttttgact attgtgtatt 4140
ctgtaacaga ttatgtataa tcatatatga tatattcaca aagagaaaac aaaaggaact 4200
tttaaaaaaa aaatcacttc acttatatta agcaatgaga tatactaaac aatgagattc 4260
tatagaatgt tctagaatgt gcacaagcgg gtttctgtgc ttttgccata gctttataac 4320
tggggataac ccttccttcg ataccaaaca ctaacaagag gaagcagaat atgagaagcc 4380
atatttttac ataggagtca gatacaaaaa gaaaaatcac tgaatgcttt tagatattga 4440
atacgttttc aggaaaatgc taaatctgat agattacgaa atatattttt agaacttgtt 4500
tagaaaggat tcagttaacc aaacaagaaa aaggcagtgc ctcacaaaga aattaagaag 4560
ttgtccgtcc cacgttacat caaattcagt tttatatagg ccatatataa tatatattta 4620
taatgtataa tttttatgta tttttcaaaa ctacaaactg gaatccaact ataaagtgtt 4680
taagaatcta cacagaatat tcaaattata gaacatgttt tttccctttg ccccataatc 4740
agtatttgcc aaattacatg caattcctta aaaactaaat cacatttggt aaaaggccta 4800
cagctttgta cttacattgt gccaaaggct gaggaaatgt tttctttcgt aattttatgt 4860
gtattgtaaa atgttctacc gtactttagt agtttgaagt ttttcaagtg cataactatt 4920
tttgaccagc agatggcgat acgcttcagt attttatgca atttttttttc acttctgaag 4980 ggaaagtgta ttataaaaaa agattttttt tttttttata aaacatgcta ctcttaattt 5040
tcatgttggt gatgaaattc ccagtggtgt ttcttaaggt tctatcttgt gccatgatga 5100
ataaaaagtt aagcaaag 5118

<210> SEQ ID NO 121
<211> LENGTH: 1427
<212> TYPE: DNA
<213> ORGANISM: Homo sapiens

<400> SEQUENCE: 121
agatgaaaat ggaaggggcg ggcgcgctag gcctagtcct ggctgggctc ccgctggagt 60
gtgcgttggg ggcggaccag gagcggtggt ctccagggag gtcgaggctg gggctcccac 120
ccggatttgg agcagggtcg ccgcggccca gctgacccgc cggcgtttgt acgttgtgtg 180
cccactcagg gagccatgga caactgtttg gcggccgcag cgctgaatgg ggtggaccga 240
cgttccctgc agcgttcagc aaggctggct ctagaagtgc tggagagggc caagaggagg 300
gcggtggact ggcatgccct ggagcgtccc aaaggctgca tgggggtcct tgcccgggag 360
gcgccccacc tagagaaaca gccggcagcc ggcccgcagc gcgttctccc gggagagaga 420
gaagagagac ccccaaccct tagtgcttcc ttcagaacaa tggctgaatt catggactat 480
acttcaagtc agtgtgggaa atattattca tctgtgccag aggaaggagg ggcaacccat 540
gtctatcgtt atcacagagg cgagtcgaag ctgcacatgt gcttggacat agggaatggt 600
cagagaaaag acagaaaaaa gacatccctt ggtcctggag gcagctatca aatatcagag 660
catgctccag aggcatccca gcctgctgag aacatctcta aggacctcta catagaagta 720
tatccaggga cctattctgt cactgtgggc tcaaatgact taaccaagaa gactcatgtg 780
gtagcagttg attctggaca aagcgtggac ctggtcttcc ctgtgtgatg ttgaccatca 840
ctgccatcac atcacctttt tttaagtagt aagaataaag ccactgtatg attctcttaa 900
tagctataca ttaatcctgt ttttagtgct gactgggtca gccttccggg aactggagtc 960
tgtctctttc agtgcttttt tgtttgtttg gttggttttt ttttgagaca gtctcactct 1020
gttgcccagg ctggagtgca gtggcgtgat ctcggctcac tgcaagttcc gcctcccggg 1080
ttcacaccat tctcctgcct cagcctcccg agtagctggc actacaggca cccgccacca 1140
tgcccggcta ttttttttgt atttttagta gagacggggt ttcaccatgt tggccaggat 1200
ggtctcgatc tcttgacctc gtgatccacc caccttggcc tcccaaagtg ttgggattac 1260
aggcgtgagc caccgcgccc ggcctcagtg cctttttttaa cttgagggtg tagaggtcct 1320
ccacgcttgt ttgcctgaaa gtaatataat gatgctgtct gaacaggttt tactgcttgc 1380
tttccaagta aaggttaatt atgataataa agagatttgg aaatgaa 1427

<210> SEQ ID NO 122
<211> LENGTH: 3316
<212> TYPE: DNA
<213> ORGANISM: Homo sapiens

<400> SEQUENCE: 122
cactctcttt ctctctccct ctggcatgca tgctgctggt aggagacccc caagtcaaca 60
ttgcttcaga aatcctttag cactcatttc tcaggagaac ttatggcttc agaatcacag 120
ctcggttttt aagatggaca taacctgtac gaccttctga tgggctttca actttgaact 180
ggatgtggac acttttctct cagatgacag aattactcca acttcccctt tgcagttgct 240
tcctttcctt gaaggtagct gtatcttatt ttctttaaaa agctttttct tccaaagcca 300
cttgccatgc cgaccgtcat tagcgcatct gtggctccaa ggacagcggc tgagccccgg 360
tccccagggc cagttcctca cccggcccag agcaaggcca ctgaggctgg gggtggaaac 420
ccaagtggca tctattcagc catcatcagc cgcaattttc ctattatcgg agtgaaagag 480
aagacattcg agcaacttca caagaaatgt ctagaaaaga aagttcttta tgtggaccct 540
gagttcccac cggatgagac ctctctcttt tatagccaga agttccccat ccagttcgtc 600
tggaagagac ctccggaaat ttgcgagaat ccccgattta tcattgatgg agccaacaga 660
actgacatct gtcaaggaga gctaggggac tgctggtttc tcgcagccat tgcctgcctg 720
accctgaacc agcaccttct tttccgagtc ataccccatg atcaaagttt catcgaaaac 780
tacgcaggga tcttccactt ccagttctgg cgctatggag agtgggtgga cgtggttata 840
gatgactgcc tgccaacgta caacaatcaa ctggttttca ccaagtccaa ccaccgcaat 900
gagttctgga gtgctctgct ggagaaggct tatgctaagc tccatggttc ctacgaagct 960
ctgaaaggtg ggaacaccac agaggccatg gaggacttca caggaggggt ggcagagttt 1020
tttgagatca gggatgctcc tagtgacatg tacaagatca tgaagaaagc catcgagaga 1080
ggctccctca tgggctgctc cattgatgat ggcacgaaca tgacctatgg aacctctcct 1140
tctggtctga acatgggga gttgattgca cggatggtaa ggaatatgga taactcactg 1200
ctccaggact cagacctcga ccccagaggc tcagatgaaa gaccgacccg gacaatcatt 1260
ccggttcagt atgagacaag aatggcctgc gggctggtca gaggtcacgc ctactctgtc 1320
acggggctgg atgaggtccc gttcaaaggt gagaaagtga agctggtgcg gctgcggaat 1380
ccgtggggcc aggtggagtg gaacggttct tggagtgata gatggaagga ctggagcttt 1440
gtggacaaag atgagaaggc ccgtctgcag caccaggtca ctgaggatgg agagttctgg 1500
atgtcctatg aggatttcat ctaccatttc acaaagttgg agatctgcaa cctcacggcc 1560
gatgctctgc agtctgacaa gcttcagacc tggacagtgt ctgtgaacga gggccgctgg 1620

-continued

```
gtacggggtt gctctgccgg aggctgccgc aacttcccag atactttctg gaccaaccct   1680

cagtaccgtc tgaagctcct ggaggaggac gatgaccctg atgactcgga ggtgatttgc   1740

agcttcctgg tggccctgat gcagaagaac cggcggaagg accggaagct aggggccagt   1800

ctcttcacca ttggcttcgc catctacgag gttcccaaag agatgcacgg gaacaagcag   1860

cacctgcaga aggacttctt cctgtacaac gcctccaagg ccaggagcaa aacctacatc   1920

aacatgcggg aggtgtccca gcgcttccgc ctgcctccca gcgagtacgt catcgtgccc   1980

tccacctacg agccccacca ggagggggaa ttcatcctcc gggtcttctc tgaaaagagg   2040

aacctctctg aggaagttga aaataccatc tccgtggatc ggccagtgaa aaagaaaaaa   2100

accaagccca tcatcttcgt ttcggacaga gcaaacagca acaaggagct gggtgtggac   2160

caggagtcag aggagggcaa aggcaaaaca agccctgata agcaaaagca gtccccacag   2220

ccacagcctg gcagctctga tcaggaaagt gaggaacagc aacaattccg gaacattttc   2280

aagcagatag caggagatga catggagatc tgtgcagatg agctcaagaa ggtccttaac   2340

acagtcgtga acaaacacaa ggacctgaag acacacgggt tcacactgga gtcctgccgt   2400

agcatgattg cgctcatgga tacagatggc tctggaaagc tcaacctgca ggagttccac   2460

cacctctgga acaagattaa ggcctggcag aaaatttca aacactatga cacagaccag   2520

tccggcacca tcaacagcta cgagatgcga aatgcagtca acgacgcagg attccacctc   2580

aacaaccagc tctatgacat cattaccatg cggtacgcag acaaacacat gaacatcgac   2640

tttgacagtt tcatctgctg cttcgttagg ctggagggca tgttcagagc ttttcatgca   2700

tttgacaagg atggagatgg tatcatcaag ctcaacgttc tggagtggct gcagctcacc   2760

atgtatgcct gaaccaggct ggcctcatcc aaagccatgc aggatcactc aggatttcag   2820

tttcaccctc tatttccaaa gccatttacc tcaaaggacc cagcagctac acccctacag   2880

gcttccaggc acctcatcag tcatgctcct cctccatttt accccctacc catccttgat   2940

cggtcatgcc tagcctgacc ctttagtaaa gcaatgaggt aggaagaaca aacccttgtc   3000

cctttgccat gtggaggaaa gtgcctgcct ctggtccgag ccgcctcggt tctgaagcga   3060

gtgctcctgc ttaccttgct ctaggctgtc tgcagaagca cctgccggtg gcactcagca   3120

cctccttgtg ctagagccct ccatcacctt cacgctgtcc caccatgggc caggaaccaa   3180

accagcactg ggttctactg ctgtggggta aactaactca gtggaatagg gctggttact   3240

ttgggctgtc caactcataa gtttggctgc attttgaaaa aagctgatct aaataaaggc   3300

atgtgtatgg ctggtc                                                   3316
```

```
<210> SEQ ID NO 123
<211> LENGTH: 2833
<212> TYPE: DNA
<213> ORGANISM: Homo sapiens

<400> SEQUENCE: 123

gaaggagctc tcttcttgct tggcagctgg accaagggag ccagtcttgg gcgctggagg     60

gcctgtcctg accatggtcc ctgcctggct gtggctgctt tgtgtctccg tcccccaggc    120

tctccccaag gcccagcctg cagagctgtc tgtggaagtt ccagaaaact atggtggaaa    180

tttcccttta tacctgacca agttgccgct gccccgtgag gggggctgaag gccagatcgt    240

gctgtcaggg gactcaggca aggcaactga gggcccattt gctatggatc cagattctgg    300

cttcctgctg gtgaccaggg ccctggaccg agaggagcag gcagagtacc agctacaggt    360

caccctggag atgcaggatg gacatgtctt gtggggtcca cagcctgtgc ttgtgcacgt    420
```

-continued

```
gaaggatgag aatgaccagg tgccccattt ctctcaagcc atctacagag ctcggctgag    480
ccggggtacc aggcctggca tccccttcct cttccttgag gcttcagacc gggatgagcc    540
aggcacagcc aactcggatc ttcgattcca catcctgagc caggctccag cccagccttc    600
cccagacatg ttccagctgg agcctcggct gggggctctg gccctcagcc ccaaggggag    660
caccagcctt gaccacgccc tggagaggac ctaccagctg ttggtacagg tcaaggacat    720
gggtgaccag gcctcaggcc accaggccac tgccaccgtg gaagtctcca tcatagagag    780
cacctgggtg tccctagagc ctatccacct ggcagagaat ctcaaagtcc tatacccgca    840
ccacatggcc caggtacact ggagtggggg tgatgtgcac tatcacctgg agagccatcc    900
cccgggaccc tttgaagtga atgcagaggg aaacctctac gtgaccagag agctggacag    960
agaagcccag gctgagtacc tgctccaggt gcgggctcag aattcccatg gcgaggacta   1020
tgcggcccct ctggagctgc acgtgctggt gatggatgag aatgacaacg tgcctatctg   1080
ccctccccgt gaccccacag tcagcatccc tgagctcagt ccaccaggta ctgaagtgac   1140
tagactgtca gcagaggatg cagatgcccc cggctccccc aattcccacg ttgtgtatca   1200
gctcctgagc cctgagcctg aggatggggt agaggggaga gccttccagg tggaccccac   1260
ttcaggcagt gtgacgctgg gggtgctccc actccgagca ggccagaaca tcctgcttct   1320
ggtgctggcc atggacctgg caggcgcaga gggtggcttc agcagcacgt gtgaagtcga   1380
agtcgcagtc acagatatca atgatcacgc ccctgagttc atcacttccc agattgggcc   1440
tataagcctc cctgaggatg tggagcccgg gactctggtg gccatgctaa cagccattga   1500
tgctgacctc gagcccgcct tccgcctcat ggattttgcc attgagaggg gagacacaga   1560
agggactttt ggcctggatt gggagccaga ctctgggcat gttagactca gactctgcaa   1620
gaacctcagt tatgaggcag ctccaagtca tgaggtggtg gtggtggtgc agagtgtggc   1680
gaagctggtg gggccaggcc caggccctgg agccaccgcc acggtgactg tgctagtgga   1740
gagagtgatg ccaccccca agttggacca ggagagctac gaggccagtg tccccatcag    1800
tgccccagcc ggctctttcc tgctgaccat ccagccctcc gaccccatca gccgaaccct   1860
caggttctcc ctagtcaatg actcagaggg ctggctctgc attgagaaat tctccgggga   1920
ggtgcacacc gcccagtccc tgcagggcgc ccagcctggg gacacctaca cggtgcttgt   1980
ggaggcccag gatacagatg agccgagact gagcgcttct gcacccctgg tgatccactt   2040
cctaaaggcc cctcctgccc cagccctgac tcttgcccct gtgccctccc aatacctctg   2100
cacaccccgc caagaccatg gcttgatcgt gagtggaccc agcaaggacc ccgatctggc   2160
cagtgggcac ggtccctaca gcttcaccct tggtcccaac cccacggtgc aacgggattg   2220
gcgcctccag actctcaatg gttcccatgc ctacctcacc ttggccctgc attgggtgga   2280
gccacgtgaa cacataatcc ccgtggtggt cagccacaat gcccagatgt ggcagctcct   2340
ggttcgagtg atcgtgtgtc gctgcaacgt ggaggggcag tgcatgcgca aggtgggccg   2400
catgaagggc atgcccacga agctgtcggc agtgggcatc cttgtaggca ccctggtagc   2460
aataggaatc ttcctcatcc tcattttcac ccactggacc atgtcaagga agaaggaccc   2520
ggatcaacca gcagacagcg tgcccctgaa ggcgactgtc tgaatggccc aggcagctct   2580
agctgggagc ttggcctctg gctccatctg agtcccctgg gagagagccc agcacccaag   2640
atccagcagg ggacaggaca gagtagaagc ccctccatct gccctggggt ggaggcacca   2700
tcaccatcac caggcatgtc tgcagagcct ggacaccaac tttatggact gcccatggga   2760
```

gtgctccaaa tgtcagggtg tttgcccaat aataaagccc cagagaactg ggctgggccc 2820
tatgggattg gta 2833

<210> SEQ ID NO 124
<211> LENGTH: 3981
<212> TYPE: DNA
<213> ORGANISM: Homo sapiens

<400> SEQUENCE: 124
tggggcttgt tccgggatcc gcagccttgc tcaggctgtg cattggtgtg gccccgaatt 60
gcacggagct gccttcctat ttcaaggaaa gacgccaagg taattttgac ccagaggagc 120
aatgatgtag ccacctccta accttccctt cttgaacccc caggtcccct cttgctgttg 180
gctgcacatc aggaaggctg tgatgggaat gaaggtgaaa acttggagat ttcacttcag 240
tcattgcttc tgcctgcaag atcatccttt aaaagtagag aagctgctct gtgtggtggt 300
taactccaag aggcagaact cgttctagaa ggaaatggat gcaagcagct ccgggggccc 360
caaacgcatg cttcctgtga tctagcccag ggaagccctt ccgtgggggc cccggctttg 420
agggatgcca ccggttctgg acgcatggct gattcctgaa tgatgatggt tcgccggggg 480
ctgcttgcgt ggatttcccg ggtggtggtt ttgctggtgc tcctctgctg tgctatctct 540
gtcctgtaca tgttggcctg caccccaaaa ggtgacgagg agcagctggc actgcccagg 600
gccaacagcc ccacggggaa ggaggggtac caggccgtcc ttcaggagtg ggaggagcag 660
caccgcaact acgtgagcag cctgaagcgg cagatcgcac agctcaagga ggagctgcag 720
gagaggagtg agcagctcag gaatgggcag taccaagcca gcgatgctgc tggcctgggt 780
ctggacagga gcccccccaga gaaaacccag gccgacctcc tggccttcct gcactcgcag 840
gtggacaagg cagaggtgaa tgctggcgtc aagctggcca cagagtatgc agcagtgcct 900
ttcgatagct ttactctaca gaaggtgtac cagctggaga ctggccttac ccgccacccc 960
gaggagaagc ctgtgaggaa ggacaagcgg gatgagttgg tggaagccat tgaatcagcc 1020
ttggagaccc tgaacaatcc tgcagagaac agccccaatc accgtcctta cacggcctct 1080
gatttcatag aagggatcta ccgaacagaa agggacaaag ggacattgta tgagctcacc 1140
ttcaaagggg accacaaaca tgaattcaaa cggctcatct tatttcgacc attcggcccc 1200
atcatgaaag tggaaaatga aaagctcaac atggccaaca cgcttatcaa tgttatcgtg 1260
cctctagcaa aaagggtgga caagttccgg cagttcatgc agaatttcag gcctgctgat 1320
gaagttttta gatgtgtgcc tttaagccct tgattgtgcg gtgttggatc ttagaagctg 1380
tgatggctca gatgcacata ttggctgagg ataaccagct aagtgatttc accagcttgt 1440
tttaaacata gaaaatccta ctgtctaatt ataaatcttg aaagatcaag ctgatttttt 1500
atttcttttt ttttgagatg gagtcttact ctgtcaccca ggctggagtg cagtggcacg 1560
aactctgctc actgcaacct tcacctccca ggttcaggga gatgtgcatt gagcaggatg 1620
ggagagtcca tctcactgtt gtttactttg ggaaagaaga aataaatgaa gtcaaaggaa 1680
tacttgaaaa cacttccaaa gctgccaact tcaggaactt taccttcatc cagctgaatg 1740
gagaattttc tcggggaaag ggacttgatg ttggagcccg cttctggaag ggaagcaacg 1800
tccttctctt tttctgtgat gtggacatct acttcacatc tgaattcctc aatacgtgta 1860
ggctgaatac acagccaggg aagaaggtat tttatccagt tcttttcagt cagtacaatc 1920
ctggcataat atacggccac catgatgcag tccctccctt ggaacagcag ctggtcataa 1980
agaaggaaac tggattttgg agagactttg gatttgggat gacgtgtcag tatcggtcag 2040

```
acttcatcaa tataggtggg tttgatctgg acatcaaagg ctggggcgga gaggatgtgc   2100
acctttatcg caagtatctc cacagcaacc tcatagtggt acggacgcct gtgcgaggac   2160
tcttccacct ctggcatgag aagcgctgca tggacgagct gaccccgag cagtacaaga   2220
tgtgcatgca gtccaaggcc atgaacgagg catcccacgg ccagctgggc atgctggtgt   2280
tcaggcacga gatagaggct caccttcgca aacagaaaca gaagacaagt agcaaaaaaa   2340
catgaactcc cagagaagga ttgtgggaga cactttttct ttccttttgc aattactgaa   2400
agtggctgca acagagaaaa gacttccata aaggacgaca aaagaattgg actgatgggt   2460
cagagatgag aaagcctccg atttctctct gttgggcttt ttacaacaga aatcaaaatc   2520
tccgctttgc ctgcaaaagt aacccagttg caccctgtga agtgtctgac aaaggcagaa   2580
tgcttgtgag attataagcc taatggtgtg gaggttttga tggtgtttac aatacactga   2640
gacctgttgt tttgtgtgct cattgaaata ttcatgattt aagagcagtt ttgtaaaaaa   2700
ttcattagca tgaaaggcaa gcatatttct cctcatatga atgagcctat cagcagggct   2760
ctagtttcta ggaatgctaa aatatcagaa ggcaggagag gagataggct tattatgata   2820
ctagtgagta cattaagtaa aataaaatgg accagaaaag aaaagaaacc ataaatatcg   2880
tgtcatattt tccccaagat taaccaaaaa taatctgctt atctttttgg ttgtcctttt   2940
aactgtctcc gtttttttct tttatttaaa aatgcacttt ttttcccttg tgagttatag   3000
tctgcttatt taattaccac tttgcaagcc ttacaagaga gcacaagttg gcctacattt   3060
ttatattttt taagaagata ctttgagatg cattatgaga actttcagtt caaagcatca   3120
aattgatgcc atatccaagg acatgccaaa tgctgattct gtcaggcact gaatgtcagg   3180
cattgagaca tagggaagga atggtttgta ctaatacaga cgtacagata ctttctctga   3240
agagtatttt cgaagaggag caactgaaca ctggaggaaa agaaaatgac actttctgct   3300
ttacagaaaa ggaaactcat tcagactggt gatatcgtga tgtacctaaa agtcagaaac   3360
cacattttct cctcagaagt agggaccgct ttcttacctg tttaaataaa ccaaagtata   3420
ccgtgtgaac caaacaatct cttttcaaaa cagggtgctc ctcctggctt ctggcttcca   3480
taagaagaaa tggagaaaaa tatatatata tatatatata ttgtgaaaga tcaatccatc   3540
tgccagaatc tagtgggatg gaagtttttg ctacatgtta tccaccccag gccaggtgga   3600
agtaactgaa ttattttta aattaagcag ttctactcga tcaccaagat gcttctgaaa   3660
attgcatttt attaccattt caaactattt tttaaaaata aatacagtta acatagagtg   3720
gtttcttcat tcatgtgaaa attattagcc agcaccagat gcatgagcta attatctctt   3780
tgagtccttg cttctgtttg ctcacagtaa actcattgtt taaaagcttc aagaacattc   3840
aagctgttgg tgtgttaaaa aatgcattgt attgatttgt actggtagtt tatgaaattt   3900
aattaaaaca caggccatga atggaaggtg gtattgcaca gctaataaaa tatgatttgg   3960
gatatgaaaa aaaaaaaaaa a                                              3981
```

```
<210> SEQ ID NO 125
<211> LENGTH: 1251
<212> TYPE: DNA
<213> ORGANISM: Homo sapiens

<400> SEQUENCE: 125

acgagccagg acatgtgcta ataatgccct aagccggtta taaagacgtg gaaattgagg     60
ggagaaaaaa aaagggaaaa aaagggtctg tccttcctgg gattcctagc cgaggccagt    120
```

-continued ctgctgccgt gtgcgtgtgc gtcagggctc tccgggcggc aatgggggct tgagagccgg 180
gtccccagcg ccgggaaggg agcgcggtgg ccgccaccgc caccgccccg gagtccggcg 240
ccgaagctgc gggcgggcgg gcgggcacca gctcggtcag gggctgcttg gcgcggcact 300
gtgcggtgca gcggcggcgc ggcgcggtgc gggcttttcc caggcgcccc ggggtcgggt 360
ggccaacggc gcggccgcgg gcgctgagcg cgaccggttc gcggtagcgg tggcggcggc 420
gtgcgtgcca ggggctgggg gctccgccgc ctctcttgcg gctcaccgag ctccgcgctt 480
ccctctctcc agggcaggcg gcttctcaga gcacaacagc tccagctggc agcatcactt 540
cccgccaatt tatccaactt ctgccaaggc tctgaaatgc caacaacgtc gaggcctgca 600
cttgatgtca agggtggcac ctcacctgcg aaggaggatg ccaaccaaga gatgagctcc 660
gtggcctact ccaaccttgc ggtgaaagat cgcaaagcag tggccattct gcactaccct 720
ggggtagcct caaatggaac caaggccagt ggggctccca ctagttcctc gggatctcca 780
ataggctctc ctacaaccac ccctcccact aaacccccat ccttcaacct gcaccccgcc 840
cctcacttgc tggctagtat gcacctgcag aaacttaata gccagtatca ggggatggct 900
gctgccactc caggccaacc cggggaggca ggacccctgc aaaactggga ctttggggcc 960
caggcgggag gggcagaatc actctctcct tctgctggtg cccagagccc tgctatcatc 1020
gattcggacc cagtggatga ggaagtgctg atgtcgctgg tggtggaact ggggttggac 1080
cgagccaatg agcttccgga gctgtggctg gggcagaatg agtttgactt cactgcggac 1140
tttccatcta gctgctaatg ccaagtgtcc ctaaagatgg aggaataaag ccaccaattc 1200
tgttgtaaat aaaaataaag ttacttacaa agagacgggc caaaaaaaaa a 1251

<210> SEQ ID NO 126
<211> LENGTH: 1930
<212> TYPE: DNA
<213> ORGANISM: Homo sapiens

<400> SEQUENCE: 126
acagctcatt gttggcagct gccgggcggt cctgccgagc tgtgagggca acggagggga 60
aataaaaggg aacggctccg aatctgcccc agcggccgct gcgagacctc ggcgccgaca 120
tcgcgacagc gaagcgcttt gcacgccagg aaggtcccct ctatgtgctg ctgagccggt 180
cctggacgcg acgagcccgc cctcggtctt cggagcagaa atcgcaaaaa cggaaggact 240
ggaaatggca gaccatatga tggccatgaa ccacgggcgc ttccccgacg gcaccaatgg 300
gctgcaccat caccctgccc accgcatggg catggggcag ttcccgagcc cccatcacca 360
ccagcagcag cagccccagc acgccttcaa cgccctaatg ggcgagcaca tacactacgg 420
cgcgggcaac atgaatgcca cgagcggcat caggcatgcg atggggccgg ggactgtgaa 480
cggagggcac cccccgagcg cgctggcccc cgcggccagg tttaacaact cccagttcat 540
gggtcccccg gtggccagcc agggaggctc cctgccggcc agcatgcagc tgcagaagct 600
caacaaccag tatttcaacc atcaccccta cccccacaac cactacatgc cggatttgca 660
ccctgctgca ggccaccaga tgaacgggac aaaccagcac ttccgagatt gcaaccccaa 720
gcacagcggc ggcagcagca cccccggcgg ctcgggcggc agcagcaccc ccggcggctc 780
tggcagcagc tcgggcggcg gcgcgggcag cagcaacagc ggcggcggca gcggcagcgg 840
caacatgccc gcctccgtgg cccacgtccc cgctgcaatg ctgccgccca atgtcataga 900
cactgatttc atcgacgagg aagttcttat gtccttggtg atagaaatgg gtttggaccg 960
catcaaggag ctgcccgaac tctggctggg gcaaaacgag tttgatttta tgacggactt 1020
cgtgtgcaaa cagcagccca gcagagtgag ctgttgactc gatcgaaacc ccggcgaaag 1080
aaatcaaacc cccaacttct tcggcgtgaa ttaaaagaaa cattccctta gacacagtat 1140
ctcacttttc agatcttgaa aggtttgaga acttggaaac aaagtaaact ataaacttgt 1200
acaaattggt tttaaaaaaa attgctgcca cttttttttc ctgtttttgt ttcgtttttg 1260
tagccttgac attcacccac ctcccttatg tagttgaaat atctagctaa cttggtcttt 1320
ttcgttgttt gtttttactc ctttccctca ctttctccag tgctcaactg ttagatatta 1380
atcttggcaa actgcttaat cttgtggatt ttgtagatgg tttcaaatga ctgaactgca 1440
ttcagattta cgagtgaaag gaaaaattgc attagttggt tgcatgaact tcgaagggca 1500
gatattactg cacaaactgc catctcgctt catttttta actatgcatt tgagtacaga 1560
ctaattttta aaatatgcta aactggaaga ttaaacagat gtgggccaaa ctgttctgga 1620
tcaggaaagt catactgttc actttcaagt tggctgtccc ccccgccgcc ccccccaccc 1680
ccatatgtac agatgataat agggtgtgga atgtcgtcag tggcaaacat ttcacagatt 1740
tttattttgt ttctgtcttc aacatttttg acactgtgct aatagttata ttcagtacat 1800
gaaaagatac tactgtgttg aaagcttttt aggaaatttt gacagtattt ttgtacaaaa 1860
catttttttg aaaaaatact tgttaattta ttctatttta atttgccaat gtcaataaaa 1920
agttaagaaa 1930

<210> SEQ ID NO 127
<211> LENGTH: 1372
<212> TYPE: DNA
<213> ORGANISM: Homo sapiens

<400> SEQUENCE: 127
ccggccgccc gcccgccgcc gccatgccct tctccaacag ccacaacgca ctgaagctgc 60
gcttcccggc cgaggacgag ttccccgacc tgagcgccca caacaaccac atggccaagg 120
tgctgacccc cgagctgtac gcggacgtgc gcgccaagag cacgccgagc ggcttcacgc 180
tggacgacgt catccagaca ggcgtggaca acccgggcca cccgtacatc atgaccgtgg 240
gctgcgtggc gggcgacgag gagtcctacg aagtgttcaa ggatctcttc gaccccatca 300
tcgaggaccg gcaccggcgc tacaagccca gcgatgacga caagaccgac ctcaaccccg 360
acaacctgca gggcggcgac gacctggacc ccaactacgt gctgagctcg cgggtggcca 420
cgggccgcag catccgtggc ttctgcctcc ccccgcactg cagccgcggg gagcgccgag 480
ccatcgagaa gctcgcggtg gaagccctgt ccagcctgga cggcgacctg gcgggccgat 540
actacgcgct caagagcatg acggaggcgg agcagcagca gctcatcgac gaccacttcc 600
tcttcgacaa gcccgtgtcg cccctgctgc tggcctcggg catggcccgc gactggcccg 660
acgccgcgcg tatctggcac aatgacaata agaccttcct ggtgtgggtc aacgaggagg 720
accacctgcg ggtcatctcc atgcagaagg ggggcaacat gaaggaggtg ttcacccgct 780
tctgcaccgg cctcacccag attgaaactc tcttcaagtc taaggactat gagttcatgt 840
ggaaccctca cctgggctac atcctcacct gcccatccaa cctgggcacc gggctgcggg 900
caggtgtcga tatcaagctg cccaacctgg gcaagcatga gaagttctcg gaggtgctta 960
agcggctgcg acttcagaag cgaggcacag gcggtgtgga cacggctgcg gtgggcgggg 1020
tcttcgacgt ctccaacgct gaccgcctgg gcttctcaga ggtggagctg gtgcagatgg 1080
tggtggacgg agtgaagctg ctcatcgaga tggaacagcg gctggagcag ggccaggcca 1140

-continued

```
tcgacgacct catgcctgcc cagaaatgaa gcccggccca cacccgacac cagccctgct   1200

gcttcctaac ttattgcctg cagtgcccac catgcacccc tcgatgttgc cgtctggcga   1260

gcccttagcc ttgctgtaag gaaggcttcc gtcacccttg gtagagttta tttttttgat   1320

ggctaagata ctgctgatgc tgaaataaac tagggttttg gcctgcaaaa aa           1372
```

```
<210> SEQ ID NO 128
<211> LENGTH: 2485
<212> TYPE: DNA
<213> ORGANISM: Homo sapiens

<400> SEQUENCE: 128

gccatggccg ggccgcgcgc gtgcgccccg ctcctgctcc tgctcctgct cggggagctt     60

ctggcggccg ccggggcgca gagagtggga ctccccggcc cccccggccc cccagggccg    120

cccgggaagc ccggccagga cggcattgac ggagaagctg gtcctccagg tctgcctggg    180

cccccgggac caaagggggc cccaggaaag ccggggaaac caggagaggc tgggctgccg    240

ggactgccgg gtgtggatgg tctgactgga cgagatggac cccctggacc caagggtgcc    300

cctggggaac ggggaagtct gggacccccg gggccgcccg ggctgggggg caaaggcctc    360

cctggacccc ccggagaggc aggagtgagc ggccccccag gtgggatcgg cctccgcggc    420

cccccgggac cttctggact ccccggcctc cctggtcccc caggacctcc cggacccccct    480

ggacacccag gagtcctccc tgaaggcgct actgaccttc agtgcccaag tatctgcccg    540

ccaggtcccc cagggccccc tggaatgcca gggttcaagg gacccactgg ctacaaaggc    600

gagcaggggg aagtcggcaa ggacggcgag aagggtgacc ctggcccccc tgggcccgcc    660

ggcctcccgg gcagcgtggg gctgcagggc ccccggggat tacgaggact gccagggcca    720

ctcgggcccc ctggggaccg gggtcccatt gggttccgag ggccgcctgg gatcccagga    780

gcgcctggga aagcgggtga ccgaggcgag aggggcccag aagggttccg cggccccaag    840

ggtgacctcg gcagacctgg tcccaaggga acccccggag tggccgggcc aagcggagag    900

ccgggcatgc cgggcaagga cggccagaat ggcgtgccag gactcgatgg ccagaaggga    960

gaggctggtc gcaacggtgc tccgggagag aagggcccca acgggctgcc gggcctccct   1020

ggacgagcgg ggtccaaagg cgagaaggga gaacggggca gagctgggga gctgggtgag   1080

gccggcccct ctggagagcc aggcgtccct ggagatgctg gcatgcctgg ggagcgcggt   1140

gaggctggcc accggggctc agcgggggcc ctcggcccac aaggccctcc cggagcccct   1200

ggtgtccgag gcttccaggg ccagaagggc agcatgggag accccggcct tccaggcccc   1260

cagggcctcc gaggtgacgt gggcgaccgg ggtccgggag gtgccgcagg ccctaaggga   1320

gaccaggggta ttgcaggttc cgacggtctt cctggggata aaggagaact gggtcccagc   1380

ggcctggtcg gacccaaagg agagtctggc agtcgagggg agctgggccc caaaggcacc   1440

cagggtccca acggcaccag cggtgttcag ggtgtccccg ggcccccccgg tcctctgggc   1500

ctgcagggcg tcccgggtgt tcctggcatc acggggaagc cgggagttcc ggggaaggag   1560

gccagcgagc agcgcatcag ggagctgtgt gggggggatga tcagcgaaca aattgcacag   1620

ttagccgcgc acctaaggaa gcctttggca cccgggtcca ttggtcggcc cggtccagct   1680

ggcccccctg ggcccccagg acccccaggc tccattggtc accctggcgc tcgaggaccc   1740

cctggatacc gcggtcccac tggggagctg ggagaccccg ggcccagagg aaaccagggt   1800

gacagaggag acaaaggcgc ggcaggagca gggctggacg ggcctgaagg agaccagggg   1860

ccccaaggac cccaaggcgt gcccggcacc agcaaggacg gccaggacgg tgctcccggc   1920
```

gagcctgggc ctcccggaga tcctgggctt ccaggtgcca ttggggccca ggggacaccg 1980
gggatctgcg acacctcagc ctgccaagga gccgtgttag gaggggtcgg ggagaaatca 2040
ggctctcgaa gctcataaaa ttcaacgtga ggaagcaagt gacaaggacg cccgaagcac 2100
agtggacggt catgaaggag cgggggtgtg gcaggcgggt gacgtccagg agagggagcg 2160
cccctggctg cccctcggcc gccgactgga cgcgcgggcc ttgccagcga gcaccctcat 2220
cgggctgtcg cctgacagca tacctcaaaa ggccctagct aataaacctg taagcccagc 2280
atttgagaga aggtagggtg tgtatatata aaaggttgtg tacaactcca cgaggtgaaa 2340
aatattcagt aacttgttta catagcattt gtgtaaagac tatgatctca tcccaataaa 2400
atgatatatt aaaccttcag attaatgact ggctacagag taacaaaaaa taaagaattt 2460
aatgtacagt aaattctctc ccata 2485

<210> SEQ ID NO 129
<211> LENGTH: 901
<212> TYPE: DNA
<213> ORGANISM: Homo sapiens

<400> SEQUENCE: 129
gggatctcgg actccctgga ccctccctcc agcccagcct cgctagctcc gcctgcggta 60
cgtgctcccg cctccgactc aaaatgcctg tctggggagg tggaaacaag tgtggggcct 120
gtgggaggac cgtgtaccac gcagaagagg tgcagtgtga tggcaggagc ttccaccgct 180
gctgctttct ctgcatggtt tgcaggaaaa atttagatag cacaacagtg gcaattcacg 240
atgaagagat ctactgcaaa tcctgctacg gaaagaagta tgggccaaaa ggctacggtt 300
atggccaggg cgctggcacg cttaacatgg accgtggcga gaggctgggc atcaaaccag 360
agagtgttca gcctcacagg cctacaacaa atccaaacac ttctaaattt gctcagaaat 420
atggaggtgc tgagaagtgt tccagatgtg gggattctgt atatgctgcc gagaagataa 480
ttggagctgg aaagccctgg cacaaaaact gtttccgatg tgcaaagtgt gggaagagtc 540
ttgaatcaac aactctgact gaaaaagaag gtgaaatcta ttgtaaagga tgctatgcaa 600
agaactttgg gcccaaggga tttggctatg gccaaggagc aggggctctt gttcatgccc 660
agtaagatgt aaaccctgaa ctaaacatca cacactgaga atctcttcat aatctaggca 720
cagataatct ttaacactaa actactgtga aattctacca gcattaagta ctgtatatcg 780
ccctgtactt ggataggctg gctaactcgt aggaagagag cactgtatgg tatccttttg 840
ctttattcac cagcattttg ggggaacatt tcttttacat tttaaataaa acttcagctt 900
g 901

<210> SEQ ID NO 130
<211> LENGTH: 2628
<212> TYPE: DNA
<213> ORGANISM: Homo sapiens

<400> SEQUENCE: 130
gaccgcggca gctcagcctc ccgccgattg tatgttccag gcctcaatga ggagtccaaa 60
catggagcca ttcaagcagc agaaggtgga ggacttttat gacatcggag aggagctggg 120
gagtggccag tttgccatcg tgaagaagtg ccgggagaag agcacggggc ttgagtatgc 180
agccaagttc atcaagaagc ggcagagccg ggcgagccgg cgcggtgtga gccgggagga 240
gatcgagcgg gaggtgagca tcctgcggca ggtgctgcac cacaatgtca tcacgctgca 300

-continued

```
cgacgtctat gagaaccgca ccgacgtggt gctcatcctt gagctagtgt ctggaggaga    360
gctcttcgat ttcctggccc agaaggagtc actgagtgag gaggaggcca ccagcttcat    420
taagcagatc ctggatgggg tgaactacct tcacacaaag aaaattgctc actttgatct    480
caagccagaa aacattatgt tgttagacaa gaatattccc attccacaca tcaagctgat    540
tgactttggt ctggctcacg aaatagaaga tggagttgaa tttaagaata tttttgggac    600
gccggaattt gttgctccag aaattgtgaa ctacgagccc ctgggtctgg aggctgacat    660
gtggagcata ggcgtcatca cctacatcct cttaagtgga gcatcccctt tcctgggaga    720
cacgaagcag gaaacactgg caaatatcac agcagtgagt tacgactttg atgaggaatt    780
cttcagccag acgagcgagc tggccaagga ctttattcgg aagcttctgg ttaaagagac    840
ccggaaacgg ctcacaatcc aagaggctct cagacacccc tggatcacgc cggtggacaa    900
ccagcaagcc atggtgcgca gggagtctgt ggtcaatctg gagaacttca ggaagcagta    960
tgtccgcagg cggtggaagc tttccttcag catcgtgtcc ctgtgcaacc acctcacccg   1020
ctcgctgatg aagaaggtgc acctgaggcc ggatgaggac ctgaggaact gtgagagtga   1080
cactgaggag gacatcgcca ggaggaaagc cctccaccca cggaggagga gcagcacctc   1140
ctaactggcc tgacctgcag tggccgccag ggaggtctgg gcccagcggg gctcccttct   1200
gtgcagactt ttggacccag ctcagcacca gcacccgggc gtcctgagca ctttgcaaga   1260
gagatgggcc caaggaattc agaagagctt gcaggcaagc caggagaccc tgggagctgt   1320
ggctgtcttc tgtggaggag gctccagcat tcccaaagct cttaattctc cataaaatgg   1380
gctttcctct gtctgccatc ctcagagtct ggggtgggag tgtggactta ggaaaacaat   1440
ataaaggaca tcctcatcat cacggggtga aggtcagact aaggcagcct tcttcacagg   1500
ctgagggggt tcagaaccag cctggccaaa aattacacca gagagacaga gtcctcccca   1560
ttgggaacag ggtgattgag gaaagtgaac cttgggtgtg agggaccaat cctgtgacct   1620
cccagaacca tggaagccag gacgtcaggc tgaccaacac ctcagacctt ctgaagcagc   1680
ccattgctgg cccgccatgt tgtaattttg ctcattttta ttaaacttct ggtttacctg   1740
atgcttggct tcttttaggg ctacccccat ctcatttcct ttagcccgtg tgcctgtaac   1800
tctgaggggg ggcacccagt ggggtgctga gtgggcagaa tctcagaagg tcctcctgaa   1860
ccgtccgcgc aggcctgcag tgggcctgcc tcctccttgc ttccctaaca ggaaggtgtc   1920
cagttcaaga gaacccaccc agagactggg agtggtggct cacgcctata atccctgcgc   1980
tttggcagtc cgaggcaggg gaattgcttg aactcaggag ttggagacca gcctgggcaa   2040
catggcaaaa cgcagtctgt acaaaaaata caaaaaatta gccaggtgta ggggtaggca   2100
cctggcatcc cagctactcc aggggctgag gtgacagcat tgcttaagcc cagaaggtcg   2160
aggctgcagt gagctgagat cacgccactg cactccagtc tgggtgacag agagagacca   2220
tatccaaaaa aaaaaaaagt tgccagagac gagtatgccc atgctccctc tacctcactg   2280
ccaccactcc tgctgttagg agctgagtgt gtctccctaa aatttctatg ttgaagtctt   2340
aacccttggt accacagaat atcactgtat ttggagatgg ggtctttaga aaggcactta   2400
aattaaaatg agctcactga tatgggcccc gatgcaatat aattggtgtc cttataagaa   2460
ggggaggtta ggacacgcag gaaagaccac atgaaggccc aggagtggga gggggaatag   2520
ccatcgacaa actaaggggg cctcagagga aaccaaccct gctgacacct caatcttaga   2580
ctctggcctc aaaaattgta agaaaataaa cttctgtctt ttaagcca                2628
```

<210> SEQ ID NO 131
<211> LENGTH: 1876
<212> TYPE: DNA
<213> ORGANISM: Homo sapiens

<400> SEQUENCE: 131
gagcttactc tggctttgcc gagatggggc tgccccagcc agggctgtgg ctgaagaggc 60
tctgggtgct cttggaggtg gctgtgcatg tggtcgtggg taaagtgctt ctgatattgt 120
ttccagacag agtcaagcgg aacatcctgg ccatgggcga gaagacgggt atgaccagga 180
acccccattt cagccacgac aactggatac caaccttttt cagcacccag tatttctggt 240
tcgtcttgaa ggtccgttgg cagcgactag aggacacgac tgagctaggg ggtctggccc 300
caaactgccc ggtggtccgc ctctcaggac agaggtgcaa catttgggag tttatgcaag 360
gtaataggcc actggtgctg aattttggaa gttgtacctg accttcattt atgttcaaat 420
ttgaccagtt caagaggctt attgaagact ttagttccat agcagatttt cttgtcattt 480
acattgaaga agcacatgca tcagatggct gggcttttaa gaacaacatg gacatcagaa 540
atcaccagaa ccttcaggat cgcctgcagg cagcccatct actgctggcc aggagccccc 600
agtgccctgt ggtggtggac accatgcaga accagagcag ccagctctac gcagcactgc 660
ctgagaggct ctacataatc caggagggca ggatcctcta caagggtaaa tctggccctt 720
ggaactacaa cccagaggaa gttcgtgctg ttctggaaaa gctccacagt taatctggac 780
agatacctca attctaggtg accaacggga gggcttctca aggcttagct ctccctgaga 840
cccagctggc ttttaccctt gacctgtgtc cctagctgaa tcactagctc agatttttct 900
gatctaagca aacaactccc agctgaggaa tgcaggccac agcacccaat caagacaaat 960
tgttattatc agaaaatgaa gcaacacttg agctgttcag gccagttccc tgttgaagaa 1020
acagttccct gttgaagaaa gtagagcctg acactgctcc cactttggag accacattcc 1080
ctgcacacgg tctttgagag agcagttgca ctctacaggc acacttctga ggtacggtat 1140
ctctctccag ccactctgat accaagtaat tcaagctggc attccttcta ttagggaaat 1200
tcattttacc caatttgcat ttatggaatt gatcatttaa gacactaaat tagtttttag 1260
aaccaattat gggaagaatt ccagttgtta ggaagagatg aggagttgga agaggaggga 1320
ttagaaacag gaggaggcag tcatcctctc cttgccaaaa gatttaaacc tgtccacatt 1380
ggtggtgatg atgggtgagt ttccatggta acacatccct aattttacca gggaagagga 1440
gagtactcac tttaccatct ttgaatatat ttcatagaaa tctagctctc tgtaccctga 1500
aatcttccac tagcctcact tttcaacaga gtcatctaga agggagggtt ggcttcccaa 1560
aagcataacc ttgaccaaac caaacaatag gcaccagcaa tgctgtcatt cagttatgca 1620
gaagctcatt tgtgaaattc tgtttctctg atttcttcgc aagtctctta atggtcattt 1680
gtgttagatt acatcaaact gatggatagc cattggtatt catctatttt aactctgtgt 1740
ctttacatat ttgtttatga tggccacagc ctaaagtaca cacggctgtg acttgattca 1800
aaagaaaatg ttataagatg cagtaaacta ataacagaat tattaaaata tatcaggcta 1860
aaaaaaaaaa aaaaaa 1876

<210> SEQ ID NO 132
<211> LENGTH: 3913
<212> TYPE: DNA
<213> ORGANISM: Homo sapiens

<400> SEQUENCE: 132

-continued

```
ctttcactgg caagagacgg agtcctgggt ttcagttcca gttgcctgcg gtgggctgtg     60
tgagtttgcc aaagtcccct gccctctctg ggtctcggtt ccctcgcctg tccacgtgag    120
gttggaggag ctgaacgccg acgtcatttt tagctaagag ggagcagggt ccccgagtcg    180
ccggcccagg gtctgcgcat ccgaggccgc gcgccctttc ccctccccca cggctcctcc    240
gggccccgca ctctgcgccc cggctgccgc ccagcgccct acaccgccct caggggcccc    300
tcgcgggctc cccccggccg ggatgccagt gccccgcgcc acgcgcgcct gctcccgcgc    360
cgcctgccct gcagcctgcc cgcggcgcct ttatacccag cgggctcggc gctcactaat    420
gtttaactcg gggccgaaac ttgccagcgg cgagtgactc caccgcccgg agcagcggtg    480
caggacgcgc gtctccgccg cccgcggtga cttctgcctg cgctccttct ctgaacgctc    540
acttccgagg agacgccgac gatgaagaca ccgtggaagg ttcttctggg actgctgggt    600
gctgctgcgc ttgtcaccat catcaccgtg cccgtggttc tgctgaacaa aggcacagat    660
gatgctacag ctgacagtcg caaaacttac actctaactg attacttaaa aaatacttat    720
agactgaagt tatactcctt aagatggatt tcagatcatg aatatctcta caaacaagaa    780
aataatatct tggtattcaa tgctgaatat ggaaacagct cagttttctt ggagaacagt    840
acatttgatg agtttggaca ttctatcaat gattattcaa tatctcctga tgggcagttt    900
attctcttag aatacaacta cgtgaagcaa tggaggcatt cctacacagc ttcatatgac    960
atttatgatt taaataaaag gcagctgatt acagaagaga ggattccaaa caacacacag   1020
tgggtcacat ggtcaccagt gggtcataaa ttggcatatg tttggaacaa tgacatttat   1080
gttaaaattg aaccaaattt accaagttac agaatcacat ggacggggaa agaagatata   1140
atatataatg gaataactga ctgggtttat gaagaggaag tcttcagtgc ctactctgct   1200
ctgtggtggt ctccaaacgg cacttttta gcatatgccc aatttaacga cacagaagtc    1260
ccacttattg aatactcctt ctactctgat gagtcactgc agtacccaaa gactgtacgg   1320
gttccatatc caaaggcagg agctgtgaat ccaactgtaa agttctttgt tgtaaataca   1380
gactctctca gctcagtcac caatgcaact tccatacaaa tcactgctcc tgcttctatg   1440
ttgatagggg atcactactt gtgtgatgtg acatgggcaa cacaagaaag aatttctttg   1500
cagtggctca ggaggattca gaactattcg gtcatggata tttgtgacta tgatgaatcc   1560
agtggaagat ggaactgctt agtggcacgg caacacattg aaatgagtac tactggctgg   1620
gttggaagat ttaggccttc agaacctcat tttacccttg atggtaatag cttctacaag   1680
atcatcagca atgaagaagg ttacagacac atttgctatt tccaaataga taaaaaagac   1740
tgcacattta ttacaaaagg cacctgggaa gtcatcggga tagaagctct aaccagtgat   1800
tatctatact acattagtaa tgaatataaa ggaatgccag gaggaaggaa tctttataaa   1860
atccaactta gtgactatac aaaagtgaca tgcctcagtt gtgagctgaa tccggaaagg   1920
tgtcagtact attctgtgtc attcagtaaa gaggcgaagt attatcagct gagatgttcc   1980
ggtcctggtc tgcccctcta tactctacac agcagcgtga atgataaagg gctgagagtc   2040
ctggaagaca attcagcttt ggataaaatg ctgcagaatg tccagatgcc ctccaaaaaa   2100
ctggacttca ttattttgaa tgaaacaaaa ttttggtatc agatgatctt gcctcctcat   2160
tttgataaat ccaagaaata tcctctacta ttagatgtgt atgcaggccc atgtagtcaa   2220
aaagcagaca ctgtcttcag actgaactgg gccacttacc ttgcaagcac agaaaacatt   2280
atagtagcta gctttgatgg cagaggaagt ggttaccaag gagataagat catgcatgca   2340
atcaacagaa gactgggaac atttgaagtt gaagatcaaa ttgaagcagc cagacaattt   2400
```

tcaaaaatgg gatttgtgga caacaaacga attgcaattt ggggctggtc atatggaggg 2460
tacgtaacct caatggtcct gggatcggga agtggcgtgt tcaagtgtgg aatagccgtg 2520
gcgcctgtat cccggtggga gtactatgac tcagtgtaca cagaacgtta catgggtctc 2580
ccaactccag aagacaacct tgaccattac agaaattcaa cagtcatgag cagagctgaa 2640
aattttaaac aagttgagta cctccttatt catggaacag cagatgataa cgttcacttt 2700
cagcagtcag ctcagatctc caaagccctg gtcgatgttg gagtggattt ccaggcaatg 2760
tggtatactg atgaagacca tggaatagct agcagcacag cacaccaaca tatatatacc 2820
cacatgagcc acttcataaa acaatgtttc tctttacctt agcacctcaa aataccatgc 2880
catttaaagc ttattaaaac tcatttttgt tttcattatc tcaaaactgc actgtcaaga 2940
tgatgatgat ctttaaaata cacactcaaa tcaagaaact taaggttacc tttgttccca 3000
aatttcatac ctatcatctt aagtagggac ttctgtcttc acaacagatt attaccttac 3060
agaagtttga attatccggt cggttttat tgtttaaaat catttctgca tcagctgctg 3120
aaacaacaaa taggaattgt ttttatggag gctttgcata gattccctga gcaggatttt 3180
aatctttttc taactggact ggttcaaatg ttgttctctt ctttaaaggg atggcaagat 3240
gtgggcagtg atgtcactag ggcagggaca ggataagagg gattagggag agaagatagc 3300
agggcatggc tgggaaccca agtccaagca taccaacacg agcaggctac tgtcagctcc 3360
cctcggagaa gagctgttca cagccagact ggcacagttt tctgagaaag actattcaaa 3420
cagtctcagg aaatcaaata tgcaaagcac tgacttctaa gtaaaaccac agcagttgaa 3480
aagactccaa agaaatgtaa gggaaactgc cagcaacgca ggcccccagg tgccagttat 3540
ggctataggt gctacaaaaa cacagcaagg gtgatgggaa agcattgtaa atgtgctttt 3600
aaaaaaaaat actgatgttc ctagtgaaag aggcagcttg aaactgagat gtgaacacat 3660
cagcttgccc tgttaaaaga tgaaaatatt tgtatcacaa atcttaactt gaaggagtcc 3720
ttgcatcaat ttttcttatt tcatttcttt gagtgtctta attaaaagaa tattttaact 3780
tccttggact cattttaaaa aatggaacat aaaatacaat gttatgtatt attattccca 3840
ttctacatac tatggaattt ctcccagtca tttaataaat gtgccttcat tttttcagaa 3900
aaaaaaaaaa aaa 3913

<210> SEQ ID NO 133
<211> LENGTH: 5795
<212> TYPE: DNA
<213> ORGANISM: Homo sapiens

<400> SEQUENCE: 133
gagcagcggc agcagcagcg gaccccggcg gcggcggcgg cgcgcggtcc cagccaggcg 60
gccccggtgt cccggccccg gtggatgcac ggctggggag gagcccatgg gccggagctg 120
aggctgcccg gggcggcggg gcgcggggca gggggcgcgg tcgaggcccg gaggcggcgg 180
cgcaggagga agcggaggag gtcgggcgct cggggcccgg gaggcgggcc gcgcagcgcc 240
gcagccccgg gctcgccatg ctcctggcct cggccgtggt ggtctgggaa tggctgaacg 300
agcacggccg ctggcgtccc tacagcccag cggtgagcca ccacatcgag gcggtggtcc 360
gcgccggccc ccgcgcgggg ggcagcgtgg tgctgggcca ggtggacagc cgtctcgcgc 420
cctacatcat cgacctgcag tccatgaacc agttccgcca agacacggga actctccgcc 480
cagttcgccg caactactac gacccctcct cggcccctgg gaagggcgtg gtgtgggagt 540

-continued

```
gggagaacga caatggctcc tggacgccct acgacatgga agtgggcatc accatccagc    600
atgcctatga gaagcagcac ccctggatcg acctcacttc cattggcttt agctacgtaa    660
ttgacttcaa caccatgggc cagatcaacc gtcagaccca gcgccaacgc cgcgtccgcc    720
ggcgcctcga cctcatctac cccatggtca cagggacctt gcctaaggct cagtcctggc    780
cagtcagccc tgggccagcc acctcgcccc ccatgtcccc ctgctcctgt ccccagtgtg    840
tcttggtgat gagtgttaag gcagccgtgg tcaatggcag cactgggccc ctacagctgc    900
cagtgacccg caagaacatg ccgcctcctg gagtggtcaa gctacccccca ctgccaggct    960
ctggggccaa gccactggac agcacaggca ccattcgagg cccactgaag accgccccat   1020
cgcaggtgat ccggagacaa gcctccagca tgcccactgg gacaaccatg ggctctcctg   1080
ccagtccccc aggacccaac agcaagaccg gaagggtggc cctggccacc ttgaatcgta   1140
ccaacctgca gcgactggcc attgcccagt cccgggtgct gatcgcctct ggggtcccca   1200
cagtcccagt gaagaaccta aatgggtcca gtcctgtcaa ccctgccttg gcaggaatca   1260
ctgggatcct catgagtgca gcggggctgc ctgtgtgtct caccaggcca ccaaagctgg   1320
tcctacaccc accccccgtc agcaagagtg aaataaaatc catcccaggg gtttccaaca   1380
caagccgcaa gaccaccaaa aaacaagcca agaaaggtaa aacccccagag gaagtgctaa   1440
aaaaatatct acagaaagtc cggcacccac cagatgagga ctgcaccatc tgtatggaac   1500
gcctcacggc cccctcaggc tacaagggcc cgcagcctac ggtaaaacct gacctggtag   1560
ggaagctgtc cagatgcggc cacgtctacc acatctactg cttggttgcc atgtacaaca   1620
atgggaacaa ggatggaagt ttgcagtgtc caacctgcaa gaccatttat ggggtgaaga   1680
caggcaccca acctccaggg aagatggagt accacctcat cccccactcc ttgcctggcc   1740
acccagactg caaaaccatc cggatcatct acagcatccc ccccggcatt cagggaccgg   1800
aacacccgaa tcctgggaag agtttcagcg cccgaggctt cccacgacac tgttaccttc   1860
cggacagcga gaaagggaga aaagttctga agctgctgct cgtggcctgg gatcgccgcc   1920
tcatttttgc cattggcacc tccagcacca caggcgagtc agacaccgtc atctggaatg   1980
aggtccacca caagacagag tttggctcta atctcactgg ccatggctac ccagatgcca   2040
attacctgga taatgtgctg gctgaactgg ctgcccaggg catctctgag gacagcactg   2100
cccaggagaa ggactgaggc cagaaaagct ttgaggtggg aggggccatg gagactgcag   2160
gacaggaagt gaggagagtg agtcaatgta gaagaagttg gtgtcctgcc ctcccaactt   2220
tctatcctcc cctcctgccc tgtgtccatc cctcatccct cccaaccaca gtgggagcca   2280
gactgaatat agcgacatca ttcataaatc tcatccaaca caaagggaga tgggatgagg   2340
gccatcctgg gtctgttccc atggagtttt tggtgctggg taggcaggaa tcccctccct   2400
accccacctc ccaagtaggg gcatggtcag cacacctagg gtatgggcag tgcttaggca   2460
ctccatatcc tggctttggg aagccggggt ttcttgcctc agccggcttc ttgctacttc   2520
cactctgctt tgagactgga gtttctgcta ttctccctct gctggaggca gggagctctc   2580
actgtgcaag gttgggggt gggcaaaggg gtgaatcact aaactgctgt gacatcagaa   2640
actgatgcct tggtgtagag caaggaagca cttcttccca agagggtcgg agaaggaaaa   2700
gcctctggga gcacattctg ctgtcatcac agtccttggc ttctctgggc cctcctctcc   2760
tcctcacagc tctcacctgt ccaaagaggc atctggttct ctcatgtgga tggatggact   2820
ctggggttcc tctttggagt ggcatcccat gatgctgttt ctagaccctc tctgatcaaa   2880
ccagagcctg catcccactg agcatctgaa ctgtcctcag ggagaggagc ccacagcctt   2940
```

-continued cttcccaact cattctagac cagctcaaag attccatgag tttcatcgag tcactgtgag 3000
tggagcccat gctgggctct gtgccctctg tgtctgtgca tgcgcgtgtg tgtgtgggcg 3060
tgtgtgcatt gctgggccag cttgaaggga aggcccgtca tgtccctgca ctctgttttg 3120
caagatgcca aaccccagtt ctgatggggc tccaacagcc aggctgtggt cctttgacgt 3180
tcctcacctg ttgccaacct atcccgtagt gaactgaaac cccaatgaag acagaactgt 3240
gcctggggag atgcaatgag gtgagggctg aactcatcct tttatatttc ttttcaagat 3300
tggatcagag ctcatctcca tccagtcttg tttctatgaa ggcttcaatc tgtttccatg 3360
caaatttgct aatcagagcc cagagctgct gggtccctca tctccctcat ctattataga 3420
ttgacttaca gcagggagag aatctcttta gctcattcct aatggagttg ggatcacaat 3480
atggtctggt ccaatctgca tcttgttgtg tcccaagacc ctatctcctc cccaacattc 3540
ttattgcctt tggctcccag taaggaacga attgggggcc agggaggaga acagggggga 3600
tcaagaaggg aaacccaatt ccccctttga aagtgggttc tttgaactat gtgtttgggg 3660
gaagttcctc tggatactaa tttgaattta tatacctcat gttttggggg tttgacgtat 3720
atatatatat atatatatgc atatatattt cataatattt ggaaggtttt tgatgctaga 3780
aaaatggaaa caagagaacc ttcaaaaatg gtacttagat gggaactgga ggccaatctt 3840
tcataaagcc agccccatag ctgcttgctg ttaggcctcc agccattttg acattggggt 3900
ggatagtcga ttcacctgcc tgtcagtcga ttcacctgcc tgtcacccag ttctgtggat 3960
gtgctggtgc tgagcctttg ctctctttcc aaatggttac agggatgttg atcagctcca 4020
ccagagggag ctctgatggg aggaattgct ctgccatcct tgtccctgtg tctcctgtcg 4080
gcaggcagcc attgtatctc accagcagac caggagactg gtcccaaggt tactgcacca 4140
cagggcaatt tcctgccata gttaggaagg aaacacctga actaaatgga agagacatcc 4200
ctgcggtgtt taatatcaca cccatgccct ttgtcaggtt accatgtaca gagattactt 4260
ggagagcctc atgccgtctc taccttcgca cactggtcaa gtatctgctg agcttcttgg 4320
ccgcaaggat gcagaaatag gctgagggtc catgggaaga aagacacaat gaggcagtag 4380
gaggtgggga agaaaagaag acagactttc aaaatggaat taggcactgg ggagagatca 4440
gtttccccac atcagggaga agaaggtata ggtggggaag ggggtggcca ggagcagaag 4500
gaagaagact caagatggaa agggagccgc tgtgcctgtg gcaataccac ttggagaggt 4560
cgacttcata ccttcaagcc ttttcccctg ggcttttgat tgtgtctgtg cccccttct 4620 tgtcctctct gcagatgccc agtaggggct acctcatcct cgtgctgttc ttgtgtggct 4680
ttctgggcag tagggatctt gaatttcctt tctaacactg tgcccggcaa ggcggggagc 4740
attcctctgc cctttgtctt gtgccaacct ggaaaggtgc agtctagatt tcagtgagaa 4800
ccctgccagc tgagccctgt gcatctacta ccttgacaca gagtgttttc ccactagaag 4860
ctctgctctg ctctcctggc ccaagtaggg gattccatgc cttccctttc atggtcttag 4920
caccagcagc ctagtttctc ccttccagag tctccaggga tgacaaattg gattggagac 4980
aaacctcgtc agatgctcat cccctaaaag gttaattgtg tatttgtggc tgcgtgtgcc 5040
tttgtgtttt cattctcttc ccatttttgt acattttggt cttctctgtg gttttatact 5100
tggtcaaaag tactcgtctt ggtattgcac tgttgtgtgc atgagaaaac tgggggaagg 5160
ctcactggta caagaaagga cccctgaccc ctttccttct ctgtggtccc cggcattaga 5220
ttgggggttc tgggagaggc aggtgaatgt cctaagtgaa ttgttctgtt tgtaactgga 5280

-continued atgtttttga agtctttggt gttgctccgt gaaaggacat cgccacctgg tgctcatgag 5340
gtgtctttgc agaacaataa atggcaaatg aacaaccaca aaattgttac tcttgttggc 5400
cttctgctgt ttgtagatta gtgcacctat ctgtgaggga tttgggttac ctccctgagt 5460
ctgtaagcaa ccacaagccc tgccactggg tgggggaagt ccctccccaa ccacttaaaa 5520 acaaatttc cacatattac ccacccacac atttgacctg gctagacttt gtttgcctaa 5580
aggaacagac cacattgctg ggaaaatgag taagtgaacg tgtgggagaa aaacactttt 5640
agaatcacga atattcactt ttaaaggtct ctttgcctgg ctgcaatata gtgtgtgttt 5700
aaattattta caggctgttg tttctcaaat aaatgtttaa tattaatcat tcccaaactg 5760
acaagaacac aaaaataaaa tgcaaataca gagcc 5795

<210> SEQ ID NO 134
<211> LENGTH: 2498
<212> TYPE: DNA
<213> ORGANISM: Homo sapiens

<400> SEQUENCE: 134
gctgagcgcc ggaggagcgt aggcagggca gcgctggcgc cagtggcgac aggagccgcg 60
cgaccggcaa aaatacacgg gaggccgtcg ccgaaaagag tccgcggtcc tctctcgtaa 120
acacactctc ctccaccggc gcctccccct ccgctctgcg cgccgcccgg ctgggcgccc 180
gaggccgctc cgactgctat gtgaccgcga ggctgcggga ggaaggggac agggaagaag 240
aggctctccc gcgggagccc ttgaggacca agtttgcggc cacttctgca ggcgtccctt 300
cttagctctc gcccgcccct ttctgcagcc taggcggccc gggttctctt ctcttcctcg 360
cgcgcccagc cgcctcggtt cccggcgacc atggtgacga tggaggagct gcgggagatg 420
gactgcagtg tgctcaaaag gctgatgaac cgggacgaga atggcggcgg cgcgggcggc 480
agcggcagcc acggcaccct ggggctgccg agcggcggca agtgcctgct gctggactgc 540
agaccgttcc tggcgcacag cgcgggctac atcctaggtt cggtcaacgt gcgctgtaac 600
accatcgtgc ggcggcgggc taagggctcc gtgagcctgg agcagatcct gcccgccgag 660
gaggaggtac gcgcccgctt gcgctccggc ctctactcgg cggtcatcgt ctacgacgag 720
cgcagcccgc gcgccgagag cctccgcgag gacagcaccg tgtcgctggt ggtgcaggcg 780
ctgcgccgca acgccgagcg caccgacatc tgcctgctca aaggcggcta tgagaggttt 840
tcctccgagt acccagaatt ctgttctaaa accaaggccc tggcagccat cccacccccg 900
gttcccccca gtgccacaga gcccttggac ctgggctgca gctcctgtgg gaccccacta 960
cacgaccagg ggggtcctgt ggagatcctt cccttcctct acctcggcag tgcctaccat 1020
gctgcccgga gagacatgct ggacgccctg ggcatcacgg ctctgttgaa tgtctcctcg 1080
gactgcccaa accactttga aggacactat cagtacaagt gcatcccagt ggaagataac 1140
cacaaggccg acatcagctc ctggttcatg gaagccatag agtacatcga tgccgtgaag 1200
gactgccgtg ggcgcgtgct ggtgcactgc caggcgggca tctcgcggtc ggccaccatc 1260
tgcctggcct acctgatgat gaagaaacgg gtgaggctgg aggaggcctt cgagttcgtt 1320
aagcagcgcc gcagcatcat ctcgcccaac ttcagcttca tggggcagct gctgcagttc 1380
gagtcccagg tgctggccac gtcctgtgct gcggaggctg ctagcccctc gggacccctg 1440
cgggagcggg gcaagacccc cgccaccccc acctcgcagt tcgtcttcag ctttccggtc 1500
tccgtgggcg tgcactcggc ccccagcagc ctgccctacc tgcacagccc catcaccacc 1560
tctcccagct gttagagccg ccctgggggc cccagaacca gagctggctc ccagcaaggg 1620
taggacgggc cgcatgcggg cagaaagttg ggactgagca gctgggagca ggcgaccgag 1680
ctccttcccc atcatttctc cttggccaac gacgaggcca gccagaatgg caataaggac 1740
tccgaataca taataaaagc aaacagaaca ctccaactta gagcaataac ggctgccgca 1800
gcagccaggg aagaccttgg tttggtttat gtgtcagttt cacttttccg atagaaattt 1860
cttacctcat ttttttaagc agtaaggctt gaagtgatga aacccacaga tcctagcaaa 1920
tgtgcccaac cagctttact aaagggggag gaagggaggg caaagggatg agaagacaag 1980
tttcccagaa gtgcctggtt ctgtgtactt gtccctttgt tgtcgttgtt gtagttaaag 2040
gaatttcatt ttttaaaaga aatcttcgaa ggtgtggttt tcatttctca gtcaccaaca 2100
gatgaataat tatgcttaat aataaagtat ttattaagac tttcttcaga gtatgaaagt 2160
acaaaaagtc tagttacagt ggatttagaa tatatttatg ttgatgtcaa acagctgagc 2220
accgtagcat gcagatgtca aggcagttag gaagtaaatg gtgtcttgta gatatgtgca 2280
aggtagcatg atgagcaact tgagtttgtt gccactgaga agcaggcggg ttgggtggga 2340
ggaggaagaa agggaagaat taggtttgaa ttgcttttta aaaaaaaaag aaaagaaaaa 2400
gacagcatct cactatgttg ccaaggctca tcttgagaag caggcgggtt gggtgggagg 2460
aggaagaaag ggaagaatta ggtttgaatt gctttttt 2498

<210> SEQ ID NO 135
<211> LENGTH: 2936
<212> TYPE: DNA
<213> ORGANISM: Homo sapiens

<400> SEQUENCE: 135
cgaaggtagc gtgtcgggga cccagactga taagacaaaa gagaatcagt cgctttgggc 60
tgcccctcca cacaacctgg gacttttaaa caaagctgtg cgcagagaaa ggcgtggaaa 120
tgccactttg agagtttgtg ctgggggatg tgagaagctc tgagacatgt gagaaggtct 180
agtattctac tagaactgga agattgctct ccgagttttg ttttgttatt ttgtttaaaa 240
aataaaaagc ttgaggccaa ggcaattcat attggctcac aggtattttt gctgtgctgt 300
gcaaggaact ctgctagctc aagattcaca atgttgaaag ccctttttcct aactatgctg 360 actctggcgc tggtcaagtc acaggacacc gaagaaacca tcacgtacac gcaatgcact 420
gacggatatg agtgggatcc tgtgagacag caatgcaaag atattgatga atgtgacatt 480
gtcccagacg cttgtaaagg tggaatgaag tgtgtcaacc actatggagg atacctctgc 540
cttccgaaaa cagcccagat tattgtcaat aatgaacagc ctcagcagga aacacaacca 600
gcagaaggaa cctcaggggc aaccaccggg gttgtagctg ccagcagcat ggcaaccagt 660
ggagtgttgc ccgggggtgg ttttgtggcc agtgctgctg cagtcgcagg ccctgaaatg 720
cagactggcc gaaataactt tgtcatccgg cggaacccag ctgaccctca gcgcattccc 780
tccaaccctt cccaccgtat ccagtgtgca gcaggctacg agcaaagtga acacaacgtg 840
tgccaagaca tagacgagtg cactgcaggg acgcacaact gtagagcaga ccaagtgtgc 900
atcaatttac ggggatcctt tgcatgtcag tgccctcctg gatatcagaa gcgaggggag 960
cagtgcgtag acatagatga atgtaccatc cctccatatt gccaccaaag atgcgtgaat 1020
acaccaggct cattttattg ccagtgcagt cctgggtttc aattggcagc aaacaactat 1080
acctgcgtag atataaatga atgtgatgcc agcaatcaat gtgctcagca gtgctacaac 1140
attcttggtt cattcatctg tcagtgcaat caaggatatg agctaagcag tgacaggctc 1200

-continued

```
aactgtgaag acattgatga atgcagaacc tcaagctacc tgtgtcaata tcaatgtgtc   1260
aatgaacctg ggaaattctc atgtatgtgc ccccagggat accaagtggt gagaagtaga   1320
acatgtcaag atataaatga gtgtgagacc acaaatgaat gccgggagga tgaaatgtgt   1380
tggaattatc atggcggctt ccgttgttat ccacgaaatc cttgtcaaga tccctacatt   1440
ctaacaccag agaaccgatg tgtttgccca gtctcaaatg ccatgtgccg agaactgccc   1500
cagtcaatag tctacaaata catgagcatc cgatctgata ggtctgtgcc atcagacatc   1560
ttccagatac aggccacaac tatttatgcc aacaccatca atacttttcg gattaaatct   1620
ggaaatgaaa atggagagtt ctacctacga caaacaagtc ctgtaagtgc aatgcttgtg   1680
ctcgtgaagt cattatcagg accaagagaa catatcgtgg acctggagat gctgacagtc   1740
agcagtatag ggaccttccg cacaagctct gtgttaagat tgacaataat agtggggcca   1800
ttttcatttt agtcttttct aagagtcaac cacaggcatt taagtcagcc aaagaatatt   1860
gttaccttaa agcactattt tatttataga tatatctagt gcatctacat ctctatactg   1920
tacactcacc cataattcaa acaattacac catggtataa agtgggcatt taatatgtaa   1980
agattcaaag tttgtcttta ttactatatg taaattagac attaatccac taaactggtc   2040
ttcttcaaga gagctaagta tacactatct ggtgaaactt ggattctttc ctataaaagt   2100
gggaccaagc aatgatgatc ttctgtggtg cttaaggaaa cttactagag ctccactaac   2160
agtctcataa ggaggcagcc atcataacca ttgaatagca tgcaagggta agaatgagtt   2220
tttaactgct ttgtaagaaa atggaaaagg tcaataaaga tatatttctt tagaaaatgg   2280
ggatctgcca tatttgtgtt ggtttttatt ttcatatcca gcctaaaggt ggttgtttat   2340
tatatagtaa taaatcattg ctgtacaata tgctggtttc tgtagggtat ttttaatttt   2400
gtcagaaatt ttagattgtg aatattttgt aaaaaacagt aagcaaaatt ttccagaatt   2460
cccaaaatga accagatatc ccctagaaaa ttatactatt gagaaatcta tggggaggat   2520
atgagaaaat aaattccttc taaaccacat tggaactgac ctgaagaagc aaactcggaa   2580
aatataataa catccctgaa ttcaggactt ccacaagatg cagaacaaaa tggataaaag   2640
gtatttcact ggagaagttt taatttctaa gtaaaattta aatcctaaca cttcactaat   2700
ttataactaa aatttctcat cttcgtactt gatgctcaca gaggaagaaa atgatgatgg   2760
tttttattcc tggcatccag agtgacagtg aacttaagca aattaccctc ctacccaatt   2820
ctatggaata ttttatacgt ctccttgttt aaaatgtcac tgctttactt tgatgtatca   2880
tatttttaaa taaaaataaa tattccttta gaagatcaaa aaaaaaaaaa aaaaaa       2936
```

<210> SEQ ID NO 136
<211> LENGTH: 3727
<212> TYPE: DNA
<213> ORGANISM: Homo sapiens

<400> SEQUENCE: 136

```
aagtgagagc agcggcagcc ggcggtgcag cagccggccg acccagagtg taagtgcgtg     60
tgctggggcg agcgggagcg ggcgaggatg ggcacaggat agaggcagag ccacccacgc    120
cgccgcggcc ccacgctggg cgacagagcc tccagttccc cttcaatggt ggcgggtcgc    180
cggagctctg atcgccggga acccttgccg ctgctgtcct gcgaccccaa gcaggtatag    240
acacgtgtgg ccgtttacgc tgtaggatcc tcattcccac tggctttgaa cattttgggg    300
acttacaatg ccgccacccg cggacatcgt caaggtggcc atagaatggc cgggcgccta    360
ccccaaactc atggaaattg atcagaaaaa accactgtct gcaataataa aggaagtctg    420
```

-continued

```
tgatgggtgg tctcttgcca accatgaata ttttgcactc cagcatgccg atagttcaaa    480
cttctatatc acagaaaaga accgcaatga gataaaaaat ggcactatcc ttcgattaac    540
cacatctcca gctcagaacg cccagcagct ccatgaacga atccagtcct cgagtatgga    600
tgccaagctg gaagccctga aggacttggc cagcctctcc cgggatgtca cgtttgccca    660
ggagtttata aacctggacg gtatctctct cctcacgcag atggtggaga gcggcactga    720
gcgataccag aaattgcaga agatcatgaa gccttgcttt ggagacatgc tgtccttcac    780
cctgacggcc ttcgttgagc tgatggacca tggcatagtg tcctgggata cattttcggt    840
ggcgttcatt aagaagatag caagttttgt gaacaagtca gccatagaca tctcgatcct    900
gcagcggtcc ttggccattt tggagtcgat ggtgctcaat agccatgacc tctaccagaa    960
agtggcgcag gagatcacca tcggccagct cattccacac ctgcaagggt cagatcaaga   1020
aatccaaacc tatactattg cagtgattaa tgcgcttttc ctgaaggctc ctgatgagag   1080
gaggcaggag atggcgaata ttttggctca gaagcaactg cgttccatca ttttaacaca   1140
tgtcatccga gcccagcggg ccatcaacaa tgagatggcg caccagctgt atgttctaca   1200
agtgctcacc tttaacctcc tggaagacag gatgatgacc aaaatggacc cccaggacca   1260
ggctcagagg gacatcatat ttgaacttcg aagaattgct tttgatgctg agtctgaacc   1320
taacaacagc agtggcagca tggagaaacg caagtccatg tacacgcgag attataagaa   1380
gcttgggttc attaatcatg tcaaccctgc catggacttc acgcagactc cacctgggat   1440
gttggctctg gacaacatgc tgtactttgc caagcaccac caagatgcct acatccggat   1500
tgtgcttgag aacagtagtc gagaagacaa gcatgaatgt ccctttggcc gcagtagtat   1560
agagctgacc aagatgctat gtgagatctt gaaagtgggc gagttgccta gtgagacctg   1620
caacgacttc cacccgatgt tcttcaccca cgacagatcc tttgaggagt tttctgcat    1680
ctgtatccag ctcctgaaca agacatggaa ggaaatgagg gcaacttctg aagacttcaa   1740
caaggtaatg caggtggtga aggagcaggt tatgagagca cttacaacca agcctagctc   1800
cctggaccag ttcaagagca aactgcagaa cctgagctac actgagatcc tgaaaatccg   1860
ccagtccgag aggatgaacc aggaagattt ccagtcccgc ccgattttgg aactaaagga   1920
gaagattcag ccagaaatct tagagctgat caaacagcaa cgcctgaacc gccttgtgga   1980
agggacctgc tttaggaaac tcaatgcccg gcggaggcaa gacaagtttt ggtattgtcg   2040
gctttcgcca aatcacaaag tcctgcatta cggagactta gaagagagtc ctcagggaga   2100
agtgccccac gattccttgc aggacaaact gccggtggca gatatcaaag ccgtggtgac   2160
gggaaaggac tgccctcata tgaaagagaa aggtgccctt aaacaaaaca aggaggtgct   2220
tgaactcgct ttctccatct tgtatgactc aaactgccaa ctgaacttca tcgctcctga   2280
caagcatgag tactgtatct ggacggatgg actgaatgcg ctactcggga aggacatgat   2340
gagcgacctg acgcggaatg acctggacac cctgctcagc atggaaatca agctccgcct   2400
cctggacctg gaaaacatcc agatccctga cgcacctccg ccgattccca aggagcccag   2460
caactatgac ttcgtctatg actgtaactg aagtggccgg gcccagacat gccccttcca   2520
aaactggaac acctagctaa caggagagag gaatgaaaac acacccacgc cttggaaccg   2580
tcctttggta aagggaagct gtgggtccac attcccttca gcatcacctc tagccctggc   2640
aactttcagc ccctagctgg catcttgctc accgccctga ttctgttcct cggctccact   2700
gcttcaggtc acttcccatg gctgcagtcc actggtggga caagagcaaa gcccactgcc   2760
```

agtaagaagg ccaaagggcc cttccatcct agccctctgc aggcatgccc ttccttccct 2820
tgggcaggaa agccagcagc cccagactgc ccaaaaactt gcccaccaga ccaagggcag 2880
tgccccaagg cccctgtctg gaggaaatgg cctagctatt tgatgagaag accaaacccc 2940
acatcctcct ttcccctctc tctagaatca tctcgcacca ccagttacac ttgaattaag 3000
atctgcgctc aaatctcctc ccacctctct ccctgctttt gccttgctct gttcctcttt 3060
ggtcccaaga gcagcagccg cagcctcctc gtgatcctcc ctagcataaa tttcccaaac 3120
agtccacagg tcccatgccc actttgcgtc tgcactgtga tcgtgacaaa tcttccctcc 3180
tcaccagcta gtctggggtt tcctctccct gccccaggcc agaactgcct tcttcatttc 3240
cacccacgct cccagcctct tagctgaaag cacaaatggt gaaatcagta gtctcgctcc 3300
atctctaata gactaaacct aaatgcctct aggacggact gttgctatcc aagcgtttgg 3360
tgttaccttc tcctgggagg tcctgctgca actcaagttc cacaggatgg tcaagctgtc 3420
agacatccaa gtttacatca ttgtaattat tactggtatt tacaatttgc aagagttttg 3480
ggttagtttt tttttttttt tttgctttgt ttttgtacaa aagagtctaa catttttttgc 3540 caaacagata tatatttaat gaaaagaaga gatacataaa tgtgtgaatt tccagttttt 3600
ttttaattat tttaatccca aacatcttcc tgaaaataac attcccttaa acatgctgtg 3660
gaataaaatg gattgtgatg atttggaaaa aaaaaaaaaa aaaaaaaaaa aaaaaaaaaa 3720
aaaaaaa 3727

<210> SEQ ID NO 137
<211> LENGTH: 4654
<212> TYPE: DNA
<213> ORGANISM: Homo sapiens

<400> SEQUENCE: 137
ggcggcggct ggaggagagc gcggtggaga gccgagcggg cgggcggcgg gtgcggagcg 60
ggcgagggag cgcgcgcggc cgccacaaag ctcgggcgcc gcggggctgc atgcggcgta 120
cctggcccgg cgcggcgact gctctccggg ctggcggggg ccggccgcga gccccggggg 180
ccccgaggcc gcagcttgcc tgcgcgctct gagccttcgc aactcgcgag caaagtttgg 240
tggaggcaac gccaagcctg agtcctttct tcctctcgtt ccccaaatcc gagggcagcc 300
cgcgggcgtc atgcccgcgc tcctccgcag cctggggtac gcgtgaagcc cgggaggctt 360
ggcgccggcg aagacccaag gaccactctt ctgcgtttgg agttgctccc cgcaaccccg 420
ggctcgtcgc tttctccatc ccgacccacg cggggcgcgg ggacaacaca ggtcgcggag 480
gagcgttgcc attcaagtga ctgcagcagc agcggcagcg cctcggttcc tgagcccacc 540
gcaggctgaa ggcattgcgc gtagtccatg cccgtagagg aagtgtgcag atgggattaa 600
cgtccacatg gagatatgga agaggaccgg ggattggtac cgtaaccatg gtcagctggg 660
gtcgtttcat ctgcctggtc gtggtcacca tggcaacctt gtccctggcc cggccctcct 720
tcagtttagt tgaggatacc acattagagc cagaagagcc accaaccaaa taccaaatct 780
ctcaaccaga agtgtacgtg gctgcgccag gggagtcgct agaggtgcgc tgcctgttga 840
aagatgccgc cgtgatcagt tggactaagg atggggtgca cttggggccc aacaatagga 900
cagtgcttat tggggagtac ttgcagataa agggcgccac gcctagagac tccggcctct 960
atgcttgtac tgccagtagg actgtagaca gtgaaacttg gtacttcatg gtgaatgtca 1020
cagatgccat ctcatccgga gatgatgagg atgacaccga tggtgcggaa gattttgtca 1080
gtgagaacag taacaacaag agagcaccat actggaccaa cacagaaaag atggaaaagc 1140
ggctccatgc tgtgcctgcg gccaacactg tcaagtttcg ctgcccagcc ggggggaacc 1200
caatgccaac catgcggtgg ctgaaaaacg ggaaggagtt taagcaggag catcgcattg 1260
gaggctacaa ggtacgaaac cagcactgga gcctcattat ggaaagtgtg gtcccatctg 1320
acaagggaaa ttatacctgt gtagtggaga atgaatacgg gtccatcaat cacacgtacc 1380
acctggatgt tgtggagcga tcgcctcacc ggcccatcct ccaagccgga ctgccggcaa 1440
atgcctccac agtggtcgga ggagacgtag agtttgtctg caaggtttac agtgatgccc 1500
agccccacat ccagtggatc aagcacgtgg aaaagaacgg cagtaaatac gggcccgacg 1560
ggctgcccta cctcaaggtt ctcaaggccg ccggtgttaa caccacggac aaagagattg 1620
aggttctcta tattcggaat gtaacttttg aggacgctgg ggaatatacg tgcttggcgg 1680
gtaattctat tgggatatcc tttcactctg catggttgac agttctgcca gcgcctggaa 1740
gagaaaagga gattacagct tccccagact acctggagat agccatttac tgcatagggg 1800
tcttcttaat cgcctgtatg gtggtaacag tcatcctgtg ccgaatgaag aacacgacca 1860
agaagccaga cttcagcagc cagccggctg tgcacaagct gaccaaacgt atcccccctgc 1920
ggagacaggt aacagtttcg gctgagtcca gctcctccat gaactccaac accccgctgg 1980
tgaggataac aacacgcctc tcttcaacgg cagacacccc catgctggca ggggtctccg 2040
agtatgaact tccagaggac ccaaaatggg agtttccaag agataagctg acactgggca 2100
agcccctggg agaaggttgc tttgggcaag tggtcatggc ggaagcagtg ggaattgaca 2160
aagacaagcc caaggaggcg gtcaccgtgg ccgtgaagat gttgaaagat gatgccacag 2220
agaaagacct ttctgatctg gtgtcagaga tggagatgat gaagatgatt gggaaacaca 2280
agaatatcat aaatcttctt ggagcctgca cacaggatgg gcctctctat gtcatagttg 2340
agtatgcctc taaaggcaac ctccgagaat acctccgagc ccggaggcca cccgggatgg 2400
agtactccta tgacattaac cgtgttcctg aggagcagat gaccttcaag gacttggtgt 2460
catgcaccta ccagctggcc agaggcatgg agtacttggc ttcccaaaaa tgtattcatc 2520
gagatttagc agccagaaat gttttggtaa cagaaaacaa tgtgatgaaa atagcagact 2580
ttggactcgc cagagatatc aacaatatag actattacaa aaagaccacc aatgggcggc 2640
ttccagtcaa gtggatggct ccagaagccc tgtttgatag agtatacact catcagagtg 2700
atgtctggtc cttcggggtg ttaatgtggg agatcttcac tttagggggc tcgccctacc 2760
cagggattcc cgtggaggaa ctttttaagc tgctgaagga aggacacaga atggataagc 2820
cagccaactg caccaacgaa ctgtacatga tgatgaggga ctgttggcat gcagtgccct 2880
cccagagacc aacgttcaag cagttggtag aagacttgga tcgaattctc actctcacaa 2940
ccaatgagga atacttggac ctcagccaac ctctcgaaca gtattcacct agttaccctg 3000
acacaagaag ttcttgttct tcaggagatg attctgtttt ttctccagac cccatgcctt 3060
acgaaccatg ccttcctcag tatccacaca taaacggcag tgttaaaaca tgaatgactg 3120
tgtctgcctg tccccaaaca ggacagcact gggaacctag ctacactgag cagggagacc 3180
atgcctccca gagcttgttg tctccacttg tatatatgga tcagaggagt aaataattgg 3240
aaaagtaatc agcatatgtg taaagattta tacagttgaa aacttgtaat cttccccagg 3300
aggagaagaa ggtttctgga gcagtggact gccacaagcc accatgtaac ccctctcacc 3360
tgccgtgcgt actggctgtg gaccagtagg actcaaggtg gacgtgcgtt ctgccttcct 3420
tgttaatttt gtaataattg gagaagattt atgtcagcac acacttacag agcacaaatg 3480
cagtatatag gtgctggatg tatgtaaata tattcaaatt atgtataaat atatattata 3540
tatttacaag gagttatttt ttgtattgat tttaaatgga tgtcccaatg cacctagaaa 3600
attggtctct ctttttttaa tagctatttg ctaaatgctg ttcttacaca taatttctta 3660
attttcaccg agcagaggtg gaaaaatact tttgctttca gggaaaatgg tataacgtta 3720
atttattaat aaattggtaa tatacaaaac aattaatcat ttatagtttt ttttgtaatt 3780
taagtggcat ttctatgcag gcagcacagc agactagtta atctattgct tggacttaac 3840
tagttatcag atcctttgaa aagagaatat ttacaatata tgactaattt ggggaaaatg 3900
aagttttgat ttatttgtgt ttaaatgctg ctgtcagacg attgttctta gacctcctaa 3960
atgccccata ttaaaagaac tcattcatag gaaggtgttt cattttggtg tgcaaccctg 4020
tcattacgtc aacgcaacgt ctaactggac ttcccaagat aaatggtacc agcgtcctct 4080
taaaagatgc cttaatccat tccttgagga cagaccttag ttgaaatgat agcagaatgt 4140
gcttctctct ggcagctggc cttctgcttc tgagttgcac attaatcaga ttagcctgta 4200
ttctcttcag tgaattttga taatggcttc cagactcttt ggcgttggag acgcctgtta 4260
ggatcttcaa gtcccatcat agaaaattga aacacagagt tgttctgctg atagttttgg 4320
ggatacgtcc atctttttaa gggattgctt tcatctaatt ctggcaggac ctcaccaaaa 4380
gatccagcct catacctaca tcagacaaaa tatcgccgtt gttccttctg tactaaagta 4440
ttgtgttttg ctttggaaac acccactcac tttgcaatag ccgtgcaaga tgaatgcaga 4500
ttacactgat cttatgtgtt acaaaattgg agaaagtatt taataaaacc tgttaatttt 4560
tatactgaca ataaaaatgt ttctacagat attaatgtta acaagacaaa ataaatgtca 4620
cgcaacttat ttttttaata aaaaaaaaaa aaaa 4654

<210> SEQ ID NO 138
<211> LENGTH: 3252
<212> TYPE: DNA
<213> ORGANISM: Homo sapiens

<400> SEQUENCE: 138
caaggaggct gctgattgtg gcccacagcc tcatctgaac gccaggagac caggataccg 60
aggcaccgga tcccctctct gtgccctggg gagccccagt gctgcccagt caccccaggg 120
ctgaggtctg cgtccctagt ggtgcaaggc ctggtaggac cacggggcag ggaatgtgag 180
cgccatctga gctcacggtg tcctgagtcg cggcttcgtg actttggcag gggcctccgg 240
accagtgacc ccagtcaaac ccagagggtc ttgggcggca gcgacgaagg aggtattcag 300
gctccaggcc aggtggggcc ggacgccccc agccatccac catggtggtg gcacacccca 360
ccgccactgc caccaccacg cccactgcca ctgtcacggc caccgttgtg atgaccacgg 420
ccaccatgga cctgcgggac tggctgttcc tctgctacgg gctcatcgcc ttcctgacgg 480
aggtcatcga cagcaccacc tgcccctcgg tgtgccgctg cgacaacggc ttcatctact 540
gcaacgaccg gggactcaca tccatccccg cagatatccc tgatgatgcc accaccctct 600
acctgcagaa caaccagatc aacaacgccg gcatccccca ggacctcaag accaaggtca 660
acgtgcaggt catctaccta tacgagaatg acctggatga gttccccatc aacctgcccc 720
gctccctccg ggagctgcac ctgcaggaca acaatgtgcg caccattgcc agggactcgc 780
tggcccgcat cccgctgctg gagaagctgc acctggatga caactccgtg tccaccgtca 840
gcattgagga ggacgccttc gccgacagca aacagctcaa gctgctcttc ctgagccgga 900
accacctgag cagcatcccc tcggggctgc cgcacacgct ggaggagctg cggctggatg 960

-continued

```
acaaccgcat ctccaccatc ccgctgcatg ccttcaaggg cctcaacagc ctgcggcgcc   1020
tggtgctgga cggtaacctg ctggccaacc agcgcatcgc cgacgacacc ttcagccgcc   1080
tacagaacct cacagagctc tcgctggtgc gcaattcgct ggccgcgcca cccctcaacc   1140
tgcccagcgc ccacctgcag aagctctacc tgcaggacaa tgccatcagc cacatcccct   1200
acaacacgct ggccaagatg cgtgagctgg agcggctgga cctgtccaac aacaacctga   1260
ccacgctgcc ccgcggcctg ttcgacgacc tggggaacct ggcccagctg ctgctcagga   1320
acaacccttg gttttgtggc tgcaacctca tgtggctgcg ggactgggtg aaggcacggg   1380
cggccgtggt caacgtgcgg ggcctcatgt gccagggccc tgagaaggtc cggggcatgg   1440
ccatcaagga cattaccagc gagatggacg agtgttttga gacggggccg cagggcggcg   1500
tggccaatgc ggctgccaag accacggcca gcaaccacgc ctctgccacc acgccccagg   1560
gttccctgtt taccctcaag gccaaaaggc cagggctgcg cctcccccgac tccaacattg  1620
actaccccat ggccacgggt gatggcgcca agaccctggc catccacgtg aaggccctga   1680
cggcagactc catccgcatc acgtggaagg ccacgctccc cgcctcctct ttccggctca   1740
gttggctgcg cctgggccac agcccagccg tgggctccat cacggagacc ttggtgcagg   1800
gggacaagac agagtacctg ctgacagccc tggagcccaa gtccacctac atcatctgca   1860
tggtcaccat ggagaccagc aatgcctacg tagctgatga gacacccgtg tgtgccaagg   1920
cagagacagc cgacagctat ggccctacca ccacactcaa ccaggagcag aacgctggcc   1980
ccatggcgag cctgcccctg gcgggcatca tcggcggggc agtggctctg gtcttcctct   2040
tcctggtcct gggggccatc tgctggtacg tgcaccaggc tggcgagctg ctgacccggg   2100
agagggccta caaccggggc agcaggaaaa aggatgacta tatggagtca gggaccaaga   2160
aggataactc catcctggaa atccgcggcc ctgggctgca gatgctgccc atcaacccgt   2220
accgcgccaa agaggagtac gtggtccaca ctatcttccc ctccaacggc agcagcctct   2280
gcaaggccac acacaccatt ggctacggca ccacgcgggg ctaccgggac ggcggcatcc   2340
ccgacataga ctactcctac acatgatgcc cgcccacccg ggctgccccg cctcagcccc   2400
agctgccctg gcgtggccat gtggctttgc ccagcctgct gcaatccaag agagcaagga   2460
agagaaattc catgggtgac tttcctccgc agaaagcaaa gtttggggag ggctgacgat   2520
tttgtagaac acaacagtga caattttttt taaaagaata gaaggcagga gggggaattc   2580
gacattgttg aagacataat ttataccaag ttatgccagt tggggaggga aggactaaaa   2640
ataatattgc aggcagggct gggttgggtt tttttttttt ccccccctgaa ctggaaggat  2700
actacctgta caacatctgt ggacacctca tgctctgttc aaggccatca caaaggaacc   2760
gccagggaga agcagccggc tctcaaagct cccacgcagc tctcccgcca ctggccactc   2820
gctggcgacc cgatggaagg ttttcaggct cctcacaaag gagagaggga agaaaagatc   2880
ttttgccctg gagatatggt cctgaaatct ctcccctggc ttattccata ccatttccct   2940
tgcagatttg cagaaacatg gcatctttca ctgcattctt tgaacaatca tgtagtcgat   3000
taaaaaaaaa aaacaaactt ttttttccta ggctgaagcc ctcttcagtt ccatgcacca   3060
cgctccgtag aagccccggc ggaagccgta gctttccctg ccacctggag gtgcatctgt   3120
ctgcctgtct atccctgtcg cggtgtctct aagtacagat gggtagatag agccacatgc   3180
acggtcctta ccgttcttct tgggtcagtt cttaccattt cctgaacaat agaattgtga   3240
aagtgttaaa aa                                                       3252
```

<210> SEQ ID NO 139
<211> LENGTH: 3005
<212> TYPE: DNA
<213> ORGANISM: Homo sapiens

<400> SEQUENCE: 139
ggtctggcac aggcacgcac actctcagta gactctttca ctcctctctc tcttcctctc 60
tcacacgttc tccaacccaa ggaggccaga cagagggacg tggtcactct ctgaaaagtt 120
caacttgaga gacaaaatgc agtggacctc cctcctgctg ctggcagggc tcttctccct 180
ctcccaggcc cagtatgaag atgaccctca ttggtggttc cactacctcc gcagccagca 240
gtccacctac tacgatccct atgaccctta cccgtatgag acctacgagc cttaccccta 300
tggggtggat gaagggccag cctacaccta cggctctcca tcccctccag atccccgcga 360
ctgcccccag gagtgcgact gcccacccaa cttccccacg gccatgtact gtgacaatcg 420
caacctcaag tacctgccct tcgttccctc ccgcatgaag tatgtgtact tccagaacaa 480
ccagatcacc tccatccagg aaggcgtctt tgacaatgcc acagggctgc tctggattgc 540
tctccacggc aaccagatca ccagtgataa ggtgggcagg aaggtcttct ccaagctgag 600
gcacctggag aggctgtacc tggaccacaa caacctgacc cggatgcccg gtcccctgcc 660
tcgatccctg agagagctcc atctcgacca caaccagatc tcacgggtcc ccaacaatgc 720
tctggagggg ctggagaacc tcacggcctt gtacctccaa cacaatgaga tccaggaagt 780
gggcagttcc atgaggggcc tccggtcact gatcttgctg gacctgagtt ataaccacct 840
tcggaaggtg cctgatgggc tgccctcagc tcttgagcag ctgtacatgg agcacaacaa 900
tgtctacacc gtccccgata gctacttccg gggggcgccc aagctgctgt atgtgcggct 960
gtcccacaac agtctaacca acaatggcct ggcctccaac accttcaatt ccagcagcct 1020
ccttgagcta gacctctcct acaaccagct gcagaagatc cccccagtca acaccaacct 1080
ggagaacctc tacctccaag gcaataggat caatgagttc tccatcagca gcttctgcac 1140
cgtggtggac gtcgtgaact tctccaagct gcaggtgctg cgcctggacg ggaacgagat 1200
caagcgcagc gccatgcctg ccgacgcgcc cctctgcctg cgccttgcca gcctcatcga 1260
gatctgagca gccctggcac cgggtactgg gcggagagcc cccgtggcat ttggcttgat 1320
ggtttggttt ggcttttgct ggaaggtcca ggatggacca tgtgacagaa gtccacgggc 1380
accctctgta gtcttctttc ctgtaggtgg ggttaggggg ggcgatcagg gacaggcagc 1440
cttctgctga ggacataggc agaagctcac tcttttccag ggacagaagt ggtggtagat 1500
ggaaggatcc ctggatgttc caaccccata aatctcacgg ctcttaagtt cttcccaatg 1560
atctgaggtc atggaacttc aaaagtggca tgggcaatag tatataacca tacttttcta 1620
acaatccctg gctgtctgtg agcagcactt gacagctctc cctctgtgct gggctggtcg 1680
tgcagttact ctgggctccc atttgttgct tctcaaaata tacctcttgc ccagctgcct 1740
cttctgaaat ccacttcacc cactccactt tcctccacag atgcctcttc tgtgccttaa 1800
gcagagtcag gagaccccaa ggcatgtgag catctgccca gcaacctgtg gagacaaccc 1860
acactgtgtc tgagggtgaa aggacaccag gagtcacttc tatacctccc taacctcacc 1920
cctggaaagc caccagattg gaggtcacca gcatgatgat aatattcatg acctgatgtg 1980
ggaggagaca gccaacctca ggcttagatc aatgtatagg gctatatttt ggcagctggg 2040
tagctctttg aaggtggata agacttcaga agaggaaagg ccagactttg cttaccatca 2100
gcatctgcaa tgggccaaac acacctcaaa ttggctgagt tgagaaagca gccccagtag 2160

```
ttccattctt gcccagcact ttctgcattc caaacagcat cctacctggg tttttatcca   2220
caaaggtagc ggccacatgg tttttaaagt atgagaaaca cagtttgtcc tctcctttta   2280
tccaagcagg aagattctat atcctgatgg tagagacaga ctccaggcag ccctggactt   2340
gctagcccaa agaaggagga tgtggttaat ctgtttcacc tggtttgtcc taaggccata   2400
gttaaaaagt accagctctg gctggggtcc gtgaagccca ggccaggcag ccaaatcttg   2460
cctgtgctgg gcatacaacc ctctgctttc acatctctga gctatatcct cattagtgaa   2520
ggtggctttt gctttatagt ttggctgggg agcacttaat tcttcccatt tcaaaaggta   2580
atgttgcctg gggcttaacc cacctgccct ttgggcaagg ttgggacaaa gccatctggg   2640
cagtcagggg caaggactgt tggaggagag ttagcccaag tataggctct gcccagatgc   2700
catcacatcc ctgatactgt gtatgctttg aagcaccttc cctgagaagg gaagagggga   2760
tctttggact acgttcttgg ctccagacct ggaatccaca aaagccaaac cagctcattt   2820
caacaaagga gctccgatgt gaggggcaag gctgcccccct gccccagggc tcttcagaaa   2880
gcatctgcat gtgaacacca tcatgccttt ataaaggatc cttattacag gaaaagcatg   2940
agtggtggct aacctgacca ataaagttat tttatgattg catctaaaaa aaaaaaaaaa   3000
aaaaa                                                                3005
```

<210> SEQ ID NO 140
<211> LENGTH: 4339
<212> TYPE: DNA
<213> ORGANISM: Homo sapiens

<400> SEQUENCE: 140

```
agagccggag gagggggaag gagggagggg agagcggtgg cggcggctgc gccgggctgt     60
gagtctctcg ccgccggagg aagatgaggc tgaagattgg gttcatctta cgcagtttgc    120
tggtggtggg aagcttcctg ggctagtgg tcctctggtc ttccctgacc ccgcggccgg    180
acgacccaag cccgctgagc aggatgaggg aagacagaga tgtcaatgac cccatgccca    240
accgaggcgg caatggacta gctcctgggg aggacagatt caaacctgtg gtaccatggc    300
ctcatgttga aggagtagaa gtggacttag agtctattag aagaataaac aaggccaaaa    360
atgaacaaga gcaccatgct ggaggagatt cccagaaaga tatcatgcag aggcagtatc    420
tcacatttaa gcctcagaca ttcacctacc atgatcctgt gcttcgccca gggatcctcg    480
gtaactttga acccaaagaa cctgagcctc ctggagtggt tggtggccct ggagagaaag    540
ccaagccatt ggttttggga ccagaattca aacaagcaat tcaagccagc attaaagagt    600
ttggatttaa catggtggca agtgacatga tctcactgga ccgcagcgtc aatgacttac    660
gccaagaaga atgcaagtat tggcattatg atgaaaactt gctcacttcg agcgttgtca    720
ttgtcttcca taatgaagga tggtcaaccc tcatgagaac agtccacagt gtaattaaaa    780
ggactccaag gaaatattta gcagaaattg tgttaattga cgatttcagt aataaagaac    840
acttaaaaga aaaactggat gaatatatta agctgtggaa tggcctagtg aaggtatttc    900
gaaatgaaag aagggaaggt ttaattcaag cacgaagtat tggtgctcag aaggctaaac    960
ttggacaggt tttgatatac cttgatgccc actgtgaggt ggcagttaac tggtatgcac   1020
cacttgtagc tcccatatct aaggacagaa ccatttgcac tgtgccgctt atagatgtca   1080
taaatggcaa cacatatgaa attatacccc aagggggtgg tgatgaagat gggtatgccc   1140
gaggagcatg ggattggagt atgctctgga aacgggtgcc tctgacccct caagagaaga   1200
```

```
gactgagaaa gacaaaaact gaaccgtatc ggtccccagc catggctggg ggattatttg   1260
ccattgaacg agagttcttc tttgaattgg gtctctatga tccaggtctc cagatttggg   1320
gtggtgaaaa ctttgagatc tcatacaaga tatggcagtg tggtggcaaa ttattatttg   1380
ttccttgttc tcgtgttgga catatctacc gtcttgaggg ctggcaagga aatcctccgc   1440
ccatttatgt tgggtcttct ccaactctga agaattatgt tagagttgtg gaggtttggt   1500
gggatgaata taaagactac ttctatgcta gtcgtcctga atcgcaggca ttaccatatg   1560
gggatatatc ggagctgaaa aaatttcgag aagatcacaa ctgcaaaagt tttaagtggt   1620
tcatggaaga aatagcttat gatatcacct cacactaccc tttgccaccc aaaaatgttg   1680
actggggaga aatcagaggc ttcgaaactg cttactgcat tgatagcatg ggaaaaacaa   1740
atggaggctt tgttgaacta ggaccctgcc acaggatggg agggaatcag cttttcagaa   1800
tcaatgaagc aaatcaactc atgcagtatg accagtgttt gacaaaggga gctgatggat   1860
caaaagttat gattacacac tgtaatctaa atgaatttaa ggaatggcag tacttcaaga   1920
acctgcacag atttactcat attccttcag gaaagtgttt agatcgctca gaggtcctgc   1980
atcaagtatt catctccaat tgtgactcca gtaaaacgac tcaaaaatgg gaaatgaata   2040
acatccatag tgtttagaga gaaaaaaata aaccaataac ctacctactg acaagtaaat   2100
ttatacagga ctgaaaaccg cctgaaacct gctgcaacta ttgttattaa ctctgtatag   2160
ctccaaacct ggaacctcct gatcagtttg aaggacattg ataaactgtg attttacaat   2220
aacattatca tctgcagtta ctgtttacaa gactgctttt accttaaact ttgtagatgt   2280
ttacatcttt ttgttgtgtt ttaagatgat gttggtaatt tgtgccttta gctctgtttt   2340
attagacaga gttaaagcat gttgtcttct ttgggattac actcaggggt ctgaaaggca   2400
gtttgatttt tatttttaac acacttgaaa aaaggttgga gtagccagac tttcatatat   2460
aacttggtga ttatcaacct gttgtgtctt tatttaattt tacatctttt tgaagcactg   2520
ccacaggtta ttagccaagg tggccttcct tcacagtcat gctgcttttt tgaaaggtga   2580
atttcaacac atttagtgcc tctttcattt ctcagtatat atttcaagag cttgtgatga   2640
aatctatagg atggtaatga tggacttgtc acctgtatgg ggaatacttt tactactcag   2700
aaatgaattt atgtgctgcc atttgctata aagttgaact ttgtatggct tgaaaaagaa   2760
atgacaatat ggaacatccc aaggctgtcc catagggttg gaagttgtgt agcattcact   2820
cccttaccta ctggcattcc cagtgccctc tgtccatacc tacttctagg attgcaaagg   2880
agtcttccaa ctagagaaaa attgtccact gacatttggg atttactttt ctccaatacc   2940
tgccaataca gaaaactatt atcagttgtt attgttatcc cttgaaagcg agggtgacaa   3000
aaacaacaaa acaccgttat aaacacatca aaggttcatt ctgactgagg taagactttc   3060
caagcccttg ttagattagg ccttataaaa cttgtgtgca ttataaccta agctgtgcaa   3120
cctgtgaagc caagagtgaa ctgatgtttc atttatattt tcatccaaat gacattatct   3180
gcacgttttt aaaatttaaa aacaaaggac tatttaaaaa tacagtttat taacaaacgt   3240
gaactacttt ctgttacatt aggtgttccc tagtgtttct taatttcttt ttagaaagtg   3300
tatttttatt agtatttttc cggtgaacag aagatttgtt tggatttaaa catttactaa   3360
gacagtacct attaggaaaa ccaaatattg caaatggtca attcgatttt aatttctcaa   3420
aagatactct gttatccaga agattaaaat gcctacattg agtgcttaaa aaaaaaaaaa   3480
caactgtgat gatgtgagca gaatggcaag taagttaagc atttttgatc ctgtaatcat   3540
ggtatcatta caatgaaagg aattcacaaa ctactgccag aggaagtttg tttttaatt   3600
```

-continued taagagggaa atataaccta taaatttgtt tcttccaagc ttagctctta aatttggaga 3660
ctcaaagtta aacatcctca acagagtttt atttataatt ttgaattgtc aatttgtatt 3720
ttgctactga tctgtgatca accattttaa ctttcatctc tagggatgtt taacatttat 3780
aattgcaaaa taaaccaact ataaaaaaag aaactaagag agaattggta ctttaattac 3840
ttgtgtgttt gcaaataggc tccattttcc atgttgagta gattataacc ttattaacta 3900
tgcataggcc taagaaaggt ggcaatgaac tgtgcatgta aattttaaat gggtactttg 3960
tgcaattcgt taaaagaaga tactctatga atatgattct atatattgaa atcagaaaac 4020
ctaccaaaca aaaacatcag aagctgctgc cataatgact attttctact gtaggctgct 4080
ttggaaataa ttcccatatc cttgctttgt aagttggtaa tatcactatg catttctaca 4140
cattttataa atttgattta tgcagatttt gatacactgt atgtttctgt agaaattgta 4200
taaatattca aaattttatt aggataaatt tgagaaactt acgtatatct taattctggg 4260
ttgcttgttt tttaggtgac aaaaataaaa tattgtattt taattcaaaa aaaaaaaaaa 4320
aaaaaaaaaa aaaaaaaaa 4339

<210> SEQ ID NO 141
<211> LENGTH: 2602
<212> TYPE: DNA
<213> ORGANISM: Homo sapiens

<400> SEQUENCE: 141
ttgcgacgct cgggtctggg tccgggtccg gacgtgcaac agaagccgtc agtggccccg 60
ctggctaaaa aagggcaagc atcggaggct cgagccagcg gccgcggcgc ttcccgacag 120
ttcctaattc ggggcgctac gccggcccca ccacctgttc ccggcagcca atggggccgc 180
ggggggcggc cggggcggag cgcggctaca aaaggcctcg ggccccgcgc gcccgcccac 240
cccgctccgg gcgcgctctc gggaaggctt ggaccgacgc ggcccagagg ccaggaacat 300
tccgcgcgtg gaccagccgg gccagggcga tgctgcgggt gcggtgtctg cgcggcggga 360
gccgcggcgc cgaggcggtg cactacatcg gatctcggct tggacgaacc ttgacaggat 420
gggtgcagcg aactttccag agcacccagg cagctacggc ttcctcccgg aactcctgtg 480
cagctgacga caaagccact gagcctctgc ccaaggactg ccctgtctct tcttacaacg 540
aatgggaccc cttagaggaa gtgatagtgg gcagagcaga aaacgcctgt gttccaccgt 600
tcaccatcga ggtgaaggcc aacacatatg aaaagtactg gccattttac cagaagcaag 660
gagggcatta ttttcccaaa gatcatttga aaaaggctgt tgctgaaatt gaagaaatgt 720
gcaatatttt aaaaacggaa ggagtgacag taaggaggcc tgaccccatt gactggtcat 780
tgaagtataa aactcctgat tttgagtcta cgggtttata cagtgcaatg cctcgagaca 840
tcctgatagt tgtgggcaat gagattatcg aggctcccat ggcatggcgt tcacgcttct 900
ttgagtaccg agcgtacagg tcaattatca aagactactt ccaccgtggc gccaagtgga 960
caacagctcc taagcccaca atggctgatg agctttataa ccaggattat cccatccact 1020
ctgtagaaga cagacacaaa ttggctgctc agggaaaatt tgtgacaact gagtttgagc 1080
catgctttga tgctgctgac ttcattcgag ctggaagaga tatttttgca cagagaagcc 1140
aggttacaaa ctacctaggc attgaatgga tgcgtaggca tcttgctcca gactacagag 1200
tgcatatcat ctcctttaaa gatcccaatc ccatgcatat tgatgctacc ttcaacatca 1260
ttggacctgg tattgtgctt tccaaccctg accgaccatg tcaccagatt gatcttttca 1320
agaaagcagg atggactatc attactcctc caacaccaat catcccagac gatcatccac 1380
tctggatgtc atccaaatgg ctttccatga atgtcttaat gctagatgaa aaacgtgtta 1440
tggtggatgc caatgaagtt ccaattcaaa agatgtttga aaagctgggt atcactacca 1500
ttaaagttaa cattcgtaat gccaattccc tgggaggagg cttccattgc tggacctgcg 1560
atgtccggcg ccgaggcacc ttacagtcct acttggactg aacaggcctg atggagcttg 1620
tggctggcct cagatacacc taagaagctt aggggcaagg ttcattctcc tgctttaaaa 1680
agtgcatgaa ctgtagtgct ttaaacaatc atctccttaa caggggtcgt aagcctggtt 1740
tgcttctatt actttcttt gacataaaga aaataacttc tgctaggtat tactctctac 1800
tcctaaagtt atttactatt tggcttcaag tataaaattt tggtgaatgt gtaccaagaa 1860
aaaattagtc acctgagtaa cttggccact aataattaac catctacctc tgtttttaat 1920
tttctttcca aaaggcagct tgaaatgttg gtcctaatct taattttttt tcctcttcta 1980
tagacttgag aatgtttttc tctaaatgag agaaagactt agaatgtaca cagatccaaa 2040
atagaatcag attatctctt tttttctaaa ggagagaaag acttagaaca tacacagatc 2100
ctaagtagaa ccaggtaatt gtctcttttt ctaataagga atttgggtaa tttttaattt 2160
tttgtttttt aaaaaaataac ctagactatg caaaacatca aagtgaattt tccatgaatg 2220
tttttaatat tctcatctca acattgtgat atatgctact aaaaaccttt tcatatacat 2280
cttacctcat ttcaagtgaa ttattttaat ctttttctct ctttccaaaa atttaggaat 2340
gtttagtgta attggatttc gctatcagtt cccatcctta agttttgata ttcaatatct 2400
gatagataca ctgcatcttt ggtcatctaa gatttgttta caaatgtgca aattatttag 2460
agcatagact ttataagcat taaaaaaaac taatggaggt aaaacctaaa tgcgatgtga 2520
aataatttta gtgttgatac cgtatgtgta tttttattct aataaacttt tgtgttccag 2580
attgaaaaaa aaaaaaaaaa aa 2602

<210> SEQ ID NO 142
<211> LENGTH: 1920
<212> TYPE: DNA
<213> ORGANISM: Homo sapiens

<400> SEQUENCE: 142
ccacagttcc tttccccgat agcttcaaat tctctgcctt ttgaaataag cctactttta 60
actggaataa ataattggtc aatctctacc tcaggtgaag aggaaccaag cctctggaaa 120
cacttaggaa caaactgtaa aaaccaaagg caattgtgta accggttaaa taagcttgct 180
ggactttgtc cctgtgtatg agttagacaa ttctttcagc tagtttgagt gacgcactga 240
ccagtgaagc gcagtgaagc agtgggaacc ggaatatcca aagagtggtt tgaaggagaa 300
agaagcattg tggctttata tcctctgggc ctgggtttcc tgaagtcacc acacatagag 360
gagagagaaa atggctgagt taaagtacat ttctggattt gggaatgagt gttcttcaga 420
ggatcctcgc tgcccaggtt ccctgccaga aggacagaat aatcctcagg tctgcccccta 480 caatctctat gctgagcagc tctcaggatc ggctttcact tgtccacgga gcaccaataa 540
gagaagctgg ctgtatagga ttctaccttc agtttctcac aagccctttg aatccattga 600
cgaaggccaa gtcactcaca actgggatga agttgatcct gatcctaacc agcttagatg 660
gaaaccattt gagattccaa aagcatctca gaagaaagta gactttgtga gtggcctgca 720
taccttgtgt ggagctggag acataaagtc taacaatggg cttgctatcc acattttcct 780
ctgcaatacc tccatggaga acagatgctt ttacaattca gatggggact tcttgattgt 840

```
tccgcagaaa gggaaccttc tcatttacac cgagtttggc aagatgcttg tacagcccaa    900
tgagatctgc gtcattcaga gaggaatgcg gttcagcata gatgtctttg aggagaccag    960
gggctacatc ttggaggtct atggtgtcca ctttgagtta cctgaccttg gaccaattgg   1020
ggccaatggc ttggccaatc ctcgtgattt cttgataccc attgcctggt atgaggatcg   1080
ccaagtacca ggtggttaca cggtcattaa taaataccag ggcaagctgt ttgctgccaa   1140
acaggatgtc tccccgttca atgttgtggc ctggcacggg aattatacac cctacaagta   1200
caacctgaag aatttcatgg ttatcaactc agtggccttt gaccatgcag acccatccat   1260
tttcacagta ttgactgcta agtctgtccg ccctggagtg gccattgctg attttgtcat   1320
cttcccacct cgatgggggg ttgctgataa gaccttcagg cctccttatt accataggaa   1380
ctgcatgagt gagttcatgg gactcatccg aggtcactat gaggcaaagc aaggtgggtt   1440
cctgccaggg ggagggagtc tacacagcac aatgaccccc catggacctg atgctgactg   1500
ctttgagaag gccagcaagg tcaagctggc acctgagagg attgccgatg gcaccatggc   1560
atttatgttt gaatcatctt taagtctggc ggtcacaaag tggggactca aggcctccag   1620
gtgtttggat gagaactacc acaagtgctg ggagccactc aagagccact tcactcccaa   1680
ctccaggaac ccagcagaac ctaattgaga ctggaacatt gctaccataa ttaagagtag   1740
atttgtgaag atttcttcag aatctcatgc tttctggtag tattggagga gggggttggt   1800
taaaatgaaa attcactttt catagtcaag taactcagaa cttttatgga aacgcatttg   1860
caaagttcta tggctgtcac cttaattact caataaactt gctggtgttc tgtggacgta   1920
```

<210> SEQ ID NO 143
<211> LENGTH: 4150
<212> TYPE: DNA
<213> ORGANISM: Homo sapiens

<400> SEQUENCE: 143

```
cttgaatctt ggggcaggaa ctcagaaaac ttccagcccg ggcagcgcgc gcttggtgca     60
agactcagga gctagcagcc cgtccccctc cgactctccg gtgccgccgc tgcctgctcc    120
cgccacccta ggaggcgcgg tgccacccac tactctgtcc tctgcctgtg ctccgtgccc    180
gaccctatcc cggcggagtc tccccatcct cctttgcttt ccgactgccc aaggcacttt    240
caatctcaat ctcttctctc tctctctctc tctctctctc tctctctctc tctctctctc    300
tctctctctc gcagggtggg gggaagagga ggaggaattc tttccccgcc taacatttca    360
agggacacaa ttcactccaa gtctcttccc tttccaagcc gcttccgaag tgctcccggt    420
gcccgcaact cctgatccca acccgcgaga ggagcctctg cgacctcaaa gcctctcttc    480
cttctccctc gcttccctcc tcctcttgct acctccacct ccaccgccac ctccacctcc    540
ggcacccacc caccgccgcc gccgccaccg gcagcgcctc ctcctctcct cctcctcctc    600
ccctcttctc tttttggcag ccgctggacg tccggtgttg atggtggcag cggcggcagc    660
ctaagcaaca gcagccctcg cagcccgcca gctcgcgctc gccccgccgg cgtccccagc    720
cctatcacct catctcccga aaggtgctgg gcagctccgg ggcggtcgag gcgaagcggc    780
tgcagcggcg gtagcggcgg cgggaggcag gatgagcgca cgcggtgagg gcgcggggca    840
gccgtccact tcagcccagg gacaacctgc cgccccagcg cctcagaaga gaggacgcgg    900
ccgccccagg aagcagcagc aagaaccaac cggtgagccc tctcctaaga gacccagggg    960
aagacccaaa ggcagcaaaa acaagagtcc ctctaaagca gctcaaaaga aagcagaagc   1020
```

-continued

```
cactggagaa aaacggccaa gaggcagacc taggaaatgg ccacaacaag ttgttcagaa   1080
gaagcctgct caggaggaaa ctgaagagac atcctcacaa gagtctgccg aagaggacta   1140
gggggcgcca acgttcgatt tctacctcag cagcagttgg atcttttgaa gggagaagac   1200
actgcagtga ccacttattc tgtattgcca tggtctttcc actttcatct ggggtggggt   1260
ggggtggggt gggggagggg ggggtggggt ggggagaaat cacataacct taaaaaggac   1320
tatattaatc accttctttg taatcccttc acagtcccag gtttagtgaa aaactgctgt   1380
aaacacaggg gacacagctt aacaatgcaa cttttaatta ctgttttctt ttttcttaac   1440
ctactaatag tttgttgatc tgataagcaa gagtgggcgg gtgagaaaaa ccgaattggg   1500
tttagtcaat cactgcactg catgcaaaca agaaacgtgt cacacttgtg acgtcgggca   1560
ttcatatagg aagaacgcgg tgtgtaacac tgtgtacacc tcaaatacca ccccaaccca   1620
ctccctgtag tgaatcctct gtttagaaca ccaaagataa ggactagata ctactttctc   1680
tttttcgtat aatcttgtag acacttactt gatgattttt aactttttat ttctaaatga   1740
gacgaaatgc tgatgtatcc tttcattcag ctaacaaact agaaaaggtt atgttcattt   1800
ttcaaaaagg gaagtaagca aacaaatatt gccaactctt ctatttatgg atatcacaca   1860
tatcagcagg agtaataaat ttactcacag cacttgtttt caggacaaca cttcattttc   1920
aggaaatcta cttcctacag agccaaaatg ccatttagca ataaataaca cttgtcagcc   1980
tcagagcatt taaggaaact agacaagtaa aattatcctc tttgtaattt aatgaaaagg   2040
tacaacagaa taatgcatga tgaactcacc taattatgag gtgggaggag cgaaatctaa   2100
atttcttttg ctatagttat acatcaattt aaaaagcaaa aaaaaaaaag ggggggcaa    2160
tctctctctg tgtctttctc tctctctctt cctctccctc tctcttttca ttgtgtatca   2220
gtttccatga aagacctgaa taccacttac ctcaaattaa gcatatgtgt tacttcaagt   2280
aatacgtttt gacataagat ggttgaccaa ggtgcttttc ttcggcttga gttcaccatc   2340
tcttcattca aactgcactt ttagccagag atgcaatata tccccactac tcaatactac   2400
ctctgaatgt tacaacgaat ttacagtcta gtacttatta catgctgcta tacacaagca   2460
atgcaagaaa aaaacttact gggtaggtga ttctaatcat ctgcagttct ttttgtacac   2520
ttaattacag ttaaagaagc aatctcctta ctgtgtttca gcatgactat gtatttttct   2580
atgttttttt aattaaaaat ttttaaaata cttgtttcag cttctctgct agatttctac   2640
attaacttga aaattttta accaagtcgc tcctaggttc ttaaggataa ttttcctcaa    2700
tcacactaca catcacacaa gatttgactg taatatttaa atattaccct ccaagtctgt   2760
acctcaaatg aattctttaa ggagatggac taattgactt gcaaagacct acctccagac   2820
ttcaaaagga atgaacttgt tacttgcagc attcatttgt tttttcaatg tttgaaatag   2880
ttcaaactgc agctaaccct agtcaaaact atttttgtaa aagacatttg atagaaagga   2940
acacgttttt acatactttt gcaaaataag taaataataa ataaaataaa agccaacctt   3000
caaagaaact tgaagctttg taggtgagat gcaacaagcc ctgcttttgc ataatgcaat   3060
caaaaatatg tgtttttaag attagttgaa tataagaaaa tgcttgacaa atattttcat   3120
gtattttaca caaatgtgat ttttgtaata tgtctcaacc agatttattt taaacgcttc   3180
ttatgtagag tttttatgcc tttctctcct agtgagtgtg ctgacttttt aacatggtat   3240
tatcaactgg gccaggaggt agtttctcat gacggctttt gtcagtatgg cttttagtac   3300
tgaagccaaa tgaaactcaa aaccatctct cttccagctg cttcagggag gtagtttcaa   3360
aggccacata cctctctgag actggcagat cgctcactgt tgtgaatcac caaaggagct   3420
```

atggagagaa ttaaaactca acattactgt taactgtgcg ttaaataagc aaataaacag 3480
tggctcataa aaataaaagt cgcattccat atctttggat gggcctttta gaaacctcat 3540
tggccagctc ataaaatgga agcaattgct catgttggcc aaacatggtg caccgagtga 3600
tttccatctc tggtaaagtt acacttttat ttcctgtatg ttgtacaatc aaaacacact 3660
actacctctt aagtcccagt atacctcatt tttcatactg aaaaaaaaag cttgtggcca 3720
atggaacagt aagaacatca taaaattttt atatatatag tttatttttg tgggagataa 3780
attttatagg actgttcttt gctgttgttg gtcgcagcta cataagactg gacatttaac 3840
ttttctacca tttctgcaag ttaggtatgt ttgcaggaga aaagtatcaa gacgtttaac 3900
tgcagttgac tttctccctg ttcctttgag tgtcttctaa ctttattctt tgttctttat 3960
gtagaattgc tgtctatgat tgtactttga atcgcttgct tgttgaaaat atttctctag 4020
tgtattatca ctgtctgttc tgcacaataa acataacagc ctctgtgatc cccatgtgtt 4080
ttgattcctg ctctttgtta cagttccatt aaatgagtaa taaagtttgg tcaaaacaga 4140
aaaaaaaaaa 4150

<210> SEQ ID NO 144
<211> LENGTH: 980
<212> TYPE: DNA
<213> ORGANISM: Homo sapiens

<400> SEQUENCE: 144
gcggcggcgg gcagcagctg cgctgcgact gctctggaag gagaggacgg ggcacaaacc 60
ctgaccatga ccccccacag gctgctgcca ccgctgctgc tgctgctagc tctgctgctc 120
gctgccagcc caggaggcgc cttggcgcgg tgcccaggct gcgggcaagg ggtgcaggcg 180
ggttgtccag ggggctgcgt ggaggaggag gatgggggt cgccagccga gggctgcgcg 240
gaagctgagg gctgtctcag gagggagggg caggagtgcg ggtctacac ccctaactgc 300 gccccaggac tgcagtgcca tccgcccaag gacgacgagg cgcctttgcg ggcgctgctg 360
ctcggccgag gccgctgcct tccggcccgc gcgcctgctg ttgcagagga gaatcctaag 420
gagagtaaac cccaagcagg cactgcccgc ccacaggatg tgaaccgcag agaccaacag 480
aggaatccag gcacctctac cacgccctcc cagcccaatt ctgcgggtgt ccaagacact 540
gagatgggcc catgccgtag acatctggac tcagtgctgc agcaactcca gactgaggtc 600
taccgagggg ctcaaacact ctacgtgccc aattgtgacc atcgaggctt ctaccggaag 660
cggcagtgcc gctcctccca ggggcagcgc cgaggtccct gctggtgtgt ggatcggatg 720
ggcaagtccc tgccagggtc tccagatggc aatggaagct cctcctgccc cactgggagt 780
agcggctaaa gctgggggat agaggggctg cagggccact ggaaggaaca tggagctgtc 840
atcactcaac aaaaaaccga ggccctcaat ccaccttcag gccccgcccc atgggcccct 900
caccgctggt tggaaagagt gttggtgttg gctggggtgt caataaagct gtgcttgggg 960
tcgctgaaaa aaaaaaaaaa 980

<210> SEQ ID NO 145
<211> LENGTH: 5190
<212> TYPE: DNA
<213> ORGANISM: Homo sapiens

<400> SEQUENCE: 145
tctgggggct cggctttgcc gcgctcgctg cacttgggcg agagctggaa cgtggaccag 60

-continued agctcggatc ccatcgcagc taccgcgatg agaggcgctc gcggcgcctg ggattttctc 120
tgcgttctgc tcctactgct tcgcgtccag acaggctctt ctcaaccatc tgtgagtcca 180
ggggaaccgt ctccaccatc catccatcca ggaaaatcag acttaatagt ccgcgtgggc 240
gacgagatta ggctgttatg cactgatccg ggctttgtca aatggacttt tgagatcctg 300
gatgaaacga atgagaataa gcagaatgaa tggatcacgg aaaaggcaga agccaccaac 360
accggcaaat acacgtgcac caacaaacac ggcttaagca attccattta tgtgtttgtt 420
agagatcctg ccaagctttt ccttgttgac cgctccttgt atgggaaaga agacaacgac 480
acgctggtcc gctgtcctct cacagaccca gaagtgacca attattccct caaggggtgc 540
caggggaagc ctcttcccaa ggacttgagg tttattcctg accccaaggc gggcatcatg 600
atcaaaagtg tgaaacgcgc ctaccatcgg ctctgtctgc attgttctgt ggaccaggag 660
ggcaagtcag tgctgtcgga aaaattcatc ctgaaagtga ggccagcctt caaagctgtg 720
cctgttgtgt ctgtgtccaa agcaagctat cttcttaggg aaggggaaga attcacagtg 780
acgtgcacaa taaaagatgt gtctagttct gtgtactcaa cgtggaaaag agaaaacagt 840
cagactaaac tacaggagaa atataatagc tggcatcacg gtgacttcaa ttatgaacgt 900
caggcaacgt tgactatcag ttcagcgaga gttaatgatt ctggagtgtt catgtgttat 960
gccaataata cttttggatc agcaaatgtc acaacaacct tggaagtagt agataaagga 1020
ttcattaata tcttccccat gataaacact acagtatttg taaacgatgg agaaaatgta 1080
gatttgattg ttgaatatga agcattcccc aaacctgaac accagcagtg gatctatatg 1140
aacagaacct tcactgataa atgggaagat tatcccaagt ctgagaatga aagtaatatc 1200
agatacgtaa gtgaacttca tctaacgaga ttaaaaggca ccgaaggagg cacttacaca 1260
ttcctagtgt ccaattctga cgtcaatgct gccatagcat ttaatgttta tgtgaataca 1320
aaaccagaaa tcctgactta cgacaggctc gtgaatggca tgctccaatg tgtggcagca 1380
ggattcccag agcccacaat agattggtat ttttgtccag gaactgagca gagatgctct 1440
gcttctgtac tgccagtgga tgtgcagaca ctaaactcat ctgggccacc gtttggaaag 1500
ctagtggttc agagttctat agattctagt gcattcaagc acaatggcac ggttgaatgt 1560
aaggcttaca acgatgtggg caagacttct gcctatttta actttgcatt taaaggtaac 1620
aacaaagagc aaatccatcc ccacaccctg ttcactcctt tgctgattgg tttcgtaatc 1680
gtagctggca tgatgtgcat tattgtgatg attctgacct acaaatattt acagaaaccc 1740
atgtatgaag tacagtggaa ggttgttgag gagataaatg gaaacaatta tgtttacata 1800
gacccaacac aacttcctta tgatcacaaa tgggagtttc ccagaaacag gctgagtttt 1860
gggaaaaccc tgggtgctgg agctttcggg aaggttgttg aggcaactgc ttatggctta 1920
attaagtcag atgcggccat gactgtcgct gtaaagatgc tcaagccgag tgcccatttg 1980
acagaacggg aagccctcat gtctgaactc aaagtcctga gttaccttgg taatcacatg 2040
aatattgtga atctacttgg agcctgcacc attggagggc ccaccctggt cattacagaa 2100
tattgttgct atggtgatct tttgaatttt ttgagaagaa aacgtgattc atttatttgt 2160
tcaaagcagg aagatcatgc agaagctgca ctttataaga atcttctgca ttcaaaggag 2220
tcttcctgca gcgatagtac taatgagtac atggacatga aacctggagt ttcttatgtt 2280
gtcccaacca aggccgacaa aaggagatct gtgagaatag gctcatacat agaaagagat 2340
gtgactcccg ccatcatgga ggatgacgag ttggccctag acttagaaga cttgctgagc 2400
ttttcttacc aggtggcaaa gggcatggct ttcctcgcct ccaagaattg tattcacaga 2460

-continued gacttggcag ccagaaatat cctccttact catggtcgga tcacaaagat ttgtgatttt 2520
ggtctagcca gagacatcaa gaatgattct aattatgtgg ttaaaggaaa cgctcgacta 2580
cctgtgaagt ggatggcacc tgaaagcatt ttcaactgtg tatacacgtt tgaaagtgac 2640
gtctggtcct atgggatttt tctttgggag ctgttctctt taggaagcag cccctatcct 2700
ggaatgccgg tcgattctaa gttctacaag atgatcaagg aaggcttccg gatgctcagc 2760
cctgaacacg cacctgctga aatgtatgac ataatgaaga cttgctggga tgcagatccc 2820
ctaaaaagac caacattcaa gcaaattgtt cagctaattg agaagcagat ttcagagagc 2880
accaatcata tttactccaa cttagcaaac tgcagcccca accgacagaa gcccgtggta 2940
gaccattctg tgcggatcaa ttctgtcggc agcaccgctt cctcctccca gcctctgctt 3000
gtgcacgacg atgtctgagc agaatcagtg tttgggtcac ccctccagga atgatctctt 3060
cttttggctt ccatgatggt tattttcttt tctttcaact tgcatccaac tccaggatag 3120
tgggcacccc actgcaatcc tgtctttctg agcacacttt agtggccgat gatttttgtc 3180
atcagccacc atcctattgc aaaggttcca actgtatata ttcccaatag caacgtagct 3240
tctaccatga acagaaaaca ttctgatttg gaaaaagaga gggaggtatg gactgggggc 3300
cagagtcctt tccaaggctt ctccaattct gcccaaaaat atggttgata gtttacctga 3360
ataaatggta gtaatcacag ttggccttca gaaccatcca tagtagtatg atgatacaag 3420
attagaagct gaaaacctaa gtcctttatg tggaaaacag aacatcatta gaacaaagga 3480
cagagtatga acacctgggc ttaagaaatc tagtatttca tgctgggaat gagacatagg 3540
ccatgaaaaa aatgatcccc aagtgtgaac aaaagatgct cttctgtgga ccactgcatg 3600
agcttttata ctaccgacct ggtttttaaa tagagtttgc tattagagca ttgaattgga 3660
gagaaggcct ccctagccag cacttgtata tacgcatcta taaattgtcc gtgttcatac 3720
atttgagggg aaaacaccat aaggtttcgt ttctgtatac aaccctggca ttatgtccac 3780
tgtgtataga agtagattaa gagccatata agtttgaagg aaacagttaa taccattttt 3840
taaggaaaca atataaccac aaagcacagt ttgaacaaaa tctcctcttt tagctgatga 3900
acttattctg tagattctgt ggaacaagcc tatcagcttc agaatggcat tgtactcaat 3960
ggatttgatg ctgtttgaca aagttactga ttcactgcat ggctcccaca ggagtgggaa 4020
aacactgcca tcttagtttg gattcttatg tagcaggaaa taaagtatag gtttagcctc 4080
cttcgcaggc atgtcctgga caccgggcca gtatctatat atgtgtatgt acgtttgtat 4140
gtgtgtagac aaatatttgg aggggtattt ttgccctgag tccaagaggg tcctttagta 4200
cctgaaaagt aacttggctt tcattattag tactgctctt gtttcttttc acatagctgt 4260
ctagagtagc ttaccagaag cttccatagt ggtgcagagg aagtggaagg catcagtccc 4320
tatgtatttg cagttcacct gcacttaagg cactctgtta tttagactca tcttactgta 4380
cctgttcctt agaccttcca taatgctact gtctcactga aacatttaaa ttttaccctt 4440
tagactgtag cctggatatt attcttgtag tttacctctt taaaaacaaa acaaaacaaa 4500
acaaaaaact ccccttcctc actgcccaat ataaaaggca aatgtgtaca tggcagagtt 4560
tgtgtgttgt cttgaaagat tcaggtatgt tgcctttatg gtttcccccct tctacatttc 4620
ttagactaca tttagagaac tgtggccgtt atctggaagt aaccatttgc actggagttc 4680
tatgctctcg cacctttcca aagttaacag attttggggt tgtgttgtca cccaagagat 4740
tgttgtttgc catactttgt ctgaaaaatt cctttgtgtt tctattgact tcaatgatag 4800

```
taagaaaagt ggttgttagt tatagatgtc taggtacttc aggggcactt cattgagagt   4860

tttgtcttgg atattcttga aagtttatat ttttataatt ttttcttaca tcagatgttt   4920

ctttgcagtg gcttaatgtt tgaaattatt ttgtggcttt ttttgtaaat attgaaatgt   4980

agcaataatg tcttttgaat attcccaagc ccatgagtcc ttgaaaatat tttttatata   5040

tacagtaact ttatgtgtaa atacataagc ggcgtaagtt taaaggatgt tggtgttcca   5100

cgtgttttat tcctgtatgt tgtccaattg ttgacagttc tgaagaattc taataaaatg   5160

tacatatata aatcaaaaaa aaaaaaaaaa                                    5190
```

<210> SEQ ID NO 146
<211> LENGTH: 7998
<212> TYPE: DNA
<213> ORGANISM: Homo sapiens

<400> SEQUENCE: 146

```
gcggcggcgg cccgagggcg acttgcgggg cgcgcaggcc gccgtgcacc cgggacgctt     60

ccccctcggg gaccctccgc gggcttctcc gccgcgccgt ccggcgggag ccggcgggac    120

cccgggcgag cggcgcgggc ggcaccatga ggcggcagtg gggcgcgctg ctgcttggcg    180

ccctgctctg cgcacacggc ctggccagca gccccgagtg tgcttgtggt cggagccact    240

tcacatgtgc agtgagtgct cttggagagt gtacctgcat ccctgcccag tggcagtgtg    300

atggagacaa tgactgcggg gaccacagcg atgaggatgg atgtatacta cctacctgtt    360

cccctcttga ctttcactgt gacaatggca agtgcatccg ccgctcctgg gtgtgtgacg    420

gggacaacga ctgtgaggat gactcggatg agcaggactg tccccccgg gagtgtgagg    480

aggacgagtt tccctgccag aatggctact gcatccggag tctgtggcac tgcgatggtg    540

acaatgactg tggcgacaac agcgatgagc agtgtgacat gcgcaagtgc tccgacaagg    600

agttccgctg tagtgacgga agctgcattg ctgagcattg gtactgcgac ggtgacaccg    660

actgcaaaga tggctccgat gaggagaact gtccctcagc agtgccagcg ccccccctgca    720

acctggagga gttccagtgt gcctatggac gctgcatcct cgacatctac cactgcgatg    780

gcgacgatga ctgtggagac tggtcagacg agtctgactg ctcctcccac cagccctgcc    840

gctctgggga gttcatgtgt gacagtggcc tgtgcatcaa tgcaggctgg cgctgcgatg    900

gtgacgcgga ctgtgatgac cagtctgatg agcgcaactg caccacctcc atgtgtacgg    960

cagaacagtt ccgctgtcac tcaggccgct gtgtccgcct gtcctggcgc tgtgatgggg   1020

aggacgactg tgcagacaac agcgatgaag agaactgtga gaatacagga agccccccaat   1080

gtgccttgga ccagttcctg tgttggaatg ggcgctgcat tgggcagagg aagctgtgca   1140

acggggtcaa cgactgtggt gacaacagcg acgaaagccc acagcagaat tgccggcccc   1200

ggacgggtga ggagaactgc aatgttaaca acggtggctg tgcccagaag tgccagatgg   1260

tgcgggggc agtgcagtgt acctgccaca caggctaccg gctcacagag gatgggcaca   1320

cgtgccaaga tgtgaatgaa tgtgccgagg aggggtattg cagccagggc tgcaccaaca   1380

gcgaaggggc tttccaatgc tggtgtgaaa caggctatga actacggccc gaccggcgca   1440

gctgcaaggc tctggggcca gagcctgtgc tgctgttcgc caatcgcatc gacatccggc   1500

aggtgctgcc acaccgctct gagtacacac tgctgcttaa caacctggag aatgccattg   1560

cccttgattt ccaccaccgc cgcgagcttg tcttctggtc agatgtcacc ctggaccgga   1620

tcctccgtgc caacctcaac ggcagcaacg tggaggaggt tgtgtctact gggctggaga   1680

gcccaggggg cctggctgtg gattgggtcc atgacaaact ctactggacc gactcaggca   1740
```

cctcgaggat tgaggtggcc aatctggatg gggcccaccg gaaagtgttg ctgtggcaga 1800
acctggagaa gccccgggcc attgccttgc atcccatgga gggtaccatt tactggacag 1860
actggggcaa caccccccgt attgaggcct ccagcatgga tggctctgga cgccgcatca 1920
ttgccgatac ccatctcttc tggcccaatg gcctcaccat cgactatgcc gggcgccgta 1980
tgtactgggt ggatgctaag caccatgtca tcgagagggc caatctggat gggagtcacc 2040
gtaaggctgt cattagccag ggcctcccgc atcccttcgc catcacagtg tttgaagaca 2100
gcctgtactg gacagactgg cacaccaaga gcatcaatag cgctaacaaa tttacgggga 2160
agaaccagga aatcattcgc aacaaactcc acttccctat ggacatccac accttgcacc 2220
cccagcgcca acctgcaggg aaaaaccgct gtggggacaa caacggaggc tgcacgcacc 2280
tgtgtctgcc cagtggccag aactacacct gtgcctgccc cactggcttc cgcaagatca 2340
gcagccacgc ctgtgcccag agtcttgaca agttcctgct tttgcccgag aggatggaca 2400
tccgtcgaat cagctttgac acagaggacc tgtctgatga tgtcatccca ctggctgacg 2460
tgcgcagtgc tgtggccctt gactgggact cccgggatga ccacgtgtac tggacagatg 2520
tcagcactga taccatcagc agggccaagt gggatggaac aggacaggag gtggtagtgg 2580
ataccagttt ggagagccca gctggcctgg ccattgattg ggtcaccaac aaactgtact 2640
ggacagatgc aggtacagac cggattgaag tagccaacac agatggcagc atgagaacag 2700
tactcatctg ggagaacctt gatcgtcctc gggacatcgt ggtggaaccc atgggcgggt 2760
acatgtattg gactgactgg ggtgcgagcc ccaagattga acgagctggc atggatgcct 2820
caggccgcca agtcattatc tcttctaatc tgacctggcc taatgggtta gctattgatt 2880
atgggtccca gcgtctatac tgggctgacg ccggcatgaa gacaattgaa tttgctggac 2940
tggatggcag taagaggaag gtgctgattg gaagccagct cccccaccca tttgggctga 3000
ccctctatgg agagcgcatc tattggactg actggcagac caagagcata cagagcgctg 3060
accggctgac agggctggac cgggagactc tgcaggagaa cctggaaaac ctaatggaca 3120
tccatgtctt ccaccgccgc cggcccccag tgtctacacc atgtgctatg gagaatggcg 3180
gctgtagcca cctgtgtctt aggtccccaa atccaagcgg attcagctgt acctgcccca 3240
caggcatcaa cctgctgtct gatggcaaga cctgctcacc aggcatgaac agtttcctca 3300
tcttcgccag gaggatagac attcgcatgg tctccctgga catcccttat tttgctgatg 3360
tggtggtacc aatcaacatt accatgaaga acaccattgc cattggagta gacccccagg 3420
aaggaaaggt gtactggtct gacagcacac tgcacaggat cagtcgtgcc aatctggatg 3480
gctcacagca tgaggacatc atcaccacag ggctacagac cacagatggg ctcgcggttg 3540
atgccattgg ccggaaagta tactggacag acacgggaac aaaccggatt gaagtgggca 3600
acctggacgg gtccatgcgg aaagtgttgg tgtggcagaa ccttgacagt ccccgggcca 3660
tcgtactgta ccatgagatg ggtttatgt actggacaga ctggggggag aatgccaagt 3720
tagagcggtc cggaatggat ggctcagacc gcgcggtgct catcaacaac aacctaggat 3780
ggcccaatgg actgactgtg gacaaggcca gctcccaact gctatgggcc gatgcccaca 3840
ccgagcgaat tgaggctgct gacctgaatg gtgccaatcg gcatacattg gtgtcaccgg 3900
tgcagcaccc atatggcctc accctgctcg actcctatat ctactggact gactggcaga 3960
ctcggagcat ccaccgtgct gacaagggta ctggcagcaa tgtcatcctc gtgaggtcca 4020
acctgccagg cctcatggac atgcaggctg tggaccgggc acagccacta ggttttaaca 4080
agtgcggctc gagaaatggc ggctgctccc acctctgctt gcctcggcct tctggcttct 4140
cctgtgcctg ccccactggc atccagctga agggagatgg gaagacctgt gatccctctc 4200
ctgagaccta cctgctcttc tccagccgtg gctccatccg gcgtatctca ctggacacca 4260
gtgaccacac cgatgtgcat gtccctgttc ctgagctcaa caatgtcatc tccctggact 4320
atgacagcgt ggatggaaag gtctattaca cagatgtgtt cctggatgtt atcaggcgag 4380
cagacctgaa cggcagcaac atggagacag tgatcgggcg agggctgaag accactgacg 4440
ggctggcagt ggactgggtg gccaggaacc tgtactggac agacacaggt cgaaatacca 4500
ttgaggcgtc caggctggat ggttcctgcc gcaaagtact gatcaacaat agcctggatg 4560
agccccgggc cattgctgtt ttccccagga aggggtacct cttctggaca gactggggcc 4620
acattgccaa gatcgaacgg gcaaacttgg atggttctga gcggaaggtc ctcatcaaca 4680
cagacctggg ttggcccaat ggccttaccc tggactatga tacccgcagg atctactggg 4740
tggatgcgca tctggaccgg atcgagagtg ctgacctcaa tgggaaactg cggcaggtct 4800
tggtcagcca tgtgtcccac ccctttgccc tcacacagca agacaggtgg atctactgga 4860
cagactggca gaccaagtca atccagcgtg ttgacaaata ctcaggccgg aacaaggaga 4920
cagtgctggc aaatgtggaa ggactcatgg atatcatcgt ggtttcccct cagcggcaga 4980
cagggaccaa tgcctgtggt gtgaacaatg gtggctgcac ccacctctgc tttgccagag 5040
cctcggactt cgtatgtgcc tgtcctgacg aacctgatag ccggccctgc tcccttgtgc 5100
ctggcctggt accaccagct cctagggcta ctggcatgag tgaaaagagc ccagtgctac 5160
ccaacacacc acctaccacc ttgtattctt caaccacccg gacccgcacg tctctggagg 5220
aggtggaagg aagatgctct gaaagggatg ccaggctggg cctctgtgca cgttccaatg 5280
acgctgttcc tgctgctcca ggggaaggac ttcatatcag ctacgccatt ggtggactcc 5340
tcagtattct gctgattttg gtggtgattg cagctttgat gctgtacaga cacaaaaaat 5400
ccaagttcac tgatcctgga atggggaacc tcacctacag caacccctcc taccgaacat 5460
ccacacagga agtgaagatt gaagcaatcc ccaaaccagc catgtacaac cagctgtgct 5520
ataagaaaga gggagggcct gaccataact acaccaagga gaagatcaag atcgtagagg 5580
gaatctgcct cctgtctggg gatgatgctg agtgggatga cctcaagcaa ctgcgaagct 5640
cacggggggg cctcctccgg gatcatgtat gcatgaagac agacacggtg tccatccagg 5700
ccagctctgg ctccctggat gacacagaga cggagcagct gttacaggaa gagcagtctg 5760
agtgtagcag cgtccatact gcagccactc cagaaagacg aggctctctg ccagacacgg 5820
gctggaaaca tgaacgcaag ctctcctcag agagccaggt ctaaatgccc acattctctt 5880
ccctgcctgc ctgttccttc tcctttatgg acgtctagtc cttgtgctcg cttacaccgc 5940
aggccccgct tctgtgtgct tgtcctcctc ctcctcccac cccataactg ttcctaagcc 6000
ttcaccggag ctgtttacca cgtgagtcca taactacctg tgcacaagaa atgatggcac 6060
atcacgagaa tttagacctg gattttacca tgaacctcac atcttgtact ccatcctggg 6120
ccccctgaaa ctgcttattc gtgattcctc accagcgtag agctccacct ccccttcccc 6180
cagtaccctc agtgcctgct tctcagtgct gatgcagctg atgacccagg actgcgctct 6240
gccccatcac agccagcatg actgcttctc tgagagaact tgcccatcag ggctgggac 6300
atgggggtgt gggtaaagac agggatgaag gatagaggct gagagaagaa ggaagaatca 6360
gcccagcagg tatgggcatc tgggaaacct ccagcctcaa gtgtgttggt aacatgaaaa 6420
agctttgggg ggtagttgga tctgggtgtc tggtccattg ctggcagtgg acattattct 6480

-continued tgccctaaga gacactgcct tttcagcagc agatactggt gagatggggg tggctcaggc 6540
tgttcttcct cctcctagaa tgtctggagc tgtttctaca ttcagataac tgggtcccct 6600
atcacaaggc tactggctaa taggaattcc ctcctggtgc caccactggc cagtaccttt 6660
cctaagtctt tgctcaaatt aaccaggttg tgagccagtg gcttgagtga atgttaggcc 6720
ttgggggctg agtctctgaa aagtctaaga agctctgcct agaccaaata tggtatacct 6780
cctgacccct ctctccctca tgtcctggga ttctggggaa gagacctaga aacaagcttt 6840
caaagaaaaa ccagaagttg tcataaatgg tcagaaagaa cgatcaggtt ggagacttgg 6900
gaaacccagg gcctaaagag aagtatccat gagggtcaaa cttcctgttg aacttcctat 6960
gttctttctc aagtgctcag ggatctaagt tagtggacag caagcctgtg gctacggggt 7020
ggtgatgttc ctcttccagc tgtcccctca gctaaggggc ttagtttcca tgtgggatgc 7080
catcacttgg ttcatgctca ttcacacaaa gggcacgtgt ctcagcctgg tatcagggaa 7140
attgagactt atttttgccc taaaacgtct ccctagctgt tcttcgtggg gttttttttgt 7200 ttgttttttt gcctaatttg ctttttctga ccaagccttg tggcaccagc aatctccaaa 7260
gtcctgtggt gggagggctg aataaataaa aatacaaaga ggtgggtaag gagtaggaag 7320
gtagagagca ccactgatga ggccctccta gcccatggca gacccagacc tcttctcccc 7380
caggaattag aagtggcagg agagaacaac aggggctggg aatggagggg agaatttcta 7440
ggggaagttt cctgagttga aacttctcct gtggttactg gtattgagaa atcagctacc 7500
aaagtgaaaa aggacaagat caattctttt ctagtcagtt ctaagactgc tagagagaga 7560
taccaggccc ttagccttgc tctcagtagc gtcagcccca gttctgagcc tccccacatt 7620
acacttaaca agcagtaaag gagtgagcac tttgggtcct tagactcatg tctggggagg 7680
aagagcaagt agaaaagtgg cattttcttg attggaaagg gggaaggatc ttattgcact 7740
tgggctgttc agaatgtaga aaggacatat ttgaggaagt atctatttga gcactgattt 7800
actctgtaaa aagcaaaatc tctctgtcct aaactaatgg aagcgattct cccatgctca 7860
tgtgtaatgg ttttaacgtt actcactgga gagattggac tttctggagt tatttaacca 7920
ctatgttcag tattttagga ctttatgata atttaatata aatttagctt ttcttaatca 7980
aaaaaaaaaa aaaaaaaa 7998

<210> SEQ ID NO 147
<211> LENGTH: 4122
<212> TYPE: DNA
<213> ORGANISM: Homo sapiens

<400> SEQUENCE: 147
gcgagcgaag ggagcgctct gggatgggac ttggagcaag cggcggcggc ggagacagag 60
gcagaggcag aagctggggc tccgtcctcg cctcccacga gcgatccccg aggagagccg 120
cggccctcgg cgaggcgaag aggccgacga ggaagacccg ggtggctgcg cccctgcctc 180
gcttcccagg cgccggcggc tgcagccttg cccctcttgc tcgccttgaa aatggaaaag 240
atgctcgcag gctgctttct gctgatcctc ggacagatcg tcctcctccc tgccgaggcc 300
agggagcggt cacgtgggag gtccatctct aggggcagac acgctcggac ccacccgcag 360
acggcccttc tggagagttc ctgtgagaac aagcgggcag acctggtttt catcattgac 420
agctctcgca gtgtcaacac ccatgactat gcaaaggtca aggagttcat cgtggacatc 480
ttgcaattct tggacattgg tcctgatgtc acccgagtgg gcctgctcca atatggcagc 540

-continued

```
actgtcaaga atgagttctc cctcaagacc ttcaagagga agtccgaggt ggagcgtgct    600
gtcaagagga tgcggcatct gtccacgggc accatgactg ggctggccat ccagtatgcc    660
ctgaacatcg cattctcaga agcagagggg gcccggcccc tgagggagaa tgtgccacgg    720
gtcataatga tcgtgacaga tgggagacct caggactccg tggccgaggt ggctgctaag    780
gcacgggaca cgggcatcct aatctttgcc attggtgtgg gccaggtaga cttcaacacc    840
ttgaagtcca ttgggagtga gccccatgag gaccatgtct tccttgtggc caatttcagc    900
cagattgaga cgctgacctc cgtgttccag aagaagttgt gcacggccca catgtgcagc    960
accctggagc ataactgtgc ccacttctgc atcaacatcc ctggctcata cgtctgcagg   1020
tgcaaacaag gctacattct caactcggat cagacgactt gcagaatcca ggatctgtgt   1080
gccatggagg accacaactg tgagcagctc tgtgtgaatg tgccgggctc cttcgtctgc   1140
cagtgctaca gtggctacgc cctggctgag gatgggaaga ggtgtgtggc tgtggactac   1200
tgtgcctcag aaaaccacgg atgtgaacat gagtgtgtaa atgctgatgg ctcctacctt   1260
tgccagtgcc atgaaggatt tgctcttaac ccagataaaa aaacgtgcac aaagatagac   1320
tactgtgcct catctaatca cggatgtcag cacgagtgtg ttaacacaga tgattcctat   1380
tcctgccact gcctgaaagg ctttaccctg aatccagata agaaaacctg cagaaggatc   1440
aactactgtg cactgaacaa accgggctgt gagcatgagt gcgtcaacat ggaggagagc   1500
tactactgcc gctgccaccg tggctacact ctggacccca atggcaaaac ctgcagccga   1560
gtggaccact gtgcacagca ggaccatggc tgtgagcagc tgtgtctgaa cacggaggat   1620
tccttcgtct gccagtgctc agaaggcttc ctcatcaacg aggacctcaa gacctgctcc   1680
cgggtggatt actgcctgct gagtgaccat ggttgtgaat actcctgtgt caacatggac   1740
agatcctttg cctgtcagtg tcctgaggga cacgtgctcc gcagcgatgg gaagacgtgt   1800
gcaaaattgg actcttgtgc tctgggggac cacggttgtg aacattcgtg tgtaagcagt   1860
gaagattcgt ttgtgtgcca gtgctttgaa ggttatatac tccgtgaaga tggaaaaacc   1920
tgcagaagga aagatgtctg ccaagctata gaccatggct gtgaacacat ttgtgtgaac   1980
agtgatgact catacacgtg cgagtgcttg gagggattcc ggctcgctga ggatgggaaa   2040
cgctgccgaa ggaaggatgt ctgcaaatca acccaccatg gctgcgaaca catttgtgtt   2100
aataatggga attcctacat ctgcaaatgc tcagagggat ttgttctagc tgaggacgga   2160
agacggtgca agaaatgcac tgaaggccca attgacctgg tctttgtgat cgatggatcc   2220
aagagtcttg gagaagagaa ttttgaggtc gtgaagcagt ttgtcactgg aattatagat   2280
tccttgacaa tttcccccaa agccgctcga gtggggctgc tccagtattc cacacaggtc   2340
cacacagagt tcactctgag aaacttcaac tcagccaaag acatgaaaaa agccgtggcc   2400
cacatgaaat acatgggaaa gggctctatg actgggctgg ccctgaaaca catgtttgag   2460
agaagtttta cccaaggaga aggggccagg ccccttttcca caagggtgcc cagagcagcc   2520
attgtgttca ccgacggacg ggctcaggat gacgtctccg agtgggccag taaagccaag   2580
gccaatggta tcactatgta tgctgttggg gtaggaaaag ccattgagga ggaactacaa   2640
gagattgcct ctgagcccac aaacaagcat ctcttctatg ccgaagactt cagcacaatg   2700
gatgagataa gtgaaaaact caagaaaggc atctgtgaag ctctagaaga ctccgatgga   2760
agacaggact ctccagcagg ggaactgcca aaaacggtcc aacagccaac agaatctgag   2820
ccagtcacca taaatatcca agacctactt tcctgttcta attttgcagt gcaacacaga   2880
tatctgtttg aagaagacaa tcttttacgg tctacacaaa agctttccca ttcaacaaaa   2940
```

-continued ccttcaggaa gccctttgga agaaaaacac gatcaatgca aatgtgaaaa ccttataatg 3000
ttccagaacc ttgcaaacga agaagtaaga aaattaacac agcgcttaga agaaatgaca 3060
cagagaatgg aagccctgga aaatcgcctg agatacagat gaagattaga aatcgcgaca 3120
catttgtagt cattgtatca cggattacaa tgaacgcagt gcagagcccc aaagctcagg 3180
ctattgttaa atcaataatg ttgtgaagta aaacaatcag tactgagaaa cctggtttgc 3240
cacagaacaa agacaagaag tatacactaa cttgtataaa tttatctagg aaaaaaatcc 3300
ttcagaattc taagatgaat ttaccaggtg agaatgaata agctatgcaa ggtattttgt 3360
aatatactgt ggacacaact tgcttctgcc tcatcctgcc ttagtgtgca atctcatttg 3420
actatacgat aaagtttgca cagtcttact tctgtagaac actggccata ggaaatgctg 3480
tttttttgta ctggacttta ccttgatata tgtatatgga tgtatgcata aaatcatagg 3540
acatatgtac ttgtggaaca agttggattt tttatacaat attaaaattc accacttcag 3600
agaatggtat tcagtgcaaa aattcttagt ttaactttaa atggaagata tgtatgtatg 3660
agaaatggcc aacatgccta tgaaaaaaat gctgaatctc atcagtaatc aggaaaatgc 3720
aggttaaaac aataccattt ttcacccatc agcttagcaa aaatgagtat atttttttaac 3780 aagtgttggt aaggatgtgg aaatgtgagg ttcttgtagt aagaatgcaa atggcactct 3840
ttgtagagta agtctgttga catctcataa aactgaaaat gcacacaacc ctgtaaatct 3900
agcaactgca ctcagttgat ttcagcccat acatacaaag agacctgcat aagaatgtta 3960
ctaggctttg taaaagcaaa aaataaggaa caacttaaac atcatcagaa ggggaactga 4020
taaactctgg tgtaatccat accacagaaa tacaacaccg catgtacagg aatgtgctac 4080
atctatacaa ataaatggtc aaactcaaaa aaaaaaaaaa aa 4122

<210> SEQ ID NO 148
<211> LENGTH: 6695
<212> TYPE: DNA
<213> ORGANISM: Homo sapiens

<400> SEQUENCE: 148
gccctcgccg cccgcggcgc cccgagcgct ttgtgagcag atgcggagcc gagtggaggg 60
cgcgagccag atgcggggcg acagctgact tgctgagagg aggcggggag gcgcggagcg 120
cgcgtgtggt ccttgcgccg ctgacttctc cactggttcc tgggcaccga aagataaacc 180
tctcataatg aaggcccccg ctgtgcttgc acctggcatc ctcgtgctcc tgtttacctt 240
ggtgcagagg agcaatgggg agtgtaaaga ggcactagca aagtccgaga tgaatgtgaa 300
tatgaagtat cagcttccca acttcaccgc ggaaacaccc atccagaatg tcattctaca 360
tgagcatcac attttccttg gtgccactaa ctacatttat gttttaaatg aggaagacct 420
tcagaaggtt gctgagtaca agactgggcc tgtgctggaa cacccagatt gtttcccatg 480
tcaggactgc agcagcaaag ccaatttatc aggaggtgtt tggaaagata acatcaacat 540
ggctctagtt gtcgacacct actatgatga tcaactcatt agctgtggca gcgtcaacag 600
agggacctgc cagcgacatg tctttcccca caatcatact gctgacatac agtcggaggt 660
tcactgcata ttctccccac agatagaaga gcccagccag tgtcctgact gtgtggtgag 720
cgccctggga gccaaagtcc tttcatctgt aaaggaccgg ttcatcaact tctttgtagg 780
caataccata aattcttctt atttcccaga tcatccattg cattcgatat cagtgagaag 840
gctaaaggaa acgaaagatg gttttatgtt tttgacggac cagtcctaca ttgatgtttt 900

-continued

```
acctgagttc agagattctt accccattaa gtatgtccat gcctttgaaa gcaacaattt    960
tatttacttc ttgacggtcc aaagggaaac tctagatgct cagacttttc acacaagaat   1020
aatcaggttc tgttccataa actctggatt gcattcctac atggaaatgc ctctggagtg   1080
tattctcaca gaaaagagaa aaaagagatc cacaaagaag gaagtgttta atatacttca   1140
ggctgcgtat gtcagcaagc ctggggccca gcttgctaga caaataggag ccagcctgaa   1200
tgatgacatt cttttcgggg tgttcgcaca aagcaagcca gattctgccg aaccaatgga   1260
tcgatctgcc atgtgtgcat tccctatcaa atatgtcaac gacttcttca acaagatcgt   1320
caacaaaaac aatgtgagat gtctccagca tttttacgga cccaatcatg agcactgctt   1380
taataggaca cttctgagaa attcatcagg ctgtgaagcg cgccgtgatg aatatcgaac   1440
agagtttacc acagctttgc agcgcgttga cttattcatg ggtcaattca gcgaagtcct   1500
cttaacatct atatccacct tcattaaagg agacctcacc atagctaatc ttgggacatc   1560
agagggtcgc ttcatgcagg ttgtggtttc tcgatcagga ccatcaaccc ctcatgtgaa   1620
ttttctcctg gactcccatc cagtgtctcc agaagtgatt gtggagcata cattaaacca   1680
aaatggctac acactggtta tcactgggaa gaagatcacg aagatcccat tgaatggctt   1740
gggctgcaga catttccagt cctgcagtca atgcctctct gccccaccct ttgttcagtg   1800
tggctggtgc cacgacaaat gtgtgcgatc ggaggaatgc ctgagcggga catggactca   1860
acagatctgt ctgcctgcaa tctacaaggt tttcccaaat agtgcacccc ttgaaggagg   1920
gacaaggctg accatatgtg gctgggactt tggatttcgg aggaataata aatttgattt   1980
aaagaaaact agagttctcc ttggaaatga gagctgcacc ttgactttaa gtgagagcac   2040
gatgaataca ttgaaatgca cagttggtcc tgccatgaat aagcatttca atatgtccat   2100
aattatttca aatggccacg ggacaacaca atacagtaca ttctcctatg tggatcctgt   2160
aataacaagt atttcgccga aatacggtcc tatggctggt ggcactttac ttactttaac   2220
tggaaattac ctaaacagtg ggaattctag acacatttca attggtggaa aaacatgtac   2280
tttaaaaagt gtgtcaaaca gtattcttga atgttatacc ccagcccaaa ccatttcaac   2340
tgagtttgct gttaaattga aaattgactt agccaaccga gagacaagca tcttcagtta   2400
ccgtgaagat cccattgtct atgaaattca tccaaccaaa tcttttatta gtacttggtg   2460
gaaagaacct ctcaacattg tcagttttct attttgcttt gccagtggtg ggagcacaat   2520
aacaggtgtt gggaaaaacc tgaattcagt tagtgtcccg agaatggtca taaatgtgca   2580
tgaagcagga aggaacttta cagtggcatg tcaacatcgc tctaattcag agataatctg   2640
ttgtaccact ccttccctgc aacagctgaa tctgcaactc cccctgaaaa ccaaagcctt   2700
tttcatgtta gatgggatcc tttccaaata ctttgatctc atttatgtac ataatcctgt   2760
gtttaagcct tttgaaaagc cagtgatgat ctcaatgggc aatgaaaatg tactggaaat   2820
taagggaaat gatattgacc ctgaagcagt taaaggtgaa gtgttaaaag ttggaaataa   2880
gagctgtgag aatatacact tacattctga agccgtttta tgcacggtcc ccaatgacct   2940
gctgaaattg aacagcgagc taaatataga gtggaagcaa gcaatttctt caaccgtcct   3000
tggaaaagta atagttcaac cagatcagaa tttcacagga ttgattgctg gtgttgtctc   3060
aatatcaaca gcactgttat tactacttgg gtttttcctg tggctgaaaa agagaaagca   3120
aattaaagat ctgggcagtg aattagttcg ctacgatgca agagtacaca ctcctcattt   3180
ggataggctt gtaagtgccc gaagtgtaag cccaactaca gaaatggttt caaatgaatc   3240
tgtagactac cgagctactt ttccagaaga tcagtttcct aattcatctc agaacggttc   3300
```

atgccgacaa gtgcagtatc ctctgacaga catgtccccc atcctaacta gtggggactc 3360
tgatatatcc agtccattac tgcaaaatac tgtccacatt gacctcagtg ctctaaatcc 3420
agagctggtc caggcagtgc agcatgtagt gattgggccc agtagcctga ttgtgcattt 3480
caatgaagtc ataggaagag ggcattttgg ttgtgtatat catgggactt tgttggacaa 3540
tgatggcaag aaaattcact gtgctgtgaa atccttgaac agaatcactg acataggaga 3600
agtttcccaa tttctgaccg agggaatcat catgaaagat tttagtcatc ccaatgtcct 3660
ctcgctcctg ggaatctgcc tgcgaagtga agggtctccg ctggtggtcc taccatacat 3720
gaaacatgga gatcttcgaa atttcattcg aaatgagact cataatccaa ctgtaaaaga 3780
tcttattggc tttggtcttc aagtagccaa aggcatgaaa tatcttgcaa gcaaaaagtt 3840
tgtccacaga gacttggctg caagaaactg tatgctggat gaaaaattca cagtcaaggt 3900
tgctgatttt ggtcttgcca gagacatgta tgataaagaa tactatagtg tacacaacaa 3960
aacaggtgca aagctgccag tgaagtggat ggctttggaa agtctgcaaa ctcaaaagtt 4020
taccaccaag tcagatgtgt ggtcctttgg cgtgctcctc tgggagctga tgacaagagg 4080
agccccacct tatcctgacg taaacacctt tgatataact gtttacttgt tgcaagggag 4140
aagactccta caacccgaat actgcccaga ccccttatat gaagtaatgc taaaatgctg 4200
gcaccctaaa gccgaaatgc gcccatcctt ttctgaactg gtgtcccgga tatcagcgat 4260
cttctctact ttcattgggg agcactatgt ccatgtgaac gctacttatg tgaacgtaaa 4320
atgtgtcgct ccgtatcctt ctctgttgtc atcagaagat aacgctgatg atgaggtgga 4380
cacacgacca gcctccttct gggagacatc atagtgctag tactatgtca aagcaacagt 4440
ccacactttg tccaatggtt ttttcactgc ctgaccttta aaaggccatc gatattcttt 4500
gctcttgcca aaattgcact attataggac ttgtattgtt atttaaatta ctggattcta 4560
aggaatttct tatctgacag agcatcagaa ccagaggctt ggtcccacag gccacggacc 4620
aatggcctgc agccgtgaca acactcctgt catattggag tccaaaactt gaattctggg 4680
ttgaattttt taaaaatcag gtaccacttg atttcatatg ggaaattgaa gcaggaaata 4740
ttgagggctt cttgatcaca gaaaactcag aagagatagt aatgctcagg acaggagcgg 4800
cagccccaga acaggccact catttagaat tctagtgttt caaaacactt ttgtgtgttg 4860
tatggtcaat aacatttttc attactgatg gtgtcattca cccattaggt aaacattccc 4920
ttttaaatgt ttgtttgttt tttgagacag gatctcactc tgttgccagg gctgtagtgc 4980
agtggtgtga tcatagctca ctgcaacctc cacctcccag gctcaagcct cccgaatagc 5040
tgggactaca ggcgcacacc accatccccg gctaattttt gtattttttg tagagacggg 5100
gttttgccat gttgccaagg ctggtttcaa actcctggac tcaagaaatc cacccacctc 5160
agcctcccaa agtgctagga ttacaggcat gagccactgc gcccagccct tataaatttt 5220
tgtatagaca ttcctttggt tggaagaata tttataggca atacagtcaa agtttcaaaa 5280
tagcatcaca caaaacatgt ttataaatga acaggatgta atgtacatag atgacattaa 5340
gaaaatttgt atgaaataat ttagtcatca tgaaatattt agttgtcata taaaaaccca 5400
ctgtttgaga atgatgctac tctgatctaa tgaatgtgaa catgtagatg ttttgtgtgt 5460 attttttaa atgaaaactc aaaataagac aagtaatttg ttgataaata tttttaaaga 5520
taactcagca tgtttgtaaa gcaggataca ttttactaaa aggttcattg gttccaatca 5580
cagctcatag gtagagcaaa gaaagggtgg atggattgaa aagattagcc tctgtctcgg 5640
tggcaggttc ccacctcgca agcaattgga aacaaaactt ttggggagtt ttattttgca 5700
ttagggtgtg ttttatgtta agcaaaacat actttagaaa caaatgaaaa aggcaattga 5760
aaatcccagc tatttcacct agatggaata gccaccctga gcagaacttt gtgatgcttc 5820
attctgtgga attttgtgct tgctactgta tagtgcatgt ggtgtaggtt actctaactg 5880
gttttgtcga cgtaaacatt taaagtgtta tattttttat aaaaatgttt atttttaatg 5940
atatgagaaa aattttgtta ggccacaaaa acactgcact gtgaacattt tagaaaaggt 6000
atgtcagact gggattaatg acagcatgat tttcaatgac tgtaaattgc gataaggaaa 6060
tgtactgatt gccaatacac cccaccctca ttacatcatc aggacttgaa gccaagggtt 6120
aacccagcaa gctacaaaga gggtgtgtca cactgaaact caatagttga gtttggctgt 6180
tgttgcagga aaatgattat aactaaaagc tctctgatag tgcagagact taccagaaga 6240
cacaaggaat tgtactgaag agctattaca atccaaatat tgccgtttca taaatgtaat 6300
aagtaatact aattcacaga gtattgtaaa tggtggatga caaaagaaaa tctgctctgt 6360
ggaaagaaag aactgtctct accagggtca agagcatgaa cgcatcaata gaaagaactc 6420
ggggaaacat cccatcaaca ggactacaca cttgtatata cattcttgag aacactgcaa 6480
tgtgaaaatc acgtttgcta tttataaact tgtccttaga ttaatgtgtc tggacagatt 6540
gtgggagtaa gtgattcttc taagaattag atacttgtca ctgcctatac ctgcagctga 6600
actgaatggt acttcgtatg ttaatagttg ttctgataaa tcatgcaatt aaagtaaagt 6660
gatgcaacat cttgtaaaaa aaaaaaaaaa aaaaa 6695

<210> SEQ ID NO 149
<211> LENGTH: 7619
<212> TYPE: DNA
<213> ORGANISM: Homo sapiens

<400> SEQUENCE: 149
actgaggcgc tggatctgtg gtcgcggctg gggacgtgcg cccgcgccac catcttcggc 60
tgaagaggca attgcttttg gatcgttcca tttacaatgg cgcagagaac tggactcgag 120
gatccagaga ggtatctctt tgtggacagg gctgtcatct acaaccctgc cactcaagct 180
gattggacag ctaaaaagct agtgtggatt ccatcagaac gccatggttt tgaggcagct 240
agtatcaaag aagaacgggg agatgaagtt atggtggagt tggcagagaa tggaaagaaa 300
gcaatggtca acaaagatga tattcagaag atgaacccac ctaagttttc caaggtggag 360
gatatggcag aattgacatg cttgaatgaa gcttccgttt tacataatct gaaggatcgc 420
tactattcag gactaatcta tacttattct ggactcttct gtgtagttat aaacccttac 480
aagaatcttc caatttactc tgagaatatt attgaaatgt acagagggaa gaagcgtcat 540
gagatgcctc cacacatcta tgctatatct gaatctgctt acagatgcat gcttcaagat 600
cgtgaggacc agtcaattct ttgcacgggt gagtcaggtg ctgggaagac agaaaataca 660
aagaaagtta ttcagtacct tgcccatgtt gcttcttcac ataaaggaag aaaggaccat 720
aatattcctg gggaacttga acggcagctt ttgcaagcaa atccaattct ggaatcattt 780
ggaaatgcga agactgtgaa aaatgataac tcatctcgtt ttggcaaatt tattcggatc 840
aactttgatg taactggcta tatcgttggg gccaacattg aaacatacct tctggaaaag 900
tctcgtgctg ttcgtcaagc aaaagatgaa cgtacttttc atatctttta ccagttgtta 960
tctggagcag gagaacacct aaagtctgat ttgcttcttg aaggatttaa taactacagg 1020
tttctctcca atggctatat tcctattccg ggacagcaag acaaagataa tttccaggag 1080

-continued

```
accatggaag caatgcacat aatgggcttc tcccatgaag agattctgtc aatgcttaaa   1140
gtagtatctt cagtgctaca gtttggaaat atttctttca aaaaggagag aaatactgat   1200
caagcttcca tgccagaaaa tacagttgcg cagaagctct gccatcttct tgggatgaat   1260
gtgatggagt ttactcgggc catcctgact ccccggatca aggtcggccg agactatgtg   1320
caaaaagccc agaccaaaga acaggcagat tttgcagtag aagcattggc aaaagctacc   1380
tatgagcggc tctttcgctg gctcgttcat cgcatcaata aagctctgga taggaccaaa   1440
cgtcagggag catctttcat tggaatcctg gatattgctg gatttgaaat ttttgagctg   1500
aactcctttg aacaactttg catcaactac accaatgaga agctgcagca gctgttcaac   1560
cacaccatgt ttatcctaga acaagaggaa taccagcgcg aaggcatcga gtggaacttc   1620
atcgatttcg ggctggatct gcagccatgc atcgacctaa tagagagacc tgcgaaccct   1680
cctggtgtac tggccctttt ggatgaagaa tgctggttcc ctaaagccac agataaaacc   1740
tttgttgaaa aactggttca agagcaaggt tcccactcca agtttcagaa acctcgacaa   1800
ttaaaagaca aagctgattt ttgcattata cattatgcag ggaaggtgga ctataaggca   1860
gatgagtggc tgatgaagaa tatggacccc ctgaatgaca acgtggccac ccttttgcac   1920
cagtcatcag acagatttgt ggcagagctt tggaaagatg tggaccgtat cgtgggtctg   1980
gatcaagtca ctggtatgac tgagacagct tttggctccg catataaaac caagaagggc   2040
atgtttcgta ccgttgggca actctacaaa gaatctctca ccaagctgat ggcaactctc   2100
cgaaacacca accctaactt tgttcgttgt atcattccaa atcacgagaa gagggctgga   2160
aaattggatc cacacctagt cctagatcag cttcgctgta atggtgtcct ggaagggatc   2220
cgaatctgtc gccagggctt ccctaaccga atagttttcc aggaattcag acagagatat   2280
gagatcctaa ctccaaatgc tattcctaaa ggttttatgg atggtaaaca ggcctgtgaa   2340
cgaatgatcc gggctttaga attggaccca aacttgtaca gaattggaca gagcaagata   2400
tttttcagag ctggagttct ggcacactta gaggaagaaa gagatttaaa aatcaccgat   2460
atcattatct tcttccaggc cgtttgcaga ggttacctgg ccagaaaggc ctttgccaag   2520
aagcagcagc aactaagtgc cttaaaggtc ttgcagcgga actgtgccgc gtacctgaaa   2580
ttacggcact ggcagtggtg gcgagtcttc acaaaggtga agccgcttct acaagtgact   2640
cgccaggagg aagaacttca ggccaaagat gaagagctgt tgaaggtgaa ggagaagcag   2700
acgaaggtgg aaggagagct ggaggagatg gagcggaagc accagcagct tttagaagag   2760
aagaatatcc ttgcagaaca actacaagca gagactgagc tctttgctga agcagaagag   2820
atgagggcaa gacttgctgc taaaaagcag gaattagaag agattctaca tgacttggag   2880
tctagggttg aagaagaaga agaaagaaac caaatcctcc aaaatgaaaa gaaaaaaatg   2940
caagcacata ttcaggacct ggaagaacag ctagacgagg aggaaggggc tcggcaaaag   3000
ctgcagctgg aaaaggtgac agcagaggcc aagatcaaga agatggaaga ggagattctg   3060
cttctcgagg accaaaattc caagttcatc aaagaaaaga aactcatgga agatcgcatt   3120
gctgagtgtt cctctcagct ggctgaagag gaagaaaagg cgaaaaactt ggccaaaatc   3180
aggaataagc aagaagtgat gatctcagat ttagaagaac gcttaaagaa ggaagaaaag   3240
actcgtcagg aactggaaaa ggccaaaaga aaactcgacg gggagacgac cgacctgcag   3300
gaccagatcg cagagctgca ggcgcagatt gatgagctca agctgcagct ggccaagaag   3360
gaggaggagc tgcagggcgc actggccaga ggtgatgatg aaacactcca taagaacaat   3420
```

-continued gcccttaaag ttgtgcgaga gctacaagcc caaattgctg aacttcagga agactttgaa 3480
tccgagaagg cttcacggaa caaggccgaa aagcagaaaa gggacttgag tgaggaactg 3540
gaagctctga aaacagagct ggaggacacg ctggacacca cggcagccca gcaggaacta 3600
cgtacaaaac gtgaacaaga agtggcagag ctgaagaaag ctcttgagga ggaaactaag 3660
aaccatgaag ctcaaatcca ggacatgaga caaagacacg caacagccct ggaggagctc 3720
tcagagcagc tggaacaggc caagcggttc aaagcaaatc tagagaagaa caagcagggc 3780
ctggagacag ataacaagga gctggcgtgt gaggtgaagg tcctgcagca ggtcaaggct 3840
gagtctgagc acaagaggaa gaagctcgac gcgcaggtcc aggagctcca tgccaaggtc 3900
tctgaaggcg acaggctcag ggtggagctg gcggagaaag caagtaagct gcagaatgag 3960
ctagataatg tctccaccct tctggaagaa gcagagaaga agggtattaa atttgctaag 4020
gatgcagcta gtcttgagtc tcaactacag gatacacagg agcttcttca ggaggagaca 4080
cgccagaaac taaacctgag cagtcggatc cggcagctgg aagaggagaa gaacagtctt 4140
caggagcagc aggaggagga ggaggaggcc aggaagaacc tggagaagca agtgctggcc 4200
ctgcagtccc agttggctga taccaagaag aaagtagatg acgacctggg aacaattgaa 4260
agtctggaag aagccaagaa gaagcttctg aaggacgcgg aggccctgag ccagcgcctg 4320
gaggagaagg cactggcgta tgacaaactg gagaagacca agaaccgcct gcagcaggag 4380
ctggacgacc tcacggtgga cctggaccac cagcgccagg tcgcctccaa cttggagaag 4440
aagcagaaga agtttgacca gctgttagca gaagagaaga gcatctctgc tcgctatgcc 4500
gaagagcggg accgggccga agccgaggcc agagagaaag aaaccaaagc cctgtcactg 4560
gcccgggccc tcgaggaagc cctggaggcc aaggaggagt ttgagaggca gaacaagcag 4620
ctccgagcag acatggaaga cctcatgagc tccaaagatg atgtgggaaa aaacgttcac 4680
gaacttgaaa aatccaaacg ggccctagag cagcaggtgg aggaaatgag gacccagctg 4740
gaggagctgg aagacgaact ccaggccacg gaagatgcca agcttcgtct ggaggtcaac 4800
atgcaggcca tgaaggcgca gttcgagaga gacctgcaaa ccagggatga gcagaatgaa 4860
gagaagaagc ggctgctgat caaacaggtg cgggagctcg aggcggagct ggaggatgag 4920
aggaaacagc gggcgcttgc tgtagcttca aagaaaaaga tggagataga cctgaaggac 4980
ctcgaagccc aaatcgaggc tgcgaacaaa gctcgggatg aggtgattaa gcagctccgc 5040
aagctccagg ctcagatgaa ggattaccaa cgtgaattag aagaagctcg tgcatccaga 5100
gatgagattt ttgctcaatc caaagagagt gaaaagaaat tgaagagtct ggaagcagaa 5160
atccttcaat tgcaggagga acttgcctca tctgagcgag cccgccgaca cgccgagcag 5220
gagagagatg agctggcgga cgagatcacc aacagcgcct ctggcaagtc cgcgctgctg 5280
gatgagaagc ggcgtctgga agctcggatc gcacagctgg aggaggagct ggaagaggag 5340
cagagcaaca tggagctgct caacgaccgc ttccgcaaga ccactctaca ggtggacaca 5400
ctgaacgccg agctagcagc cgagcgcagc gccgcccaga agagtgacaa tgcacgccag 5460
caactggagc ggcagaacaa ggagctgaag gccaagctgc aggaactcga gggtgctgtc 5520
aagtctaagt tcaaggccac catctcagcc ctggaggcca agattgggca gctggaggag 5580
cagcttgagc aggaagccaa ggaacgagca gccgccaaca aattagtccg tcgcactgag 5640
aagaagctga aagaaatctt catgcaggtt gaggatgagc gtcgacacgc ggaccagtat 5700
aaagagcaga tggagaaggc caacgctcgg atgaagcagc ttaaacgcca gctggaggaa 5760
gcagaagaag aagcgacgcg tgccaacgca tctcggcgta aactccagcg ggaactggat 5820
gatgccaccg aggccaacga gggcctgagc cgcgaggtca gcaccctgaa gaaccggctg 5880
aggcggggtg gccccatcag cttctcttcc agccgatctg gccggcgcca gctgcacctt 5940
gaaggagctt ccctggagct ctccgacgat gacacagaaa gtaagaccag tgatgtcaac 6000
gagacgcagc caccccagtc agagtaaagt tgcaggaagc cagaggaggc aatacagtgg 6060
gacagttagg aatgcacccg gggcctcctg cagatttcgg aaattggcaa gctacgggat 6120
tccttcctga aagatcaact gtgtcttaag gctctccagc ctatgcatac tgtatcctgc 6180
ttcagactta ggtacaattg ctcccctttt tatatataga cacacacagg acacatatat 6240
taaacagatt gtttcatcat tgcatctatt ttccatatag tcatcaagag accattttat 6300
aaaacatggt aagacccttt ttaaaacaaa ctccaggccc ttggttgcgg gtcgctgggt 6360
tattggggca gcgccgtggt cgtcactcag tcgctctgca tgctctctgt catacagaca 6420
ggtaacctag ttctgtgttc acgtggcccc cgactcctca gccacatcaa gtctcctaga 6480
ccactgtgga ctctaaactg cacttgtctc tctcatttcc ttcaaataat gatcaatgct 6540
atttcagtga gcaaactgtg aaaggggctt tggaaagagt aggaggggtg ggctggatcg 6600
gaagcaacac ccatttgggg ttaccatgtc catcccccaa ggggggccct gcccctcgag 6660
tcgatggtgt cccgcatcta ctcatgtgaa ctggccttgg cgagggctgg tctgtgcata 6720
gaagggatag tggccacact gcagctgagg ccccaggtgg cagccatgga tcatgtagac 6780
ttccagatgg tctcccgaac cgcctggctc tgccggcgcc ctcctcacgt caggagcaag 6840
cagccgtgga cccctaagcc gagctggtgg aaggcccctc cctgtcgcca gccgggccct 6900
catgctgacc ttgcaaattc agccgctgct ttgagcccaa aatgggaata ttggttttgt 6960
gtccgaggct tgttccaagt ttgtcaatga ggtttatgga gcctccagaa cagatgccat 7020
cttcctgaat gttgacatgc cagtgggtgt gactccttca tttttccttc tcccttccct 7080
ttggacagtg ttacagtgaa cacttagcat cctgtttttg gttggtagtt aagcaaactg 7140
acattacgga aagtgcctta gacactacag tactaagaca atgttgaata tatcattcgc 7200
ctctataaca atttaatgta ttcagttttg actgtgcttc atatcatgta cctctctagt 7260
caaagtggta ttacagacat tcagtgacaa tgaatcagtg ttaattctaa atccttgatc 7320
ctctgcaatg tgcttgaaaa cacaaacctt ttgggttaaa agctttaaca tctattagga 7380
agaatttgtc ctgtgggttt ggaatcttgg attttccccc tttatgaact gtactggctg 7440
ttgaccacca gacacctgac cgcaaatatc ttttcttgta ttcccatatt tctagacaat 7500
gatttttgta agacaataaa tttattcatt atagatattt gcgcctgctc tgtttacttg 7560
aagaaaaaag cacccgtgga gaataaagag acctcaataa acaagaataa tcatgtgaa 7619

<210> SEQ ID NO 150
<211> LENGTH: 1752
<212> TYPE: DNA
<213> ORGANISM: Homo sapiens

<400> SEQUENCE: 150
atgtcttatg gtgaaattga aggtaaattc ttgggaccta gagaagaagt aacgagtgag 60
ccacgctgta aaaaattgaa gtcaaccaca gagtcgtatg tttttcacaa tcatagtaat 120
gctgattttc acagaatcca agagaaaact ggaaatgatt gggtccctgt gaccatcatt 180
gatgtcagag gacatagtta tttgcaggag aacaaaatca aaactacaga tttgcataga 240
cctttgcatg atgagatgcc tggtaataga ccagatgtta ttgaatccat tgattcacag 300

-continued gttttacagg aagcacgtcc tccattagta tccgcagacg atgagatata tagcacaagt 360
aaagcattta taggacccat ttacaaaccc cctgagaaaa agaaacgtaa tgaagggagg 420
aatgaggcac atgttctaaa tggtataaat gacagaggag gacaaaaaga gaaacagaaa 480
tttaactctg aaaaatcaga gattgacaat gaattattcc agttttacaa agaaattgaa 540
gagcttgaaa aggaaaaaga tggttttgag aacagttgta aagaatctga accttctcag 600
gaacaatttg ttccatttta tgagggtcat aataatggtc tcttaaaacc tgatgaagaa 660
aagaaagatc ttagtaataa agctatgcca tcacattgtg attatcagca gaacttgggg 720
aatgagccag acaaatatcc ctgtaatgga caagtaatac ctacattttg tgacacttca 780
tttacttctt tcaggcctga atggcagtca gtatatcctt ttatagtgcc ctatggtccc 840
cctcttccca gtttgaacta tcatttaaac attcagagat tcagtggtcc accaaatcca 900
ccatcaaata ttttccaagc ccaagatgac tctcagatac aaaatggata ttatgtaaat 960
aattgtcatg ttaactggaa ttgcatgact tttgatcaga acaatgaata tactgactgt 1020
agtgagaata ggagtagtgt tcatccctct ggaaatggct gcagtatgca agatcgatat 1080
gtgagtaatg gtttctgtga agtcagagaa agatgctgga aagatcattg tatggacaag 1140
cataatggaa cagacaggtt tgtgaaccag cagtttcaag aggaaaagtt aaataaattg 1200
cagaagttac ttattctttt aagaggtctg cctggttctg ggaaaacaac attgtctcga 1260
attctgcttg gtcagaatcg tgatggcatt gtgttcagca ctgatgacta ttttcaccat 1320
caagatgggt acaggtataa tgttaatcaa cttggtgatg cccatgactg gaaccagaac 1380
agagcaaaac aagctatcga tcagggaaga tctccagtta taatagataa cactaatata 1440
caagcttggg aaatgaagcc atatgtggaa gtggccatag gaaaaggata cagagtagag 1500
tttcatgaac ctgaaacttg gtggaaattt gatcctgaag aattagaaaa gaggaataaa 1560
catggtgtgt ctcgaaagaa gattgctcag atgttggatc gttatgaata tcaaatgtcc 1620
atttctattg taatgaattc agtggaacca tcacacaaaa gcacacaaag acctcctcct 1680
ccacagggga gacagaggtg gggaggctct cttggctcac ataatcgtgt ctgtgtcaca 1740
aataatcatt aa 1752

<210> SEQ ID NO 151
<211> LENGTH: 1758
<212> TYPE: DNA
<213> ORGANISM: Homo sapiens

<400> SEQUENCE: 151
ctgctgtctg cggaggaaac tgcatcgacg gacggccgcc cagctacggg aggacctgga 60
gtggcactgg gcgcccgacg gaccatcccc gggacccgcc tgcccctcgg cgccccgccc 120
cgccgggccg ctccccgtcg ggttccccag ccacagcctt acctacgggc tcctgactcc 180
gcaaggcttc cagaagatgc tcgaaccacc ggccggggcc tcggggcagc agtgagggag 240
gcgtccagcc ccccactcag ctcttctcct cctgtgccag gggctccccg ggggatgagc 300
atggtggttt tccctcggag ccccctggct cgggacgtct gagaagatgc cggtcatgag 360
gctgttccct tgcttcctgc agctcctggc cgggctggcg ctgcctgctg tgcccccccca 420 gcagtgggcc ttgtctgctg ggaacggctc gtcagaggtg gaagtggtac ccttccagga 480
agtgtggggc cgcagctact gccgggcgct ggagaggctg gtggacgtcg tgtccgagta 540
ccccagcgag gtggagcaca tgttcagccc atcctgtgtc tccctgctgc gctgcaccgg 600
ctgctgcggc gatgagaatc tgcactgtgt gccggtggag acggccaatg tcaccatgca 660
gctcctaaag atccgttctg gggaccggcc ctcctacgtg gagctgacgt tctctcagca 720
cgttcgctgc gaatgccggc ctctgcggga gaagatgaag ccggaaagga ggagacccaa 780
gggcaggggg aagaggagga gagagaagca gagacccaca gactgccacc tgtgcggcga 840
tgctgttccc cggaggtaac ccaccccttg gaggagagag accccgcacc cggctcgtgt 900
atttattacc gtcacactct tcagtgactc ctgctggtac ctgccctcta tttattagcc 960
aactgtttcc ctgctgaatg cctcgctccc ttcaagacga ggggcaggga aggacaggac 1020
cctcaggaat tcagtgcctt caacaacgtg agagaaagag agaagccagc cacagacccc 1080
tgggagcttc cgctttgaaa gaagcaagac acgtggcctc gtgaggggca agctaggccc 1140
cagaggccct ggaggtctcc aggggcctgc agaaggaaag aagggggccc tgctacctgt 1200
tcttgggcct caggctctgc acagacaagc agcccttgct ttcggagctc ctgtccaaag 1260
tagggatgcg gatcctgctg gggccgccac ggcctggctg gtgggaaggc cggcagcggg 1320
cggaggggat ccagccactt ccccctcttc ttctgaagat cagaacattc agctctggag 1380
aacagtggtt gcctgggggc ttttgccact ccttgtcccc cgtgatctcc cctcacactt 1440
tgccatttgc ttgtactggg acattgttct ttccggccaa ggtgccacca ccctgccccc 1500
cctaagagac acatacagag tgggccccgg gctggagaaa gagctgcctg gatgagaaac 1560
agctcagcca gtggggatga ggtcaccagg ggaggagcct gtgcgtccca gctgaaggca 1620
gtggcagggg agcaggttcc ccaagggccc tggcaccccc acaagctgtc cctgcagggc 1680
catctgactg ccaagccaga ttctcttgaa taaagtattc tagtgtggaa aaaaaaaaaa 1740
aaaaaaaaaa aaaaaaaa 1758

<210> SEQ ID NO 152
<211> LENGTH: 1622
<212> TYPE: DNA
<213> ORGANISM: Homo sapiens

<400> SEQUENCE: 152
gtttaagtag aatcctcaag cttggcctca gagtactatg aggcttctga atccaggaat 60
aagactgctc ttggatttac tctctttgta ttgcatgtca aaggcaacag aactggacca 120
agaaaattca taactttttg cgtttgtttc tactaagatg acatcataca tggctattga 180
tggcagtgct cttgttccct tgcgtcagaa gcccaggagg aaaactcaag gttttctcac 240
gatgagtcgg aggaggatat cgtgtaaaga tctgggccat gctgactgcc aagggtggct 300
gtataagaaa aaggaaaagg gaagtttcct aagcaacaaa tggaaaaagt tctgggtgat 360
actgaagggg tcgtcactgt actggtatag caatcaaatg gcagagaaag ctgatggatt 420
tgtcaacctg cctgatttca ctgtggaaag agcatctgaa tgcaagaaaa agcatgcttt 480
taagatcagc catccacaga tcaagacctt ttattttgca gctgagaatg tgcaggaaat 540
gaacgtgtgg ttaaataaac ttggatcggc tgtaatccat caggaatcca ctacaaagga 600
tgaagaatgt tacagtgaaa gtgaacagga agatccagaa atagctgcgg agacaccacc 660
ccctcctcac gcttcccaga ctcagtcttt gactgcacag caggcatctt catcctcacc 720
cagcctgagt ggaacgtcgt attctttctc ttccctggaa aatacagtga agacacccag 780
cagttttcct tcctccttat ctaaagagag acaatccttg cctgacacag ttaacagttt 840
gtctgctgct gaagatgagg gacaaccaat aacgtttgct gtgcaagttc attcacctgt 900
accctcagag gcaggcatcc acaaggccct ggaaaacagt tttgtcacat cagaaagtgg 960

-continued

```
atttttgaac tctttatcta gtgatgatac ttcttcattg agtagcaatc atgaccatct   1020

tactgtccca gataagcctg ctggatcaaa gatcatggac aaagaagaga caaaagtgtc   1080

tgaagatgat gaaatggaga agctgtacaa atcattagag caagctagtc tatctcctct   1140

tggggaccga cgaccttcga ctaaaaagga gttgagaaaa tcctttgtta agcggtgtaa   1200

aaatccatct ataaacgaga aactccacaa aatccgaaca ttgaatagca cattaaagtg   1260

taaagaacat gatctggcca tgattaacca gttgctggat gacccgaagc tgacagccag   1320

gaaatacaga gagtggaaag tcatgaacac cctgctgatc caggacatct atcagcagca   1380

gcgggcttcg cctgcccctg atgacactga tgacaccccc caggaactca agaaatcacc   1440

ttcttctccc tctgttgaaa attccatttg agacaaagtc agggttttct cctcttatat   1500

tttatcacaa gcaactcttc aagatgttgc aaaagcttac atttttcctt aaaaggaaaa   1560

ctgaaaccca gtccttcaag catcagcttc ccatctaaag atgcacgtta gatgaagata   1620

at                                                                  1622
```

<210> SEQ ID NO 153
<211> LENGTH: 3730
<212> TYPE: DNA
<213> ORGANISM: Homo sapiens

<400> SEQUENCE: 153

```
gtgtgaaggg ggggtccggg gggcgggtcc ctgtgccgct gacgtcccga gcagtgctgg     60

gaagtatagg ctgtgttgtc acgccggtgt cagtctgatg aagattggca tcaggtgaag    120

tctggagcag gacttctgag gctttctatc ctccatgctg ctcactagaa aaggggctgt    180

gaactgtgct ttggctctag cagacaggaa gaaattctgg cccagctgga agtagaaaga    240

ggggagtgag tctcctgagg accatctcag aggccccggg atcacccgaa cagtcctcca    300

tgtgaatcaa tcccatgatg caacatgcct ccccagcccc cgctctgacg atgatggcca    360

cgcagaatgt cccgcccccca ccctaccagg acagcccaca gatgacggca accgcccagc    420

caccctccaa ggcccaggct gtccacatct ctgcccctc agctgctgcc agcacacctg    480

tgcccagtgc ccccatcgac ccccaggccc agctggaggc tgacaagcga gctgtataca    540

ggcaccctct tttcccgctc ctgacgctgc tgtttgagaa atgtgaacag gccacccagg    600

gctctgagtg catcacctcc gccagctttg atgtggacat cgagaacttt gtccaccagc    660

aggaacagga gcacaaaccc ttcttcagcg atgacccaga actggacaat ctgatggtga    720

aggcaatcca ggtcctgaga atccacctgc tggagctgga gaaagtcaat gaactctgca    780

aggacttttg taaccgttac atcacctgcc tcaaaaccaa gatgcacagc gacaacctgc    840

tcaggaatga tctagggggg ccctactccc ccaaccagcc ctccatcaac cttcactcac    900

aggacctcct gcagaattcc cccaattcca tgtccggagt ctccaataac ccccaggggga    960

ttgtggtccc agcctcagcg ctccagcagg gcaacatcgc catgacaacc gtcaactcac   1020

aagttgtgtc aggtggagcc ttataccaac cggttaccat ggtaacctcc cagggtcagg   1080

tggtcaccca agcaatcccc cagggagcca tccagatcca gaacacacag gttaaccttg   1140

acctcacctc cctcctggac aatgaggata agaagtccaa gaacaaacga ggagtcttgc   1200

ccaagcatgc caccaatata atgcgttctt ggctcttcca gcatctcatg caccccctacc   1260

ccacggagga tgagaagagg cagatcgcag cccagaccaa cctcaccctc ctgcaagtaa   1320

acaactggtt catcaatgcc cggaggcgca tcctgcagcc catgcttgat gccagcaacc   1380

cagatcctgc ccccaaagcc aagaagatca agtctcagca ccggcccacc caaagattct   1440
```

```
ggcccaactc catcgctgcg ggggtgctgc agcagcaggg cggtgcccca gggacaaacc   1500
ccgatggttc catcaacttg gacaacctgc agtccctgtc ctcagacagt gccaccatgg   1560
ccatgcagca ggctatgatg gctgcacacg atgactcatt ggatgggaca gaagaagagg   1620
atgaggatga gatggaagag gaggaggagg aggagctgga ggaggaggtc gacgagctgc   1680
agacgacaaa tgtcagcgac ctgggcttgg aacacagtga ctccctggag tagtcgggca   1740
gcccagatgg cactgatcac tgagcaggag aggagtgtcg ccgggaggcc ttcagggtgg   1800
gggggaaggg gacatgggca ggaagcaccg agggagttgg gccctagctt ccccaaatca   1860
gtagcttgaa gaaaggcaaa ggagacacct gttccttccc aaccaccgag cttcaatgag   1920
gaccccagcc ccacttccct ggaactgccg aggactctgt ttggcggggc cagtcgagca   1980
gcctgtgtgg aaagacagga gtgagatctg gactcaccaa atccctgagg atagatggca   2040
cccatggccc ccacccacgg aaggacttga gttgtttaca agccctgcac tgaggcagat   2100
tggtgctgtt cgcagagtag gcctttgccc gggggcagac ttagaaggaa ggggagagac   2160
aaagggggac tgagtttcat ccccagaagt ttctcagctc ctttgacaga cattcaaggg   2220
caggagggag ccccaaagca taaccagtgg ccagaggagt gggagggcct gaggcatcac   2280
atcttgcaga tcagaatggg atggaatcca ccaggctcca gctcatccct ccaaggccct   2340
gtctctgcgc acagcaacca tggacatggg agaaagggat gggagccaca gtgcccttca   2400
ctctctcctg gaaaccaact gtaagctggt gggctcaacc tgtgggaggt taagaggagt   2460
cccttctggg ttgactccaa gagccaagga gatggcagac cctgggctag gaaccatatg   2520
gaggtgactt tgaggccaca gctgtcccta ggtgatcaca gaacttagct cctttaacaa   2580
caggacaatg gtttttacc ctagatgttc ccaccttcag tgctccacgc cctccataga   2640
ccttcagaga aggtgaaacc aggttatctg ggaatctttc cagcccgcag gtcgccacgg   2700
ccatcccttt gctcccagcc tggctccatc agcctccagc ttcctttctt cattctgtcc   2760
ttcagggaag gcagaagaaa cattggaaag catctagtcc agtgggaagc caggggttgg   2820
agaaggtgct acatccctct tcccatcaat atcctaaatg tgggggaggg cccagagaat   2880
ggcacccaag agcctgcggg gatgcccatc ccacacaccc cacccagctg ttctaaccct   2940
gctatccaca gccctggagg aactggggct cctggaagga ggaggaggct ctccactgtc   3000
caccctaaca catacctcc cacccacctt ccagaccccc ttggttggca ccctctcctc   3060
cggttccctc tcaccccatg gctgtgaatg acaggacagg tcacacgtgt gttttccatt   3120
gggtttaatt taatggacgt gcagtttcat ttgtaaattg tgcattggcc acctccttca   3180
gtggcaggat gtgagtggct acctggctca actggagggg accccttggg ccctctgggg   3240
cttcccctcc cccacctggt tggggtagag caaaaggatg gtcactcttc cgaggtctcc   3300
ctgaaatgaa tgtatttctc ccccaaaaga gctgatattt aatgttttaa taaggatttt   3360
tgagaaacaa ataaccttat ttataatctg ggtgatccaa tcatttttta ctccctttg   3420
atgccataca tagaggaaag tctagctttt ttggcgtgag acttttgcaa tgtgcagtgg   3480
gataaaatgc atttcctttt ctggttcgtt tttcttgtta acacgcgcac acagacacac   3540
acacacaccg ttccactcac cacctggaca ggcgtccccc agcacggaca cactggcaca   3600
caggtgccca catctcttcc tctcagcccc tccacctgcc taatgttatg caacctcctt   3660
ctgatgtatc caccaaacca gtactgaatg tggccgagac gttttcagta aatcttatta   3720
cctaccgtaa                                                          3730
```

<210> SEQ ID NO 154
<211> LENGTH: 4499
<212> TYPE: DNA
<213> ORGANISM: Homo sapiens

<400> SEQUENCE: 154
acacatgcat agctcttagc ttctgtgtaa gaagttgtga gctccttctg gaaacatttg 60
cagttacatt aagtaaagtg taaatgcaca tgaatggcag cttatagaga accaccttgt 120
aaccagtata caggtacaac tacagctctt cagaaattgg aaggttttgc tagccggtta 180
tttcatagac actctaaagg tactgcacat gatcagaaaa cagctctgga aaatgacagc 240
cttcatttct ctgaacatac tgccttatgg gacagatcaa tgaaagagtt tctagccaaa 300
gccaaagaag actttttgaa aaaatgggag aatccaactc agaataatgc cggacttgaa 360
gattttgaaa ggaaaaaaac ccttggaaca ggttcatttg gaagagtcat gttggtaaaa 420
cacaaagcca ctgaacagta ttatgccatg aagatcttag ataagcagaa ggttgttaaa 480
ctgaagcaaa tagagcatac tttgaatgag aaaagaatat tacaggcagt gaattttcct 540
ttccttgttc gactggagta tgcttttaag gataattcta atttatacat ggttatggaa 600
tatgtccctg ggggtgaaat gttttcacat ctaagaagaa ttggaaggtt cagtgagccc 660
catgcacggt tctatgcagc tcagatagtg ctaacattcg agtacctcca ttcactagac 720
ctcatctaca gagatctaaa acctgaaaat ctcttaattg accatcaagg ctatatccag 780
gtcacagact ttgggtttgc caaaagagtt aaaggcagaa cttggacatt atgtggaact 840
ccagagtatt tggctccaga aataattctc agcaagggct acaataaggc agtggattgg 900
tgggcattag gagtgctaat ctatgaaatg gcagctggct atcccccatt ctttgcagac 960
caaccaattc agatttatga aaagattgtt tctggaaagg tccgattccc atcccacttc 1020
agttcagatc tcaaggacct tctacggaac ctgctgcagg tggatttgac caagagattt 1080
ggaaatctaa agaatggtgt cagtgatata aaaactcaca agtggtttgc cacgacagat 1140
tggattgcta tttaccagag gaaggttgaa gctccattca taccaaagtt tagaggctct 1200
ggagatacca gcaactttga tgactatgaa gaagaagata tccgtgtctc tataacagaa 1260
aaatgtgcaa aagaatttgg tgaattttaa agaggaacaa gatgacatct gagctcacac 1320
tcagtgtttg cactctgttg agagataagg tagagctgag accgtccttg ttgaagcagt 1380
tacctagttc cttcattcca acgactgagt gaggtcttta ttgccatcat cccgtgtgcg 1440
cactctgcat ccacctatgt aacaaggcac cgctaagcaa gcattgtctg tgccataaca 1500
cagtactaga ccactttctt acttctcttt gggttgtctt tctcctctcc tatatccatt 1560
tcttcctttt ccaatttcat tggttttctc taaacagtgc tccattttat tttgttggtg 1620
tttcagatgg gcagtgttat ggctacgtga tatttgaagg gaaggataag tgttgctttc 1680
agtagttatt gccaatattg ttgttggtca atggcttgaa gataaacttt ctaataatta 1740
ttatttcttt gagtagctca gacttggttt tgccaaaact cttggtaatt tttgaagata 1800
gactgtctta tcaccaagga aatttataca aattaagact aactttcttg gaattcacta 1860
ttctggcaat aaattttggt agactaatac agtacagcta gacccagaaa tttggaaggc 1920
tgtagatcag aggttctagt tccctttccc tccttttata tcctcctctc cttgagtaat 1980
gaagtgacca gcctgtgtag tgtgacaaac gtgtctcatt cagcaggaaa aactaatgat 2040
atggatcatc acccagattc tctcacttgg taccagcatt tctgtaggta ttagagaaga 2100
gttctaagtt ttctaaacct taactgttcc ttaaggattt tagccagtat tttaatagaa 2160

```
catgattaat gaaagtgaca aattttaaat tttctctaat agtcctcatc ataaactttt   2220
taaaggaaaa taagcaaact aaaaagaaca ttggtttaga taaatactta tactttgcaa   2280
agtcaaaaat ggcttgattt ttggaaacaa tatagaggta ttcatattta aatgagggtt   2340
tacatttgtt ttgttttgta accgttaaaa agaagttgtt tccagctaat tattgtggtg   2400
tactatattt gtgagcctag ggtaggggca ctgctgcaac ttctgctttc atcccatgcc   2460
tcatcaatga ggaaagggaa caaagtgtat aaaactgcca caattgtatt ttaattttga   2520
ggtatgatat tttcagatat ttcataattt ctaacctctg ttctctcagt aaacagaatg   2580
tctgatcgat catgcagata caatgttggt atttgagagg ttagtttttt tcctacactt   2640
tttttgcca actgacttaa caacattgct gtcaggtgga aatttcaagc acttttgcac   2700
atttagttca gtgtttgttg agaatccatg gcttaaccca cttgttttgc tattttttc   2760
tttgctttta attttcccca tctgatttta tctctgcgtt tcagtgacct accttaaaac   2820
aacacacgag aagagttaaa ctgggttcat tttaatgatc aatttacctg catataaaat   2880
ttatttttaa tcaagctgat cttaatgtat ataatcattc tatttgcttt attatcggtg   2940
caggtaggtc attaacacca cttcttttca tctgtaccac accctggtga aacctttgaa   3000
gacataaaaa aaacctgtct gagatgttct ttctaccaat ctatatgtct ttcggttatc   3060
aagtgtttct gcatggtaat gtcatgtaaa tgctgatatt gatttcactg gtccatctat   3120
atttaaaacg tgcaagaaaa aaataaaata ctctgctcta gcaagttttg tgtaacaaag   3180
gcatatcgtc atgttaataa atttaaaaca tcattcgtat aaaatatttt aattttcttg   3240
tatttcattt agacccaaga acatgctgac caatgtgttc tatatgtaaa ctacaaattc   3300
tatggtagct ttgttgtata ttattgtaaa attattttaa taagtcatgg ggatgacaat   3360
ttgattatta caatttagtt ttcagtaatc aaaaagattt ctatgaattc taaaaaatat   3420
ttttttctat gaaattacta gtgcccagct gtagaatcta ccttaggtag atgatcccta   3480
gacatacgtt ggttttgagg gctattcagc cattccattt tactctctat ttaaaggccg   3540
tgagcaagct tgtcatgagc aaatatgtca agggagtcaa tttctgacca atcaagtaca   3600
ctaaattaga atatttttaa agtatgtaac attcccagtt tcagccacaa tttagccaag   3660
aataagataa aaacttgaat aagaagtaag tagcataaat cagtatttaa cctaaaatta   3720
catatttgaa acagaagata ttatgttatg ctcagtaaat aattaagaga tggcattgtg   3780
taagaaggag ccctagactg aaagtcaaga catctgaatt tcaggctgga aaactatcag   3840
tatgatctca gcctcagttc tcttgtctgt aaaatggaag aactggatta ggcagtttgt   3900
aagattcctc ctaactttca cagtcgatga caagattgtc tttttatctg atattttgaa   3960
gggtatattg ctttgaagta agtctcaata aggcaatata ttttagggca tctttcttct   4020
tatctctgac agtgttctta aaattatttg aatatcataa gagccttggt gtctgtccta   4080
attcctttct cactcaccga tgctgaatac ccagttgaat caaactgtca acctaccaaa   4140
aacgatattg tggcttatgg gtattgctgt ctcattcttg gtatattctt gtgttaactg   4200
cccattggcc tgaaaatact cattgtaagc ctgaaaaaaa aaatctttcc cactgttttt   4260
tctgcttgtt gtaagaatca aatgaaataa tgtatgtgaa agcaccttgt aaactgtaac   4320
ctatcaatgt aaaatgttaa ggtgtgttgt tatttcatta attacttctt tgtttagaat   4380
ggaatttcct atgcactact gtagctagga aatgctgaaa acaactgtgt tttttaatta   4440
atcaataact gcaaaattaa agtaccttca atggataaga caaaaaaaaa aaaaaaaaa    4499
```

<210> SEQ ID NO 155
<211> LENGTH: 3595
<212> TYPE: DNA
<213> ORGANISM: Homo sapiens

<400> SEQUENCE: 155
tttggaaacg tcacactgtg gaggaaaagc agcaactagg gagctggtga agaaggatgt 60
ctcagcagtg tttactaggc ctccaacact agagcccatc ccccagctcc gaaaagcttc 120
ctggaaatgt ccttgttatc acttcccctc tcgggctggg cgctgggagc gggcggtctc 180
ctccgccccc ggctgttccg ccgaggctcg ctgggtcgct ggcgccgccg cgcagcacgg 240
ctcagaccga ggcgcacagg ctcgcagctc cgcggcgcct agcgctccgg tccccgccgc 300
gacgcgccac cgtccctgcc ggcgcctccg cgcgcttcga aatgagggtc ctgggtgggc 360
gctgcggggc gctgctggcg tgtctcctcc tagtgcttcc cgtctcagag gcaaactttt 420
tgtcaaagca acaggcttca caagtcctgg ttaggaagcg tcgtgcaaat tctttacttg 480
aagaaaccaa acagggtaat cttgaaagag aatgcatcga agaactgtgc aataaagaag 540
aagccaggga ggtctttgaa aatgacccgg aaacggatta tttttatcca aaatacttag 600
tttgtcttcg ctcttttcaa actgggttat tcactgctgc acgtcagtca actaatgctt 660
atcctgacct aagaagctgt gtcaatgcca ttccagacca gtgtagtcct ctgccatgca 720
atgaagatgg atatatgagc tgcaaagatg gaaaagcttc ttttacttgc acttgtaaac 780
caggttggca aggagaaaag tgtgaatttg acataaatga atgcaaagat ccctcaaata 840
taaatggagg ttgcagtcaa atttgtgata atacacctgg aagttaccac tgttcctgta 900
aaaatggttt tgttatgctt tcaaataaga aagattgtaa agatgtggat gaatgctctt 960
tgaagccaag catttgtggc acagctgtgt gcaagaacat cccaggagat tttgaatgtg 1020
aatgccccga aggctacaga tataatctca aatcaaagtc ttgtgaagat atagatgaat 1080
gctctgagaa catgtgtgct cagctttgtg tcaattaccc tggaggttac acttgctatt 1140
gtgatgggaa gaaaggattc aaacttgccc aagatcagaa gagttgtgag gttgtttcag 1200
tgtgccttcc cttgaacctt gacacaaagt atgaattact ttacttggcg gagcagtttg 1260
caggggttgt tttatattta aaatttcgtt tgccagaaat cagcagattt tcagcagaat 1320
ttgatttccg gacatatgat tcagaaggcg tgatactgta cgcagaatct atcgatcact 1380
cagcgtggct cctgattgca cttcgtggtg gaaagattga agttcagctt aagaatgaac 1440
atacatccaa aatcacaact ggaggtgatg ttattaataa tggtctatgg aatatggtgt 1500
ctgtggaaga attagaacat agtattagca ttaaaatagc taaagaagct gtgatggata 1560
taaataaacc tggacccctt tttaagccgg aaaatggatt gctggaaacc aaagtatact 1620
ttgcaggatt ccctcggaaa gtggaaagtg aactcattaa accgattaac cctcgtctag 1680
atggatgtat acgaagctgg aatttgatga agcaaggagc ttctggaata aaggaaatta 1740
ttcaagaaaa acaaaataag cattgcctgg ttactgtgga gaagggctcc tactatcctg 1800
gttctggaat tgctcaattt cacatagatt ataataatgt atccagtgct gagggttggc 1860
atgtaaatgt gaccttgaat attcgtccat ccacgggcac tggtgttatg cttgccttgg 1920
tttctggtaa caacacagtg ccctttgctg tgtccttggt ggactccacc tctgaaaaat 1980
cacaggatat tctgttatct gttgaaaata ctgtaatata tcggatacag gccctaagtc 2040
tatgttccga tcaacaatct catctggaat ttagagtcaa cagaaacaat ctggagttgt 2100
cgacaccact taaaatagaa accatctccc atgaagacct tcaaagacaa cttgccgtct 2160

```
tggacaaagc aatgaaagca aaagtggcca catacctggg tggccttcca gatgttccat   2220

tcagtgccac accagtgaat gccttttata atggctgcat ggaagtgaat attaatggtg   2280

tacagttgga tctggatgaa gccatttcta aacataatga tattagagct cactcatgtc   2340

catcagtttg gaaaaagaca aagaattctt aaggcatctt ttctctgctt ataatacctt   2400

ttccttgtgt gtaattatac ttatgtttca ataacagctg aagggtttta tttacaatgt   2460

gcagtctttg attattttgt ggtcctttcc tgggattttt aaaaggtcct ttgtcaagga   2520

aaaaaattct gttgtgatat aaatcacagt aaagaaattc ttacttctct tgctatctaa   2580

gaatagtgaa aaataacaat tttaaatttg aatttttttc ctacaaatga cagtttcaat   2640

ttttgtttgt aaaactaaat tttaatttta tcatcatgaa ctagtgtcta aatacctatg   2700

tttttttcag aaagcaagga agtaaactca aacaaaagtg cgtgtaatta aatactatta   2760

atcataggca gatactattt tgtttatgtt tttgtttttt tcctgatgaa ggcagaagag   2820

atggtggtct attaaatatg aattgaatgg agggtcctaa tgccttattt caaaacaatt   2880

cctcaggggg aacagctttg gcttcatctt tctcttgtgt ggcttcacat ttaaaccagt   2940

atctttattg aattagaaaa caagtgggac atattttcct gagagcagca caggaatctt   3000

cttcttggca gctgcagtct gtcaggatga gatatcagat taggttggat aggtggggaa   3060

atctgaagtg ggtacatttt ttaaattttg ctgtgtgggt cacacaaggt ctacattaca   3120

aaagacagaa ttcagggatg gaaaggagaa tgaacaaatg tgggagttca tagttttcct   3180

tgaatccaac ttttaattac cagagtaagt tgccaaaatg tgattgttga agtacaaaag   3240

gaactatgaa aaccagaaca aattttaaca aaaggacaac cacagaggga tatagtgaat   3300

atcgtatcat tgtaatcaaa gaagtaagga ggtaagattg ccacgtgcct gctggtactg   3360

tgatgcattt caagtggcag ttttatcacg tttgaatcta ccattcatag ccagatgtgt   3420

atcagatgtt tcactgacag tttttaacaa taaattcttt tcactgtatt ttatatcact   3480

tataataaat cggtgtataa ttttaaaatg catgtgaata tctttattat atcaactgtt   3540

tgaataaaac aaaattacat aatagacatt taactcttca aaaaaaaaaa aaaaa        3595
```

<210> SEQ ID NO 156
<211> LENGTH: 11687
<212> TYPE: DNA
<213> ORGANISM: Homo sapiens

<400> SEQUENCE: 156

```
aacaaagagc acgcggcgct ggccgccggc actcgcgccc tgaggctgcg gccccggagc     60

gcccggcggc ggtttcggcg cgcggccggg ctggcgatgg aagatggaag gaaggagcgc    120

agcggcagag acatttgttt gggtgaacaa tgcatctgca cattcccaga gtgttgccaa    180

ggccaaatat gaatttttat ttggcagatc tgaagggaaa gctccagata ctagtgatca    240

tggaggaagc actttactcc caccaaatgt cacaaatgaa tttccagaat atgggaccat    300

ggaggaaggt ggagaaggcc taagggcttc tctggaattt gatggtgagg ctctgccatg    360

ccacccacaa gagcagcagg gtgtccagcc tcttactggc tgccactctg ggctcgacag    420

tgttacagaa ggaccaaaag atgtcagaga ggccccctct caaagtcatc tcaaggaaca    480

aagtttacag cccattgact ctttgatttc agctctgaaa gccacagaag ccagaatcat    540

ttccggaaca ttacaggcta caaaggtact ggaccaagat gctgtttcta gtttttcagt    600

tcagcaggtg gaaaaagagc tggacactgc cagtcgtaaa acacagagag tcaacaaaac    660
```

```
gctccctgct ggccaaaaaa atttaccaga aatacctctt tcagctgaag taacaacgga    720
ggaaagtttt tatttgagca tccagaaaga tctcaccgcg ctgttaactg gagacactca    780
ggcagagatt tcccagataa tgaataatgg gaggaaaggg gctgtctgtg tgcaggagcc    840
atcttgtcct ttggcctccc tcgggagctc agcagtgacc tgccactctg caggcagtgt    900
tggtttcttg aaagagcaga ggtctgctct tgggagagag cacccagggg gatgtgatcg    960
aagcagctcc atgggacgcc caggccgggt caaacatgtg gaatttcaag gagtggaaat   1020
actgtggaca ggaggagaca agagagagac ccagcatcct atagattttg agacatcact   1080
gcaaagaaca gcctctcctg acagcaaaga gtcttccaaa gtgccacgcc atctcatctc   1140
atcagctggt ttgtgtaatt caagtagttt aactgagaat gtttgggatg aatcctggaa   1200
agctccttca gagaggcctg gcactagctc ggggacattt tcccctgtgc gtcttgatga   1260
gagtggagag gatgaagtct tcctacagga aaacaaacag catcttgaga agacacctaa   1320
accagagaga gacagggaaa ggatcagcga acaagaggag cacgttaagg gggaagatga   1380
agacatcctt gggcctggat atacggagga ctccaccgac gtgtacagct cccagtttga   1440
aaccattttg gacaacactt ctttatacta cagtgcagag tccctggaga cattatactc   1500
agagcctgat agctatttta gctttgaaat gcccctcact ccaatgatac aacagcgcat   1560
taaagaaggt ggtcagttct tggagaggac atcaggggga ggacatcagg atatcctgag   1620
tgtgtctgca gatggtggca tcgtgatggg ctattctagt ggcgtcacca atgggctgaa   1680
tgatgccagc gactccatct acacgaaagg caccccggag attgctttct ggggaagcaa   1740
tgctggggtg aaaacaacac ggctagaagc tcattctgaa atggggagca ctgaaatttt   1800
ggaaaaggag accccagaaa atctcagtaa tggtaccagc agcaatgtgg aagcagccaa   1860
aaggttggcc aaacgccttt atcagctgga cagattcaaa agatcagatg ttgcaaaaca   1920
ccttggcaag aacaacgaat ttagcaaact agttgcagaa gaatatctga agtttttga    1980
ttttacagga atgacgctgg atcagtcact caggtatttc tttaaagcat tctctcttgt   2040
gggagaaact caagaacgag agagagtttt aatacacttc tccaatagat atttttattg   2100
taacccagat accattgctt cacaagatgg agtccattgc cttacctgtg caataatgct   2160
tcttaatacc gatctacatg gccacaatat tggaaagaag atgacctgtc aggagttcat   2220
tgcaaatctg caaggggtaa atgagggtgt tgatttctcc aaggatctgc tgaaagctct   2280
gtacaactca atcaagaatg agaagcttga atgggcagta gatgatgaag agaaaaaaaa   2340
gtctccctca gaaagtactg aggagaaagc taacggaaca catccaaaga ccatcagtcg   2400
tattggaagt actactaacc catttttgga cattcctcat gatccaaatg ctgctgtgta   2460
caaaagtgga ttcttggctc ggaaaattca tgcagatatg gatggaaaga agactccaag   2520
aggaaaacga ggatggaaaa ccttttatgc tgtactgaag ggaacagttc tttacttgca   2580
aaaggatgaa tacaagccag aaaaggcctt gtctgaagag gacttgaaaa acgctgtgag   2640
tgtgcaccac gcattggcat ccaaggccac ggactatgag aagaaaccaa acgtgtttaa   2700
acttaaaact gccgactgga gggtcttgct ttttcaaact cagagcccag aggaaatgca   2760
agggtggata aacaaaatca attgtgtggc agctgtattt tctgcaccac catttccagc   2820
agcaatcggc tctcagaaga agtttagccg cccacttctg cctgccacta caacaaaact   2880
gtctcaggag gagcaactga agtcacatga aagtaagctg aagcagatca ccaccgagct   2940
ggccgagcac cgctcatatc cccccgacaa gaaggtcaaa gccaaggacg tcgatgagta   3000
caaactgaaa gaccactatc tggagtttga gaaaacccgc tatgaaatgt atgtcagcat   3060
```

tctcaaggaa ggaggcaaag agctactgag taacgatgaa agcgaggctg caggactgaa 3120
gaagtcgcac tcgagtcctt cgctgaaccc ggatacttct ccaatcactg ccaaagtcaa 3180
gcgtaacgtg tcagagagga aggatcaccg acctgaaaca ccaagcatta agcaaaaagt 3240
tacttagagt ccatctgcgg ccaggaagtg ctggtcatgg agcaaaatag ggtttttcaa 3300
gatctttctg gtaatccgtg aatatattta aaaaaaaaaa gtctgtgaca aaacggtgca 3360
ttagtaattt tttctattgt atatttttgt tagtttctgt acagattgtc tttgctcttg 3420
atttcttttg ctttgatgat ttttgcaact tgatagctaa tgcacctttt ctgtgaggag 3480
gaggggatcg tgatttcaga atgaattatg tatcccttct cttttggttt tctcttgttt 3540
gcagtctgct cagttgtttt atgtattctc atatcaactg ttaaactttt ttttaaggtt 3600
aaagaattta atccattgtg aaacacttaa ctggacaaac tgtagtttta gtaaattcta 3660
gctggagtta atatacgcct ttatatgtga aatcttgccc agtcacagag gtagaattga 3720
gcactcacag atgctccagt aagaatcaca gtgctgggaa tctagttgct ccaatatgag 3780
gcagcttcat gtgcagctta gcacttgttg ttgagatcgg accctgctgg aagcagggaa 3840
aagaagcgtg aagatcgtag gattgagaac ttagggaagc acattagctt gcttgaagtg 3900
ctgattccat ttcagccaag caagggaaag aggaagtgga gtcattttgc ctttgaaggc 3960
tgaggaaaga ttgataccca gttaattttg tttgctaaag gatgggggca ataatcggcc 4020
cttgaggagc tgcagcagta ggcatgtgct cagtctgcag gaattgttac ctcactccca 4080
cagggtctag actagaaatc catcatctct atcgttgata tccttccatc caggaataga 4140
tttttcttac tctacatatg tgtgtgtgcg tgcgtgtgtg tgcgtgtgtg ggcatggggt 4200
tgtgtcctgg ttgtgatatt gaggtcttcc ttcctaacaa attaatacta aaatgaaaca 4260
gcttttcttg tgtccttaag acaaaataag gaaggaaaac gtagctgcag ttgtccacga 4320
tggatattgg ttctttaaaa tatatctgaa agtagtagtc agaatgaatt atggttggaa 4380
aactgaggaa tcttctggtt gcaggtgcaa agtgactttg tttattcttg tctcagtctc 4440
cttgatagcc acttcactct gctactactc aactttctcc taaaaatact tcatctattt 4500
tcagtccttt ctttctgtct actcaaaatg gttctattaa ctttgcagtc atgagcttgt 4560
tccagttaca gtccctttga agttcagggt gataaacaga atattcttct gtagaggaag 4620
agaaaggagt gaaagtttag cccactgaga cctagagctt tgtgatttcc taaccttgaa 4680
actctgtaat ccctaaagtt aaaatctccg caagtggcac aacttcagaa ctaatagtat 4740
cactttgatt tttctttttc ctcccttaga aagtttctct agttctatag tttatttgtt 4800
gaaggtacta tgaccaaaga atcagctgct ctacaggaat agcatggttc cagtgaatta 4860
gagaaaacct gctgtaaagc catggtagtg tctaagtggt atgttattat gatgtactag 4920
catttattta cagaattatt tattaacgtt tacttccttc ccctctgtaa atgtccatga 4980
ctattgccca gagaaggctt acccctctct agggttgcag ttgctttctt tgtaataagt 5040
attttgccac acctgtaaaa aaaaaaacct cacttttaac tctctgcctt gtttgggtaa 5100
aggcagtaac taagtttatg tttcagaact gcaaaacaaa caggatagtt accaatatgg 5160
cccatgtatc agattgattt ttgtagcctc tcactgaatc caacatatcc acaagcaagt 5220
tatctgtctt tctacctgat aatctaaatt atcaggatat ttgttttctg cctaaatgtt 5280
tatactaagc cgaggggaga gaggtaccta gaccatgtca tctacaagct tcagtaacta 5340
aagaaaaagg aacttccctg agtggcttga atgtgtttgc ccacagtcta tatctatgta 5400

-continued

```
tatagaatgt ctgtatgtat tttacttatt taatatacat tgaatggtac cttgctacag   5460
tatttctgac atttagagta gtgttgaaat actcggctag catcagcacc actatagcac   5520
tgtccgtgtc atatgagtca ctaatattaa ctccagggac ttctggatag gctaatagat   5580
cattggatac gaagggctct tttgaagctt cagtatacca tgtttgcata gtttatcttt   5640
aaaaacaact ttaaaggttc ttttgtgagc caggatctca gactgccgta gcatgatgct   5700
gtccatcttt agcgcatggg ctgagaacac ctcttccctg aggcttctga aggttgctgt   5760
ctgtcatgag tgcatgaagg aggccaagag tttatgctat gggaggaaac agtcactgat   5820
ttgcctagat tctgagagtc tggcccatag ccaaccacat tttcctttgg gataatttat   5880
ttcctgtggc atctagccag aagaaattga ggatgtttcc tttcacagct gctccaagcc   5940
tgttgcccaa ttcacggtac aagggagcac cccttccctt tcctctgaag gtacgccacc   6000
cacctccgtc gcccacctca gcgcccagga gccttgggac ttccttccat atgataaatc   6060
attcttcttc acgtcaatac acttcatatt aatttctagt acagaaaatc ttgacagcta   6120
tcagaatgcc ttggtcatag tgttgttgca aaattgacca tacaggtggc ccatgtataa   6180
aatctgaatt ttaggggttt gtccccacct cgcatgctgg cttttacagg gaggtgtctg   6240
ggattcctca ttagcaatca aaacttaatt actgggatgc agagtcctta ctttatcgcc   6300
agcccgtagg catttctgaa gtgcactttt ttgaaacatc attttgctaa ctctcagcag   6360
tgtctaatta aactgagcaa tacttttgtg aattttaatt aatctcagca aaaccatgat   6420
gggagagagt cctctgatgg aaatgtagtc cctggattat gtgtaacctt tttattcctc   6480
ttagatgcag aggatagaaa gcattttttg gtgcagtggt cttgtggcaa acacaagacc   6540
ctctatgcgt ctccaactgt tatcctaatc tagaaaatga ggactggccc ctgggcaaaa   6600
gtgacatgag gaatttactc tggaagagga aaatctgggt ggctttccaa ggctaagata   6660
ggtttgtatt tcaccctgtg gccaagctac agaacttctg agattgtgga agaatttttg   6720
caaccagcag ggaaagaggc ctcttactgc ctaaacacaa agttacactg agcttttcta   6780
ctgtcctttg cctattgctc cctctatcat gtaaagatct gggaaggatg agaggcaggg   6840
cctgcttgtc atgagctgca ctcttttctt tttaactaat cattgacaat tggaagaaaa   6900
ttgacgttaa agaagtttct ccattgtctt actaacaaaa ccttttgggt ttcattaatt   6960
gtccttgaaa ttgagttcct ttggcatttt tccttgcagt catcagttaa gcatgttgca   7020
tcctgaattc acagaagttt agctttgcag gtttgaatct ctgtaattta actcccgtgg   7080
acttggtcga gttttcagca ggttgggagc cacctctctt catttcagca gtgagtcatc   7140
ccttgacttt tcaaatgaca gaatttttcc caattgtaaa attagcactg taaaacaaag   7200
aaccaaagtg gcatcctaag agttgttaaa cctgaagtct agtttatgag gaattgtcca   7260
agttggagtt taaatagtat ctgcttttgt ctcaaagcat ctaagttatt ctgacagaaa   7320
atggtaagtc agctttgcag gcagatgcgc ctctgggcct cctaccttgc tccacagctt   7380
tctggccatc ttgtctccca ggccatgcca ctgctctgcc acatgtcagc aaatttcttt   7440
ccaccagtct tatagcatct tacatgatca aatcatcaca gaataacccc gtgatagatt   7500
attgatagca atagagaggg gctttgtcac tgatttttct ctcagattcc ttttccatct   7560
ctcatccata aaggaaggac tgaaatccaa aggcattctc cttttgtacc tacagtatcc   7620
agaacccacg tgggcagcct tctgcttatg acaataattg gcccattgca tgcagagaga   7680
atgtcttcat agagagaatg tcattaaata cttgaatctg catgacagtt tgacttgaat   7740
gcaacagcag gaaaattttg caagttacat aattgtatat acagtaggtt ttcttaagtc   7800
```

tcttcggttc atcctttgta atttgtgtgt gtatctgtag tattgcaggc ttttggagac 7860
tattcttaca ggcagtatgt cagtcatcaa agaaaatgct gtcacctgcc attgttgtat 7920
ttgtgggtat ttatagttgt atgtatgtaa atgcatcagt gtgtagattg catatcagtg 7980
tatggtacat gtacatcaaa attatttttg tccttaatca gtgtgatatg aaaagcaagt 8040
acaacctcat aggactgatt atataatgaa gttgttgaga gtatatatag tggtattgtt 8100
ttattaaact taaactcaaa taatattttg attaaaattt ttaataagac tttatgctag 8160
aaaattcttt gagctttgaa tcaccagggc aaaaatgact ttcaactaac cttgtgaatc 8220
ttttgcagtg tactgtgtgc aataccaagg gcatagctcc ctgtaatttg ggaaatacag 8280
aaagaaaaga aaaaaaaaaa aaaaggcagc ctgtgcagtc ttagtaactt tagtattaag 8340
agcacttaaa gtcaaactga caattttggg cttattacaa aatgtgatgc tttaaagcac 8400
acgttcttta ttgttgttgt aattagtcca taaaaaatat agctttcgga agaattaagt 8460
acccaccata tcatttatgt atttgtgtat gttttacggg agatcaaacc actctcgtgg 8520
tgccgcatcc gtactcgctt gacttggaag aaatatcaca agcactaaag tatatcaggg 8580
catcccagga ttgggtactg tatcctaggt ttgcagttgc agaaattagc atctagtgtc 8640
acaggtaaaa gaatttcagg accaggttta aactttattt taaatatttt tatacttagg 8700 tctcttttc ctgcctctcc ccaaagaaga gccactggcc ttagttgttt gagcttactg 8760
cttatattat agagtgtaaa taggtaacta gagactaaaa ttttattaac cagcatgttt 8820
ggtatattta aagcagtgac tgagtgtgtt tgagtgagtg gctgagtgca gtgtcttttg 8880
tttaaacaca ctgcctcgtg tctttgtagc tgattcagag agtttgaatt gtggggtggg 8940
agactaactt cagctccagg ctgcagtaat gtgttggtag ttacacttga ggcatttttt 9000
tgttgttgtt aattaactct atagtctcaa actatttttg caaatatatc atttttccta 9060
attggttctt gacgtgcagt ggactggctc tgtgaatgat tggcagggtc ttagttttgc 9120
gagagtattt ccttctaaga attattgtga tctgcagaaa cagccatttg attcaaaaat 9180
catgtagaaa aggagtagga gaagcaaaac gtttcatttt tgggccttaa ccatttgaaa 9240
tgtttggact ttaaacataa agccatggag tttataaagc caagtaacca tttgatatgg 9300
ataataatat ctactctaga gagagtatat atatgcacat tgatttttaa tgctgttaag 9360
atacttttgt aaaactgtag gaacaagagt aattagacca aattgaagct taggggacag 9420
taaagtggtt gctttccatt tagggtaacc atgcatgtgg ttagtcctct cctcctgaga 9480
ttcagaacca gttgactgtc cccttaggtg tataaggaga aaagttgaca tgtctgggac 9540
ctctgacatg tgtacacatg cttgcacaca tgcacacaca gtgaatgttt taagttatac 9600
aaacataaga ccttaagatg caaagagcca gaatattcta aagaggtgat gaacagaggg 9660
ggtggaaact gcatcacaga tgttttccaa gggccagggt ggaatctgag ctctagtgtc 9720
tgactttgag atgcattata tttttaacac ataaatgagg ggatccatat cacattcttt 9780
cttgtggacc accaaattga aggctttctt gtaattcaca agcagcagct ctccagcatc 9840
tctccgtagc ctgggtgaag tcccagaagc tggtgtgcat cattttccaa ggtggcagag 9900
ctgcttgctc tgcagatcat tcctttgaga gaggagtaca agtgaagaaa caaggaggca 9960
cttcctgtag gagcactgat gtgccttgtc cacactcccc tctgagcttt actggtaaga 10020
gagctccgac tgaacatgct gagcagttga gcacttttcc atcagcaaca acagcgagga 10080
tggaaatgga aaggaaccga actaaaatgc atttcccttt gcagggcaga gagctaagct 10140
cttaggaata gtgttataga aataagcacc ctaacttcaa ttcctgaaaa tgttggttaa 10200
tggagagaat tttggagttt cacttaatat tttcccatcg gtcgccataa ataagtcttc 10260
aggcgctcct agaagagtcc cagcccaagg ctcgattaag gaccacactg caggtctgag 10320
gctcactgct ctgagtcctg aacaccagag ccctgcagag agtggtgata acacatcatc 10380
tctgcaaaga ggaacctctc ccccggccgc cacttcactc aggcttctac tgagcagcaa 10440
ggacagcctg ggtttcaaat gccacttccc ctgctttagg gatccaggtg tcctgatagc 10500
gtgaccctgc tgaggcaagg tatcaactcc gagagtgact gagtcactga gcgtggcaca 10560
tgaacaaacg tcatgacaaa gattctctga gtgaagttaa caccacgtat tttacctttg 10620
caaaaaacaa actggcaccc tgagttctaa ctacggacgg acgatatctt tgcctccaca 10680
cccagattcc tggaaatggc taacgtttcc tttctagggg aagggtcgag gaatactcaa 10740
gtgctagctt agcagctttg ttcagtccag atcagagctg ttaggtaaag gcctaaccac 10800
ctccctgcag tctcttatat ctcaagcttt aggaacccat ttctaaatgt acactagcgg 10860
agaatttata ttgtcagcct tgattaccat aggacaggca gaaaggcgat aatttgtatc 10920
ttttaatata aaagaagctt ttaacttttc cagcctatta taataactga gttatattca 10980
ctgtggctca aactaattgg cattgtggaa catttcttta ccttcaaagt tttctccacc 11040
aatcatttca gttctattgc agtcctggtg ccatatgtcc cctgcaaatt gtgaaagtaa 11100
ttagtgacaa aatagcagcc tgctcctttt caatggcgaa actgtcggca ttagcagttt 11160
tgggtaagct ggcggtacta taacacgtac tggaaacctg ttcctcatca ccacctacca 11220
gattctggaa atgccgtctt ctagaaaacg atggcgtttg tggtggtctt cttttgaaag 11280
gaacagtaat ttgtgtggat attgttaaag tgtttaaaga atattttgac aattaagttt 11340
acattttaca attgctttat tttttattaa aatagttgta tataaatatt accctatttc 11400
actgttgttc aagtaaatct aaaccttgta gacaagtgag tcatctgata tgtatagaag 11460
ctgtgatata tagagtacat ttattgtgta aatgtttatg aatataattg ttcctgtgtt 11520
tttataagtt ggggatattt tgttgtttta cggcaacaaa atttattgca tttaaatggt 11580
ttttatgtaa tagaaatcac gcaaaatagt gaaggattta aaatatgtat atgatacatg 11640
taaatgtaca aactttagaa agaaataaat ccaacaaatt tcaatca 11687

<210> SEQ ID NO 157
<211> LENGTH: 1719
<212> TYPE: DNA
<213> ORGANISM: Homo sapiens

<400> SEQUENCE: 157
ggcgatggga aggcgggcgc agtcgaccca agggtggaga agagggaagg cgaaggacgc 60
gcgttcccgg gctcgtgacc gccagcggcc cggggaaccc gctcccagac agactcggag 120
agatggcagg cggaagacac cggcgcgtcg tgggcaccct ccacctgctg ctgctggtgg 180
ccgccctgcc ctgggcatcc aggggggtca gtccgagtgc ctcagcctgg ccagaggaga 240
agaattacca ccagccagcc attttgaatt catcggctct tcggcaaatt gcagaaggca 300
ccagtatctc tgaaatgtgg caaaatgact tacagccatt gctgatagag cgatacccgg 360
gatcccctgg aagctatgct gctcgtcagc acatcatgca gcgaattcag aggcttcagg 420
ctgactgggt cttggaaata gacaccttct tgagtcagac accctatggg taccggtctt 480
tctcaaatat catcagcacc ctcaatccca ctgctaaacg acatttggtc ctcgcctgcc 540
actatgactc caagtatttt tcccactgga acaacagagt gtttgtagga gccactgatt 600

```
cagccgtgcc atgtgcaatg atgttggaac ttgctcgtgc cttagacaag aaactccttt    660
ccttaaagac tgtttcagac tccaagccag atttgtcact ccagctgatc ttctttgatg    720
gtgaagaggc ttttcttcac tggtctcctc aagattctct ctatgggtct cgacacttag    780
ctgcaaagat ggcatcgacc ccgcacccac ctggagcgag aggcaccagc caactgcatg    840
gcatggattt attggtctta ttggatttga ttggagctcc aaacccaacg tttcccaatt    900
tttttccaaa ctcagccagg tggttcgaaa gacttcaagc aattgaacat gaacttcatg    960
aattgggttt gctcaaggat cactctttgg aggggcggta tttccagaat tacagttatg   1020
gaggtgtgat tcaggatgac catattccat ttttaagaag aggtgttcca gttctgcatc   1080
tgataccgtc tcctttccct gaagtctggc acaccatgga tgacaatgaa gaaaatttgg   1140
atgaatcaac cattgacaat ctaaacaaaa tcctacaagt ctttgtgttg gaatatcttc   1200
atttgtaata ctctgattta gtttaggata attggttcta gaattgaatt caaaagtcaa   1260
ggcatcattt aaaataatct gatttcagac aaatgctgtg tggaaacatc tatcctatag   1320
atcatcctat tcttatgtgt ctttggttat cagatcaatt acagaataat tgtgttgtga   1380
tattgtgtcc taaattgctc attaattttt atttacagat tgaaaaagag ggaccgtgta   1440
aagaaaatgg aaaataaata tctttcaaag actcttttag ataaacacga tgaggcaaaa   1500
tcaggttcat tcattcaacg atagtttctc aacagtactt aaatagcggt tggaaaacgt   1560
agccttcatt ttatgatttt ttcatatgtg gaaatctatt acatgtaata caaaacaaac   1620
atgtagtttg aaggcggtca gatttctttg agaaatcttt gtagagttaa ttttatggaa   1680
attaaaatca gaattaaatg ctaaaaaaaa aaaaaaaaa                          1719
```

<210> SEQ ID NO 158
<211> LENGTH: 2824
<212> TYPE: DNA
<213> ORGANISM: Homo sapiens

<400> SEQUENCE: 158

```
gttttgaaag ttgatggagc gaactgcttt tccaaagact cttttgaaaa actttttaag     60
taggccattc tgactttaac atttctcttt gtcttaacat tagacaaaaa gtaaccttcc    120
tgaagaggac atgtgattgg aagttgtcaa ttgttgaagc attggtaact ccagtctcta    180
acgttttaga aaatcataac aagcggttct ctaccctgta aaggtgaact actgagttct    240
tcattatgtc tgatggagat tatgattacc tcatcaagtt tttagctttg ggagactctg    300
gtgtagggaa gaccagtgta ctttaccaat atacagatgg taaatttaac tccaaattta    360
tcacaacagt gggcattgat ttcagggaaa aaagagtggt gtacagagcc agtgggccgg    420
atggagccac tggcagaggc cagagaatcc acctgcagtt atgggacaca gcagggcagg    480
agaggtttcg tagcttaacg acagcgttct tcagagatgc tatgggtttt cttctacttt    540
ttgatctgac aaatgagcaa agtttcctca atgtcagaaa ctggataagc cagctacaga    600
tgcatgcata ttgtgaaaac ccagatatag tgctgtgtgg aaacaagagt gatctggagg    660
accagagagt agtgaaagag gaggaagcca tagcactcgc agagaaatat ggaatcccct    720
actttgaaac tagtgctgcc aatgggacaa acataagcca agcaattgag atgcttctgg    780
acctgataat gaagcgaatg gaacggtgtg tggacaagtc ctggattcct gaaggagtgg    840
tgcgatcaaa tggtcatgcc tctacggatc agttaagtga agaaaaggag aaagggggcat    900
gtggctgttg agaagtcaag taagcgacat agtagttcag gtggcccatg cctgggatct    960
```

-continued

```
tctctatgat tgatacatgg cacagtgaga gattaatggg cattgtgtac aaattgcttc   1020

tcaccatccc cattagacct acgaataaag catccggttc taaaattaat ttgttgcagc   1080

tttgtaaata tttctttaag attcagcctg agagttagga gaaatatttc agagccaaaa   1140

gtgccttata caaccttagc ctattatagt aaatcattca aggattcaga attttgcagt   1200

cacagaagag tgtatttatt atgtagaatg aatgagggta ctgtcacctg ccttaatgta   1260

ggtaggccca gagtcttaca tttaagatct tacatgcagt tataaaaccg ccacagtctt   1320

caatccagat ttgaagactc atgccatagg tgacattcta aaataccatt aaagccactt   1380

aaatgttaaa taagaatata catgcacatc agctcaatgt ctttgagtat taattttatg   1440

taagcattct atttaacatg aatataggac aaatcatggc tatatctata gaccttggat   1500

aaactggatt gaccaattat acactcacgg tgactttttt attggtggga aggggattgg   1560

ggtggggcag gctggcttaa tgtaatatga gcaaccaaag tgggacttct gtctccccgc   1620

tatattccca ttgctctgaa tggttgattg aagggtcagg gaactagatt ttatggcttt   1680

agttcactgt gattgtacat ttatacttgg cctatgtgct ggccgcacct gaacatagct   1740

ggtgcttatg ccgagttatt tgcgatgagt aaatatttag tttctttttc ttcatattta   1800

taatgttgat ctggcatcct caggctgcag ctttattagc ttataactta ctcatctcta   1860

tctttaccag caggctctgt attgttgata tttgcaactt gttttgcttt tccattggtg   1920

gaattgaaat aattagtttt taattacata agatgcctgt ttgctatttg gtggaagata   1980

gatgttcata ttgaagcagt cacatttgta ctgtagttca ataaaagaaa aatgaagtat   2040

tctgtagcct atatttttca tagagctcat gagcatttac tgtacttgct gggtcttgcc   2100

aagatcattt attccgctgc attgccaaag tgtcttcata ccaaattaaa ggtggtttta   2160

atatatgttt catggaagtt gtttataaaa ttcaaaggta tttcatttag gtgaaaagtc   2220

ttatttatta aagtggtttg aataaagtag atcaaaactt ccagagatct taatggctat   2280

ataggaagaa atatcactca ccataattta aataaagaat aaaaatactt gtattttgtg   2340

gtggcaaatg tttggtagaa ctgtaattag aaaaatacaa gtatatttgc gtgatggtta   2400

cactagaagc ccagacttta cgactacaca atatattcat gtatctaaac tgtacttgta   2460

ccccctaaat ttatttttaa aaaaggaaaa ataaaagtat catgaaaaaa cctatttttt   2520

tttccactgt ccttccacta ctcccataac aaacttatcc atggttggta aaattttaca   2580

tatttctatc cttgaaatga aggcttcttt taaattccaa agaagtcatg gaggcctgtg   2640

catttgaatt gtatatgcta gtgaggaaaa gatttagaca tttcaagagc agggttggcc   2700

aggcgcggtg gctcacacct gtaatcccag cactttggga ggccgaggag ggcggatcac   2760

gaggtcagga gatcgagacc atcctggcta acacagtgaa accccatctc tactaaaaaa   2820

aaaa                                                                 2824
```

<210> SEQ ID NO 159
<211> LENGTH: 1856
<212> TYPE: DNA
<213> ORGANISM: Homo sapiens

<400> SEQUENCE: 159

```
gtggcaagag tagcggtgac ggcggcggcg gcggcggcgg cagcattatg cgtgattact     60

gacaggcacc agctgctgcc gccacagccg tctcaaacgc actatgtgga ctctccgatc    120

tagaggcaga ttcctgacta atcccagagg gctggcccag cctgtgctcc ccgggctgct    180

aggaagcgat gaccactctt gttagcccaa gttgaagaaa gccgggctgt gcctgggagc    240
```

```
cgagagaggc ggtaatattt agaagctgca caggagagga acatgaactg acgagtaaac    300
atgtatggaa attattctca cttcatgaag tttcccgcag gctatggagg ctcccctggc    360
cacactggct ctacatccat gagcccatca gcagccttgt ccacagggaa gccaatggac    420
agccacccca gctacacaga taccccagtg agtgccccac ggactctgag tgcagtgggg    480
accccccctca atgccctggg ctctccatat cgagtcatca cctctgccat gggcccaccc    540
tcaggagcac ttgcagcgcc tccaggaatc aacttggttg ccccacccag ctctcagcta    600
aatgtggtca acagtgtcag cagttcagag gacatcaagc ccttaccagg gcttcccggg    660
attggaaaca tgaactaccc atccaccagc cccggatctc tggttaaaca catctgtgcc    720
atctgtggag acagatcctc aggaaagcac tacggggtat acagttgtga aggctgcaaa    780
gggttcttca agaggacgat aaggaaggac ctcatctaca cgtgtcggga taataaagac    840
tgcctcattg acaagcgtca gcgcaaccgc tgccagtact gtcgctatca gaagtgcctt    900
gtcatgggca tgaagaggga agctgtgcaa gaagaaagac agaggagccg agagcgagct    960
gagagtgagg cagaatgtgc taccagtggt catgaagaca tgcctgtgga gaggattcta   1020
gaagctgaac ttgctgttga accaaagaca gaatcctatg gtgacatgaa tatggagaac   1080
tcgacaaatg accctgttac caacatatgt catgctgctg acaagcagct tttcaccctc   1140
gttgaatggg ccaagcgtat tccccacttc tctgacctca ccttggagga ccaggtcatt   1200
ttgcttcggg cagggtggaa tgaattgctg attgcctctt tctcccaccg ctcagtttcc   1260
gtgcaggatg gcatccttct ggccacgggt ttacatgtcc accggagcag tgcccacagt   1320
gctggggtcg gctccatctt tgacagagtc ctaactgagc tggtttccaa aatgaaagac   1380
atgcagatgg acaagtcgga actgggatgc ctgcgagcca ttgtactctt taacccagat   1440
gccaagggcc tgtccaaccc ctctgaggtg gagactctgc gagagaaggt ttatgccacc   1500
cttgaggcct acaccaagca gaagtatccg gaacagccag gcaggtttgc caagctgctg   1560
ctgcgcctcc cagctctgcg ttccattggc ttgaaatgcc tggagcacct cttcttcttc   1620
aagctcatcg gggacacccc cattgacacc ttcctcatgg agatgttgga gaccccgctg   1680
cagatcacct gagccccacc agccacagcc tccccaccca ggatgacccc tgggcaggtg   1740
tgtgtggacc cccaccctgc actttcctcc acctcccacc ctgacccccct tcctgtcccc   1800
aaaatgtgat gcttataata aagaaaacct ttctacacat gaaaaaaaaa aaaaaa       1856
```

<210> SEQ ID NO 160
<211> LENGTH: 2640
<212> TYPE: DNA
<213> ORGANISM: Homo sapiens

<400> SEQUENCE: 160

```
actcgccgca gcctgcgcgc cttctccagt ccgcggtgcc atggccccccg cccgtctgtt     60
cgcgctgctg ctgttcttcg taggcggagt cgccgagtcg atccgagaga ctgaggtcat    120
cgaccccccag gacctcctag aaggccgata cttctccgga gccctaccag acgatgagga    180
tgtagtgggg cccgggcagg aatctgatga ctttgagctg tctggctctg gagatctgga    240
tgacttggaa gactccatga tcggccctga agttgtccat cccttggtgc ctctagataa    300
ccatatccct gagagggcag ggtctgggag ccaagtcccc accgaaccca agaaactaga    360
ggagaatgag gttatcccca agagaatctc acccgttgaa gagagtgagg atgtgtccaa    420
caaggtgtca atgtccagca ctgtgcaggg cagcaacatc tttgagagaa cggaggtcct    480
```

ggcagctctg attgtgggtg gcatcgtggg catcctcttt gccgtcttcc tgatcctact 540
gctcatgtac cgtatgaaga agaaggatga aggcagctat gacctgggca agaaacccat 600
ctacaagaaa gcccccacca atgagttcta cgcgtgaagc ttgcttgtgg gcactggctt 660
ggactttagc ggggagggaa gccaggggat tttgaagggt ggacattagg gtagggtgag 720
gtcaacctaa tactgacttg tcagtatctc cagctctgat tacctttgaa gtgttcagaa 780
gagacattgt cttctactgt tctgccaggt tcttcttgag ctttgggcct cagttgccct 840
ggcagaaaaa tggattcaac ttggcctttc tgaaggcaag actgggattg gatcacttct 900
taaacttcca gttaagaatc taggtccgcc ctcaagccca tactgaccat gcctcatcca 960
gagctcctct gaagccaggg ggctaacgga tgttgtgtgg agtcctggct ggaggtcctc 1020
ccccagtggc cttcctccct tcctttcaca gccggtctct ctgccaggaa atgggggaag 1080
gaactagaac cacctgcacc ttgagatgtt tctgtaaatg ggtacttgtg atcacactac 1140
gggaatctct gtggtatata cctggggcca ttctaggctc tttcaagtga cttttggaaa 1200
tcaacctttt ttatttgggg gggaggatgg ggaaaagagc tgagagttta tgctgaaatg 1260
gatttataga atatttgtaa atctattttt agtgtttgtt cgttttttta actgttcatt 1320
cctttgtgca gagtgtatat ctctgcctgg gcaagagtgt ggaggtgccg aggtgtcttc 1380
attctctcgc acatttccac agcacctgct aagtttgtat ttaatggttt ttgtttttgt 1440
ttttgtttgt ttcttgaaaa tgagagaaga gccggagaga tgatttttat taattttttt 1500
tttttttttt tttttttact atttatagct ttagataggg cctcccttcc cctcttcttt 1560
ctttgttctc tttcattaaa ccccttcccc agtttttttt ttatacttta aaccccgctc 1620
ctcatggcct tggccctttc tgaagctgct tcctcttata aaatagcttt tgccgaaaca 1680
tagttttttt ttagcagatc ccaaaatata atgaagggga tggtgggata tttgtgtctg 1740
tgttcttata atatattatt attcttcctt ggttctagaa aaatagataa atatattttt 1800
ttcaggaaat agtgtggtgt ttccagtttg atgttgctgg gtggttgagt gagtgaattt 1860
tcatgtggct gggtgggttt ttgccttttt ctcttgccct gttcctggtg ccttctgatg 1920
gggctggaat agttgaggtg gatggttcta ccctttctgc cttctgtttg ggacccagct 1980
ggtgttcttt ggtttgcttt cttcaggctc tagggctgtg ctatccaata cagtaaccac 2040
atgcggctgt ttaaagttaa gccaattaaa atcacataag attaaaaatt ccttcctcag 2100
ttgcactaac cacgtttcta gaggcgtcac tgtatgtagt tcatggctac tgtactgaca 2160
gcgagagcat gtccatctgt tggacagcac tattctagag aactaaactg gcttaacgag 2220
tcacagcctc agctgtgctg ggacgaccct tgtctccctg ggtagggggg ggggaatggg 2280
ggagggctga tgaggcccca gctggggcct gttgtctggg accctccctc tcctgagagg 2340
ggaggcctgg tggcttagcc tgggcaggtc gtgtctcctc ctgaccccag tggctgcggt 2400
gaggggaacc accctccctt gctgcaccag tggccattag ctcccgtcac cactgcaacc 2460
cagggtccca gctggctggg tcctcttctg cccccagtgc ccttcccctt gggctgtgtt 2520
ggagtgagca cctcctctgt aggcacctct cacactgttg tctgttactg attttttttg 2580
ataaaaagat aataaaacct ggtactttct aaaaaaaaaa aaaaaaaaaa aaaaaaaaaa 2640

<210> SEQ ID NO 161
<211> LENGTH: 3300
<212> TYPE: DNA
<213> ORGANISM: Homo sapiens

<400> SEQUENCE: 161

-continued

```
tgggcaggaa ctgggcactg tgcccagggc atgcactgcc tccacgcagc aaccctcaga      60
gtcctgagct gaaccaagaa ggaggagggg gtcgggcctc cgaggaaggc ctagccgctg     120
ctgctgccag gaattccagg ttggaggggc ggcaacctcc tgccagcctt caggccactc     180
tcctgtgcct gccagaagag acagagcttg aggagagctt gaggagagca ggaaagcctc     240
ccccgttgcc cctctggatc cactgcttaa atacggacga ggacagggcc ctgtctcctc     300
agcttcaggc accaccactg acctgggaca gtgaatcgac aatgccgtct tctgtctcgt     360
ggggcatcct cctgctggca ggcctgtgct gcctggtccc tgtctccctg gctgaggatc     420
cccagggaga tgctgcccag aagacagata catcccacca tgatcaggat cacccaacct     480
tcaacaagat cacccccaac ctggctgagt tcgccttcag cctataccgc cagctggcac     540
accagtccaa cagcaccaat atcttcttct ccccagtgag catcgctaca gcctttgcaa     600
tgctctccct ggggaccaag gctgacactc acgatgaaat cctggagggc ctgaatttca     660
acctcacgga gattccggag gctcagatcc atgaaggctt ccaggaactc ctccgtaccc     720
tcaaccagcc agacagccag ctccagctga ccaccggcaa tggcctgttc ctcagcgagg     780
gcctgaagct agtggataag tttttggagg atgttaaaaa gttgtaccac tcagaagcct     840
tcactgtcaa cttcggggac accgaagagg ccaagaaaca gatcaacgat tacgtggaga     900
agggtactca agggaaaatt gtggatttgg tcaaggagct tgacagagac acagtttttg     960
ctctggtgaa ttacatcttc tttaaaggca aatgggagag accctttgaa gtcaaggaca    1020
ccgaggaaga ggacttccac gtggaccagg tgaccaccgt gaaggtgcct atgatgaagc    1080
gtttaggcat gtttaacatc cagcactgta agaagctgtc cagctgggtg ctgctgatga    1140
aatacctggg caatgccacc gccatcttct tcctgcctga tgaggggaaa ctacagcacc    1200
tggaaaatga actcacccac gatatcatca ccaagttcct ggaaaatgaa gacagaaggt    1260
ctgccagctt acatttaccc aaactgtcca ttactggaac ctatgatctg aagagcgtcc    1320
tgggtcaact gggcatcact aaggtcttca gcaatggggc tgacctctcc ggggtcacag    1380
aggaggcacc cctgaagctc tccaaggccg tgcataaggc tgtgctgacc atcgacgaga    1440
aagggactga agctgctggg gccatgtttt tagaggccat acccatgtct atcccccccg    1500
aggtcaagtt caacaaaccc tttgtcttct taatgattga acaaaatacc aagtctcccc    1560
tcttcatggg aaaagtggtg aatcccaccc aaaaataact gcctctcgct cctcaacccc    1620
tcccctccat ccctggcccc ctccctggat gacattaaag aagggttgag ctggtccctg    1680
cctgcatgtg actgtaaatc cctcccatgt tttctctgag tctccctttg cctgctgagg    1740
ctgtatgtgg gctccaggta acagtgctgt cttcgggccc cctgaactgt gttcatggag    1800
catctggctg ggtaggcaca tgctgggctt gaatccaggg gggactgaat cctcagctta    1860
cggacctggg cccatctgtt tctggagggc tccagtcttc cttgtcctgt cttggagtcc    1920
ccaagaagga atcacagggg aggaaccaga taccagccat gaccccaggc tccaccaagc    1980
atcttcatgt ccccctgctc atcccccact cccccccacc cagagttgct catcctgcca    2040
gggctggctg tgcccacccc aaggctgccc tcctgggggc cccagaactg cctgatcgtg    2100
ccgtggccca gttttgtggc atctgcagca acacaagaga gaggacaatg tcctcctctt    2160
gacccgctgt cacctaacca gactcgggcc ctgcacctct caggcacttc tggaaaatga    2220
ctgaggcaga ttcttcctga agcccattct ccatggggca acaaggacac ctattctgtc    2280
cttgtccttc catcgctgcc ccagaaagcc tcacatatct ccgtttagaa tcaggtccct    2340
```

tctccccaga tgaagaggag ggtctctgct ttgttttctc tatctcctcc tcagacttga 2400
ccaggcccag caggccccag aagaccatta ccctatatcc cttctcctcc ctagtcacat 2460
ggccataggc ctgctgatgg ctcaggaagg ccattgcaag gactcctcag ctatgggaga 2520
ggaagcacat cacccattga cccccgcaac ccctcccttt cctcctctga gtcccgactg 2580
gggccacatg cagcctgact tctttgtgcc tgttgctgtc cctgcagtct tcagagggcc 2640
accgcagctc cagtgccacg gcaggaggct gttcctgaat agcccctgtg gtaagggcca 2700
ggagagtcct tccatcctcc aaggccctgc taaaggacac agcagccagg aagtcccctg 2760
ggcccctagc tgaaggacag cctgctccct ccgtctctac caggaatggc cttgtcctat 2820
ggaaggcact gccccatccc aaactaatct aggaatcact gtctaaccac tcactgtcat 2880
gaatgtgtac ttaaaggatg aggttgagtc ataccaaata gtgatttcga tagttcaaaa 2940
tggtgaaatt agcaattcta catgattcag tctaatcaat ggataccgac tgtttcccac 3000
acaagtctcc tgttctctta agcttactca ctgacagcct ttcactctcc acaaatacat 3060
taaagatatg gccatcacca agccccctag gatgacacca gacctgagag tctgaagacc 3120
tggatccaag ttctgacttt tccccctgac agctgtgtga ccttcgtgaa gtcgccaaac 3180
ctctctgagc cccagtcatt gctagtaaga cctgcctttg agttggtatg atgttcaagt 3240
tagataacaa aatgtttata cccattagaa cagagaataa atagaactac atttcttgca 3300

<210> SEQ ID NO 162
<211> LENGTH: 4038
<212> TYPE: DNA
<213> ORGANISM: Homo sapiens

<400> SEQUENCE: 162
tgggggcggt ggcagggccg gtgggcggtg gcggctcccg gtctcggctc gggcacggcc 60
ctgggcaggc cgcccgccag ccgcaggggc gctcctgagc ttcgcggggc cgcagtccgg 120
gatgcctgcg cgaagggagg ggcgaagggc cggccgttgc cgacgtgggt gttaagtggc 180
cgccccagcc ggcgacccgg agccgagagc gggcggcgga gcctgagctg gacgcggcca 240
cgccggcgcg gcgggatatg tggtgcctgt cataagctcc agagagctgc cttccacaag 300
accagcagaa gagtgggcaa acatgaaatc caatcctgct atccaggctg ccattgacct 360
cacagcgggg gctgcaggag gtacagcatg tgtactgacc gggcagccct ttgacacaat 420
gaaagtgaag atgcagacgt tccctgacct gtaccggggc ctcaccgact gctgcctgaa 480
gacttactcc caggtgggct tccgtggctt ctacaagggt accagtccag cactaatcgc 540
caacatcgct gagaactcag tcctcttcat gtgctacggc ttctgccagc aggtggtgcg 600
gaaagtggct ggattggaca agcaggcaaa gctgagtgat ctgcagaatg cagccgccgg 660
ttccttcgcc tctgcctttg ctgcactggt gctctgcccc acggagctcg tgaagtgccg 720
gctgcagacc atgtatgaga tggagacatc agggaagata gccaagagcc agaatacagt 780
gtggtctgtc atcaaaagta ttcttaggaa agatggcccc ttggggttct accatggact 840
ctcaagcact ttacttcgag aagtaccagg ctatttcttc ttcttcggtg gctatgaact 900
gagccggtcc ttttttgcat cagggagatc aaaagatgaa ttaggccctg tacctttgat 960
gttaagtggt ggagttggtg ggatttgcct ctggcttgcg gtataccccag tggattgtat 1020 caaatccaga attcaagttc tttccatgtc tggaaaacag gcaggattta tcagaacctt 1080
tataaatgtt gtgaaaaatg aaggaataac ggccttatat tctggactga aacctactat 1140
gattcgagca ttccctgcca atggagcact ctttttggcc tacgaatata gcaggaagtt 1200
gatgatgaac cagttggaag catactgaag tgtcttggtg ggcctgagcc aagcacaggt 1260
gtttgaggac tacagttcat ctcagggttt cttggagtac aagaccagtg tgaagttatt 1320
ctgatttctt gggaattttg ctttttgtct tcccttctac cctacatctt aaactttatg 1380
gaagaacctc tattttgcat catatcattt ctgtccataa ttgtactgaa atagaaaagt 1440
gaccgctctt gctcttggta aaatatagag tggtcagtag ccttatgcac ctaattcaaa 1500
aggtggaata tagttctgtc agggctttta cgtaaacctc cacttgtaca tgcaatttgg 1560
acagttatgt gttgagggaa atacagtttg gtaccttgtt tatttcaaat atcagaaaaa 1620
cccagaggtg atcatttctc atgaagatgc ttataaatgg ttgcttaacc cattctagat 1680
gtagggtctg cttaatgtgt gtacttttct aagtggttga ttattttta ttttttgat 1740
acagagtctc actctgtcac ccagactgga gtgcagtggc acgatctcgg ctcactgcaa 1800
cctccgcctc ctgggttcaa gcgattctct cacctcagcc tcctgagtag ctgggattac 1860
aggtacgcgc caccatgtcc agctaatttt ttttggtatt ttttgtagag acgaggtttc 1920
accatgttgt ccaggttggt ctcgaactcc tgacctcaag tgatccgccc acctcggcct 1980
cccaaagtgc tgggattact ggtgtgagcc accatgccca gccagtggtt gaatttttta 2040
aaaagtgttc atggggtgct tgaaaactaa aatatccttc tagatttgta agacagtata 2100
cctgcatact ggtgtggctt ccacacttga gtaaaagctt cagagtaggt atcctagatt 2160
tccccaagat gctctactct taaaatagtg ccattcattt tctaggtggg atcatattcc 2220
acgctgacta tattgctagg ggtggcccag agggtcaggc ctttgggaaa tagcatggcc 2280
tttaccagct tcccttctct cccaaagaac ttcccttctt gggctttaga ttgaggaagg 2340
ggctgagtgg taggcggtgc tgctgtgctc tgatgaagac ccatgtggct agcaacagcg 2400
cttacctttt gtctctgggt cctggcctgg ggccatcaat ccactttggg ccactcactg 2460
tctgctctgc ctccaccaat cagaaaccct tccaaggaac agtgagagcc aaagccaaga 2520
gaagccttct tccctgtttg gtgattgtgt gacagtgggt gaacctctct cagagagaac 2580
tagaaagaac tcagtgcttg tactccacag tgagtaatgt caggtctgac ccatcctgaa 2640
gcctgtcttg ccatgctttt acagtgttgg aggcttctac atttggtact tgcagtcagt 2700
aagtcttaat gatgactgta tatgtgatat gagtttataa agcaatggaa cataagaaaa 2760
gcaattgtag gccaggcgca gtggctcacg cctataatcc cagcactttg ggaggctgag 2820
gcgggcgggt cacaaggtca ggagttcgag aacagcctga ccaacatggt gaaaccccat 2880
ctctactaaa aatacaaaaa ttagctgggc gtggtggcac gtgcctgtaa tcccagctac 2940
tcaggaggct gaggcaggag aatcgcttga acccgggagg cagaggttgc agtgaactga 3000
gattgtgcca ctgcactcca gactgggtga cacagcgaga cttcatctca aaaaaaaaaa 3060
gaaaagaaaa gcaattgtac ttcactatgc catatgtatg tattcactga ccaaaaattc 3120
actgaccaac caaccaaact ccacacttca tctgatcccc catagacttg gggatggaca 3180
gctgttcttt ggccatatgg tataagagga tcattcttgt cactacttaa gttagcctca 3240
tcattttgtg ctgctccaac accagcaggg tatctcccaa taaagtgttc ctaagcagcc 3300
tgtatactga gtgcaagcag gctatcaatt ttaataatag tccataccat gtatgtgttt 3360
ctgtcagcag aatgtacatg ttgtacaaaa cctccaggtt ccttaagctt tttgctgtcc 3420
atgaatcctc tgtggcaact gtaatcacag agccagaagc cagagggcca gggatatgag 3480
aggctgacaa acatcagggg acatctgggg aggagatccc tgtcatgtct cttgtgccat 3540
ggagctatta tggctggtct tccatttgct ttttctttaa gtgaaaacca tttttctact 3600
ttgcttttct ctccatactt aaatggtcag tagctactga gtggtgcttt atctgaatag 3660
gcctggatcg aagtaaaata gaaatgggac tggctttcca caggaagtaa actgcttcag 3720
agcccacagt cccctgctca gtgtccggaa agaagtcagt catccctgtt ggcagtaaat 3780
cttcccacag gccgtccatt agagatttaa ctagatatgt tcaatagaaa gagtctgagg 3840
caagtggaaa tgaggaacgg aaacttaggt tgggagaata ttttttttt attcattctg 3900 tttgcttaat tcagagtaca gtttgtgcta tttcatatct gtactccagg cagaaatata 3960
acttgaaaat actgtgtcta aagaaatttc agtgttctat cattaaatta tttacttaat 4020
aaaaaaaaaa aaaaaaa 4038

<210> SEQ ID NO 163
<211> LENGTH: 7693
<212> TYPE: DNA
<213> ORGANISM: Homo sapiens

<400> SEQUENCE: 163
gcggcggcgg ccgcggtggc agcgaaggcg gcggcggcgg cggcagtggc agtggccgct 60
gcagccccac actccgccgc caaactggag gagcgacgga agccagaccc caggaggatg 120
gaggatgaag ctgtcctgga cagaggggct tccttcctca agcatgtgtg tgatgaagaa 180
gaagtagaag gccaccatac catttacatc ggagtccatg tgccgaagag ttacaggaga 240
aggagacgtc acaagagaaa gacagggcac aaagaaaaga aggaaaagga gagaatctct 300
gagaactact ctgacaaatc agatattgaa aatgctgatg aatccagcag cagcatccta 360
aaacctctca tctctcctgc tgcagaacgc atccgattca tcttgggaga ggaggatgac 420
agcccagctc cccctcagct cttcacggaa ctggatgagc tgctggccgt ggatgggcag 480
gagatggagt ggaaggaaac agccaggtgg atcaagtttg aagaaaaagt ggaacagggt 540
ggggaaagat ggagcaagcc ccatgtggcc acattgtccc ttcatagttt atttgagctg 600
aggacatgta tggagaaagg atccatcatg cttgatcggg aggcttcttc tctcccacag 660
ttggtggaga tgattgttga ccatcagatt gagacaggcc tattgaaacc tgaacttaag 720
gataaggtga cctatacttt gctccggaag caccggcatc aaaccaagaa atccaacctt 780
cggtccctgg ctgacattgg gaagacagtc tccagtgcaa gtaggatgtt taccaaccct 840
gataatggta gcccagccat gacccatagg aatctgactt cctccagtct gaatgacatt 900
tctgataaac cggagaagga ccagctgaag aataagttca tgaaaaaatt gccacgtgat 960
gcagaagctt ccaacgtgct tgttggggag gttgactttt tggatactcc tttcattgcc 1020
tttgttaggc tacagcaggc tgtcatgctg ggtgccctga ctgaagttcc tgtgcccaca 1080
aggttcttgt tcattctctt aggtcctaag gggaaagcca agtcctacca cgagattggc 1140
agagccattg ccaccctgat gtctgatgag gtgttccatg acattgctta taaagcaaaa 1200
gacaggcacg acctgattgc tggtattgat gagttcctag atgaagtcat cgtccttcca 1260
cctggggaat gggatccagc aattaggata gagcctccta agagtcttcc atcctctgac 1320
aaaagaaaga atatgtactc aggtggagag aatgttcaga tgaatgggga tacgccccat 1380
gatggaggtc acggaggagg aggacatggg gattgtgaag aattgcagcg aactggacgg 1440
ttctgtggtg gactaattaa agacataaag aggaaagcgc catttttttgc cagtgatttt 1500 tatgatgctt taaatattca agctctttcg gcaattctct tcatttatct ggcaactgta 1560
actaatgcta tcacttttgg aggactgctt ggggatgcca ctgacaacat gcagggcgtg 1620
ttggagagtt tcctgggcac tgctgtctct ggagccatct tttgcctttt tgctggtcaa 1680
ccactcacta ttctgagcag caccggacct gtcctagttt ttgagaggct tctatttaat 1740
ttcagcaagg acaataattt tgactatttg gagtttcgcc tttggattgg cctgtggtcc 1800
gccttcctat gtctcatttt ggtagccact gatgccagct tcttggttca atacttcaca 1860
cgtttcacgg aggagggctt ttcctctctg attagcttca tctttatcta tgatgctttc 1920
aagaagatga tcaagcttgc agattactac cccatcaact ccaacttcaa agtgggctac 1980
aacactctct tttcctgtac ctgtgtgcca cctgacccag ctaatatctc aatatctaat 2040
gacaccacac tggccccaga gtatttgcca actatgtctt ctactgacat gtaccataat 2100
actacctttg actgggcatt tttgtcgaag aaggagtgtt caaaatacgg aggaaacctc 2160
gtcgggaaca actgtaattt tgttcctgat atcacactca tgtcttttat cctcttcttg 2220
ggaacctaca cctcttccat ggctctgaaa aaattcaaaa ctagtcctta ttttccaacc 2280
acagcaagaa aactgatcag tgattttgcc attatcttgt ccattctcat cttttgtgta 2340
atagatgccc tagtaggcgt ggacacccca aaactaattg tgccaagtga gttcaagcca 2400
acaagtccaa accgaggttg gttcgttcca ccgtttggag aaaacccctg gtgggtgtgc 2460
cttgctgctg ctatcccggc tttgttggtc actatactga ttttcatgga ccaacaaatt 2520
acagctgtga ttgtaaacag gaaagaacat aaactcaaga aaggagcagg gtatcacttg 2580
gatctctttt gggtggccat cctcatggtt atatgctccc tcatggctct tccgtggtat 2640
gtagctgcta cggtcatctc cattgctcac atcgacagtt tgaagatgga gacagagact 2700
tctgcacctg gagaacaacc aaagtttcta ggagtgaggg aacaaagagt cactggaacc 2760
cttgtgttta ttctgactgg tctgtcagtc tttatggctc ccatcttgaa gtttataccc 2820
atgcctgtac tctatggtgt gttcctgtat atgggagtag catcccttaa tggtgtgcag 2880
ttcatggatc gtctgaagct gcttctgatg cctctgaagc atcagcctga cttcatctac 2940
ctgcgtcatg ttcctctgcg cagagtccac ctgttcactt tcctgcaggt gttgtgtctg 3000
gccctgcttt ggatcctcaa gtcaacggtg gctgctatca tttttccagt aatgatcttg 3060
gcacttgtag ctgtcagaaa aggcatggac tacctcttct cccagcatga cctcagcttc 3120
ctggatgatg tcattccaga aaaggacaag aaaaagaagg aggatgagaa gaaaaagaaa 3180
aagaagaagg gaagtctgga cagtgacaat gatgattctg actgcccata ctcagaaaaa 3240
gttccaagta ttaaaattcc aatggacatc atggaacagc aacctttcct aagcgatagc 3300
aaaccttctg acagagaaag atcaccaaca ttccttgaac gccacacatc atgctgataa 3360
aattcctttc cttcagtcac tcggtatgcc aagtcctcct agaactccag taaaagttgt 3420
gcctcaaatt agaatagaac ttgaacctga agacaatgat tatttctgga ggagcaaggg 3480
aacagaaact acattgtaac ctgtttgtct ttcttaaaac tgacatttgt tgttaatgtc 3540
atttgttttt gtttggctgt ttgtttattt tttaactttt atttcgtctc agtttttggt 3600
cacaggccaa ataatacagc gctctctctg cttctctctt gcatagatac aatcaagaca 3660
atagtgcacc gttccttaaa aacagcatct gaggaatccc ccttttgttc ttaaactttc 3720
agatgtgtcc tttgataacc aaattctgtc actcaagaca cagacacgca cagaccctgt 3780
cctttgcctc tattaagcag aggatggaag tattaaggat tttgtaacac cttttatgaa 3840
aatgttgaag gaacttaaaa ctttagcttt ggagctgtgc ttactggctt gtctttgtct 3900
ggtagaacaa accttgacct ccagacagag tcccttctca cttatagagc tctccaggac 3960

```
tggaaaaagt gctgctattt taacttgctc ttgcttgtaa atcctaatct tagagttatc   4020
aaaagaagaa aaaactgaag gtactttact ccctatagag aaaccattgc catcattgta   4080
gcaagtgctg gaatgtccct tttttcctat gcaacttttt ttaacccttt aatgaactta   4140
tctgttgagt acattgaaga atatttttct tcctagattt tgttgtttaa attatggggc   4200
ctaacctgcc acttattttt tgtcaatttt taaaactttt ttttaattac tgtaaagaaa   4260
atgaattttt tcctgcagca ggaaacatag ttttgagtag ttctacctct tatttgtagc   4320
tgccaggctt tctgtaaaaa ttgtattgta tataatgtga tttttacaca tacatacaca   4380
cacaaataca caatctctag ggtaagccag aaggcaagat cagattaaaa acaccatgtt   4440
tctaagcatc catttttccc tttctttaaa agaaacttaa ctgttctatg aaggagattg   4500
agggagaaga gacaaactcc tatgtcatga gaataaccga tgttctgata atagtagcat   4560
ctaggtacag atgctggttg tattaccacg tcaatgtcct atgcagtatt gttagacatt   4620
ttctcatttt gaaatatttg tgtgtttgtg tatgtgctct gtgccatggc tggtgtatat   4680
atgtgcaatg ttagaaggca aaagagtgat ggtaggcaga gggcaaagtc attgaatctc   4740
ttatgccagt tttcataaaa cccaaaccac atatgaaaaa atccattaag ggtccaagaa   4800
gtctgtccat atgaaaatga gggtaaatat agtttatttc ccaggtatca gtcattataa   4860
ttgatataat agctctaaca tgcaatataa aattcatagg agtattaata gcccatttac   4920
acatctataa aatgtaatgg gattgcagag ctgcagagta cagtgtaaca gtactctcat   4980
gcaatttttt tcaggatgca aaggcaatta ttctttgtaa gcgggacatt tagaatatat   5040
ttgtgtacat attatatgta tgtatatttc aaagtaccac actgaaaatt agacatttat   5100
taaccaaatt taacgtggta tttaaaggta atatttttaa tatgatacat tacatattgt   5160
gaatgtatac taaaaaaaca ttttaaatgt taaaattata atttcagatt catataacca   5220
caactgtgat atatcctaac tataaccagt tgttgagggg tatactagaa gcagaatgaa   5280
accacatttt ttggtttgat aatatgcact tattgactcc cactcattgt tatgttaatt   5340
aagttattat tctgtctcct tgtaattttg attacaaaaa ttttattatc ctgagttagc   5400
tgttactttt acagtacctg atactcctaa aacttttaac ttatacaaat tagtcaataa   5460
tgaccccaat tttttcatta aaataatagt ggtgaattat atgttattgt gttaaaacct   5520
cacttgccaa attctggctt cacatttgta tttagggcta tccttaaaat gatgagtcta   5580
tattatctag ctttctatta ccctaatata aactggtata agaagacttt cctttttttct   5640
ttatgcatgg aagcatcaat aaattgttta aaaaccatgt atagtaaatt cagcttaacc   5700
cgtgatcttc ttaagttaaa ggtacttttg ttttataaaa gctctagata aaactttctt   5760
ttctgatcat gaatcaagta tctgtggttt catgcccctc tctatacctt tcaaagaact   5820
cctgaagcaa cttaactcat catttcagcc tctgagtaga ggtaaaacct atgtgtactt   5880
ctgtttatga tccatattga tatttatgac atgaacacag aatagtacct tacatttgct   5940
aaacagacag ttaatatcaa atcctttcaa tattctggga acccagggaa gtttttaaaa   6000
atgtcattac tttcaaagga acagaagtag ttaaccaaac taacaagcaa aacctgaggt   6060
ttacctagtg acaccaaatt atcggtattt taactgaatt tacccattga ctaagaatga   6120
accagatttg gtggtggttt tgtttctatg caaactggac acaaattaca acagtaaatt   6180
tttttataag tgcttctccc ttctccatga tgtgacttcc ggagataaag gattcaaaag   6240
ataaagacaa agtacgctca gagttgttaa ccagaaagtc ctggctgtgg ttgcagaaac   6300
actgttggaa gaaaagagat gactaagtca agtgtctgcc ttatcaaaag agcaaaaatg   6360
```

```
cctctggttt tgtgtttggg agaaaaatat cttggacgca ctgttttcct tgataaaagt   6420

catcttctct actgtgtgaa atgaatactt ggaattctaa ttgttttgtg tgccaggggc   6480

agtaatgtcc ctgcctcttc tcccaatcaa ggttgaggag tggggctggg gagaggactt   6540

aactgactta agaagtagga aaacaaaaac ctctctcctc agccttccac ctccaagaga   6600

ggaggaaaaa cagttgtctg ctgtctgtaa ttcagtttgc gtgtatttta tgctcatgca   6660

ccaacccata cagagtaaat cttttatcaa ctatatactg gtgtttaata gagaatgatt   6720

gtcttccgag tttttggtt ccttttttaa ctgtgttaaa gtacttgaaa tgtattgact   6780

gctgactata ttttaaaaac aaaatgaaat aatttgagtt gtattacaga ggttgacatt   6840

gttcagggat gggacaaagc cttcttcaat ccttttcata ctacttaatg attttggtgc   6900

aggaacctga gatttctga tttatatttc atgatatttc acatttgctc ttcacagcat   6960

gagcatgaag cccagtggca ccaaatggct gggtacaatc aagtgatatt ttgtagcacc   7020

tcactatctg aaaggccatg agttttcaga tgatttcatt gagcttcatt gcagcctgaa   7080

attttaaaaa agttgtgtaa tacgccaacc agtcaagttg tgttttggcc agagatttag   7140

atatgtccaa tttcctggct catttcattg tgctctatgg gtacgtataa aaagcaagaa   7200

ttctgtttcc taggcaaaca ttgcaactca gggctaaagt catccagtga aacttttaga   7260

gccagaagta actttgtccc agtcctacaa tgtgaaaaga gtgaatagtt gcctcttttt   7320

agccatttc atggctggta catattcgta cgcattactt ttcagaatca atacgcactt   7380

tcagatattc ttatttttat tctcttaagt ctttattaac tttggagaga gaaatgatgc   7440

atctttttat tttaaatgaa gtagatcaac atggtggaac aaaatgataa agaacagaaa   7500

acatttcaat atattactaa taacttttc caatataaat cctaaaattc ctataacata   7560

gtattttaca gttttatgaa gctttctatt gtgactttta tggaattaag agatgaagaa   7620

gatgagatat tttagcattt atatttttca aaattatatg tatacttaaa aataaagtaa   7680

ctttatgcat tta                                                      7693
```

<210> SEQ ID NO 164
<211> LENGTH: 7949
<212> TYPE: DNA
<213> ORGANISM: Homo sapiens

<400> SEQUENCE: 164

```
gggagaggga gacgcaggcg gcgaaacggc agaggagccg agccccctcc gcccaaggcg     60

ccctccctcc gtccgcgcac aggcgccgtc gcttggagga gcaaggtgcc tcccagcccg    120

caggggcgcc gcgcgcaagc ccgcgggctc ttcggtggct ctgccccggg actgcacctg    180

gaggcggccc cggacgggga tggtcagcgg ctgctgccgt ctggctcgcg agcgggacgc    240

tgtgagggca ccatggcgct gactcccggg tgggggtcct cggcggggcc ggtccggccg    300

gagctctggc tgctgctgtg ggcagccgcg tggcgcctgg gtgcctcggc gtgccccgcc    360

ctctgcacct gcaccggaac cacggtggac tgccacggca cggggctgca ggccattccc    420

aagaatatac ctcggaacac cgagcgcctg gaactcaatg gcaacaacat cactcggatc    480

cataagaatg actttgcggg gctcaagcag ctgcgggtgc tgcagctgat ggagaaccag    540

attggagcag tggaacgtgg tgcttttgat gacatgaagg agctggagcg gctgcgactg    600

aaccgaaacc agctgcacat gttaccggaa ctgctgttcc agaacaacca ggctttgtca    660

agactggact tgagtgagaa cgccatccag gccatcccca ggaaagcttt tcggggagct    720
```

-continued

```
acggacctta aaaatttaca gctggacaag aaccagatca gctgcattga ggaaggggcc    780
ttccgtgctc tgcgggggct ggaggtgctg accctgaaca acaacaatat caccaccatc    840
cccgtgtcca gcttcaacca tatgcccaag ctacggacct tccgcctgca ctccaaccac    900
ctgttttgcg actgccacct ggcctggctc tcgcagtggc tgaggcagcg gccaaccatc    960
gggctcttca cccagtgctc gggcccagcc agcctgcgtg gcctcaatgt ggcagaggtc   1020
cagaagagtg agttcagctg ctcaggccag ggagaagcgg ggcgcgtgcc cacctgcacc   1080
ctgtcctccg gctcctgccc ggccatgtgc acctgcagca atggcatcgt ggactgtcgt   1140
ggaaaaggcc tcactgccat cccggccaac ctgcccgaga ccatgacgga gatacgcctg   1200
gagctgaacg gcatcaagtc catccctcct ggagccttct caccctacag aaagctacgg   1260
aggatagacc tgagcaacaa tcagatcgct gagattgcac ccgacgcctt ccagggcctc   1320
cgctccctga actcgctggt cctctatgga aacaagatca cagacctccc ccgtggtgtg   1380
tttggaggcc tatacaccct acagctcctg ctcctgaatg ccaacaagat caactgcatc   1440
cggcccgatg ccttccagga cctgcagaac ctctcactgc tctccctgta tgacaacaag   1500
atccagagcc tcgccaaggg cactttcacc tccctgcggg ccatccagac tctgcacctg   1560
gcgcagaacc ctttcatttg cgactgtaac ctcaagtggc tggcagactt cctgcgcacc   1620
aatcccatcg agacgagtgg tgcccgctgt gccagtcccc ggcgcctcgc caacaagcgc   1680
atcgggcaga tcaagagcaa gaagttccgg tgctcagcca aagagcagta cttcattcca   1740
ggcacggagg attaccagct gaacagcgag tgcaacagcg acgtggtctg tccccacaag   1800
tgccgctgtg aggccaacgt ggtggagtgc tccagcctga agctcaccaa gatccctgag   1860
cgcatccccc agtccacggc agaactgcga ttgaataaca atgagatttc catcctggag   1920
gccactggga tgtttaaaaa acttacacat ctgaagaaaa tcaatctgag caacaacaag   1980
gtgtcagaaa ttgaagatgg ggccttcgag ggcgcagcct ctgtgagcga gctgcaccta   2040
actgccaacc agctggagtc catccggagc ggcatgttcc ggggtctgga tggcttgagg   2100
accctaatgc tgcggaacaa ccgcatcagc tgcatccaca acgacagctt cacgggcctg   2160
cgcaacgtcc ggctcctctc gctctacgac aaccagatca ccaccgtatc cccaggagcc   2220
ttcgacaccc tccagtccct ctccacactg aatctcctgg ccaacccttt caactgcaac   2280
tgccagctgg cctggctagg aggctggcta cggaagcgca agatcgtgac ggggaacccg   2340
cgatgccaga accctgactt tttgcggcag attcccctgc aggacgtggc cttccctgac   2400
ttcaggtgtg aggaaggcca ggaggagggg ggctgcctgc cccgcccaca gtgcccacag   2460
gagtgcgcct gcctggacac cgtggtccga tgcagcaaca agcacctgcg ggccctgccc   2520
aagggcattc ccaagaatgt cacagaactc tatttggacg ggaaccagtt cacgctggtt   2580
ccgggacagc tgtctacctt caagtacctg cagctcgtgg acctgagcaa caacaagatc   2640
agttccttaa gcaattcctc cttcaccaac atgagccagc tgaccactct gatcctcagc   2700
tacaatgccc tgcagtgcat cccgcctttg gccttccagg gactccgctc cctgcgcctg   2760
ctgtctctcc acggcaatga catctccacc ctccaagagg gcatctttgc agacgtgacc   2820
tccctgtctc acctggccat tggtgccaac cccctatact gtgactgcca cctccgctgg   2880
ctgtccagct gggtgaagac tggctacaag gaaccgggca ttgctcgttg tgctgggccc   2940
caggacatgg agggcaagct gctcctcacc acgcctgcca agaagtttga atgccaaggt   3000
cctccaacgc tggctgtcca ggccaagtgt gatctctgct tgtccagtcc gtgccagaac   3060
cagggcacct gccacaacga ccccccttgag gtgtacaggt gcgcctgccc cagcggctat   3120
```

aagggtcgag actgtgaggt gtccctggac agctgttcca gtggcccctg tgaaaatggg 3180
ggcacctgcc atgcacagga gggcgaggat gccccgttca cgtgctcctg tcccaccggc 3240
tttgaaggac caacctgtgg ggtgaacaca gatgactgtg tggatcatgc ctgtgccaat 3300
gggggcgtct gtgtggatgg tgtgggcaac tacacctgcc agtgccccct gcagtatgag 3360
ggaaaggcct gtgagcagct ggtggacttg tgctctccgg atctgaaccc atgtcaacac 3420
gaggcccagt gtgtgggcac cccggatggg cccaggtgtg agtgcatgcc aggttatgca 3480
ggtgacaact gcagtgagaa ccaggatgac tgcagggacc accgctgcca gaatggggcc 3540
cagtgtatgg atgaagtcaa cagctactcc tgcctctgtg ctgagggcta cagtggacag 3600
ctctgtgaga tccctcccca tctgcctgcc cccaagagcc cctgtgaggg gactgagtgc 3660
cagaatgggg ccaactgtgt ggaccagggc aacaggcctg tgtgccagtg cctcccaggc 3720
ttcggtggcc ctgagtgtga gaagttgctc agtgtcaact ttgtggatcg ggacacttac 3780
ctgcagttca ctgacctgca aaactggcca cgggccaaca tcacgttgca ggtctccacg 3840
gcagaggaca atgggatcct tctgtacaac ggggacaacg accacattgc agttgagctg 3900
taccagggcc atgtgcgtgt cagctacgac ccaggcagct accccagctc tgccatctac 3960
agtgctgaga cgatcaacga tggcaattc cacaccgttg agctggttgc ctttgaccag 4020
atggtgaatc tctccattga tggcgggagc cccatgacca tggacaactt tggcaaacat 4080
tacacgctca acagcgaggc gccactctat gtgggaggga tgcccgtgga tgtcaactca 4140
gctgccttcc gcctgtggca gatcctcaac ggcaccggct tccacggttg catccgaaac 4200
ctgtacatca acaacgagct gcaggacttc accaagacgc agatgaagcc aggcgtggtg 4260
ccaggctgcg aaccctgccg caagctctac tgcctgcatg gcatctgcca gcccaatgcc 4320
accccagggc ccatgtgcca ctgcgaggct ggctgggtgg gcctgcactg tgaccagccc 4380
gctgacggcc cctgccatgg ccacaagtgt gtccatgggc aatgcgtgcc cctcgacgct 4440
ctttcctaca gctgccagtg ccaggatggg tactcggggg cactgtgcaa ccaggccggg 4500
gccctggcag agccctgcag aggcctgcag tgcctgcatg gccactgcca ggcctcaggc 4560
accaaggggg cacactgtgt gtgtgacccc ggcttttcgg gcgagctgtg tgagcaagag 4620
tccgagtgcc ggggggaccc tgtccgggac tttcaccagg tccagagggg ctatgccatc 4680
tgccagacca cgcgcccccct gtcatgggtg gagtgccggg gctcgtgccc aggccagggc 4740
tgctgccagg gccttcggct gaagcggagg aagttcacct ttgagtgcag cgatgggacc 4800
tcttttgccg aggaggtgga aaagcccacc aagtgtggct gtgccctctg cgcatagcgc 4860
tgggcgtgga caggccggtg agggcgggca aggggcccca gccgctgcag cagcggagac 4920
agtcgccagc agctgggctg gggtgcaggt catcacagga cggctcctgg gcagctgggc 4980
cctcctgggt ggggtggtgc cagagcagcc ttttaaaagc aaattgcgcc atagctgggg 5040
gcagcggggg tgggcgaggc ctgagctgcg ggctgccctc tccggaagtg ccttgcacaa 5100
ataggcgctt aataaatatt tgttgagtga atgtgtgcgt gaggtcaggc caagaagtgc 5160
agaacgatga cacccctcct tacctgctat ctgaatctgg agaagaaaaa tgacagcctt 5220
ccaaaccaac ccttcccttt ggcctgtggc ccaggctggc ttggaactgg gtctgtggcc 5280
ccagaagcct cttacccctc tgcgggcaac catgaagtac tgtcagcctc cccgggaagc 5340
cagcctggtt cattctgctg ctacagaatc tgctggtggt aggccaggct ctggagcggg 5400
ggtgccgcct cctgctggcc agggagggtc ggacccttgc cccctgggct gactggcagc 5460
tctgcagcca cggcttggga acgaggctgt gggtggaggt ggttcttagg accaggcctc 5520
tgaatcctaa agttctagca tgactactgt agctgcgagg gcttatgtgg aggaaacagt 5580
cacaggggct gctcagggtg gcagacccca ctaaagaggg cagagggttc tttgctctag 5640
ataaacaaac atcatctgcc tccagacact ggccacagta ggagtattgg tcctgggctt 5700
ccccagccac cagtcagcca caagctgtcg gtgacctatt ggtagaggga ctgggtgtga 5760
gggtctgggc cagggtgctt gacctgggag cagctggttc agagtccttc acaccgcagg 5820
ccagtaggga gcagtggaag ggacagtgct ccaggcattg ggaagtccct gctggctcta 5880
tcactcgggg caaacttctc cccacctggg ccttgggttc ttcagctata aaatggccag 5940
aggtgggggg cgggatgact aaaggaacag tgcagactcc cccactgtgg tcttgggagg 6000
ccagaggagt tagaagacct atctatctat ctatctatct acattgatca catcaaaagt 6060
atttatgtgc ctaacccggg gctggggatt gtggacgttc tggcctaatg gacagatgtg 6120
aactcatccc agagcatcgc aggaatgacc aggatgcccg ggaagagttg agctgagtgg 6180
gggctccagc cacagacagc ggcccaggcc agggagttgc tggcaacgaa ggagccagtg 6240
gtggaagaag aagaggccct gaatatacga ttgcctgccc acgttgtctt ctcttccata 6300
cacagtgaaa atgtagaaag atggtttgtg aggccaaact gtgaatgggc taaagggagg 6360
caaagttgca ctctccttcc ccagagggct caccaagagg gcacaccccc gggggttctg 6420
gtgggcaacg gggtgagca tgtccctgcc ctggctccct ccatctgtga ccaggaggca 6480
tggctgggtg tatgttcagg tgaggctcag agtggcattg tgtccctgtc ccctgcccag 6540
ggcagtgagg ggagcccttg atgctgatta gaaggctaga actggggtag aggtgcctgg 6600
catgtctcat gccatgggga ctcaatctag caactgtgag tcctggggtc cctgtgatgg 6660
gaagagggca gtgccctgcc caatgtggca ggtgtcctca tggcaggatc tgcccctcac 6720 caggggggctg ggatctactt gcttggagct ctgagcaagg ccacaatgcc cgccccccacc 6780 cccaagtaga ctgcagcctg ggcctcatgg ggcttctccc aggcccacat ggcatccctc 6840
tctgagtttc caggccaccg tgggaccctg cagagcatct gcaccgggct ggatagggca 6900
gaaaagctca agggcagcta gcttgcctct tccctggaag aaaggtgctc tgggactcac 6960
caaccctgag aaagatagct ttcctggcca ccaccattcc ccaccaccct ggagaagcca 7020
attcccaggc ttgaagggca ctggctggca ggaggcctct tcattctgca ggaggtggaa 7080
aggacacctg tagacaggtg atgctcaccc ctcacctggc gccatggggc tgggaggtga 7140
gcggctggca tgtttgttcc tagggagcac catgtgagct taaggctccc ctgaccggcc 7200
ccaccacatg gcccagcctc ctagcacagc agcgctgacc tcagtgcagt ctgaggattg 7260
gaatccacca tgagatgatg tgagagctgt gtgccccagg atcaactttt tctccaactt 7320
ggccatcagc cagcgagttg ctaaggacct gagtcagcac tcacgttgcc tattcacact 7380
ccgcttgaaa gtccggaagg tggctactgc aaaatcaccc ctctgagaag tcctctctcc 7440
acatcttgtc cccctttgtg aagaccccta gttcgctctg cattttaggc atgaagagat 7500
acagcagggt gcgtccggag ggagctgtgg ccttgcaaca ccactggcaa cagggccggg 7560
gctcccggtg aaggtgtcag gaagtggaaa aggctggact ttgtctcctc tttgcctgct 7620
ggtagcctaa ccgcaaaagt atctctttat acagaatact tacagattct aatatatatt 7680
tgtatttcat tttgttacag tatttttata tgttaaagtc aacatccagc gtcttgtttt 7740
gcctttcaga tgctatgtgg tcgtggcacg ttttgttggg ggtttctgta gtcgtcttgt 7800
ttggatcaac tcctagaggc tggtttagaa caggcccatg agggagctgc acctgccctg 7860
gaagtattgt tttagactat gtcgatattg tctgttgtct tccatgtgaa catgacattg 7920
agtcactctg caaaaaaaaa aaaaaaaaa 7949

<210> SEQ ID NO 165
<211> LENGTH: 7924
<212> TYPE: DNA
<213> ORGANISM: Homo sapiens

<400> SEQUENCE: 165
gccactaccc gctgcggagt gaacggtgtg gagcggaggc cgcggaggct cctcggtcct 60
tcagcacccc tcggcccgac gcacccacgc ccctcacccc ccgagagccg aaaatggacc 120
caagtggggt caaagtgctg gaaacagcag aggacatcca ggagaggcgg cagcaggtcc 180
tagaccgata ccaccgcttc aaggaactct caacccttag gcgtcagaag ctggaagatt 240
cctatcgatt ccagttcttt caaagagatg ctgaagagct ggagaaatgg atacaggaaa 300
aacttcagat tgcatctgat gagaattata aagacccaac caacttgcag ggaaagcttc 360
agaagcatca agcatttgaa gctgaagtgc aggccaactc aggagccatt gttaagctgg 420
atgaaactgg aaacctgatg atctcagaag ggcattttgc atctgaaacc atacggaccc 480
gtttgatgga gctgcaccgc cagtgggaat tacttttgga gaagatgcga gaaaaaggaa 540
tcaaactgct gcaggcccag aagttggtgc agtacttacg agaatgtgag gacgtgatgg 600
actggatcaa tgacaaggaa gcaattgtta cttctgaaga gctgggccag gatctggagc 660
atgtagaggt tttacagaag aaatttgaag agtttcaaac agatatggct gctcatgaag 720
aaagagttaa tgaagtgaac cagtttgctg ccaaactcat acaggagcag caccctgagg 780
aggaactgat caagactaag caggatgaag tcaatgcagc ctggcagcgg ctgaagggcc 840
tggctctgca gaggcagggg aagctctttg gggcagcaga agttcagcgc tttaacaggg 900
atgtggatga gactatcagt tggattaagg aaaaggagca gttaatggcc tctgatgatt 960
ttggccgaga cctggcaagt gttcaggctc tgcttcggaa gcacgagggt ctggagagag 1020
atcttgctgc tctagaagac aaggtcaaag ccctgtgtgc tgaggctgac cgcctgcaac 1080
agtcccaccc tctgagtgca acacagattc aagtgaagcg agaggaactg attacaaact 1140
gggagcagat ccgcaccttg gcggcagaga gacatgcacg gctcaatgat tcatacaggc 1200
ttcaacgctt ccttgctgac ttccgtgacc tcaccagctg ggtgactgag atgaaagccc 1260
tcatcaatgc agatgagctt gccagtgatg tggctggggc tgaagccctg ctagatagac 1320
accaagagca caagggtgaa attgatgccc atgaagacag cttcaaatct gcagatgaat 1380
ctggacaggc actgcttgct gctggtcact atgcctcaga tgaagtgagg gagaagctga 1440
ccgtcctttc cgaggagaga gcggcgctgc tggagctgtg ggagctgcgc aggcagcagt 1500
acgagcagtg catggacctg cagctcttct accgggacac tgagcaggtg gacaactgga 1560
tgagcaagca ggaggcgttc ctgttgaatg aagacttggg agattccttg gatagtgtgg 1620
aagcgcttct taagaagcac gaagactttg agaaatccct tagtgcccag gaggaaaaga 1680
ttacagcatt agatgaattt gcaaccaagc taattcagaa caaccactat gcaatggaag 1740
atgtggccac tcgccgagat gctctgttga gccgccgcaa tgcccttcac gagagagcca 1800
tgcgtcgccg ggcccagcta gccgattctt tccatctgca gcagtttttc cgtgattctg 1860
atgagctcaa gagttgggtc aatgagaaga tgaaaactgc cacagatgaa gcttataaag 1920
atccatccaa cctacaagga aaagtacaga agcatcaggc ttttgaggct gagctctcag 1980

-continued

```
caaaccagag ccgaattgat gccttggaga aagctggcca aaagctgatt gatgtcaacc   2040
actatgccaa ggatgaagtg gcagctcgta tgaatgaggt gatcagtttg tggaagaaac   2100
tgctagaggc cactgaactg aaaggaataa agcttcgtga agccaaccag caacagcaat   2160
ttaatcgcaa tgttgaggat attgaattgt ggctatatga agtagaaggt cacttggctt   2220
cggatgatta cggcaaagat cttaccaatg tgcagaacct ccagaagaaa catgccctgc   2280
tagaggcaga tgtggctgct caccaggacc gaattgatgg catcaccatt caggcccgcc   2340
agttccaaga tgctggccat tttgatgcag aaaacatcaa gaagaaacag gaagccctcg   2400
tggctcgcta tgaggcactc aaggagccca tggttgcccg gaagcagaag ctggccgatt   2460
ctctgcggtt gcagcagctc ttccgggatg ttgaggatga ggagacgtgg attcgagaga   2520
aagagcccat tgccgcatct accaacagag gtaaggattt aattggggtc cagaatctgc   2580
taaagaaaca tcaagcctta caagcagaaa ttgctggaca tgaaccacgc atcaaagcag   2640
ttacacagaa ggggaatgcc atggtggagg aaggccattt tgctgcagag gatgtgaagg   2700
ccaagcttca cgagctgaac caaaagtggg aggcactgaa agccaaagct tcccagcgtc   2760
ggcaggacct ggaggactct ctgcaggccc agcagtactt tgctgatgct aacgaggctg   2820
aatcctggat gcgggagaag gaacccattg tgggcagcac tgactatggc aaggacgaag   2880
actctgctga ggctctactg aagaaacacg aagctttgat gtcagatctc agtgcctacg   2940
gcagcagcat ccaggctttg cgagaacaag cacagtcctg ccggcaacaa gtggccccca   3000
cggatgatga gactgggaag gagctggtct tggctctcta cgactatcag gagaagagtc   3060
cccgagaggt caccatgaag aagggagata tccttacctt actcaacagc accaacaagg   3120
attggtggaa agtggaagtg aacgatcgtc agggttttgt gccggctgcg tacgtgaaga   3180
aattggaccc cgcccagtca gcctcccggg agaatctcct ggaggagcaa ggcagcatag   3240
cactgcggca ggagcagatt gacaatcaga cacgcataac taaggaggcc ggcagtgtat   3300
ctctgcgtat gaagcaggtg gaagaactat atcattctct gctggaactg ggtgagaagc   3360
gtaaaggcat gttggagaag agttgcaaga agtttatgtt gttccgtgaa gcgaatgaac   3420
tacagcaatg gatcaatgag aaggaagccg ctctgacaag tgaggaggtc ggagcagact   3480
tggagcaggt tgaggtgctc cagaagaagt ttgatgactt ccagaaggac ctgaaggcca   3540
atgagtcacg gttgaaggac attaacaagg tagctgaaga cctggagtct gaaggtctca   3600
tggcagagga ggtgcaggct gtgcaacaac aggaagtgta tggcatgatg cccagggatg   3660
aaactgattc caagacagcc tccccgtgga agtctgctcg tctgatggtt cacaccgtgg   3720
ccacctttaa ttccatcaag gagctgaatg agcgctggcg gtccctacag cagctggccg   3780
aggaacggag ccagctcttg ggcagcgccc atgaagtaca gaggttccac agagatgctg   3840
atgaaaccaa agaatggatt gaagagaaga atcaagctct aaacacagac aattatggac   3900
atgatctcgc cagtgtccag gccctgcaac gcaagcatga gggcttcgag agggaccttg   3960
cggctctcgg tgacaaggta aactcccttg gtgaaacagc agagcgcctg atccagtccc   4020
atcccgagtc agcagaagac ctgcaggaaa agtgcacaga gttaaaccag gcctggagca   4080
gcctggggaa acgtgcagat cagcgcaagg caaagttggg tgactcccac gacctgcagc   4140
gcttccttag cgatttccgg gacctcatgt cttggatcaa tggaatacgg gggttggtgt   4200
cctcagatga gctagccaag gatgtcaccg gagctgaggc attgctggag cgacaccagg   4260
aacaccggac agaaatcgat gccagggctg gcactttcca ggcatttgag cagtttggac   4320
agcagctgtt ggctcacgga cactatgcca gccctgagat caagcagaaa cttgatattc   4380
```

-continued

```
ttgaccagga gcgtgcagac ctggagaagg cctgggttca gcgcaggatg atgctggatc   4440
agtgccttga actgcagctg ttccatcggg actgtgagca agctgagaac tggatggctg   4500
cccgggaggc cttcttgaat accgaagaca aaggagactc actggacagc gtagaggctc   4560
tgatcaaaaa acatgaagac tttgacaaag cgattaacgt ccaggaagag aagattgctg   4620
ctctgcaggc ctttgccgac cagctcatcg ctgccggcca ttatgccaag ggagacattt   4680
ctagccggcg caatgaggtc ttggacaggt ggcgacgtct gaaagcccag atgattgaga   4740
aaaggtcaaa gctaggagaa tctcaaaccc tccaacagtt cagccgggat gtggatgaga   4800
ttgaggcttg gatcagtgaa aaattgcaaa cagcgagtga tgagtcgtac aaggatccca   4860
ccaacatcca gctttccaag ctgctgagca agcaccagaa gcaccaggct tttgaagcag   4920
agctgcatgc caacgctgac cggatccgtg gggttatcga catgggcaac tccctcattg   4980
aacgtggagc ctgtgccggc agtgaggatg ctgtcaaggc ccgcctggct gccttagctg   5040
accagtggca gttcttggtg caaaagtcag cggaaaagag ccagaaactg aaagaagcca   5100
acaagcagca gaacttcaac acagggatca aggactttga cttctggctg tctgaggtgg   5160
aggccctgct ggcatccgaa gattatggca aagacctggc ttctgtgaac aacctgctga   5220
aaaagcatca actgctggaa gcagatatat ctgcccatga ggatcgcctg aaggacctga   5280
acagccaggc agacagcctg atgaccagca gtgccttcga cacctcccaa gtaaaggaca   5340
agagggacac catcaacggg cgcttccaga agatcaagag catggcggcc tcccggcgag   5400
ccaagctgaa tgaatcccat cgcctgcacc agttcttccg ggacatggat gacgaggagt   5460
cctggatcaa ggagaagaag ctgctggtgg gctcagagga ctacggccgg gacctaaccg   5520
gcgtgcagaa cctgaggaag aagcacaagc ggctggaagc agaactggct gcgcatgagc   5580
cggctattca gggtgtcctg gacactggca agaagctgtc cgatgacaac accatcggga   5640
aagaggagat ccagcagcgg ctggcgcagt ttgtggagca ctggaaagag ctgaagcagc   5700
tggcagctgc ccggggtcag cggctggaag agtccttgga atatcagcag tttgtagcca   5760
atgtggaaga ggaagaagcc tggatcaatg agaaaatgac cctggtggcc agcgaagatt   5820
atggcgacac tcttgccgcc atccagggct tactgaagaa acatgaagct tttgagacag   5880
acttcaccgt ccacaaggat cgcgtgaatg atgtctgcac caatggacaa gacctcatta   5940
agaagaacaa tcaccatgag gagaacatct cttcaaagat gaagggcctg aacgggaaag   6000
tgtcagacct ggagaaagct gcagcccaga gaaaggcgaa gctggatgag aactcggcct   6060
tccttcagtt caactggaag gcggacgtgg tggagtcctg gatcggtgaa aaggagaaca   6120
gcttgaagac agatgattat ggccgagacc tgtcttctgt gcagacgctc ctcaccaaac   6180
aggaaacttt tgacgctggg ctgcaggcct tccagcagga aggcattgcc aacatcactg   6240
ccctcaaaga tcagcttctc gccgccaaac acgttcagtc caaggccatc gaggcccggc   6300
acgcctccct catgaagagg tggagccagc ttctggccaa ctcagccgcc cgcaagaaga   6360
agcttctgga ggctcagagt cacttccgca aggtggagga cctcttcctg accttcgcca   6420
aaaaggcttc tgccttcaac agctggtttg aaaatgcaga ggaggactta acagaccccg   6480
tgcgctgcaa ctccttggaa gaaatcaaag ctttgcgcga ggcccacgac gccttccgct   6540
cctccctcag ctctgcccag gctgacttca accagctggc cgagctggac cgccagatca   6600
agagcttccg cgtagcctcc aacccctaca cctggtttac catggaggcc ctggaggaga   6660
cctggaggaa cctacagaaa atcatcaagg agagggagct ggagctgcag aaggaacagc   6720
```

ggcggcagga ggagaacgac aagctgcgcc aggagtttgc ccagcacgcc aacgccttcc 6780
accagtggat ccaagagacc aggacatacc tcctcgatgg gtcctgtatg gtggaagagt 6840
cggggaccct cgaatcccag cttgaagcta ccaaacgcaa gcaccaggaa atccgagcca 6900
tgagaagtca gctcaaaaag atcgaggacc tgggggccgc catggaggag gccctcatcc 6960
tggacaacaa gtacacggag cacagcaccg tgggcctcgc ccagcagtgg gaccagctgg 7020
accagctggg catgcgcatg cagcacaacc tggagcagca gatccaggcc aggaacacaa 7080
caggtgtgac tgaggaggcc ctcaaagaat tcagcatgat gtttaaacac tttgacaagg 7140
acaagtctgg caggctgaac catcaggagt tcaaatcttg cctgcgctcc ctgggctatg 7200
acctgcccat ggtggaggaa ggggaacctg accctgagtt cgaggcaatc ctggacacgg 7260
tggatccgaa cagagatggc catgtctcct tgcaagaata catggctttc atgatcagcc 7320
gcgaaactga gaacgtcaag tccagcgagg agattgagag cgccttccgg gccctcagct 7380
cagagggaaa gccttacgtg accaaggagg agctctacca gaacctgacc cgggaacaag 7440
ccgactactg cgtctcccac atgaagccct acgtggacgg caagggccgc gagctcccca 7500
ccgcgttcga ctacgtggag ttcacccgct cgcttttcgt gaactgagcc actccctggg 7560
tcacccaccc ctcgctgctt gccctgcgtc gccttgctgc atgtccgctc ctctgtgtgc 7620
tctcactttc cactgtaacc ttaagcctgc ttagcttgga ataagactta ggagaaaatg 7680
gtgcttcact aacccgcttc cggtccagtc acaatcatca tgtcactgtg gggacccaga 7740
tctgtgtctt gaagcagctg ccctcattcc gacttcagaa aatcgaagca gctggctcct 7800
ccccttgttc tctctcccac cctcccccaa atctgttttc atgtaaaaga caaataaatg 7860
atgacttccc ccaaaaaaaa aaaaaaaaaa aaaaaaaaaa aaaaaaaaaa aaaaaaaaaa 7920
aaaa 7924

<210> SEQ ID NO 166
<211> LENGTH: 9306
<212> TYPE: DNA
<213> ORGANISM: Homo sapiens

<400> SEQUENCE: 166
gggttcggag cgcgaagccg ccgctgggtc ctcggcgcgc cccgcgtctg cgcttgctgc 60
cgcgccccgg tcggcgcgct gggagttcca gccatgctct tctggcacac gcagcccgag 120
cactacaacc agcacaactc cggcagctac ctgcgtgatg tgctcgctct gcccatcttc 180
aagcaggagg aaccccagct gtcccccgag aacgaggccc gcctgccacc cctgcaatat 240
gtgttgtgtg ctgccacgtc cccagccgtg aagctgcatg aagagacgct gacctacctc 300
aaccaaggtc agtcttatga aatccgacta ctggagaatc ggaagctggg agactttcaa 360
gatctgaaca caaaatatgt caagagcatc atccgtgtgg tcttccatga ccgccggctg 420
cagtatacgg agcaccagca gctggagggc tggcggtgga gtcggccagg ggaccggatc 480
ctggacatcg atattccact gtctgttggt atcttggacc ccagggccag cccgacccag 540
ctgaatgcag tcgagttttt gtgggaccct gcgaagagag cttctgcatt cattcaggta 600
cactgcatca gcacagaatt cacccccagg aagcacgggg gcgagaaggg agtgcccttt 660
cgagtccaga ttgacacgtt taagcagaac gagaatgggg agtacacgga gcacctgcac 720
tcagccagct gccagatcaa ggtgttcaag ccgaagggag ccgatcggaa acagaagact 780
gaccgggaga agatggagaa aagaactgcc caagagaagg agaaatacca gccgtcctat 840
gaaaccacca tcctcacaga gtgctctcca tggcccgacg tggcctacca ggtgaacagc 900
gccccgtccc caagctacaa tggttctcca aacagctttg gcctcggcga aggcaacgcc 960
tctccgaccc acccggtgga ggccctgccc gtgggcagtg accacctgct cccatcagct 1020
tcgatccagg atgcccagca gtggcttcac cgcaacaggt tctcgcagtt ctgccggctc 1080
tttgccagct tctcaggtgc tgacttgctg aagatgtccc gagatgattt ggtccagatc 1140
tgtggtcccg cagatgggat ccggctcttc aacgccatca aaggccggaa tgtgaggcca 1200
aagatgacca tttatgtctg tcaggagctg gagcagaatc gagtgcccct gcagcagaag 1260
cgggacggca gtggagacag caacctgtct gtgtaccacg ccatcttcct ggaagagctg 1320
accaccttgg agctgattga gaagatcgcc aacctgtaca gcatctcccc ccagcacatc 1380
caccgagtct accggcaggg ccccacgggc atccatgtgg tggtgagcaa cgagatggtg 1440
cagaacttcc aagatgaatc ctgttttgtc ctcagcacaa ttaaagctga gagcaatgat 1500
ggctaccaca tcatcctgaa atgtggactc tgagcagcag tggacctcat acctgtctcc 1560
agctcccagc cctgtggatc cccgtggatg tagacattgc cccactgtaa gctgtggcct 1620
caccaggcaa gctgaggcca ggagggaccc tgcccagtct gtgaaagcta cagagcacca 1680
accagcagaa gcctgtggac accaagtacg gtgtacagaa agccagtggc tcctttctcc 1740
cttcctcttg gcctccagat tttgaatggt tccttgttct tttctattgg tccaaccctg 1800
acgttctaaa agggcaaaca gtggagacgt ctgctctgaa atccctcatc ccttagttgg 1860
aagctgattg ggtatcttgg tgctgcctgt attggtccct tctgaccact ctcctgcctc 1920
cagagaaagc tctgcttcac cctggaagct ggtaccttta cctcctcctc tgggagttgg 1980
ctgcatggcc agcactgccg acttgatggg agcagtttgc cctcattctc ctgtttcagg 2040
tttgcttccc ttctcagtga ccctggtgag catccgcctt tcctgttctt ggatgaattg 2100
atgggagtgg ggctattctg tgccttctac ctctttcttc tctacgttgt ttctaaggat 2160
ctgctgctgc ggaacccaaa gatgtgctcc tgtctctgca ctggcgcatt ggcatggtag 2220
atgccacaat gtatgtgcac ggcctttctc agagacatta gttctgaggc cctttgtggg 2280
gaggttaggg ggatggtaat agaaaaagac tattttattt cctggcaatc acgggtaagg 2340
aggattagga atgagtattc cattcctagg tgtcatcaga tgaccttgac caccacaata 2400
ccaggccctc ttggatggac ttatagaaag ttagagaaga ccttgttgaa ccgctgctaa 2460
acttgccaca ggagcgatgt gttttctctg agtgcccctc acttacatgt ttatctttgt 2520
ttgtagaggc tatgtttagg atattttgcc tgcatcagaa tgggtgcatc atctttctta 2580
atggcctaac tatcgggaaa tttgagtgtc agtaactgtg gtagactcag aaattcgtct 2640
ttgtcttgcc tctggttcct gggatccagt gatctctact ggcccagggc ttcagctctt 2700
ggttaattta ggttcatggg gaaccctctg accacctgaa tgggatgtca tagcttctaa 2760
atggagcttc tgtggaatga agtgctagac tgaaggacta ccagaataaa acagggtcta 2820
caatggggag aacttgtttt atagatgagg aaaccaaggc tcagaggggc aaagtcacct 2880
gcatggtagc acatagtgat agggtagcga tataaattta tcatataaac caggacatct 2940
cggaataaaa ggggctctgt tagtcattat gttgggtaat agccgtggca ttcctacaga 3000
acagagtgag gacaggctcc tgattcctct tccttcttta gaggagaagc ggggagtggg 3060
ttaactaaca gctttattga gatgtcattc acatgccatt cagtttaccc attgctagtg 3120
tccaattgta ttcacagaac caccatcaat tcacagaatt acagtcaacg ttggtacatt 3180
ttcatcaccc ccagtaaaac cccgtaccct tggtctgtca ctcctgcttt cctaactcct 3240

-continued

```
gcagtccaag gcagccatga atctactttc tatgtaagat taacctactc tggacatttc   3300
atatatctgg aatcatgtga tatctctttt gtgactggct tcttccactg aatgttttct   3360
agggccgtcc aagttgagga tgtatcagta cttcattctt ttgtattgct gaataatact   3420
tcattgtata gatagaccac atttgtttat tgattcatca gttgatggac atttgtgtgt   3480
ttttactttt tggctactct gaatgatgct gctatgaaca tatttctaca agattttgtg   3540
tggacatatg ttttcatttc ttttagcaat atacatagga gtggaattgc taggtcttac   3600
agtaactccg tgttttaact ttttgagaaa ctgccagact gttttctata gcagctgtac   3660
cattttacat tcccaccagc aatgtatcca ggtttcaatt tgtctacatc ctcatcaaca   3720
cttgctatta tctgtctttt tgcttttagc atcctaatga gtatgaaatg ctatcttgtg   3780
gttttgattt gcattcccct gatggcaact gatgctgagt gtcttttcct gtgcttacgg   3840
gccatgcgta tttctttgga gaaaggtcta tccaggtcct ttgcctattt ttaattgagt   3900
tgtctttttt tttttaagtt ttctgttttc ctaaccacta gactaccagg gatgagcctt   3960
ctttttatta ttgagttggg tgagctattt gtatattcta gacgccagtc ttttatcagg   4020
tatatgactg gtaaaaatgt tctccccttc tgtggattgt tttcagtttc ttgttggtgt   4080
cctttgagac acaaaacttt ttaactttga tgatttccaa gatacgtatt tttttctat    4140
tgtcacttgt gcttttggtg ccatatctag aaaaccattg cctaatccaa ggtcaagaag   4200
attaatgcct gtgttttctt ctaagaacta tacttttagt tctcacaatg gtctttgatc   4260
catttcgagt atatttttat atatgatgtg atgtaggggt ccagcttcat tcttttgctt   4320
gtggatctcc acttgtccca ctgctgatta ttgagaaaaa tatcctttct ccacggaatt   4380
gtcttggcat ccttgctaaa ggcctctgct tcttactgga tcttctttcc tgggacatgg   4440
tgtcgttggg aagcttacct tttttttttt tttacttagt ctgtgtttgg ttccaccagt   4500
tttatgctgc ctttctactc tgttcttgct gtctccctct ttacctgagt caacggtact   4560
gagtcctatc tctctctgat gttccccagt cttccttggt gcatgttcta gctccacaca   4620
ctagtccttg gaggaaggtt gagaccaatg atttcctgtt atgagtcatg aggaaactga   4680
atcacctaga agtggaataa tgtgctcagg gtcaccatag cccattagtg gaaggaccag   4740
gactagacct ttagtcttct gaggtccagc cccttaggct gtctgtcatc actgtaccca   4800
agtgatgtca ctaccaaggc caaatgatgg tgggctaaat tttaattctc aaaagtgtag   4860
gaggctaata ttgtcttcta agttccaaaa gaagatgtaa taaaagtctg ttaccttaag   4920
tgtgctatta gtagagtctt ccatttttct ggcatgcccc tggcatctgc tcttcttacc   4980
ttctcgtggt tgtagttaaa gcttatagct tatgaaagaa tagaaaataa taaataccaa   5040
aaaaaagtac acatggtaat ttggtaccaa aatatctcag ctgcctaatt tagcagctca   5100
tcccttccac aggggtcaga tgagctaaag ctccaggttt tatttttcat ttgattgaca   5160
tacagaaaag ccatagccct tcccacagct gtccagggtc tttcctgtga gtccggaggt   5220
gctggcctat tgagcaggac agctcttccc agggcattcc caccaacctg tggcttctga   5280
actgtagctt ctttttacag tgaaccccag agggaaataa gacagacaca tgtgctcagg   5340
ccaccatctt gaactggaag cccaaagctg agttccttac tcttaggtcg tcacggtttt   5400
tgcggggtat ctgcaaggtt gagataaacc ctttcctgtt taccaggttg tcctttctgg   5460
atgaagggac agaggctgtt gaatggagga ataataggtt tgctggagga ggggcatggt   5520
atgcctgtgg aaaggacagg atggggtggg gaggtcgagg ctttgacttg gggtcctaaa   5580
caaaggtcag gtgttgccct agtgacctct tgcccagaca gcccagagcc ccttacacag   5640
```

agctattaac ctagggaagg ctttaccagc agtggactgg agccagccag ggtcacaagt 5700
ttccaagtcc agcattgctt caggggctgg cctgagtaac tgaagatctg aaaatcatta 5760
acaagtcgat gaaataaacg gaaaagcctc ttaggctgtt gtcagtggag cagagggaga 5820
aagtccctag gcgctcagag ggggtgagaa agcagtggat gattgggcgg gggtggggga 5880
ttagatgttg acactgcctg gggtgtagga agaggaacag agaacccaga gtcagggtcc 5940
tagatcccag accctcgctc agtatgagtc tctttgcctc tctgggtctc tatctcctcc 6000
tcttacaaat acaggcttgg tgatctctga agatggcacc aacctgccat gaaatgaatc 6060
tgaggggttt tcccattttt ccctccatca aaatcgtaca aaaagctgga cgtggtggcc 6120
catgcctcta atcctagcat tttgggaggc cgaggtggga gaatcacttg acgccaagag 6180
ttcgagacca gcctgggcat cgtagtgaga ctccatctct gtctttttga aaataaaaaa 6240
tctttgaaaa ttgcacaaca ggcaggagac ctttacgtgt gcccatcctg gttgtacaca 6300
gtgccaccag tgctcctgca gtgcaaggcg gcatgcttct tgacatgggt cagattgtgt 6360
ccatcgtgtc tttgggaatc agccctagct cctaactggg ctgactactt cctccgcaaa 6420
cttatggggg ctcccagata ttccttgcca gccaggggcc agacacagtg caggcacagt 6480
ctgtgtcatt ggtgcacatg tgcgtgttta catgtgtacc tgggttcctt cccttgccca 6540
tgaatttgcc atgagcacag ccagaagcag cctcagcttg gcaaggtgtg gagatgactg 6600
ctgttccctt cgcatttggg gaaaacaggc tccctcggta gctcgatgat cctcttttga 6660
tcttgtgtga cctcctggag agtggatgaa gctggtggcc ttagcttttc tagacagtgt 6720
aagtggcact gggcaaggcc cccagagcag ggcaaggtct ctagagcggg tctcccacat 6780
gactggcttc acacaggcac ttccgctcgg gttgcatgct ctgtgtcatc ttaccggtcc 6840
agggttgcag gtaggaaatg tttgtaccct cttctgattg ccacctcctt cccatcgccc 6900
cttagggaca gggcttgagg gccagtgagg cgctggtcag gcaccccagg cctccttggg 6960
acctgcccag gggcaccctg agagctcctg aaaccccccac ttagcttcca gacctttctg 7020
caaaagctcc tcctggcttt cctccctccc ccaatctatg ggtcacagct aacagatctg 7080
agggcaactg ctgtgctagt ggccagggct gcacctgcca tccccggctc tgccacttta 7140
gggccttcta gaggcagtgt ccttaggaag tagctctgag gcatgggttt tctgctcctg 7200
tgcagggcag ctgatgggat aaggtgggga aggacggtca gtgcttgggc cccagctggc 7260
cagcctggcg atggggaaac caaaccatgt cccccagcga agggccagag tgggaacctg 7320
tcctcatgcc cttcgtcctg aggagccctg aggtgggcag caggggccag gggaagtttt 7380
caggccttca tcaaagagaa caacatcctc agctccgcac ccctcatcct gtatcagcac 7440
ttaccggtgt gtgactgccc ttgtcagcta gcatacggtg ggcccacctg gcccactggc 7500
tgtttatgcc actgatttat gatagggaat attatctttg aacccaatga agtgttttct 7560
cccccatcac aaaaaaaaaa attcttattt ttagtagaca tgtatttacc aaaaatatgt 7620
actcaattat tgtattttgg attttatcaa tttaaaaatt gtggaaattt gtttgctctt 7680
acgccaacat aatattgatt ttgcctcttg gctctgaaag cccaaaatat ttaccgtcta 7740
gcccgttaca gaaaaagtct gctgactact gagccagacc tccattacct ccatccctgt 7800
tggattattt aaagaaagcc tcagacagta agggcttttt taaaagaata aaatgacttg 7860
gtttgcgctt ggaagcaggg gaagcattca gatgagcggt ttctgcatta accctgccta 7920
tcacgcatct cgtgtcctgt gtggctggcg agcccccctt ggaaggttct ggtgcttcag 7980

-continued

```
ctggctcctg cagagtccac cccgcctcgt ggtgggaatg cagagccctt tgctttcctt   8040

cttgccgcct gcttcctgtt cctggggacc cgctgggcct ttggtctgca tcccctggcc   8100

aggtccctca gggttgatgc gtggagaagg actttgagca gtggtgggca gcagtggcct   8160

cctggccagc tcacactctt gtcctgggag gggcagcctg atctcacctc cacctagtac   8220

cttggggact gaggaccttt tggcttctct ggagcctgca agcctcttcc catgtgtcca   8280

gctgctcttc ctgctacaaa ggggactgct cacagtggcc tcagcttggt ggttttgagg   8340

ggccgccccc cggccctcca taagggtatc ctgggcctga gaattctgca tctgccattg   8400

gaggatggac agcctcaaat ggaaggagtc ccacgggaga tgggtccgag gtccggctgt   8460

ggccatccag ccccctgtgg cttgtccagc ctctgtgcac ccctggtgtc ttcactccag   8520

gggcagacag cagccactgc agttcctttc ttcgtgagta acagtagtga tagcagctgg   8580

ggctaacagg ctaggctttg tgttctgcgc atttggtcag cttctcactc gatcctccct   8640

aaagcaatgg ggaggccccc actagcccag ttttcaggaa gtcaactggg aggttagatg   8700

ggggccaggg tcccacagct actgatggcc cgagccaggt tgagcttcct ggtgtccagt   8760

ccggatccca cttgcagatc tcatgctctc agataggtgg gacaagttct tttgtcacag   8820

tgctggctct gtcctgaggc ctcattgctg gctgggtgtg ctctgctggg aaaagctttg   8880

cggggcttgc ttggttaacc acagaagaga aggggactgt ttggggtgcc tctctgcagc   8940

ctccccgtgc tgggtggaag cacggttact gtgttctcta atgttcatgt atttaaaatg   9000

atttctttct aaagatgtaa cctccacacc tttctccaga ttgggtgact cttttctaaa   9060

ggtggtggga gtatctgtcg gggtggtgtg gcccttggat gggtcaggtg ggtgtgagag   9120

gtcctgggga ggtgggcgtt gagctcaaag ttgtcctact gccatgtttt tgtacctgaa   9180

ataaagcata ttttgcactt gttactgtac catagtgcgg acgagaagtc tgtatgtggg   9240

atctgtgctt gggttagaat gcaaataaaa ctcacatttg taagaaaaaa aaaaaaaaaa   9300

aaaaaa                                                              9306
```

<210> SEQ ID NO 167
<211> LENGTH: 7218
<212> TYPE: DNA
<213> ORGANISM: Homo sapiens

<400> SEQUENCE: 167

```
gccccgcatc gtgcccggcc ccgtcgcgga gatcccggac gaccgtcgcg ggttgatggt     60

cgcattccag atgtaaacag cttcagaagc ctgacggtca tatggtagaa tcactgtgga    120

ctgagaccca cctttctaga cctgaagccc aggaggagga agaggaggct ggttggtacc    180

atgggcataa tgctctgaat cctagtctct cacctagtat gtgagcagtc cctgcagatg    240

gcccatttgg agatcttgac aaagcctctt ctgtttccaa tggggttttt ggcgcattct    300

cacagactta gatgaaactg tgatggccac cgcagggggc aggtgctgac atcgtcccca    360

gccctgtggc tgttcatccg gacatcattt ccaacctcaa tatctaaatg ccacagtgct    420

cttggagcaa gttgggctgg ggaccactgt tgccttttaa gaccataaaa ccatgggaaa    480

cgcagaaagt caacatgtag agcacgagtt ttatggagaa aagcatgcca gcctggggcg    540

caagcacact tcccgctccc tgcgcctctc gcacaagacg cggaggacca ggcacgcttc    600

ctcggggaag gtgatccaca ggaactccga agtgagcacc cgatccagca gcaccccccag    660

catcccccag tccctggctg aaaatggcct ggagcccttc tcccaagatg gtaccctaga    720

agacttcggg agccccatct gggtggaccg agtggacatg ggcttgagac ctgtgtctta    780
```

cactgactct tctgtcactc ccagcgtaga cagcagcatc gtcctcacag cagcctctgt 840
gcagagcatg ccagacactg aggagagcag gctttacggg gatgacgcta catatttggc 900
tgagggaggc aggaggcagc attcctatac atccaatggg cccactttca tggagacggc 960
gagctttaag aagaaacgct ccaaatctgc agacatctgg cgggaggaca gcctggaatt 1020
ctcactctct gatctgagcc aagaacattt aacaagcaac gaagaaatct tgggttccgc 1080
cgaagagaag gactgcgagg aggctcgggg gatggaaacg cgggcgagtc cgcggcagct 1140
cagcacctgt cagagagcca attccttggg tgacttgtat gctcagaaaa actctggagt 1200
gacagcaaac ggggggccgg ggagcaaatt tgcaggctac tgtcggaatt tggtgtctga 1260
tattcccaat cttgcaaacc ataagatgcc accagctgct gctgaagaga ctcctccgta 1320
cagtaattat aacacacttc cctgtaggaa atctcactgt ctctctgaag gtgccaccaa 1380
cccacaaatt agccatagca acagcatgca aggcagaaga gctaaaacaa ctcaggatgt 1440
taatgcaggc gagggcagtg agtttgcaga cagtgggatt gaaggggcca ctaccgacac 1500
ggacctcctg tccaggcgat ctaatgccac caactccagc tactcaccca ccacaggccg 1560
ggcctttgtg ggcagcgaca gcggcagcag ctccaccggg gatgcggctc gtcagggggt 1620
gtacgagaac ttccggcggg agctggagat gagcaccacc aacagcgaga gcctggagga 1680
ggccggctcg gcgcacagcg atgagcagag cagcggcacc ctgagctctc cgggccagtc 1740
ggacatcctg ctgaccgccg cacagggcac ggtgcgcaag gccggcgccc tggccgtcaa 1800
gaacttcctg gtgcacaaga agaacaagaa ggtggagtca gccacccgga ggaagtggaa 1860
gcactactgg gtgtccctga aggatgcac gctatttttc tacgagagcg acggcaggtc 1920
tgggatagac cacaacagca tccccaaaca cgccgtctgg gtggagaaca gcattgtgca 1980
ggcggtgcct gagcacccca agaaggactt tgtcttctgc ctcagcaatt ccctgggtga 2040
tgccttcctt tttcagacca ctagccagac ggagcttgaa aactggatca ccgccatcca 2100
ctctgcctgc gccactgcgg tcgcgaggca ccaccacaag gaagacacgc tccgactcct 2160
gaaatcagag atcaaaaaac tggaacagaa gattgacatg gatgaaaaga tgaagaaaat 2220
gggtgaaatg cagctgtctt cagtcactga ctcaaagaaa aagaaaacaa tattagatca 2280
gatctttgtc tgggagcaaa atctcgagca gttccaaatg gacctgtttc gtttccgctg 2340
ttatttagcc agccttcagg gtggggagct gccaaacccc aaaaggcttc tcgcttttgc 2400
aagtcgacca acgaaagtgg ccatgggccg ccttggaatc ttttcggtat catcgtttca 2460
tgccctggtg gcagcacgca ctggtgaaac tggagtgaga agacgtactc aggccatgtc 2520
cagatccgcg agcaagcgaa ggagcaggtt ttcttctctg tggggtctgg atactacctc 2580
caaaaagaag cagggacggc caagcatcaa tcaggtgttt ggagagggaa ccgaagctgt 2640
aaagaaatct ttagagggaa tatttgatga cattgttcca gatggcaaga gggagaaaga 2700
agtggtctta cctaacgttc accagcacaa ccctgactgc gacatttggg tccacgagta 2760
tttcactcca tcctggttct gtctgcccaa taatcagcct gccctgacgg tcgtccggcc 2820
aggcgacact gcacgggaca ccctggagct gatttgcaag acacatcaac tggatcattc 2880
tgctcattac ctgcgcctga aatttctaat agaaaacaaa atgcagctct atgttccaca 2940
gcccgaggaa gacatctatg agctgctgta caaagaaatt gaaatctgtc caaaagtcac 3000
tcagagcatc cacattgaga agtcagatac agctgctgat acttacgggt tttcactttc 3060
ttctgtggaa gaagatggta ttcgaaggct gtacgtgaat agtgtgaagg aaaccggttt 3120

-continued

```
agcttccaag aaaggcctga aagcaggaga tgagattctt gagatcaata atcgtgctgc   3180
tgacgccctg aactcttcta tgctcaaaga tttcctctca cagccctcgc tgggcctcct   3240
ggtgaggacc taccccgagc tggaggaagg agtggagctg ctggaaagcc cgccccaccg   3300
agtggacggc cctgccgacc ttggcgagag ccccctcgcc tttctcacca gcaacccagg   3360
gcacagcctt tgcagcgagc agggcagcag tgctgagacc gctccagagg agaccgaggg   3420
gccagacttg gaatcctcag atgagactga tcacagcagc aagagtacag aacaggtggc   3480
cgcattttgc cgcagtttgc atgagatgaa cccctctgac cagagcccat ctcctcagga   3540
ctccacgggg cctcagctgg cgaccatgag acaactctcg gatgcagata agctgcgcaa   3600
ggtgatctgc gagctcctgg agacggagcg cacctacgtg aaggatttaa actgtcttat   3660
ggagagatac ctaaagcctc ttcaaaaaga aacttttctc acccaggatg agcttgacgt   3720
gctttttgga aatttaacgg aaatggtaga gtttcaagta gaattcctta aaactctaga   3780
agatggagtg agactggtac ctgatttgga aaagcttgag aaggttgatc aatttaagaa   3840
agtgctgttc tctctggggg gatcattcct gtattatgct gaccgcttca agctctacag   3900
tgccttctgc gccagccaca caaaagttcc caaggtcctg gtgaaagcca agacagacac   3960
ggctttcaag gcattcttgg atgcccagaa cccgaagcag cagcactcat ccacgctgga   4020
gtcgtacctc atcaagccca tccagaggat cctcaagtac ccacttctgc tcagggagct   4080
gttcgccctg accgatgcgg agagcgagga gcactaccac ctggacgtgg ccatcaagac   4140
catgaacaag gttgccagtc acatcaatga gatgcagaaa atccatgaag agtttggggc   4200
tgtgtttgac cagctgattg ctgaacagac tggtgagaaa aaagaggttg cagatctgag   4260
catgggagac ctgcttttgc acactaccgt gatctggctg aacccgccgg cctcgctggg   4320
caagtggaaa aaggaaccag agttggcagc attcgtcttc aaaactgctg tggtccttgt   4380
gtataaagat ggttccaaac agaagaagaa acttgtagga tctcacaggc tttccattta   4440
tgaggactgg gaccccttca gatttcgaca catgatcccc acggaagcgc tgcaggttcg   4500
agctttggcg agtgcagatg cagaggcaaa tgccgtgtgt gaaattgtcc atgtaaaatc   4560
cgagtctgaa gggaggccgg agagggtctt tcacttgtgc tgcagctccc cagagagccg   4620
aaaggatttc ctaaaggctg tgcattcaat cctgcgtgat aagcacagaa gacagctcct   4680
caaaaccgag agccttccct catcccagca atatgtccct tttggaggca aaagattgtg   4740
tgcactgaag ggggccaggc cggccatgag cagggcagtg tctgccccaa gcaagtctct   4800
tgggaggagg aggcggcggc tggctcgaaa caggtttacc attgattctg atgccgtctc   4860
cgcaagcagc ccggagaaag agtcccagca gccccccggt ggtggggaca ctgaccgatg   4920
ggtagaggag cagtttgatc ttgctcagta tgaggagcaa gatgacatca aggagacaga   4980
catcctcagt gacgatgatg agttctgtga gtccgtgaag ggtgcctcag tggacagaga   5040
cctgcaggag cggcttcagg ccacctccat cagtcagcgg gaaagaggcc ggaaaaccct   5100
ggatagtcac gcgtcccgca tggcacagct caagaagcaa gctgccctgt cggggatcaa   5160
tggaggcctg gagagcgcaa gcgaggaagt catttgggtt aggcgtgaag actttgcccc   5220
ctccaggaaa ctgaacactg agatctgact gcgtcacctg ccccgtagag aatgtgtgta   5280
gatacttcct gccctaactc tgcccaccct cctgtaccgt cgacaagaat gtccccttag   5340
gtcgcgctct tgcacacacg gttttggcag ctgacttggt tctgaagcca tgtagccacc   5400
caactttgtc attttcaaca acatcagaaa gaattgatca gaatcccaaa taagcttgag   5460
tcctatcttc tgtatattac taagggcttt tatttattct caataaatca gggcctgaac   5520
```

aattaaaaga aaaaagattc tatagcactg gaaagcaaat caccccagga gttaacggat 5580
gtacaacaga ttaatttaag ggatagtagc acacacacga tccttctatc tgaaatcagt 5640
ctcctagctg gggaaacctc tttcacacac aaaatgaaat gtgtacagct tgccgtgttc 5700
tgactgtacc cttccctctt ccatgtctga gaatctccgt gtattttaag aatgtgtgag 5760
gagagggtgg cgattcatgt ttcaatgagc ctcttttttt ttttccttcc tgttttggtc 5820
tatggctggt cttactctgt gtccatgttc ggaagctcta gttttgcata gaattataga 5880
gatgccaaac tctttgaaaa gagatccaaa tttatcgctt gagagaaaga aaagaaacac 5940
tattttttgt attttacctg agatacaggg gcacaaatag atgagaattt tacagtgtta 6000
gtgtatgtat ccctgagcct aaaaaatgag gatataacct tttacagaga gagtgaggcg 6060
tggtggtttt atatttatat atgaaaggcc agcaagctca tgcgaaggat atacttttct 6120
tccaaaaagc ggattttttt tttttaatgt ttgaatctat atttgagatg ggagtttggt 6180
tggattaaac atgacacccc ggtgggcggt gtgtgtgtct gttgcacatg gcagggaggg 6240
gagcctcctt ctcatggggt tgccatggtg atcattggtt tttccatcaa aattgcatct 6300
tcatccatag attaccttcc ccttccctga cagtccataa ccaaaccttt aaacagaaca 6360
acctctttaa aaacttctct tgtgtttaac actttcttca tgccaacgaa acagggtaaa 6420
catgctcaaa acattaacag tctaaacaga tatccaaata ctaagaagaa aaacaagtta 6480
tagcactttc aatttttttt ttttttttaa aaaaaggttt atagcttttt cttttcccat 6540
gtcacaatgt ccacttccta agaagggttt aaaatactat gaaaactttc tttttgggga 6600
aaatatctat ttggtgtttg acacatcagt aggtacttta aagacctgaa ttttatagta 6660
gctttaggag ttatatttta taaaaatcag ttatgacttt atatttccag acaatagaga 6720
gttcagtaca tcatgctctt gtgcctctgc ctgcttttcc tgcgttccca ccctgtattc 6780
cccccgcctt tcgggtttcc agggcttcga gcttgatctt ttgaaagttt tattctatta 6840
aatttttgct atatcttctg gttttctgaa aaagctttag aatggtttct ataccctttg 6900
tatcactgca tttttccata tcatctccgg ttcgatcgcg tccagatgga aaacggaagc 6960
agaggcttct aatcgtcgca tttactggct ccagtgcaac acatccatct gaaaacactc 7020
ggaagtctgg tgcttggaga gggtgccatt gtctcttgta cataaggtca tgacgtgtct 7080
atgtcaaaag ttcttatata tttcttttat aagctgaaag aaggtctatt tttatgtttt 7140
taggtctatg aatggaacgt tgtaaatgct tgtcaaacaa taaaaataac gaaaagtgaa 7200
aaaaaaaaaa aaaaaaaa 7218

<210> SEQ ID NO 168
<211> LENGTH: 931
<212> TYPE: DNA
<213> ORGANISM: Homo sapiens

<400> SEQUENCE: 168
tttcgtcggc ccgccccttg gcttctgcac tgatggtggg tggatgagta atgcatccag 60
gaagcctgga ggcctgtggt ttccgcaccc gctgccaccc ccgcccctag cgtggacatt 120
tatcctctag cgctcaggcc ctgccgccat cgccgcagat ccagcgccca gagagacacc 180
agagaaccca ccatggcccc ctttgagccc ctggcttctg gcatcctgtt gttgctgtgg 240
ctgatagccc ccagcagggc ctgcacctgt gtcccacccc acccacagac ggccttctgc 300
aattccgacc tcgtcatcag ggccaagttc gtggggacac cagaagtcaa ccagaccacc 360

```
ttataccagc gttatgagat caagatgacc aagatgtata aagggttcca agccttaggg    420

gatgccgctg acatccggtt cgtctacacc cccgccatgg agagtgtctg cggatacttc    480

cacaggtccc acaaccgcag cgaggagttt ctcattgctg gaaaactgca ggatggactc    540

ttgcacatca ctacctgcag ttttgtggct ccctggaaca gcctgagctt agctcagcgc    600

cggggcttca ccaagaccta cactgttggc tgtgaggaat gcacagtgtt tccctgttta    660

tccatcccct gcaaactgca gagtggcact cattgcttgt ggacggacca gctcctccaa    720

ggctctgaaa agggcttcca gtcccgtcac cttgcctgcc tgcctcggga gccagggctg    780

tgcacctggc agtccctgcg gtcccagata gcctgaatcc tgcccggagt ggaagctgaa    840

gcctgcacag tgtccaccct gttcccactc ccatctttct tccggacaat gaaataaaga    900

gttaccaccc agcagaaaaa aaaaaaaaaa a                                    931


<210> SEQ ID NO 169
<211> LENGTH: 7697
<212> TYPE: DNA
<213> ORGANISM: Homo sapiens

<400> SEQUENCE: 169

agaatgggaa actgccttgg gagaagcccc aagtgagccc aagggcgcag agcagaagga     60

ccctggagtg taagagccta gattgcaagc ctggcaggag gagccggaag aattaacctc    120

gagtctgcac gcttttaaga acaaggcctt taaaaaatcc aaagtgtgtg gagtttgcaa    180

acaaattatt gacggtcaag gtatttcatg ccgagcctgc aagtattcct gccacaagaa    240

atgtgaagcc aaggtggtga ttccctgcgg tgtgcaagtc cgactggaac aggctccagg    300

gagttccacg ctgtccagtt ctctctgccg tgataaacct ctgcggcccg tcatcctgag    360

tcccaccatg gaggagggcc atgggctgga cctcacttac atcacggagc gcatcatcgc    420

tgtgtccttc cctgccggct gctctgagga gtcctacctg cacaacctac aggaggtcac    480

gcgcatgctc aagtccaagc acggggacaa ctacctggta tttaaccttt cagaaaagag    540

atatgacctt acgaagctta acccaaagat catggatgtg ggctggccag agctccacgc    600

accgcccctg gataagatgt gtaccatatg caaggcgcag gagtcctggc tgaacagcaa    660

cctccagcat gtggtcgtca ttcactgcag gggcgggaaa ggacgcatag gagtggtcat    720

atcatcctac atgcatttca ccaacgtctc agccagcgcc gaccaggccc ttgacaggtt    780

tgcaatgaag aagttttatg atgacaaagt ttcagcttta atgcagcctt cccaaaaacg    840

gtatgttcag ttcctcagtg ggctcctgtc cggatcggtg aaaatgaatg cctctcccct    900

gttcctgcat tttgtcatcc tccacggcac ccccaacttc gacacaggtg gagtgtgccg    960

gccctttctg aagctctacc aagccatgca gcctgtgtac acctccggga tctacaacgt   1020

tggcccagaa aaccccagca ggatctgcat cgtcatcgag ccggcccagc ttctgaaggg   1080

agatgtcatg gtgaaatgct accacaagaa ataccgctcg gccacccgtg acgtcatttt   1140

ccgcctgcag tttcacactg ggctgtgca gggctacggg ctggtgtttg ggaaggagga    1200

tctggacaat gccagcaaag atgaccgttt tcctgactat gggaaggttg aattagtctt   1260

ctctgccacg cctgagaaga ttcaagggtc cgaacacttg tacaacgacc acggtgtgat   1320

tgtggactac aacacaacag acccactgat acgctgggac tcgtacgaga acctcagtgc   1380

agatggagaa gtgctacaca cgcagggccc tgtcgatggc agcctttacg cgaaggtgag   1440

gaagaaaagc tcctcggatc ctggcatccc aggtggcccc caggcaatcc cggccaccaa   1500

cagcccagac cacagtgacc acaccttgtc tgtcagcagt gactccggcc actctacagc   1560
```

```
ctctgccagg acggataaga cggaagagcg cctggcccca ggaaccagga ggggcctgag   1620
tgcccaggag aaggcagagt tggaccagct gctcagtggc tttggcctgg aagatcctgg   1680
aagctccctc aaggaaatga ctgatgctcg aagcaagtac agtgggaccc gccacgtggt   1740
gccagcccag gttcacgtga atggagacgc tgctctgaag gatcgggaga cagacattct   1800
ggatgacgag atgccccacc acgacctgca cagtgtggac agccttggga ccctgtcctc   1860
ctcggaaggg cctcagtcgg cccacctggg tcccttcacc tgccacaaga gcagccagaa   1920
ctcactccta tctgacggtt ttggcagcaa cgttggtgaa gatccgcagg gcaccctcgt   1980
tccggacctg ggccttggca tggacggccc ctatgagcgg gagcggactt ttgggagtcg   2040
agagcccaag cagccccagc ccctgctgag aaagccctca gtgtccgccc agatgcaggc   2100
ctatgggcag agcagctact ccacacagac ctgggtgcgc cagcagcaga tggttgtagc   2160
tcaccagtat agcttcgccc cagatgggga ggcccggctg gtgagccgct gccctgcaga   2220
caatcctggc ctcgtccagg cccagcccag agtgccactc acccccaccc gagggaccag   2280
cagtagggtg gctgtccaga ggggtgtagg cagtgggcca catcccccctg acacacagca   2340
gccctctccc agcaaagcgt tcaaacccag gtttccagga gaccaggttg tgaatggagc   2400
cggcccagag ctgagcacag gcccctcccc aggctcgccc accctggaca tcgaccagtc   2460
catcgagcag ctcaacaggc tgatcctgga gctggatccc accttcgagc ccatccctac   2520
ccacatgaac gccctcggta gccaggccaa tggctctgtg tctccagaca gcgtgggagg   2580
tgggctccgg gcaagcagca ggctgcctga cacaggagag ggccccagca gggccaccgg   2640
gcggcaaggc tcctctgctg aacagcccct gggcgggaga ctcaggaagc tgagcctggg   2700
gcagtacgac aacgatgctg gggggcagct gcccttctcc aaatgtgcat ggggaaaggc   2760
tggtgtggac tatgccccaa acctgccgcc attcccctca ccagcggacg tcaaagagac   2820
gatgacccct ggctatcccc aggacctcga tattatcgat ggcagaattt taagtagcaa   2880
ggagtccatg tgttcaactc cagcatttcc tgtgtctcca gagacaccgt atgtgaaaac   2940
agcgctgcgc catcctccgt tcagcccacc tgagcccccg ctgagcagcc cagccagtca   3000
gcacaaagga ggacgtgaac cacgaagctg ccctgagacg ctcactcacg ctgtggggat   3060
gtcagagagc cccatcggac ccaaatccac gatgctccgg gctgatgcgt cctcgacgcc   3120
ctcctttcag caggcttttg cttcttcctg caccatttcc agcaacggcc ctgggcagag   3180
gagagagagc tcctcttctg cagaacgcca gtgggtggag agcagcccca agcccatggt   3240
ttccctgctg gggagcggcc ggcccaccgg aagtcccctc agcgctgagt tctccggtac   3300
caggaaggac tccccagtgc tgtcctgctt cccgccgtca gagctccagg ctcctttcca   3360
cagccatgag ctgtccctag cagagccacc ggactccctg gcgcctccca gcagccaggc   3420
cttcctgggc ttcggcaccg ccccagtggg aagtggcctt ccgcccgagg aggacctggg   3480
ggccttgctg gccaattctc atggagcgtc accgaccccc agcatcccgc tgacagcgac   3540
aggggctgcc gacaatggct tcctgtccca caactttctc acggtggcgc ctggacacag   3600
cagccaccac agtccaggcc tgcagggcca gggtgtgacc ctgcccgggc agccacccct   3660
ccctgagaag aagcgggcct cggagggggga tcgttctttg ggctcagtct ctccctcctc   3720
cagtggcttc tccagcccgc acagcgggag caccatcagt atccccttcc caaatgtcct   3780
tcccgacttt tccaaggctt cagaagcggc ctcacctctg ccagatagtc caggtgataa   3840
acttgtgatc gtgaaatttg ttcaagacac ttccaagttc tggtacaagg cggatatttc   3900
```

aagagaacaa gccatcgcca tgttgaagga caaggagccg ggctcattca ttgttcgaga 3960
cagccattcc ttccgagggg cctatggcct ggccatgaag gtggccacgc cccaccttc 4020 agtcctgcag ctgaacaaga aagctggaga tttggccaat gaactcgtcc ggcacttttt 4080
gatcgagtgt accccgaagg gagtgcggtt gaaagggtgc tcgaatgaac catatttcgg 4140
gagcctgacg gccttggtgt gccagcattc catcacgccc ttggccttgc cgtgcaagct 4200
gcttatccca gagagagatc cattggagga aatagcagaa agttctcccc agacggcagc 4260
caattcagca gctgagctgt tgaagcaggg ggcagcctgc aatgtgtggt acttgaactc 4320
tgtggagatg gagtccctca ccggccacca ggcgatccag aaggccctga gcatcaccct 4380
ggtccaggag cctccacctg tgtccacagt tgtgcacttc aaggtgtcag cccagggcat 4440
caccctgaca gacaatcaga ggaagctctt cttccggagg cattaccccg tgaacagtgt 4500
gattttctgt gccttggacc cacaagacag gaagtggatc aaagatggcc cttcctcaaa 4560
agtctttgga tttgtggccc ggaagcaggg cagtgccacg gataatgtgt gccacctgtt 4620
tgcagagcat gaccctgagc agcctgccag tgccattgtc aacttcgtat caaaggtcat 4680
gattggttcc ccaaagaagg tctgagaact cccctccctc cctggaccca ccgatgcctc 4740
tcgaagccct ggagacagcc gttgggtgag ggtggggccc ccacttttta ccaaactagt 4800
aaacctgaca ttccaggccc atgaggggaa agaggatctt ccagctctgc aaaaacaaga 4860
acaaacaaca tcaccgtgaa ttggcctttc ctgaaagtga cttatctgac acatctctgt 4920
agccacatgc tttttgggta gaagaagctg ggcatgggtg caccccaccc cctagggtcc 4980
ccatgggaaa gggacatgca aggaaacagc acagaacacg aggtggtccc catgtccctg 5040
gcacactagc attccggggg atgaggaatc cccagccctt gaggcagagg tgccgagtga 5100
ctgccatgct tcgcccgtcc gcatgggcgc ttctgtccag ctgcacccga ggccgggggt 5160
ttccctcacc tcggtcttcc caagatggag atgctaacga aactgagaag ggggcgtatg 5220
tttgacgaag gtttgtgcaa gtcaggccct tctggaacac agcagggcct acaacgaggg 5280
gcctttgcga tgggctgtga ggatgggggt ggtgggaaga attggccacg ttggagaccc 5340
catgccaccc caccatggtg agtgctctgt gcctcctgct cacctgtggt gagctgggcg 5400
agctgggcga gctgggcgag ctgggctggg gagagcctgt gaggaccgag aggagaaatg 5460
agaagaagga acaaaaatat tatttctatg taatttatat tttacttatg ccaaattatt 5520
tatgataatt tgccattgct atactgtacc agtgtcaaat gctgcagcct gccaagctgt 5580
gattttgtga ggcttgtccc tatgtaggat gcaccgcagg cccctggcca ctgaaagagt 5640
gtgcagtgga ctgtgggtct cccatatgcg gtgccgccca aaggtggctt tgcctcaagc 5700
aacctaccct gatgttttac tcattggaat gtttttcccc gattgtggat gacttctttt 5760
ctgatggaga gagtccagga gggatggaaa actcctggat ttaagctcag catcccccac 5820
atgggctttt cgatcatctt caggcctgaa gctgcacgac ctgaagttcg cctgcattta 5880
tcagccctct ttgtgctgct ccttgccacc ttggggttcc tgctggggac catgtgtggt 5940
tgtggcatgt gtgagcagaa gggaggatga ggaaaaagag aagaaacccc ggtactgaca 6000
agctgttttt gagtgccact gtttgccatc atctaagcca ctgaatcaag tgtatttcag 6060
gcttatttca acattccaat gccctggttt tcctgcttga atctgttcgt ggtcaaaggt 6120
ttgggggaat ttgtgaccct ggaacatccc cagagtgaaa gatggagctg ggccacatca 6180
gaataaggcc ttggccccat cctctcacag cctaggtgct ctgcaggcat gctgactgtc 6240
ctgattgcga tccagcccga aattccctcc tctgctttca aaagtcaaat cccccattct 6300

-continued

```
taggccacac tggtgtcaca agctcctgtc agggagctgg ggtttgggaa tgtgctttgt   6360

gaactctgct ttaaagtgag gggccgagga aaacttagaa acaggcagag ttggaagcag   6420

ccaaatcaca gtgggtgttg tgtgtgtgtg cgtgtgtgca tgcgtgcgtg tatgcgtgtg   6480

tgaaagcagg tggaccattc cactttttag ctcctattga tgcaccaaac caagtgcctc   6540

atttctgtgc caaatgtttg ccttggtcgt tgtggacctc cttctctaac ttgcggtggc   6600

atgactgtca ggaggtgctg gcattttcag cagatcctca tgtgttgacc ctgatgtctt   6660

tagcagaggc ctctagcatc tcggtttttc atccactgca ggaatgtggc cacagggagc   6720

agaggtttgt actttcccca agaggtcctc atcctgagac ggtctctacc catgtttaac   6780

ccaaagagtg caggccaggt tccttatcct tctgatgaag gatgagagag ctcatttaga   6840

agtcagagca aactagggtc tcagtattga gaaacgcagc ctgccaggga atcacagaga   6900

catcggggtg cccgcgatgg ccctcatgaa gccatgcctc gacggcattc aggaagccct   6960

gcaaacgtgc tttttgaact cattggccag gtgtgatttt tacacaaggt aaacgtggtc   7020

aagggcatcg gggaatttgc tccaagcaga tagctccctc tgaggaacca aaggaagcaa   7080

gtttccacga tttctgaaga gctggtatag gaagtttctt tcttcctttt gtgttacatg   7140

tgcattaaac agaacaagct gtgtgtcatc acagattgta ctgtgggctc agaaaccgtg   7200

agagagcccc caccgtggac accggctcta gggccacagg aaaaggaacg tttccaggca   7260

ttttgtctcc agggctcccg ctggacaggc acgtactgcc ctggggagta aatgcggaga   7320

gttcacgaac tgtgcccaac gcatgttata gccagggtcc tactaactac tcagtaaaag   7380

aacgtattgt tgtattcctc cagtgttaag ctatagccat gttaaaagtc actgtgcatt   7440

tattctcagc atcaaatacc ttgtaacgtc ttctctgcct tgttagtgca tatttttact   7500

tttctgatac tgtaaagaat atatccagta tgtaaatgaa tgttctataa atcttttgta   7560

tagtcatttt ctctgctcct taaatatcat ctctattcag agtataataa aattatgaac   7620

ttggtaaaaa aaaaaaaaaa aaaaaaaaaa aaaaaaaaaa aaaaaaaaaa aaaaaaaaaa   7680

aaaaaaaaaa aaaaaaa                                                  7697
```

```
<210> SEQ ID NO 170
<211> LENGTH: 2579
<212> TYPE: DNA
<213> ORGANISM: Homo sapiens

<400> SEQUENCE: 170

ggccctggct gccgccgctg cctcgtccgg actcggagag gacttgggag ggacagcggc     60

gctgggaggt ggcttagcag agactttcca gcaactgctg cccaggactt tttttttttt    120

ttttcttttt cccaggaggc ggcgacggcg gcggcggggg gagaggaaga gaaagaagcg    180

tctccagctg aagccaatgc agccctccgg ctctccgcga agaagttccc tgccccgatg    240

agcccccgcc gtgcgtcccc gactatcccc aggcgggcgt ggggcaccgg gcccagcgcc    300

gacgatcgct gccgttttgc ccttgggagt aggatgtggt gaaaggatgg ggcttctccc    360

ttacggggct cacaatggcc agagaagatt ccgtgaagtg tctgcgctgc ctgctctacg    420

ccctcaatct gctcttttgg ttaatgtcca tcagtgtgtt ggcagtttct gcttggatga    480

gggactacct aaataatgtt ctcactttaa ctgcagaaac gagggtagag gaagcagtca    540

ttttgactta ctttcctgtg gttcatccgg tcatgattgc tgtttgctgt ttccttatca    600

ttgtggggat gttaggatat tgtggaacgg tgaaaagaaa tctgttgctt cttgcatggt    660
```

```
actttggaag tttgcttgtc attttctgtg tagaactggc ttgtggcgtt tggacatatg    720

aacaggaact tatggttcca gtacaatggt cagatatggt cactttgaaa gccaggatga    780

caaattatgg attacctaga tatcggtggc ttactcatgc ttggaatttt tttcagagag    840

agtttaagtg ctgtggagta gtatatttca ctgactggtt ggaaatgaca gagatggact    900

ggcccccaga ttcctgctgt gttagagaat tcccaggatg ttccaaacag gcccaccagg    960

aagatctcag tgacctttat caagagggtt gtgggaagaa aatgtattcc tttttgagag   1020

gaaccaaaca actgcaggtg ctgaggtttc tgggaatctc cattggggtg acacaaatcc   1080

tggccatgat tctcaccatt actctgctct gggctctgta ttatgataga agggagccgg   1140

ggacagacca aatgatgtcc ttgaagaatg acaactctca gcacctgtca tgtccctcag   1200

tagaactgtt gaaaccaagc ctgtcaagaa tctttgaaca cacatccatg gcaaacagct   1260

ttaatacaca ctttgagatg gaggagttat aaaaagaaat gtcacagaag aaaaccacaa   1320

acttgtttta ctggacttgt gaatttttga gtacatacta tgtgtttcag aaatatgtag   1380

aaataaaaat gttgccataa aataacacct aagcatatac tattctatgc tttaaaatga   1440

ggatggaaaa gtttcatgtc ataagtcacc acctggacaa taattgatgc ccttaaaatg   1500

ctgaagacag atgtcatacc cactgtgtag cctgtgtatg acttttactg aacacagtta   1560

tgttttgagg cagcatggtt tgattagcat ttccgcatcc atgcaaacga gtcacatatg   1620

gtgggactgg agccatagta aaggttgatt tacttctacc aactagtata taaagtacta   1680

attaaatgct aacataggaa gttagaaaat actaataact tttattactc agcgatctat   1740

tcttctgatg ctaaataaat tatatatcag aaaactttca atattggtga ctacctaaat   1800

gtgatttttg ctggttacta aaatattctt accacttaaa agagcaagct aacacattgt   1860

cttaagctga tcagggattt tttgtatata agtctgtgtt aaatctgtat aattcagtcg   1920

atttcagttc tgataatgtt aagaataacc attatgaaaa ggaaaatttg tcctgtatag   1980

catcattatt tttagccttt cctgttaata aagctttact attctgtcct gggcttatat   2040

tacacatata actgttattt aaatacttaa ccactaattt tgaaaattac cagtgtgata   2100

cataggaatc attattcaga atgtagtctg gtctttagga agtattaata agaaaatttg   2160

cacataactt agttgattca gaaaggactt gtatgctgtt tttctcccaa atgaagactc   2220

tttttgacac taaacacttt ttaaaaagct tatctttgcc ttctccaaac aagaagcaat   2280

agtctccaag tcaatataaa ttctacagaa aatagtgttc tttttctcca gaaaaatgct   2340

tgtgagaatc attaaaacat gtgacaattt agagattctt tgttttattt cactgattaa   2400

tatactgtgg caaattacac agattattaa attttttttac aagagtatag tatatttatt  2460

tgaaatggga aaagtgcatt ttactgtatt ttgtgtattt tgtttatttc tcagaatatg   2520

gaaagaaaat taaaatgtgt caataaatat tttctagaga gtaaaaaaaa aaaaaaaaa    2579
```

<210> SEQ ID NO 171
<211> LENGTH: 1796
<212> TYPE: DNA
<213> ORGANISM: Homo sapiens

<400> SEQUENCE: 171

```
ggtcagctga gttcgccggc ccagggcagg cggggcccga gcctagcggt aacccccggg     60

cagggcgggg ccgctcgcag actccatatg agattcacct cgcaggtggt tccctcattc    120

gagtgctccg gcgcacagac ccgcgccccg ccgtctgcga gcctcccgag agccgtccct    180

tcgtccggcc ctggagcatt gcgtttgtcg ccggtgtcgc agtgcgagga tggcgccgcg    240
```

```
ggtgtagcgg ctctctgcgc aggccgagtg ggcccagaga agcgaggaac tccgcagctc    300
gtcgacacgt ctcgtctcct gtcccaattc agggcttggt gaggtgactc gcggtcgcgg    360
gtgactcgcc ggcaggacac tgcctggaac gcctggagcg cctcccactg cagacgtctg    420
tccgcctcca gccgctctcc tctgacgggt cctgcctcag ttggcggaat ggcggccacg    480
ggagccaatg cagagaaagc tgaaagtcac aatgattgcc ccgtcagact tttaaatcca    540
aacatagcaa aaatgaaaga agatattctc tatcatttca atctcaccac tagcagacac    600
aatttcccag ccttgtttgg agatgtgaag tttgtgtgtg ttggtggaag cccctcccgg    660
atgaaagcct tcatcaggtg cgttggtgca gagctgggcc ttgactgccc aggtagagac    720
tatcccaaca tctgtgcggg aactgaccgc tatgccatgt ataaagtagg accggtgctg    780
tctgtcagtc atggtatggg cattccttct atctcaatca tgttgcatga gctcataaag    840
ctgctgtact atgcccggtg ctccaacgtc actatcatcc gcattggcac ttctggtggg    900
ataggtctgg agcccggcac tgtggtcata acagagcagg cagtggatac ctgcttcaag    960
gcagagtttg agcagattgt cctggggaag cgggtcatcc ggaaaacgga ccttaacaag   1020
aagctggtgc aggagctgtt gctgtgttct gcagagctga gcgagttcac cacagtggtg   1080
gggaacacca tgtgcacctt ggacttctat gaagggcaag gccgtctgga tggggctctc   1140
tgctcctaca cggagaagga caagcaggcg tatctggagg cagcctatgc agccggcgtc   1200
cgcaatatcg agatggagtc ctcggtgttt gccgccatgt gcagcgcctg cggcctccaa   1260
gcggccgtgg tgtgtgtcac cctcctgaac cgcctggaag gggaccagat cagcagccct   1320
cgcaatgtgc tcagcgagta ccagcagagg ccgcagcggc tggtgagcta cttcatcaag   1380
aagaaactga gcaaggcctg agcgctgccc tgcacctccg cagacctgct gtgatgactt   1440
gccattaaaa gcattgtcca aaatcccctg ttgtgtggac tttgagcaca ctttacacaa   1500
gaatctagaa aatcagatcg cgattaagag acagagaatc ttggattaac cgcatgggag   1560
atgttcttcc ttttgaagtt tcattggagc attttcaatg atgttagcct gatttggggt   1620
ttcttcaaga acattctacc aaatttttgt actatttcta gggaaatttt tcagacttta   1680
aaattctaat ggtagtcaga tttcatgtca ctaaacaaga aatctgacaa tagtgccagg   1740
aaactaattt cctgatacat taaaaaaatt ccatgcaaaa aaaaaaaaaa aaaaaa       1796
```

<210> SEQ ID NO 172
<211> LENGTH: 3443
<212> TYPE: DNA
<213> ORGANISM: Homo sapiens

<400> SEQUENCE: 172

```
gtgctttact gcgcgctctg gtactgctgt ggctccccgt cctggtgcgg gacctgtgcc     60
ccgcgcttca gccctccccg cacagcctac tgattcccct gccgcccttg ctcacctcct    120
gctcgccatg gagtcgctgg ttttcgcgcg gcgctccggc cccactccct cggccgcaga    180
gctagcccgg ccgctggcgg aagggctgat caagtcgccc aagcccctaa tgaagaagca    240
ggcggtgaag cggcaccacc acaagcacaa cctgcggcac cgctacgagt tcctggagac    300
cctgggcaaa ggcacctacg ggaaggtgaa gaaggcgcgg gagagctcgg ggcgcctggt    360
ggccatcaag tcaatccgga aggacaaaat caaagatgag caagatctga tgcacatacg    420
gagggagatt gagatcatgt catcactcaa ccaccctcac atcattgcca tccatgaagt    480
gtttgagaac agcagcaaga tcgtgatcgt catggagtat gccagccggg gcgaccttta    540
```

-continued tgactacatc agcgagcggc agcagctcag tgagcgcgaa gctaggcatt tcttccggca 600
gatcgtctct gccgtgcact attgccatca gaacagagtt gtccaccgag atctcaagct 660
ggagaacatc ctcttggatg ccaatgggaa tatcaagatt gctgacttcg gcctctccaa 720
cctctaccat caaggcaagt tcctgcagac attctgtggg agccccctct atgcctcgcc 780
agagattgtc aatgggaagc cctacacagg cccagaggtg gacagctggt ccctgggtgt 840
tctcctctac atcctggtgc atggcaccat gccctttgat gggcatgacc ataagatcct 900
agtgaaacag atcagcaacg gggcctaccg ggagccacct aaaccctctg atgcctgtgg 960
cctgatccgg tggctgttga tggtgaaccc cacccgccgg gccaccctgg aggatgtggc 1020
cagtcactgg tgggtcaact ggggctacgc cacccgagtg ggagagcagg aggctccgca 1080
tgagggtggg caccctggca gtgactctgc ccgcgcctcc atggctgact ggctccggcg 1140
ttcctcccgc cccctcctgg agaatggggc caaggtgtgc agcttcttca agcagcatgc 1200
acctggtggg ggaagcacca cccctggcct ggagcgccag cattcgctca agaagtcccg 1260
caaggagaat gacatggccc agtctctcca cagtgacacg gctgatgaca ctgcccatcg 1320
ccctggcaag agcaacctca agctgccaaa gggcattctc aagaagaagg tgtcagcctc 1380
tgcagaaggg gtacaggagg accctccgga gctcagccca atccctgcga gcccagggca 1440
ggctgccccg ctgctcccca agaagggcat tctcaagaag ccccgacagc gcgagtctgg 1500
ctactactcc tctcccgagc ccagtgaatc tggggagctc ttggacgcag gcgacgtgtt 1560
tgtgagtggg gatcccaagg agcagaagcc tccgcaagct tcagggctgc tcctccatcg 1620
caaaggcatc ctcaaactca atggcaagtt ctcccagaca gccttggagc tcgcggcccc 1680
caccaccttc ggctccctgg atgaactcgc cccacctcgc cccctggccc gggccagccg 1740
accctcaggg gctgtgagcg aggacagcat cctgtcctct gagtcctttg accagctgga 1800
cttgcctgaa cggctcccag agccccccact gcggggctgt gtgtctgtgg acaacctcac 1860
ggggcttgag gagcccccct cagagggccc tggaagctgc ctgaggcgct ggcggcagga 1920
tcctttgggg gacagctgct tttccctgac agactgccag gaggtgacag cgacctaccg 1980
acaggcactg agggtctgct caaagctcac ctgagtggag taggcattgc cccagcccgg 2040
tcaggctctc agatgcagct ggttgcaccc cgaggggaga tgccttctcc cccacctccc 2100
aggacctgca tcccagctca gaaggctgag agggtttgca gtggagccct gagcagggct 2160
ggatatggga agtaggcaaa tgaaatgcgc caagggttca gtgtctgtct tcagccctgc 2220
tgaacgaaga ggatactaaa gagaggggaa cgggaatgcc cgcgacagag tccacattgc 2280
ctgtttcttg tgtacatggg ggggccacag agacctggaa agagaactct cccagggccc 2340
atctcctgca tcccatgaat actctgtaca catggtgcct tctaaggaca gctccttccc 2400
tactcattcc ctgcccaagt ggggccagac ctctttacac acacattccc gttcctacca 2460
accaccagaa ctggatggtg gcacccctaa tgtgcatgag gcatcctggg aatggtctgg 2520
agtaacgctt cgttattttt atttttattt ttatttattt atttattttt ttgagacgga 2580
gtttcgctct tggtgcccag gctagagtgc aatggcgcga tctcagctca cctcaacctc 2640
cgcctcccgg gttcaagcga ttctcctgcc tcagcctccc tagtagctgg gattacaggc 2700
gcccgccacc atgcccggct aattttgtat ttttagtaga gacagggttt ctccatgttg 2760
gtcaggctgg tctcaaactc ccgacctcag gtgatccacc cacctcggcc tcccaaagtg 2820
ctgggattac aggcgtgagc caccgcgccc cacctaaccc ttccttattt agcctaggag 2880
taagagaaca caatctctgt ttcttcaatg gttctcttcc cttttccatc ctccaaacct 2940

-continued

```
ggcctgagcc tcctgaagtt gctgctgtga atctgaaaga cttgaaaagc ctccgcctgc   3000

tgtgtggact tcatctcaag gggcccagcc tcctctggac tccaccttgg acctcagtga   3060

ctcagaactt ctgcctctaa gctgctctaa agtccagact atggatgtgt tctctaggcc   3120

ttcaggactc tagaatgtcc atatttattt ttatgttctt ggctttgtgt tttaggaaaa   3180

gtgaatcttg ctgttttcaa taatgtgaat gctatgttct gggaaaatcc actatgacat   3240

ctaagttttg tgtacagaga gatatttttg caactatttc cacctcctcc cacaaccccc   3300

cacactccac tccacactct tgagtctctt tacctaatgg tctctaccta atggacctcc   3360

gtggccaaaa agtaccatta aaaccagaaa ggtgattgga aaaaaaaaaa aaaaaaaaaa   3420

aaaaaaaaaa aaaaaaaaaa aaa                                           3443
```